United States Patent
Matsuoka et al.

(10) Patent No.: US 12,310,955 B2
(45) Date of Patent: May 27, 2025

(54) CYCLIC AMIDE COMPOUNDS FOR RABIES TREATMENT AND METHOD THEREOF

(71) Applicant: Irimajiri Therapeutics Inc., Kochi (JP)

(72) Inventors: Shigeru Matsuoka, Yufu (JP); Akira Katoh, Yufu (JP); Tadashi Mishina, Fujisawa (JP); Kentaro Yamada, Yufu (JP); Atsushi Yoshimori, Fujisawa (JP); Toshimasa Ishizaki, Yufu (JP); Akira Nishizono, Yufu (JP); Hiroyuki Kouji, Fujisawa (JP)

(73) Assignee: Irimajiri Therapeutics Inc., Kochi (JP)

( * ) Notice: Subject to any disclaimer, the term of this patent is extended or adjusted under 35 U.S.C. 154(b) by 704 days.

(21) Appl. No.: 17/596,101

(22) PCT Filed: Jun. 3, 2020

(86) PCT No.: PCT/JP2020/021940
§ 371 (c)(1),
(2) Date: Dec. 2, 2021

(87) PCT Pub. No.: WO2020/246503
PCT Pub. Date: Dec. 10, 2020

(65) Prior Publication Data
US 2022/0331300 A1    Oct. 20, 2022

(51) Int. Cl.
A61K 31/439    (2006.01)
A61P 31/14    (2006.01)

(52) U.S. Cl.
CPC ............ *A61K 31/439* (2013.01); *A61P 31/14* (2018.01)

(58) Field of Classification Search
CPC ...... A61K 31/439; A61P 31/14; C07D 471/18
See application file for complete search history.

(56) References Cited

U.S. PATENT DOCUMENTS

| | | | |
|---|---|---|---|
| 2018/0273527 A1 | 9/2018 | Krogstad et al. | |
| 2022/0331300 A1 | 10/2022 | Matsuoka et al. | |

FOREIGN PATENT DOCUMENTS

| | | | |
|---|---|---|---|
| EP | 838 901 A1 | 6/2021 | |
| JP | 2003-510352 A | 3/2003 | |
| JP | 6890865 B1 | 6/2021 | |
| WO | 01/24785 A2 | 4/2001 | |
| WO | WO 2017053604 A1 | 3/2017 | |
| WO | WO 2019067623 A1 | 4/2019 | |
| WO | 2020/036211 A1 | 2/2020 | |

OTHER PUBLICATIONS

Extended European Search Report, dated Jan. 20, 2023, for European Patent Application No. 20818114.9. (8 pages).
Bromley et al., "Tandem inverse electron demand Diels-Alder, retro-Diels-Alder and intramolecular Diels-Alder sequences: one-pot synthesis of diaza-polycycles," *Tetrahedron* 63:6004-6014, 2007.
Craven et al., "Design, synthesis and decoration of molecular scaffolds for exploitation in the production of alkaloid-like libraries," *Bioorganic & Medicinal Chemistry* 23:2629-2635, 2015.
International Search Report and Written Opinion (w/ English Translation), dated Aug. 25, 2020, for International Application No. PCT/JP2020/021940. (11 pages).
Murrison et al., "Synthesis of Skeletally Diverse Alkaloid-Like Small Molecules," *Eur. J. Org. Chem.* 2354-2359, 2011.
Office Action (w/ English Translation), dated Jan. 5, 2021, for Japanese Application No. 2020-547016. (10 pages).

*Primary Examiner* — Kamal A Saeed
(74) *Attorney, Agent, or Firm* — Seed IP Law Group LLP

(57) ABSTRACT

The present disclosure provides compounds useful in the treatment and prevention of rabies. The present disclosure provides compounds represented by formula XXIF or XXIB

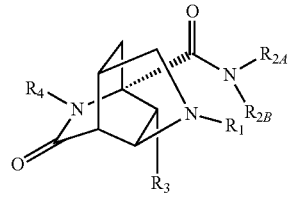

Formula XXIF

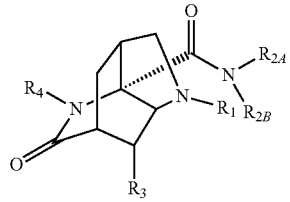

Formula XXIB

[in the formulas, $R_1$, $R_{2A}$, $R_{2B}$, $R_3$, and $R_4$ are as defined in the specification], solvates or pharmaceutically acceptable salts thereof, the use of these compounds, solvates or pharmaceutically acceptable salts thereof to treat or prevent rabies, pharmaceutical compositions including these compounds, solvates or pharmaceutically acceptable salts thereof, and a method for treating and preventing rabies using the same.

32 Claims, No Drawings

CYCLIC AMIDE COMPOUNDS FOR RABIES TREATMENT AND METHOD THEREOF

TECHNICAL FIELD

The present disclosure relates to a novel fused tricyclic compound that is useful as a medicament, an enantiomer thereof, or a pharmaceutically acceptable salt thereof, or a solvate thereof. More specifically, the present disclosure relates to a pharmaceutical composition comprising the fused tricyclic compound or an enantiomer thereof, or a pharmaceutically acceptable salt thereof, or a solvate thereof. The present disclosure also relates to a therapeutic agent comprising the fused tricyclic compound or an enantiomer thereof, or a pharmaceutically acceptable salt thereof, or a solvate thereof.

BACKGROUND ART

Rabies is an infection induced by a rabies virus. The mortality after the onset in humans is almost 100%. While over 15 million people worldwide are vaccinated post-exposure for the prophylaxis of rabies every year, the worldwide number of fatalities due to rabies is about 55,000 annually. An effective therapeutic method for rabies has not yet been established. There is still a demand for the establishment thereof.

SUMMARY OF INVENTION

Solution to Problem

The present disclosure provides a compound and a method for the treatment of rabies.

The technical matters of the present disclosure were completed by the inventors from finding that the compounds represented by the following formula IF, IB, IIF, IIB, XXIF, XXIB, XXIIF, XXIIB, XXIIIF, or XXIIIB and the structural formulae related thereto, or a pharmaceutically acceptable salt thereof (hereinafter, also referred to as "the compound(s) of the disclosure") can achieve the objects as a result of diligent study.

The present disclosure provides the following items.

[Item 1A]

A compound represented by formula XXIF:

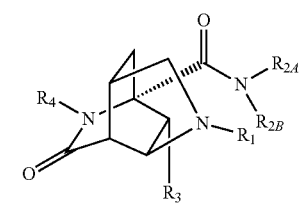

Formula XXIF

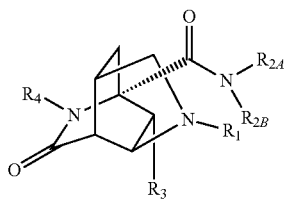

or an enantiomer thereof, or a salt thereof, or a solvate thereof, wherein $R_1$, $R_3$, and $R_4$ are each independently
hydrogen,
an optionally substituted hydrocarbon group,
an optionally substituted heterocycle,
optionally substituted carbonyl, or
an optionally substituted functional group, and $R_{2A}$ and $R_{2B}$ are each independently
hydrogen,
an optionally substituted hydrocarbon group,
an optionally substituted heterocycle,
optionally substituted carbonyl, or
an optionally substituted functional group, or $R_{2A}$ and $R_{2B}$, together with the nitrogen atom to which they are attached, form a heterocycle, wherein the heterocycles are each independently optionally substituted.

[Item 1B]

A compound represented by formula XXIF:

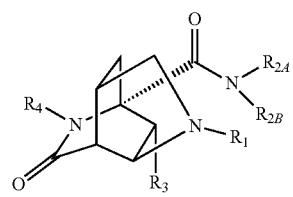

Formula XXIF

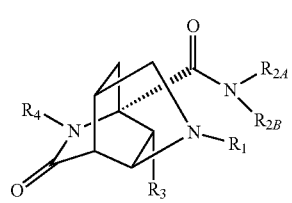

or an enantiomer thereof, or a salt thereof, or a solvate thereof, wherein $R_1$, $R_3$, and $R_4$ are each independently
hydrogen,
optionally substituted alkyl,
optionally substituted alkenyl,
optionally substituted alkynyl,
optionally substituted cycloalkyl,
optionally substituted heterocycloalkyl,
optionally substituted aryl,
optionally substituted heteroaryl, or
optionally substituted carbonyl, and $R_{2A}$ and $R_{2B}$ are each independently
hydrogen,
optionally substituted alkyl,
optionally substituted alkenyl,
optionally substituted alkynyl,
optionally substituted cycloalkyl,
optionally substituted heterocycloalkyl,
optionally substituted aryl,
optionally substituted heteroaryl, or
optionally substituted carbonyl, or $R_{2A}$ and $R_{2B}$, together with the nitrogen atom to which they are attached, form a non-aryl heterocycle or a heteroaryl ring,
wherein the non-aryl heterocycle and the heteroaryl ring are each independently optionally substituted.

[Item 2A]
A compound represented by formula XXIB:

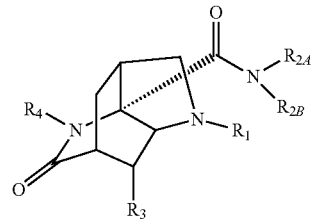

Formula XXIB

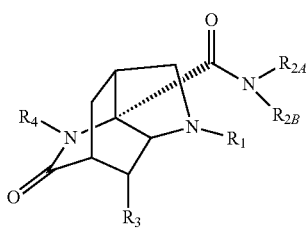

or an enantiomer thereof, or a salt thereof, or a solvate thereof, wherein
$R_1$, $R_3$, and $R_4$ are each independently
hydrogen,
an optionally substituted hydrocarbon group,
an optionally substituted heterocycle,
optionally substituted carbonyl, or
an optionally substituted functional group, and
$R_{2A}$ and $R_{2B}$ are each independently
hydrogen,
an optionally substituted hydrocarbon group,
an optionally substituted heterocycle,
optionally substituted carbonyl, or
an optionally substituted functional group, or
$R_{2A}$ and $R_{2B}$, together with the nitrogen atom to which they are attached, form a heterocycle, wherein the heterocycles are each independently optionally substituted.

[Item 2B]
A compound represented by formula XXIB:

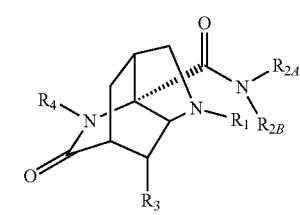

Formula XXIB

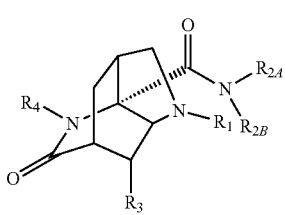

or an enantiomer thereof, or a salt thereof, or a solvate thereof, wherein
$R_1$, $R_3$, and $R_4$ are each independently
hydrogen,
optionally substituted alkyl,
optionally substituted alkenyl,
optionally substituted alkynyl,
optionally substituted cycloalkyl,
optionally substituted heterocycloalkyl,
optionally substituted aryl,
optionally substituted heteroaryl, or
optionally substituted carbonyl, and
$R_{2A}$ and $R_{2B}$ are each independently
hydrogen,
optionally substituted alkyl,
optionally substituted alkenyl,
optionally substituted alkynyl,
optionally substituted cycloalkyl,
optionally substituted heterocycloalkyl,
optionally substituted aryl,
optionally substituted heteroaryl, or
optionally substituted carbonyl, or
$R_{2A}$ and $R_{2B}$, together with the nitrogen atom to which they are attached, form a non-aryl heterocycle or a heteroaryl ring,
wherein the non-aryl heterocycle and the heteroaryl ring are each independently optionally substituted.

[Item 3A]
The compound or an enantiomer thereof, or a salt thereof, or a solvate thereof according to any one of the preceding items, wherein
the alkyl, alkenyl, alkynyl, cycloalkyl, heterocycloalkyl, aryl, heteroaryl, and carbonyl of $R_1$, $R_3$, and $R_4$ are each independently optionally substituted with one to the maximum substitutable number of the same or different substituents selected from substituent group I, and
the alkyl, alkenyl, alkynyl, cycloalkyl, heterocycloalkyl, aryl, heteroaryl, carbonyl, and the non-aryl heterocycle and the heteroaryl ring of $R_{2A}$ and $R_{2B}$ are each independently optionally substituted with one to the maximum substitutable number of the same or different substituents selected from substituent group I.

[Item 4A]
The compound or an enantiomer thereof, or a salt thereof, or a solvate thereof according to any one of the preceding items, wherein
$R_1$, $R_3$, and $R_4$ are each independently
hydrogen,
optionally substituted alkyl,
optionally substituted cycloalkyl,
optionally substituted heterocycloalkyl,
optionally substituted aryl,
optionally substituted heteroaryl, or
optionally substituted carbonyl, and
$R_{2A}$ and $R_{2B}$ are each independently
hydrogen,
optionally substituted alkyl,
optionally substituted cycloalkyl,
optionally substituted heterocycloalkyl,
optionally substituted aryl,
optionally substituted heteroaryl, or
optionally substituted carbonyl, or
$R_{2A}$ and $R_{2B}$, together with the nitrogen atom to which they are attached, form a non-aryl heterocycle or a heteroaryl ring,
wherein the non-aryl heterocycle and the heteroaryl ring are each independently optionally substituted.

[Item 4B]
The compound or an enantiomer thereof, or a salt thereof, or a solvate thereof according to any one of the preceding items, wherein
$R_1$, $R_3$, and $R_4$ are each independently
hydrogen,
optionally substituted $C_{1-12}$ alkyl,
optionally substituted $C_{3-10}$ cycloalkyl,
optionally substituted 5- to 10-membered heterocycloalkyl,
optionally substituted $C_{6-10}$ aryl,
optionally substituted 5- to 10-membered heteroaryl, or
optionally substituted carbonyl, and
$R_{2A}$ and $R_{2B}$ are each independently
hydrogen,
optionally substituted $C_{1-12}$ alkyl,
optionally substituted $C_{3-10}$ cycloalkyl,
optionally substituted 5- to 10-membered heterocycloalkyl,
optionally substituted $C_{6-10}$ aryl,
optionally substituted 5- to 10-membered heteroaryl, or
optionally substituted carbonyl, or
$R_{2A}$ and $R_{2B}$, together with the nitrogen atom to which they are attached, form a 5- to 10-membered non-aryl heterocycle or a 5- to 10-membered heteroaryl ring,
wherein the non-aryl heterocycle and the heteroaryl ring are each independently optionally substituted.

[Item 5A]
The compound or an enantiomer thereof, or a salt thereof, or a solvate thereof according to any one of the preceding items, wherein
$R_1$, $R_3$, and $R_4$ are each independently
hydrogen,
optionally substituted alkyl,
optionally substituted arylalkyl,
optionally substituted heteroarylalkyl,
optionally substituted cycloalkyl,
optionally substituted heterocycloalkyl,
optionally substituted aryl,
formyl,
optionally substituted alkylcarbonyl,
optionally substituted alkoxycarbonyl,
optionally substituted arylcarbonyl,
optionally substituted aryloxycarbonyl,
optionally substituted heteroarylcarbonyl,
optionally substituted heteroaryloxycarbonyl,
optionally substituted cycloalkylcarbonyl,
optionally substituted cycloalkyloxycarbonyl,
optionally substituted heterocycloalkylcarbonyl,
optionally substituted heterocycloalkyloxycarbonyl,
carbamoyl,
optionally substituted alkylcarbamoyl,
optionally substituted alkoxycarbamoyl,
optionally substituted arylcarbamoyl,
optionally substituted heteroarylcarbamoyl,
optionally substituted cycloalkylcarbamoyl, or
optionally substituted heterocycloalkylcarbamoyl,
wherein the groups of $R_1$, $R_3$, and $R_4$ are optionally substituted with one to the maximum substitutable number of the same or different substituents selected from substituent group II, and
$R_{2A}$ and $R_{2B}$ are each independently
hydrogen,
optionally substituted alkyl,
optionally substituted arylalkyl,
optionally substituted cycloalkyl,
optionally substituted heterocycloalkyl,
formyl,
optionally substituted alkylcarbonyl,
optionally substituted alkoxycarbonyl,
optionally substituted arylcarbonyl,
optionally substituted aryloxycarbonyl,
optionally substituted heteroarylcarbonyl,
optionally substituted heteroaryloxycarbonyl,
optionally substituted cycloalkylcarbonyl,
optionally substituted cycloalkyloxycarbonyl,
optionally substituted heterocycloalkylcarbonyl,
optionally substituted heterocycloalkyloxycarbonyl,
carbamoyl,
optionally substituted alkylcarbamoyl,
optionally substituted alkoxycarbamoyl,
optionally substituted arylcarbamoyl,
optionally substituted heteroarylcarbamoyl,
optionally substituted cycloalkylcarbamoyl, or
optionally substituted heterocycloalkylcarbamoyl,
wherein the groups of $R_{2A}$ and $R_{2B}$ are optionally substituted with one to the maximum substitutable number of the same or different substituents selected from substituent group II, or
$R_{2A}$ and $R_{2B}$, together with the nitrogen atom to which they are attached, form a non-aryl heterocycle or a heteroaryl ring,
wherein the non-aryl heterocycle and the heteroaryl ring are each independently optionally substituted with one to the maximum substitutable number of the same or different substituents selected from substituent group II.

[Item 5B]
The compound or an enantiomer thereof, or a salt thereof, or a solvate thereof according to any one of the preceding items, wherein
$R_1$, $R_3$, and $R_4$ are each independently
hydrogen,
optionally substituted $C_{1-12}$ alkyl,
optionally substituted $C_{6-10}$ aryl $C_{1-12}$ alkyl,
optionally substituted 5- to 10-membered heteroaryl $C_{1-12}$ alkyl,
optionally substituted $C_{3-10}$ cycloalkyl,
optionally substituted 5- to 10-membered heterocycloalkyl,
optionally substituted $C_{6-10}$ aryl,
formyl,
optionally substituted $C_{1-12}$ alkylcarbonyl,
optionally substituted $C_{1-12}$ alkoxycarbonyl,
optionally substituted $C_{6-10}$ arylcarbonyl,
optionally substituted $C_{6-10}$ aryloxycarbonyl,
optionally substituted 5- to 10-membered heteroarylcarbonyl,
optionally substituted 5- to 10-membered heteroaryloxycarbonyl,
optionally substituted $C_{3-10}$ cycloalkylcarbonyl,
optionally substituted $C_{3-10}$ cycloalkyloxycarbonyl,
optionally substituted 5- to 10-membered heterocycloalkylcarbonyl,
optionally substituted 5- to 10-membered heterocycloalkyloxycarbonyl,
carbamoyl,
optionally substituted $C_{1-12}$ alkylcarbamoyl,
optionally substituted $C_{1-12}$ alkoxycarbamoyl,
optionally substituted $C_{6-10}$ arylcarbamoyl,
optionally substituted 5- to 10-membered heteroarylcarbamoyl,
optionally substituted $C_{3-10}$ cycloalkylcarbamoyl, or optionally substituted 5- to 10-membered heterocycloalkylcarbamoyl,
wherein the groups of $R_1$, $R_3$, and $R_4$ are optionally substituted with one to the maximum substitutable number of the same or different substituents selected from substituent group III, and
$R_{2A}$ and $R_{2B}$ are each independently
  hydrogen,
  optionally substituted $C_{1-12}$ alkyl,
  optionally substituted $C_{6-10}$ aryl $C_{1-12}$ alkyl,
  optionally substituted $C_{3-10}$ cycloalkyl,
  optionally substituted 5- to 10-membered heterocycloalkyl,
  formyl,
  optionally substituted $C_{1-12}$ alkylcarbonyl,
  optionally substituted $C_{1-12}$ alkoxycarbonyl,
  optionally substituted $C_{6-10}$ arylcarbonyl,
  optionally substituted $C_{6-10}$ aryloxycarbonyl,
  optionally substituted 5- to 10-membered heteroarylcarbonyl,
  optionally substituted 5- to 10-membered heteroaryloxycarbonyl,
  optionally substituted $C_{3-10}$ cycloalkylcarbonyl,
  optionally substituted $C_{3-10}$ cycloalkyloxycarbonyl,
  optionally substituted 5- to 10-membered heterocycloalkylcarbonyl,
  optionally substituted 5- to 10-membered heterocycloalkyloxycarbonyl,
  carbamoyl,
  optionally substituted $C_{1-12}$ alkylcarbamoyl,
  optionally substituted $C_{1-12}$ alkoxycarbamoyl,
  optionally substituted $C_{6-10}$ arylcarbamoyl,
  optionally substituted 5- to 10-membered heteroarylcarbamoyl,
  optionally substituted $C_{3-10}$ cycloalkylcarbamoyl, or
  optionally substituted 5- to 10-membered heterocycloalkylcarbamoyl,
wherein the groups of $R_{2A}$ and $R_{2B}$ are optionally substituted with one to the maximum substitutable number of the same or different substituents selected from substituent group III, or
$R_{2A}$ and $R_{2B}$, together with the nitrogen atom to which they are attached, form a 5- to 10-membered non-aryl heterocycle or a 5- to 10-membered heteroaryl ring,
wherein the non-aryl heterocycle and the 5- to 10-membered heteroaryl ring are each independently optionally substituted with one to the maximum substitutable number of the same or different substituents selected from substituent group V.

[Item 6A]

The compound or an enantiomer thereof, or a salt thereof, or a solvate thereof according to any one of the preceding items, wherein
$R_1$ and $R_4$ are each independently
  hydrogen,
  optionally substituted alkyl,
  optionally substituted arylalkyl,
  optionally substituted heteroarylalkyl,
  optionally substituted cycloalkyl,
  optionally substituted heterocycloalkyl,
  formyl,
  optionally substituted alkylcarbonyl,
  optionally substituted alkoxycarbonyl,
  optionally substituted arylcarbonyl,
  optionally substituted aryloxycarbonyl,
  optionally substituted cycloalkylcarbonyl,
  optionally substituted cycloalkyloxycarbonyl,
  optionally substituted heterocycloalkylcarbonyl,
  optionally substituted heterocycloalkyloxycarbonyl,
  carbamoyl,
  optionally substituted alkylcarbamoyl,
  optionally substituted alkoxycarbamoyl,
  optionally substituted arylcarbamoyl,
  optionally substituted heteroarylcarbamoyl,
  optionally substituted cycloalkylcarbamoyl, or
  optionally substituted heterocycloalkylcarbamoyl,
wherein the groups of $R_1$ and $R_4$ are optionally substituted with one to the maximum substitutable number of the same or different substituents selected from substituent group III.

[Item 6B]

The compound or an enantiomer thereof, or a salt thereof, or a solvate thereof according to any one of the preceding items, wherein
$R_1$ and $R_4$ are each independently
  hydrogen,
  optionally substituted $C_{1-12}$ alkyl,
  optionally substituted $C_{6-10}$ aryl $C_{1-12}$ alkyl,
  optionally substituted 5- to 10-membered heteroaryl $C_{1-12}$ alkyl,
  optionally substituted $C_{3-10}$ cycloalkyl,
  optionally substituted 5- to 10-membered heterocycloalkyl,
  formyl,
  optionally substituted $C_{1-12}$ alkylcarbonyl,
  optionally substituted $C_{1-12}$ alkoxycarbonyl,
  optionally substituted $C_{6-10}$ arylcarbonyl,
  optionally substituted $C_{6-10}$ aryloxycarbonyl,
  optionally substituted $C_{3-10}$ cycloalkylcarbonyl,
  optionally substituted $C_{3-10}$ cycloalkyloxycarbonyl,
  optionally substituted 5- to 10-membered heterocycloalkylcarbonyl,
  optionally substituted 5- to 10-membered heterocycloalkyloxycarbonyl,
  carbamoyl,
  optionally substituted $C_{1-12}$ alkylcarbamoyl,
  optionally substituted $C_{1-12}$ alkoxycarbamoyl,
  optionally substituted $C_{6-10}$ arylcarbamoyl,
  optionally substituted 5- to 10-membered heteroarylcarbamoyl,
  optionally substituted $C_{3-10}$ cycloalkylcarbamoyl, or
  optionally substituted 5- to 10-membered heterocycloalkylcarbamoyl,
wherein the groups of $R_1$ and $R_4$ are optionally substituted with one to the maximum substitutable number of the same or different substituents selected from substituent group III.

[Item 7A]

The compound or an enantiomer thereof, or a salt thereof, or a solvate thereof according to any one of the preceding items, wherein
$R_1$ and $R_4$ are each independently
  hydrogen,
  optionally substituted alkyl,
  optionally substituted arylalkyl,
  optionally substituted heteroarylalkyl,
  optionally substituted heterocycloalkyl,
  formyl,
  optionally substituted alkylcarbonyl,
  optionally substituted alkoxycarbonyl,
  optionally substituted arylcarbonyl, or
  optionally substituted aryloxycarbonyl, wherein t the groups of $R_1$ and $R_4$ are optionally substituted with one to the maximum substitutable number of the same or different substituents selected from substituent group III.

[Item 7B]

The compound or an enantiomer thereof, or a salt thereof, or a solvate thereof according to any one of the preceding items, wherein $R_1$ and $R_4$ are each independently
hydrogen,
optionally substituted $C_{1-12}$ alkyl,
optionally substituted $C_{6-10}$ aryl $C_{1-12}$ alkyl,
optionally substituted 5- to 10-membered heteroaryl $C_{1-12}$ alkyl,
optionally substituted 5- to 10-membered heterocycloalkyl,
formyl,
optionally substituted $C_{1-12}$ alkylcarbonyl,
optionally substituted $C_{1-12}$ alkoxycarbonyl,
optionally substituted $C_{6-10}$ arylcarbonyl, or
optionally substituted $C_{6-10}$ aryloxycarbonyl,
wherein the groups of $R_1$ and $R_4$ are optionally substituted with one to the maximum substitutable number of the same or different substituents selected from substituent group III.

[Item 7C]

The compound or an enantiomer thereof, or a salt thereof, or a solvate thereof according to any one of the preceding items, wherein $R_1$ and $R_4$ are each independently
hydrogen,
optionally substituted $C_{1-12}$ alkyl,
optionally substituted $C_{6-10}$ aryl $C_{1-6}$ alkyl,
optionally substituted 5- to 10-membered heteroaryl $C_{1-6}$ alkyl,
optionally substituted 5- to 10-membered heterocycloalkyl,
formyl,
optionally substituted $C_{1-12}$ alkylcarbonyl,
optionally substituted $C_{1-12}$ alkoxycarbonyl,
optionally substituted $C_{6-10}$ arylcarbonyl, or
optionally substituted $C_{6-10}$ aryloxycarbonyl,
wherein the groups of $R_1$ and $R_4$ are optionally substituted with one to the maximum substitutable number of the same or different substituents selected from substituent group III.

[Item 8A]

The compound or an enantiomer thereof, or a salt thereof, or a solvate thereof according to any one of the preceding items, wherein $R_1$ is
hydrogen;
alkyl;
alkyl substituted with one to the maximum substitutable number of the same or different substituents selected from the group consisting of hydroxy, substituted oxy, formyl, substituted carbonyl, amino, substituted amino, cycloalkyl, and substituted cycloalkyl;
arylalkyl;
arylalkyl substituted with one to the maximum substitutable number of the same or different substituents selected from the group consisting of halogen, alkyl, substituted alkyl, hydroxy, substituted oxy, amino, substituted amino, and nitro;
heteroarylalkyl;
heteroarylalkyl substituted with one to the maximum substitutable number of the same or different substituents selected from the group consisting of halogen, alkyl, substituted alkyl, hydroxy, substituted oxy, amino, substituted amino, and nitro;
cycloalkyl;
substituted cycloalkyl;
heterocycloalkyl;
substituted heterocycloalkyl; or
substituted carbonyl,
wherein the substituted oxy, substituted carbonyl, substituted amino, substituted cycloalkyl, substituted heterocycloalkyl, and substituted alkyl each independently have one to the maximum substitutable number of the same or different substituents selected from substituent group IV.

[Item 8B]

The compound or an enantiomer thereof, or a salt thereof, or a solvate thereof according to any one of the preceding items, wherein $R_1$ is
hydrogen;
alkyl;
alkyl substituted with one to the maximum substitutable number of the same or different substituents selected from the group consisting of hydroxy, alkoxy, haloalkoxy, formyl, carboxy, carbamoyl, alkylcarbonyl, alkoxycarbonyl, amino, amidinoamino, alkoxycarbonyl-substituted amidinoamino, alkoxycarbonylamino, cycloalkyl, and halocycloalkyl;
arylalkyl;
arylalkyl substituted with one to the maximum substitutable number of the same or different substituents selected from the group consisting of halogen, alkyl, haloalkyl, hydroxy, alkoxy, haloalkoxy, arylalkoxy, amino, alkylamino, (alkyl)$_2$amino, cycloalkylcarbonylamino, and nitro;
heteroarylalkyl;
heteroarylalkyl substituted with one to the maximum substitutable number of the same or different substituents selected from the group consisting of halogen, alkyl, haloalkyl, hydroxy, alkoxy, haloalkoxy, arylalkoxy, amino, alkylamino, (alkyl)$_2$amino, cycloalkylcarbonylamino, and nitro;
cycloalkyl;
halocycloalkyl;
heterocycloalkyl;
alkylcarbonyl;
arylalkylcarbonyl;
alkoxycarbonyl;
arylcarbonyl; or
aryloxycarbonyl.

[Item 8C]

The compound or an enantiomer thereof, or a salt thereof, or a solvate thereof according to any one of the preceding items, wherein $R_1$ is
hydrogen;
$C_{1-12}$ alkyl;
$C_{1-12}$ alkyl substituted with one to the maximum substitutable number of the same or different substituents selected from the group consisting of $C_{1-12}$ alkoxy, $C_{1-12}$ haloalkoxy, formyl, carboxy, carbamoyl, $C_{1-12}$ alkylcarbonyl, $C_{1-12}$ alkoxycarbonyl, $C_{1-12}$ haloalkoxycarbonyl, amidinoamino, $C_{1-12}$ alkoxycarbonyl-substituted amidinoamino, $C_{1-12}$ alkoxycarbonylamino, hydroxy, $C_{3-10}$ cycloalkyl, and $C_{3-10}$ halocycloalkyl;

$C_{6-10}$ aryl $C_{1-12}$ alkyl;

$C_{6-10}$ aryl $C_{1-12}$ alkyl substituted with one to the maximum substitutable number of the same or different substituents selected from the group consisting of halogen, $C_{1-12}$ alkyl, $C_{1-12}$ haloalkyl, hydroxy, $C_{1-12}$ alkoxy, $C_{1-12}$ haloalkoxy, $C_{6-10}$ aryl $C_{1-12}$ alkoxy, amino, $C_{1-12}$ alkylamino, $(C_{1-12}$ alkyl$)_2$amino, $C_{3-10}$ cycloalkylcarbonylamino, nitro, and hydroxy;

5- to 10-membered heteroaryl $C_{1-12}$ alkyl;

5- to 10-membered heteroaryl $C_{1-12}$ alkyl substituted with one to the maximum substitutable number of the same or different substituents selected from the group consisting of halogen, $C_{1-12}$ alkyl, $C_{1-12}$ haloalkyl, hydroxy, $C_{1-12}$ alkoxy, $C_{1-12}$ haloalkoxy, $C_{6-10}$ aryl $C_{1-12}$ alkoxy, amino, $C_{1-12}$ alkylamino, $(C_{1-12}$ alkyl$)_2$amino, $C_{3-10}$ cycloalkylcarbonylamino, nitro, and hydroxy;

$C_{3-10}$ cycloalkyl;

5- to 10-membered heterocycloalkyl;

$C_{1-12}$ alkylcarbonyl;

$C_{6-10}$ aryl $C_{1-12}$ alkylcarbonyl;

$C_{1-12}$ alkoxycarbonyl;

$C_{6-10}$ arylcarbonyl; or $C_{6-10}$ aryloxycarbonyl.

[Item 8D]

The compound or an enantiomer thereof, or a salt thereof, or a solvate thereof according to any one of the preceding items, wherein $R_1$ is hydrogen;

$C_{1-12}$ alkyl;

$C_{1-12}$ alkyl substituted with one to the maximum substitutable number of the same or different substituents selected from the group consisting of $C_{1-6}$ alkoxy, $C_{1-6}$ haloalkoxy, formyl, carboxy, carbamoyl, $C_{1-6}$ alkylcarbonyl, $C_{1-6}$ alkoxycarbonyl, $C_{1-6}$ haloalkoxycarbonyl, amidinoamino, $C_{1-6}$ alkoxycarbonyl-substituted amidinoamino, $C_{1-6}$ alkoxycarbonylamino, hydroxy, $C_{3-10}$ cycloalkyl, and $C_{3-10}$ halocycloalkyl;

$C_{6-10}$ aryl $C_{1-6}$ alkyl;

$C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, hydroxy, $C_{1-6}$ alkoxy, $C_{1-6}$ haloalkoxy, $C_{6-10}$ aryl $C_{1-6}$ alkoxy, amino, $C_{1-6}$ alkylamino, $(C_{1-6}$ alkyl$)_2$amino, $C_{3-10}$ cycloalkylcarbonylamino, nitro, and hydroxy;

5- to 10-membered heteroaryl $C_{1-6}$ alkyl substituted with one to the maximum substitutable number of the same or different substituents selected from the group consisting of halogen, $C_{1-6}$ alkyl, $C_{1-6}$ haloalkyl, hydroxy, $C_{1-6}$ alkoxy, $C_{1-6}$ haloalkoxy, $C_{6-10}$ aryl $C_{1-6}$ alkoxy, amino, $C_{1-6}$ alkylamino, $(C_{1-6}$ alkyl$)_2$amino, $C_{3-10}$ cycloalkylcarbonylamino, nitro, and hydroxy;

$C_{3-10}$ cycloalkyl;

5- to 10-membered heterocycloalkyl;

$C_{1-6}$ alkylcarbonyl;

$C_{6-10}$ aryl $C_{1-6}$ alkylcarbonyl;

$C_{1-6}$ alkoxycarbonyl;

$C_{6-10}$ arylcarbonyl; or $C_{6-10}$ aryloxycarbonyl.

[Item 9A]

The compound or an enantiomer thereof, or a salt thereof, or a solvate thereof according to any one of the preceding items, wherein $R_3$ is alkyl;

alkyl substituted with one to the maximum substitutable number of the same or different substituents selected from the group consisting of hydroxy, substituted oxy, substituted carbonyl, amino, substituted amino, cycloalkyl, and substituted cycloalkyl;

arylalkyl;

arylalkyl substituted with one to the maximum substitutable number of the same or different substituents selected from the group consisting of halogen, alkyl, substituted alkyl, hydroxy, and substituted oxy;

aryl; or substituted aryl, wherein the substituted oxy, substituted carbonyl, substituted amino, substituted cycloalkyl, substituted alkyl, and substituted aryl each independently have one to the maximum substitutable number of the same or different substituents selected from substituent group IV.

[Item 9B]

The compound or an enantiomer thereof, or a salt thereof, or a solvate thereof according to any one of the preceding items, wherein $R_3$ is alkyl;

alkyl substituted with one to the maximum substitutable number of the same or different substituents selected from the group consisting of hydroxy, alkoxy, haloalkoxy, trialkylsilyloxy, carboxy, carbamoyl, alkoxycarbonyl, haloalkoxycarbonyl, amino, amidinoamino, alkoxycarbonyl-substituted amidinoamino, alkoxycarbonylamino, haloalkoxycarbonylamino, cycloalkyl, and halocycloalkyl;

arylalkyl;

arylalkyl substituted with one to the maximum substitutable number of the same or different substituents selected from the group consisting of halogen, alkyl, haloalkyl, hydroxy, alkoxy, and haloalkoxy; or aryl.

[Item 9C]

The compound or an enantiomer thereof, or a salt thereof, or a solvate thereof according to any one of the preceding items, wherein $R_3$ is $C_{1-12}$ alkyl;

$C_{1-12}$ alkyl substituted with one to the maximum substitutable number of the same or different substituents selected from the group consisting of hydroxy, $C_{1-12}$ alkoxy, $C_{1-12}$ haloalkoxy, tri-$C_{1-12}$ alkylsilyloxy, carboxy, carbamoyl, $C_{1-12}$ alkoxycarbonyl, $C_{1-12}$ haloalkoxycarbonyl, amino, amidinoamino, $C_{1-12}$ alkoxycarbonyl-substituted amidinoamino, $C_{1-12}$ alkoxycarbonylamino, $C_{1-12}$ haloalkoxycarbonylamino, $C_{3-10}$ cycloalkyl, and $C_{3-10}$ halocycloalkyl;

$C_{6-10}$ aryl $C_{1-12}$ alkyl;

$C_{6-10}$ aryl $C_{1-12}$ alkyl substituted with one to the maximum substitutable number of the same or different substituents selected from the group consisting of halogen, $C_{1-12}$ alkyl, $C_{1-12}$ haloalkyl, hydroxy, $C_{1-12}$ alkoxy, and $C_{1-12}$ haloalkoxy; or $C_{6-10}$ aryl.

[Item 9D]

The compound or an enantiomer thereof, or a salt thereof, or a solvate thereof according to any one of the preceding items, wherein $R_3$ is
- $C_{1-12}$ alkyl;
- $C_{1-12}$ alkyl substituted with one to the maximum substitutable number of the same or different substituents selected from the group consisting of hydroxy, $C_{1-6}$ alkoxy, $C_{1-6}$ haloalkoxy, tri-$C_{1-6}$ alkylsilyloxy, carboxy, carbamoyl, $C_{1-6}$ alkoxycarbonyl, $C_{1-6}$ haloalkoxycarbonyl, amino, amidinoamino, $C_{1-6}$ alkoxycarbonyl-substituted amidinoamino, $C_{1-6}$ alkoxycarbonylamino, $C_{1-6}$ haloalkoxycarbonylamino, $C_{3-10}$ cycloalkyl, and $C_{3-10}$ halocycloalkyl;
- $C_{6-10}$ aryl $C_{1-6}$ alkyl;
- $C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, hydroxy, $C_{1-6}$ alkoxy, and $C_{1-6}$ haloalkoxy; or
- $C_{6-10}$ aryl.

[Item 10A]

The compound or an enantiomer thereof, or a salt thereof, or a solvate thereof according to any one of the preceding items, wherein $R_{2A}$ and $R_{2B}$ are each independently
- hydrogen;
- alkyl;
- alkyl substituted with one to the maximum substitutable number of the same or different substituents selected from the group consisting of hydroxy, substituted oxy, amino, substituted amino, cycloalkyl, and substituted cycloalkyl;
- arylalkyl;
- arylalkyl substituted with one to the maximum substitutable number of the same or different substituents selected from the group consisting of halogen, alkyl, substituted alkyl, hydroxy, and substituted oxy;
- cycloalkyl;
- substituted cycloalkyl;
- heterocycloalkyl; or
- substituted heterocycloalkyl, wherein the substituted oxy, substituted amino, substituted alkyl, substituted cycloalkyl, and substituted heterocycloalkyl each independently have one to the maximum substitutable number of the same or different substituents selected from substituent group IV, or $R_{2A}$ and $R_{2B}$, together with the nitrogen atom to which they are attached, form a non-aryl heterocycle, wherein the non-aryl heterocycle is optionally substituted with one to the maximum substitutable number of the same or different substituents selected from substituent group VI.

[Item 10B]

The compound or an enantiomer thereof, or a salt thereof, or a solvate thereof according to any one of the preceding items, wherein $R_{2A}$ and $R_{2B}$ are each independently
- hydrogen;
- alkyl;
- alkyl substituted with one to the maximum substitutable number of the same or different substituents selected from the group consisting of hydroxy, alkoxy, carboxy, alkoxycarbonyl, amino, amidinoamino, amidinoamino, alkoxycarbonyl-substituted alkoxycarbonylamino, cycloalkyl, and halocycloalkyl;
- arylalkyl;
- arylalkyl substituted with one to the maximum substitutable number of the same or different substituents selected from the group consisting of halogen, alkyl, haloalkyl, hydroxy, alkoxy, and haloalkoxy;
- cycloalkyl;
- alkyl-substituted cycloalkyl; or
- heterocycloalkyl, or $R_{2A}$ and $R_{2B}$, together with the nitrogen atom to which they are attached, form a non-aryl heterocycle, wherein the non-aryl heterocycle is optionally substituted with one to the maximum substitutable number of the same or different substituents selected from substituent group VI.

[Item 10C]

The compound or an enantiomer thereof, or a salt thereof, or a solvate thereof according to any one of the preceding items, wherein $R_{2A}$ and $R_{2B}$ are each independently hydrogen;
- $C_{1-12}$ alkyl;
- $C_{1-12}$ alkyl substituted with one to the maximum substitutable number of the same or different substituents selected from the group consisting of hydroxy, $C_{1-12}$ alkoxy, carboxy, $C_{1-12}$ alkoxycarbonyl, amino, amidinoamino, $C_{1-12}$ alkoxycarbonyl-substituted amidinoamino, $C_{1-12}$ alkoxycarbonylamino, $C_{3-10}$ cycloalkyl, and $C_{3-10}$ halocycloalkyl;
- $C_{6-10}$ aryl $C_{1-12}$ alkyl;
- $C_{6-10}$ aryl $C_{1-12}$ alkyl substituted with one to the maximum substitutable number of the same or different substituents selected from the group consisting of halogen, $C_{1-12}$ alkyl, $C_{1-12}$ haloalkyl, hydroxy, $C_{1-12}$ alkoxy, and $C_{1-12}$ haloalkoxy;
- $C_{3-10}$ cycloalkyl;
- $C_{1-12}$ alkyl-substituted $C_{3-10}$ cycloalkyl; or
- 5- to 10-membered heterocycloalkyl, or $R_{2A}$ and $R_{2B}$, together with the nitrogen atom to which they are attached, form a 5- or 6-membered non-aryl heterocycle, wherein the non-aryl heterocycle is optionally substituted with one to the maximum substitutable number of the same or different substituents selected from substituent group VI.

[Item 10D]

The compound or an enantiomer thereof, or a salt thereof, or a solvate thereof according to any one of the preceding items, wherein $R_{2A}$ and $R_{2B}$ are each independently
- hydrogen;
- $C_{1-12}$ alkyl;
- $C_{1-12}$ alkyl substituted with one to the maximum substitutable number of the same or different substituents selected from the group consisting of hydroxy, $C_{1-6}$ alkoxy, carboxy, $C_{1-6}$ alkoxycarbonyl, amino, amidinoamino, $C_{1-6}$ alkoxycarbonyl-substituted amidinoamino, $C_{1-6}$ alkoxycarbonylamino, $C_{3-10}$ cycloalkyl, and $C_{3-10}$ halocycloalkyl;
- $C_{6-10}$ aryl $C_{1-6}$ alkyl;
- $C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, hydroxy, $C_{1-6}$ alkoxy, and $C_{1-6}$ haloalkoxy;

$C_{3-10}$ cycloalkyl;

$C_{1-6}$ alkyl-substituted $C_{3-10}$ cycloalkyl; or 5- to 10-membered heterocycloalkyl, or $R_{2A}$ and $R_{2B}$, together with the nitrogen atom to which they are attached, form a 5- or 6-membered non-aryl heterocycle, wherein the non-aryl heterocycle is optionally substituted with one to the maximum substitutable number of the same or different substituents selected from substituent group VI.

[Item 11A]

The compound or an enantiomer thereof, or a salt thereof, or a solvate thereof according to any one of the preceding items, wherein $R^4$ is hydrogen, alkyl, or substituted alkyl, wherein the substituted alkyl has one to the maximum substitutable number of the same or different substituents selected from the group consisting of halogen, carboxy, carbamoyl, amino, alkylamino, aryl, nitroaryl, and alkoxycarbonylamino.

[Item 11B]

The compound or an enantiomer thereof, or a salt thereof, or a solvate thereof according to any one of the preceding items, wherein $R^4$ is hydrogen, $C_{1-12}$ alkyl, or substituted $C_{1-12}$ alkyl, wherein the substituted $C_{1-12}$ alkyl has one to the maximum substitutable number of the same or different substituents selected from the group consisting of halogen, carboxy, carbamoyl, amino, $C_{1-12}$ alkylamino, $C_{6-10}$ aryl, nitro-$C_{6-10}$ aryl, and $C_{1-12}$ alkoxycarbonylamino.

[Item 11C]

The compound or an enantiomer thereof, or a salt thereof, or a solvate thereof according to any one of the preceding items, wherein $R^4$ is hydrogen or alkyl.

[Item 11D]

The compound or an enantiomer thereof, or a salt thereof, or a solvate thereof according to any one of the preceding items, wherein $R^4$ is hydrogen or $C_{1-12}$ alkyl.

[Item 12A]

The compound or an enantiomer thereof, or a salt thereof, or a solvate thereof according to any one of the preceding items, wherein $R_1$ is hydrogen, methyl, propyl, isopropyl, isobutyl, sec-butyl, isopentyl, hexyl, amidinoaminopropyl, (tert-butoxycarbonyl-substituted amidinoamino) propyl, tert-butoxyethyl, tert-butoxypropyl, tert-butoxycarbonylethyl, carboxyethyl, hydroxyethyl, hydroxypropyl, tert-butoxycarbonylaminopropyl, cyclopentylmethyl, cyclohexylmethyl, cycloheptylmethyl, 5,6,7,8-tetrahydronaphthalenylmethyl, benzyl, phenylethyl, naphthalenylmethyl, fluorobenzyl, chlorobenzyl, methylbenzyl, dimethylbenzyl, tert-butylbenzyl, methoxybenzyl, ethoxybenzyl, tert-butoxybenzyl, trifluoromethylbenzyl, (trifluoromethoxy)benzyl, benzyloxybenzyl, aminobenzyl, (dimethylamino)benzyl, (cyclopentylcarbonylamino)benzyl, 6-methyl-1H-indol-3-ylmethyl, 6-fluoro-1H-indol-3-ylmethyl, 1-tert-butoxycarbonyl-6-methyl-1H-indol-3-ylmethyl, 1-tert-butoxycarbonyl-6-fluoro-1H-indol-3-ylmethyl, nitrobenzyl, hydroxybenzyl, cyclohexyl, isovaleryl, phenylacetyl, benzoyl, isopropyloxycarbonyl, phenoxycarbonyl, or tetrahydro-2H-pyranyl.

[Item 12B]

The compound or an enantiomer thereof, or a salt thereof, or a solvate thereof according to any one of the preceding items, wherein $R_{2A}$ is hydrogen, and $R_{2B}$ is isopropyl, isobutyl, sec-butyl, pentyl, isopentyl, hexyl, heptyl, amidinoaminopropyl, (tert-butoxycarbonyl-substituted amidinoamino) propyl, (tert-butoxycarbonyl)ethyl, tert-butoxyethyl, methoxybutyl, carboxyethyl, hydroxyethyl, (tert-butoxycarbonylamino) propyl, cyclopentylmethyl, cyclohexylmethyl, cycloheptylmethyl, (1,2,3,4-tetrahydronaphthalenyl)methyl, 2,2,6,6-tetramethylpiperidinyl, benzyl, phenylethyl, naphthalenylmethyl, fluorobenzyl, chlorobenzyl, (fluorophenyl)ethyl, methylbenzyl, tert-butoxybenzyl, hydroxybenzyl, β-hydroxyphenethyl, α-hydroxymethylphenethyl, cyclopentyl, cyclohexyl, or methylcyclohexyl, or $R_{2A}$ and $R_{2B}$, together with the nitrogen atom to which they are attached, form a pyrrolidine ring.

[Item 12C]

The compound or an enantiomer thereof, or a salt thereof, or a solvate thereof according to any one of the preceding items, wherein $R_3$ is propyl, isobutyl, isopentyl, hexyl, amidinoaminopropyl, (tert-butoxycarbonyl-substituted amidinoamino) propyl, (tert-butoxycarbonyl)ethyl, carboxyethyl, hydroxyethyl, (tert-butyldimethylsilyloxy)ethyl, (tert-butoxycarbonylamino)propyl, cyclopentylmethyl, cyclohexylmethyl, cyclohexylethyl, benzyl, naphthalenylmethyl, phenylethyl, naphthalenylethyl, chlorobenzyl, methylbenzyl, (methylphenyl)ethyl, (isopropylphenyl)ethyl, tert-butoxybenzyl, hydroxybenzyl, or phenyl.

[Item 12D]

The compound or an enantiomer thereof, or a salt thereof, or a solvate thereof according to any one of the preceding items, wherein $R^4$ is hydrogen or methyl.

[Item 13A]

The compound or an enantiomer thereof, or a salt thereof, or a solvate thereof according to any one of the preceding items, wherein $R_1$ is alkyl, substituted arylalkyl, or substituted heteroarylalkyl, $R_{2A}$ is hydrogen, $R_{2B}$ is alkyl, arylalkyl, substituted arylalkyl, or optionally substituted cycloalkylalkyl, $R_3$ is alkyl, and $R_4$ is hydrogen.

[Item 13B]

The compound or an enantiomer thereof, or a salt thereof, or a solvate thereof according to any one of the preceding items, wherein $R_1$ is alkyl, alkyl-substituted arylalkyl, chloro-substituted arylalkyl, alkoxy-substituted arylalkyl, heteroarylalkyl substituted with Boc and alkyl, or heteroarylalkyl substituted with Boc and halogen, $R_{2A}$ is hydrogen, $R_{2B}$ is alkyl, arylalkyl, fluoro-substituted arylalkyl, chloro-substituted arylalkyl, or cycloalkylalkyl, and $R_3$ is alkyl.

[Item 13C]

The compound or an enantiomer thereof, or a salt thereof, or a solvate thereof according to any one of the preceding items, wherein $R_1$ is $C_{1-12}$ alkyl, $C_{1-12}$ alkyl-substituted $C_{6-10}$ aryl $C_{1-12}$ alkyl, chloro-substituted $C_{6-10}$ aryl $C_{1-12}$ alkyl, $C_{1-12}$ alkoxy-substituted $C_{6-10}$ aryl $C_{1-12}$ alkyl, 5- to 10-membered heteroaryl $C_{1-12}$ alkyl substituted with Boc and $C_{1-12}$ alkyl, or 5- to 10-membered heteroaryl $C_{1-12}$ alkyl substituted with Boc and halogen, $R_{2A}$ is hydrogen, $R_{2B}$ is $C_{1-12}$ alkyl, $C_{6-10}$ aryl $C_{1-12}$ alkyl, fluoro-substituted $C_{6-10}$ aryl $C_{1-12}$ alkyl, chloro-substituted $C_{6-10}$ aryl $C_{1-12}$ alkyl, or $C_{3-10}$ cycloalkyl $C_{1-12}$ alkyl, and $R_3$ is $C_1$-12 alkyl.

[Item 13D]

The compound or an enantiomer thereof, or a salt thereof, or a solvate thereof according to any one of the preceding items, wherein $R_1$ is isobutyl, isopentyl, methylbenzyl, t-butylbenzyl, chlorobenzyl, methoxybenzyl, 1-tert-butoxycarbonyl-6-methyl-1H-indol-3-ylmethyl, or 6-fluoro-1H-indol-3-ylmethyl, $R_{2A}$ is hydrogen, $R_{2B}$ is isobutyl, benzyl, fluorobenzyl, chlorobenzyl, or cycloheptylmethyl, and $R_3$ is isobutyl or isopentyl.

[Item 14A]

The compound or an enantiomer thereof, or a salt thereof, or a solvate thereof according to any one of the preceding items, wherein the compound is a compound selected from the group consisting of compound numbers I-1 to I-50, II-1 to II-50, IF-51 to IF-800, and IB-51 to IB-832.

[Item 14B]

The compound or an enantiomer thereof, or a salt thereof, or a solvate thereof according to any one of the preceding items, wherein the compound is a compound selected from the group consisting of compound numbers I-1 to I-50, II-1 to II-50, IF-51 to IF-411, and IB-51 to IB-425.

[Item 15]

An antiviral agent against a virus in the Lyssavirus genus, comprising the compound or a pharmaceutically acceptable salt thereof according to any one of the preceding items.

[Item 16]

The antiviral agent according to any one of the preceding items, wherein the virus in the Lyssavirus genus comprises a rabies virus.

[Item 17]

A medicament comprising the compound or a pharmaceutically acceptable salt thereof according to any one of the preceding items.

[Item 18]

The medicament according to any one of the preceding items, which is a preventive drug or therapeutic drug for rabies.

[Item 19]

A pharmaceutical composition comprising the compound or a pharmaceutically acceptable salt thereof according to any one of the preceding items and a pharmaceutically acceptable carrier.

[Item 20]

A pharmaceutical composition for preventing or treating rabies, comprising the compound or a pharmaceutically acceptable salt thereof according to any one of the preceding items and a pharmaceutically acceptable carrier.

[Item 21]

A method for preventing or treating rabies, characterized by administering, to a patient in need thereof, a therapeutically effective amount of the compound or a pharmaceutically acceptable salt thereof according to any one of the preceding items, the antiviral agent according to any one of the preceding items, the medicament according to any one of the preceding items, or the pharmaceutical composition according to any one of the preceding items.

[Item 22]

Use of the compound or a pharmaceutically acceptable salt thereof according to any one of the preceding items or the antiviral agent according to any one of the preceding items, for the manufacture of a medicament for preventing or treating rabies.

The present disclosure also provides the following items.

[Item A1]

A compound represented by formula IF:

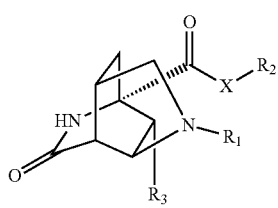

(IF)

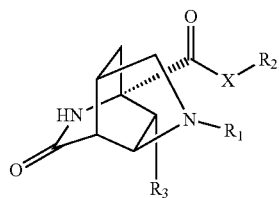

Formula IF or an enantiomer thereof, or a salt thereof, or a solvate thereof, wherein $R_1$ and $R_2$ are each independently optionally substituted alkyl, optionally substituted cycloalkyl, or optionally substituted heterocycloalkyl, $R_3$ is optionally substituted alkyl, optionally substituted alkenyl, optionally substituted alkynyl, optionally substituted aryl, optionally substituted heteroaryl, optionally substituted cycloalkyl, or optionally substituted heterocycloalkyl, and X is —NH—.

[Item A2]

A compound represented by formula IB:

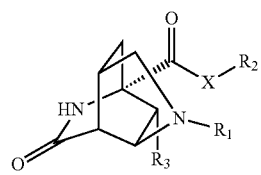

Formula IF

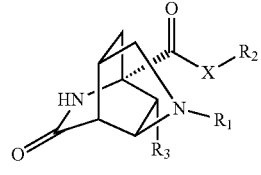

Formula IF or an enantiomer thereof, or a salt thereof, or a solvate thereof, wherein $R_1$ and $R_2$ are each independently optionally substituted alkyl, optionally substituted cycloalkyl, or optionally substituted heterocycloalkyl, $R_3$ is optionally substituted alkyl, optionally substituted alkenyl, optionally substituted alkynyl, optionally substituted aryl, optionally substituted heteroaryl, optionally substituted cycloalkyl, or optionally substituted heterocycloalkyl, and X is —NH—.

[Item A3]

The compound or an enantiomer thereof, or a salt thereof, or a solvate thereof according to any one of the preceding items, wherein $R_1$ and $R_2$ are each independently optionally substituted alkyl, optionally substituted cycloalkyl, or optionally substituted heterocycloalkyl, and $R_3$ is optionally substituted alkyl, optionally substituted alkenyl, or optionally substituted aryl.

[Item A4]

The compound or an enantiomer thereof, or a salt thereof, or a solvate thereof according to any one of the preceding items, wherein $R_1$ and $R_2$ are each independently optionally substituted alkyl, optionally substituted cycloalkyl, or optionally substituted heterocycloalkyl, and $R_3$ is optionally substituted alkyl or optionally substituted aryl.

[Item A5]

The compound or an enantiomer thereof, or a salt thereof, or a solvate thereof according to any one of the preceding items, wherein $R_1$, $R_2$, and $R_3$ are each independently alkyl optionally substituted with a hydroxyl group, a carboxyl group, a carbamoyl group, an amino group, or an amidinoamino group, optionally substituted cycloalkylalkyl, optionally substituted arylalkyl, or optionally substituted heteroarylalkyl.

[Item A6]

The compound or an enantiomer thereof, or a salt thereof, or a solvate thereof according to any one of the preceding items, wherein $R_1$, $R_2$, and $R_3$ are each independently alkyl optionally substituted with a hydroxyl group, a carboxyl group, a carbamoyl group, an amino group, or an amidinoamino group; optionally substituted cycloalkylalkyl; optionally substituted $C_{6-10}$ aryl $C_{1-6}$ alkyl; or optionally substituted 5- to 10-membered heteroaryl $C_{1-6}$ alkyl.

[Item A7]

The compound or an enantiomer thereof, or a salt thereof, or a solvate thereof according to any one of the preceding items, wherein $R_1$, $R_2$, and $R_3$ are each independently alkyl optionally substituted with a hydroxyl group, a carboxyl group, a carbamoyl group, an amino group, or an amidinoamino group; optionally substituted cycloalkylalkyl; optionally substituted $C_6$ aryl $C_{1-6}$ alkyl; or optionally substituted 5- or 6-membered heteroaryl $C_{1-6}$ alkyl.

[Item A8]

The compound or an enantiomer thereof, or a salt thereof, or a solvate thereof according to any one of the preceding items, wherein $R_1$, $R_2$, and $R_3$ are each independently alkyl optionally substituted with a hydroxyl group, a carboxyl group, a carbamoyl group, an amino group, or an amidinoamino group; optionally substituted cycloalkylalkyl; optionally substituted benzyl; or optionally substituted 5- or 6-membered heteroarylmethyl.

[Item A9]

The compound or an enantiomer thereof, or a salt thereof, or a solvate thereof according to any one of the preceding items, wherein $R_1$, $R_2$, and $R_3$ are each independently alkyl optionally substituted with a hydroxyl group, a carboxyl group, a carbamoyl group, an amino group, or an amidinoamino group; cycloalkylalkyl; optionally substituted benzyl; or optionally substituted 5- or 6-membered heteroarylmethyl.

[Item A10]

The compound or an enantiomer thereof, or a salt thereof, or a solvate thereof according to any one of the preceding items, wherein $R_1$ is alkyl or optionally substituted benzyl.

[Item A11]

The compound or an enantiomer thereof, or a salt thereof, or a solvate thereof according to any one of the preceding items, wherein $R_1$ and $R_2$ are each independently $C_{1-6}$ alkyl optionally substituted with a hydroxyl group, a carboxyl group, a carbamoyl group, an amino group, or an amidinoamino group; optionally substituted $C_{3-6}$ cycloalkyl $C_{1-6}$ alkyl; optionally substituted $C_{6-10}$ aryl $C_{1-6}$ alkyl; optionally substituted 5- to 10-membered heteroaryl $C_{1-6}$ alkyl; or optionally substituted 4- to 6-membered heterocycloalkyl $C_{1-6}$ alkyl.

[Item A12]

The compound or an enantiomer thereof, or a salt thereof, or a solvate thereof according to any one of the preceding items, wherein $R_1$ and $R_2$ are each independently $C_{1-6}$ alkyl optionally substituted with a hydroxyl group, a carboxyl group, a carbamoyl group, an amino group, or an amidinoamino group; optionally substituted $C_{3-6}$ cycloalkyl $C_{1-6}$ alkyl; or optionally substituted $C_{6-10}$ aryl $C_{1-6}$ alkyl.

[Item A13]

The compound or an enantiomer thereof, or a salt thereof, or a solvate thereof according to any one of the preceding items, wherein $R_2$ is optionally substituted $C_{6-10}$ aryl $C_{1-6}$ alkyl.

[Item A14]

The compound or an enantiomer thereof, or a salt thereof, or a solvate thereof according to any one of the preceding items, wherein $R_2$ is optionally substituted $C_6$ aryl $C_{1-6}$ alkyl.

[Item A15]

The compound or an enantiomer thereof, or a salt thereof, or a solvate thereof according to any one of the preceding items, wherein $R_2$ is optionally substituted benzyl.

[Item A16]

The compound or an enantiomer thereof, or a salt thereof, or a solvate thereof according to any one of the preceding items, wherein $R_1$ is $C_{1-6}$ alkyl optionally substituted with a hydroxyl group, a carboxyl group, a carbamoyl group, an amino group, or an amidinoamino group; optionally substituted $C_{3-6}$ cycloalkyl $C_{1-6}$ alkyl; optionally substituted $C_6$ aryl $C_{1-6}$ alkyl; or optionally substituted 5- or 6-membered heteroaryl $C_{1-6}$ alkyl.

[Item A17]

The compound or an enantiomer thereof, or a salt thereof, or a solvate thereof according to any one of the preceding items, wherein $R_1$ is $C_{1-6}$ alkyl optionally substituted with a hydroxyl group, a carboxyl group, a carbamoyl group, an amino group, or an amidinoamino group or optionally substituted benzyl.

[Item A18]

The compound or an enantiomer thereof, or a salt thereof, or a solvate thereof according to any one of the preceding items, wherein R; is alkyl optionally substituted with a hydroxyl group, a carboxyl group, a carbamoyl group, an amino group, or an amidinoamino group; optionally substituted $C_{6-10}$ arylalkyl; substituted $C_{2-6}$ alkenyl; or optionally substituted $C_{6-10}$ aryl.

[Item A19]

The compound or an enantiomer thereof, or a salt thereof, or a solvate thereof according to any one of the preceding items, wherein $R^3$ is alkyl optionally substituted with a hydroxyl group, a carboxyl group, a carbamoyl group, an amino group, or an amidinoamino group; or optionally substituted $C_{6-10}$ arylalkyl.

[Item A20]

The compound or an enantiomer thereof, or a salt thereof, or a solvate thereof according to any one of the preceding items, wherein $R^3$ is alkyl.

[Item A21]

The compound or an enantiomer thereof, or a salt thereof, or a solvate thereof according to any one of the preceding items, wherein $R^3$ is $C_{1-6}$ alkyl optionally substituted with a hydroxyl group, a carboxyl group, a carbamoyl group, an amino group, or an amidinoamino group; or optionally substituted $C_{6-10}$ aryl $C_{1-6}$ alkyl.

[Item A22]

The compound or an enantiomer thereof, or a salt thereof, or a solvate thereof according to any one of the preceding items, wherein $R_1$ and $R_2$ are each independently $C_{1-6}$ alkyl; hydroxy-substituted $C_{1-6}$ alkyl; carbamoyl-substituted $C_{1-6}$ alkyl; amidinoamino-substituted $C_{1-6}$ alkyl; carboxy-substituted $C_{1-6}$ alkyl; $C_{6-10}$ aryl $C_{1-6}$ alkyl; $C_{1-4}$ alkyl-substituted $C_{6-10}$ aryl $C_{1-6}$ alkyl; hydroxy-substituted $C_{6-10}$ aryl $C_{1-6}$ alkyl; halogen-substituted $C_{6-10}$ aryl $C_{1-6}$ alkyl; $C_{1-4}$ alkoxy-substituted $C_{6-10}$ aryl $C_{1-6}$ alkyl; $C_{1-4}$ alkoxycarbonyl-substituted $C_{1-6}$ alkyl; $C_{6-10}$ aryl $C_{1-6}$ alkyl substituted with $C_{1-4}$ alkyl-substituted amino, or $C_{3-6}$ cycloalkyl $C_{1-6}$ alkyl.

[Item A23]

The compound or an enantiomer thereof, or a salt thereof, or a solvate thereof according to any one of the preceding items, wherein $R_2$ is hydroxy-substituted $C_{1-6}$ alkyl; carbamoyl-substituted $C_{1-6}$ alkyl; amidinoamino-substituted $C_{1-6}$ alkyl; carboxy-substituted $C_{1-6}$ alkyl; $C_{6-10}$ aryl $C_{1-6}$ alkyl; $C_{1-4}$ alkyl-substituted $C_{6-10}$ aryl $C_{1-6}$ alkyl; hydroxy-substituted $C_{6-10}$ aryl $C_{1-6}$ alkyl; halogen-substituted $C_{6-10}$ aryl $C_{1-6}$ alkyl; $C_{1-4}$ alkoxy-substituted $C_{6-10}$ aryl $C_{1-6}$ alkyl; $C_{1-4}$ alkoxycarbonyl-substituted $C_{1-6}$ alkyl; $C_{6-10}$ aryl $C_{1-6}$ alkyl substituted with $C_{1-4}$ alkyl-substituted amino; or $C_{3-6}$ cycloalkyl $C_{1-6}$ alkyl.

[Item A24]

The compound or an enantiomer thereof, or a salt thereof, or a solvate thereof according to any one of the preceding items, wherein $R_2$ is $C_{6-10}$ aryl $C_{1-6}$ alkyl; $C_{1-4}$ alkyl-substituted $C_{6-10}$ aryl $C_{1-6}$ alkyl; hydroxy-substituted $C_{6-10}$ aryl $C_{1-6}$ alkyl; halogen-substituted $C_{6-10}$ aryl $C_{1-6}$ alkyl; $C_{1-4}$ alkoxy-substituted $C_{6-10}$ aryl $C_{1-6}$ alkyl; or $C_{6-10}$ aryl $C_{1-6}$ alkyl substituted with $C_{1-4}$ alkyl-substituted amino.

[Item A25]

The compound or an enantiomer thereof, or a salt thereof, or a solvate thereof according to any one of the preceding items, wherein $R^3$ is $C_{1-6}$ alkyl; hydroxy-substituted $C_{1-6}$ alkyl; carbamoyl-substituted $C_{1-6}$ alkyl; amidinoamino-substituted $C_{1-6}$ alkyl; carboxy-substituted $C_{1-6}$ alkyl; $C_{6-10}$ aryl $C_{1-6}$ alkyl; $C_{1-4}$ alkyl-substituted $C_{6-10}$ aryl $C_{1-6}$ alkyl; hydroxy-substituted $C_{6-10}$ aryl $C_{1-6}$ alkyl; halogen-substituted $C_{6-10}$ aryl $C_{1-6}$ alkyl; $C_{1-4}$ alkoxy-substituted $C_{6-10}$ aryl $C_{1-6}$ alkyl; $C_{1-4}$ alkoxycarbonyl-substituted $C_{1-6}$ alkyl; $C_{6-10}$ aryl $C_{1-6}$ alkyl substituted with $C_{1-4}$ alkyl-substituted amino; or $C_{3-6}$ cycloalkyl $C_{1-6}$ alkyl.

[Item A26]

The compound or an enantiomer thereof, or a salt thereof, or a solvate thereof according to any one of the preceding items, wherein $R^3$ is $C_{1-6}$ alkyl; hydroxy-substituted $C_{1-6}$ alkyl; carbamoyl-substituted $C_{1-6}$ alkyl; amidinoamino-substituted $C_{1-6}$ alkyl; carboxy-substituted $C_{1-6}$ alkyl; $C_{1-4}$ alkoxycarbonyl-substituted $C_{1-6}$ alkyl; or $C_{3-6}$ cycloalkyl $C_{1-6}$ alkyl.

[Item A27]

The compound or an enantiomer thereof, or a salt thereof, or a solvate thereof according to any one of the preceding items, wherein $R_1$ and $R_2$ are each independently $C_{1-6}$ alkyl; $C_{6-10}$ aryl $C_{1-6}$ alkyl; $C_{1-6}$ alkyl-substituted $C_{6-10}$ aryl $C_{1-6}$ alkyl; $C_{1-6}$ alkoxy-substituted $C_{6-10}$ aryl $C_{1-6}$ alkyl; $C_{1-6}$ haloalkoxy-substituted $C_{6-10}$ aryl $C_{1-6}$ alkyl; hydroxy-substituted $C_{6-10}$ aryl $C_{1-6}$ alkyl; halogen-substituted $C_{6-10}$ aryl $C_{1-6}$ alkyl; $C_{6-10}$ aryl $C_{1-6}$ alkyl substituted with $C_{1-6}$ alkyl-substituted amino; $C_{5-6}$ cycloalkyl; $C_{1-6}$ alkyl-substituted $C_{5-6}$ cycloalkyl; or optionally substituted 5- or 6-membered heterocyclyl, and $R_3$ is $C_{1-6}$ alkyl; $C_{6-10}$ aryl $C_{1-6}$ alkyl; $C_{1-6}$ alkyl-substituted $C_{6-10}$ aryl $C_{1-6}$ alkyl; halogen-substituted $C_{6-10}$ aryl $C_{1-6}$ alkyl; $C_{1-6}$ haloalkoxy-substituted $C_{6-10}$ aryl $C_{1-6}$ alkyl; $C_{1-6}$ alkoxy-substituted $C_{6-10}$ aryl $C_{1-6}$ alkyl; hydroxy-substituted $C_{6-10}$ aryl $C_{1-6}$ alkyl; $C_{6-10}$ aryl $C_{1-6}$ alkyl substituted with $C_{1-6}$ alkyl-substituted amino; $C_{6-10}$ aryl; $C_{1-4}$ alkyl-substituted $C_{6-10}$ aryl; or halogen-substituted $C_{6-10}$ aryl.

[Item A28]

The compound or an enantiomer thereof, or a salt thereof, or a solvate thereof according to any one of the preceding items, wherein $R_1$ and $R_2$ are each independently methyl; n-propyl; isobutyl; isopentyl; benzyl; methyl- or t-butyl-substituted benzyl; fluoro- or chloro-substituted benzyl; methoxy- or ethoxy-substituted benzyl; trifluoromethoxy-substituted benzyl; hydroxy-substituted benzyl; dimethylamino-substituted benzyl; cyclohexyl; methyl-substituted cyclohexyl; tetrahydro-2H-pyran-4-yl; or 2,2,6,6-tetramethylpiperidin-4-yl, and $R_3$ is methyl; n-propyl; isobutyl; isopentyl; benzyl; methyl- or t-butyl-substituted benzyl; fluoro- or chloro-substituted benzyl; methoxy- or ethoxy-substituted benzyl; trifluoromethoxy-substituted benzyl; hydroxy-substituted benzyl; dimethylamino-substituted benzyl; or phenyl.

[Item A29]

The compound or an enantiomer thereof, or a salt thereof, or a solvate thereof according to any one of the preceding items, wherein $R_2$ is $C_6$ aryl $C_{1-6}$ alkyl; $C_{1-6}$ alkyl-substituted $C_6$ aryl $C_{1-6}$ alkyl; $C_{1-6}$ alkoxy-substituted $C_6$ aryl $C_{1-6}$ alkyl; $C_{1-6}$ haloalkoxy-substituted $C_6$ aryl $C_{1-6}$ alkyl; hydroxy-substituted $C_6$ aryl $C_{1-6}$ alkyl; halogen-substituted $C_6$ aryl $C_1$-6 alkyl; or $C_6$ aryl $C_{1-6}$ alkyl substituted with $C_{1-6}$ alkyl-substituted amino.

[Item A30]

The compound or an enantiomer thereof, or a salt thereof, or a solvate thereof according to any one of the preceding items, wherein $R_2$ is benzyl; methyl- or t-butyl-substituted benzyl; methoxy- or ethoxy-substituted benzyl; trifluoromethoxy-substituted benzyl; hydroxy-substituted benzyl; fluoro- or chloro-substituted benzyl; or dimethylamino-substituted benzyl.

[Item A31]

The compound or an enantiomer thereof, or a salt thereof, or a solvate thereof according to any one of the preceding items, wherein $R_1$ is $C_{1-6}$ alkyl; $C_6$ aryl $C_{1-6}$ alkyl; $C_{1-6}$ alkyl-substituted $C_6$ aryl $C_{1-6}$ alkyl; $C_{1-6}$ alkoxy-substituted $C_6$ aryl $C_{1-6}$ alkyl; $C_{1-6}$ haloalkoxy-substituted $C_6$ aryl $C_{1-6}$ alkyl; hydroxy-substituted $C_6$ aryl $C_{1-6}$ alkyl; halogen-substituted $C_6$ aryl $C_{1-6}$ alkyl; or $C_6$ aryl $C_{1-6}$ alkyl substituted with $C_{1-6}$ alkyl-substituted amino.

[Item A32]

The compound or an enantiomer thereof, or a salt thereof, or a solvate thereof according to any one of the preceding items, wherein $R_1$ is methyl; isobutyl; isopentyl; benzyl; methyl- or t-butyl-substituted benzyl; methoxy- or ethoxy-substituted benzyl; trifluoromethoxy-substituted benzyl; hydroxy-substituted benzyl; fluoro- or chloro-substituted benzyl; or dimethylamino-substituted benzyl.

[Item A33]

The compound or an enantiomer thereof, or a salt thereof, or a solvate thereof according to any one of the preceding items, wherein $R^3$ is $C_{1-6}$ alkyl; $C_6$ aryl $C_{1-6}$ alkyl; $C_{1-6}$ alkyl-substituted $C_6$ aryl $C_{1-6}$ alkyl; halogen-substituted $C_6$ aryl $C_1$-6 alkyl; $C_{1-6}$ haloalkoxy-substituted $C_6$ aryl $C_{1-6}$ alkyl; $C_{1-6}$ alkoxy-substituted $C_6$ aryl $C_{1-6}$ alkyl; hydroxy-substituted $C_6$ aryl $C_{1-6}$ alkyl; or $C_6$ aryl $C_{1-6}$ alkyl substituted with $C_{1-6}$ alkyl-substituted amino.

[Item A34]

The compound or an enantiomer thereof, or a salt thereof, or a solvate thereof according to any one of the preceding items, wherein $R^3$ is propyl; isobutyl; isopentyl; benzyl; methyl- or t-butyl-substituted benzyl; fluoro- or chloro-substituted benzyl; methoxy- or ethoxy-substituted benzyl; trifluoromethoxy-substituted benzyl; hydroxy-substituted benzyl; or dimethylamino-substituted benzyl.

[Item A35]

The compound or an enantiomer thereof, or a salt thereof, or a solvate thereof according to any one of the preceding items, wherein $R^3$ is $C_{1-6}$ alkyl; $C_6$ aryl $C_{1-6}$ alkyl; or halogen-substituted $C_6$ aryl $C_{1-6}$ alkyl.

[Item A36]

The compound or an enantiomer thereof, or a salt thereof, or a solvate thereof according to any one of the preceding items, wherein $R^3$ is propyl; isobutyl; isopentyl; benzyl; or chloro-substituted benzyl.

[Item A37]

The compound or an enantiomer thereof, or a salt thereof, or a solvate thereof according to any one of the preceding items, wherein $R^3$ is $C_{1-6}$ alkyl.

[Item A38]

The compound or an enantiomer thereof, or a salt thereof, or a solvate thereof according to any one of the preceding items, wherein $R_1$ and $R_2$ are each independently methyl, ethyl, n-propyl, isopropyl, isobutyl, isopentyl, benzyl, 4-methylbenzyl, 4-(t-butyl)benzyl, 4-fluorobenzyl, 3-chlorobenzyl, 4-chlorobenzyl, 4-methoxybenzyl, 4-ethoxybenzyl, 4-hydroxybenzyl, 3-hydroxybenzyl, 4-(dimethylamino)benzyl, 4-(trifluoromethoxy)benzyl, cyclohexyl, trans-4-methylcyclohexyl, tetrahydro-2H-pyran-4-yl, or 2,2,6,6-tetramethylpiperidin-4-yl, and $R_3$ is methyl, ethyl, n-propyl, isopropyl, isobutyl, isopentyl, benzyl, 4-methylbenzyl, 4-(t-butyl)benzyl, 4-fluorobenzyl, 3-chlorobenzyl, 4-chlorobenzyl, 4-methoxybenzyl, 4-ethoxybenzyl, 4-hydroxybenzyl, 3-hydroxybenzyl, 4-(dimethylamino)benzyl, 4-(trifluoromethoxy)benzyl, or phenyl.

[Item A39]

The compound or an enantiomer thereof, or a salt thereof, or a solvate thereof according to any one of the preceding items, wherein $R_2$ is isobutyl, isopentyl, benzyl, 4-fluorobenzyl, 4-chlorobenzyl, 4-hydroxybenzyl, 3-hydroxybenzyl, cyclohexyl, tetrahydro-2H-pyran-4-yl, or 2,2,6,6-tetramethylpiperidin-4-yl.

[Item A40]

The compound or an enantiomer thereof, or a salt thereof, or a solvate thereof according to any one of the preceding items, wherein $R_2$ is benzyl, 4-fluorobenzyl, 4-chlorobenzyl, 4-hydroxybenzyl, or 3-hydroxybenzyl.

[Item A41]

The compound or an enantiomer thereof, or a salt thereof, or a solvate thereof according to any one of the preceding items, wherein $R_1$ is methyl, isobutyl, isopentyl, benzyl, 4-methylbenzyl, 4-(t-butyl)benzyl, 3-chlorobenzyl, 4-chlorobenzyl, 4-methoxybenzyl, 4-ethoxybenzyl, 4-hydroxybenzyl, 4-(dimethylamino)benzyl, cyclohexyl, or trans-4-methylcyclohexyl.

[Item A42]

The compound or an enantiomer thereof, or a salt thereof, or a solvate thereof according to any one of the preceding items, wherein $R_1$ is methyl, isobutyl, isopentyl, benzyl, 4-methylbenzyl, 4-(t-butyl)benzyl, 3-chlorobenzyl, 4-chlorobenzyl, 4-methoxybenzyl, 4-ethoxybenzyl, 4-hydroxybenzyl, or 4-(dimethylamino)benzyl.

[Item A43]

The compound or an enantiomer thereof, or a salt thereof, or a solvate thereof according to any one of the preceding items, wherein $R^3$ is n-propyl, isobutyl, isopentyl, benzyl, 4-chlorobenzyl, or phenyl.

[Item A44]

The compound or an enantiomer thereof, or a salt thereof, or a solvate thereof according to any one of the preceding items, wherein $R^3$ is n-propyl, isobutyl, or isopentyl.

[Item A45]

The compound or an enantiomer thereof, or a salt thereof, or a solvate thereof according to any one of the preceding items, wherein $R_2$ is benzyl, $R_1$ is isobutyl, methoxy-substituted benzyl, methyl-substituted benzyl, t-butyl-substituted benzyl, or chloro-substituted benzyl, and $R_3$ is isobutyl.

[Item A46]

The compound or an enantiomer thereof, or a salt thereof, or a solvate thereof according to any one of the preceding items, wherein $R_2$ is benzyl, $R_1$ is methoxy-substituted benzyl or chloro-substituted benzyl, and $R_3$ is isobutyl.

[Item A47]

The compound or an enantiomer thereof, or a salt thereof, or a solvate thereof according to any one of the preceding items, wherein $R_2$ is benzyl, $R_1$ is 4-methoxybenzyl or 3-chlorobenzyl, and $R_3$ is isobutyl.

[Item A48]

The compound or an enantiomer thereof, or a salt thereof, or a solvate thereof according to any one of the preceding items, wherein the compound is a compound of formula IF, $R_2$ is benzyl, $R_1$ is 4-methoxybenzyl, and $R_3$ is isobutyl.

[Item A49]

The compound or an enantiomer thereof, or a salt thereof, or a solvate thereof according to any one of the preceding items, wherein the compound is a compound of formula IB, $R_2$ is benzyl, $R_1$ is 4-methoxybenzyl, and $R_3$ is isobutyl.

[Item A50]

The compound or an enantiomer thereof, or a salt thereof, or a solvate thereof according to any one of the preceding items, wherein $R_2$ is benzyl or chloro-substituted benzyl, and $R_1$ and $R_3$ are each independently isobutyl or isopentyl.

[Item A51]

The compound or an enantiomer thereof, or a salt thereof, or a solvate thereof according to any one of the preceding items, wherein $R_2$ is benzyl, $R_1$ is isopentyl, and $R_3$ is isobutyl.

[Item A52]

The compound or an enantiomer thereof, or a salt thereof, or a solvate thereof according to any one of the preceding items, wherein the compound is a compound of formula IB, $R_2$ is benzyl or 4-chlorobenzyl, and $R_1$ and $R_3$ are both isobutyl.

[Item A53]

The compound or an enantiomer thereof, or a salt thereof, or a solvate thereof according to any one of the preceding items, wherein the compound is a compound of formula IB, $R_2$ is benzyl, $R_1$ is isobutyl, and $R_3$ is isopentyl.

[Item A54]

The compound or an enantiomer thereof, or a salt thereof, or a solvate thereof according to any one of the preceding items, wherein the compound represented by formula IF is selected from the group consisting of (3S*,3aR*,6S*,7R*,7aR*)-N-benzyl-1-(4-chlorobenzyl)-7-isobutyl-4-oxooctahydro-6H-3,6-methanopyrrolo[3,2-c]pyridine-6-carboxamide, (3S*,3aR*,6S*,7R*,7aR*)-N-benzyl-1-(3-chlorobenzyl)-7-isobutyl-4-oxooctahydro-6H-3,6-methanopyrrolo[3,2-c]pyridine-6-carboxamide, (3S*,3aR*,6S*,7R*,7aR*)-N-benzyl-7-isobutyl-1-(4-methoxybenzyl)-4-oxooctahydro-6H-3,6-methanopyrrolo[3,2-c]pyridine-6-carboxamide, (3S*,3aR*,6S*,7R*,7aR*)-N-benzyl-7-isobutyl-1-(4-methylbenzyl)-4-oxooctahydro-6H-3,6-methanopyrrolo[3,2-c]pyridine-6-carboxamide, (3S*,3aR*,6S*,7R*,7aR*)-1-benzyl-N, 7-diisobutyl-4-oxooctahydro-6H-3,6-methanopyrrolo[3,2-c]pyridine-6-carboxamide, (3S*,3aR*,6S*,7R*,7aR*)-7-benzyl-N-isobutyl-1-isopentyl-4-oxooctahydro-6H-3,6-methanopyrrolo[3,2-c]pyridine-6-carboxamide, (3S*,3aR*,6S*,7R*,7aR*)-7-(4-chlorobenzyl)-N, 1-diisobutyl-4-oxooctahydro-6H-3,6-methanopyrrolo[3,2-c]pyridine-6-carboxamide, (3S*,3aR*, 6S*,7R*,7aR*)-N-benzyl-1-(4-hydroxybenzyl)-7-isobutyl- 4-oxooctahydro-6H-3,6-methanopyrrolo[3,2-c]pyridine-6-carboxamide, (3S*,3aR*,6S*,7R*,7aR*)-7-benzyl-1-isobutyl-N-isopentyl-4-oxooctahydro-6H-3,6-methanopyrrolo[3,2-c]pyridine-6-carboxamide, (3S*,3aR*,6S*,7R*,7aR*)-7-benzyl-N, 1-diisobutyl-4-oxooctahydro-6H-3,6-methanopyrrolo[3,2-c]pyridine-6-carboxamide, (3S*,3aR*,6S*,7R*,7aR*)-N-benzyl-1,7-diisobutyl-4-oxooctahydro-6H-3,6-methanopyrrolo[3,2-c]pyridine-6-carboxamide, (3S*,3aR*,6S*,7R*,7aR*)-N-(4-chlorobenzyl)-1,7-diisobutyl-4-oxooctahydro-6H-3,6-methanopyrrolo[3,2-c]pyridine-6-carboxamide, (3S*,3aR*,6S*,7R*,7aR*)-N-benzyl-1-isobutyl-7-isopentyl-4-oxooctahydro-6H-3,6-methanopyrrolo[3,2-c]pyridine-6-carboxamide, (3S*,3aR*,6S*,7R*,7aR*)-N-benzyl-7-isobutyl-1-isopentyl-4-oxooctahydro-6H-3,6-methanopyrrolo[3,2-c]pyridine-6-carboxamide, (3S*,3aR*,6S*,7R*,7aR*)-N-benzyl-1-(4-(dimethylamino)benzyl)-7-isobutyl-4-oxooctahydro-6H-3,6-methanopyrrolo[3,2-c]pyridine-6-carboxamide, (3S*,3aR*,6S*,7R*,7aR*)-N-benzyl-1-(4-hydroxybenzyl)-7-isopentyl-4-oxooctahydro-6H-3,6-methanopyrrolo[3,2-c]pyridine-6-carboxamide, (3S*,3aR*,6S*,7R*,7aR*)-N-(4-fluorobenzyl)-7-isobutyl-1-isopentyl-4-oxooctahydro-6H-3,6-methanopyrrolo[3,2-c]pyridine-6-carboxamide, (3S*,3aR*,6S*,7R*,7aR*)-N-benzyl-7-isobutyl-4-oxo-1-(4-(trifluoromethoxy)benzyl) octahydro-6H-3,6-methanopyrrolo[3,2-c]pyridine-6-carboxamide, (3S*,3aR*,6S*,7R*,7aR*)-N-benzyl-1-(4-ethoxybenzyl)-7-isobutyl-4-oxooctahydro-6H-3,6-methanopyrrolo[3,2-c]pyridine-6-carboxamide, (3S*,3aR*,6S*,7R*,7aR*)-1-benzyl-N-(4-hydroxybenzyl)-7-isobutyl-4-oxooctahydro-6H-3,6-methanopyrrolo[3,2-c]pyridine-6-carboxamide, (3S*,3aR*,6S*,7R*,7aR*)-N-(4-hydroxybenzyl)-7-isobutyl-1-(4-methoxybenzyl)-4-oxooctahydro-6H-3,6-methanopyrrolo[3,2-c]pyridine-6-carboxamide, (3S*,3aR*,6S*,7R*,7aR*)-1-(4-(dimethylamino)benzyl)-N-(3-hydroxybenzyl)-7-isobutyl-4-oxooctahydro-6H-3,6-methanopyrrolo[3,2-c]pyridine-6-carboxamide, (3S*,3aR*,6S*,7R*,7aR*)-1-(4-(dimethylamino)benzyl)-N-(4-hydroxybenzyl)-7-isobutyl-4-oxooctahydro-6H-3,6-methanopyrrolo[3,2-c]pyridine-6-carboxamide, (3S*,3aR*,6S*,7R*,7aR*)-1-benzyl-N-cyclohexyl-4-oxo-7-propyloctahydro-6H-3,6-methanopyrrolo[3,2-c]pyridine-6-carboxamide, (3S*,3aR*,6S*,7R*,7aR*)-1,7-dibenzyl-N-((1R,4S)-4-methylcyclohexyl)-4-oxooctahydro-6H-3,6-methanopyrrolo[3,2-c]pyridine-6-carboxamide, (3S*,3aR*,6S*,7R*,7aR*)-1,7-dibenzyl-4-oxo-N-(2,2,6,6-tetramethylpiperidin-4-yl) octahydro-6H-3,6-methanopyrrolo[3,2-c]pyridine-6-carboxamide, and (3S*,3aR*,6S*,7R*,7aR*)-N-benzyl-1-isobutyl-4-oxo-7-phenyloctahydro-6H-3,6-methanopyrrolo[3,2-c]pyridine-6-carboxamide.

[Item A55]

The compound or an enantiomer thereof, or a salt thereof, or a solvate thereof according to any one of the preceding items, wherein the compound represented by formula IB is selected from the group consisting of (3S*,3aS*,6R*,7R*,7aS*)-N, 7-dibenzyl-1-methyl-5-oxooctahydro-3aH-3,6-methanopyrrolo[3,2-b]pyridine-3a-carboxamide, (3S*,3aS*,6R*,7R*,7aS*)-N-benzyl-1-(4-chlorobenzyl)-7-isobutyl-5-oxooctahydro-3aH-3,6-methanopyrrolo[3,2-b]pyridine-3a-carboxamide, (3S*,3aS*,6R*,7R*,7aS*)-N-benzyl-1-(3-chlorobenzyl)-7-isobutyl-5-oxooctahydro-3aH-3,6-methanopyrrolo[3,2-b]pyridine-3a-carboxamide, (3S*,3aS*,6R*,7R*,7aS*)-N-benzyl-7-isobutyl-1-(4-methoxybenzyl)-5-oxooctahydro-3aH-3,6-methanopyrrolo[3,2-b]pyridine-3a-carboxamide, (3S*,3aS*,6R*,7R*,7aS*)-N-benzyl-7-isobutyl-1-(4-methylbenzyl)-5-oxooctahydro-3aH-3,6-methanopyrrolo[3,2-b]pyridine-3a-carboxamide, (3S*,3aS*,6R*,7R*,7aS*)-1-benzyl-N, 7-diisobutyl-5-oxooctahydro-3aH-3,6-methanopyrrolo[3,2-b]pyridine-3a-carboxamide, (3S*,3aS*,6R*,7R*,7aS*)-7-benzyl-N-isobutyl-1-isopentyl-5-oxooctahydro-3aH-3,6-methanopyrrolo[3,2-b]pyridine-3a-carboxamide, (3S*,3aS*,6R*,7R*,7aS*)-7-(4-chlorobenzyl)-N, 1-diisobutyl-5-oxooctahydro-3aH-3,6-methanopyrrolo[3,2-b]pyridine-3a-carboxamide, (3R*,3aS*,6R*,7R*,7aS*)-7-benzyl-N, 1-diisobutyl-5-oxooctahydro-3aH-3,6-methanopyrrolo[3,2-b]pyridine-3a-carboxamide, (3S*,3aS*,6R*,7R*,7aS*)-N-(4-chlorobenzyl)-1,7-diisobutyl-5-oxooctahydro-3aH-3,6-methanopyrrolo[3,2-b]pyridine-3a-carboxamide, (3S*,3aS*,6R*,7R*,7aS*)-N-benzyl-1-(4-hydroxybenzyl)-7-isobutyl-5-oxooctahydro-3aH-3,6-methanopyrrolo[3,2-b]pyridine-3a-carboxamide, (3S*,3aS*,6R*,7R*,7aS*)-7-benzyl-1-isobutyl-N-isopentyl-5-oxooctahydro-3aH-3,6-methanopyrrolo[3,2-b]pyridine-3a-carboxamide, (3S*,3aS*,6R*,7R*,7aS*)-N-benzyl-1,7-diisobutyl-5-oxooctahydro-3aH-3,6-methanopyrrolo[3,2-b]pyridine-3a-carboxamide, (3S*,3aS*,6R*,7R*,7aS*)-N-benzyl-1-isobutyl-7-isopentyl-5-oxooctahydro-3aH-3,6-methanopyrrolo[3,2-b]pyridine-3a-carboxamide, (3S*,3aS*,6R*,7R*,7aS*)-N-benzyl-7-isobutyl-1-isopentyl-5-oxooctahydro-3aH-3,6-methanopyrrolo[3,2-b]pyridine-3a-carboxamide, (3S*,3aS*,6R*,7R*,7aS*)-N-benzyl-7-isobutyl-1-isopentyl-5-oxooctahydro-3aH-3,6-methanopyrrolo[3,2-b]pyridine-3a-carboxamide, (3S*,3aS*,6R*,7R*,7aS*)-N-benzyl-1-(4-(dimethylamino)benzyl)-7-isobutyl-5-oxooctahydro-3aH-3,6-methanopyrrolo[3,2-b]pyridine-3a-carboxamide, (3S*,3aS*,6R*,7R*,7aS*)-N-benzyl-1-(4-(tert-butyl)benzyl)-7-isobutyl-5-oxooctahydro-3aH-3,6-methanopyrrolo[3,2-b]pyridine-3a-carboxamide, (3S*,3aS*,6R*,7R*,7aS*)-N-benzyl-1-(4-hydroxybenzyl)-7-isopentyl-5-oxooctahydro-3aH-3,6-methanopyrrolo[3,2-b]pyridine-3a-carboxamide, (3S*,3aS*,6R*,7R*,7aS*)-N-(4-chlorobenzyl)-7-isobutyl-1-isopentyl-5-oxooctahydro-3aH-3,6-methanopyrrolo[3,2-b]pyridine-3a-carboxamide, (3S*,3aS*,6R*,7R*,7aS*)-N-(4-fluorobenzyl)-7-isobutyl-1-isopentyl-5-oxooctahydro-3aH-3,6-methanopyrrolo[3,2-b]pyridine-3a-carboxamide, (3S*,3aS*,6R*,7R*,7aS*)-N-benzyl-7-isobutyl-5-oxo-1-(4-(trifluoromethoxy)benzyl) octahydro-3aH-3,6-methanopyrrolo[3,2-b]pyridine-3a-carboxamide, (3S*,3aS*,6R*,7R*,7aS*)-N-benzyl-1-(4-ethoxybenzyl)-7-isobutyl-5-oxooctahydro-3aH-3,6-methanopyrrolo[3,2-b]pyridine-3a-carboxamide, (3S*,3aS*,6R*,7R*,7aS*)-1-benzyl-N-(4-hydroxybenzyl)-7-isobutyl-5-oxooctahydro-3aH-3,6-methanopyrrolo[3,2-b]pyridine-3a-carboxamide, (3S*,3aS*,6R*,7R*,7aS*)-N-(4-hydroxybenzyl)-7-isobutyl-1-(4-methoxybenzyl)-5-oxooctahydro-3aH-3,6-methanopyrrolo[3,2-b]pyridine-3a-carboxamide, (3S*,3aS*,6R*,7R*,7aS*)-1-(4-(dimethylamino)benzyl)-N-(3-hydroxybenzyl)-7-isobutyl-5-oxooctahydro-3aH-3,6-methanopyrrolo[3,2-b]pyridine-3a-carboxamide, (3S*,3aS*,6R*,7R*,7aS*)-1-(4-(dimethylamino)benzyl)-N-(4-hydroxybenzyl)-7-isobutyl-5-oxooctahydro-3aH-3,6-methanopyrrolo[3,2-b]pyridine-3a-carboxamide, (3S*,3aS*,6R*,7R*,7aS*)-1-benzyl-N-cyclohexyl-5-oxo-7-propyloctahydro-3aH-3,6-methanopyrrolo[3,2-b]pyridine-3a-carboxamide, (3S*,3aS*,6R*,7R*,7aS*)-1,7-dibenzyl-N-((1R,4S)-4-methylcyclohexyl)-5-oxooctahydro-3aH-3,6-methanopyrrolo[3,2-b]pyridine-3a-carboxamide, (3S*,3aS*,6R*,7R*,7aS*)-1,7-dibenzyl-5-oxo-N-(2,2,6,6-tetramethylpiperidin-4-yl) octahydro-3aH-3,6-methanopyrrolo[3,2-b]pyridine-3a-carboxamide, (3S*,3aS*,6R*,7R*,7aS*)-N-benzyl-1-cyclohexyl-7-isobutyl-5- oxooctahydro-3aH-3,6-methanopyrrolo[3,2-b]pyridine-3a-carboxamide, (3S*,3aS*,6R*,7S*,7aS*)-N-benzyl-1-cyclohexyl-5-oxo-7-phenyloctahydro-3aH-3,6-methanopyrrolo[3,2-b]pyridine-3a-carboxamide, (3S*, 3aS*,6R*,7S*,7aS*)-N-benzyl-5-oxo-7-phenyl-1-(tetrahydro-2H-pyran-4-yl) octahydro-3aH-3,6-methanopyrrolo[3,2-b]pyridine-3a-carboxamide, and (3S*, 3aS*,6R*,7S*,7aS*)-N-benzyl-1-isobutyl-5-oxo-7-phenyloctahydro-3aH-3,6-methanopyrrolo[3,2-b]pyridine-3a-carboxamide.

[Item A56]

An antiviral agent against a virus in the Lyssavirus genus, comprising the compound or a pharmaceutically acceptable salt thereof, or a solvate thereof according to any one of the preceding items.

[Item A57]

The antiviral agent according to item 56, wherein the virus in the Lyssavirus genus comprises a rabies virus.

[Item A58]

A medicament comprising the compound or a pharmaceutically acceptable salt thereof, or a solvate thereof according to any one of the preceding items.

[Item A59]

The medicament according to item 58, which is a preventive drug or therapeutic drug for rabies.

[Item A60]

A pharmaceutical composition comprising the compound or a pharmaceutically acceptable salt thereof, or a solvate thereof according to any one of the preceding items and a pharmaceutically acceptable carrier.

[Item A61]

The pharmaceutical composition of item 60 for preventing or treating rabies.

[Item A62]

A method for preventing or treating rabies, comprising administering, to a subject in need thereof, the compound or a pharmaceutically acceptable salt thereof, or a solvate thereof according to any one of the preceding items, or the pharmaceutical composition according to item 60 or 61.

[Item A63]

Use of the compound or a pharmaceutically acceptable salt thereof, or a solvate thereof according to any one of the preceding items, for the manufacture of a medicament for preventing or treating rabies.

[Item A64]

The compound or a pharmaceutically acceptable salt thereof, or a solvate thereof according to any one of the preceding items, for use in preventing or treating rabies.

The present disclosure further provides the following items.

[Item B1A]

A compound represented by formula XXIF:

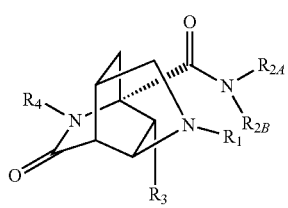

(XXIF)

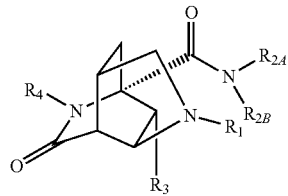

Formula XXIF or an enantiomer thereof, or a salt thereof, or a solvate thereof, wherein $R_1$, $R_3$, and $R_4$ are each independently hydrogen, an optionally substituted hydrocarbon group, an optionally substituted heterocycle, optionally substituted carbonyl, or an optionally substituted functional group, and $R_{2A}$ and $R_{2B}$ are each independently hydrogen, an optionally substituted hydrocarbon group, an optionally substituted heterocycle, optionally substituted carbonyl, or an optionally substituted functional group, or $R_{2A}$ and $R_{2B}$, together with the nitrogen atom to which they are attached, form a heterocycle, wherein the heterocycles are each independently optionally substituted. [Item B1B]

A compound represented by formula XXIF:

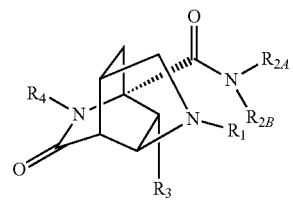

(XXIF)

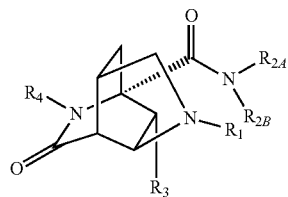

Formula XXIF or an enantiomer thereof, or a salt thereof, or a solvate thereof, wherein $R_1$, $R_3$, and $R_4$ are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl, and $R_{2A}$ and $R_{2B}$ are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl, or $R_{2A}$ and $R_{2B}$, together with the nitrogen atom to which they are attached, form a non-aryl heterocycle or a heteroaryl ring, wherein the non-aryl heterocycle and the heteroaryl ring are each independently optionally substituted.

[Item B2A]

A compound represented by formula XXIB:

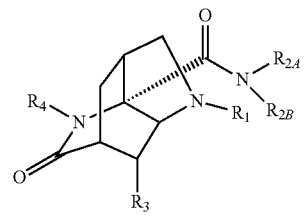

(XXIB)

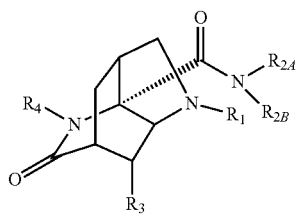

Formula XXIB or an enantiomer thereof, or a salt thereof, or a solvate thereof, wherein $R_1$, $R_3$, and $R_4$ are each independently hydrogen, an optionally substituted hydrocarbon group, an optionally substituted heterocycle, optionally substituted carbonyl, or an optionally substituted functional group, and $R_{2A}$ and $R_{2B}$ are each independently hydrogen, an optionally substituted hydrocarbon group, an optionally substituted heterocycle, optionally substituted carbonyl, or an optionally substituted functional group, or $R_{2A}$ and $R_{2B}$, together with the nitrogen atom to which they are attached, form a heterocycle, wherein the heterocycles are each independently optionally substituted.

[Item B2B]

A compound represented by formula XXIB:

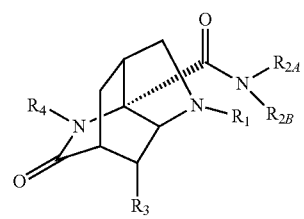

(XXIB)

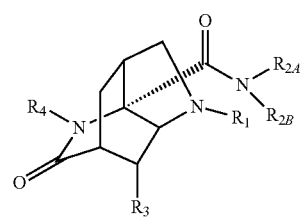

(XXIB)

or an enantiomer thereof, or a salt thereof, or a solvate thereof, wherein $R_1$, $R_3$, and Ry are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl, and $R_{2A}$ and $R_{2B}$ are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl, or $R_{2A}$ and $R_{2B}$, together with the nitrogen atom to which they are attached, form a non-aryl heterocycle or a heteroaryl ring, wherein the non-aryl heterocycle and the heteroaryl ring are each independently optionally substituted.

[Item B3A]

The compound or an enantiomer thereof, or a salt thereof, or a solvate thereof according to any one of the preceding items, wherein the alkyl, alkenyl, alkynyl, cycloalkyl, heterocycloalkyl, aryl, heteroaryl, and carbonyl of $R_1$, $R_3$, and $R_4$ are each independently optionally substituted with one to the maximum substitutable number of the same or different substituents selected from substituent group I, and the alkyl, alkenyl, alkynyl, cycloalkyl, heterocycloalkyl, aryl, heteroaryl, carbonyl, and the non-aryl heterocycle and the heteroaryl ring of $R_{2A}$ and $R_{2B}$ are each independently optionally substituted with one to the maximum substitutable number of the same or different substituents selected from substituent group I. [Item B4A]

The compound or an enantiomer thereof, or a salt thereof, or a solvate thereof according to any one of the preceding items, wherein $R_1$, $R_3$, and $R_4$ are each independently hydrogen, optionally substituted alkyl, optionally substituted cycloalkyl, optionally substituted heterocycloalkyl, optionally substituted aryl, optionally substituted heteroaryl, or optionally substituted carbonyl, and $R_{2A}$ and $R_{2B}$ are each independently hydrogen, optionally substituted alkyl, optionally substituted cycloalkyl, optionally substituted heterocycloalkyl, optionally substituted aryl, optionally substituted heteroaryl, or optionally substituted carbonyl, or $R_{2A}$ and $R_{2B}$, together with the nitrogen atom to which they are attached, form a non-aryl heterocycle or a heteroaryl ring, wherein the non-aryl heterocycle and the heteroaryl ring are each independently optionally substituted.

[Item B4B]

The compound or an enantiomer thereof, or a salt thereof, or a solvate thereof according to any one of the preceding items, wherein $R_1$, $R_3$, and are each independently hydrogen, optionally substituted $C_{1-12}$ alkyl, optionally substituted $C_{3-10}$ cycloalkyl, optionally substituted 5- to 10-membered heterocycloalkyl, optionally substituted $C_{6-10}$ aryl, optionally substituted 5- to 10-membered heteroaryl, or optionally substituted carbonyl, and $R_{2A}$ and $R_{2B}$ are each independently hydrogen, optionally substituted $C_{1-12}$ alkyl, optionally substituted $C_{3-10}$ cycloalkyl, optionally substituted 5- to 10-membered heterocycloalkyl, optionally substituted $C_{6-10}$ aryl, optionally substituted 5- to 10-membered heteroaryl, or optionally substituted carbonyl, or $R_{2A}$ and $R_{2B}$, together with the nitrogen atom to which they are attached, form a 5- to 10-membered non-aryl heterocycle or a 5- to 10-membered heteroaryl ring, wherein the non-aryl heterocycle and the heteroaryl ring are each independently optionally substituted.

[Item B5A]

The compound or an enantiomer thereof, or a salt thereof, or a solvate thereof according to any one of the preceding items, wherein $R_1$, $R_3$, and $R_4$ are each independently hydrogen, optionally substituted alkyl, optionally substituted arylalkyl, optionally substituted cycloalkyl, optionally substituted heterocycloalkyl, optionally substituted aryl, formyl, optionally substituted alkylcarbonyl, optionally substituted alkoxycarbonyl, optionally substituted arylcarbonyl, optionally substituted aryloxycarbonyl, optionally substituted heteroarylcarbonyl, optionally substituted heteroaryloxycarbonyl, optionally substituted cycloalkylcarbonyl, optionally substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted heterocycloalkylcarbamoyl, wherein the groups of $R_1$, $R_3$, and $R_4$ are optionally substituted with one to the maximum substitutable number of the same or different substituents selected from substituent group II, and $R_{2A}$ and $R_{2B}$ are each independently hydrogen, optionally substituted alkyl, optionally substituted arylalkyl, optionally substituted cycloalkyl, optionally substituted heterocycloalkyl, formyl, optionally substituted alkylcarbonyl, optionally substituted alkoxycarbonyl, optionally substituted arylcarbonyl, optionally substituted aryloxycarbonyl, optionally substituted heteroarylcarbonyl, optionally substituted heteroaryloxycarbonyl, optionally substituted cycloalkylcarbonyl, optionally substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted wherein the groups of $R_{2A}$ and $R_{2B}$ are optionally substituted with one to the maximum substitutable number of the same or different substituents selected from substituent group II, or $R_{2A}$ and $R_{2B}$, together with the nitrogen atom to which they are attached, form a non-aryl heterocycle or a heteroaryl ring, wherein the non-aryl heterocycle and the heteroaryl ring are each independently optionally substituted with one to the maximum substitutable number of the same or different substituents selected from substituent group II.

[Item B5B]

The compound or an enantiomer thereof, or a salt thereof, or a solvate thereof according to any one of the preceding items, wherein $R_1$, $R_3$, and $R_4$ each independently hydrogen, are optionally substituted $C_{1-12}$ alkyl, optionally substituted $C_{6-10}$ aryl $C_{1-12}$ alkyl, optionally substituted $C_{3-10}$ cycloalkyl, optionally substituted 5- to 10-membered heterocycloalkyl, optionally substituted $C_{6-10}$ aryl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted 5- to 10-membered heteroarylcarbonyl, optionally substituted 5- to 10-membered heteroaryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered wherein the groups of $R_1$, $R_3$, and $R_4$ are optionally substituted with one to the maximum substitutable number of the same or different substituents selected from substituent group III, and $R_{2A}$ and $R_{2B}$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, optionally substituted 5- to 10-membered heterocycloalkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted 5- to 10-membered heteroarylcarbonyl, optionally substituted 5- to 10-membered heteroaryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered heterocycloalkylcarbamoyl, wherein the groups of $R_{2A}$ and $R_{2B}$ are optionally substituted with one to the maximum substitutable number of the same or different substituents selected from substituent group III, or $R_{2A}$ and $R_{2B}$, together with the nitrogen atom to which they are attached, form a 5- to 10-membered non-aryl heterocycle or a 5- to 10-membered heteroaryl ring, wherein the non-aryl heterocycle and the 5- to 10-membered heteroaryl ring are each independently optionally substituted with one to the maximum substitutable number of the same or different substituents selected from substituent group V.

[Item B6A]

The compound or an enantiomer thereof, or a salt thereof, or a solvate thereof according to any one of the preceding items, wherein $R_1$ and $R_4$ are each independently hydrogen, optionally substituted alkyl, optionally substituted arylalkyl, optionally substituted cycloalkyl, optionally substituted heterocycloalkyl, formyl, optionally substituted alkylcarbonyl, optionally substituted alkoxycarbonyl, optionally substituted arylcarbonyl, optionally substituted aryloxycarbonyl, optionally substituted cycloalkylcarbonyl, optionally substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted heterocycloalkylcarbamoyl, wherein the groups of $R_1$ and $R_4$ are optionally substituted with one to the maximum substitutable number of the same or different substituents selected from substituent group III.

[Item B6B]

The compound or an enantiomer thereof, or a salt thereof, or a solvate thereof according to any one of the preceding items, wherein $R_1$ and $R_4$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, optionally substituted 5- to 10-membered heterocycloalkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered heterocycloalkylcarbamoyl, wherein the groups of $R_1$ and $R_4$ are optionally substituted with one to the maximum substitutable number of the same or different substituents selected from substituent group III.

[Item B7A]

The compound or an enantiomer thereof, or a salt thereof, or a solvate thereof according to any one of the preceding items, wherein $R_1$ and $R_4$ are each independently hydrogen, optionally substituted alkyl, optionally substituted arylalkyl, optionally substituted heterocycloalkyl, formyl, optionally substituted alkylcarbonyl, optionally substituted alkoxycarbonyl, optionally substituted arylcarbonyl, or optionally substituted aryloxycarbonyl, wherein the groups of $R_1$ and $R_4$ are optionally substituted with one to the maximum substitutable number of the same or different substituents selected from substituent group III.

[Item B7B]

The compound or an enantiomer thereof, or a salt thereof, or a solvate thereof according to any one of the preceding items, wherein $R_1$ and $R_4$ are each independently hydrogen, optionally substituted $C_{1-12}$ alkyl, optionally substituted $C_{6-10}$ aryl $C_{1-6}$ alkyl, optionally substituted 5- to 10-membered heterocycloalkyl, formyl, optionally substituted $C_{1-12}$ alkylcarbonyl, optionally substituted $C_{1-12}$ alkoxycarbonyl, optionally substituted $C_{6-10}$ arylcarbonyl, or optionally substituted $C_{6-10}$ aryloxycarbonyl, wherein the groups of $R_1$ and $R_4$ are optionally substituted with one to the maximum substitutable number of the same or different substituents selected from substituent group III.

[Item B8A]

The compound or an enantiomer thereof, or a salt thereof, or a solvate thereof according to any one of the preceding items, wherein $R_1$ is hydrogen;

alkyl;

alkyl substituted with one to the maximum substitutable number of the same or different substituents selected from the group consisting of hydroxy, substituted oxy, formyl, substituted carbonyl, amino, substituted amino, cycloalkyl, and substituted cycloalkyl;

arylalkyl;

arylalkyl substituted with one to the maximum substitutable number of the same or different substituents selected from the group consisting of halogen, alkyl, substituted alkyl, hydroxy, substituted oxy, amino, substituted amino, and nitro;

cycloalkyl;

substituted cycloalkyl;

heterocycloalkyl;

substituted heterocycloalkyl; or substituted carbonyl, wherein the substituted oxy, substituted carbonyl, substituted amino, substituted cycloalkyl, substituted heterocycloalkyl, and substituted alkyl each independently have one to the maximum substitutable number of the same or different substituents selected from substituent group IV.

[Item B8B]

The compound or an enantiomer thereof, or a salt thereof, or a solvate thereof according to any one of the preceding items, wherein $R_1$ is hydrogen;

alkyl;

alkyl substituted with one to the maximum substitutable number of the same or different substituents selected from the group consisting of hydroxy, alkoxy, haloalkoxy, formyl, carboxy, carbamoyl, alkylcarbonyl, alkoxycarbonyl, amino, amidinoamino, alkoxycarbonyl-substituted amidinoamino, alkoxycarbonylamino, cycloalkyl, and halocycloalkyl;

arylalkyl;

arylalkyl substituted with one to the maximum substitutable number of the same or different substituents selected from the group consisting of halogen, alkyl, haloalkyl, hydroxy, alkoxy, haloalkoxy, amino, alkylamino, (alkyl)$_2$amino, cycloalkylcarbonylamino, and nitro;

cycloalkyl;

halocycloalkyl;

heterocycloalkyl;

alkylcarbonyl;

arylalkylcarbonyl;

alkoxycarbonyl;

arylcarbonyl; or aryloxycarbonyl.

[Item B8C]

The compound or an enantiomer thereof, or a salt thereof, or a solvate thereof according to any one of the preceding items, wherein $R_1$ is hydrogen;

$C_{1-12}$ alkyl;

$C_{1-12}$ alkyl substituted with one to the maximum substitutable number of the same or different substituents selected from the group consisting of $C_{1-6}$ alkoxy, $C_{1-6}$ haloalkoxy, formyl, carboxy, carbamoyl, $C_{1-6}$ alkylcarbonyl, $C_{1-6}$ alkoxycarbonyl, $C_{1-6}$ haloalkoxycarbonyl, amidinoamino, $C_{1-6}$ alkoxycarbonyl-substituted amidinoamino, $C_{1-6}$ alkoxycarbonylamino, hydroxy, $C_{3-10}$ cycloalkyl, and $C_{3-10}$ halocycloalkyl;

$C_{6-10}$ aryl $C_{1-6}$ alkyl;

$C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, hydroxy, $C_{1-6}$ alkoxy, $C_{1-6}$ haloalkoxy, amino, $C_{1-6}$ alkylamino, $(C_{1-6}$ alkyl$)_2$amino, $C_{3-10}$ cycloalkylcarbonylamino, nitro, and hydroxy;

$C_{3-10}$ cycloalkyl;

5- to 10-membered heterocycloalkyl;

$C_{1-6}$ alkylcarbonyl;

$C_{6-10}$ aryl $C_{1-6}$ alkylcarbonyl;

$C_{1-6}$ alkoxycarbonyl;

$C_{6-10}$ arylcarbonyl; or $C_{6-10}$ aryloxycarbonyl.

[Item B9A]

The compound or an enantiomer thereof, or a salt thereof, or a solvate thereof according to any one of the preceding items, wherein $R_3$ is alkyl;

alkyl substituted with one to the maximum substitutable number of the same or different substituents selected from the group consisting of hydroxy, substituted oxy, substituted carbonyl, amino, substituted amino, cycloalkyl, and substituted cycloalkyl;

arylalkyl;

arylalkyl substituted with one to the maximum substitutable number of the same or different substituents selected from the group consisting of halogen, alkyl, substituted alkyl, hydroxy, and substituted oxy;

aryl; or substituted aryl, wherein the substituted oxy, substituted carbonyl, substituted amino, substituted cycloalkyl, substituted alkyl, and substituted aryl each independently have one to the maximum substitutable number of the same or different substituents selected from substituent group IV.

[Item B9B]

The compound or an enantiomer thereof, or a salt thereof, or a solvate thereof according to any one of the preceding items, wherein $R_3$ is alkyl;

alkyl substituted with one to the maximum substitutable number of the same or different substituents selected from the group consisting of hydroxy, alkoxy, haloalkoxy, trialkylsilyloxy, carboxy, carbamoyl, alkoxycarbonyl, haloalkoxycarbonyl, amino, amidinoamino, alkoxycarbonyl-substituted amidinoamino, alkoxycarbonylamino, haloalkoxycarbonylamino, cycloalkyl, and halocycloalkyl;

arylalkyl;

arylalkyl substituted with one to the maximum substitutable number of the same or different substituents selected from the group consisting of halogen, alkyl, haloalkyl, hydroxy, alkoxy, and haloalkoxy; or aryl.

[Item B9C]

The compound or an enantiomer thereof, or a salt thereof, or a solvate thereof according to any one of the preceding items, wherein $R_3$ is $C_{1-12}$ alkyl;

$C_{1-12}$ alkyl substituted with one to the maximum substitutable number of the same or different substituents selected from the group consisting of hydroxy, $C_{1-6}$ alkoxy, $C_{1-6}$ haloalkoxy, tri-$C_{1-6}$ alkylsilyloxy, carboxy, carbamoyl, $C_{1-6}$ alkoxycarbonyl, $C_{1-6}$ haloalkoxycarbonyl, amino, amidinoamino, $C_{1-6}$ alkoxycarbonyl-substituted amidinoamino, $C_{1-6}$ alkoxycarbonylamino, $C_{1-6}$ haloalkoxycarbonylamino, $C_{3-10}$ cycloalkyl, and $C_{3-10}$ halocycloalkyl;

$C_{6-10}$ aryl $C_{1-6}$ alkyl;

$C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, hydroxy, $C_{1-6}$ alkoxy, and $C_{1-6}$ haloalkoxy; or $C_{6-10}$ aryl.

[Item B10A]

The compound or an enantiomer thereof, or a salt thereof, or a solvate thereof according to any one of the preceding items, wherein $R_{2A}$ and $R_{2B}$ are each independently hydrogen;

alkyl;

alkyl substituted with one to the maximum substitutable number of the same or different substituents selected from the group consisting of hydroxy, substituted oxy, amino, substituted amino, cycloalkyl, and substituted cycloalkyl;

arylalkyl;

arylalkyl substituted with one to the maximum substitutable number of the same or different substituents selected from the group consisting of halogen, alkyl, substituted alkyl, hydroxy, and substituted oxy;

cycloalkyl;

substituted cycloalkyl;

heterocycloalkyl; or substituted heterocycloalkyl, wherein the substituted oxy, substituted amino, substituted alkyl, substituted cycloalkyl, and substituted heterocycloalkyl each independently have one to the maximum substitutable number of the same or different substituents selected from substituent group IV, or $R_{2A}$ and $R_{2B}$, together with the nitrogen atom to which they are attached, form a non-aryl heterocycle, wherein the non-aryl heterocycle is optionally substituted with one to the maximum substitutable number of the same or different substituents selected from substituent group VI.

[Item B10B]

The compound or an enantiomer thereof, or a salt thereof, or a solvate thereof according to any one of the preceding items, wherein
$R_{2A}$ and $R_{2B}$ are each independently hydrogen;
alkyl;
alkyl substituted with one to the maximum substitutable number of the same or different substituents selected from the group consisting of hydroxy, alkoxy, carboxy, alkoxycarbonyl, amino, amidinoamino, alkoxycarbonyl-substituted amidinoamino, alkoxycarbonylamino, cycloalkyl, and halocycloalkyl;
arylalkyl;
arylalkyl substituted with one to the maximum substitutable number of the same or different substituents selected from the group consisting of halogen, alkyl, haloalkyl, hydroxy, alkoxy, and haloalkoxy;
cycloalkyl;
alkyl-substituted cycloalkyl; or
heterocycloalkyl, or
$R_{2A}$ and $R_{2B}$, together with the nitrogen atom to which they are attached, form a non-aryl heterocycle, wherein the non-aryl heterocycle is optionally substituted with one to the maximum substitutable number of the same or different substituents selected from substituent group VI.

[Item B10C]

The compound or an enantiomer thereof, or a salt thereof, or a solvate thereof according to any one of the preceding items, wherein
$R_{2A}$ and $R_{2B}$ are each independently
hydrogen;
$C_{1-12}$ alkyl;
$C_{1-12}$ alkyl substituted with one to the maximum substitutable number of the same or different substituents selected from the group consisting of hydroxy, $C_{1-6}$ alkoxy, carboxy, $C_{1-6}$ alkoxycarbonyl, amino, amidinoamino, $C_{1-6}$ alkoxycarbonyl-substituted amidinoamino, $C_{1-6}$ alkoxycarbonylamino, $C_{3-10}$ cycloalkyl, and $C_{3-10}$ halocycloalkyl;
$C_{6-10}$ aryl $C_{1-6}$ alkyl;
$C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, hydroxy, $C_{1-6}$ alkoxy, and $C_{1-6}$ haloalkoxy;
$C_{3-10}$ cycloalkyl;
$C_{1-6}$ alkyl-substituted $C_{3-10}$ cycloalkyl; or
5- to 10-membered heterocycloalkyl, or
$R_{2A}$ and $R_{2B}$, together with the nitrogen atom to which they are attached, form a 5- or 6-membered non-aryl heterocycle, wherein the non-aryl heterocycle is optionally substituted with one to the maximum substitutable number of the same or different substituents selected from substituent group VI.

[Item B11A]

The compound or an enantiomer thereof, or a salt thereof, or a solvate thereof according to any one of the preceding items, wherein $R^4$ is hydrogen, alkyl, or substituted alkyl, wherein the substituted alkyl has one to the maximum substitutable number of the same or different substituents selected from the group consisting of halogen, carboxy, carbamoyl, amino, alkylamino, aryl, nitroaryl, and alkoxycarbonylamino.

[Item B11B]

The compound or an enantiomer thereof, or a salt thereof, or a solvate thereof according to any one of the preceding items, wherein $R^4$ is hydrogen or alkyl.

[Item B11C]

The compound or an enantiomer thereof, or a salt thereof, or a solvate thereof according to any one of the preceding items, wherein $R^4$ is hydrogen or $C_{1-12}$ alkyl.

[Item B12A]

The compound or an enantiomer thereof, or a salt thereof, or a solvate thereof according to any one of the preceding items, wherein $R_1$ is hydrogen, methyl, propyl, isopropyl, isobutyl, sec-butyl, isopentyl, hexyl, (tert-butoxycarbonyl-substituted amidinoamino) propyl, tert-butoxyethyl, tert-butoxypropyl, tert-butoxycarbonylethyl, carboxyethyl, hydroxyethyl, hydroxypropyl, tert-butoxycarbonylaminopropyl, cyclopentylmethyl, cyclohexylmethyl, 5,6,7,8-tetrahydronaphthalenylmethyl, benzyl, 2-phenylethyl, chlorobenzyl, naphthalenylmethyl, fluorobenzyl, methylbenzyl, dimethylbenzyl, tert-butylbenzyl, methoxybenzyl, ethoxybenzyl, tert-butoxybenzyl, (trifluoromethoxy)benzyl, aminobenzyl, (dimethylamino)benzyl, (cyclopentylcarbonylamino)benzyl, nitrobenzyl, hydroxybenzyl, cyclohexyl, isovaleryl, phenylacetyl, benzoyl, isopropyloxycarbonyl, phenoxycarbonyl, or tetrahydro-2H-pyranyl.

[Item B12B]

The compound or an enantiomer thereof, or a salt thereof, or a solvate thereof according to any one of the preceding items, wherein
$R_{2A}$ is hydrogen, and
$R_{2B}$ is isopropyl, isobutyl, sec-butyl, pentyl, isopentyl, hexyl, heptyl, amidinoaminopropyl, (tert-butoxycarbonyl-substituted amidinoamino) propyl, (tert-butoxycarbonyl)ethyl, tert-butoxyethyl, carboxyethyl, hydroxyethyl, (tert-butoxycarbonylamino) propyl, cyclopentylmethyl, cyclohexylmethyl, (1,2,3,4-tetrahydronaphthalenyl)methyl, 2,2,6,6-tetramethylpiperidinyl, benzyl, phenylethyl, naphthalenylmethyl, fluorobenzyl, chlorobenzyl, (fluorophenyl)ethyl, methylbenzyl, tert-butoxybenzyl, hydroxybenzyl, β-hydroxyphenethyl, α-hydroxymethylphenethyl, cyclopentyl, cyclohexyl, or methylcyclohexyl, or $R_{2A}$ and $R_{2B}$, together with the nitrogen atom to which they are attached, form a pyrrolidine ring.

[Item B12C]

The compound or an enantiomer thereof, or a salt thereof, or a solvate thereof according to any one of the preceding items, wherein $R^3$ is propyl, isobutyl, isopentyl, hexyl, amidinoaminopropyl, (tert-butoxycarbonyl-substituted amidinoamino) propyl, (tert-butoxycarbonyl)ethyl, carboxyethyl, hydroxyethyl, (tert-butyldimethylsilyloxy)ethyl, (tert-butoxycarbonylamino) propyl, cyclopentylmethyl, cyclohexylmethyl, cyclohexylethyl, benzyl, naphthalenylmethyl, naphthalenylethyl, chlorobenzyl, (methylphenyl)ethyl, (isopropylphenyl)ethyl, tert-butoxybenzyl, hydroxybenzyl, or phenyl.

[Item B12D]

The compound or an enantiomer thereof, or a salt thereof, or a solvate thereof according to any one of the preceding items, wherein $R^4$ is hydrogen or methyl.

[Item B13A]

The compound or an enantiomer thereof, or a salt thereof, or a solvate thereof according to any one of the preceding items, wherein the compound is a compound selected from the group consisting of compound numbers I-1 to 1-50, II-1 to II-50, IF-51 to IF-411, and IB-51 to IB-425.

[Item B12]

An antiviral agent against a virus in the Lyssavirus genus, comprising the compound or a pharmaceutically acceptable salt thereof according to any one of the preceding items.

[Item B13]

The antiviral agent according to any one of the preceding items, wherein the virus in the Lyssavirus genus comprises a rabies virus.

[Item B14] A medicament comprising the compound or a pharmaceutically acceptable salt thereof according to any one of the preceding items.

[Item B15]

The medicament according to any one of the preceding items, which is a preventive drug or therapeutic drug for rabies.

[Item B16]

A pharmaceutical composition comprising the compound or a pharmaceutically acceptable salt thereof according to any one of the preceding items and a pharmaceutically acceptable carrier.

[Item B17]

A pharmaceutical composition for preventing or treating rabies, comprising the compound or a pharmaceutically acceptable salt thereof according to any one of the preceding items and a pharmaceutically acceptable carrier.

[Item B18]

A method for preventing or treating rabies, characterized by administering, to a patient in need thereof, a therapeutically effective amount of the compound or a pharmaceutically acceptable salt thereof according to any one of the preceding items, the antiviral agent according to any one of the preceding items, the medicament according to any one of the preceding items, or the pharmaceutical composition according to any one of the preceding items.

[Item B19]

Use of the compound or a pharmaceutically acceptable salt thereof according to any one of the preceding items or the antiviral agent according to any one of the preceding items, for the manufacture of a medicament for preventing or treating rabies.

The present disclosure is intended so that one or more of the features described above can be provided not only as the explicitly disclosed combinations, but also as other combinations thereof. Additional embodiments and advantages of the present disclosure are recognized by those skilled in the art by reading and understanding the following detailed description as needed.

Advantageous Effects of Invention

The compounds of the present disclosure exhibit an excellent antiviral action on viruses in the Lyssavirus genus including the rabies virus. Therefore, the compounds of the present disclosure are useful as a therapeutic agent and/or prophylactic agent for rabies.

DESCRIPTION OF EMBODIMENTS

Hereinafter, the present disclosure is described in more detail.

Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present disclosure pertains. In case of a contradiction, the present specification (including the definitions) takes precedence.

(Definitions)

The terms and the general technology used in the present disclosure are first described.

As used herein, the term "group" refers to a monovalent group, unless especially noted otherwise. Examples of a group that is not a monovalent group include alkylene group (divalent) and the like. The term "group" may also be abbreviated in the following description of substituents or the like.

As used herein, the number of substituents when a group is defined as "optionally substituted" or "substituted" is not particularly limited as long as it is substitutable and is one or more. The description for each group is also applicable when the substituent is a part of or a substituent on another substituent, unless specifically noted otherwise.

As used herein, "maximum substitutable number" is the maximum number of substituents that a group can have. The number can vary for each group. For example, the number is 3 for a methyl group, 5 for an ethyl group, 7 for a benzyl group, and 11 for a naphthalenyl ethyl group.

For a group that is modified by "optionally substituted" or "substituted" herein, any portion of the group can be substituted. For example, "optionally substituted arylalkyl" and "substituted arylalkyl" can have the aryl moiety substituted, the alkyl moiety substituted, or both the aryl moiety and the alkyl moiety substituted.

As used herein, the substituent used when "optionally substituted" can be one or more of the same or different substituents selected from any one of the following substituent groups I to VI. While the types of atoms within a substituent associated with attachment are not particularly limited by the type of substituent, if the atom to which a substituent attaches is an oxygen atom, a nitrogen atom, or a sulfur atom, the atom is limited to and selected from those with an attachment point in the following substituents that is a carbon atom.

Substituent group I consists of halogen, hydroxy, oxo, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureido, amidino, amidinoamino, unsubstituted or substituted alkyl, unsubstituted or substituted alkenyl, unsubstituted or substituted alkynyl, unsubstituted or substituted aryl, unsubstituted or substituted cycloalkyl, unsubstituted or substituted heteroaryl, unsubstituted or substituted heterocycloalkyl, unsubstituted or substituted alkyloxy, unsubstituted or substituted alkenyloxy, unsubstituted or substituted alkynyloxy, unsubstituted or substituted aryl- or substituted cycloalkyl-$L_X$-oxy, $L_X$-oxy, unsubstituted unsubstituted or substituted heteroaryl-$L_X$-Oxy, unsubstituted or substituted heterocycloalkyl-$L_X$-oxy, unsubstituted or substituted alkyloxyalkyl, unsubstituted or substituted alkenyloxyalkyl, unsubstituted or substituted alkynyloxyalkyl, unsubstituted or substituted aryloxyalkyl, unsubstituted or substituted cycloalkyloxyalkyl, unsubstituted or substituted heteroaryloxyalkyl, unsubstituted or substituted heterocycloalkyloxyalkyl, unsubstituted or substituted alkyloxyalkyloxy, unsubstituted or substituted alkenyloxyalkyloxy, unsubstituted or substituted alkynyloxyalkyloxy, unsubstituted or substituted aryloxyalkyloxy, unsubstituted or substituted cycloalkyloxyalkyloxy, unsubstituted or substituted heteroaryloxyalkyloxy, unsubstituted or substituted heterocycloalkyloxyalkyloxy, unsubstituted or substituted alkylcarbonyl, unsubstituted or substituted alkenylcarbonyl, unsubstituted or substituted alkynylcarbonyl, unsubstituted or substituted aryl-$L_X$-carbonyl, unsubstituted or substituted cycloalkyl-$L_X$-carbonyl, unsubstituted or substituted heteroaryl-$L_X$-carbonyl, unsubstituted or substituted heterocycloalkyl-$L_X$-carbonyl, unsubstituted or substituted alkylcarbonyloxy, unsubstituted or substituted alkenylcarbonyloxy, unsubstituted or substituted alkynylcarbonyloxy, unsubstituted or substituted aryl-$L_X$-carbonyloxy, unsubstituted or substituted cycloalkyl-$L_X$-carbonyloxy, unsubstituted or substituted heteroaryl-$L_X$-carbonyloxy, unsubstituted or substituted heterocycloalkyl-$L_X$-carbonyloxy, unsubstituted or substituted alkylcarbonylamino, unsubstituted or substituted alkenylcarbonylamino, unsubstituted or substituted alkynylcarbonylamino, unsubstituted or substituted aryl-$L_X$-carbonylamino, unsubstituted or substituted cycloalkyl-$L_X$-carbonylamino, unsubstituted or substituted heteroaryl-$L_X$-carbonylamino, unsubstituted or substituted heterocycloalkyl-$L_X$-carbonylamino, unsubstituted or substituted alkylcarbonylthio, unsubstituted or substituted alkenylcarbonylthio, unsubstituted or substituted alkynylcarbonylthio, unsubstituted or substituted aryl-$L_X$-carbonylthio, unsubstituted or substituted cycloalkyl-$L_X$-carbonylthio, unsubstituted or substituted heteroaryl-$L_X$-carbonylthio, unsubstituted or substituted heterocycloalkyl-$L_X$-carbonylthio, unsubstituted or substituted alkylcarbonylimino, unsubstituted or substituted alkenylcarbonylimino, unsubstituted or substituted alkynylcarbonylimino, unsubstituted or substituted aryl-$L_X$-carbonylimino, unsubstituted or substituted cycloalkyl-$L_X$-carbonylimino, unsubstituted or substituted heteroaryl-$L_X$-carbonylimino, unsubstituted or substituted heterocycloalkyl-$L_X$-carbonylimino, unsubstituted or substituted alkylthio, unsubstituted or substituted alkenylthio, unsubstituted or substituted alkynylthio, unsubstituted or substituted aryl-$L_X$-thio, unsubstituted or substituted cycloalkyl-$L_X$-thio, unsubstituted or substituted heteroaryl-$L_X$-thio, unsubstituted or substituted heterocycloalkyl-$L_X$-thio, unsubstituted or substituted alkylamino, unsubstituted or substituted alkenylamino, unsubstituted or substituted alkynylamino, unsubstituted or substituted aryl-$L_X$-amino, unsubstituted or substituted cycloalkyl-$L_X$-amino, unsubstituted or substituted heteroaryl-$L_X$-amino, unsubstituted or substituted heterocycloalkyl-$L_X$-amino, unsubstituted or substituted alkylsulfonyl, unsubstituted or substituted alkenylsulfonyl, unsubstituted or substituted alkynylsulfonyl, unsubstituted or substituted aryl-$L_X$-sulfonyl, unsubstituted or substituted cycloalkyl-$L_X$-sulfonyl, unsubstituted or substituted heteroaryl-$L_X$-sulfonyl, unsubstituted or substituted heterocycloalkyl-$L_X$-sulfonyl, unsubstituted or substituted alkylsulfonylamino, unsubstituted or substituted alkenylsulfonylamino, unsubstituted or substituted alkynylsulfonylamino, unsubstituted or substituted aryl-$L_X$-sulfonylamino, unsubstituted or substituted cycloalkyl-$L_X$-sulfonylamino, unsubstituted or substituted heteroaryl-$L_X$-sulfonylamino, unsubstituted or substituted heterocycloalkyl-$L_X$-sulfonylamino, unsubstituted or alkylimino, unsubstituted or substituted alkenylimino, unsubstituted or substituted alkynylimino, unsubstituted or substituted aryl-$L_X$-imino, unsubstituted or substituted cycloalkyl-$L_X$-imino, unsubstituted or substituted heteroaryl-$L_X$-imino, unsubstituted or substituted heterocycloalkyl-$L_X$-imino, unsubstituted or substituted alkyloxyimino, unsubstituted or substituted alkenyloxyimino, unsubstituted or substituted alkynyloxyimino, unsubstituted or substituted aryl-$L_X$-oxyimino, unsubstituted or substituted cycloalkyl-$L_X$-oxyimino, unsubstituted or substituted heteroaryl-$L_X$-oxyimino, unsubstituted or substituted heterocycloalkyl-$L_X$-oxyimino, unsubstituted or substituted alkyloxycarbonyl, unsubstituted or substituted alkenyloxycarbonyl, unsubstituted or substituted alkynyloxycarbonyl, unsubstituted or substituted aryl-$L_X$-oxycarbonyl, unsubstituted or substituted cycloalkyl-$L_X$-oxycarbonyl, unsubstituted or substituted heteroaryl-$L_X$-oxycarbonyl, unsubstituted or substituted heterocycloalkyl-$L_X$-oxycarbonyl, unsubstituted or substituted alkyloxycarbonylamino, alkenyloxycarbonylamino, unsubstituted or substituted unsubstituted or substituted alkynyloxycarbonylamino, unsubstituted or substituted aryl-$L_X$-oxycarbonylamino, unsubstituted or substituted cycloalkyl-$L_X$-oxycarbonylamino, unsubstituted or substituted heteroaryl-$L_X$-oxycarbonylamino, unsubstituted or substituted heterocycloalkyl-$L_X$-oxycarbonylamino, unsubstituted or substituted alkylsulfanyl, unsubstituted or substituted alkenylsulfanyl, unsubstituted or substituted alkynylsulfanyl, unsubstituted or substituted aryl-$L_X$-sulfanyl, unsubstituted or substituted cycloalkyl-$L_X$-sulfanyl, unsubstituted or substituted heteroaryl-$L_X$-sulfanyl, unsubstituted or substituted heterocycloalkyl-$L_X$-sulfanyl, unsubstituted or substituted alkylsulfinyl, unsubstituted or substituted alkenylsulfinyl, unsubstituted or substituted alkynylsulfinyl, unsubstituted or substituted aryl-$L_X$-sulfinyl, unsubstituted or substituted cycloalkyl-$L_X$-sulfinyl, unsubstituted or substituted heteroaryl-$L_X$-sulfinyl, unsubstituted or substituted heterocycloalkyl-$L_X$-sulfinyl, unsubstituted or substituted alkylcarbamoyl, unsubstituted or substituted alkenylcarbamoyl, unsubstituted or substituted alkynylcarbamoyl, unsubstituted or substituted aryl-$L_X$-carbamoyl, unsubstituted or substituted cycloalkyl-$L_X$-carbamoyl, unsubstituted or substituted heteroaryl-$L_X$-carbamoyl, unsubstituted or substituted heterocycloalkyl-$L_X$-carbamoyl, unsubstituted or substituted alkylsulfamoyl, unsubstituted or substituted alkenylsulfamoyl, unsubstituted or substituted alkynylsulfamoyl, unsubstituted or substituted aryl-$L_X$-sulfamoyl, unsubstituted or substituted cycloalkyl-$L_X$-sulfamoyl, unsubstituted or substituted heteroaryl-$L_X$-unsubstituted or substituted heterocycloalkyl-$L_X$-sulfamoyl, wherein $L_X$ is a single bond or unsubstituted or substituted alkylene, wherein the substituted alkyl, substituted alkenyl, substituted alkynyl, substituted aryl, substituted sulfamoyl, and cycloalkyl, substituted heteroaryl, substituted heterocycloalkyl, and substituted alkylene moieties (fully or partially) in the substituent group each independently have one to the maximum substitutable number of the same or different substituents selected from the group consisting of halogen, hydroxy, oxo, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureido, amidino, amidinoamino, alkyl, alkenyl, alkynyl, aryl, cycloalkyl, heteroaryl, heterocycloalkyl, alkyloxy, alkenyloxy, alkynyloxy, aryl-$L_X$-oxy, cycloalkyl-heteroaryl-$L_X$-oxy, heterocycloalkyl-$L_X$-oxy, $L_X$-oxy, alkyloxyalkyl, alkenyloxyalkyl, alkynyloxyalkyl, aryloxyalkyl, cycloalkyloxyalkyl, heteroaryloxyalkyl, heterocycloalkyloxyalkyl, alkyloxyalkyloxy, alkenyloxyalkyloxy, alkynyloxyalkyloxy, aryloxyalkyloxy, cycloalkyloxyalkyloxy, heteroaryloxyalkyloxy, heterocycloalkyloxyalkyloxy, alkylcarbonyl, alkenylcarbonyl, alkynylcarbonyl, aryl-$L_X$-carbonyl, cycloalkyl-$L_X$-carbonyl, heteroaryl-$L_X$-carbonyl, heterocycloalkyl-$L_X$-carbonyl, alkylcarbonyloxy, alkenylcarbonyloxy, alkynylcarbonyloxy, aryl-$L_X$-carbonyloxy, cycloalkyl-$L_X$-carbonyloxy, heteroaryl-heterocycloalkyl-$L_X$-carbonyloxy, $L_X$-carbonyloxy, alkylcarbonylamino, alkenylcarbonylamino, alkynylcarbonylamino, aryl-$L_X$-carbonylamino, cycloalkyl-$L_X$-carbonylamino, heteroaryl-$L_X$-carbonylamino, heterocycloalkyl-$L_X$-carbonylamino, alkylcarbonylthio, alkenylcarbonylthio, alkynylcarbonylthio, aryl-$L_X$-carbonylthio, cycloalkyl-$L_X$-carbonylthio, heteroaryl-$L_X$-carbonylthio, heterocycloalkyl-$L_X$-carbonylthio, alkylcarbonylimino, alkenylcarbonylimino, alkynylcarbonylimino, aryl-$L_X$-carbonylimino, cycloalkyl-$L_X$-carbonylimino, heteroaryl-$L_X$-carbonylimino, heterocycloalkyl-$L_X$-carbonylimino, alkylthio, alkenylthio, alkynylthio, aryl-$L_X$-thio, cycloalkyl-$L_X$-thio, heteroaryl-$L_X$-thio, heterocycloalkyl-$L_X$-thio, alkylamino, alkenylamino, alkynylamino, alkynylamino, aryl-$L_X$-amino, cycloalkyl-$L_X$-amino, heteroaryl-$L_X$-amino, heterocycloalkyl-$L_X$-amino, alkylsulfonyl, alkenylsulfonyl, alkynylsulfonyl, aryl-$L_X$-sulfonyl, cycloalkyl-$L_X$-sulfonyl, heteroaryl-$L_X$-sulfonyl, heterocycloalkyl-$L_X$-sulfonyl, alkylsulfonylamino, alkenylsulfonylamino, alkynylsulfonylamino, aryl-$L_X$-sulfonylamino, cycloalkyl-$L_X$-sulfonylamino, heteroaryl-$L_X$-sulfonylamino, heterocycloalkyl-$L_X$-sulfonylamino, alkylimino, alkenylimino, alkynylimino, aryl-$L_X$-imino, cycloalkyl-$L_X$-imino, heteroaryl-$L_X$-imino, heterocycloalkyl-$L_X$-imino, alkyloxyimino, alkenyloxyimino, alkynyloxyimino, aryl-$L_X$-oxyimino, cycloalkyl-$L_X$-oxyimino, heteroaryl-$L_X$-oxyimino, heterocycloalkyl-$L_X$-oxyimino, alkyloxycarbonyl, alkenyloxycarbonyl, alkynyloxycarbonyl, aryl-$L_X$-oxycarbonyl, cycloalkyl-$L_X$-oxycarbonyl, heteroaryl-$L_X$-oxycarbonyl, heterocycloalkyl-$L_X$-oxycarbonyl, alkyloxycarbonylamino, alkenyloxycarbonylamino, alkynyloxycarbonylamino, aryl-$L_X$-oxycarbonylamino, cycloalkyl-$L_X$-oxycarbonylamino, heteroaryl-$L_X$-oxycarbonylamino, heterocycloalkyl-$L_X$-oxycarbonylamino, alkylsulfanyl, alkenylsulfanyl, alkynylsulfanyl, aryl-$L_X$-sulfanyl, cycloalkyl-$L_X$-sulfanyl, heteroaryl-$L_X$-sulfanyl, heterocycloalkyl-$L_X$-sulfanyl, alkylsulfinyl, alkenylsulfinyl, alkynylsulfinyl, aryl-$L_X$-sulfinyl, cycloalkyl-$L_X$-sulfinyl, heteroaryl-$L_X$-sulfinyl, heterocycloalkyl-$L_X$-sulfinyl, alkylcarbamoyl, alkenylcarbamoyl, alkynylcarbamoyl, aryl-$L_X$-carbamoyl, cycloalkyl-$L_X$-carbamoyl, heteroaryl-$L_X$-carbamoyl, heterocycloalkyl-$L_X$-carbamoyl, alkylsulfamoyl, alkenylsulfamoyl, alkynylsulfamoyl, aryl-$L_X$-sulfamoyl, cycloalkyl-$L_X$-sulfamoyl, heteroaryl-$L_X$-sulfamoyl, and heterocycloalkyl-$L_X$-sulfamoyl.

Substituent group II consists of halogen, hydroxy, oxo, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureido, amidino, amidinoamino, unsubstituted or substituted $C_{1-12}$ alkyl, unsubstituted or substituted $C_{2-12}$ alkenyl, unsubstituted or substituted $C_{2-12}$ alkynyl, unsubstituted or substituted $C_{6-10}$ aryl, unsubstituted or substituted $C_{3-10}$ cycloalkyl, unsubstituted or substituted 5- to 10-membered heteroaryl, unsubstituted or substituted 5- to 10-membered heterocycloalkyl, unsubstituted or substituted $C_{1-12}$ alkyloxy, unsubstituted or substituted $C_{2-12}$ alkenyloxy, unsubstituted or substituted $C_{2-12}$ alkynyloxy, unsubstituted or substituted $C_{6-10}$ aryl-$L_X$-oxy, unsubstituted or substituted $C_{3-10}$ cycloalkyl-$L_X$-oxy, unsubstituted or substituted 5- to 10-membered heteroaryl-$L_X$-oxy, unsubstituted or substituted 5- to 10-membered heterocycloalkyl-$L_X$-oxy, unsubstituted or substituted $C_{1-12}$ alkyloxy $C_{1-12}$ alkyl, unsubstituted or substituted $C_{2-12}$ alkenyloxy $C_{1-12}$ alkyl, unsubstituted or substituted $C_{2-12}$ alkynyloxy $C_{1-12}$ alkyl, unsubstituted or substituted $C_{6-10}$ aryloxy $C_{1-12}$ alkyl, unsubstituted or substituted $C_{3-10}$ cycloalkyloxy $C_{1-12}$ alkyl, unsubstituted or substituted 5- to 10-membered heteroaryloxy $C_{1-12}$ alkyl, unsubstituted or substituted 5- to 10-membered heterocycloalkyloxy $C_{1-12}$ alkyl, unsubstituted or substituted $C_{1-12}$ alkyloxy $C_{1-12}$ alkyloxy, unsubstituted or substituted $C_{2-12}$ alkenyloxy $C_{1-12}$ alkyloxy, unsubstituted or substituted $C_{2-12}$ alkynyloxy $C_{1-12}$ alkyloxy, unsubstituted or substituted $C_{6-10}$ aryloxy $C_{1-12}$ alkyloxy, unsubstituted or substituted $C_{3-10}$ cycloalkyloxy $C_{1-12}$ alkyloxy, unsubstituted or substituted 5- to 10-membered heteroaryloxy $C_{1-12}$ alkyloxy, unsubstituted or substituted 5- to 10-membered heterocycloalkyloxy $C_{1-12}$ alkyloxy, unsubstituted or substituted $C_{1-12}$ alkylcarbonyl, unsubstituted or substituted $C_{2-12}$ alkenylcarbonyl, unsubstituted or substituted $C_{2-12}$ alkynylcarbonyl, unsubstituted or substituted $C_{6-10}$ aryl-$L_X$-carbonyl, unsubstituted or substituted $C_{3-10}$ cycloalkyl-$L_X$-carbonyl, unsubstituted or substituted 5- to 10-membered heteroaryl-$L_X$-carbonyl, unsubstituted or substituted 5- to 10-membered heterocycloalkyl-$L_X$-carbonyl, unsubstituted or substituted $C_{1-12}$ alkylcarbonyloxy, unsubstituted or substituted $C_{2-12}$ alkenylcarbonyloxy, unsubstituted or substituted $C_{2-12}$ alkynylcarbonyloxy, unsubstituted or substituted $C_{6-10}$ aryl-$L_X$-carbonyloxy, unsubstituted or substituted $C_{3-10}$ cycloalkyl-$L_X$-carbonyloxy, unsubstituted or substituted 5- to 10-membered heteroaryl-$L_X$-carbonyloxy, unsubstituted or substituted 5- to 10-membered heterocycloalkyl-$L_X$-carbonyloxy, unsubstituted or substituted $C_{1-12}$ alkylcarbonylamino, unsubstituted or substituted $C_{2-12}$ alkenylcarbonylamino, unsubstituted or substituted $C_{2-12}$ alkynylcarbonylamino, unsubstituted or substituted $C_{6-10}$ aryl-$L_X$-carbonylamino, unsubstituted or substituted $C_{3-10}$ cycloalkyl-$L_X$-carbonylamino, unsubstituted or substituted 5- to 10-membered heteroaryl-$L_X$-carbonylamino, unsubstituted or substituted 5- to 10-membered heterocycloalkyl-$L_X$-carbonylamino, unsubstituted or substituted $C_{1-12}$ alkylcarbonylthio, unsubstituted or substituted $C_{2-12}$ alkenylcarbonylthio, unsubstituted or substituted $C_{2-12}$ alkynylcarbonylthio, unsubstituted or substituted $C_{6-10}$ aryl-$L_X$-carbonylthio, unsubstituted or substituted $C_{3-10}$ cycloalkyl-$L_X$-carbonylthio, unsubstituted or substituted 5- to 10-membered heteroaryl-$L_X$-carbonylthio, unsubstituted or substituted 5- to 10-membered heterocycloalkyl-$L_X$-carbonylthio, unsubstituted or substituted $C_{1-12}$ alkylcarbonylimino, unsubstituted or substituted $C_{2-12}$ alkenylcarbonylimino, unsubstituted or substituted $C_{2-12}$ alkynylcarbonylimino, unsubstituted or substituted $C_{6-10}$ aryl-$L_X$-carbonylimino, unsubstituted or substituted $C_{3-10}$ cycloalkyl-$L_X$-carbonylimino, unsubstituted or substituted 5- to 10-membered heteroaryl-$L_X$-carbonylimino, unsubstituted or substituted 5- to 10-membered heterocycloalkyl-$L_X$-carbonylimino, unsubstituted or substituted $C_{1-12}$ alkylthio, unsubstituted or substituted $C_{2-12}$ alkenylthio, unsubstituted or substituted $C_{2-12}$ alkynylthio, unsubstituted or substituted $C_{6-10}$ aryl-$L_X$-thio, unsubstituted or substituted $C_{3-10}$ cycloalkyl-$L_X$-thio, unsubstituted or substituted 5- to 10-membered heteroaryl-$L_X$-thio, unsubstituted or substituted 5- to 10-membered heterocycloalkyl-$L_X$-thio, unsubstituted or substituted $C_{1-12}$ alkylamino, unsubstituted or substituted $C_{2-12}$ alkenylamino, unsubstituted or substituted $C_{2-12}$ alkynylamino, unsubstituted or substituted $C_{2-12}$ alkynylamino, unsubstituted or substituted $C_{6-10}$ aryl-$L_X$-amino, unsubstituted or substituted $C_{3-10}$ cycloalkyl-$L_X$-amino, unsubstituted or substituted 5- to 10-membered heteroaryl-$L_X$-amino, unsubstituted or substituted 5- to 10-membered heterocycloalkyl-$L_X$-amino, unsubstituted or substituted C$_{1-12}$ alkylsulfonyl, unsubstituted or substituted C$_{2-12}$ alkenylsulfonyl, unsubstituted or substituted C$_{2-12}$ alkynylsulfonyl, unsubstituted or substituted C$_{6-10}$ aryl-L$_X$-sulfonyl, unsubstituted or substituted C$_{3-10}$ cycloalkyl-L$_X$-sulfonyl, unsubstituted or substituted 5- to 10-membered heteroaryl-L$_X$-sulfonyl, unsubstituted or substituted 5- to 10-membered heterocycloalkyl-L$_X$-sulfonyl, unsubstituted or substituted C$_{1-12}$ alkylsulfonylamino, unsubstituted or substituted C$_{2-12}$ alkenylsulfonylamino, unsubstituted or substituted C$_{2-12}$ alkynylsulfonylamino, unsubstituted or substituted C$_{6-10}$ aryl-L$_X$-sulfonylamino, unsubstituted or substituted C$_{3-10}$ cycloalkyl-L$_X$-sulfonylamino, unsubstituted or substituted 5- to 10-membered heteroaryl-L$_X$-sulfonylamino, unsubstituted or substituted 5- to 10-membered heterocycloalkyl-L$_X$-sulfonylamino, unsubstituted or substituted C$_{1-12}$ alkylimino, unsubstituted or substituted C$_2$-12 alkenylimino, unsubstituted or substituted C$_{2-12}$ alkynylimino, unsubstituted or substituted C$_{6-10}$ aryl-L$_X$-imino, unsubstituted or substituted C$_{3-10}$ cycloalkyl-L$_X$-imino, unsubstituted or substituted 5- to 10-membered heteroaryl-L$_X$-imino, unsubstituted or substituted 5- to 10-membered heterocycloalkyl-L$_X$-imino, unsubstituted or substituted C$_{1-12}$ alkyloxyimino, unsubstituted or substituted C$_{2-12}$ alkenyloxyimino, unsubstituted or substituted C$_{2-12}$ alkynyloxyimino, unsubstituted or substituted C$_{6-10}$ aryl-L$_X$-oxyimino, unsubstituted or substituted C$_{3-10}$ cycloalkyl-L$_X$-oxyimino, unsubstituted or substituted 5- to 10-membered heteroaryl-L$_X$-oxyimino, unsubstituted or substituted 5- to 10-membered heterocycloalkyl-L$_X$-oxyimino, unsubstituted or substituted C$_{1-12}$ alkyloxycarbonyl, unsubstituted or substituted C$_{2-12}$ alkenyloxycarbonyl, unsubstituted or substituted C$_{2-12}$ alkynyloxycarbonyl, unsubstituted or substituted C$_{6-10}$ aryl-L$_X$-oxycarbonyl, unsubstituted or substituted C$_{3-10}$ cycloalkyl-L$_X$-oxycarbonyl, unsubstituted or substituted 5- to 10-membered heteroaryl-L$_X$-oxycarbonyl, unsubstituted or substituted 5- to 10-membered heterocycloalkyl-L$_X$-oxycarbonyl, unsubstituted or substituted C$_{1-12}$ alkyloxycarbonylamino, unsubstituted or substituted C$_{2-12}$ alkenyloxycarbonylamino, unsubstituted or substituted C$_{2-12}$ alkynyloxycarbonylamino, unsubstituted or substituted C$_{6-10}$ aryl-L$_X$-oxycarbonylamino, unsubstituted or substituted C$_{3-10}$ cycloalkyl-L$_X$-oxycarbonylamino, unsubstituted or substituted 5- to 10-membered heteroaryl-L$_X$-oxycarbonylamino, unsubstituted or substituted 5- to 10-membered heterocycloalkyl-L$_X$-oxycarbonylamino, unsubstituted or substituted C$_{1-12}$ alkylsulfanyl, unsubstituted or substituted C$_{2-12}$ alkenylsulfanyl, unsubstituted or substituted C$_{2-12}$ alkynylsulfanyl, unsubstituted or substituted C$_{6-10}$ aryl-L$_X$-sulfanyl, unsubstituted or substituted C$_{3-10}$ cycloalkyl-L$_X$-sulfanyl, unsubstituted or substituted 5- to 10-membered heteroaryl-L$_X$-sulfanyl, unsubstituted or substituted 5- to 10-membered heterocycloalkyl-L$_X$-sulfanyl, unsubstituted or substituted C$_{1-12}$ alkylsulfinyl, unsubstituted or substituted C$_{2-12}$ alkenylsulfinyl, unsubstituted or substituted C$_{2-12}$ alkynylsulfinyl, unsubstituted or substituted C$_{6-10}$ aryl-L$_X$-sulfinyl, unsubstituted or substituted C$_{3-10}$ cycloalkyl-L$_X$-sulfinyl, unsubstituted or substituted 5- to 10-membered heteroaryl-L$_X$-sulfinyl, unsubstituted or substituted 5- to 10-membered heterocycloalkyl-L$_X$-sulfinyl, unsubstituted or substituted C$_{1-12}$ alkylcarbamoyl, unsubstituted or substituted C$_{2-12}$ alkenylcarbamoyl, unsubstituted or substituted C$_{2-12}$ alkynylcarbamoyl, unsubstituted or substituted C$_{6-10}$ aryl-L$_X$-carbamoyl, unsubstituted or substituted C$_{3-10}$ cycloalkyl-L$_X$-carbamoyl, unsubstituted or substituted 5- to 10-membered heteroaryl-L$_X$-carbamoyl, unsubstituted or substituted 5- to 10-membered heterocycloalkyl-L$_X$-carbamoyl, unsubstituted or substituted C$_{1-12}$ alkylsulfamoyl, unsubstituted or substituted C$_{2-12}$ alkenylsulfamoyl, unsubstituted or substituted C$_{2-12}$ alkynylsulfamoyl, unsubstituted or substituted C$_{6-10}$ aryl-L$_X$-sulfamoyl, unsubstituted or substituted C$_{3-10}$ cycloalkyl-L$_X$-sulfamoyl, unsubstituted or substituted 5- to 10-membered heteroaryl-L$_X$-sulfamoyl, and unsubstituted or substituted 5- to 10-membered heterocycloalkyl-L$_X$-sulfamoyl, wherein L$_X$ is a single bond or unsubstituted or substituted C$_{1-12}$ alkylene, wherein the substituted C$_{1-12}$ alkyl, substituted C$_{2-12}$ alkenyl, substituted C$_{2-12}$ alkynyl, substituted C$_{6-10}$ aryl, substituted C$_{3-10}$ cycloalkyl, substituted 5- to 10-membered heteroaryl, substituted 5- to 10-membered heterocycloalkyl, and substituted alkylene moieties (fully or partially) in the substituent group each independently have one to the maximum substitutable number of the same or different substituents selected from the group consisting of halogen, hydroxy, oxo, carboxy, amino, imino, hydroxyamino, hydroxyimino, formyl, formyloxy, carbamoyl, sulfamoyl, sulfanyl, sulfino, sulfo, thioformyl, thiocarboxy, dithiocarboxy, thiocarbamoyl, cyano, nitro, nitroso, azide, hydrazino, ureido, amidino, amidinoamino, C$_{1-12}$ alkyl, C$_{1-12}$ haloalkyl, C$_{2-12}$ alkenyl, C$_{2-12}$ alkynyl, C$_{6-10}$ aryl, C$_{3-10}$ cycloalkyl, 5- to 10-membered heteroaryl, 5- to 10-membered heterocycloalkyl, C$_{1-12}$ alkyloxy, C$_{1-12}$ haloalkyloxy, C$_{2-12}$ alkenyloxy, C$_{2-12}$ alkynyloxy, C$_{6-10}$ aryl-L$_X$-oxy, C$_{3-10}$ cycloalkyl-L$_X$-oxy, 5- to 10-membered heteroaryl-L$_X$-oxy, 5- to 10-membered heterocycloalkyl-L$_X$-oxy, C$_{1-12}$ alkyloxyalkyl, C$_{2-12}$ alkenyloxyalkyl, C$_{2-12}$ alkynyloxyalkyl, C$_{6-10}$ aryloxyalkyl, C$_3$-10 cycloalkyloxyalkyl, 5- to 10-membered heteroaryloxyalkyl, 5- to 10-membered heterocycloalkyloxyalkyl, C$_{1-12}$ alkyloxyalkyloxy, C$_{2-12}$ alkenyloxyalkyloxy, C$_{2-12}$ alkynyloxyalkyloxy, C$_{6-10}$ aryloxyalkyloxy, C$_{3-10}$ cycloalkyloxyalkyloxy, 5- to 10-membered heteroaryloxyalkyloxy, 5- to 10-membered heterocycloalkyloxyalkyloxy, C$_{1-12}$ alkylcarbonyl, C$_{2-12}$ alkenylcarbonyl, C$_{2-12}$ alkynylcarbonyl, C$_{6-10}$ aryl-L$_X$-carbonyl, C$_{3-10}$ cycloalkyl-L$_X$-carbonyl, 5- to 10-membered heteroaryl-L$_X$-carbonyl, 5- to 10-membered heterocycloalkyl-L$_X$-carbonyl, C$_{1-12}$ alkylcarbonyloxy, C$_{2-12}$ alkenylcarbonyloxy, C$_{2-12}$ alkynylcarbonyloxy, C$_{6-10}$ aryl-L$_X$-carbonyloxy, C$_{3-10}$ cycloalkyl-L$_X$-carbonyloxy, 5- to 10-membered heteroaryl-L$_X$-carbonyloxy, 5- to 10-membered heterocycloalkyl-L$_X$-carbonyloxy, C$_{1-12}$ alkylcarbonylamino, C$_{2-12}$ alkenylcarbonylamino, C$_{2-12}$ alkynylcarbonylamino, C$_{6-10}$ aryl-L$_X$-carbonylamino, C$_{3-10}$ cycloalkyl-L$_X$-carbonylamino, 5- to 10-membered heteroaryl-L$_X$-carbonylamino, 5- to 10-membered heterocycloalkyl-L$_X$-carbonylamino, C$_{1-12}$ alkylcarbonylthio, C$_{2-12}$ alkenylcarbonylthio, C$_{2-12}$ alkynylcarbonylthio, C$_{6-10}$ aryl-L$_X$-carbonylthio, C$_{3-10}$ cycloalkyl-L$_X$-carbonylthio, 5- to 10-membered heteroaryl-L$_X$-carbonylthio, 5- to 10-membered heterocycloalkyl-L$_X$-carbonylthio, C$_{1-12}$ alkylcarbonylimino, C$_{2-12}$ alkenylcarbonylimino, C$_{2-12}$ alkynylcarbonylimino, C$_{6-10}$ aryl-L$_X$-carbonylimino, C$_{3-10}$ cycloalkyl-L$_X$-carbonylimino, 5- to 10-membered heteroaryl-L$_X$-carbonylimino, 5- to 10-membered heterocycloalkyl-L$_X$-carbonylimino, C$_{1-12}$ alkylthio, C$_{2-12}$ alkenylthio, C$_{2-12}$ alkynylthio, C$_{6-10}$ aryl-L$_X$-thio, C$_{3-10}$ cycloalkyl-L$_X$-thio, 5- to 10-membered heteroaryl-L$_X$-thio, 5- to 10-membered heterocycloalkyl-L$_X$-thio, C$_{1-12}$ alkylamino, C$_{2-12}$ alkenylamino, C$_{2-12}$ alkynylamino, C$_{2-12}$ alkynylamino, C$_{6-10}$ aryl-L$_X$-amino, C$_{3-10}$ cycloalkyl-L$_X$-amino, 5- to 10-membered heteroaryl-L$_X$-amino, 5- to 10-membered heterocycloalkyl-L$_X$-amino, C$_{1-12}$ alkylsulfonyl, C$_{2-12}$ alkenylsulfonyl, C$_{2-12}$ alkynylsulfonyl, C$_{6-10}$ aryl-L$_X$-sulfonyl, C$_{3-10}$ cycloalkyl-L$_X$-sulfonyl, 5- to 10-membered heteroaryl-L$_X$-sulfonyl, 5- to 10-membered heterocycloalkyl-L$_X$-sulfonyl, C$_{1-12}$ alkylsulfonylamino, C$_{2-12}$ alkenylsulfonylamino, C$_{2-12}$ alkynylsulfonylamino, $C_{6-10}$ aryl-$L_X$-sulfonylamino, $C_{3-10}$ cycloalkyl-$L_X$-sulfonylamino, 5- to 10-membered heteroaryl-$L_X$-sulfonylamino, 5- to 10-membered heterocycloalkyl-$L_X$-sulfonylamino, $C_{1-12}$ alkylimino, $C_{2-12}$ alkenylimino, $C_{2-12}$ alkynylimino, $C_{6-10}$ aryl-$L_X$-imino, $C_{3-10}$ cycloalkyl-$L_X$-imino, 5- to 10-membered heteroaryl-$L_X$-imino, 5- to 10-membered heterocycloalkyl-$L_X$-imino, $C_{1-12}$ alkyloxyimino, $C_{2-12}$ alkenyloxyimino, $C_{2-12}$ alkynyloxyimino, $C_{6-10}$ aryl-$L_X$-oxyimino, $C_{3-10}$ cycloalkyl-$L_X$-oxyimino, 5- to 10-membered heteroaryl-$L_X$-oxyimino, 5- to 10-membered heterocycloalkyl-$L_X$-oxyimino, $C_{1-12}$ alkyloxycarbonyl, $C_{2-12}$ alkenyloxycarbonyl, $C_{2-12}$ alkynyloxycarbonyl, $C_{6-10}$ aryl-$L_X$-oxycarbonyl, $C_{3-10}$ cycloalkyl-$L_X$-oxycarbonyl, 5- to 10-membered heteroaryl-$L_X$-oxycarbonyl, 5- to 10-membered heterocycloalkyl-$L_X$-oxycarbonyl, $C_{1-12}$ alkyloxycarbonylamino, $C_{2-12}$ alkenyloxycarbonylamino, $C_{2-12}$ alkynyloxycarbonylamino, $C_{6-10}$ aryl-$L_X$-oxycarbonylamino, $C_{3-10}$ cycloalkyl-$L_X$-oxycarbonylamino, 5- to 10-membered heteroaryl-$L_X$-oxycarbonylamino, 5- to 10-membered heterocycloalkyl-$L_X$-oxycarbonylamino, $C_{1-12}$ alkylsulfanyl, $C_{2-12}$ alkenylsulfanyl, $C_{2-12}$ alkynylsulfanyl, $C_{6-10}$ aryl-$L_X$-sulfanyl, $C_{3-10}$ cycloalkyl-$L_X$-sulfanyl, 5- to 10-membered heteroaryl-$L_X$-sulfanyl, 5- to 10-membered heterocycloalkyl-$L_X$-sulfanyl, $C_{1-12}$ alkylsulfinyl, $C_{2-12}$ alkenylsulfinyl, $C_{2-12}$ alkynylsulfinyl, $C_{6-10}$ aryl-$L_X$-sulfinyl, $C_{3-10}$ cycloalkyl-$L_X$-sulfinyl, 5- to 10-membered heteroaryl-$L_X$-sulfinyl, 5- to 10-membered heterocycloalkyl-$L_X$-sulfinyl, $C_{1-12}$ alkylcarbamoyl, $C_{2-12}$ alkenylcarbamoyl, $C_{2-12}$ alkynylcarbamoyl, $C_{6-10}$ aryl-$L_X$-carbamoyl, $C_{3-10}$ cycloalkyl-$L_X$-carbamoyl, 5- to 10-membered heteroaryl-$L_X$-carbamoyl, 5- to 10-membered heterocycloalkyl-$L_X$-carbamoyl, $C_{1-12}$ alkylsulfamoyl, $C_{2-12}$ alkenylsulfamoyl, $C_{2-12}$ alkynylsulfamoyl, $C_{6-10}$ aryl-$L_X$-sulfamoyl, $C_{3-10}$ cycloalkyl-$L_X$-sulfamoyl, 5- to 10-membered heteroaryl-$L_X$-sulfamoyl, and 5- to 10-membered heterocycloalkyl-$L_X$-sulfamoyl.

Substituent group III consists of halogen, hydroxy, carboxy, amino, carbamoyl, nitro, amidinoamino, alkyl, aryl, cycloalkyl, heteroaryl, alkyloxy, alkylcarbonyl, cycloalkylcarbonyl, alkylcarbonylamino, cycloalkylcarbonylamino, alkylamino, cycloalkylalkylamino, alkyloxycarbonyl, and trialkylsilyloxy, and these groups of the substituent group are optionally substituted with one to the maximum substitutable number of the same or different substituents selected from the group consisting of halogen, hydroxy, carboxy, amino, carbamoyl, nitro, alkyl, haloalkyl, aryl, haloaryl, alkyloxy, haloalkyloxy, and alkyloxycarbonyl.

Substituent group III is preferably substituent group III', which consists of halogen, hydroxy, carboxy, amino, carbamoyl, nitro, amidinoamino, $C_{1-12}$ alkyl, $C_{6-10}$ aryl, $C_{3-10}$ cycloalkyl, 5- to 10-membered heteroaryl, $C_{1-12}$ alkyloxy, $C_{1-12}$ alkylcarbonyl, $C_{3-10}$ cycloalkylcarbonyl, $C_{1-12}$ alkylcarbonylamino, $C_{3-10}$ cycloalkylcarbonylamino, $C_{1-12}$ alkylamino, $C_{3-10}$ cycloalkyl $C_{1-6}$ alkylamino, $C_{1-12}$ alkyloxycarbonyl, and tri-$C_{1-6}$ alkylsilyloxy, wherein these groups of the substituent group are optionally substituted with one to the maximum substitutable number of the same or different substituents selected from the group consisting of halogen, hydroxy, carboxy, amino, carbamoyl, nitro, $C_{1-12}$ alkyl, $C_{1-12}$ haloalkyl, $C_{6-10}$ aryl, $C_{6-10}$ haloaryl, $C_{1-12}$ alkyloxy, $C_{1-12}$ haloalkyloxy, and $C_{1-12}$ alkyloxycarbonyl.

Substituent group IV consists of halogen, hydroxy, carboxy, amino, carbamoyl, nitro, amidino, alkyl, aryl, cycloalkyl, heteroarylheterocycloalkyl, arylalkyl, cycloalkylalkyl, alkyloxy, aryloxy, alkylcarbonyl, cycloalkylcarbonyl, alkyloxycarbonyl, and trialkylsilyloxy, and these groups of the substituent group are optionally substituted with one to the maximum substitutable number of the same or different substituents selected from the group consisting of halogen, hydroxy, carboxy, amino, carbamoyl, nitro, alkyl, haloalkyl, alkyloxy, haloalkyloxy, and alkyloxycarbonyl.

Substituent group IV is preferably substituent group IV', which consists of halogen, hydroxy, carboxy, amino, carbamoyl, nitro, amidino, $C_{1-6}$ alkyl, $C_{6-10}$ aryl, $C_{3-10}$ cycloalkyl, 5- to 10-membered heteroaryl, 5- to 10-membered heterocycloalkyl, $C_{6-10}$ aryl $C_{1-6}$ alkyl, $C_3$-10 cycloalkyl $C_{1-6}$ alkyl, $C_{1-6}$ alkyloxy, $C_{6-10}$ aryloxy, $C_{1-6}$ alkylcarbonyl, $C_{3-10}$ cycloalkylcarbonyl, $C_{1-6}$ alkyloxycarbonyl, and tri-$C_{1-6}$ alkylsilyloxy, and these groups of the substituent group are each independently and optionally substituted with one to the maximum substitutable number of the same or different substituents selected from the group consisting of halogen, hydroxy, carboxy, amino, carbamoyl, nitro, $C_{1-6}$ alkyl, $C_{1-6}$ haloalkyl, $C_{1-6}$ alkyloxy, $C_{1-6}$ haloalkyloxy, and $C_{1-6}$ alkyloxycarbonyl.

Substituent group V consists of halogen, hydroxy, carboxy, amino, formyl, carbamoyl, cyano, nitro, amidino, amidinoamino, alkyl, aryl, cycloalkyl, heteroaryl, heterocycloalkyl, alkyloxy, aryloxy, cycloalkyloxy, heteroaryloxy, heterocycloalkyloxy, alkyloxyoxy, alkylamino, arylamino, cycloalkylamino, heteroarylamino, heterocycloalkylamino, formyl, alkylcarbonyl, arylcarbonyl, cycloalkylcarbonyl, heteroarylcarbonyl, heterocycloalkylcarbonyl, alkyloxycarbonyl, aryloxycarbonyl, cycloalkyloxycarbonyl, heteroaryloxycarbonyl, heterocycloalkyloxycarbonyl, alkylcarbamoyl, arylcarbamoyl, cycloalkylcarbamoyl, heteroarylcarbamoyl, and heterocycloalkylcarbamoyl, wherein these groups of the substituent group are each independently and optionally substituted with one to the maximum substitutable number of the same or different substituents selected from the group consisting of halogen, hydroxy, carboxy, amino, formyl, carbamoyl, cyano, nitro, amidino, amidinoamino, alkyl, alkyloxy, haloalkyl, haloalkyloxy, alkylamino, formyl, alkylcarbonyl, alkyloxycarbonyl, and alkylcarbamoyl.

Substituent group V is preferably substituent group V', which consists of halogen, hydroxy, carboxy, amino, formyl, carbamoyl, cyano, nitro, amidino, amidinoamino, $C_{1-12}$ alkyl, $C_{6-10}$ aryl, $C_{3-10}$ cycloalkyl, 5- to 10-membered heteroaryl, 5- to 10-membered heterocycloalkyl, $C_{1-12}$ alkyloxy, $C_{6-10}$ aryloxy, $C_{3-10}$ cycloalkyloxy, 5- to 10-membered heteroaryloxy, 5- to 10-membered heterocycloalkyloxy, $C_{1-12}$ alkylamino, $C_{6-10}$ arylamino, $C_{3-10}$ cycloalkylamino, 5- to 10-membered heteroarylamino, 5- to 10-membered heterocycloalkylamino, formyl, $C_{1-12}$ alkylcarbonyl, $C_{6-10}$ arylcarbonyl, $C_{3-10}$ cycloalkylcarbonyl, 5- to 10-membered heteroarylcarbonyl, 5- to 10-membered heterocycloalkylcarbonyl, $C_{1-12}$ alkyloxycarbonyl, $C_{6-10}$ aryloxycarbonyl, $C_{3-10}$ cycloalkyloxycarbonyl, 5- to 10-membered heteroaryloxycarbonyl, 5- to 10-membered heterocycloalkyloxycarbonyl, $C_{1-12}$ alkylcarbamoyl, $C_{6-10}$ arylcarbamoyl, $C_{3-10}$ cycloalkylcarbamoyl, 5- to 10-membered heteroarylcarbamoyl, and 5- to 10-membered heterocycloalkylcarbamoyl, wherein these groups of the substituent group are each independently and optionally substituted with one to the maximum substitutable number of the same or different substituents selected from the group consisting of halogen, hydroxy, carboxy, amino, formyl, carbamoyl, cyano, nitro, amidino, amidinoamino, $C_{1-6}$ alkyl, $C_{1-6}$ alkyloxy, $C_{1-6}$ haloalkyl, $C_{1-6}$ haloalkyloxy, $C_{1-6}$ alkylamino, formyl, $C_{1-6}$ alkylcarbonyl, $C_{1-6}$ alkyloxycarbonyl, and $C_{1-6}$ alkylcarbamoyl.

Substituent group VI consists of halogen, hydroxy, carboxy, amino, formyl, carbamoyl, cyano, nitro, amidino, amidinoamino, alkyl, alkyloxy, haloalkyl, haloalkyloxy, alkylamino, formyl, alkylcarbonyl, alkyloxycarbonyl, and alkylcarbamoyl.

Substituent group VI is preferably substituent group VI', which consists of halogen, hydroxy, carboxy, amino, formyl, carbamoyl, cyano, nitro, amidino, amidinoamino, $C_{1-6}$ alkyl, $C_{1-6}$ alkyloxy, $C_{1-6}$ haloalkyl, $C_{1-6}$ haloalkyloxy, $C_{1-6}$ alkylamino, formyl, $C_{1-6}$ alkylcarbonyl, $C_{1-6}$ alkyloxycarbonyl, and $C_{1-6}$ alkylcarbamoyl.

As used herein, examples of substituents used when "optionally substituted" include substituent group α and substituent group β. Substituent group α can be substituent group α1, substituent group α2, or substituent group α3. Substituent group β can be substituent group β1, substituent group 32, or substituent group 3. Substituents used when "optionally substituted" can be selected from substituent group α1, and substitution can be performed with 1 to 5 of the same or different substituents. While the types of atoms within a substituent associated with attachment are not particularly limited by the type of substituent, if the atom to which a substituent attaches is an oxygen atom, a nitrogen atom, or a sulfur atom, the substituent is limited to those with an attaching atom that is a carbon atom from the following substituents.

Substituent group α1 includes
1) halogen atom
2) hydroxyl group
3) carboxyl group
4) cyano group
5) $C_{1-6}$ alkyl
6) $C_{2-6}$ alkenyl
7) $C_{2-6}$ alkynyl
8) $C_{1-6}$ alkoxy
9) $C_{1-6}$ alkylthio
10) $C_{1-6}$ alkylcarbonyl
11) $C_{1-6}$ alkylsulfonyl
(however, each substituent from 5) to 11) is optionally substituted with 1 to 5 of the same or different substituents selected from substituent group (1)
12) $C_{3-10}$ alicyclic group
13) $C_{3-10}$ alicyclic oxy
14) $C_{6-10}$ aryloxy
15) 5- to 6-membered heteroaryloxy
16) 4- to 10-membered non-aryl heterocyclyloxy
17) $C_{3-10}$ alicyclic thio
18) $C_{6-10}$ arylthio
19) 5- to 6-membered heteroarylthio
20) 4- to 10-membered non-aryl heterocyclylthio
21) $C_{6-10}$ aryl
22) 5- to 6-membered heteroaryl
23) 4- to 10-membered non-aryl heterocycle
24) $C_{3-10}$ alicyclic carbonyl
25) $C_{6-10}$ arylcarbonyl
26) 5- to 6-membered heteroarylcarbonyl
27) 4- to 10-membered non-aryl heterocyclylcarbonyl
28) $C_{3-10}$ alicyclic sulfonyl
29) $C_{6-10}$ aryl sulfonyl
30) 5- to 6-membered heteroarylsulfonyl
31) 4- to 10-membered non-aryl heterocyclylsulfonyl
(however, each substituent from 12) to 31) is optionally substituted with 1 to 5 substituents in substituent group β1 or 5) $C_{1-6}$ alkyl)
32) —$NR^{10a}R^{11a}$
33) —$SO_2$—$NR^{10b}R^{11b}$
34) —$NR^{10c}$—C(=O)$R^{11c}$
35) —$NR^{10d}$—C(=O)O$R^{11d}$
36) —$NR^{12a}$—C(=O)$NR^{10e}R^{11e}$
37) —$NR^{10i}$—$SO_2$—$R^{11i}$
38) —$NR^{12v}$—$SO_2$—$NR^{10j}R^{11j}$
39) —C(=O)O$R^{10k}$
40) —C(=O)$NR^{10l}R^{11k}$
41) —C(=O)$NR^{10m}OR^{11l}$
42) —C(=O)$NR^{12d}$—$NR^{10n}R^{11m}$
43) —C(=$NR^{13a}$)$R^{10a}$
44) —C(=$NR^{13c}$)$NR^{10t}R^{11q}$
45) —C(=$NR^{13d}$)$NR^{12f}$—$NR^{10u}R^{11r}$
46) —$NR^{17c}$—C(=$NR^{13k}$)$R^{17d}$
47) —$NR^{12g}$—C(=$NR^{13e}$)—$NR^{10v}R^{11s}$
48) —$NR^{14}$—C(=$NR^{13f}$)—$NR^{12h}$—$NR^{10w}R^{11t}$
49) —OC(=O)$R_{10x}$
50) —OC(=O)O$R^{10y}$
51) —OC(=O)$NR^{10z1}R^{11u}$
52) —$NR^{12i}$—$NR^{10z2}R^{11v}$
53) —$NR^{10z3}OR^{11w}$, and
54) protecting group, and substituent group β1 is a group consisting of
1) halogen atom,
2) hydroxyl group,
3) carboxyl group,
4) cyano group,
5) $C_{3-10}$ alicyclic group,
6) $C_{1-6}$ alkoxy,
7) $C_{3-10}$ alicyclic oxy,
8) $C_{1-6}$ alkylthio,
9) 5- to 6-membered heteroarylthio,
10) $C_{6-10}$ aryl,
11) 5- to 6-membered heteroaryl,
12) 4- to 10-membered non-aryl heterocycle,
13) $C_{1-6}$ alkylcarbonyl,
14) $C_{3-10}$ alicyclic carbonyl,
15) $C_{6-10}$ arylcarbonyl,
16) 5- to 6-membered heteroarylcarbonyl,
17) 4- to 10-membered non-aryl heterocyclylcarbonyl,
18) —$NR^{15a}R^{16a}$,
19) —$SO_2$—$NR^{15b}R^{16b}$,
20) —$NR^{15c}$—C(=O)$R^{16c}$
21) —$NR^{17a}$—C(=O)$NR^{15d}R^{16d}$
22) —C(=O)$NR^{15e}R^{16e}$,
23) —C(=$NR^{13g}$)$R^{15f}$,
24) —C(=$NR^{13h}$)$NR^{15g}R^{16f}$
25) —$NR^{16g}$—C(=$NR^{13i}$)$R^{15h}$
26) —$NR^{17b}$—C(=$NR^{13j}$)—$NR^{15i}R^{16h}$, and
27) protecting group
(however, each substituent from 5) to 17) in substituent group β1 is optionally substituted with 1 to 5 substituents selected from the group consisting of a halogen atom, hydroxyl group, cyano group, carboxyl group, and —$NR^{18a}R^{18b}$), wherein $R^{13a}$, $R^{13c}$, $R^{13d}$, $R^{13e}$, $R^{13f}$, $R^{13g}$, $R^{13h}$, $R^{13i}$, $R^{13j}$, and $R^{13k}$ are each independently the same or different hydrogen atom, hydroxyl group, $C_{1-6}$ alkyl, $C_{1-6}$ alkoxy, or $C_{1-6}$ alkoxycarbonyl, $R^{10a}$, $R^{10b}$, $R^{10c}$, $R^{10d}$, $R^{10e}$, $R^{10i}$, $R^{10j}$, $R^{10k}$, $R^{10l}$, $R^{10m}$, $R^{10n}$, $R^{10s}$, $R^{10t}$, $R^{10u}$, $R^{10v}$, $R^{10w}$, $R^{10x}$, $R^{10y}$, $R^{10z1}$, $R^{10z2}$, $R^{10z3}$, $R^{11a}$, $R^{11b}$, $R^{11c}$, $R^{11d}$, $R^{11e}$, $R^{11i}$, $R^{11j}$, $R^{11k}$, $R^{11l}$, $R^{11m}$, $R^{11q}$, $R^{11r}$, $R^{11s}$, $R^{11t}$, $R^{11u}$, $R^{11v}$, $R^{11w}$, $R^{12a}$, $R^{12c}$, $R^{12d}$, $R^{12f}$, $R^{12g}$, $R^{12h}$, $R^{12i}$, $R^{14}$, $R^{15a}$, $R^{15b}$, $R^{15c}$, $R^{15d}$, $R^{15e}$, $R^{15f}$, $R^{15g}$, $R^{15h}$, $R^{15i}$, $R^{16a}$, $R^{16b}$, $R^{16c}$, $R^{16d}$, $R^{16e}$, $R^{16f}$, $R^{16g}$, $R^{16h}$, $R^{17a}$, $R^{17b}$, $R^{17c}$, and $R^{17d}$ are each independently the same or different hydrogen atom, $C_{1-6}$ alkyl (the $C_{1-6}$ alkyl is optionally substituted with 1 to 3 of the same or different substituents selected from a hydroxyl group, cyano group, $C_{1-6}$ alkoxy, and —$NR^{18a}R^{18b}$), or $C_{1-6}$ alkoxycarbonyl, and $R^{18a}$ and $R^{18b}$ are each independently the same or different hydrogen atom or $C_{1-6}$ alkyl.

In an exemplary embodiment, hydrogen of any hydroxyl group in substituent groups α1 and β1 is optionally substituted with a protecting group.

Examples of preferred substituents as the substituent used when "optionally substituted" herein include the following.

Substituent group α2 preferably includes
1) halogen atom
2) hydroxyl group
3) carboxyl group
4) cyano group
5) $C_{1-6}$ alkyl
6) $C_{1-6}$ alkoxy
7) $C_{1-6}$ alkylthio
8) $C_{1-6}$ alkylcarbonyl
(however, each substituent from 5) to 8) is optionally substituted with 1 to 5 same or different substituents selected from substituent group (2)
9) $C_{3-10}$ alicyclic group
10) $C_{3-10}$ alicyclic oxy
11) $C_{6-10}$ aryloxy
12) 5- to 6-membered heteroaryloxy
13) 4- to 10-membered non-aryl heterocyclyloxy
14) $C_{3-10}$ alicyclic thio
15) $C_{6-10}$ arylthio
16) 5- to 6-membered heteroarylthio
17) 4- to 10-membered non-aryl heterocyclylthio
18) $C_{6-10}$ aryl
19) 5- to 6-membered heteroaryl
20) 4- to 10-membered non-aryl heterocycle
21) $C_{3-10}$ alicyclic carbonyl
22) $C_{6-10}$ arylcarbonyl
23) 5- to 6-membered heteroarylcarbonyl
24) 4- to 10-membered non-aryl heterocyclylcarbonyl
(however, each substituent from 9) to 24) is optionally substituted with 1 to 5 substituents in substituent group β2 or 1) $C_{1-6}$ alkyl)
25) —$NR^{10a}R^{11a}$
26) —$SO_2$—$NR^{10b}R^{11b}$
27) —$NR^{10c}$—$C(=O)R^{11c}$
28) —$NR^{12a}$—$C(=O)NR^{10d}R^{11d}$
29) —$NR^{10e}$—$SO_2$—$R^{11e}$
30) —$NR^{12b}$—$SO_2$—$NR^{10f}R^{11f}$
31) —$C(=O)NR^{10g}R^{11g}$
32) —$C(=NR^{13a})R^{10h}$
33) —$C(=NR^{13b})NR^{10i}R^{11h}$
34) —$NR^{11f2}$—$C(=NR^{13c})R^{10g2}$, and
35) —$NR^{12c}$—$C(=NR^{13f})$—$NR^{10j}R^{11i}$, and
substituent group β2 is preferably a group consisting of
1) halogen atom
2) hydroxyl group
3) cyano group
4) $C_{3-10}$ alicyclic group
5) $C_{1-6}$ alkoxy
6) $C_{1-6}$ alkylthio
7) 5- to 6-membered heteroarylthio
8) 5- to 6-membered heteroaryl
9) 4- to 10-membered non-aryl heterocycle
10) $C_{1-6}$ alkylcarbonyl
11) $C_{3-10}$ alicyclic carbonyl
12) $C_{6-10}$ arylcarbonyl
13) 5- to 6-membered heteroarylcarbonyl
14) 4- to 10-membered non-aryl heterocyclylcarbonyl
15) —$NR^{15a}R^{16a}$
16) —$NR^{15b}$—$C(=O)R^{16b}$
17) —$NR^{17a}$—$C(=O)NR^{15c}R^{16c}$
18) —$C(=O)NR^{15d}R^{16a}$
19) —$C(=NR^{13e})R^{15e}$
20) —$C(=NR^{13f})NR^{15f}R^{16e}$
21) —$NR^{16f}$—$C(=NR^{13g})R^{15g}$
22) —$NR^{17b}$—$C(=NR^{13h})$—$NR^{15h}R^{16g}$
(however, each substituent from 4) to 14) in substituent group 32 is optionally substituted with 1 to 5 substituents selected from the group consisting of a halogen atom, hydroxyl group, cyano group, carboxyl group, and —$NR^{18a}R^{18b}$, $R^{13a}$, $R^{13b}$, $R^{13c}$, $R^{13d}$, $R^{13e}$, $R^{13f}$, $R^{13g}$, and $R^{13h}$ are each independently the same or different hydrogen atom, hydroxyl group, $C_{1-6}$ alkyl, $C_{1-6}$ alkoxy, or $C_{1-6}$ alkoxycarbonyl, $R^{10a}$, $R^{10b}$, $R^{10c}$, $R^{10d}$, $R^{10e}$, $R^{10f}$, $R^{10g}$, $R^{10g2}$, $R^{10h}$, $R^{10i}$, $R^{10j}$, $R^{11a}$, $R^{11b}$, $R^{11c}$, $R^{11d}$, $R^{11e}$, $R^{11f}$, $R^{11f2}$, $R^{11g}$, $R^{11h}$, $R^{11i}$, $R^{12a}$, $R^{12b}$, $R^{12c}$, $R^{15a}$, $R^{15b}$, $R^{15c}$, $R^{15d}$, $R^{15e}$, $R^{15f}$, $R^{15g}$, $R^{15h}$, $R^{16a}$, $R^{16b}$, $R^{16c}$, $R^{16d}$, $R^{16e}$, $R^{16f}$, $R^{16g}$, $R^{17a}$, and $R^{17b}$ are each independently the same or different hydrogen atom, $C_{1-6}$ alkyl (the $C_{1-6}$ alkyl is optionally substituted with 1 to 3 same or different substituents selected from a hydroxyl group, cyano group, $C_{1-6}$ alkoxy, and —$NR^{18a}R^{18b}$), or $C_{1-6}$ alkoxycarbonyl, and $R^{18a}$ and $R^{18b}$ are each independently the same or different hydrogen atom or $C_{1-6}$ alkyl.

In an exemplary embodiment, hydrogen of any hydroxy group in substituent groups α2 and β2 is optionally substituted with a protecting group.

Examples of more preferred substituents used when "optionally substituted" herein include the following substituents.

Substituent group α3 more preferably includes
1) halogen atom
2) hydroxyl group
3) cyano group
4) $C_{1-6}$ alkyl
5) $C_{1-6}$ alkoxy
6) $C_{1-6}$ alkylthio
7) $C_{1-6}$ alkylcarbonyl
(however, each substituent from 4) to 7) is optionally substituted with 1 to 5 same or different substituents selected from substituent group (3)
8) $C_{3-10}$ alicyclic group
9) 5- to 6-membered heteroaryloxy
10) 4- to 10-membered non-aryl heterocyclyloxy
11) 5- to 6-membered heteroarylthio
12) 4- to 10-membered non-aryl heterocyclylthio
13) $C_{6-10}$ aryl
14) 5- to 6-membered heteroaryl
15) 4- to 10-membered non-aryl heterocycle
(however, each substituent from 8) to 15) is optionally substituted with 1 to 5 substituents in substituent group β3 or 1) $C_{1-6}$ alkyl)
16) —$NR^{10a}R^{11a}$
17) —$NR^{11b}$—$C(=O)R^{10b}$
18) —$NR^{12a}$—$C(=O)NR^{10c}R^{11c}$
19) —$C(=O)NR^{10d}R^{11d}$
20) —$C(=NR^{13a})R^{10e}$
21) —$C(=NR^{13b})NR^{10f}R^{11e}$
22) —$NR^{11f}$—$C(=NR^{13c})R^{10g}$, and
23) —$NR^{12b}$—$C(=NR^{13d})$—$NR^{10h}R^{11g}$, and
substituent group β3 is more preferably 1) halogen atom,
2) hydroxyl group,
3) cyano group,
4) —NR$^{15a}$R$^{16a}$,
5) —NR$^{15b}$—C(=O)R$^{16b}$,
6) —NR$^{17a}$—C(=O)NR$^{15c}$R$^{16c}$,
7) —C(=O)NR$^{15d}$R$^{16d}$,
8) —C(=NR$^{13e}$)R$^{15e}$,
9) —C(=NR$^{13f}$)NR$^{15f}$R$^{16e}$,
10) —NR$^{16f}$—C(=NR$^{13g}$)R$^{15g}$, and
11) —NR$^{17b}$—C(=NR$^{13h}$)—NR$^{15h}$R$^{16g}$, wherein
R$^{13a}$, R$^{13b}$, R$^{13c}$, R$^{13d}$, R$^{13e}$, R$^{13f}$, R$^{13g}$, and R$^{13h}$ are each independently the same or different hydrogen atom, hydroxyl group, $C_{1-6}$ alkyl, $C_{1-6}$ alkoxy, or $C_{1-6}$ alkoxycarbonyl,
R$^{10a}$, R$^{10b}$, R$^{10c}$, R$^{10d}$, R$^{10e}$, R$^{10f}$, R$^{10g}$, R$^{10h}$, R$^{11a}$, R$^{11b}$, R$^{11c}$, R$^{11d}$, R$^{11e}$, R$^{11f}$, R$^{11g}$, R$^{12a}$, R$^{12b}$, R$^{15a}$, R$^{15b}$, R$^{15c}$, R$^{15d}$, R$^{15e}$, R$^{15f}$, R$^{15g}$, R$^{15h}$, R$^{16a}$, R$^{16b}$, R$^{16c}$, R$^{16d}$, R$^{16e}$, R$^{16f}$, R$^{16g}$, R$^{17a}$, and R$^{17b}$ are each independently the same or different hydrogen atom, $C_{1-6}$ alkyl (the $C_{1-6}$ alkyl is optionally substituted with 1 to 3 same or different substituents selected from hydroxyl group, cyano group, $C_{1-6}$ alkoxy, and —NR$^{18a}$R$^{18b}$), or $C_{1-6}$ alkoxycarbonyl, and
R$^{18a}$ and R$^{18b}$ are each independently the same or different hydrogen atom or $C_{1-6}$ alkyl.

In an exemplary embodiment, hydrogen of any hydroxyl group in substituent groups α3 and β3 is optionally substituted with a protecting group.

In an exemplary embodiment, a hydroxyl group in the aforementioned substituent group (e.g., α (α1 or the like) β (β1 or the like), or I to VI) is also optionally substituted with a protecting group. In an exemplary embodiment, an amino group in substituent groups I to VI is also optionally protected with a nitrogen protecting group.

As used herein, "$C_{1-6}$" means that the number of carbon atoms is 1 to 6. The same applies to other numbers. For example, "$C_{1-4}$" means that the number of carbon atoms is 1 to 4, and "$C_{1-3}$" means that the number of carbon atoms is 1 to 3. A description with a limitation in the number of carbons herein is only a preferred numerical range. It is intended so that groups with a substituent with a number of carbons other than the number of carbons specified in the present disclosure are also within the scope of the present disclosure.

As used herein, "hydrocarbon group" is also referred to as a hydrocarbyl group, referring to a group generated by removing at least one hydrogen from "hydrocarbon" comprising at least one carbon and at least one hydrogen.

As used herein, "functional group" refers to any group conferring some type of functionality, encompassing a carboxyl group, nitrile group, carbonyl group, hydroxyl group, amino group, imino group, nitro group, halogen group, as well as alkyl group, and more broadly acid anhydrides and groups formed by a bond such as an ester bond, amide bond, or ether bond.

As used herein, "heteroatom" refers to atoms other than carbon atoms and hydrogen atoms such as oxygen atoms, nitrogen atoms, and sulfur atoms. A group comprising a heteroatom is also known as a hetero . . . group (e.g., heteroaryl group (means that an aryl group comprises at least a heteroatom) or heterocyclic group (means that a cyclic group (carbon ring group) comprises at least one heteroatom)) or the like.

As used herein, "halogen atom" is an atom belonging to the halogen group, referring to a fluorine atom, chlorine atom, bromine atom, iodine atom, or the like, and is preferably a fluorine atom or chlorine atom. A "halogen atom" is also referred to as "halogen" or "halo".

As used herein, "hydroxyl group" is a monovalent group of —OH. This group is also referred to as a "hydroxy group" or "hydroxy".

As used herein, "carboxyl group" is a monovalent group of —COOH. This group is also referred to as a "carboxy group", "carboxy", or "carboxyl".

As used herein, "cyano group" is a monovalent group of —CN.

As used herein, "amino" is a monovalent group of —NH$_2$. This group is also referred to as an "amino group".

As used herein, "alkyl" refers to a linear or branched saturated aliphatic hydrocarbon group. "$C_{1-12}$ alkyl" is an alkyl group with 1 to 12 carbon atoms. Examples thereof include, but are not limited to, $C_{1-6}$ alkyl, heptyl, iso-heptyl, octyl, iso-octyl, nonyl, iso-nonyl, decyl, iso-decyl, undecyl, isoundecyl, dodecyl, iso-dodecy, and the like. "$C_{1-12}$ alkyl" is an alkyl group with 1 to 12 carbon atoms. "$C_{1-6}$ alkyl" is an alkyl group with 1 to 6 carbon atoms, which is preferably "$C_{1-4}$ alkyl", more preferably "$C_{1-3}$ alkyl", and still more preferably "$C_{1-2}$ alkyl". Specific examples of "$C_1$-4 alkyl" include methyl, ethyl, n-propyl, isopropyl, n-butyl, isobutyl, tert-butyl, sec-butyl, and the like. Specific examples of "$C_{1-6}$ alkyl" include, but are not limited to, $C_1$-4 alkyl, n-pentyl, isopentyl, neopentyl, tert-pentyl, 1,2-dimethylpropyl, n-hexyl, and the like. Specific examples of "$C_{1-12}$ alkyl" include, but are not limited to, $C_{1-6}$ alkyl, n-heptyl, isoheptyl, n-octyl, isooctyl, n-nonyl, n-decanyl, n-undecyl, n-dodecyl, and the like.

As used herein, "alkenyl" refers to a linear or branched unsaturated aliphatic hydrocarbon group comprising at least one carbon-carbon double bond. "$C_{2-12}$ alkenyl" is an alkenyl group with 2 to 12 carbon atoms. Examples thereof include, but are not limited to, heptenyl, isoheptenyl, octenyl, isooctenyl, nonenyl, isononenyl, decenyl, isodecenyl, undecenyl, isoundecenyl, dodecenyl, isododecenyl, and the like. "$C_{2-6}$ alkenyl" is an alkenyl group with 2 to 6 carbon atoms. Preferred examples thereof include "$C_{2-4}$ alkenyl". Specific examples of "$C_{2-6}$ alkenyl" include, but are not limited to, vinyl, 1-propenyl, 2-propenyl, 1-butenyl, 2-butenyl, 3-butenyl, 2-methyl-1-propenyl, 2-methyl-2-propenyl, and the like.

As used herein, "alkynyl" refers to a linear or branched unsaturated aliphatic hydrocarbon group comprising at least one carbon-carbon triple bond. "$C_{2-12}$ alkynyl" is an alkynyl group with 2 to 12 carbon atoms. Examples thereof include, but are not limited to, heptynyl, isoheptynyl, octynyl, isooctynyl, nonynyl, isononynyl, decynyl, isodecynyl, undecynyl, isoundecynyl, dodecynyl, isododecynyl, and the like. "$C_{2-6}$ alkynyl" is an alkynyl group with 2 to 6 carbon atoms. Preferred examples thereof include "$C_{2-4}$ alkynyl". Specific examples of "$C_{2-6}$ alkynyl" include, but are not limited to, ethynyl, 1-propynyl, 2-propynyl, 1-butynyl, 1-methyl-2-propynyl, 3-butynyl, 1-pentynyl, 1-hexynyl, and the like.

As used herein, "aryl" refers to a monovalent group of a monocyclic or bicyclic aromatic hydrocarbon ring. "$C_{6-10}$ aryl" refers to an aryl group with 6 to 10 carbon atoms. Examples of "aryl" include, but are not limited to, $C_6$ aryl, $C_{10}$ aryl, and the like. Specific examples of $C_6$ aryl include, but are not limited to, phenyl and the like. Specific examples of $C_{10}$ aryl include, but are not limited to, 1-naphthyl, 2-naphthyl, and the like.

An aryl group as a substituent or a portion thereof may be fused to an alicyclic group. For example, a phenyl group may be fused to a cyclohexane ring to form a 1,2,3,4-tetrahydronaphthalenyl group. In such a case, one of the possible carbon atoms on a benzene ring attaches to the backbone, or to a group near the backbone, or to its atom. An aryl group encompasses 5,6,7,8-tetrahydronaphthalen-1-yl and 5,6,7,8-tetrahydronaphthalen-2-yl.

As used herein, "arylalkyl" refers to alkyl substituted with at least one aryl. "$C_{6-10}$ aryl $C_{1-6}$ alkyl" refers to $C_{1-6}$ alkyl substituted with at least one $C_{6-10}$ aryl. Specific examples of $C_{6-10}$ aryl $C_{1-6}$ alkyl include, but are not limited to, benzyl (i.e., phenyl-$CH_2$—), phenethyl (i.e., phenyl-$CH_2CH_2$—), 1-phenylethyl, naphthalen-1-ylmethyl, naphthalen-2-ylmethyl, 2-(naphthalen-1-yl)ethyl, 2-(naphthalen-2-yl)ethyl, 1-(naphthalen-1-yl)ethyl, 1-(naphthalen-2-yl)ethyl, and the like.

As used herein, "(optionally substituted amino)-arylalkyl" refers to arylalkyl substituted with an optionally substituted amino group, wherein the alkyl group, the aryl group, or both is substituted with an amino group. An amino group of an arylalkyl group may be unsubstituted, or substituted with 1, 2, or 3 substituents, such as optionally substituted alkyl (e.g., unsubstituted $C_{1-6}$ alkyl, $C_3$-6 cycloalkyl-$C_{1-6}$ alkyl, $C_3$-6 cycloalkylcarbonyl, or the like). Examples of (optionally substituted amino)-$C_{6-10}$ aryl $C_{1-6}$ alkyl include, but are not limited to, (di(alkyl)amino)benzyl, ((cycloalkylalkyl)amino)benzyl, ((cycloalkylcarbonyl)amino)benzyl, ((carbamoylalkyl)carbonylamino)benzyl, ((carboxyalkyl)carbonyl)aminobenzyl, (di(alkyl)amino) naphthalenylmethyl, ((cycloalkylalkyl)amino) naphthalenylmethyl, ((cycloalkylcarbonyl)amino) naphthalenylmethyl, ((carbamoylalkyl)carbonylamino) naphthalenylmethyl, ((carboxyalkyl)carbonyl)aminonaphthalenylmethyl, and the like.

As used herein, the aryl moiety of "arylthio" is defined the same as the aforementioned aryl. Preferred examples of "$C_{6-10}$ arylthio" include "$C_6$ or $C_{10}$ arylthio". Specific examples of "$C_{6-10}$ aryloxy" include, but are not limited to, phenylthio, 1-naphthylthio, 2-naphthylthio, and the like.

As used herein, "aryl sulfonyl" refers to sulfonyl substituted with the aforementioned "aryl". "$C_{6-10}$ aryl sulfonyl" is preferably "$C_6$ or $C_{10}$ aryl sulfonyl". Specific examples of "$C_{6-10}$ aryl sulfonyl" include, but are not limited to, phenylsulfonyl, 1-naphthylsulfonyl, 2-naphthylsulfonyl, and the like.

As used herein, "heteroaryl" refers to a monovalent group of a monocyclic or bicyclic aromatic heterocycle comprising 1 to 4 same or different heteroatoms selected from the group consisting of an oxygen atom, nitrogen atom, and sulfur atom.

As used herein, "5- to 6-membered heteroaryl" refers to a monovalent group of a monocyclic aromatic heterocycle consisting 5 to 6 atoms, comprising 1 to 4 same or different heteroatoms selected from the group consisting of an oxygen atom, nitrogen atom, and sulfur atom. Specific examples of "5- to 6-membered heteroaryl" include, but are not limited to, pyrrolyl, furyl, thienyl, pyrazolyl, imidazolyl, oxazolyl, isoxazolyl, oxadiazolyl, thiazolyl, isothiazolyl, thiadiazolyl, tetrazolyl, pyridyl, furyl, pyridazinyl, pyrimidinyl, pyrazinyl, and the like.

As used herein, "5- to 10-membered heteroaryl" refers to a monovalent group of a monocyclic or bicyclic aromatic heterocycle consisting of 5 to 10 atoms, comprising 1 to 4 same or different heteroatoms selected from the group consisting of an oxygen atom, nitrogen atom, and sulfur atom. Specific examples of "5- to 10-membered heteroaryl" include, but are not limited to, 5- to 6-membered heteroaryl, quinolyl, isoquinolyl, naphthyridinyl, quinoxalinyl, cinnolinyl, quinazolinyl, phthalazinyl, imidazopyridyl, imidazothiazolyl, imidazooxazolyl, benzothiazolyl, benzoxazolyl, benzoimidazolyl, indolyl, isoindolyl, indazolyl, pyrrolopyridyl, thienopyridyl, furopyridyl, benzothiadiazolyl, benzoxadiazolyl, pyridopyrimidinyl, benzofuryl, benzothienyl, benzo[1,3]dioxole, thienofuryl, chromenyl, chromanyl, coumarinyl, quinolonyl, and the like.

As used herein, "heteroarylalkyl" refers to alkyl substituted with at least one heteroaryl. "5- to 10-membered heteroaryl $C_{1-6}$ alkyl" refers to $C_{1-6}$ alkyl substituted with at least one 5- to 10-membered heteroaryl. Specific examples of 5- to 10-membered heteroaryl $C_{1-6}$ alkyl include, but are not limited to, pyridin-2-ylmethyl, pyridin-4-ylmethyl, 2-(quinolin-8-yl)ethyl, 2-(quinolin-5-yl)ethyl, 2-(quinoxalin-5-yl)ethyl, 1H-indol-3-ylmethyl, 2-(1H-indol-3-yl)ethyl, and the like.

As used herein, "alicyclic group" refers to a monovalent group of a monocyclic, bicyclic, or tricyclic non-aromatic hydrocarbon ring, including those that have a partially unsaturated bond, those that have a partially crosslinked structure, those that are partially a spiro, and those having 1, 2, or more carbonyl structures. An "alicyclic group" encompasses cycloalkyl, cycloalkenyl, and cycloalkynyl. "$C_{3-20}$ alicyclic group" is preferably a "$C_{3-10}$ alicyclic group", more preferably a "$C_{3-6}$ alicyclic group". Specific examples of "$C_{3-20}$ alicyclic group" include, but are not limited to, cyclopropyl, cyclobutyl, cyclopentyl, cyclohexyl, cycloheptyl, cyclooctyl, cyclohexadinyl, cycloheptadinyl, cyclooctadinyl, adamantyl, norbornyl, and the like.

An alicyclic group can be a fused ring between a non-aryl ring and an aryl and/or heteroaryl ring. For example, cycloalkyl fused with $C_{6-10}$ aryl or 5- to 6-membered heteroaryl is encompassed by an alicyclic group. Examples of fused alicyclic groups include a monovalent group with one hydrogen atom removed from 1,2,3,4-tetrahydronaphthalene, indane, 1,2,3,4-tetrahydroanthracene, and 5,6,7,8-tetrahydroquinoline. Specific examples thereof include 1,2,3,4-tetrahydronaphthalen-1-yl, 1,2,3,4-tetrahydronaphthalen-2-yl, indan-1-yl, indan-2-yl, 5,6,7,8-tetrahydroquinolin-5-yl, 5,6,7,8-tetrahydroquinolin-6-yl, and the like. A fused alicyclic group attaches from any one of the possible cyclic structure atoms on a non-aryl ring to the backbone.

As used herein, "$C_{3-10}$ alicyclic group" refers to a substituent with "$C_{3-10}$ alicyclic group" that is a monovalent group among the aforementioned "$C_{3-20}$ alicyclic group".

As used herein, "alicyclic oxy" refers to an (alicyclic group) —O— group, and the alicyclic moiety is defined the same as an alicyclic group. "$C_{3-6}$ alicyclic oxy" refers to a ($C_{3-6}$ alicyclic group) —O— group, and the $C_{3-6}$ alicyclic moiety is defined the same as a $C_{3-6}$ alicyclic group. "$C_{3-6}$ alicyclic oxy" is preferably "$C_3$-s alicyclic oxy". Specific examples of "$C_{3-6}$ alicyclic oxy" include, but are not limited to, cyclopropyloxy, cyclobutyloxy, cyclopentyloxy, cyclohexyloxy, and the like.

As used herein, "alicyclic carbonyl" refers to carbonyl substituted with the "alicyclic group" described above. "$C_{3-10}$ alicyclic carbonyl" is preferably "$C_{3-6}$ alicyclic carbonyl". Specific examples of "$C_{3-10}$ alicyclic carbonyl" include, but are not limited to, cyclopropylcarbonyl, cyclobutylcarbonyl, cyclopentylcarbonyl, cyclohexylcarbonyl, and the like.

As used herein, "alicyclic thio" refers to an (alicyclic group) —S— group, and the alicyclic moiety is defined the same as above. "$C_{3-10}$ alicyclic thio" is preferably "$C_{3-6}$ alicyclic thio". Specific examples of "$C_{3-6}$ alicyclic thio" include, but are not limited to, cyclopropylthio, cyclobutylthio, cyclopentylthio, cyclohexylthio, and the like.

As used herein, "alicyclic sulfonyl" refers to a sulfonyl group substituted with the "alicyclic group" described above. "$C_{3-10}$ alicyclic sulfonyl" is preferably "$C_{3-6}$ alicyclic sulfonyl". Specific examples of "$C_{3-10}$ alicyclic sulfonyl" include, but are not limited to, cyclopropylsulfonyl, cyclobutylsulfonyl, cyclopentylsulfonyl, cyclohexylsulfonyl, and the like.

As used herein, "cycloalkyl" refers to a non-aromatic saturated hydrocarbon ring group, including those that have a partially crosslinked structure, those that are partially spiro, those having 1, 2, or more carbonyl structures. "$C_{3-20}$ cycloalkyl" refers to monocyclic or bicyclic cycloalkyl with 3 to 20 carbon atoms. "$C_{3-6}$ cycloalkyl" refers to monocyclic cycloalkyl with 3 to 6 carbon atoms. Specific examples of $C_{3-6}$ cycloalkyl include, but are not limited to, cyclopropyl, cyclobutyl, cyclopentyl, and cyclohexyl. "$C_{3-10}$ cycloalkyl" refers to a monocyclic or bicyclic cycloalkyl with 3 to 10 carbon atoms. Specific examples of $C_{3-10}$ cycloalkyl include, but are not limited to, $C_{3-6}$ cycloalkyl, cycloheptyl, cyclooctyl, cyclononyl, cyclodecyl, bicyclo[4.1.0]heptyl, bicyclo[3.3.0]octyl, bicyclo[4.2.0]octyl, bicyclo[4.3.0]nonyl, decahydronaphthyl, and the like.

A cycloalkyl group can be fused to aryl and/or heteroaryl ring as a substituent or a portion thereof. For example, a cyclohexyl group can be fused to a benzene ring to form a 1,2,3,4-tetrahydronaphthalenyl group. In such a case, one of the possible carbon atoms on the cyclohexane ring attaches to the backbone, to a group near the backbone, or to its atom. A cycloalkyl group encompasses 1,2,3,4-tetrahydronaphthalen-1-yl, 1,2,3,4-tetrahydronaphthalen-2-yl, indan-1-yl, indan-2-yl, 5,6,7,8-tetrahydroquinolin-5-yl, and 5,6,7,8-tetrahydroquinolin-6-yl.

As used herein, "cycloalkylalkyl" refers to alkyl substituted with at least one cycloalkyl. "$C_{3-10}$ cycloalkyl $C_{1-6}$ alkyl" refers to $C_{1-6}$ alkyl substituted with at least one $C_{3-10}$ cycloalkyl, and "$C_{3-6}$ cycloalkyl $C_{1-6}$ alkyl" refers to $C_{1-6}$ alkyl substituted with at least one $C_{3-6}$ cycloalkyl. Specific examples of $C_{3-6}$ cycloalkyl $C_{1-6}$ alkyl include, but are not limited to, cyclopropylmethyl, cyclobutylmethyl, cyclopentylmethyl, cyclohexylmethyl, 2-cyclopropylethyl, 2-cyclobutylethyl, 2-cyclopentylethyl, 2-cyclohexylethyl, 3-cyclopropylpropyl, 3-cyclobutylpropyl, 3-cyclopentylpropyl, 3-cyclohexylpropyl, and the like. Specific examples of $C_{3-10}$ cycloalkyl $C_{1-6}$ alkyl include, but are not limited to, $C_{3-6}$ cycloalkylmethyl, $C_{3-6}$ cycloalkylethyl, cycloheptylmethyl, cycloheptylethyl, cyclooctylmethyl, cyclooctylethyl, cyclononylmethyl, cyclononylethyl, cyclodecylmethyl, cyclodecylethyl, and the like.

As used herein, "heterocycloalkyl" refers to a non-aromatic saturated or partially unsaturated heterocycle comprised of 3 or more atoms, comprising 1, 2, or more same or different heteroatoms selected from the group consisting of an oxygen atom, nitrogen atom, and sulfur atom, including those that have a partially crosslinked structure and those that are partially spiro. "Heterocycloalkyl" encompasses "non-aryl heterocycle". Heterocycloalkyl can have a structure where a non-aromatic heterocycle is fused to an aryl ring and/or heteroaryl ring.

As used herein, "non-aryl heterocycle" refers to a monocyclic or bicyclic non-aromatic heterocycle comprised of 3 or more atoms, comprising 1, 2, or more same or different heteroatoms selected from the group consisting of an oxygen atom, nitrogen atom, and sulfur atom, including saturated non-aryl heterocycles, those that have a partially unsaturated attachment, those that have a partially crosslinked structure, and those that are partially spiro. A non-aryl heterocycle can form a fused ring with aryl or heteroaryl. For example, a non-aryl heterocycle fused to $C_{6-10}$ aryl or 5- to 6-membered heteroaryl is also encompassed by a heterocycle. 1, 2, or more carbonyl, thiocarbonyl, sulfinyl, or sulfonyl can be comprised to constitute the non-aryl heterocycle. For example, lactam, thiolactam, lactone, thiolactone, cyclic imide, cyclic carbamate, cyclic thiocarbamate, and other cyclic groups are also encompassed by the non-aryl heterocycle. In this regard, an oxygen atom of carbonyl, sulfinyl, and sulfonyl and a sulfur atom of thiocarbonyl are not included in the number of members of the ring (ring size) or the number of heteroatoms constituting the ring.

As used herein, "4- to 10-membered non-aryl heterocycle" refers to a substituent with "4- to 10-membered non-aryl heterocycle" that is a monovalent group among the "non-aryl heterocycle" described above.

As used herein, the non-aryl heterocycle moiety of "non-aryl heterocyclyloxy" is defined the same as the "4- to 10-membered non-aryl heterocycle" described above. "4- to 10-membered non-aryl heterocyclyloxy" is preferably "4- to 6-membered non-aryl heterocyclyloxy". Specific examples of "4- to 10-membered non-aryl heterocyclyloxy" include, but are not limited to, tetrahydrofuranyloxy, tetrahydropyranyloxy, azetidinyloxy, pyrrolidinyloxy, piperidinyloxy, and the like.

As used herein, the non-aryl heterocycle moiety of "non-aryl heterocyclylthio" is defined the same as the "non-aryl heterocycle" described above. "4- to 10-membered non-aryl heterocyclylthio" is preferably "4- to 6-membered non-aryl heterocyclylthio". Specific examples of "4- to 10-membered non-aryl heterocyclylthio" include, but are not limited to, tetrahydropyranylthio, piperidinylthio, and the like.

As used herein, "non-aryl heterocyclylcarbonyl" refers to a carbonyl group substituted with the "non-aryl heterocycle" described above. "4- to 10-membered non-aryl heterocyclylcarbonyl" is preferably "4- to 6-membered non-aryl heterocyclylcarbonyl". Specific examples of "4- to 10-membered non-aryl heterocyclylcarbonyl" include, but are not limited to, azetidinylcarbonyl, pyrrolidinylcarbonyl, piperidinylcarbonyl, morpholinylcarbonyl, and the like.

As used herein, "non-aryl heterocyclylsulfonyl" refers to a sulfonyl group substituted with the "non-aryl heterocycle" described above. "4- to 10-membered non-aryl heterocyclylsulfonyl" is preferably "4- to 6-membered non-aryl heterocyclylsulfonyl". Specific examples of "4- to 10-membered non-aryl heterocyclylsulfonyl" include, but are not limited to, azetidinylsulfonyl, pyrrolidinylsulfonyl, piperidinylsulfonyl, morpholinylsulfonyl, and the like.

As used herein, "5- or 6-membered heterocycloalkyl" and "5- to 6-membered heterocycloalkyl" refer to heterocycloalkyl comprised of 5 to 6 cyclic atoms, comprising 1, 2, or more same or different heteroatoms selected from the group consisting of an oxygen atom, nitrogen atom, and sulfur atom.

As used herein, "heterocycloalkylalkyl" refers to alkyl substituted with at least one heterocycloalkyl.

As used herein, "alkylcarbonyl" is a monovalent group of —C(=O)-alkyl. Preferred examples of alkylcarbonyl include $C_{1-6}$ alkylcarbonyl. Specific examples of $C_{1-6}$ alkylcarbonyl include, but are not limited to, acetyl ($CH_3C(=O)—$), n-propanoyl ($CH_3CH_2C(=O)—$), n-butanoyl ($CH_3CH_2CH_2C(=O)—$), n-pentanoyl ($CH_3(CH_2)_3C(=O)—$), n-hexanoyl ($CH_3(CH_2)_4C(=O)—$), n-heptanoyl ($CH_3(CH_2)_5C(=O)—$), and the like.

As used herein, "alkoxy" is a monovalent group of —O-alkyl. Preferred examples of alkoxy include $C_{1-6}$ alkoxy (i.e., $C_{1-6}$ alkyl-O—), $C_{1-4}$ alkoxy (i.e., $C_{1-4}$ alkyl-O—), and the like. Specific examples of $C_{1-4}$ alkoxy include methoxy ($CH_3O—$), ethoxy ($CH_3CH_2O—$), n-propoxy ($CH_3(CH_2)_2O—$), isopropoxy (($CH_3)_2CHO—$), n-butoxy ($CH_3(CH_2)_3O—$), isobutoxy (($CH_3)_2CHCH_2O—$), tert-butoxy ((CH$_3$)$_3$CO—), sec-butoxy (CH$_3$CH$_2$CH(CH$_3$)O—), and the like. Specific examples of C$_{1-6}$ alkoxy include, but are not limited to, C$_{1-4}$ alkoxy, n-pentyloxy (CH$_3$(CH$_2$)$_4$O—), isopentyloxy ((CH$_3$)$_2$CHCH$_2$CH$_2$O—), neopentyloxy ((CH$_3$)$_3$CCH$_2$O—), tert-pentyloxy (CH$_3$CH$_2$C(CH$_3$)$_2$O—), 1,2-dimethylpropoxy (CH$_3$CH(CH$_3$)CH(CH$_3$)O—), and the like.

As used herein, "alkoxycarbonyl" is a monovalent group of —C(=O)—O-alkyl. Examples of alkoxycarbonyl include, but are not limited to, C$_{1-6}$ alkoxycarbonyl, preferably C$_{1-4}$ alkoxycarbonyl. Specific examples of C$_{1-4}$ alkoxycarbonyl include methoxycarbonyl, ethoxycarbonyl, n-propoxycarbonyl, isopropoxycarbonyl, n-butoxycarbonyl, sec-butoxycarbonyl, tert-butoxycarbonyl, isobutoxycarbonyl, and the like. Specific examples of C$_{1-6}$ alkoxycarbonyl include, but are not limited to, C$_{1-4}$ alkoxycarbonyl, n-pentyloxycarbonyl, isopentyloxycarbonyl, neopentyloxycarbonyl, tert-pentyloxycarbonyl, 1,2-dimethylpropyloxycarbonyl, n-hexyloxycarbonyl, and the like.

As used herein, "alkoxycarbonylamino" is a monovalent group of —NH—C(=O)—O-alkyl. Examples of alkoxycarbonylamino include, but are not limited to, C$_{1-6}$ alkoxycarbonylamino, preferably C$_{1-4}$ alkoxycarbonylamino. Specific examples of C$_{1-4}$ alkoxycarbonylamino include methoxycarbonylamino, ethoxycarbonylamino, n-propoxycarbonylamino, isopropoxycarbonylamino, n-butoxycarbonylamino, sec-butoxycarbonylamino, tert-butoxycarbonylamino, isobutoxycarbonylamino, and the like. Specific examples of C$_{1-6}$ alkoxycarbonylamino include, but are not limited to, C$_{1-4}$ alkoxycarbonylamino, n-pentyloxycarbonylamino, isopentyloxycarbonylamino, neopentyloxycarbonylamino, tert-pentyloxycarbonylamino, 1,2-dimethylpropyloxycarbonylamino, n-hexyloxycarbonylamino, and the like.

As used herein, "haloalkyl" is a monovalent group of halogenated alkyl, having one or more hydrogen on an alkyl group substituted with halogen. The term "perhaloalkyl" refers to haloalkyl with all hydrogen on the alkyl group substituted with halogen. For example, perfluoroethyl is —CF$_2$CF$_3$, and perchloro-n-propyl is —CCl$_2$CCl$_2$CCl$_3$. Examples of haloalkyl include C$_{1-6}$ haloalkyl, C$_{1-4}$ haloalkyl, C$_{1-3}$ haloalkyl, and the like. Specific examples of C$_{1-3}$ alkyl include, but are not limited to, fluoromethyl, chloromethyl, bromomethyl, difluoromethyl, dichloromethyl, dibromomethyl, trifluoromethyl, trichloromethyl, tribromomethyl, fluorochloromethyl, difluorochloromethyl, fluorodichloromethyl, fluoroethyl, chloroethyl, bromoethyl, trifluoroethyl, trichloroethyl, tribromoethyl, perfluoroethyl, perchloroethyl, perbromoethyl, perfluoropropyl, perchloropropyl, perbromopropyl, perfluoroisopropyl, perchloroisopropyl, perbromoisopropyl, and the like. Specific examples of C$_{1-4}$ alkyl include, but are not limited to, C$_{1-3}$ haloalkyl, perfluorobutyl, perchlorobutyl, perbromobutyl, perfluoroisobutyl, perfluoro-t-butyl, and the like. Specific examples of C$_{1-6}$ alkyl include, but are not limited to, C$_{1-4}$ haloalkyl, perfluoro-n-pentyl, perfluoroisopentyl, perfluoroneopentyl, perfluoro-tert-pentyl, perfluoro-1,2-dimethylpropyl, and the like.

As used herein, "haloalkoxy" as well as "haloalkyloxy" is a monovalent group of —O-haloalkyl with one or more hydrogen on the alkyl group substituted with halogen. The term "perhaloalkoxy" refers to haloalkoxy with all hydrogen on the alkyl group substituted with halogen. For example, perfluoroethoxy is —OCF$_2$CF$_3$, and perchloro-n-propoxy is —OCCl$_2$CCl$_2$CCl$_3$. Preferred examples of haloalkoxy include C$_{1-6}$ haloalkoxy, C$_{1-4}$ haloalkoxy, C$_{1-3}$ haloalkoxy, and the like. Specific examples of C$_{1-3}$ alkoxy include, but are not limited to, fluoromethoxy, chloromethoxy, bromomethoxy, difluoromethoxy, dichloromethoxy, dibromomethoxy, trifluoromethoxy, trichloromethoxy, tribromomethoxy, fluorochloromethoxy, difluorochloromethoxy, fluorodichloromethoxy, fluoroethoxy, chloroethoxy, bromoethoxy, trifluoroethoxy, trichloroethoxy, tribromoethoxy, perfluoroethoxy, perchloroethoxy, perbromoethoxy, perfluoropropoxy, perchloropropoxy, perbromopropoxy, perfluoroisopropoxy, perchloroisopropoxy, perbromoisopropoxy, and the like. Specific examples of C$_{1-4}$ alkoxy include, but are not limited to, C$_{1-3}$ haloalkoxy, perfluorobutoxy, perchlorobutoxy, perbromobutoxy, perfluoroisobutoxy, perfluoro-t-butoxy, and the like. Specific examples of C$_{1-6}$ alkoxy include, but are not limited to, C$_{1-4}$ haloalkoxy, perfluoro-n-pentyloxy, perfluoroisopentyloxy, perfluoroneopentyloxy, perfluoro-tert-pentyloxy, perfluoro-1,2-dimethylpropoxy, and the like.

As used herein, "alkylsulfonyl" refers to a sulfonyl group substituted with the "alkyl" described above. "C$_{1-6}$ alkylsulfonyl" is preferably "C$_{1-4}$ alkylsulfonyl". Specific examples of "C$_{1-6}$ alkylsulfonyl" include, but are not limited to, methylsulfonyl, propionylsulfonyl, butyrylsulfonyl, and the like.

As used herein, the alkyl moiety of "alkylthio" is defined the same as the alkyl described above. Examples of "C$_{1-6}$ alkylthio" include "C$_{1-4}$ alkylthio", and preferred examples thereof include "C$_{1-3}$ alkylthio". Specific examples of "C$_{1-6}$ alkylthio" include, but are not limited to, methylthio, ethylthio, n-propylthio, n-butylthio, isopropylthio, isobutylthio, tert-butylthio, sec-butylthio, isopentylthio, neopentylthio, tert-pentylthio, 1,2-dimethylpropylthio, and the like.

As used herein, "arylcarbonyl" is a monovalent group of —C(=O)-aryl. Preferred examples of arylcarbonyl include C$_{6-10}$ arylcarbonyl. Specific examples of C$_{6-10}$ arylcarbonyl include, but are not limited to, benzoyl (i.e., phenyl-C(=O)—), 1-naphthylcarbonyl, 2-naphthylcarbonyl, and the like.

As used herein, the aryl moiety of "aryloxy" is defined the same as the aryl described above. Preferred examples of "C$_{6-10}$ aryloxy" include "C$_6$ or C$_{10}$ aryloxy". Specific examples of "C$_{6-10}$ aryloxy group" include, but are not limited to, a phenoxy group, 1-naphthyloxy group, 2-naphthyloxy group, and the like.

As used herein, "heteroarylcarbonyl" is a monovalent group of —C(=O)-heteroaryl.

As used herein, "heteroarylcarbonyl group" refers to a carbonyl group substituted with the "heteroaryl" described above. Specific examples of "5- to 6-membered heteroarylcarbonyl group" include, but are not limited to, pyrazoylcarbonyl group, triazoylcarbonyl group, thiazoylcarbonyl group, thiadiazoylcarbonyl group, pyridylcarbonyl group, pyridazoylcarbonyl group, and the like.

As used herein, the heteroaryl moiety of the "heteroaryloxy group" is defined the same as the "heteroaryl" described above. The 5- to 6-membered heteroaryl moiety of the "5- to 6-membered heteroaryloxy group" is defined the same as "5-membered heteroaryl" or "6-membered heteroaryl", respectively. Specific examples of "5- to 6-membered heteroaryloxy group" include, but are not limited to, a pyrazoyloxy group, triazoyloxy group, thiazoyloxy group, thiadiazoyloxy group, pyridyloxy group, pyridazoyloxy group, and the like.

As herein, the heteroaryl moiety of a "heteroarylthio group" is defined the same as the "heteroaryl" described above. The 5- to 6-membered heteroaryl moiety of "5- to 6-membered heteroarylthio group" is defined the same as "5-membered heteroaryl" or "6-membered heteroaryl", respectively. Specific examples of "5- to 6-membered heteroarylthio group" include, but are not limited to, pyrazoylthio group, triazoylthio group, thiazoylthio group, thiadiazoylthio group, pyridylthio group, pyridazoylthio group, and the like.

As used herein, the heteroaryl moiety of a "heteroarylsulfonyl group" is defined the same as the "heteroaryl" described above. A "5- to 6-membered heteroarylsulfonyl group" refers to a sulfonyl group substituted with the "5- to 6-membered heteroaryl" described above. Specific examples of "5- to 6-membered heteroarylsulfonyl group" include, but are not limited to, pyrazoylsulfonyl group, triazoylsulfonyl group, thiazoylsulfonyl group, thiadiazoylsulfonyl group, pyridylsulfonyl group, pyridazoylsulfonyl group, and the like.

As used herein, "acyl" refers to a monovalent group of —C(=O)—$R_{acyl}$, wherein $R_{acyl}$ is hydrogen, optionally substituted alkyl, optionally substituted alkenyl, optionally substituted alkynyl, optionally substituted aryl, optionally substituted heteroaryl, or optionally substituted heterocycloalkyl. Specific examples of acyl include, but are not limited to, formyl, groups exemplified as alkylcarbonyl, arylcarbonyl, and heteroarylcarbonyl, and the like.

As used herein, "optionally substituted carbonyl" group refers to a monovalent group of —C(=O)— (hydrogen or any group selected from a substituent group described herein). Examples of "optionally substituted carbonyl" group include, but are not limited to, formyl, and optionally substituted carbamoyl, alkylcarbonyl, alkoxycarbonyl, alkenylcarbonyl, alkenyloxycarbonyl, alkynylcarbonyl, alkynyloxycarbonyl, arylcarbonyl, aryloxycarbonyl, cycloalkylcarbonyl, cycloalkyloxycarbonyl, heteroarylcarbonyl, heteroaryloxycarbonyl, heterocycloalkylcarbonyl, heterocycloalkyloxycarbonyl, and the like. A carbonyl group substituted with hydrogen is a formyl group. A carbonyl group substituted with amino is a carbamoyl group.

As used herein, "optionally substituted oxy" group refers to a monovalent group of —O— (hydrogen or any group selected from a substituent group described herein). Examples of "optionally substituted oxy" group include, but are not limited to, hydroxy, and optionally substituted alkyloxy, alkenyloxy, alkynyloxy, aryloxy, heteroaryloxy, heterocycloalkyloxy, alkylcarbonyloxy, alkenylcarbonyloxy, alkynylcarbonyloxy, arylcarbonyloxy, heteroarylcarbonyloxy, heterocycloalkylcarbonyloxy, and the like. An oxy group substituted with hydrogen is a hydroxy group.

As used herein, "carbamoyl" is a monovalent group of —C(=O)—$NH_2$.

As used herein, "amidinoamino" is a monovalent group of —NH—C(=NH)—$NH_2$. "Amidinoamino" group is also referred to as a "guanidine" group or "guanidyl" group. Such terms are interchangeably used.

As used herein, the phrase "a substituent-substituted group" means that the group is substituted with at least one substituent. For example, "hydroxy-substituted $C_{1-6}$ alkyl" refers to $C_{1-6}$ alkyl that has at least one hydroxy substitution.

As used herein, "carbamoyl-substituted $C_{1-6}$ alkyl" is $C_{1-6}$ alkyl substituted with at least one —C(=O)—$NH_2$ group. Examples of "carbamoyl-substituted $C_{1-6}$ alkyl" include, but are not limited to, carbamoyl-substituted $C_{1-4}$ alkyl, 6-amino-6-oxohexyl (i.e., $H_2NC(=O)—(CH_2)_5$— or carbamoylpentyl), 7-amino-7-oxoheptyl (i.e., $H_2NC(=O)—(CH_2)_6$— or carbamoylhexyl), and the like. Specific examples of "carbamoyl-substituted $C_{1-4}$ alkyl" include, but are not limited to, 2-amino-2-oxoethyl (i.e., $H_2NC(=O)—CH_2$- or carbamoylmethyl), 3-amino-3-oxopropyl (i.e., $H_2NC(=O)—CH_2CH_2$- or carbamoylethyl), 4-amino-4-oxobutyl (i.e., $H_2NC(=O)—(CH_2)_3$— or carbamoylpropyl), 5-amino-5-oxopentyl (i.e., $H_2NC(=O)—(CH_2)_4$— or carbamoylbutyl), and the like.

As used herein, "amidinoamino-substituted alkyl" or "guanidino-substituted alkyl" is alkyl substituted with at least one-NH—C(=NH)—$NH_2$ group, wherein the nitrogen atom of the amidinoamino group can be protected with a nitrogen protecting group (e.g., tert-butoxycarbonyl group). Examples of "amidinoamino-substituted $C_{1-6}$ alkyl" include, but are not limited to, "amidinoamino-substituted $C_{1-4}$ alkyl" and the like. Specific examples of "amidinoamino-substituted $C_{1-4}$ alkyl" include, but are not limited to, (amidinoamino)methyl, 2-(amidinoamino)ethyl, 3-(amidinoamino) propyl, 4-(amidinoamino)butyl, and the like. Specific examples of "amidinoamino-substituted $C_{1-6}$ alkyl" include, but are not limited to, amidinoamino-substituted $C_{1-4}$ alkyl, 5-(amidinoamino) pentyl, 6-(amidinoamino) hexyl, and the like. Examples of amidinoamino groups protected with a nitrogen protecting group include

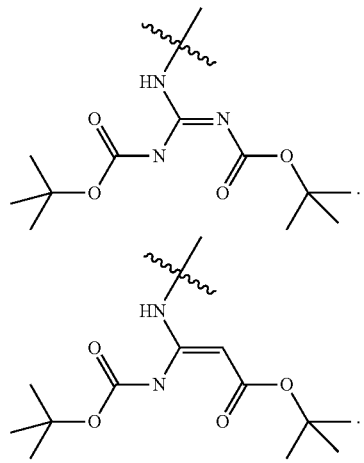

As used herein, "amidinoamino" is synonymous with "guanidino".

As used herein, "carboxy-substituted alkyl" is alkyl substituted with at least one-COOH group. Examples of "carboxy-substituted $C_{1-6}$ alkyl" include, but are not limited to, carboxy-substituted $C_{1-4}$ alkyl, 5-carboxypentyl, 6-carboxyhexyl, and the like. Specific examples of "carboxy-substituted $C_{1-4}$ alkyl" include, but are not limited to, carboxymethyl, 2-carboxyethyl, 3-carboxypropyl, 4-carboxybutyl, and the like.

As used herein, "arylalkyl substituted with alkyl-substituted amino" is arylalkyl substituted with at least one alkyl-substituted amino. Specific examples of $C_{1-6}$ alkyl-substituted amino include, but are not limited to, —NH($CH_3$), —N($CH_3$)$_2$, —NH($CH_2CH_3$), —N($CH_2CH_3$)$_2$, —NH(($CH_2$)$_2CH_3$), —N(($CH_2$)$_2CH_3$)$_2$, —NH(CH($CH_3$)$_2$), —N(CH($CH_3$)$_2$)$_2$, —NH(($CH_2$) 3 $CH_3$), —N(($CH_2$)$_3CH_3$)$_2$, —NH($CH_2$CH($CH_3$)$_2$), —N($CH_2$CH($CH_3$)$_2$)$_2$, —NH (($CH_2$)$_4CH_3$), —N(($CH_2$)$_4CH_3$)$_2$, —NH(($CH_2$)$_5CH_3$), —N(($CH_2$)$_5CH_3$)$_2$, and the like. As used herein, "alkyl-substituted amino" is synonymous with "alkylamino".

A "protecting group" refers to a group of atoms that blocks, reduces, or prevents reactivity of a functional group when attached to a reactive functional group in a molecule. The compound of the disclosure can have a substitution with a protecting group when appropriate or needed at any of $R^1$ to $R^4$ or any position of a substituent thereof or other substituents or the like. Compounds comprising such a protecting group are also within the scope of the present disclosure. Typically, a protecting group can be selectively removed during a synthesis process if desired. Examples of protecting groups are found in Greene and Wuts, Protective Groups in Organic Chemistry, 5th Edition, 2014, John Wiley & Sons, NY and Harrison et al., Compendium of Synthetic Organic Methods, Vol. 1 to 8, John Wiley & Sons, NY, or the like. As used herein, a "protecting group" can fall under the definitions for 1) to 53) of substituent α and 1) to 26) of substituent β. In such a case, "54) protecting group" can be described as "54) protecting group other than 1) to 53)" in substituent group α1, and "27) protecting group" can be described as "protecting group other than 1) to 26)" in substituent group β1. Representative examples of nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilylethanesulfonyl ("TES"), trityl and substituted trityl group, allyloxycarbonyl, 9-fluorenylmethyloxycarbonyl ("FMOC"), nitro-veratryloxycarbonyl ("NVOC"), groups represented by "Protect" herein, and the like. Representative examples of hydroxyl protecting groups include, but are not limited to, groups that acylate (esterify) or alkylate a hydroxyl group, such as benzyl and trityl ether, as well as alkyl ether, tetrahydropyranyl ether, trialkylsilyl ether (e.g., TMS, triethylsilyl, t-butyldimethylsilyl (TBDMS), and triisopropylsilyl (TIPS)), alkyldiarylsilyl ether (e.g., t-butyldiphenylsilyl (TBDPS)), triarylsilyl ether (e.g., triphenylsilyl), glycol ether (e.g., ethylene glycol ether, propylene glycol ether, and the like), and allyl ether.

An amino group of the compound of the disclosure (e.g., amino group of the backbone, amino group as a substituent, amino group in a substituent of said compound, or the like) can be protected with a nitrogen protecting group or a group represented by "Protect". An amino group in a substituent listed in a substituent group can be further protected with a nitrogen protecting group or a group represented by "Protect". A protected substituent can also be used as a substituent.

A hydroxy group of the compound of the disclosure (e.g., hydroxy group as a substituent, a hydroxy group in a substituent of said compound, a hydroxy group in a substituent group described above, or the like) can also be protected with a protecting group of a hydroxy group. A hydroxy group in a substituent listed in a substituent group can be further protected with a hydroxyl protecting group (silyl ether or the like) described herein. A protected substituent can also be used as a substituent.

(Preferred Embodiments)

The preferred embodiments of the present disclosure are described hereinafter. It is understood that the embodiments provided hereinafter for are provided the better understanding of the present disclosure, so that the scope of the present disclosure should not be limited by the following descriptions. Thus, it is apparent that those skilled in the art can refer to the descriptions herein to make appropriate modifications within the scope of the present disclosure. It is also understood that the following embodiments of the present disclosure can be used individually or as a combination.

(Compound and Composition of the Disclosure)

In one aspect, the compound of the disclosure can be exemplified as a compound represented by formula XXIF:

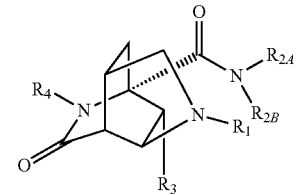

(XXIF)

Formula XXIF

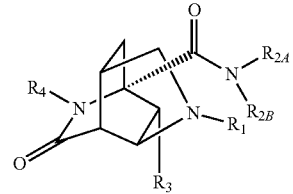

or an enantiomer thereof, or a salt thereof, or a solvate thereof, wherein $R_1$, $R_3$, and $R_4$ are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl, and $R_{2A}$ and $R_{2B}$ are each independently hydrogen, optionally substituted alkyl, optionally substituted alkenyl, optionally substituted alkynyl, optionally substituted cycloalkyl, optionally substituted heterocycloalkyl, optionally substituted aryl, optionally substituted heteroaryl, or optionally substituted carbonyl, or $R_{2A}$ and $R_{2B}$, together with the nitrogen atom to which they are attached, form a non-aryl heterocycle or heteroaryl ring, wherein the non-aryl heterocycle and the heteroaryl ring are each independently and optionally substituted.

If one of $R_{2A}$ or $R_{2B}$ is hydrogen herein, it is understood that the same definition as $R_2$ described herein can be used.

In another aspect, the compound of the disclosure can be exemplified as a compound represented by formula XXIB:

[Chemical Formula 13]

Formula XXIB

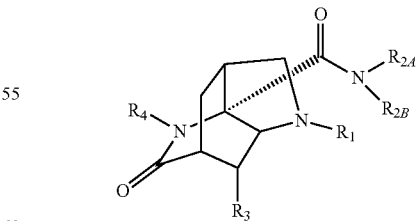

or an enantiomer thereof, or a salt thereof, or a solvate thereof, wherein $R_1$, $R_{2a}$, $R_{2B}$, and $R_3$ are defined the same as those for formula XXIF described herein.

In one embodiment, the alkyl, alkenyl, alkynyl, cycloalkyl, heterocycloalkyl, aryl, heteroaryl, and carbonyl of $R_1$, $R_3$, and $R_4$ are each independently and optionally substituted with one to the maximum substitutable number of the same or different substituents selected from substituent group I, and the alkyl, alkenyl, alkynyl, cycloalkyl, heterocycloalkyl, aryl, heteroaryl, carbonyl, and the non-aryl heterocycle and the heteroaryl ring of $R_{2A}$ and $R_{2B}$ are each independently and optionally substituted with one to the maximum substitutable number of the same or different substituents selected from substituent group I.

In one embodiment, $R_1$, $R_3$, and $R_4$ are each independently hydrogen, optionally substituted alkyl, optionally substituted cycloalkyl, optionally substituted heterocycloalkyl, optionally substituted aryl, optionally substituted heteroaryl, or optionally substituted carbonyl, and $R_{2A}$ and $R_{2B}$ are each independently hydrogen, optionally substituted alkyl, optionally substituted cycloalkyl, optionally substituted heterocycloalkyl, optionally substituted aryl, optionally substituted heteroaryl, or optionally substituted carbonyl, or $R_{2A}$ and $R_{2B}$, together with the nitrogen atom to which they are attached, form a non-aryl heterocycle or heteroaryl ring, wherein the non-aryl heterocycle and the heteroaryl ring are each independently and optionally substituted.

In one embodiment, $R_1$, $R_3$, and $R_4$ are each independently hydrogen, optionally substituted $C_{1-12}$ alkyl, optionally substituted $C_{3-10}$ cycloalkyl, optionally substituted 5- to 10-membered heterocycloalkyl, optionally substituted $C_{6-10}$ aryl, optionally substituted 5- to 10-membered heteroaryl, or optionally substituted carbonyl, and $R_{2A}$ and $R_{2B}$ are each independently hydrogen, optionally substituted $C_{1-12}$ alkyl, optionally substituted $C_{3-10}$ cycloalkyl, optionally substituted 5- to 10-membered heterocycloalkyl, optionally substituted $C_{6-10}$ aryl, optionally substituted 5- to 10-membered heteroaryl, or optionally substituted carbonyl, or $R^{2A}$ and $R^{2B}$, together with the nitrogen atom to which they are attached, form a 5- to 10-membered non-aryl heterocycle or 5- to 10-membered heteroaryl ring, wherein the non-aryl heterocycle and the heteroaryl ring are each independently and optionally substituted.

In one embodiment, $R^1$, $R^3$, and $R^4$ are each independently
hydrogen,
optionally substituted alkyl,
optionally substituted arylalkyl,
optionally substituted heteroarylalkyl,
optionally substituted cycloalkyl,
optionally substituted heterocycloalkyl,
optionally substituted aryl,
formyl,
optionally substituted alkylcarbonyl,
optionally substituted alkoxycarbonyl,
optionally substituted arylcarbonyl,
optionally substituted aryloxycarbonyl,
optionally substituted heteroarylcarbonyl,
optionally substituted heteroaryloxycarbonyl,
optionally substituted cycloalkylcarbonyl,
optionally substituted cycloalkyloxycarbonyl,
optionally substituted heterocycloalkylcarbonyl,
optionally substituted heterocycloalkyloxycarbonyl,
carbamoyl,
optionally substituted alkylcarbamoyl,
optionally substituted alkoxycarbamoyl,
optionally substituted arylcarbamoyl,
optionally substituted heteroarylcarbamoyl,
optionally substituted cycloalkylcarbamoyl, or
optionally substituted heterocycloalkylcarbamoyl wherein the groups of $R_1$, $R_3$, and $R_4$ are optionally substituted with one to the maximum substitutable number of the same or different substituents selected from substituent group II, and $R_{2A}$ and $R_{2B}$ are each independently
hydrogen,
optionally substituted alkyl,
optionally substituted arylalkyl,
optionally substituted cycloalkyl,
optionally substituted heterocycloalkyl,
formyl,
optionally substituted alkylcarbonyl,
optionally substituted alkoxycarbonyl,
optionally substituted arylcarbonyl,
optionally substituted aryloxycarbonyl,
optionally substituted heteroarylcarbonyl,
optionally substituted heteroaryloxycarbonyl,
optionally substituted cycloalkylcarbonyl,
optionally substituted cycloalkyloxycarbonyl,
optionally substituted heterocycloalkylcarbonyl,
optionally substituted heterocycloalkyloxycarbonyl,
carbamoyl,
optionally substituted alkylcarbamoyl,
optionally substituted alkoxycarbamoyl,
optionally substituted arylcarbamoyl,
optionally substituted heteroarylcarbamoyl,
optionally substituted cycloalkylcarbamoyl, or
optionally substituted heterocycloalkylcarbamoyl, wherein the groups of $R^{2A}$ and are optionally substituted with one to the maximum substitutable number of the same or different substituents selected from substituent group II, or $R^{2A}$ and $R^{2B}$, together with the nitrogen atom to which they are attached, form a non-aryl heterocycle or a heteroaryl ring, wherein the non-aryl heterocycle and the heteroaryl ring are each independently optionally substituted with one to the maximum substitutable number of the same or different substituents selected from substituent group II.

In one embodiment, $R^1$, $R^3$, and $R^4$ are each independently hydrogen, optionally substituted alkyl, optionally substituted arylalkyl, optionally substituted cycloalkyl, optionally substituted heterocycloalkyl, optionally substituted aryl, formyl, optionally substituted alkylcarbonyl, optionally substituted alkoxycarbonyl, optionally substituted arylcarbonyl, optionally substituted aryloxycarbonyl, optionally substituted heteroarylcarbonyl, optionally substituted heteroaryloxycarbonyl, optionally substituted cycloalkylcarbonyl, optionally substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted heterocycloalkylcarbamoyl, wherein the groups of $R_1$, $R_3$, and $R_4$ are optionally substituted with one to the maximum substitutable number of the same or different substituents selected from substituent group II, and $R_{2A}$ and $R_{2B}$ are each independently hydrogen, optionally substituted alkyl, optionally substituted arylalkyl, optionally substituted cycloalkyl, optionally substituted heterocycloalkyl, formyl, optionally substituted alkylcarbonyl, optionally substituted alkoxycarbonyl, optionally substituted arylcarbonyl, optionally substituted aryloxycarbonyl, optionally substituted heteroarylcarbonyl, optionally substituted heteroaryloxycarbonyl, optionally substituted cycloalkylcarbonyl, optionally substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted heterocycloalkylcarbamoyl, wherein the groups of $R_{2A}$ and $R_{2B}$ are optionally substituted with one to the maximum substitutable number of the same or different substituents selected from substituent group II, or $R_{2A}$ and $R_{2B}$, together with the nitrogen atom to which they are attached, form a non-aryl heterocycle or heteroaryl ring, wherein the non-aryl heterocycle and the heteroaryl ring are each independently optionally substituted with one to the maximum substitutable number of the same or different substituents selected from substituent group II.

In one embodiment,
$R^1$, $R^3$, and $R^4$ are each independently
hydrogen,
optionally substituted $C_{1-12}$ alkyl,
optionally substituted $C_{6-10}$ aryl $C_{1-12}$ alkyl,
optionally substituted 5- to 10-membered heteroaryl $C_{1-12}$ alkyl,
optionally substituted $C_{3-10}$ cycloalkyl,
optionally substituted 5- to 10-membered heterocycloalkyl,
optionally substituted $C_{6-10}$ aryl,
formyl,
optionally substituted $C_{1-12}$ alkylcarbonyl,
optionally substituted $C_{1-12}$ alkoxycarbonyl,
optionally substituted $C_{6-10}$ arylcarbonyl,
optionally substituted $C_{6-10}$ aryloxycarbonyl,
optionally substituted 5- to 10-membered heteroarylcarbonyl,
optionally substituted 5- to 10-membered heteroaryloxycarbonyl,
optionally substituted $C_{3-10}$ cycloalkylcarbonyl,
optionally substituted $C_{3-10}$ cycloalkyloxycarbonyl,
optionally substituted 5- to 10-membered heterocycloalkylcarbonyl,
optionally substituted 5- to 10-membered heterocycloalkyloxycarbonyl,
carbamoyl,
optionally substituted $C_{1-12}$ alkylcarbamoyl,
optionally substituted $C_{1-12}$ alkoxycarbamoyl,
optionally substituted $C_{6-10}$ arylcarbamoyl,
optionally substituted 5- to 10-membered heteroarylcarbamoyl,
optionally substituted $C_{3-10}$ cycloalkylcarbamoyl, or
optionally substituted 5-10-membered to heterocycloalkylcarbamoyl,
wherein the groups of $R^1$, $R^3$, and $R^4$ are optionally substituted with one to the maximum substitutable number of the same or different substituents selected from substituent group III, and $R^{2A}$ and $R^{2B}$ are each independently
hydrogen,
optionally substituted $C_{1-12}$ alkyl,
optionally substituted $C_{6-10}$ aryl $C_{1-12}$ alkyl,
optionally substituted $C_{3-10}$ cycloalkyl,
optionally substituted 5- to 10-membered heterocycloalkyl,
formyl,
optionally substituted $C_{1-12}$ alkylcarbonyl,
optionally substituted $C_{1-12}$ alkoxycarbonyl,
optionally substituted $C_{6-10}$ arylcarbonyl,
optionally substituted $C_{6-10}$ aryloxycarbonyl,
optionally substituted 5- to 10-membered heteroarylcarbonyl,
optionally substituted 5- to 10-membered heteroaryloxycarbonyl,
optionally substituted $C_{3-10}$ cycloalkylcarbonyl,
optionally substituted $C_{3-10}$ cycloalkyloxycarbonyl,
optionally substituted 5- to 10-membered heterocycloalkylcarbonyl,
optionally substituted 5- to 10-membered heterocycloalkyloxycarbonyl,
carbamoyl,
optionally substituted $C_{1-12}$ alkylcarbamoyl,
optionally substituted $C_{1-12}$ alkoxycarbamoyl,
optionally substituted $C_{6-10}$ arylcarbamoyl,
optionally substituted 5- to 10-membered heteroarylcarbamoyl,
optionally substituted $C_{3-10}$ cycloalkylcarbamoyl, or
optionally substituted 5- to 10-membered heterocycloalkylcarbamoyl,
wherein the groups of $R^{2A}$ and $R^{2B}$ are optionally substituted with one to the maximum substitutable number of the same or different substituents selected from substituent group III, or $R^{2A}$ and $R^{2B}$, together with the nitrogen atom to which they are attached, form a 5- to 10-membered non-aryl heterocycle or a 5- to 10-membered heteroaryl ring, wherein the non-aryl heterocycle and the 5- to 10-membered heteroaryl ring are each independently optionally substituted with one to the maximum substitutable number of the same or different substituents selected from substituent group V.

In one embodiment, $R^1$, $R^3$, and $R^4$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, optionally substituted 5- to 10-membered heterocycloalkyl, optionally substituted $C_{6-10}$ aryl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted 5- to 10-membered heteroarylcarbonyl, optionally 5-substituted to 10-membered heteroaryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered heterocycloalkylcarbamoyl, wherein the groups of $R^1$, $R^3$, and $R^4$ are optionally substituted with one to the maximum substitutable number of the same or different substituents selected from substituent group III, and $R_{2A}$ and $R_{2B}$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, optionally substituted 5- to 10-membered heterocycloalkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted 5- to 10-membered heteroarylcarbonyl, optionally substituted 5- to 10-membered heteroaryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered heterocycloalkylcarbamoyl, wherein the groups of $R_{2A}$ and $R_{2B}$ are optionally substituted with one to the maximum substitutable number of the same or different substituents selected from substituent group III, or $R_{2A}$ and $R_{2B}$, together with the nitrogen atom to which they are attached, form a 5- to 10-membered non-aryl heterocycle or a 5- to 10-membered heteroaryl ring, wherein the non-aryl heterocycle and the 5- to 10-membered heteroaryl ring are each independently optionally substituted with one to the maximum substitutable number of the same or different substituents selected from substituent group V.

In one embodiment, $R^1$ and $R^4$ are each independently hydrogen,
optionally substituted alkyl,
optionally substituted arylalkyl,
optionally substituted heteroarylalkyl,
optionally substituted cycloalkyl,
optionally substituted heterocycloalkyl,
formyl,
optionally substituted alkylcarbonyl,
optionally substituted alkoxycarbonyl,
optionally substituted arylcarbonyl,
optionally substituted aryloxycarbonyl,
optionally substituted cycloalkylcarbonyl,
optionally substituted cycloalkyloxycarbonyl,
optionally substituted heterocycloalkylcarbonyl,
optionally substituted heterocycloalkyloxycarbonyl,
carbamoyl,
optionally substituted alkylcarbamoyl,
optionally substituted alkoxycarbamoyl,
optionally substituted arylcarbamoyl,
optionally substituted heteroarylcarbamoyl,
optionally substituted cycloalkylcarbamoyl, or
optionally substituted heterocycloalkylcarbamoyl,
wherein the groups of $R_1$ and $R_4$ are optionally substituted with one to the maximum substitutable number of the same or different substituents selected from substituent group III.

In one embodiment, $R_1$ and $R_4$ are each independently hydrogen, optionally substituted alkyl, optionally substituted arylalkyl, optionally substituted cycloalkyl, optionally substituted heterocycloalkyl, formyl, optionally substituted alkylcarbonyl, optionally substituted alkoxycarbonyl, optionally substituted arylcarbonyl, optionally substituted aryloxycarbonyl, optionally substituted cycloalkylcarbonyl, optionally substituted substituted cycloalkyloxycarbonyl, optionally substituted heterocycloalkylcarbonyl, optionally substituted heterocycloalkyloxycarbonyl, carbamoyl, optionally substituted alkylcarbamoyl, optionally substituted alkoxycarbamoyl, optionally substituted arylcarbamoyl, optionally substituted heteroarylcarbamoyl, optionally substituted cycloalkylcarbamoyl, or optionally substituted heterocycloalkylcarbamoyl, wherein the groups of $R_1$ and $R_4$ are optionally substituted with one to the maximum substitutable number of the same or different substituents selected from substituent group III.

In one embodiment, $R_1$ and $R_4$ are each independently
hydrogen,
optionally substituted $C_{1-12}$ alkyl,
optionally substituted $C_{6-10}$ aryl $C_{1-12}$ alkyl,
optionally substituted 5- to 10-membered heteroaryl $C_{1-12}$ alkyl,
optionally substituted $C_{3-10}$ cycloalkyl,
optionally substituted 5- to 10-membered heterocycloalkyl,
formyl,
optionally substituted $C_{1-12}$ alkylcarbonyl,
optionally substituted $C_{1-12}$ alkoxycarbonyl,
optionally substituted $C_{6-10}$ arylcarbonyl,
optionally substituted $C_{6-10}$ aryloxycarbonyl,
optionally substituted $C_{3-10}$ cycloalkylcarbonyl,
optionally substituted $C_{3-10}$ cycloalkyloxycarbonyl,
optionally substituted 5- to 10-membered heterocycloalkylcarbonyl,
optionally substituted 5- to 10-membered heterocycloalkyloxycarbonyl,
carbamoyl,
optionally substituted $C_{1-12}$ alkylcarbamoyl,
optionally substituted $C_{1-12}$ alkoxycarbamoyl,
optionally substituted $C_{6-10}$ arylcarbamoyl,
optionally substituted 5- to 10-membered heteroarylcarbamoyl,
optionally substituted $C_{3-10}$ cycloalkylcarbamoyl, or
optionally substituted 5- to 10-membered heterocycloalkylcarbamoyl,
wherein the groups of $R_1$ and $R_4$ are optionally substituted with one to the maximum substitutable number of the same or different substituents selected from substituent group III.

In one embodiment, $R_1$ and $R_4$ are each independently hydrogen, optionally substituted $C_{1-12}$ alkyl, optionally substituted $C_{6-10}$ aryl $C_{1-12}$ alkyl, optionally substituted $C_{3-10}$ cycloalkyl, optionally substituted 5- to 10-membered heterocycloalkyl, formyl, optionally substituted $C_{1-12}$ alkylcarbonyl, optionally substituted $C_{1-12}$ alkoxycarbonyl, optionally substituted $C_{6-10}$ arylcarbonyl, optionally substituted $C_{6-10}$ aryloxycarbonyl, optionally substituted $C_{3-10}$ cycloalkylcarbonyl, optionally substituted $C_{3-10}$ cycloalkyloxycarbonyl, optionally substituted 5- to 10-membered heterocycloalkylcarbonyl, optionally substituted 5- to 10-membered heterocycloalkyloxycarbonyl, carbamoyl, optionally substituted $C_{1-12}$ alkylcarbamoyl, optionally substituted $C_{1-12}$ alkoxycarbamoyl, optionally substituted $C_{6-10}$ arylcarbamoyl, optionally substituted 5- to 10-membered heteroarylcarbamoyl, optionally substituted $C_{3-10}$ cycloalkylcarbamoyl, or optionally substituted 5- to 10-membered heterocycloalkylcarbamoyl, wherein the groups of $R_1$ and $R_4$ are optionally substituted with one to the maximum substitutable number of the same or different substituents selected from substituent group III.

In one embodiment, $R_1$ and $R_4$ are each independently
hydrogen,
optionally substituted alkyl,
optionally substituted arylalkyl,
optionally substituted heteroarylalkyl,
optionally substituted heterocycloalkyl, formyl,
optionally substituted alkylcarbonyl,
optionally substituted alkoxycarbonyl,
optionally substituted arylcarbonyl, or
optionally substituted aryloxycarbonyl,
wherein the groups of $R_1$ and $R_4$ are optionally substituted with one to the maximum substitutable number of the same or different substituents selected from substituent group III.

In one embodiment, $R_1$ and $R_4$ are each independently hydrogen, optionally substituted alkyl, optionally substituted arylalkyl, optionally substituted heterocycloalkyl, formyl, optionally substituted alkylcarbonyl, optionally substituted alkoxycarbonyl, optionally substituted arylcarbonyl, or optionally substituted aryloxycarbonyl, wherein the groups of $R_1$ and $R_4$ are optionally substituted with one to the maximum substitutable number of the same or different substituents selected from substituent group III.

In one embodiment, $R_1$ and $R_4$ are each independently
hydrogen,
optionally substituted $C_{1-12}$ alkyl,
optionally substituted $C_{6-10}$ aryl $C_{1-12}$ alkyl,
optionally substituted 5- to 10-membered heteroaryl $C_{1-12}$ alkyl,
optionally substituted 5- to 10-membered heterocycloalkyl,
formyl,
optionally substituted $C_{1-12}$ alkylcarbonyl,
optionally substituted $C_{1-12}$ alkoxycarbonyl,
optionally substituted $C_{6-10}$ arylcarbonyl, or
optionally substituted $C_{6-10}$ aryloxycarbonyl,
wherein the groups of $R_1$ and $R_4$ are optionally substituted with one to the maximum substitutable number of the same or different substituents selected from substituent group III.

In one embodiment, $R_1$ and $R_4$ are each independently
hydrogen,
optionally substituted $C_{1-12}$ alkyl,
optionally substituted $C_{6-10}$ aryl $C_{1-6}$ alkyl,
optionally substituted 5- to 10-membered heteroaryl $C_{1-6}$ alkyl,
optionally substituted 5- to 10-membered heterocycloalkyl,
formyl,
optionally substituted $C_{1-12}$ alkylcarbonyl,
optionally substituted $C_{1-12}$ alkoxycarbonyl,
optionally substituted $C_{6-10}$ arylcarbonyl, or
optionally substituted $C_{6-10}$ aryloxycarbonyl,
wherein the groups of $R_1$ and $R_4$ are optionally substituted with one to the maximum substitutable number of the same or different substituents selected from substituent group III.

In one embodiment, $R_1$ and $R_4$ are each independently hydrogen, optionally substituted $C_{1-12}$ alkyl, optionally substituted $C_{6-10}$ aryl $C_{1-6}$ alkyl, optionally substituted 5- to 10-membered heterocycloalkyl, formyl, optionally substituted $C_{1-12}$ alkylcarbonyl, optionally substituted $C_{1-12}$ alkoxycarbonyl, optionally substituted $C_{6-10}$ arylcarbonyl, or optionally substituted $C_{6-10}$ aryloxycarbonyl, wherein the groups of $R_1$ and $R_4$ are optionally substituted with one to the maximum substitutable number of the same or different substituents selected from substituent group III.

In one embodiment, $R_1$ is
hydrogen;
alkyl;
alkyl substituted with one to the maximum substitutable number of the same or different substituents selected from the group consisting of hydroxy, substituted oxy, formyl, substituted carbonyl, amino, substituted amino, cycloalkyl, and substituted cycloalkyl;
arylalkyl;
arylalkyl substituted with one to the maximum substitutable number of the same or different substituents selected from the group consisting of halogen, alkyl, substituted alkyl, hydroxy, substituted oxy, amino, substituted amino, and nitro;
heteroarylalkyl;
heteroarylalkyl substituted with one to the maximum substitutable number of the same or different substituents selected from the group consisting of halogen, alkyl, substituted alkyl, hydroxy, substituted oxy, amino, substituted amino, and nitro;
cycloalkyl;
substituted cycloalkyl;
heterocycloalkyl;
substituted heterocycloalkyl; or
substituted carbonyl,
wherein the substituted oxy, substituted carbonyl, substituted amino, substituted cycloalkyl, substituted heterocycloalkyl, and substituted alkyl each independently have one to the maximum substitutable number of the same or different substituents selected from substituent group IV.

In one embodiment, $R_1$ is
hydrogen,
alkyl,
alkyl substituted with one to the maximum substitutable number of the same or different substituents selected from the group consisting of hydroxy, substituted oxy, formyl, substituted carbonyl, amino, substituted amino, cycloalkyl, and substituted cycloalkyl,
arylalkyl,
arylalkyl substituted with one to the maximum substitutable number of the same or different substituents selected from the group consisting of halogen, alkyl, substituted alkyl, hydroxy, substituted oxy, amino, substituted amino, and nitro,
cycloalkyl, substituted cycloalkyl, heterocycloalkyl, substituted heterocycloalkyl, or substituted carbonyl,
wherein the substituted oxy, substituted carbonyl, substituted amino, substituted cycloalkyl, substituted heterocycloalkyl, and substituted alkyl each independently have one to the maximum substitutable number of the same or different substituents selected from substituent group IV.

In one embodiment, $R_1$ is
hydrogen;
alkyl;
alkyl substituted with one to the maximum substitutable number of the same or different substituents selected from the group consisting of hydroxy, alkoxy, haloalkoxy, formyl, carboxy, carbamoyl, alkylcarbonyl, alkoxycarbonyl, amino, amidinoamino, alkoxycarbonyl-substituted amidinoamino, alkoxycarbonylamino, cycloalkyl, and halocycloalkyl;
arylalkyl;
arylalkyl substituted with one to the maximum substitutable number of the same or different substituents selected from the group consisting of halogen, alkyl, haloalkyl, hydroxy, alkoxy, haloalkoxy, arylalkoxy, amino, alkylamino, (alkyl)$_2$amino, cycloalkylcarbonylamino, and nitro;

heteroarylalkyl;
heteroarylalkyl substituted with one to the maximum substitutable number of the same or different substituents selected from the group consisting of halogen, alkyl, haloalkyl, hydroxy, alkoxy, haloalkoxy, arylalkoxy, amino, alkylamino, (alkyl)$_2$amino, cycloalkylcarbonylamino, and nitro;
cycloalkyl;
halocycloalkyl;
heterocycloalkyl;
alkylcarbonyl;
arylalkylcarbonyl;
alkoxycarbonyl;
arylcarbonyl; or
aryloxycarbonyl.

In one embodiment, $R_1$ is
hydrogen,
alkyl,
alkyl substituted with one to the maximum substitutable number of the same or different substituents selected from the group consisting of hydroxy, alkoxy, haloalkoxy, formyl, carboxy, carbamoyl, alkylcarbonyl, alkoxycarbonyl, amino, amidinoamino, alkoxycarbonyl-substituted amidinoamino, alkoxycarbonylamino, cycloalkyl, and halocycloalkyl,
arylalkyl,
arylalkyl substituted with one to the maximum substitutable number of the same or different substituents selected from the group consisting of halogen, alkyl, haloalkyl, hydroxy, alkoxy, haloalkoxy, amino, alkylamino, (alkyl)$_2$amino, cycloalkylcarbonylamino, and nitro,
cycloalkyl, halocycloalkyl, heterocycloalkyl, alkylcarbonyl, arylalkylcarbonyl, alkoxycarbonyl, arylcarbonyl, or aryloxycarbonyl.

In one embodiment, $R_1$ is
hydrogen;
$C_{1-12}$ alkyl;
$C_{1-12}$ alkyl substituted with one to the maximum substitutable number of the same or different substituents selected from the group consisting of $C_{1-12}$ alkoxy, $C_{1-12}$ haloalkoxy, formyl, carboxy, carbamoyl, $C_{1-12}$ alkylcarbonyl, $C_{1-12}$ alkoxycarbonyl, $C_{1-12}$ haloalkoxycarbonyl, amidinoamino, $C_{1-12}$ alkoxycarbonyl-substituted amidinoamino, $C_{1-12}$ alkoxycarbonylamino, hydroxy, $C_{3-10}$ cycloalkyl, and $C_{3-10}$ halocycloalkyl;
$C_{6-10}$ aryl $C_{1-12}$ alkyl;
$C_{6-10}$ aryl $C_{1-12}$ alkyl substituted with one to the maximum substitutable number of the same or different substituents selected from the group consisting of halogen, $C_{1-12}$ alkyl, $C_{1-12}$ haloalkyl, hydroxy, $C_{1-12}$ alkoxy, $C_{1-12}$ haloalkoxy, $C_{6-10}$ aryl $C_{1-12}$ alkoxy, amino, $C_{1-12}$ alkylamino, ($C_{1-12}$ alkyl)$_2$amino, $C_{3-10}$ cycloalkylcarbonylamino, nitro, and hydroxy;
5- to 10-membered heteroaryl $C_{1-12}$ alkyl;
5- to 10-membered heteroaryl $C_{1-12}$ alkyl substituted with one to the maximum substitutable number of the same or different substituents selected from the group consisting of halogen, $C_{1-12}$ alkyl, $C_{1-12}$ haloalkyl, hydroxy, $C_{1-12}$ alkoxy, $C_{1-12}$ haloalkoxy, $C_{6-10}$ aryl $C_{1-12}$ alkoxy, amino, $C_{1-12}$ alkylamino, ($C_{1-12}$ alkyl)$_2$amino, $C_{3-10}$ cycloalkylcarbonylamino, nitro, and hydroxy;
$C_{3-10}$ cycloalkyl;
5- to 10-membered heterocycloalkyl;
$C_{1-12}$ alkylcarbonyl;
$C_{6-10}$ aryl $C_{1-12}$ alkylcarbonyl;
$C_{1-12}$ alkoxycarbonyl;
$C_{6-10}$ arylcarbonyl; or
$C_{6-10}$ aryloxycarbonyl.

In one embodiment, $R_1$ is
hydrogen;
$C_{1-12}$ alkyl;
$C_{1-12}$ alkyl substituted with one to the maximum substitutable number of the same or different substituents selected from the group consisting of $C_{1-6}$ alkoxy, $C_{1-6}$ haloalkoxy, formyl, carboxy, carbamoyl, $C_{1-6}$ alkylcarbonyl, $C_{1-6}$ alkoxycarbonyl, $C_{1-6}$ haloalkoxycarbonyl, amidinoamino, $C_{1-6}$ alkoxycarbonyl-substituted amidinoamino, $C_{1-6}$ alkoxycarbonylamino, hydroxy, $C_{3-10}$ cycloalkyl, and $C_{3-10}$ halocycloalkyl;
$C_{6-10}$ aryl $C_{1-6}$ alkyl;
$C_{6-10}$ aryl $C_{1-6}$ alkyl substituted with one to the substitutable number of the same or different maximum substituents selected from the group consisting of halogen, $C_{1-6}$ alkyl, $C_{1-6}$ haloalkyl, hydroxy, $C_{1-6}$ alkoxy, $C_{1-6}$ haloalkoxy, $C_{6-10}$ aryl $C_{1-6}$ alkoxy, amino, $C_{1-6}$ alkylamino, ($C_{1-6}$ alkyl)$_2$amino, $C_{3-10}$ cycloalkylcarbonylamino, nitro, and hydroxy;
5- to 10-membered heteroaryl $C_{1-6}$ alkyl substituted with one to the maximum substitutable number of the same or different substituents selected from the group consisting of halogen, $C_{1-6}$ alkyl, $C_{1-6}$ haloalkyl, hydroxy, $C_{1-6}$ alkoxy, $C_{1-6}$ haloalkoxy, $C_{6-10}$ aryl $C_{1-6}$ alkoxy, amino, $C_{1-6}$ alkylamino, ($C_{1-6}$ alkyl)$_2$amino, $C_{3-10}$ cycloalkylcarbonylamino, nitro, and hydroxy;
$C_{3-10}$ cycloalkyl;
5- to 10-membered heterocycloalkyl;
$C_{1-6}$ alkylcarbonyl;
$C_{6-10}$ aryl $C_{1-6}$ alkylcarbonyl;
$C_{1-6}$ alkoxycarbonyl;
$C_{6-10}$ arylcarbonyl; or
$C_{6-10}$ aryloxycarbonyl.

In one embodiment, $R_1$ is
hydrogen,
$C_{1-12}$ alkyl,
$C_{1-12}$ alkyl substituted with one to the maximum substitutable number of the same or different substituents selected from the group consisting of $C_{1-6}$ alkoxy, $C_{1-6}$ haloalkoxy, formyl, carboxy, carbamoyl, $C_{1-6}$ alkylcarbonyl, $C_{1-6}$ alkoxycarbonyl, $C_{1-6}$ haloalkoxycarbonyl, amidinoamino, $C_{1-6}$ alkoxycarbonyl-substituted amidinoamino, $C_{1-6}$ alkoxycarbonylamino, hydroxy, $C_{3-10}$ cycloalkyl, and $C_{3-10}$ halocycloalkyl,
$C_{6-10}$ aryl $C_{1-6}$ alkyl,
$C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, hydroxy, $C_{1-6}$ alkoxy, $C_{1-6}$ haloalkoxy, amino, $C_{1-6}$ alkylamino, ($C_{1-6}$ alkyl)$_2$amino, $C_{3-10}$ cycloalkylcarbonylamino, nitro, and hydroxy,
$C_{3-10}$ cycloalkyl, 5- to 10-membered heterocycloalkyl, $C_{1-6}$ alkylcarbonyl, $C_{6-10}$ aryl $C_{1-6}$ alkylcarbonyl, $C_{1-6}$ alkoxycarbonyl, $C_{6-10}$ arylcarbonyl, or $C_{6-10}$ aryloxycarbonyl.

In one embodiment, $R_3$ is
alkyl,
alkyl substituted with one to the maximum substitutable number of the same or different substituents selected from the group consisting of hydroxy, substituted oxy, substituted carbonyl, amino, substituted amino, cycloalkyl, and substituted cycloalkyl, arylalkyl,
arylalkyl substituted with one to the maximum substitutable number of the same or different substituents selected from the group consisting of halogen, alkyl, substituted alkyl, hydroxy, and substituted oxy,
aryl, or
substituted aryl,
wherein the substituted oxy, substituted carbonyl, substituted amino, substituted cycloalkyl, substituted alkyl, and substituted aryl each independently have one to the maximum substitutable number of the same or different substituents selected from substituent group IV.

In one embodiment, $R_3$ is
alkyl,
alkyl substituted with one to the maximum substitutable number of the same or different substituents selected from the group consisting of hydroxy, alkoxy, haloalkoxy, trialkylsilyloxy, carboxy, carbamoyl, alkoxycarbonyl, haloalkoxycarbonyl, amino, amidinoamino, alkoxycarbonyl-substituted amidinoamino, alkoxycarbonylamino, haloalkoxycarbonylamino, cycloalkyl, and halocycloalkyl,
arylalkyl,
arylalkyl substituted with one to the maximum substitutable number of the same or different substituents selected from the group consisting of halogen, alkyl, haloalkyl, hydroxy, alkoxy, and haloalkoxy, or aryl.

In one embodiment, $R_3$ is
$C_{1-12}$ alkyl,
$C_{1-12}$ alkyl substituted with one to the maximum substitutable number of the same or different substituents selected from the group consisting of hydroxy, $C_{1-6}$ alkoxy, $C_{1-6}$ haloalkoxy, tri-$C_{1-6}$ alkylsilyloxy, carboxy, carbamoyl, $C_{1-6}$ alkoxycarbonyl, $C_{1-6}$ haloalkoxycarbonyl, amino, amidinoamino, $C_{1-6}$ alkoxycarbonyl-substituted amidinoamino, $C_{1-6}$ alkoxycarbonylamino, $C_{1-6}$ haloalkoxycarbonylamino, $C_{3-10}$ cycloalkyl, and $C_{3-10}$ halocycloalkyl,
$C_{6-10}$ aryl $C_{1-6}$ alkyl,
$C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, hydroxy, $C_{1-6}$ alkoxy, and $C_{1-6}$ haloalkoxy, or
$C_{6-10}$ aryl.

In one embodiment, $R_{2A}$ and $R_{2B}$ are each independently
hydrogen,
alkyl,
alkyl substituted with one to the maximum substitutable number of the same or different substituents selected from the group consisting of hydroxy, substituted oxy, amino, substituted amino, cycloalkyl, and substituted cycloalkyl,
arylalkyl,
arylalkyl substituted with one to the maximum substitutable number of the same or different substituents selected from the group consisting of halogen, alkyl, substituted alkyl, hydroxy, and substituted oxy,
cycloalkyl,
substituted cycloalkyl, heterocycloalkyl, or substituted heterocycloalkyl,
wherein the substituted oxy, substituted amino, substituted alkyl, substituted cycloalkyl, and substituted heterocycloalkyl each independently have one to the maximum substitutable number of the same or different substituents selected from substituent group IV, or $R_{2A}$ and $R_{2B}$, together with the nitrogen atom to which they are attached, form a non-aryl heterocycle, wherein the non-aryl heterocycle is optionally substituted with one to the maximum substitutable number of the same or different substituents selected from substituent group VI.

In one embodiment, $R_{2A}$ and $R_{2B}$ are each independently
hydrogen,
alkyl,
alkyl substituted with one to the maximum substitutable number of the same or different substituents selected from the group consisting of hydroxy, alkoxy, carboxy, alkoxycarbonyl, amino, amidinoamino, alkoxycarbonyl-substituted amidinoamino, alkoxycarbonylamino, cycloalkyl, and halocycloalkyl,
arylalkyl,
arylalkyl substituted with one to the maximum substitutable number of the same or different substituents selected from the group consisting of halogen, alkyl, haloalkyl, hydroxy, alkoxy, and haloalkoxy,
cycloalkyl,
alkyl-substituted cycloalkyl, or
heterocycloalkyl, or
$R_{2A}$ and $R_{2B}$, together with the nitrogen atom to which they are attached, form a non-aryl heterocycle, wherein the non-aryl heterocycle is optionally substituted with one to the maximum substitutable number of the same or different substituents selected from substituent group VI.

In one embodiment, $R_{2A}$ and $R_{2B}$ are each independently
hydrogen;
$C_{1-12}$ alkyl;
$C_{1-12}$ alkyl substituted with one to the maximum substitutable number of the same or different substituents selected from the group consisting of hydroxy, $C_{1-12}$ alkoxy, carboxy, $C_{1-12}$ alkoxycarbonyl, amino, amidinoamino, $C_{1-12}$ alkoxycarbonyl-substituted amidinoamino, $C_{1-12}$ alkoxycarbonylamino, $C_{3-10}$ cycloalkyl, and $C_{3-10}$ halocycloalkyl;
$C_{6-10}$ aryl $C_{1-12}$ alkyl;
$C_{6-10}$ aryl $C_{1-12}$ alkyl substituted with one to the maximum substitutable number of the same or different substituents selected from the group consisting of halogen, $C_{1-12}$ alkyl, $C_{1-12}$ haloalkyl, hydroxy, $C_{1-12}$ alkoxy, and $C_{1-12}$ haloalkoxy;
$C_{3-10}$ cycloalkyl;
$C_{1-12}$ alkyl-substituted $C_{3-10}$ cycloalkyl; or
5- to 10-membered heterocycloalkyl, or
$R_{2A}$ and $R_{2B}$, together with the nitrogen atom to which they are attached, form a 5- or 6-membered non-aryl heterocycle, wherein the non-aryl heterocycle is optionally substituted with one to the maximum substitutable number of the same or different substituents selected from substituent group VI.

In one embodiment, $R_{2A}$ and $R_{2B}$ are each independently
hydrogen,
$C_{1-12}$ alkyl,
$C_{1-12}$ alkyl substituted with one to the maximum substitutable number of the same or different substituents selected from the group consisting of hydroxy, $C_{1-6}$ alkoxy, carboxy, $C_{1-6}$ alkoxycarbonyl, amino, amidinoamino, $C_{1-6}$ alkoxycarbonyl-substituted amidinoamino, $C_{1-6}$ alkoxycarbonylamino, $C_{3-10}$ cycloalkyl, and $C_{3-10}$ halocycloalkyl,
$C_{6-10}$ aryl $C_{1-6}$ alkyl,
$C_{6-10}$ aryl $C_{1-6}$ alkyl substituted with one to the maximum substitutable number of the same or different substituents selected from the group consisting of halogen, $C_{1-6}$ alkyl, $C_{1-6}$ haloalkyl, hydroxy, $C_{1-6}$ alkoxy, and $C_{1-6}$ haloalkoxy, $C_{3-10}$ cycloalkyl, $C_{1-6}$ alkyl-substituted $C_{3-10}$ cycloalkyl, or 5- to 10-membered heterocycloalkyl, or $R_{2A}$ and $R_{2B}$, together with the nitrogen atom to which they are attached, form a 5- or 6-membered non-aryl heterocycle, wherein the non-aryl heterocycle is optionally substituted with one to the maximum substitutable number of the same or different substituents selected from substituent group VI.

In one embodiment, $R_4$ is hydrogen, alkyl, or substituted alkyl, wherein the substituted alkyl has one to the maximum substitutable number of the same or different substituents selected from the group consisting of halogen, carboxy, carbamoyl, amino, alkylamino, aryl, nitroaryl, and alkoxycarbonylamino.

In one embodiment, $R_4$ is hydrogen, alkyl, or substituted alkyl, wherein the substituted alkyl has one to the maximum substitutable number of the same or different substituents selected from the group consisting of halogen, carboxy, carbamoyl, amino, $C_{1-6}$ alkylamino, $C_{6-10}$ aryl, nitro-$C_{6-10}$ aryl, and $C_{1-6}$ alkoxycarbonylamino.

In one embodiment, $R_4$ is hydrogen, $C_{1-12}$ alkyl, or substituted $C_{1-12}$ alkyl, wherein the substituted $C_{1-12}$ alkyl has one to the maximum substitutable number of the same or different substituents selected from the group consisting of halogen, carboxy, carbamoyl, amino, $C_{1-12}$ alkylamino, $C_{6-10}$ aryl, nitro-$C_{6-10}$ aryl, and $C_{1-12}$ alkoxycarbonylamino.

In one embodiment, $R_4$ is hydrogen or alkyl.

In one embodiment, $R_4$ is hydrogen or $C_{1-12}$ alkyl.

In one embodiment, $R_1$ is hydrogen, methyl, propyl, isopropyl, isobutyl, sec-butyl, isopentyl, hexyl, amidinoaminopropyl, (tert-butoxycarbonyl-substituted amidinoamino) propyl, tert-butoxyethyl, tert-butoxypropyl, tert-butoxycarbonylethyl, carboxyethyl, hydroxyethyl, hydroxypropyl, tert-butoxycarbonylaminopropyl, cyclopentylmethyl, cyclohexylmethyl, cycloheptylmethyl, 5,6,7,8-tetrahydronaphthalenylmethyl, benzyl, phenylethyl, naphthalenylmethyl, fluorobenzyl, chlorobenzyl, methylbenzyl, dimethylbenzyl, tert-butylbenzyl, methoxybenzyl, ethoxybenzyl, tert-butoxybenzyl, trifluoromethylbenzyl, (trifluoromethoxy)benzyl, benzyloxybenzyl, aminobenzyl, (dimethylamino)benzyl, (cyclopentylcarbonylamino)benzyl, 6-methyl-1H-indol-3-ylmethyl, 6-fluoro-1H-indol-3-ylmethyl, 1-tert-butoxycarbonyl-6-methyl-1H-indol-3-ylmethyl, 1-tert-butoxycarbonyl-6-fluoro-1H-indol-3-ylmethyl, nitrobenzyl, hydroxybenzyl, cyclohexyl, isovaleryl, phenylacetyl, benzoyl, isopropyloxycarbonyl, phenoxycarbonyl, or tetrahydro-2H-pyranyl.

In one embodiment, $R_1$ is hydrogen, methyl, propyl, isopropyl, isobutyl, sec-butyl, isopentyl, hexyl, (tert-butoxycarbonyl-substituted amidinoamino) propyl, tert-butoxyethyl, tert-butoxypropyl, tert-butoxycarbonylethyl, carboxyethyl, hydroxyethyl, hydroxypropyl, tert-butoxycarbonylaminopropyl, cyclopentylmethyl, cyclohexylmethyl, 5,6,7,8-tetrahydronaphthalenylmethyl, benzyl, 2-phenylethyl, naphthalenylmethyl, fluorobenzyl, chlorobenzyl, methylbenzyl, dimethylbenzyl, tert-butylbenzyl, methoxybenzyl, ethoxybenzyl, tert-butoxybenzyl, (trifluoromethoxy)benzyl, aminobenzyl, (dimethylamino)benzyl, (cyclopentylcarbonylamino)benzyl, nitrobenzyl, hydroxybenzyl, cyclohexyl, isovaleryl, phenylacetyl, benzoyl, isopropyloxycarbonyl, or phenoxycarbonyl.

In one embodiment, $R_{2A}$ is hydrogen, and $R_{2B}$ is isopropyl, isobutyl, sec-butyl, pentyl, isopentyl, hexyl, heptyl, amidinoaminopropyl, (tert-butoxycarbonyl-substituted amidinoamino) propyl, (tert-butoxycarbonyl)ethyl, tert-butoxyethyl, methoxybutyl, carboxyethyl, hydroxyethyl, (tert-butoxycarbonylamino) propyl, cyclopentylmethyl, cyclohexylmethyl, cycloheptylmethyl, (1,2,3,4-tetrahydronaphthalenyl)methyl, 2,2,6,6-tetramethylpiperidinyl, benzyl, phenylethyl, naphthalenylmethyl, fluorobenzyl, chlorobenzyl, (fluorophenyl)ethyl, methylbenzyl, tert-butoxybenzyl, hydroxybenzyl, β-hydroxyphenethyl, α-hydroxymethylphenethyl, cyclopentyl, cyclohexyl, or methylcyclohexyl, or $R_{2A}$ and $R_{2B}$, together with the nitrogen atom to which they are attached, form a pyrrolidine ring.

In one embodiment, $R_{2A}$ is hydrogen, and $R_{2B}$ is isopropyl, isobutyl, pentyl, isopentyl, hexyl, heptyl, (tert-butoxycarbonyl-substituted amidinoamino) propyl, tert-butoxyethyl, hydroxyethyl, (tert-butoxycarbonylamino) propyl, cyclopentylmethyl, cyclohexylmethyl, (1,2,3,4-tetrahydronaphthalenyl)methyl, 2,2,6,6-tetramethylpiperidinyl, benzyl, phenylethyl, naphthalenylmethyl, fluorobenzyl, chlorobenzyl, (fluorophenyl)ethyl, methylbenzyl, tert-butoxybenzyl, hydroxybenzyl, β-hydroxyphenethyl, α-hydroxymethylphenethyl, cyclopentyl, cyclohexyl, or methylcyclohexyl, or $R_{2A}$ and $R_{2B}$, together with the nitrogen atom to which they are attached, form a pyrrolidine ring.

In one embodiment, $R_3$ is propyl, isobutyl, isopentyl, hexyl, amidinoaminopropyl, (tert-butoxycarbonyl-substituted amidinoamino) propyl, (tert-butoxycarbonyl)ethyl, carboxyethyl, hydroxyethyl, (tert-butyldimethylsilyloxy) ethyl, (tert-butoxycarbonylamino) propyl, cyclopentylmethyl, cyclohexylmethyl, cyclohexylethyl, benzyl, naphthalenylmethyl, phenylethyl, naphthalenylethyl, chlorobenzyl, methylbenzyl, (methylphenyl)ethyl, (isopropylphenyl)ethyl, tert-butoxybenzyl, hydroxybenzyl, or phenyl.

In one embodiment, $R_3$ is propyl, isobutyl, isopentyl, hexyl, (tert-butoxycarbonyl-substituted amidinoamino) propyl, (tert-butoxycarbonyl)ethyl, carboxyethyl, hydroxyethyl, (tert-butyldimethylsilyloxy)ethyl, (tert-butoxycarbonylamino) propyl, cyclopentylmethyl, cyclohexylmethyl, cyclohexylethyl, benzyl, naphthalenylmethyl, (naphthalenyl)ethyl, chlorobenzyl, (methylphenyl)ethyl, (isopropylphenyl)ethyl, tert-butoxybenzyl, hydroxybenzyl, or phenyl.

In one embodiment, $R_4$ is hydrogen or $C_{1-6}$ alkyl. In one embodiment, $R_4$ is hydrogen or methyl. In one embodiment, $R_4$ is hydrogen. In one embodiment, $R_4$ is methyl.

In one embodiment, $R_1$ is alkyl, substituted arylalkyl, or substituted heteroarylalkyl, $R_{2A}$ is hydrogen, $R_{2B}$ is alkyl, arylalkyl, substituted arylalkyl, or optionally substituted cycloalkylalkyl, $R_3$ is alkyl, and $R_4$ is hydrogen.

In one embodiment, $R_1$ is alkyl, alkyl-substituted arylalkyl, chloro-substituted arylalkyl, alkoxy-substituted arylalkyl, heteroarylalkyl substituted with Boc and alkyl, or heteroarylalkyl substituted with Boc and halogen, $R_{2A}$ is hydrogen, $R_{2B}$ is alkyl, arylalkyl, fluoro-substituted arylalkyl, chloro-substituted arylalkyl, or cycloalkylalkyl, and $R_3$ is alkyl.

In one embodiment, $R_1$ is $C_{1-12}$ alkyl, $C_{1-12}$ alkyl-substituted $C_{6-10}$ aryl $C_{1-12}$ alkyl, chloro-substituted $C_{6-10}$ aryl $C_{1-12}$ alkyl, $C_{1-12}$ alkoxy-substituted $C_{6-10}$ aryl $C_{1-12}$ alkyl, 5- to 10-membered heteroaryl $C_{1-12}$ alkyl substituted with Boc and $C_{1-12}$ alkyl, or 5- to 10-membered heteroaryl $C_{1-12}$ alkyl substituted with Boc and halogen, $R_{2A}$ is hydrogen, $R_{2B}$ is $C_{1-12}$ alkyl, $C_{6-10}$ aryl $C_{1-12}$ alkyl, fluoro-substituted $C_{6-10}$ aryl $C_{1-12}$ alkyl, chloro-substituted $C_{6-10}$ aryl $C_{1-12}$ alkyl, or $C_{3-10}$ cycloalkyl $C_{1-12}$ alkyl, and $R_3$ is $C_1$-12 alkyl.

In one embodiment, $R_1$ isobutyl, is isopentyl, methylbenzyl, t-butylbenzyl, chlorobenzyl, methoxybenzyl, 1-tert-butoxycarbonyl-6-methyl-1H-indol-3-ylmethyl, or 6-fluoro-1H-indol-3-ylmethyl, $R_{2A}$ is hydrogen, $R_{2B}$ is isobutyl, benzyl, fluorobenzyl, chlorobenzyl, or cycloheptylmethyl, and $R_3$ is isobutyl or isopentyl.

In some embodiments, the compound of the disclosure can be exemplified as a compound represented by formula IF:

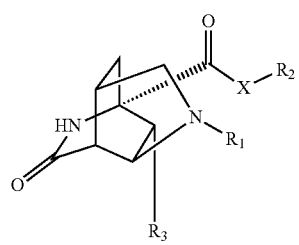

(IF)

or an enantiomer thereof, or a salt thereof, or a solvate thereof, wherein
$R_1$ and $R_2$ are each independently optionally substituted alkyl, optionally substituted cycloalkyl, or optionally substituted heterocycloalkyl,
$R_3$ is optionally substituted alkyl, optionally substituted alkenyl, optionally substituted alkynyl, optionally substituted aryl, optionally substituted heteroaryl, optionally substituted cycloalkyl, or optionally substituted heterocycloalkyl, and
X is —NH—.

In one embodiment, $R_1$ and $R_2$ are each independently optionally substituted alkyl, optionally substituted cycloalkyl, or optionally substituted heterocycloalkyl, and
$R_3$ is optionally substituted alkyl, optionally substituted alkenyl, or optionally substituted aryl.

In one embodiment, $R_1$ and $R_2$ are each independently optionally substituted optionally substituted cycloalkyl, or optionally substituted heterocycloalkyl, and $R_3$ is optionally substituted alkyl or optionally substituted aryl.

In one embodiment, $R_1$, $R_2$, and $R_3$ are each independently alkyl optionally substituted with a hydroxyl group, a carboxyl group, a carbamoyl group, an amino group, or an amidinoamino group, optionally substituted cycloalkylalkyl, optionally substituted arylalkyl, or optionally substituted heteroarylalkyl.

In one embodiment, $R_1$, $R_2$, and $R_3$ are each independently alkyl optionally substituted with a hydroxyl group, a carboxyl group, a carbamoyl group, an amino group, or an amidinoamino group, optionally substituted cycloalkylalkyl, optionally substituted $C_{6-10}$ aryl $C_{1-6}$ alkyl, or optionally substituted 5- to 10-membered heteroaryl $C_{1-6}$ alkyl.

In one embodiment, $R_1$, $R_2$, and $R_3$ are each independently alkyl optionally substituted with a hydroxyl group, a carboxyl group, a carbamoyl group, an amino group, or an amidinoamino group, optionally substituted cycloalkylalkyl, optionally substituted $C_6$ aryl $C_{1-6}$ alkyl, or optionally substituted 5- or 6-membered heteroaryl $C_{1-6}$ alkyl.

In one embodiment, $R_1$, $R_2$, and $R_3$ are each independently alkyl optionally substituted with a hydroxyl group, a carboxyl group, a carbamoyl group, an amino group, or an amidinoamino group, optionally substituted cycloalkylalkyl, optionally substituted benzyl, or optionally substituted 5- or 6-membered heteroarylmethyl.

In one embodiment, $R_1$, $R_2$, and $R_3$ are each independently alkyl optionally substituted with a hydroxyl group, a carboxyl group, a carbamoyl group, an amino group, or an amidinoamino group, cycloalkylalkyl, optionally substituted benzyl, or optionally substituted 5- or 6-membered heteroarylmethyl.

In one embodiment, $R_1$ and $R_2$ are each independently $C_{1-6}$ alkyl, $C_{6-10}$ aryl $C_{1-6}$ alkyl, $C_{1-6}$ alkyl-substituted $C_{6-10}$ aryl $C_{1-6}$ alkyl, $C_{1-6}$ alkoxy-substituted $C_{6-10}$ aryl $C_{1-6}$ alkyl, $C_{1-6}$ haloalkoxy-substituted $C_{6-10}$ aryl $C_{1-6}$ alkyl, hydroxy-substituted $C_{6-10}$ aryl $C_{1-6}$ alkyl, halogen-substituted $C_{6-10}$ aryl $C_{1-6}$ alkyl, $C_{6-10}$ aryl $C_{1-6}$ alkyl substituted with $C_{1-6}$ alkyl-substituted amino, $C_{5-6}$ cycloalkyl, $C_{1-6}$ alkyl-substituted $C_5$-6 cycloalkyl, or optionally substituted 5- or 6-membered heterocyclyl, and
$R_3$ is $C_{1-6}$ alkyl, $C_{6-10}$ aryl $C_{1-6}$ alkyl, $C_{1-6}$ alkyl-substituted $C_{6-10}$ aryl $C_{1-6}$ alkyl, halogen-substituted $C_{6-10}$ aryl $C_{1-6}$ alkyl, $C_{1-6}$ haloalkoxy-substituted $C_{6-10}$ aryl $C_{1-6}$ alkyl, $C_{1-6}$ alkoxy-substituted $C_{6-10}$ aryl $C_{1-6}$ alkyl, hydroxy-substituted $C_{6-10}$ aryl $C_{1-6}$ alkyl, $C_{6-10}$ aryl $C_{1-6}$ alkyl substituted with $C_{1-6}$ alkyl-substituted amino, $C_{6-10}$ aryl, $C_{1-4}$ alkyl-substituted $C_{6-10}$ aryl, or halogen-substituted $C_{6-10}$ aryl.

In one embodiment, $R_1$ and $R_2$ are each independently methyl, n-propyl, isobutyl, isopentyl, benzyl, methyl- or t-butyl-substituted benzyl, fluoro- or chloro-substituted benzyl, methoxy- or ethoxy-substituted benzyl, trifluoromethoxy-substituted benzyl, hydroxy-substituted benzyl, dimethylamino-substituted benzyl, cyclohexyl, methyl-substituted cyclohexyl, tetrahydro-2H-pyran-4-yl, or 2,2,6,6-tetramethylpiperidin-4-yl, and
$R_3$ is methyl, n-propyl, isobutyl, isopentyl, benzyl, methyl- or t-butyl-substituted benzyl, fluoro- or chloro-substituted benzyl, methoxy- or ethoxy-substituted benzyl, trifluoromethoxy-substituted benzyl, hydroxy-substituted benzyl, dimethylamino-substituted benzyl, or phenyl.

In one embodiment, $R_1$ and $R_2$ are each independently methyl, ethyl, n-propyl, isopropyl, isobutyl, isopentyl, benzyl, 4-methylbenzyl, 4-(t-butyl)benzyl, 4-fluorobenzyl, 3-chlorobenzyl, 4-chlorobenzyl, 4-methoxybenzyl, 4-ethoxybenzyl, 4-hydroxybenzyl, 3-hydroxybenzyl, 4-(dimethylamino)benzyl, 4-(trifluoromethoxy)benzyl, cyclohexyl, trans-4-methylcyclohexyl, tetrahydro-2H-pyran-4-yl, or 2,2,6,6-tetramethylpiperidin-4-yl, and
$R_3$ is methyl, ethyl, n-propyl, isopropyl, isobutyl, isopentyl, benzyl, 4-methylbenzyl, 4-(t-butyl)benzyl, 4-fluorobenzyl, 3-chlorobenzyl, 4-chlorobenzyl, 4-methoxybenzyl, 4-ethoxybenzyl, 4-hydroxybenzyl, 3-hydroxybenzyl, 4-(dimethylamino)benzyl, 4-(trifluoromethoxy)benzyl, or phenyl.

In one embodiment, $R_1$ and $R_2$ are each independently $C_{1-6}$ alkyl optionally substituted with a hydroxyl group, a carboxyl group, a carbamoyl group, an amino group, or an amidinoamino group, optionally substituted $C_{3-6}$ cycloalkyl $C_{1-6}$ alkyl, optionally substituted $C_{6-10}$ aryl $C_{1-6}$ alkyl, optionally substituted 5- to 10-membered heteroaryl $C_{1-6}$ alkyl, or optionally substituted 4- to 6-membered heterocycloalkyl $C_{1-6}$ alkyl.

In one embodiment, $R_1$ and $R_2$ are each independently $C_{1-6}$ alkyl optionally substituted with a hydroxyl group, a carboxyl group, a carbamoyl group, an amino group, or an amidinoamino group, optionally substituted $C_{3-6}$ cycloalkyl $C_{1-6}$ alkyl, or optionally substituted $C_{6-10}$ aryl $C_{1-6}$ alkyl.

In one embodiment, $R_1$ and $R_2$ are each independently $C_{1-6}$ alkyl, hydroxy-substituted $C_{1-6}$ alkyl, carbamoyl-substituted $C_{1-6}$ alkyl, amidinoamino-substituted $C_{1-6}$ alkyl, carboxy-substituted $C_{1-6}$ alkyl, $C_{6-10}$ aryl $C_{1-6}$ alkyl, $C_{1-4}$ alkyl-substituted $C_{6-10}$ aryl $C_{1-6}$ alkyl, hydroxy-substituted $C_{6-10}$ aryl $C_{1-6}$ alkyl, halogen-substituted $C_{6-10}$ aryl $C_{1-6}$ alkyl, $C_{1-4}$ alkoxy-substituted $C_{6-10}$ aryl $C_{1-6}$ alkyl, $C_{1-4}$ alkoxycarbonyl-substituted $C_{1-6}$ alkyl, $C_{6-10}$ aryl $C_{1-6}$ alkyl substituted with $C_{1-4}$ alkyl-substituted amino, or $C_{3-6}$ cycloalkyl $C_{1-6}$ alkyl.

In one embodiment, $R_2$ is optionally substituted $C_{6-10}$ aryl $C_{1-6}$ alkyl. In one embodiment, $R_2$ is optionally substituted $C_6$ aryl $C_{1-6}$ alkyl. In one embodiment, $R_2$ is optionally substituted benzyl.

In one embodiment, $R_2$ is each independently hydroxy-substituted $C_{1-6}$ alkyl, carbamoyl-substituted $C_{1-6}$ alkyl, amidinoamino-substituted $C_{1-6}$ alkyl, carboxy-substituted $C_{1-6}$ alkyl, $C_{6-10}$ aryl $C_{1-6}$ alkyl, $C_{1-4}$ alkyl-substituted $C_{6-10}$ aryl $C_{1-6}$ alkyl, hydroxy-substituted $C_{6-10}$ aryl $C_{1-6}$ alkyl, halogen-substituted $C_{6-10}$ aryl $C_{1-6}$ alkyl, $C_{1-4}$ alkoxy-substituted $C_{6-10}$ aryl $C_{1-6}$ alkyl, $C_{1-4}$ alkoxycarbonyl-substituted $C_{1-6}$ alkyl, $C_{6-10}$ aryl $C_{1-6}$ alkyl substituted with $C_{1-4}$ alkyl-substituted amino, or $C_{3-6}$ cycloalkyl $C_{1-6}$ alkyl.

In one embodiment, $R_2$ is $C_{6-10}$ aryl $C_{1-6}$ alkyl, $C_{1-4}$ alkyl-substituted $C_{6-10}$ aryl $C_{1-6}$ alkyl, hydroxy-substituted $C_{6-10}$ aryl $C_{1-6}$ alkyl, halogen-substituted $C_{6-10}$ aryl $C_{1-6}$ alkyl, $C_{1-4}$ alkoxy-substituted $C_{6-10}$ aryl $C_{1-6}$ alkyl, or $C_{6-10}$ aryl $C_{1-6}$ alkyl substituted with $C_{1-4}$ alkyl-substituted amino.

In one embodiment, $R_2$ is $C_6$ aryl $C_{1-6}$ alkyl, $C_{1-6}$ alkyl-substituted $C_6$ aryl $C_{1-6}$ alkyl, $C_{1-6}$ alkoxy-substituted $C_6$ aryl $C_{1-6}$ alkyl, $C_{1-6}$ haloalkoxy-substituted $C_6$ aryl $C_{1-6}$ alkyl, hydroxy-substituted $C_6$ aryl $C_{1-6}$ alkyl, halogen-substituted $C_6$ aryl $C_{1-6}$ alkyl, or $C_6$ aryl $C_{1-6}$ alkyl substituted with $C_{1-6}$ alkyl-substituted amino.

In one embodiment, $R_2$ is benzyl, methyl- or t-butyl-substituted benzyl, methoxy- or ethoxy-substituted benzyl, trifluoromethoxy-substituted benzyl, hydroxy-substituted benzyl, fluoro- or chloro-substituted benzyl, or dimethylamino-substituted benzyl.

In one embodiment, $R_2$ is isobutyl, isopentyl, benzyl, 4-fluorobenzyl, 4-chlorobenzyl, 4-hydroxybenzyl, 3-hydroxybenzyl, cyclohexyl, tetrahydro-2H-pyran-4-yl, or 2,2,6,6-tetramethylpiperidin-4-yl.

In one embodiment, $R_2$ is benzyl, 4-fluorobenzyl, 4-chlorobenzyl, 4-hydroxybenzyl, or 3-hydroxybenzyl.

In one embodiment, $R_2$ is 5- or 6-membered heteroaryl-substituted $C_{1-6}$ alkyl. In one embodiment, the 5- or 6-membered heteroaryl group in 5- or 6-membered heteroaryl-substituted alkyl of $R_2$ can be selected from the group consisting of thienyl, pyrrolyl, thiazolyl, isothiazolyl, pyrazolyl, imidazolyl, furanyl, oxazolyl, isoxazolyl, oxadiazolyl, thiadiazolyl, triazolyl, tetrazolyl, pyridyl, pyridazinyl, pyrimidinyl, and pyrazinyl. In one embodiment, $R_2$ is pyridyl-substituted methyl, or thienyl-substituted methyl.

In one embodiment, $C_{10}$ aryl-substituted $C_{1-6}$ alkyl. In one embodiment, $R_2$ is 1-naphthylmethyl or 2-naphthylmethyl. In one embodiment, $R_2$ is 1-naphthylmethyl.

In one embodiment, $R_1$ is alkyl or optionally substituted benzyl, wherein the alkyl is unsubstituted.

In one embodiment, $R_1$ is $C_{1-6}$ alkyl optionally substituted with a hydroxyl group, a carboxyl group, a carbamoyl group, an amino group, or an amidinoamino group, optionally substituted $C_{3-6}$ cycloalkyl $C_{1-6}$ alkyl, optionally substituted $C_6$ aryl $C_{1-6}$ alkyl, or optionally substituted 5- or 6-membered heteroaryl $C_{1-6}$ alkyl.

In one embodiment, $R_1$ is $C_{1-6}$ alkyl optionally substituted with a hydroxyl group, a carboxyl group, a carbamoyl group, an amino group, or an amidinoamino group, or optionally substituted benzyl.

In one embodiment, $R_1$ is $C_{1-6}$ alkyl, $C_6$ aryl $C_{1-6}$ alkyl, $C_{1-6}$ alkyl-substituted $C_6$ aryl $C_{1-6}$ alkyl, $C_{1-6}$ alkoxy-substituted $C_6$ aryl $C_{1-6}$ alkyl, $C_{1-6}$ haloalkoxy-substituted $C_6$ aryl $C_{1-6}$ alkyl, hydroxy-substituted $C_6$ aryl $C_{1-6}$ alkyl, halogen-substituted $C_6$ aryl $C_{1-6}$ alkyl, or $C_6$ aryl $C_{1-6}$ alkyl substituted with $C_{1-6}$ alkyl-substituted amino.

In one embodiment, $R_1$ is methyl, isobutyl, isopentyl, benzyl, methyl- or t-butyl-substituted benzyl, methoxy- or ethoxy-substituted benzyl, trifluoromethoxy-substituted benzyl, hydroxy-substituted benzyl, fluoro- or chloro-substituted benzyl, or dimethylamino-substituted benzyl.

In one embodiment, $R_1$ is methyl, isobutyl, isopentyl, benzyl, 4-methylbenzyl, 4-(t-butyl)benzyl, 3-chlorobenzyl, 4-chlorobenzyl, 4-methoxybenzyl, 4-ethoxybenzyl, 4-hydroxybenzyl, 4-(dimethylamino)benzyl, cyclohexyl, or trans-4-methylcyclohexyl.

In one embodiment, $R_1$ is methyl, isobutyl, isopentyl, benzyl, 4-methylbenzyl, 4-(t-butyl)benzyl, 3-chlorobenzyl, 4-chlorobenzyl, 4-methoxybenzyl, 4-ethoxybenzyl, 4-hydroxybenzyl, or 4-(dimethylamino)benzyl.

In one embodiment, $R_1$ is $C_{3-6}$ cycloalkyl $C_{1-6}$ alkyl.

In one embodiment, the $C_{3-6}$ cycloalkyl group in $C_{3-6}$ cycloalkyl $C_{1-6}$ alkyl of $R_1$ can be selected from the group consisting of cyclopropyl, cyclobutyl, cyclopentyl, and cyclohexyl, and the $C_{1-6}$ alkyl group can be selected from the group consisting of methyl, ethyl, n-propyl, isopropyl, n-butyl, isobutyl, tert-butyl, sec-butyl, n-pentyl, isopentyl, neopentyl, tert-pentyl, 1,2-dimethylpropyl, and n-hexyl.

In one embodiment, $R_1$ is cyclopropylmethyl, cyclobutylmethyl, cyclopentylmethyl, cyclohexylmethyl, cyclopropylethyl, cyclobutylethyl, cyclopentylethyl, or cyclohexylethyl.

In one embodiment, $R_1$ is cyclopropylmethyl or cyclohexylmethyl.

In one embodiment, $R_3$ is alkyl optionally substituted with a hydroxyl group, a carboxyl group, a carbamoyl group, an amino group, or an amidinoamino group, optionally substituted $C_{6-10}$ arylalkyl, optionally substituted $C_{2-6}$ alkenyl, or optionally substituted $C_{6-10}$ aryl.

In one embodiment, $R_3$ is alkyl optionally substituted with a hydroxyl group, a carboxyl group, a carbamoyl group, an amino group, or an amidinoamino group, or optionally substituted $C_{6-10}$ arylalkyl.

In one embodiment, $R_3$ is optionally substituted alkyl. In one embodiment, $R_3$ is alkyl, wherein the alkyl is unsubstituted. In one embodiment, $R_3$ is optionally substituted $C_{1-6}$ alkyl. $R_3$ is $C_{1-6}$ alkyl.

In one embodiment, $R_3$ is $C_{1-6}$ alkyl optionally substituted with a hydroxyl group, a carboxyl group, a carbamoyl group, an amino group, or an amidinoamino group, or optionally substituted $C_{6-10}$ aryl $C_{1-6}$ alkyl.

In one embodiment, $R_3$ is $C_{1-6}$ alkyl, hydroxy-substituted $C_{1-6}$ alkyl, carbamoyl-substituted $C_{1-6}$ alkyl, amidinoamino-substituted $C_{1-6}$ alkyl, carboxy-substituted $C_{1-6}$ alkyl, $C_{6-10}$ aryl $C_{1-6}$ alkyl, $C_{1-4}$ alkyl-substituted $C_{6-10}$ aryl $C_{1-6}$ alkyl, hydroxy-substituted $C_{6-10}$ aryl $C_{1-6}$ alkyl, halogen-substituted $C_{6-10}$ aryl $C_{1-6}$ alkyl, $C_{1-4}$ alkoxy-substituted $C_{6-10}$ aryl $C_{1-6}$ alkyl, $C_{1-4}$ alkoxycarbonyl-substituted $C_{1-6}$ alkyl, $C_{6-10}$ aryl $C_{1-6}$ alkyl substituted with $C_{1-4}$ alkyl-substituted amino, or $C_{3-6}$ cycloalkyl $C_{1-6}$ alkyl.

In one embodiment, $R_3$ is $C_{1-6}$ alkyl, hydroxy-substituted $C_{1-6}$ alkyl, carbamoyl-substituted $C_{1-6}$ alkyl, amidinoamino-substituted $C_{1-6}$ alkyl, carboxy-substituted $C_{1-6}$ alkyl, $C_{1-4}$ alkoxycarbonyl-substituted $C_{1-6}$ alkyl, or $C_{3-6}$ cycloalkyl $C_{1-6}$ alkyl.

In one embodiment, $R_3$ is $C_{1-6}$ alkyl, $C_6$ aryl $C_{1-6}$ alkyl, $C_{1-6}$ alkyl-substituted $C_6$ aryl $C_{1-6}$ alkyl, halogen-substituted $C_6$ aryl $C_{1-6}$ alkyl, $C_{1-6}$ haloalkoxy-substituted $C_6$ aryl $C_{1-6}$ alkyl, $C_{1-6}$ alkoxy-substituted $C_6$ aryl $C_{1-6}$ alkyl, hydroxy-substituted $C_6$ aryl $C_{1-6}$ alkyl, or $C_6$ aryl $C_{1-6}$ alkyl substituted with $C_{1-6}$ alkyl-substituted amino.

In one embodiment, $R_3$ is n-propyl, isobutyl, isopentyl, benzyl, methyl- or t-butyl-substituted benzyl, fluoro- or chloro-substituted benzyl, methoxy- or ethoxy-substituted benzyl, trifluoromethoxy-substituted benzyl, hydroxy-substituted benzyl, or dimethylamino-substituted benzyl.

In one embodiment, $R_3$ is $C_{1-6}$ alkyl, $C_6$ aryl $C_{1-6}$ alkyl, or halogen-substituted $C_6$ aryl $C_{1-6}$ alkyl.

In one embodiment, $R_3$ is n-propyl, isobutyl, isopentyl, benzyl, or chloro-substituted benzyl.

In one embodiment, $R_3$ is $C_{1-6}$ alkyl.

In one embodiment, $R_3$ is n-propyl, isobutyl, isopentyl, benzyl, 4-chlorobenzyl, or phenyl.

In one embodiment, Ra is n-propyl, isobutyl, or isopentyl.

In one embodiment, $R_3$ is $C_{3-6}$ cycloalkyl $C_{1-6}$ alkyl.

In one embodiment, the $C_{3-6}$ cycloalkyl group in $C_{3-6}$ cycloalkyl $C_{1-6}$ alkyl of $R_3$ can be selected from the group consisting of cyclopropyl, cyclobutyl, cyclopentyl, and cyclohexyl, and the $C_{1-6}$ alkyl group can be selected from the group consisting of methyl, ethyl, n-propyl, isopropyl, n-butyl, isobutyl, tert-butyl, sec-butyl, n-pentyl, isopentyl, neopentyl, tert-pentyl, 1,2-dimethylpropyl, and n-hexyl.

In one embodiment, $R_3$ is cyclopropylmethyl.

In one embodiment, $R_3$ is $C_{2-6}$ alkenyl.

In one embodiment, $R_3$ can be selected from the group consisting of 1-propenyl, 1-butenyl, 1-pentenyl, 1-hexenyl, 2-methyl-1-propenyl, 2-methyl-1-butenyl, 2-ethyl-1-butenyl, and 2-methyl-1-pentenyl.

In one embodiment, $R_3$ is 2-methyl-1-propenyl.

In one embodiment, $R_2$ is benzyl, $R_1$ is isobutyl, methoxy-substituted benzyl, methyl-substituted benzyl, t-butyl-substituted benzyl, or chloro-substituted benzyl, and $R_3$ is isobutyl.

In one embodiment, $R_2$ is benzyl, $R_1$ is methoxy-substituted benzyl or chloro-substituted benzyl, and $R_3$ is isobutyl.

In one embodiment, $R_2$ is benzyl, $R_1$ is 4-methoxybenzyl or 3-chlorobenzyl, and $R_3$ is isobutyl.

In one embodiment, $R_2$ in the compound of formula IF is benzyl, $R_1$ is 4-methoxybenzyl, and $R_3$ is isobutyl.

In one embodiment, $R_2$ in the compound of formula IB is benzyl, $R_1$ is 4-methoxybenzyl, and $R_3$ is isobutyl.

In one embodiment, $R_2$ is benzyl or chloro-substituted benzyl, and $R_1$ and $R_3$ are each independently isobutyl or isopentyl.

In one embodiment, $R_2$ is benzyl, $R_1$ is isopentyl, and $R_3$ is isobutyl.

In one embodiment, $R_2$ in the compound of formula IB is benzyl or 4-chlorobenzyl, and $R_1$ and $R_3$ are both isobutyl.

In one embodiment, $R_2$ in the compound of formula IB is benzyl, $R_1$ is isobutyl, and $R_3$ is isopentyl.

Preferred combinations of substituents $R_1$, $R_2$, and $R_3$ in compounds of formulae IF and IB of the disclosure are shown in the following table.

TABLE 1

| Combination No. | $R_1$ | $R_2$ | $R_3$ |
|---|---|---|---|
| 1 | methyl | benzyl | benzyl |
| 2 | 4-chlorobenzyl | benzyl | isobutyl |
| 3 | 3-chlorobenzyl | benzyl | isobutyl |
| 4 | 4-methoxybenzyl | benzyl | isobutyl |
| 5 | 4-methyl benzyl | benzyl | isobutyl |
| 6 | benzyl | isobutyl | isobutyl |
| 7 | isopentyl | isobutyl | benzyl |
| 8 | isobutyl | isobutyl | 4-chlorobenzyl |
| 9 | isobutyl | isobutyl | benzyl |
| 10 | 4-hydroxybenzyl | benzyl | isobutyl |
| 11 | isobutyl | isopentyl | benzyl |
| 12 | isobutyl | isobutyl | benzyl |
| 13 | isobutyl | benzyl | isobutyl |
| 14 | isobutyl | 4-chlorobenzyl | isobutyl |
| 15 | isobutyl | benzyl | isopentyl |
| 16 | isopentyl | benzyl | isobutyl |
| 17 | 4-(dimethylamino)benzyl | benzyl | isobutyl |
| 18 | 4-(tert-butyl)benzyl | benzyl | isobutyl |
| 19 | 4-hydroxybenzyl | benzyl | isopentyl |
| 20 | isopentyl | 4-chlorobenzyl | isobutyl |
| 21 | isopentyl | 4-fluorobenzyl | isobutyl |
| 22 | 4-(trifluoromethoxy)benzyl | benzyl | isobutyl |
| 23 | 4-ethoxybenzyl | benzyl | isobutyl |
| 24 | benzyl | 4-hydroxybenzyl | isobutyl |
| 25 | 4-methoxybenzyl | 4-hydroxybenzyl | isobutyl |
| 26 | 4-(dimethylamino)benzyl | 3-hydroxybenzyl | isobutyl |
| 27 | 4-(dimethylamino)benzyl | 4-hydroxybenzyl | isobutyl |
| 28 | benzyl | cyclohexyl | n-propyl |
| 29 | benzyl | trans-4-methylcyclohexyl | benzyl |
| 30 | benzyl | 2,2,6,6-tetramethylpiperidin-4-yl | benzyl |
| 31 | cyclohexyl | benzyl | isobutyl |
| 32 | cyclohexyl | benzyl | phenyl |
| 33 | tetrahydro-2H-pyran-4-yl | benzyl | phenyl |
| 34 | isobutyl | benzyl | phenyl |

Preferred combinations of substituents R₁, R₂, R₃ and X in the compounds of formulae IF and IB of the disclosure are shown below in the form of (R₁, R₂, R₃)=(M, N, Q), wherein R₁ (M) is selected from M1 to M15, R₂ (N) is selected from N1 to N11, and R₃ (Q) is selected from Q1 to Q6.

TABLE 2

| No. | Substituent | Symbol R₁ | R₂ | R₃ |
|---|---|---|---|---|
| 1 | isobutyl | M1 | N1 | Q1 |
| 2 | isopentyl | M2 | N2 | Q2 |
| 3 | benzyl | M3 | N3 | Q3 |
| 4 | 4-fluorobenzyl | — | N4 | — |
| 5 | 4-chlorobenzyl | M4 | N5 | Q4 |
| 6 | 3-chlorobenzyl | M5 | — | — |
| 7 | 4-hydroxybenzyl | M6 | N6 | — |
| 8 | 3-hydroxybenzyl | — | N7 | — |
| 9 | 4-methylbenzyl | M7 | — | — |
| 10 | 4-tert-butyl benzyl | M8 | — | — |
| 11 | 4-methoxybenzyl | M9 | — | — |
| 12 | 4-ethoxybenzyl | M10 | — | — |
| 13 | 4-(trifluoromethoxy)benzyl | M11 | — | — |
| 14 | 4-(dimethylamino)benzyl | M12 | — | — |
| 15 | cyclohexyl | M13 | N8 | — |
| 16 | trans-4-methylcyclohexyl | — | N9 | — |
| 17 | methyl | M14 | — | — |
| 18 | n-propyl | — | — | Q5 |
| 19 | phenyl | — | — | Q6 |
| 20 | 2,2,6,6-tetra methyl pi peridin-4-yl | — | N10 | — |
| 21 | tetrahydro-2H-pyran-4-yl | M15 | — | — |

Preferred combinations of substituents R₁, R₂, and R₃ (R₁, R₂, R₃)=(M1, N1, Q1), (M1, N1, Q2), (M1, N1, Q3), (M1, N1, Q4), (M1, N1, Q5), (M1, N1, Q6), (M1, N2, Q1), (M1, N2, Q2), (M1, N2, Q3), (M1, N2, Q4), (M1, N2, Q5), (M1, N2, Q6), (M1, N3, Q1), (M1, N3, Q2), (M1, N3, Q3), (M1, N3, Q4), (M1, N3, Q5), (M1, N3, Q6), (M1, N4, Q1), (M1, N4, Q2), (M1, N4, Q3), (M1, N4, Q4), (M1, N4, Q5), (M1, N4, Q6), (M1, N5, Q1), (M1, N5, Q2), (M1, N5, Q3), (M1, N5, Q4), (M1, N5, Q5), (M1, N5, Q6), (M1, N6, Q1), (M1, N6, Q2), (M1, N6, Q3), (M1, N6, Q4), (M1, N6, Q5), (M1, N6, Q6), (M1, N7, Q1), (M1, N7, Q2), (M1, N7, Q3), (M1, N7, Q4), (M1, N7, Q5), (M1, N7, Q6), (M1, N8, Q1), (M1, N8, Q2), (M1, N8, Q3), (M1, N8, Q4), (M1, N8, Q5), (M1, N8, Q6), (M1, N9, Q1), (M1, N9, Q2), (M1, N9, Q3), (M1, N9, Q4), (M1, N9, Q5), (M1, N9, Q6), (M1, N10, Q1), (M1, N10, Q2), (M1, N10, Q3), (M1, N10, Q4), (M1, N10, Q5), (M1, N10, Q6), (M2, N1, Q1), (M2, N1, Q2), (M2, N1, Q3), (M2, N1, Q4), (M2, N1, Q5), (M2, N1, Q6), (M2, N2, Q1), (M2, N2, Q2), (M2, N2, Q3), (M2, N2, Q4), (M2, N2, Q5), (M2, N2, Q6), (M2, N3, Q1), (M2, N3, Q2), (M2, N3, Q3), (M2, N3, Q4), (M2, N3, Q5), (M2, N3, Q6), (M2, N4, Q1), (M2, N4, Q2), (M2, N4, Q3), (M2, N4, Q4), (M2, N4, Q5), (M2, N4, Q6), (M2, N5, Q1), (M2, N5, Q2), (M2, N5, Q3), (M2, N5, Q4), (M2, N5, Q5), (M2, N5, Q6), (M2, N6, Q1), (M2, N6, Q2), (M2, N6, Q3), (M2, N6, Q4), (M2, N6, Q5), (M2, N6, Q6), (M2, N7, Q1), (M2, N7, Q2), (M2, N7, Q3), (M2, N7, Q4), (M2, N7, Q5), (M2, N7, Q6), (M2, N8, Q1), (M2, N8, Q2), (M2, N8, Q3), (M2, N8, Q4), (M2, N8, Q5), (M2, N8, Q6), (M2, N9, Q1), (M2, N9, Q2), (M2, N9, Q3), (M2, N9, Q4), (M2, N9, Q5), (M2, N9, Q6), (M2, N10, Q1), (M2, N10, Q2), (M2, N10, Q3), (M2, N10, Q4), (M2, N10, Q5), (M2, N10, Q6), (M3, N1, Q1), (M3, N1, Q2), (M3, N1, Q3), (M3, N1, Q4), (M3, N1, Q5), (M3, N1, Q6), (M3, N2, Q1), (M3, N2, Q2), (M3, N2, Q3), (M3, N2, Q4), (M3, N2, Q5), (M3, N2, Q6), (M3, N3, Q1), (M3, N3, Q2), (M3, N3, Q3), (M3, N3, Q4), (M3, N3, Q5), (M3, N3, Q6), (M3, N4, Q1), (M3, N4, Q2), (M3, N4, Q3), (M3, N4, Q4), (M3, N4, Q5), (M3, N4, Q6), (M3, N5, Q1), (M3, N5, Q2), (M3, N5, Q3), (M3, N5, Q4), (M3, N5, Q5), (M3, N5, Q6), (M3, N6, Q1), (M3, N6, Q2), (M3, N6, Q3), (M3, N6, Q4), (M3, N6, Q5), (M3, N6, Q6), (M3, N7, Q1), (M3, N7, Q2), (M3, N7, Q3), (M3, N7, Q4), (M3, N7, Q5), (M3, N7, Q6), (M3, N8, Q1), (M3, N8, Q2), (M3, N8, Q3), (M3, N8, Q4), (M3, N8, Q5), (M3, N8, Q6), (M3, N9, Q1), (M3, N9, Q2), (M3, N9, Q3), (M3, N9, Q4), (M3, N9, Q5), (M3, N9, Q6), (M3, N10, Q1), (M3, N10, Q2), (M3, N10, Q3), (M3, N10, Q4), (M3, N10, Q5), (M3, N10, Q6), (M4, N1, Q1), (M4, N1, Q2), (M4, N1, Q3), (M4, N1, Q4), (M4, N1, Q5), (M4, N1, Q6), (M4, N2, Q1), (M4, N2, Q2), (M4, N2, Q3), (M4, N2, Q4), (M4, N2, Q5), (M4, N2, Q6), (M4, N3, Q1), (M4, N3, Q2), (M4, N3, Q3), (M4, N3, Q4), (M4, N3, Q5), (M4, N3, Q6), (M4, N4, Q1), (M4, N4, Q2), (M4, N4, Q3), (M4, N4, Q4), (M4, N4, Q5), (M4, N4, Q6), (M4, N5, Q1), (M4, N5, Q2), (M4, N5, Q3), (M4, N5, Q4), (M4, N5, Q5), (M4, N5, Q6), (M4, N6, Q1), (M4, N6, Q2), (M4, N6, Q3), (M4, N6, Q4), (M4, N6, Q5), (M4, N6, Q6), (M4, N7, Q1), (M4, N7, Q2), (M4, N7, Q3), (M4, N7, Q4), (M4, N7, Q5), (M4, N7, Q6), (M4, N8, Q1), (M4, N8, Q2), (M4, N8, Q3), (M4, N8, Q4), (M4, N8, Q5), (M4, N8, Q6), (M4, N9, Q1), (M4, N9, Q2), (M4, N9, Q3), (M4, N9, Q4), (M4, N9, Q5), (M4, N9, Q6), (M4, N10, Q1), (M4, N10, Q2), (M4, N10, Q3), (M4, N10, Q4), (M4, N10, Q5), (M4, N10, Q6), (M5, N1, Q1), (M5, N1, Q2), (M5, N1, Q3), (M5, N1, Q4), (M5, N1, Q5), (M5, N1, Q6), (M5, N2, Q1), (M5, N2, Q2), (M5, N2, Q3), (M5, N2, Q4), (M5, N2, Q5), (M5, N2, Q6), (M5, N3, Q1), (M5, N3, Q2), (M5, N3, Q3), (M5, N3, Q4), (M5, N3, Q5), (M5, N3, Q6), (M5, N4, Q1), (M5, N4, Q2), (M5, N4, Q3), (M5, N4, Q4), (M5, N4, Q5), (M5, N4, Q6), (M5, N5, Q1), (M5, N5, Q2), (M5, N5, Q3), (M5, N5, Q4), (M5, N5, Q5), (M5, N5, Q6), (M5, N6, Q1), (M5, N6, Q2), (M5, N6, Q3), (M5, N6, Q4), (M5, N6, Q5), (M5, N6, Q6), (M5, N7, Q1), (M5, N7, Q2), (M5, N7, Q3), (M5, N7, Q4), (M5, N7, Q5), (M5, N7, Q6), (M5, N8, Q1), (M5, N8, Q2), (M5, N8, Q3), (M5, N8, Q4), (M5, N8, Q5), (M5, N8, Q6), (M5, N9, Q1), (M5, N9, Q2), (M5, N9, Q3), (M5, N9, Q4), (M5, N9, Q5), (M5, N9, Q6), (M5, N10, Q1), (M5, N10, Q2), (M5, N10, Q3), (M5, N10, Q4), (M5, N10, Q5), (M5, N10, Q6), (M6, N1, Q1), (M6, N1, Q2), (M6, N1, Q3), (M6, N1, Q4), (M6, N1, Q5), (M6, N1, Q6), (M6, N2, Q1), (M6, N2, Q2), (M6, N2, Q3), (M6, N2, Q4), (M6, N2, Q5), (M6, N2, Q6), (M6, N3, Q1), (M6, N3, Q2), (M6, N3, Q3), (M6, N3, Q4), (M6, N3, Q5), (M6, N3, Q6), (M6, N4, Q1), (M6, N4, Q2), (M6, N4, Q3), (M6, N4, Q4), (M6, N4, Q5), (M6, N4, Q6), (M6, N5, Q1), (M6, N5, Q2), (M6, N5, Q3), (M6, N5, Q4), (M6, N5, Q5), (M6, N5, Q6), (M6, N6, Q1), (M6, N6, Q2), (M6, N6, Q3), (M6, N6, Q4), (M6, N6, Q5), (M6, N6, Q6), (M6, N7, Q1), (M6, N7, Q2), (M6, N7, Q3), (M6, N7, Q4), (M6, N7, Q5), (M6, N7, Q6), (M6, N8, Q1), (M6, N8, Q2), (M6, N8, Q3), (M6, N8, Q4), (M6, N8, Q5), (M6, N8, Q6), (M6, N9, Q1), (M6, N9, Q2), (M6, N9, Q3), (M6, N9, Q4), (M6, N9, Q5), (M6, N9, Q6), (M6, N10, Q1), (M6, N10, Q2), (M6, N10, Q3), (M6, N10, Q4), (M6, N10, Q5), (M6, N10, Q6), (M7, N1, Q1), (M7, N1, Q2), (M7, N1, Q3), (M7, N1, Q4), (M7, N1, Q5), (M7, N1, Q6), (M7, N2, Q1), (M7, N2, Q2), (M7, N2, Q3), (M7, N2, Q4), (M7, N2, Q5), (M7, N2, Q6), (M7, N3, Q1), (M7, N3, Q2), (M7, N3, Q3), (M7, N3, Q4), (M7, N3, Q5), (M7, N3, Q6), (M7, N4, Q1), (M7, N4, Q2), (M7, N4, Q3), (M7, N4, Q4), (M7, N4, Q5), (M7, N4, Q6), (M7, N5, Q1), (M7, N5, Q2), (M7, N5, Q3), (M7, N5, Q4), (M7, N5, Q5), (M7, N5, Q6), (M7, N6, Q1), (M7, N6, Q2), (M7, N6, Q3), (M7, N6, Q4), (M7, N6, Q5), (M7, N6, Q6), (M7, N7, Q1), (M7, N7, Q2), (M7, N7, Q3), (M7, N7, Q4), (M7, N7, Q5), (M7, N7, Q6), (M7, N8, Q1), (M7, N8, Q2), (M7, N8, Q3), (M7, N8, Q4), (M7, N8, Q5), (M7, N8, Q6), (M7, N9, Q1), (M7, N9, Q2), (M7, N9, Q3), (M7, N9, Q4), (M7, N9, Q5), (M7, N9, Q6), (M7, N10, Q1), (M7, N10, Q2), (M7, N10, Q3), (M7, N10, Q4), (M7, N10, Q5), (M7, N10, Q6), (M8, N1, Q1), (M8, N1, Q2), (M8, N1, Q3), (M8, N1, Q4), (M8, N1, Q5), (M8, N1, Q6), (M8, N2, Q1), (M8, N2, Q2), (M8, N2, Q3), (M8, N2, Q4), (M8, N2, Q5), (M8, N2, Q6), (M8, N3, Q1), (M8, N3, Q2), (M8, N3, Q3), (M8, N3, Q4), (M8, N3, Q5), (M8, N3, Q6), (M8, N4, Q1), (M8, N4, Q2), (M8, N4, Q3), (M8, N4, Q4), (M8, N4, Q5), (M8, N4, Q6), (M8, N5, Q1), (M8, N5, Q2), (M8, N5, Q3), (M8, N5, Q4), (M8, N5, Q5), (M8, N5, Q6), (M8, N6, Q1), (M8, N6, Q2), (M8, N6, Q3), (M8, N6, Q4), (M8, N6, Q5), (M8, N6, Q6), (M8, N7, Q1), (M8, N7, Q2), (M8, N7, Q3), (M8, N7, Q4), (M8, N7, Q5), (M8, N7, Q6), (M8, N8, Q1), (M8, N8, Q2), (M8, N8, Q3), (M8, N8, Q4), (M8, N8, Q5), (M8, N8, Q6), (M8, N9, Q1), (M8, N9, Q2), (M8, N9, Q3), (M8, N9, Q4), (M8, N9, Q5), (M8, N9, Q6), (M8, N10, Q1), (M8, N10, Q2), (M8, N10, Q3), (M8, N10, Q4), (M8, N10, Q5), (M8, N10, Q6), (M9, N1, Q1), (M9, N1, Q2), (M9, N1, Q3), (M9, N1, Q4), (M9, N1, Q5), (M9, N1, Q6), (M9, N2, Q1), (M9, N2, Q2), (M9, N2, Q3), (M9, N2, Q4), (M9, N2, Q5), (M9, N2, Q6), (M9, N3, Q1), (M9, N3, Q2), (M9, N3, Q3), (M9, N3, Q4), (M9, N3, Q5), (M9, N3, Q6), (M9, N4, Q1), (M9, N4, Q2), (M9, N4, Q3), (M9, N4, Q4), (M9, N4, Q5), (M9, N4, Q6), (M9, N5, Q1), (M9, N5, Q2), (M9, N5, Q3), (M9, N5, Q4), (M9, N5, Q5), (M9, N5, Q6), (M9, N6, Q1), (M9, N6, Q2), (M9, N6, Q3), (M9, N6, Q4), (M9, N6, Q5), (M9, N6, Q6), (M9, N7, Q1), (M9, N7, Q2), (M9, N7, Q3), (M9, N7, Q4), (M9, N7, Q5), (M9, N7, Q6), (M9, N8, Q1), (M9, N8, Q2), (M9, N8, Q3), (M9, N8, Q4), (M9, N8, Q5), (M9, N8, Q6), (M9, N9, Q1), (M9, N9, Q2), (M9, N9, Q3), (M9, N9, Q4), (M9, N9, Q5), (M9, N9, Q6), (M9, N10, Q1), (M9, N10, Q2), (M9, N10, Q3), (M9, N10, Q4), (M9, N10, Q5), (M9, N10, Q6), (M10, N1, Q1), (M10, N1, Q2), (M10, N1, Q3), (M10, N1, Q4), (M10, N1, Q5), (M10, N1, Q6), (M10, N2, Q1), (M10, N2, Q2), (M10, N2, Q3), (M10, N2, Q4), (M10, N2, Q5), (M10, N2, Q6), (M10, N3, Q1), (M10, N3, Q2), (M10, N3, Q3), (M10, N3, Q4), (M10, N3, Q5), (M10, N3, Q6), (M10, N4, Q1), (M10, N4, Q2), (M10, N4, Q3), (M10, N4, Q4), (M10, N4, Q6), (M10, N5, Q1), (M10, N5, Q2), (M10, N5, Q3), (M10, N5, Q4), (M10, N5, Q5), (M10, N5, Q6), (M10, N6, Q2), (M10, N6, Q3), (M10, N6, Q4), (M10, N6, Q5), (M10, N6, Q6), (M10, N7, Q1), (M10, N7, Q2), (M10, N7, Q3), (M10, N7, Q4), (M10, N7, Q5), (M10, N7, Q6), (M10, N8, Q1), (M10, N8, Q2), (M10, N8, Q3), (M10, N8, Q4), (M10, N8, Q5), (M10, N8, Q6), (M10, N9, Q1), (M10, N9, Q2), (M10, N9, Q3), (M10, N9, Q4), (M10, N9, Q5), (M10, N9, Q6), (M10, N10, Q1), (M10, N10, Q2), (M10, N10, Q3), (M10, N10, Q4), (M10, N10, Q5), (M10, N10, Q6), (M11, N1, Q1), (M11, N1, Q2), (M11, N1, Q3), (M11, N1, Q4), (M11, N1, Q5), (M11, N1, Q6), (M11, N2, Q1), (M11, N2, Q2), (M11, N2, Q3), (M11, N2, Q4), (M11, N2, Q5), (M11, N2, Q6), (M11, N3, Q1), (M11, N3, Q2), (M11, N3, Q3), (M11, N3, Q4), (M11, N3, Q5), (M11, N3, Q6), (M11, N4, Q1), (M11, N4, Q2), (M11, N4, Q3), (M11, N4, Q4), (M11, N4, Q5), (M11, N4, Q6), (M11, N5, Q1), (M11, N5, Q2), (M11, N5, Q3), (M11, N5, Q4), (M11, N5, Q5), (M11, N5, Q6), (M11, N6, Q1), (M11, N6, Q2), (M11, N6, Q3), (M11, N6, Q4), (M11, N6, Q5), (M11, N6, Q6), (M11, N7, Q1), (M11, N7, Q2), (M11, N7, Q3), (M11, N7, Q4), (M11, N7, Q5), (M11, N7, Q6), (M11, N8, Q1), (M11, N8, Q2), (M11, N8, Q3), (M11, N8, Q4), (M11, N8, Q5), (M11, N8, Q6), (M11, N9, Q1), (M11, N9, Q2), (M11, N9, Q3), (M11, N9, Q4), (M11, N9, Q5), (M11, N9, Q6), (M11, N10, Q1), (M11, N10, Q2), (M11, N10, Q3), (M11, N10, Q4), (M11, N10, Q5), (M11, N10, Q6), (M12, N1, Q1), (M12, N1, Q2), (M12, N1, Q3), (M12, N1, Q4), (M12, N1, Q5), (M12, N1, Q6), (M12, N2, Q1), (M12, N2, Q2), (M12, N2, Q3), (M12, N2, Q4), (M12, N2, Q5), (M12, N2, Q6), (M12, N3, Q1), (M12, N3, Q2), (M12, N3, Q3), (M12, N3, Q4), (M12, N3, Q5), (M12, N3, Q6), (M12, N4, Q1), (M12, N4, Q2), (M12, N4, Q3), (M12, N4, Q4), (M12, N4, Q5), (M12, N4, Q6), (M12, N5, Q1), (M12, N5, Q2), (M12, N5, Q3), (M12, N5, Q4), (M12, N5, Q5), (M12, N5, Q6), (M12, N6, Q1), (M12, N6, Q2), (M12, N6, Q3), (M12, N6, Q4), (M12, N6, Q5), (M12, N6, Q6), (M12, N7, Q1), (M12, N7, Q2), (M12, N7, Q3), (M12, N7, Q4), (M12, N7, Q5), (M12, N7, Q6), (M12, N8, Q1), (M12, N8, Q2), (M12, N8, Q3), (M12, N8, Q4), (M12, N8, Q5), (M12, N8, Q6), (M12, N9, Q1), (M12, N9, Q2), (M12, N9, Q3), (M12, N9, Q4), (M12, N9, Q5), (M12, N9, Q6), (M12, N10, Q1), (M12, N10, Q2), (M12, N10, Q3), (M12, N10, Q4), (M12, N10, Q5), (M12, N10, Q6), (M13, N1, Q1), (M13, N1, Q2), (M13, N1, Q3), (M13, N1, Q4), (M13, N1, Q5), (M13, N1, Q6), (M13, N2, Q1), (M13, N2, Q2), (M13, N2, Q3), (M13, N2, Q4), (M13, N2, Q5), (M13, N2, Q6), (M13, N3, Q1), (M13, N3, Q2), (M13, N3, Q3), (M13, N3, Q4), (M13, N3, Q5), (M13, N3, Q6), (M13, N4, Q1), (M13, N4, Q2), (M13, N4, Q3), (M13, N4, Q4), (M13, N4, Q5), (M13, N4, Q6), (M13, N5, Q1), (M13, N5, Q2), (M13, N5, Q3), (M13, N5, Q4), (M13, N5, Q5), (M13, N5, Q6), (M13, N6, Q1), (M13, N6, Q2), (M13, N6, Q3), (M13, N6, Q4), (M13, N6, Q5), (M13, N6, Q6), (M13, N7, Q1), (M13, N7, Q2), (M13, N7, Q3), (M13, N7, Q4), (M13, N7, Q5), (M13, N7, Q6), (M13, N8, Q1), (M13, N8, Q2), (M13, N8, Q3), (M13, N8, Q4), (M13, N8, Q5), (M13, N8, Q6), (M13, N9, Q1), (M13, N9, Q2), (M13, N9, Q3), (M13, N9, Q4), (M13, N9, Q5), (M13, N9, Q6), (M13, N10, Q1), (M13, N10, Q2), (M13, N10, Q3), (M13, N10, Q4), (M13, N10, Q5), (M13, N10, Q6), (M14, N1, Q1), (M14, N1, Q2), (M14, N1, Q3), (M14, N1, Q4), (M14, N1, Q5), (M14, N1, Q6), (M14, N2, Q1), (M14, N2, Q2), (M14, N2, Q3), (M14, N2, Q4), (M14, N2, Q5), (M14, N2, Q6), (M14, N3, Q1), (M14, N3, Q2), (M14, N3, Q3), (M14, N3, Q4), (M14, N3, Q5), (M14, N3, Q6), (M14, N4, Q1), (M14, N4, Q2), (M14, N4, Q3), (M14, N4, Q4), (M14, N4, Q5), (M14, N4, Q6), (M14, N5, Q1), (M14, N5, Q2), (M14, N5, Q3), (M14, N5, Q4), (M14, N5, Q5), (M14, N5, Q6), (M14, N6, Q1), (M14, N6, Q2), (M14, N6, Q3), (M14, N6, Q4), (M14, N6, Q5), (M14, N6, Q6), (M14, N7, Q1), (M14, N7, Q2), (M14, N7, Q3), (M14, N7, Q4), (M14, N7, Q5), (M14, N7, Q6), (M14, N8, Q1), (M14, N8, Q2), (M14, N8, Q3), (M14, N8, Q4), (M14, N8, Q5), (M14, N8, Q6), (M14, N9, Q1), (M14, N9, Q2), (M14, N9, Q3), (M14, N9, Q4), (M14, N9, Q5), (M14, N9, Q6), (M14, N10, Q1), (M14, N10, Q2), (M14, N10, Q3), (M14, N10, Q4), (M14, N10, Q5), (M14, N10, Q6), (M15, N1, Q1), (M15, N1, Q2), (M15, N1, Q3), (M15, N1, Q4), (M15, N1, Q5), (M15, N1, Q6), (M15, N2, Q1), (M15, N2, Q2), (M15, N2, Q3), (M15, N2, Q4), (M15, N2, Q5), (M15, N2, Q6), (M15, N3, Q1), (M15, N3, Q2), (M15, N3, Q3), (M15, N3, Q4), (M15, N3, Q5), (M15, N3, Q6), (M15, N4, Q1), (M15, N4, Q2), (M15, N4, Q3), (M15, N4, Q4), (M15, N4, Q5), (M15, N4, Q6), (M15, N5, Q1), (M15, N5, Q2), (M15, N5, Q3), (M15, N5, Q4), (M15, N5, Q5), (M15, N5, Q6), (M15, N6, Q1), (M15, N6, Q2), (M15, N6, Q3), (M15, N6, Q4), (M15, N6, Q5), (M15, N6, Q6), (M15, N7, Q1), (M15, N7, Q2), (M15, N7, Q3), (M15, N7, Q4), (M15, N7, Q5), (M15, N7, Q6), (M15, N8, Q1), (M15, N8, Q2), (M15, N8, Q3), (M15, N8, Q4), (M15, N8, Q5), (M15, N8, Q6), (M15, N9, Q1), (M15, N9, Q2), (M15, N9, Q3), (M15, N9, Q4), (M15, N9, Q5), (M15, N9, Q6), (M15, N10, Q1), (M15, N10, Q2), (M15, N10, Q3), (M15, N10, Q4), (M15, N10, Q5), (M15, N10, Q6)

In some embodiments, the compound of the disclosure can be exemplified as a compound represented by formula IB:

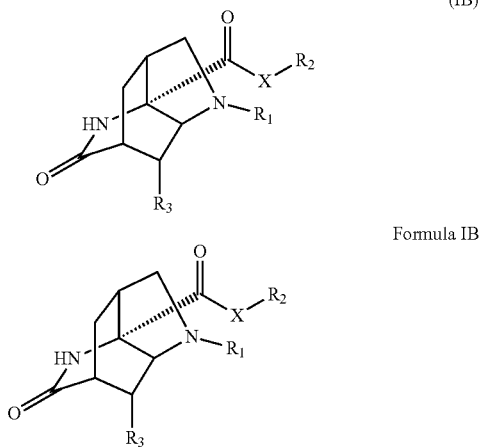

Formula IB or an enantiomer thereof, or a salt thereof, or a solvate thereof, wherein $R_1$, $R_2$, and $R_3$ are defined the same as those for formula IF, and X is —NH—.

The compound of the disclosure is further described hereinafter.

While the compound of the disclosure can have enantiomers and stereoisomers such as tautomers and geometric isomers depending on the type of substituent, they are also encompassed by the present disclosure. Specifically, if there is one or more asymmetric carbon atoms in the compound of the disclosure, there is a diastereomer or enantiomer, and a mixture of such a diastereomer and enantiomer, and isolated diastereomers and enantiomers are also encompassed by the compound of the disclosure.

The present disclosure is also intended to encompass various hydrates, solvates, and crystalline polymorphisms.

Furthermore, the compound of the disclosure can be substituted with an isotope (e.g., $^2H$ (or D), $^3H$ (or T), $^{11}C$, $^{13}C$, $^{14}C$, $^{13}N$, $^{15}N$, $^{15}O$, $^{35}S$, $^{18}F$, $^{125}I$, or the like). These compounds are also encompassed by the compound of the disclosure.

Furthermore, the scope of the present disclosure encompasses prodrugs of the compound of the disclosure. In the present disclosure, a prodrug refers to a derivative that yields a compound represented by formula IF, IB, IIF, IIB, XXIF, XXIB, XXIIF, XXIIB, XXIIIF, or XXIIIB described herein by, for example, acid hydrolysis or enzymatic degradation in the body. For example, if a compound represented by formula IF, IB, IIF, IIB, XXIF, XXIB, XXIIF, XXIIB, XXIIIF, or XXIIIB described herein has a hydroxyl group, amino group, or carboxyl group, these groups can be modified by a conventional method to manufacture a prodrug. Prodrug technologies are described in, for example, C. G. Wermuth, "The Practice of Medicinal Chemistry", 4th Ed., Academic Press, (2015), Chapter 28.

Examples for compounds having a carboxy group include compounds whose carboxyl group is modified to be an alkoxycarbonyl group, alkylthiocarbonyl group, or alkylaminocarbonyl group.

Examples of compounds having an amino group include compounds whose amino group is substituted with an alkanoyl group to be an alkanoylamino group, compounds substituted with an alkoxycarbonyl group to be an alkoxycarbonylamino group, compounds modified to have an alkanoyloxymethylamino group, and compounds modified to have hydroxylamine.

Examples for compounds having a hydroxyl group include compounds whose hydroxyl group is substituted with an alkanoyl group to be an alkanoyloxy group, phosphate ester, or alkanoyloxymethyloxy group.

Examples of the alkyl moiety of a group used for preparing a prodrug thereof include the alkyl group. The alkyl group is optionally substituted with, for example, an alkoxy group or the like. Preferred examples thereof include the following.

For compounds whose carboxyl group is modified to be an alkoxycarbonyl group, examples thereof include alkoxycarbonyl such as methoxycarbonyl and ethoxycarbonyl, and alkoxycarbonyl substituted with an alkoxy group such as methoxymethoxycarbonyl, ethoxymethoxycarbonyl, 2-methoxyethoxycarbonyl, and 2-methoxyethoxymethoxycarbonyl, or pivaloyloxymethoxycarbonyl.

As used herein, "pharmaceutically acceptable salt" refers to an acid addition salt or base addition salt which is pharmaceutically acceptable for use. Specific examples of "pharmaceutically acceptable salts" include, but are not limited to, acid addition salts such as acetate, propionate, butyrate, formate, trifluoroacetate, maleate, fumarate, tartrate, citrate, stearate, succinate, ethylsuccinate, malonate, lactobionate, gluconate, glucoheptonate, benzoate, methanesulfonate, benzenesulfonate, para-toluenesulfonate (tosylate), laurylsulfate, malate, ascorbate, mandelate, saccharinate, xinafoate, pamoate, cinnamate, adipate, cysteine salt, N-acetyl cysteine salt, hydrochloride, hydrobromide, phosphate, sulfate, hydroiodide, nicotinate, oxalate, picrate, thiocyanate, undecanoate, acrylic acid polymer salt, and carboxyvinyl polymer; inorganic base addition salts such as lithium salt, sodium salt, potassium salt, and calcium salt; organic base addition salts such as morpholine and piperidine; amino acid addition salts such as aspartic acid and glutamic acid; and the like.

The phrase "compound or an enantiomer thereof, or a salt thereof, or a solvate thereof" refers to a compound, an enantiomer of the compound, a salt of the compound, a salt of the enantiomer, a solvate of the compound, a solvate of the enantiomer, a solvate of the salt of the compound, or a solvate of the salt of the enantiomer.

As used herein, a therapeutic agent for "preventing" rabies refers to a compound that reduces the manifestation of a disorder or condition in a treated subject compared to an untreated subject, or delays the onset of one or more symptoms or alleviates the severity of rabies compared to an untreated subject.

The term "treat" includes preventive and/or therapeutic treatment. The term "preventive or therapeutic" treatment includes administration, to a host, of one or more compounds or pharmaceutical compositions of the invention, which is approved in the art. When administered prior to a clinical diagnosis of an undesirable condition (e.g., disease of a host animal or other undesirable conditions), treatment is preventive (i.e., for protection of the host from developing the undesirable condition), whereas when administered after a diagnosis of an undesirable condition, treatment is therapeutic (i.e., intended for ameliorating, recovering from, or stabilizing an existing undesirable condition or side effect thereof).

The term "prodrug" is intended to encompass compounds that are converted into the therapy activation agent (e.g., compound of formula I) of the disclosure under physiological conditions. A general method for preparing a prodrug is a method of including one or more selected portions for exposing a desired molecule by hydrolysis under physiological conditions. In another embodiment, a prodrug is converted by enzymatic activity of a host animal. For example, esters and carbonate (e.g., alcohol or carboxylic acid ester or carbonate) are preferred prodrugs of the present disclosure. In a specific embodiment, some of the formulations presented in the above table or all of the compounds of formulae IF, IB, XXIF, and XXIB can be replaced with a suitable corresponding prodrug, wherein, for example, hydroxyl in the parent compound is given as an ester or carbonate, or carboxylic acid in the parent compound is given as an ester.

Pharmaceutical Composition

The composition and method of the present disclosure can be utilized for treating an individual in need thereof. In a specific embodiment, an individual is a mammal such as a human or non-human mammal. If administered to an animal such as a human, the composition or compound is preferably administered as a pharmaceutical composition preferably comprising, for example, the compound of the disclosure and a pharmaceutically acceptable carrier. Pharmaceutically acceptable carriers are well known in the art. Examples thereof include aqueous solutions such as water and buffered saline, and other solvents and vehicles such as glycol, glycerol, oil such as olive oil, and organic esters for injection. In a preferred embodiment, an aqueous solution does not, or substantially does not, contain a pyrogen if such a pharmaceutical composition is for administration to a human, especially for administration through an invasive route (e.g., route such as injection or implantation that avoids transport or diffusion through the epithelial barrier). An excipient can be selected, for example, to achieve delayed release of an agent or to selectively target one or more cells, tissues, or organs. A pharmaceutical composition can be a unit dose, such as a tablet, capsule (including sprinkle capsule and gelatin capsule), granule, lyophilized form for reconstitution, powder, liquid agent, syrup, suppository, injection, or the like. A composition can also be in a transdermal delivery system such as a skin patch. A composition can also be a suitable liquid agent for topical administration, such as an eye drop.

A pharmaceutically acceptable carrier can comprise a physiologically acceptable agent, which has an effect of, for example, stabilizing, increasing the solubility, or increasing the absorption of a compound such as the compound of the disclosure. Examples of such a physiologically acceptable agent include carbohydrates such as glucose, sucrose, and dextran, antioxidants such as ascorbic acid and glutathione, chelating agents, low molecular weight proteins, other stabilizers, excipients, and the like. Selection of a pharmaceutically acceptable carrier including physiologically acceptable carrier is dependent on, for example, the route of administration of a composition. A preparation or pharmaceutical composition can be a self-emulsifying drug delivery system or self-microemulsifying drug delivery system. A pharmaceutical composition (preparation) can also be a liposome or other polymer matrix, and a compound of the disclosure can be incorporated therein. A liposome such as a liposome comprising a phospholipid or another lipid is a non-toxic, physiologically acceptable, and metabolizable carrier that is relatively easy to prepare and administer.

The phrase "pharmaceutically acceptable" refers to a compound, material, composition, and/or dosage form that is suitable for use in contact with human or animal tissue without excessive toxicity, stimulation, allergic reaction, other problems, or complications, with a reasonable risk-reward ratio, within the scope of a sound medical judgment, upon use herein.

As used herein, the phrase "pharmaceutically acceptable carrier" refers to a pharmaceutically acceptable material, composition, or vehicle such as a liquid or solid filler, diluent, excipient, solvent, or capsule material. Each carrier must be "acceptable" in terms of being compatible with other ingredients of a formulation and unharmful to a patient. Some examples of materials that can act as a pharmaceutically acceptable carrier include the following: (1) saccharide such as lactose, glucose, and sucrose; (2) starch such as corn starch and potato starch; (3) cellulose and derivatives thereof such as sodium carboxymethylcellulose, ethyl cellulose, and cellulose acetate; (4) powder tragacanth; (5) malt; (6) gelatin; (7) talc; (8) excipients such as cocoa butter and suppository wax; (9) oil such as peanut oil, cottonseed oil, safflower oil, sesame oil, olive oil, corn oil, and soybean oil; (10) glycol such as propylene glycol; (11) polyol such as glycerin, sorbitol, mannitol, and polyethylene glycol; (12) esters such as ethyl oleate and ethyl laurate; (13) agar; (14) buffer such as magnesium hydroxide and aluminum hydroxide; (15) alginic acid; (16) pyrogen-free water; (17) isotonic saline; (18)Ringer's solution; (19) ethyl alcohol; (20) phosphate buffer; and (21) other nontoxic compatible substances that are used in pharmaceutical formulations.

A pharmaceutical composition (preparation) can be administered to a subject through any of several routes of administration including, for example, oral administration (e.g., oral medicine, tablet, capsule (including sprinkle capsule and gelatin capsule), bolus, powder, granule, or paste agent for application on the tongue in an aqueous or non-aqueous liquid agent of suspension); absorption through an oral mucous membrane (e.g., sublingual administration); rectal, through the anus, or vaginal administration (e.g., as a pessary, cream, foam, or the like); parenteral administration (including intramuscular, intravenous, subcutaneous, and intraspinal cavity administration as, for example, sterilized liquid agent or suspension); intranasal administration; intraperitoneal administration; subcutaneous administration; transdermal administration (e.g., as a patch applied to the skin); topical administration (e.g., cream, ointment, or spray applied to the skin, and eye drop); and the like. A compound can also be formulated for inhalation. In a specific embodiment, a compound only needs to be dissolved or suspended in sterilized water. Details for suitable routes of administration and composition that are suited thereto can be found in, for example, U.S. Pat. Nos. 6,110,973, 5,731,000, 5,541,231, 5,427,798, 5,358,970, and 4,172,896, and patents cited therein.

A formulation can be provided in a convenient unit dosage form and prepared by any method that is well known in the pharmaceutical field. The amount of active ingredient that can form a unit dose in combination with a carrier varies depending on the host being treated or specific dosing mode. The amount of active ingredient that can form a unit dose in combination with a carrier is generally an amount of compound that results in a therapeutic effect. In general, such an amount is in the range of about 1 percent to about 99 percent active ingredient, preferably about 5 percent to about 70 percent active ingredient, and most preferably about 10 percent to about 30 percent active ingredient with respect to 100 percent.

A method of preparing such formulations or compositions comprises associating an active compound such as the compound of the disclosure with a carrier and optionally one or more secondary ingredients. In general, a formulation is prepared by associating the compound of the disclosure with a liquid carrier or a finely divided solid carrier or both in a uniform and dense manner and then optionally molding a product.

The formulation of the present disclosure that is suitable for oral administration can be in a form of a capsule (including sprinkle capsule and gelatin capsule), cachet, pill, tablet, lozenge (flavored base, generally using sucrose and acacia or tragacanth), lyophilized formulation, powder, granule, liquid agent or suspension in an aqueous or non-aqueous liquid, oil-in-water or water-in-oil liquid emulsion, elixir or syrup, pastille (using an inert base such as gelatin or glycerin, or sucrose and acacia), and/or mouthwash. Each of them contains a determined amount of the compound of the disclosure as an active ingredient. The composition or compound can also be administered as a bolus, lozenge, or paste.

To prepare a solid dosage form for oral administration (capsule (including sprinkle capsule and gelatin capsule), tablet, pill, sugar-coated tablet, powder, granule, or the like), an active ingredient is mixed with one or more pharmaceutically acceptable carriers such as sodium citrate or calcium monohydrogen phosphate, and/or one of the following: (1) a filler or bulking agent such as starch, lactose, sucrose, glucose, mannitol, and/or silicic acid; (2) binding agent, such as carboxymethyl cellulose, alginate, gelatin, polyvinylpyrrolidone, sucrose, and/or acacia; (3) moisturizing agent such as glycerol; (4) disintegrant such as agar, calcium carbonate, potato starch or tapioca starch, alginic acid, specific silicate, and sodium carbonate; (5) dissolution retardant such as paraffin; (6) absorption promoting agent such as a quaternary ammonium compound; (7) humectant such as cetyl alcohol and glycerol monostearate; (8) absorbent such as kaolin or bentonite clay; (9) lubricant such as talc, calcium stearate, magnesium stearate, solid polyethylene glycol, sodium lauryl sulfate, or a mixture thereof; (10) complexing agent such as modified or unmodified cyclodextrin; and (11) colorant. For a capsule (including sprinkle capsule and gelatin capsule), tablet, and pill, a pharmaceutical composition can also comprise a buffer. A same type of solid composition can also use an excipient such as lactose or milk sugar, high molecular weight polyethylene glycol, and the like as a filler in a soft or hard filled gelatin capsule.

A tablet can be prepared by compressing or molding the active ingredient together with one or more optional secondary ingredients. A compressed tablet can be prepared by using a binding agent (e.g., gelatin or hydroxypropyl methylcellulose), lubricant, inert diluent, preservative, disintegrant (e.g., sodium carboxymethyl starch or crosslinked sodium carboxymethylcellulose), surface activator, or dispersant. A molded tablet can be prepared by molding a mixture of a powder compound moisturized with an inert liquid diluent in a suitable instrument.

A tablet or other solid dosage form of a pharmaceutical composition such as a sugar-coated tablet, capsule (including sprinkle capsule and gelatin capsule), pill, or granule can be optionally notched or prepared using a coating or shell such as an enteric coating or other coating that is known in pharmaceutical product formulation technologies. The tablet or solid dosage form can also be formulated to provide sustained release or controlled release of the active ingredient by using, for example, hydroxypropyl methylcellulose, other polymer matrix, liposome, and/or microsphere, which contains the active ingredient, at different ratios to provide a desired release profile. The tablet or solid dosage form can be sterilized, for example, by filtration through a bacteria retaining filter or by incorporating a sterilizing agent in a form of a sterilized solid composition that can be dissolved in sterilized water or another medium for sterilized injection immediately prior to use. These compositions can also be a composition, which optionally comprises an emulsifying agent and releases an active ingredient(s) only at, or preferentially at, a specific part of a digestive tract, optionally in a delayed manner. Examples of embedded composition that can be used include polymeric substances and wax. An active ingredient can be in a microcapsule form by using one or more types of excipients described above when suitable.

Examples of liquid dosage forms that are useful for oral administration include a pharmaceutically acceptable emulsion, lyophilized form for reconstitution, microemulsion, liquid agent, suspension, syrup, and elixir. In addition to the active ingredient, a liquid dosage form can comprise an inert diluent that is commonly used in the art such as water or another solvent, cyclodextrin or a derivative thereof, solubilizing agent or emulsifying agent such as ethyl alcohol, isopropyl alcohol, ethyl carbonate, ethyl acetate, benzyl alcohol, benzyl benzoate, propylene glycol, 1,3-butylene glycol, oil (especially, cottonseed oil, peanut oil, corn oil, germ oil, olive oil, castor oil, or sesame oil), glycerol, tetrahydrofuryl alcohol, polyethylene glycol, sorbitan fatty acid ester, a mixture thereof, or the like.

In addition to an inert diluent, an oral composition can also comprise an adjuvant such as a humectant, emulsifying agent, suspending agent, sweetener, flavoring agent, colorant, fragrance, preservative, and the like.

In addition to an active compound, a suspension can comprise a suspending agent such as ethoxylated isostearyl alcohol, polyoxyethylene sorbitol, sorbitan ester, microcrystalline cellulose, aluminum metahydroxide, bentonite, agar, tragacanth, mixture thereof, or the like.

A formulation of a pharmaceutical composition for rectal, vaginal, or urethral administration can be given as a suppository, which can be prepared by mixing one or more active compounds with one or more suitable non-stimulatory excipients or carriers, including for example, cocoa butter, polyethylene glycol, suppository wax, salicylate, or the like. The formulation is a solid at room temperature, but a liquid at body temperature, so that the formulation melts in the rectum or vaginal cavity and releases an active compound.

A formulation of a pharmaceutical composition for oral administration can be given as a mouthwash, oral spray, or oral ointment.

Instead of or in addition, the composition can be formulated for delivery via a catheter, stent, wire, or another intracavity device. Delivery via such a device can be particularly useful for delivery to the bladder, urethra, urinary tract, rectum, or intestine.

A formulation that is suitable for transvaginal administration includes a pessary, tampon, cream, gel, paste, foam, or spray formulation, which comprises a carrier that is known to be suitable in the art.

A dosage form for topical or transdermal administration includes powder, spray agent, ointment, paste, cream, lotion, gel, liquid agent, patch, and inhalant. An active compound can be mixed with a pharmaceutically acceptable carrier and any preservative, buffer, or aerosol agent that may be needed under sterilized conditions.

In addition to an active compound, an ointment, paste, cream, and gel can contain an excipient such as an animal or vegetable oil and fat, wax, paraffin, starch, tragacanth, cellulose derivative, polyethylene glycol, silicone, bentonite, silicic acid, talc, zinc oxide, mixture thereof, or the like.

In addition to an active compound, powder and spray can contain an excipient such as lactose, talc, silicic acid, aluminum hydroxide, calcium silicate, polyamide powder, mixture thereof, or the like. A spray can further contain conventional aerosol agent such as chlorofluorohydrocarbon or volatile unsubstituted hydrocarbon such as butane or propane.

A transdermal patch has given an advantage of providing controlled delivery of the compound of the disclosure to the body. Such a dosage form can be prepared by dissolving or dispersing an active compound in a suitable medium. The flux of a compound crossing the skin can be increased by using an absorption enhancing agent. Such a flux rate can be controlled either by providing a rate controlling membrane or by dispersing a compound within a polymer matrix or gel.

An ophthalmic formulation, ophthalmic ointment, powder, liquid agent, and the like are also envisioned to be within the scope of the present disclosure. Exemplary ophthalmic formulations are described in US Patent Application Publication Nos. 2005/0080056, 2005/0059744, 2005/0031697, and 2005/004074, and U.S. Pat. No. 6,583,124 (content of which is incorporated herein by reference). When desirable, a liquid ophthalmic formulation has the same property as a lachrymal fluid, aqueous humor, or vitreous humor, or is compatible with such fluids. The preferred route of administration is administration to the affected part (e.g., topical administration such as eye drops or administration through an implant).

As used herein, the phrases "parenteral administration" and "parenterally administered" refer to an administration mode other than enteral and topical administration and generally to injections. Examples thereof include, but are not limited to, intravenous, intramuscular, intraarterial, intraspinal cavity, intracapsular, intraorbital, intracardial, intradermal, intraperitoneal, transtracheal, subcutaneous, subepidermal, intraarticular, subcapsular, subarachnoidal, intraspinal, and intrasternum injection and infusion. A pharmaceutical composition that is suitable for parenteral administration comprises one or more active compounds in combination with one or more pharmaceutically acceptable, sterile, isotonic, aqueous or non-aqueous liquid agent, dispersion, suspension, or emulsion, or sterile powder that can be reconstituted in a sterile injection liquid agent or dispersion immediately prior to use, which can comprise an antioxidant, buffer, bacteriostatic agent, solute for isotonizing the target recipient blood and formulation, or suspending agent or thickening agent.

Examples of suitable aqueous and non-aqueous carriers that can be used in the pharmaceutical composition of the present disclosure include water, ethanol, polyol (e.g., glycerol, propylene glycol, polyethylene glycol, and the like), suitable mixtures thereof, vegetable oil such as olive oil, organic ester for injection such as ethyl oleate, and the like. A suitable fluidity can be maintained, for example, by using a coating material such as lecithin, by maintaining a required particle size for a dispersion, and by using a surfactant.

These compositions can also comprise an adjuvant such as a preservative, humectant, emulsifying agent, or dispersant. Various antimicrobial agents and antifungal agents such as paraben, chlorobutanol, and phenol sorbic acid can be included to ensure prevention of microbial action. It is also desirable to include an isotonizing agent such as a saccharide or sodium chloride in the composition. In addition, long-term absorption in a form of a pharmaceutical product for injection can be induced by including an agent for delaying absorption, such as aluminum monostearate or gelatin.

In some cases, it is desirable to delay absorption of a drug from subcutaneous injection or intramuscular injection in order to prolong the effect of the drug. This can be accomplished by using a liquid suspension of a crystalline or amorous material with poor water solubility. Accordingly, the drug absorption rate can be dependent on the dissolution rate thereof, and the rate can be dependent on the crystal size and crystalline form. Delayed absorption of a drug form that is parenterally administered can be accomplished by dissolving or suspending a drug in an oil vehicle.

A depot form of injection is prepared by forming a microcapsule matrix of a target compound in a biodegradable polymer (e.g., polylactide-polyglycolide or the like). The drug release rate can be controlled in accordance with the drug to polymer ratio and the property of the specific polymer used. Examples of other biodegradable polymers include poly(orthoester) and poly(anhydride). A formulation for depot injection is prepared by encapsulating a drug within a liposome or microemulsion that is compatible with body tissue.

For use in the method of the present disclosure, the active compound itself can be given, or 0.1 to 99.5% (more preferably 0.5 to 90%) of active ingredient can be given as a pharmaceutical composition in combination with a pharmaceutically acceptable carrier.

A method of introduction can also provide a drug with a refillable device or a biodegradable device. In recent years, various sustained release polymer devices have been developed and tested in vivo for controlled delivery of a drug including proteinaceous biological formulations. An implant for sustained release of a compound at a specific target site can be formed by using various biocompatible polymers (including hydrogel) including both a biodegradable polymer and a non-biodegradable polymer.

An amount of active ingredient that is effective to achieve a desired therapeutic response for a specific patient, composition, and mode of administration without toxicity to the specific patient can be obtained by changing the actual dosage level of the active ingredient in a pharmaceutical composition.

The selected dosage level is dependent on various factors including the activity of the specific compound or combination of compounds, ester, salt, or amide thereof used, route of administration, dosing time, discharge rate of the specific compound(s) used, period of continued treatment, other drugs, compound, and/or substance used in combination with the specific compound(s) used, age, sex, body weight, condition, overall health condition, and medical record of patient receiving treatment, and same type of factors that are well-known in the medical field.

Those skilled in the art who are physicians or veterinarians can readily determine and prescribe a therapeutically effective amount of the pharmaceutical composition that is required. For example, a physician or veterinarian can start the dose of a pharmaceutical composition or compound from a level that is lower than the level required to achieve a desired therapeutic effect and gradually increase the dosage until the desired effect is achieved. "Therapeutically effective amount" refers to a concentration of a compound that is sufficient to result in manifestation of the desired therapeutic effect. It is generally understood that the effective amount of compound varies depending on the body weight, sex, age, and medical record of the subject. Examples of other factors affecting the effective amount include, but are not limited to, the severity of the condition of a patient, disorder being treated, stability of compound, and, if desirable, another type of therapeutic agent co-administered with the compound of the disclosure. A greater total dose can be delivered by multiple administrations of the agent. A method of determining the potency and dosage is known to those skilled in the art (Isselbacher et al., (1996) Harrison's Principles of Internal Medicine, 13th edition, pages 1814 to 1882, which is incorporated herein by reference).

A suitable daily dose of an active compound used in the composition and method of the present disclosure is an amount of the compound, which is the lowest dose that is effective to generate a therapeutic effect. Such an effective dose is generally dependent on the factors described above.

When desirable, the effective daily dose of the active compound can be optionally administered in a unit dosage form divided into 1, 2, 3, 4, 5, 6, or more doses administered separately at a suitable interval throughout a day. In a specific embodiment of the present disclosure, an active compound can be administered two or three times daily. In a preferred embodiment, an active compound is administered once daily.

A patient who receives such a treatment can be any animal requiring the treatment, including primates, especially humans, and other mammals such as horses, cows, pigs, and sheep, and poultry and all pets.

In a specific embodiment, the compound of the disclosure can be used alone or administered concomitantly with another type of therapeutic agent. As used herein, the phrase "administered concomitantly" refers to any form of administration of two or more different therapeutic compounds, which administers a second compound while a previously administered therapeutic compound is still effective in the body (e.g., two compounds are simultaneously effective in the body of a patient, and this can include a synergistic effect of the two compounds). For example, different therapeutic compounds can be administered in the same formulation or separate formulations, simultaneously or sequentially. In a specific embodiment, different therapeutic compounds can be administered within 1 hour, within 12 hours, within 24 hours, within 36 hours, within 48 hours, within 72 hours, or within one week of each other. Thus, an individual receiving such treatment can benefit from a combined effect of different therapeutic compounds.

In a specific embodiment, concomitant administration of the compound of the disclosure and one or more additional therapeutic agent(s) or (i.e., one more additional chemotherapeutic agent(s)) provides improved potency compared to administration of each of the compound of the disclosure (e.g., compound of formula IF, IB, XXIF, or XXIB) and one or more additional therapeutic agent(s) individually. In such a specific embodiment, concomitant administration provides a synergistic effect, wherein the synergistic effect refers the sum of the effects of each individual administration of the compound of the disclosure and one or more additional therapeutic agents(s).

In one embodiment, the compound of the disclosure can be administered directly, or as a formulation, medicament, or a pharmaceutical composition using a suitable dosage form, by oral or parenteral administration. Specific examples of such dosage forms include, but are not limited to, tablets, capsules, powdered agents, granules, liquid agents, suspension, injection agents, patch-on agents, poultice, and the like. These formulations can be manufactured by a known method using an additive that is commonly used as a pharmaceutical additive.

As these additives, an excipient, disintegrant, binding agent, fluidizer, lubricant, coating agent, solubilizing agent, solubilizing promotor, thickener, dispersant, stabilizer, sweetener, flavoring agent, or the like can be used depending on the objective. Specific examples of these additives include, but are not limited to, lactose, mannitol, crystalline cellulose, low-substituted hydroxypropyl cellulose, corn starch, partially pregelatinized starch, carmellose calcium, croscarmellose sodium, hydroxypropyl cellulose, hydroxypropyl methylcellulose, polyvinyl alcohol, magnesium stearate, sodium stearyl fumarate, polyethylene glycol, propylene glycol, titanium oxide, talc, and the like.

The dosage of the compound of the disclosure is appropriately selected depending on the subject targeted for administration, route of administration, disease, age of subject, body weight, and symptom. For example, the dosage is 0.01 mg as the lower limit (preferably 100 mg) and 10000 mg as the upper limit (preferably 6000 mg) per day for adults for oral administration. This amount can be administered once daily, or divided into several doses.

In one embodiment, the compound of the disclosure is a compound with an antiviral activity for a virus in the Lyssavirus genus. The virus in the Lyssavirus genus comprises a rabies virus, Lagos bat virus, mokola virus, Duvenhage virus, European bat 1 lyssavirus, European bat 2 lyssavirus, Australian bat lyssavirus, and the like. The virus in the Lyssavirus genus preferably comprises a rabies virus.

The timing of dosing of the compound of the disclosure and therapeutic agents thereof is not limited. The compound and therapeutic agent can be administered concurrently or sequentially to a subject being administered therewith. The compound of the disclosure and therapeutic agent thereof can be formulated as a combined agent. The dosage of the therapeutic agent can be appropriately selected based on the clinically used dose. The ratio of the compound of the disclosure and therapeutic agent thereof can be appropriately selected depending on the subject of administration, route of administration, target disease, symptom, combination, or the like.

In one embodiment of the present disclosure, the compound of the disclosure can be combined and administered concurrently or at different times upon use of a pharmaceutical composition. Such a pharmaceutical composition is also within the scope of the present disclosure.

Such a medicament, formulation, or pharmaceutical composition can be manufactured by mixing the compound of the disclosure and/or an addition agent (e.g., anti-rabies gamma globulin formulation, antimicrobial agent, antiviral agent (e.g., ribavirin, amantadine, or the like), sedative (e.g., ketamine, midazolam, or the like) or the like) with any suitable component, together or separately, as a combined agent, or as separate agents using any technology that is known in the art. An appropriate formulation such as a tablet, capsule, powder, granule, liquid agent, suspension, injection, patch, or poultice can be formulated by using any technology that is known in the art. If the compound of the disclosure and/or an addition agent (e.g., anti-rabies gamma globulin formulation, antimicrobial agent, antiviral agent (e.g., ribavirin, amantadine, or the like), sedative (e.g., ketamine, midazolam, or the like) or the like) are prepared as separate agents, they can be provided as a kit of two agents. The kit can provide one of the components as a single agent, with instructions (package insert or the like) instructing to combine and administer the other component (for the compound of the disclosure, the additional agent; for the addition agent (e.g., anti-rabies gamma globulin formulation, antimicrobial agent, antiviral agent (e.g., ribavirin, amantadine, or the like), sedative (e.g., ketamine, midazolam, or the like) or the like), the compound of the disclosure) concurrently or at different times.

If the compound of the disclosure is used as an active ingredient of a medicament, the compound is intended for use in not just humans, but also animals other than humans (cat, dog, cow, horse, bat, fox, mongoose, raccoon, and the like).

(Preventive or Therapeutic Method)

The present disclosure also provides a method of preventing or treating rabies, comprising administering, to a subject in need thereof, a compound of formula IF, formula IB, formula XXIF, or formula XXIB or a pharmaceutically acceptable t thereof, or a solvate thereof, or a pharmaceutical composition comprising the same. In one embodiment, a method of preventing or treating rabies comprises administering, to a subject in need thereof, a therapeutically effective amount of a compound of formula IF, formula IB, formula XXIF, or formula XXIB or a pharmaceutically acceptable salt thereof, or a solvate thereof, or a pharmaceutical composition comprising the same.

(Use for Prevention or Treatment)

One embodiment of the present disclosure provides use of a compound of formula IF, formula IB, formula XXIF, or formula XXIB or a pharmaceutically acceptable salt thereof, or a solvate thereof, for the manufacture of a medicament for preventing or treating rabies.

The present disclosure also provides a compound of formula IF, formula IB, formula XXIF, or formula XXIB or a pharmaceutically acceptable salt thereof, or a solvate thereof, for use in preventing or treating rabies.

(Method of Manufacturing the Compound of the Disclosure)

Hereinafter, the method of manufacturing the compound of the disclosure is described with examples, but the present disclosure is not limited thereto.

The compound of the disclosure can be manufactured by, for example, the following manufacturing methods, but are not limited to such methods. These manufacturing methods can be appropriately improved upon based on the expertise of those skilled in the art of organic synthetic chemistry. Salts of the compounds used as a raw material can be used in the following manufacturing method, as long as the reaction is not affected.

In the following manufacturing methods, even if use of a protecting group is not specifically described, a functional group other than those at the reaction point can be protected as needed and deprotected after the completion of a reaction or after a series of reactions to obtain a compound of interest if one of the functional groups other than those at the reaction point is altered under the reaction condition or if it is unsuitable for post-reaction processing. Common protecting groups described in the document (Peter G. M. Wuts, "Greene's Protective Groups in Organic Synthesis", 5th Ed., John Wiley & Sons, Inc., Hoboken, New Jersey (2014)) or the like can be used as the protecting groups used in these processes. A protecting group can be introduced or removed by a method that is commonly used in organic synthetic chemistry (e.g., method described in the aforementioned document or the like) or a method in accordance thereto.

The starting material and intermediate in the following manufacturing methods can be purchased as a commercially available product or are available by synthesis in accordance with a method described in a known document or a known method from a known compound. Salts of the starting material and intermediate can also be used, as long as the reaction is not affected.

The intermediate and compound of interest in the following manufacturing methods can also be converted into another compound encompassed by the present disclosure by appropriately converting their functional groups. A functional group can be converted in doing so by a method that is commonly used in organic synthetic chemistry (e.g., method described in R. C. Larock, "Comprehensive Organic Transformations", 2nd Ed., John Wiley and Sons, Inc., New York (1999) or the like) or a method in accordance therewith.

An inert solvent in the following manufacturing methods refers to a solvent that does not react with a raw material, reagent, base, acid, catalyst, ligand, or the like used in the reaction (hereinafter, also referred to as "raw material or the like used in the reaction"). A solvent used in each step can be used as an inert solvent even if the solvent reacts with the raw material or the like used in the reaction, as long as the reaction of interest proceeds to result in a compound of interest.

The overview of compound synthesis related to the present disclosure is shown below. "B" and "F" following the Roman numerical compound number indicate that a 5-membered ring comprising nitrogen is located in the "back" and "front", respectively. In other words, a —C(=O)NH—$R_2$ group attached to a 5-membered ring comprising nitrogen referred to as "back", and a —C(=O)NH—$R_2$ that is not attached to a 5-membered ring comprising nitrogen is referred to as "front".

Synthesis Scheme 1
Synthesis of Compound III

Compound III can be manufactured by, for example, the following manufacturing method.

(1) Route 1-1 Synthesis from compound VII and compound VIII

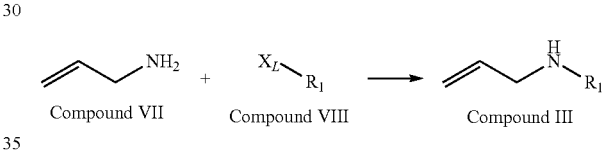

(2) Route 1-2 Synthesis from Compound VII and Compound VIII Through Protection of Amine

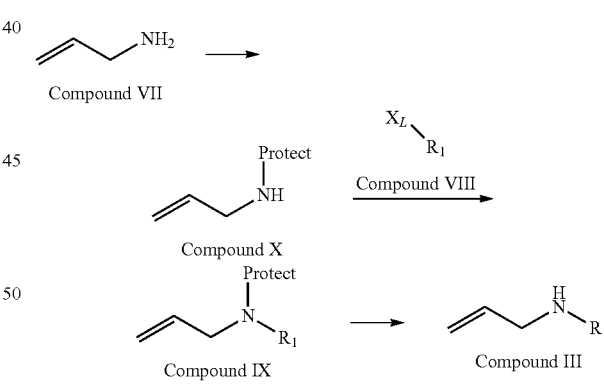

(3) Route 1-3 Synthesis from Compound XI and Compound XII

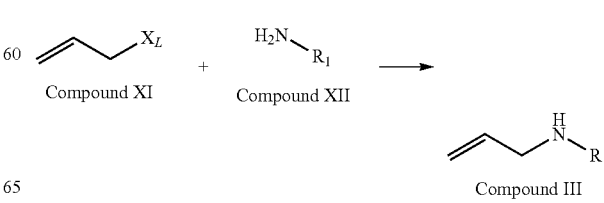

wherein $X_L$ represents a leaving group in a nucleophilic substitution reaction. Examples thereof include halogen (e.g., chlorine, bromine, or iodine), sulfate esters (—$OSO_3H$ and the like), and sulfonyl-O— groups (e.g., methanesulfonyl-O—, toluenesulfonyl-O—, and the like).

(4) Route 1-4 Synthesis from Compound XI and Compound XIII

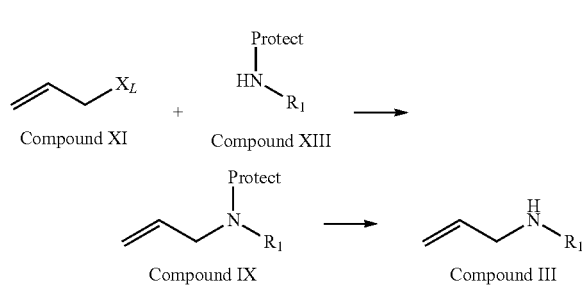

(5) Route 1-5 Synthesis from Compound VII and Compound XIV

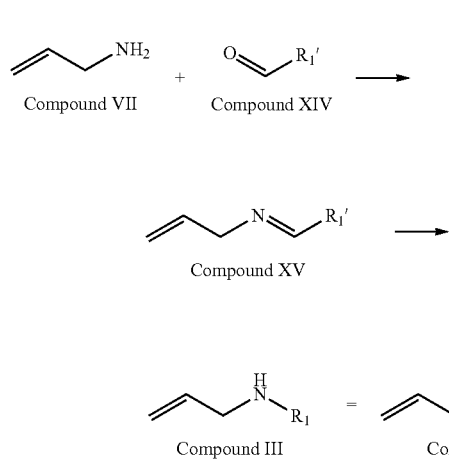

wherein if $R_1$ in compound III can be expressed as —$CH_2$—$R_1$', $R_1$ in compound III can be replaced with —$CH_2$—$R_1$' to express compound III as compound III'.

In the formula, $R_1$ is as defined in item 1 or A1 herein, and "Protect" is a protecting group of amino group. Examples of protecting groups of an amino group include an ethoxycarbonyl group, tert-butoxycarbonyl group, acetyl group, benzoyl group, trifluoroacetyl group, benzyloxycarbonyl group, 3- or 4-chlorobenzyloxycarbonyl group, triphenylmethyl group, methanesulfonyl group, p-toluenesulfonyl group, trimethylsilyl group, benzyloxycarbonyl group, 3- or 4-chlorobenzyloxycarbonyl group, benzylsulfonyl group, benzyl group, 4-nitrobenzyl group, 4-methoxybenzyl group, methyl group, ethyl group, and the like.

A compound that is commercially available or a compound manufactured by a known method can be used as a starting raw material compound.
Synthesis Scheme 2
Synthesis of Compound V A compound of formula V can be manufactured by, for example, the following manufacturing method.

(1) Route 2-1 Synthesis from Compound XVI and Compound XVII

[Chemical Formula 21]

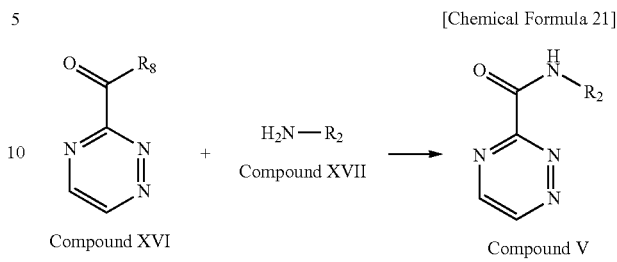

wherein $R_8$ indicates alkoxy, aryloxy, hydroxy, or halogen. This synthesis is achieved by various reactions known to those skilled in the art. If $R_2$ is aryl, compound V can be synthesized in accordance with the method described in C. W. Cheung, M. L. Ploeger, and X. Hu, Nature Communications 2017, 8, 14878.

(2) Route 2-2 Synthesis from Compound XVIII

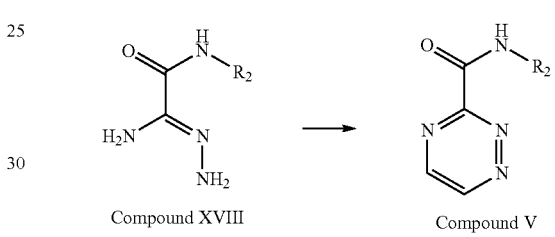

wherein $R_2$ is as defined in item 1 or A1 herein.

A compound that is commercially available or a compound that is manufactured by a known method can be used as the starting compound.
Synthesis Scheme 3
Synthesis of Compound VI A compound of formula VI can be manufactured from compound III and compound IV by, for example, the following manufacturing method.

[Chemical Formula 23]

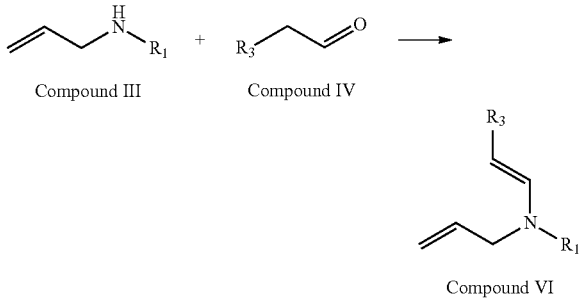

wherein $R_1$ and $R_3$ are as defined in item 1 or A1 herein.
Synthesis Scheme 4
Compound of Formula IIF and Compound of Formula IIB-Route 1

A compound of formula IIF and compound of formula IIB can be manufactured, for example, from three components through one-pot synthesis in accordance with a known method (e.g., method described in Bioorg. Med. Chem. 23

(2015) 2629-2635, Tetrahedron 63 (2007) 6004-6014, Eur. J. Org. Chem. 2009, 2185-2189, Eur. J. Org. Chem. 2011, 2354-2359 or the like).

known method (e.g., the method described in RSC Advances, 2012, 2, 5536-5538 or Tetrahedron Lett. 50 (2009) 3436-3438 or the like). X in the following formulae is —NH—.

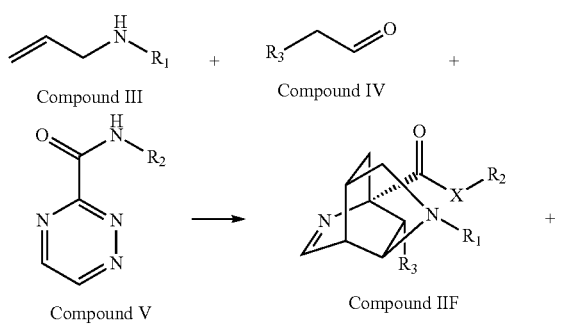

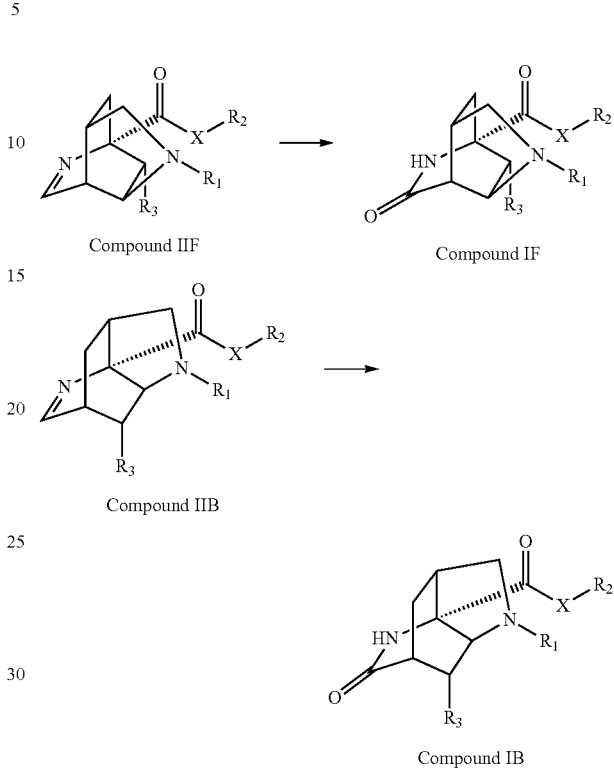

wherein $R_1$, $R_2$, and Ry are as defined in item 1 or A1 herein, and X is —NH—.

Synthesis Scheme 5

Compound of Formula IIF and Compound of Formula IIB-Route 2

A compound of formula IIF and compound of formula IIB can be manufactured, for example, from two components as described below.

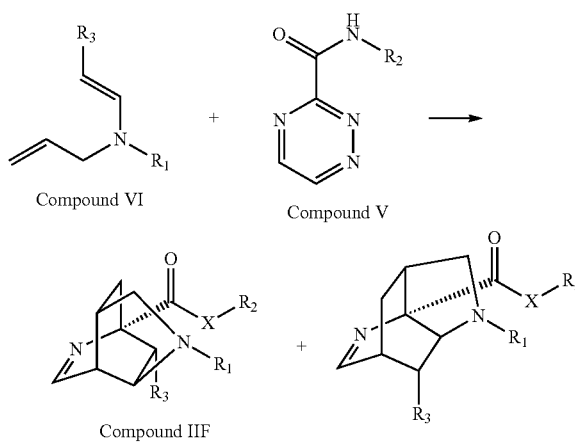

wherein $R_1$, $R_2$, and R; are as defined in item 1 or A1 herein, and X is —NH—.

Synthesis Scheme 6
Synthesis of Compound IF and Compound IB
Step 6-1
Oxidation of Imine Compound IF (i.e., compound of formula IF) or compound IB (i.e., compound of formula IB) can be manufactured, for example, from compound IIF (i.e., compound of formula IIF) or compound IIB (i.e., compound of formula IIB) by oxidation as described below in accordance with a Synthesis Scheme 7
Synthesis of Compound V'

A compound of formula V' can be manufactured by, for example, the following manufacturing method.

(1) Route 7-1 Synthesis from Compound XVI and Compound XVII'

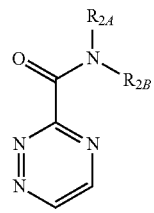

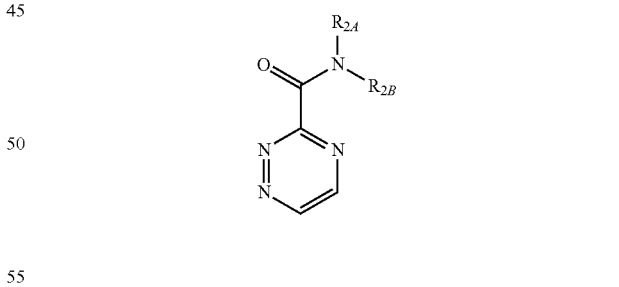

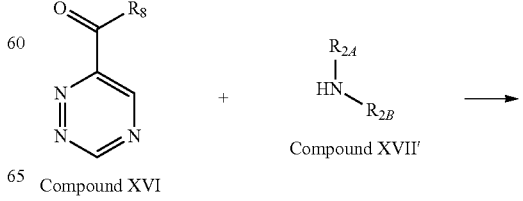

-continued

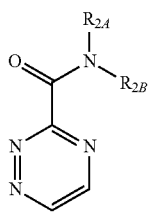
Compound V'

A compound of formula V' can be manufactured under the same condition as Route 2-1 of Synthesis Scheme 2. $R_8$ indicates alkoxy, aryloxy, hydroxy, or halogen.

(2) Route 7-2 Synthesis from compound XVIII'

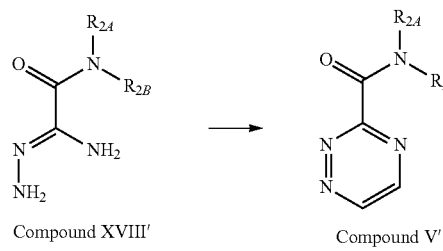

Compound XVIII'   Compound V' wherein $R_2$ is as defined in item 1 or item A1 herein.

A compound that is commercially available or a compound manufactured by a known method can be used as a starting raw material compound.

Synthesis Scheme 8
Compound of Formula XXIIF and Compound of Formula XXIIB-Route 1

A compound of formula XXIIF and a compound of formula XXIIB can be manufactured through one-pot synthesis from three components in accordance with, for example, a known method (e.g., method described in Bioorg. Med. Chem. 23 (2015) 2629-2635, Tetrahedron 63 (2007) 6004-6014, or Eur. J. Org. Chem. 2009, 2185-2189, Eur. J. Org. Chem. 2011, 2354-2359 or the like).

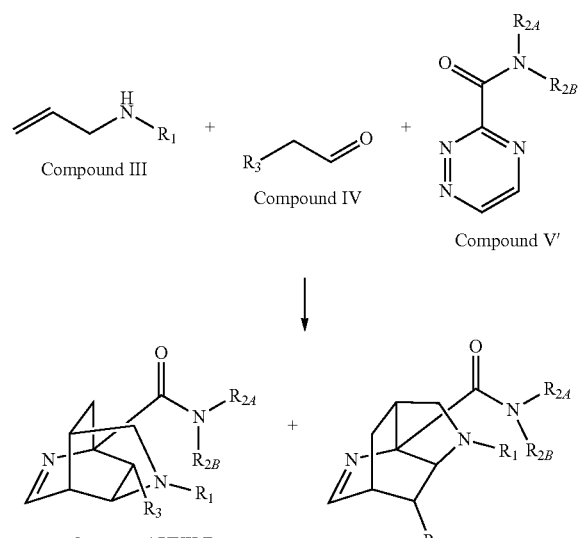

Compound III + Compound IV + Compound V'

Compound XXII F + Compound XXII B wherein $R_1$, $R_{2A}$, $R_{2B}$, and $R_3$ are as defined in item 1 or item A1 herein.

Synthesis Scheme 9
Compound of Formula XXIIF and Compound of Formula XXIIB-Route 2

A compound of formula XXIIF and compound of formula XXIIB can be manufactured, for example, from two components as described below.

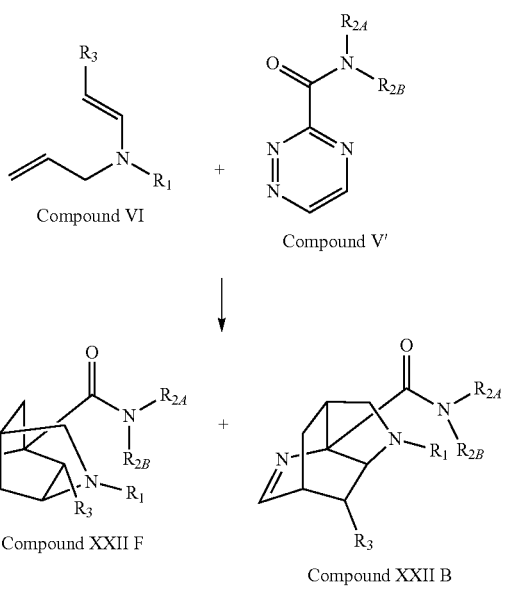

Compound VI + Compound V'

Compound XXII F + Compound XXII B

Synthesis Scheme 10
Synthesis of Compound XXIF and Compound XXIB by Oxidation of Imine Compound XXIF (i.e., compound of formula XXIF) or compound XXIB (i.e., compound of formula XXIB) can be manufactured, for example, from compound XXIIF (i.e., compound of formula XXIIF) or compound XXIIB (i.e., compound of formula XXIIB) by the following oxidation in accordance with, for example, a known method (e.g., method described in RSC Advances, 2012, 2, 5536-5538, Tetrahedron Lett. 50 (2009) 3436-3438 or the like).

[Chemical Formula 31]

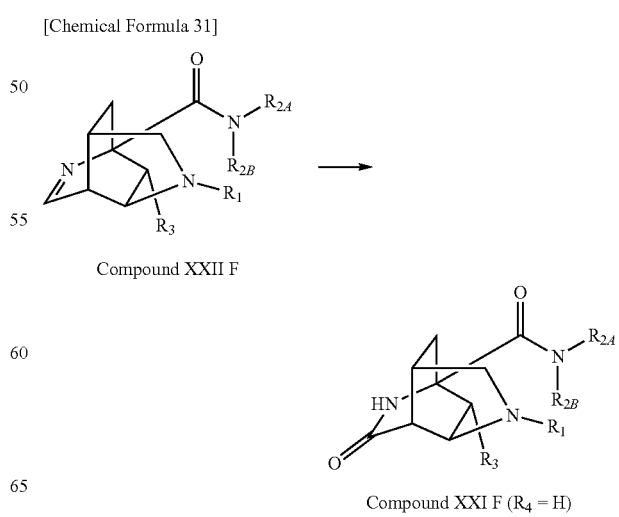

Compound XXII F

Compound XXI F ($R_4$ = H)

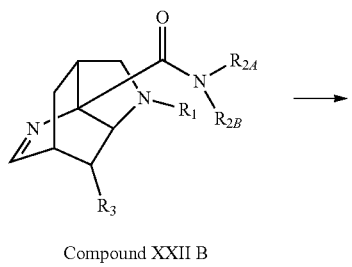

Compound XXII B

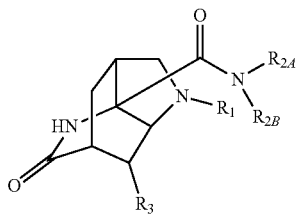

Compound XXI B (R$_4$ = H)

Synthesis Scheme 11
Synthesis of Intermediates XXIIIF and XXIIIB

For example, intermediates XXIIIF and XXIIIB can be respectively manufactured as follows.

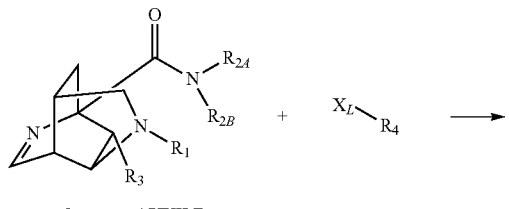

Compound XXII F

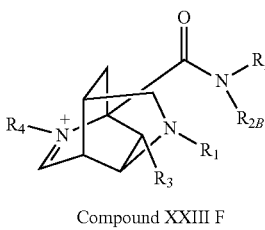

Compound XXIII F

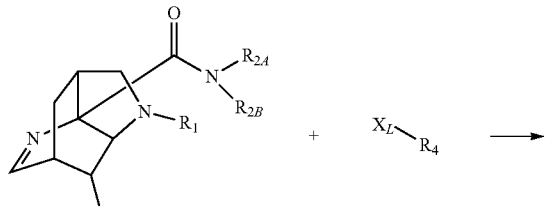

Compound XXII B

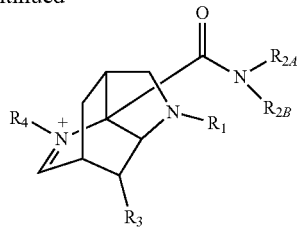

Compound XXIII B wherein $X_L$ represents a leaving group in a nucleophilic substitution reaction. Examples thereof include halogen (e.g., chlorine, bromine, and iodine), sulfate esters (—SO$_3$H), and sulfonyl-O— groups (e.g., methanesulfonyl-O—, toluenesulfonyl-O—, and the like).

Synthesis Scheme 12
Synthesis of Compounds XXIF and XXIB Wherein R$_4$ is not Hydrogen For example, compound XXIF and compound XXIB wherein R$_4$ is not hydrogen can be manufactured as follows from, for example, intermediate compounds XXIIIF and XXIIIB, respectively.

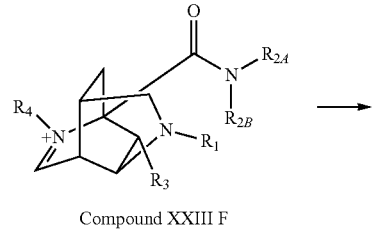

Compound XXIII F

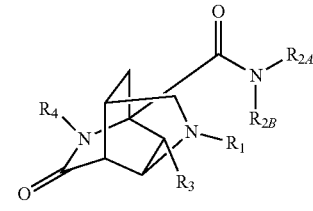

Compound XXI F

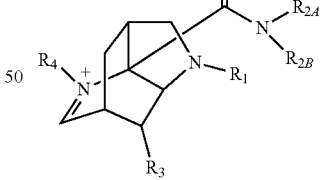

Compound XXIII B

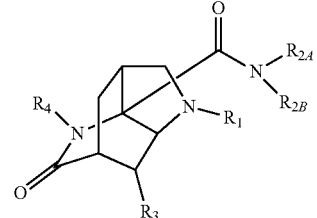

Compound XXI B

By being subjected to suitable chemical reaction conditions, compounds XXIF, XXIB, XXIIF, and XXIIB having various groups in $R_1$, $R_{2A}$, $R_{2B}$, $R_3$, and $R_4$ can be synthesized.

Synthesis Scheme 13

Synthesis of Compounds XXIF and XXIB Via Conversion of $R_1$

Compound XXI F

Compound XXI F ($R_1$ = H)

Compound XXI F

Compound XXI B

Compound XXI B ($R_1$ = H)

Compound XXI B

The group at $R_1$ of compounds XXIF, XXIB, XXIIF, and XXIIB can be converted to hydrogen by a suitable chemical reaction, and hydrogen can be further converted to different $R_1'$.

The intermediate and compound of interest in the manufacturing methods described above can be isolated and purified by subjecting them to a purification method that is commonly used in organic synthesis chemistry (e.g., neutralization, filtration, extraction, washing, drying, concentration, recrystallization, various chromatography, or the like). Each intermediate can also be subjected to the subsequent reaction without any particular purification.

Optically active forms of the compound of the disclosure can be manufactured by using an optically active starting material or intermediate, or by optically resolving a racemate of the final product or intermediate. Examples of optional resolution methods include, but are not limited to, separation method using an optically active column or a separation method such as fractional crystallization method. A diastereomer of the compound of the disclosure can be manufactured by, for example, but not limited to, a separation method such as column chromatography or fractional crystallization.

A pharmaceutically acceptable salt of a compound represented by formula IF, IB, IIF, IIB, XXIF, XXIB, XXIIF, XXIIB, XXIIIF, or XXIIIB can be manufactured by, for example, but not limited to, mixing a compound represented by formula IF, IB, IIF, IIB, XXIF, XXIB, XXIIF, XXIIB, XXIIIF, or XXIIIB with a pharmaceutically acceptable acid or base in a solvent such as water, methanol, ethanol, 2-propanol, ethyl acetate, or acetone.

(Medicament)

In one aspect, the present disclosure provides a medicament (composition) for treating, preventing, or managing an infection of a virus in the Lyssavirus genus and/or a disease, disorder, or symptom induced by a viral infection. Such a medicament or pharmaceutical composition can be used in the preparation of individual single unit dosage forms. The pharmaceutical composition and dosage form of the present disclosure comprise the compound of the disclosure or a pharmaceutically acceptable salt, solvate, or stereoisomer thereof, and optionally an additional active substance. The pharmaceutical composition and dosage form of the present disclosure can further comprise one or more carriers, excipients, or diluents.

The pharmaceutical composition and dosage form of the present disclosure can also comprise one or more additional active substances or components. As a result, the pharmaceutical composition and dosage form of the present disclosure can comprise the compound of the disclosure or a pharmaceutically acceptable salt, solvate, or stereoisomer thereof, and at least one second active substance. An example of any second active substance is disclosed herein.

Viruses in the Lyssavirus genus that can be targeted in the present disclosure comprise a rabies virus, Lagos bat virus, mokola virus, Duvenhage virus, European bat 1 lyssavirus, European bat 2 lyssavirus, Australian bat lyssavirus, and the like. The virus in the Lyssavirus genus preferably comprises a rabies virus.

In one embodiment, the compound of the disclosure can be administered directly or as a formulation, medicament, or pharmaceutical composition using a suitable dosage form, through oral administration or parenteral administration (e.g., transmucosal (e.g., sublingual, transnasal, transvaginal, intracystic, transrectal, transpreputial, intraocular, cheek, or intra-aural), non-parenteral (e.g., subcutaneous, intravenous, bolus injection, intramuscular, or intraarterial), topical (e.g., eye drop other ophthalmic preparation), transdermal, or transepidermal administration). Specific examples of such dosage forms include, but are not limited to, tablet, caplet, capsule such as a soft gelatin capsule with elasticity, cachet, troche, powder, lozenge, granule, liquid agent, dispersion, suppository, aerosol (e.g., transnasal aerosol or inhalant), gel, suspension (e.g., aqueous or non-aqueous liquid suspension, oil-in-water liquid emulsion, or water-in-oil liquid emulsion), elixir, injection, patch, poultice, and the like. These formulations can be manufactured by a known method using an additive that is commonly used as a pharmaceutical additive. The present disclosure can also be a liquid dosage form suitable for oral or transmucosal administration to a patient including elixir, a liquid dosage form suitable for parenteral administration to a patient, an ophthalmic preparation suitable for eye drops or other topical administration, an aseptic solid (e.g., crystalline or amorphous solid) that can be reconstituted to provide a liquid dosage form suitable for parenteral administration to a patient, or the like. The present disclosure can be administered as a single unit dosage form.

As the additive that can be used in the present disclosure, an excipient, disintegrant, binding agent, fluidizer, lubricant, coating agent, solubilizing agent, solubilizing promotor, thickener, dispersant, stabilizer, sweetener, flavoring agent, or the like can be used depending on the objective. Specific examples of these additives include, but are not limited to, lactose, mannitol, crystalline cellulose, low-substituted hydroxypropyl cellulose, corn starch, partially pregelatinized starch, carmellose calcium, croscarmellose sodium, hydroxypropyl cellulose, hydroxypropyl methylcellulose, polyvinyl alcohol, magnesium stearate, sodium stearyl fumarate, polyethylene glycol, propylene glycol, titanium oxide, talc, and the like.

The composition, shape, and type of the composition and dosage form of the present disclosure typically vary depending on the application thereof. For example, a dosage form used in quick therapy of a disease can contain a large amount of one or more active ingredients, which is an amount greater than the amount of dosage form used in chronic therapy of the disease. Likewise, a parenteral dosage form can comprise one or more active ingredients at a smaller amount, and the content of the active ingredient is less than the oral dosage form used in therapy of the disease. These and other methods with specific dosage forms that are different from each other encompassed by the present disclosure are obvious to those skilled in the art. See, for example, Remington's Pharmaceutical Sciences, 18th Ed., Mack Publishing, Easton, PA (1990).

The dosage of the compound of the disclosure is appropriately selected depending on the subject who is administered with the compound, route of administration, disease, subject's age, body weight, and symptom. For example, the dosage, for oral administration, is 0.01 mg (preferably 100 mg) as the lower limit, and 10000 mg (preferably 6000 mg) as the upper limit per day to an adult. This amount can be administered once daily or in several separate doses.

In one embodiment, the pharmaceutical composition of the present disclosure that is suitable for oral administration can be presented as individual dosage form such as, but not limited to, tablet (e.g., chewable tablet), caplet, capsule, and liquid agent (e.g., flavored syrup). A typical oral dosage form of the present disclosure is prepared by forming a complete mixture combining at least one excipient and an active ingredient in accordance with normal drug formulation technology. An excipient can be in various forms in accordance with the form of a preparation that is desirable for administration. Non-limiting examples of excipients suitable for use in oral liquid or aerosol dosage form include water, glycol, oil, alcohol, flavoring agent, preservative, and colorant. Non-limiting examples of excipients suitable for use in a solid oral dosage form (e.g., powder, tablet, capsule, or caplet) include starch, saccharide, microcrystalline cellulose, diluent, granulating agent, lubricant, binding agent, and disintegrant.

Non-limiting examples of excipients that can be used in the oral dosage form of the present disclosure include binding agent, filler, disintegrant, and lubricant. Non-limiting examples of binding agents suitable for use in a pharmaceutical composition and dosage form include corn starch, potato starch, other starches, gelatin, natural and synthetic rubber such as acacia gum, sodium alginate, alginic acid, other alginate, tragacanth powder, guar gum, cellulose, and derivatives thereof (e.g., ethyl cellulose, cellulose acetate, carboxymethylcellulose calcium, and sodium carboxymethylcellulose), polyvinylpyrrolidone, pregelatinized methylcellulose, starch, hydroxypropyl methylcellulose, microcrystalline cellulose, and mixtures thereof.

Non-limiting examples of fillers suitable for use in the pharmaceutical composition and dosage form disclosed herein include talc, calcium carbonate (e.g., granule or powder), microcrystalline cellulose, powdered cellulose, dextran, kaolin, mannitol, silicic acid, sorbitol, starch, pregelatinized starch, and mixtures thereof. The binding agent or filter in the pharmaceutical composition of the present disclosure is typically present at about 50 to about 99% by mass of the pharmaceutical composition of dosage form.

Non-limiting examples of disintegrants that can be used in the pharmaceutical composition and dosage form of the present disclosure include agar, alginic acid, calcium carbonate, microcrystalline cellulose, sodium croscarmellose, crospovidone, polacrilin potassium, sodium carboxymethyl starch, potato or tapioca starch, other starches, pregelatinized starch, other starches, clay, other algin, other cellulose, gum, and mixtures thereof.

Non-limiting examples of lubricants that can be used in the pharmaceutical composition and dosage form of the present disclosure include calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional examples of lubricants include Syloid silica gel, coagulated aerosol of synthetic silica, CAB-O-SIL (pyrogenic silicon dioxide product, sold by Cabot (Boston, MA)), and mixtures thereof. A lubricant, if any, is typically used at an amount of about less than 1% by mass of the pharmaceutical composition of dosage form into which it is incorporated.

An effective ingredient or active ingredient of the present disclosure can be administered through release controlling means or through a delivery device or dosage . . . form that is well known to those skilled in the art. Non-limiting examples of release controlling means or delivery devices include those disclosed in US Patent Nos. 3, 845, 770, 3,916,899, 3,536,809, 3,598,123, 4,008,719, 5,674,533, 5,059,595, 5,591,767, 5,120,548, 5,073,543, 5,639,476, 5,354,556, and 5,733,566, which are incorporated herein by reference. It is possible to provide delayed release or release control of one or more active ingredients using, for example, hydropropylmethyl cellulose, other polymer matrices, gel, permeable membrane, osmotic pressure system, multilayer coating, microparticles, liposome, microsphere or combination thereof in order to provide a desirable release profile at various ratios using such a dosage form. A suitable release control formulation that is known to those skilled in the art, including those disclosed herein, can be readily selected for use with the effective ingredient or active ingredient of the present disclosure. Thus, the present disclosure is not limited thereto, but encompasses unit dosage forms that are suitable for oral administration such as, without limitation, tablets, capsules, gelcaps, and caplets, which are prepared to be compatible with release control.

A parenteral dosage form can be administered to a patient through various routes that include, but are not limited to, subcutaneous, intravenous (including bolus injection), intramuscular, and intraatrial administration. Since such administration typically circumvents the natural defense of a patient against contaminants, a parenteral dosage form is preferably aseptic or sterilizable prior to administration to the patient. Non-limiting examples of the parental dosage form include a liquid agent that can be directly injected, a dried product which is readily dissolved or suspended in a pharmaceutically acceptable vehicle for injection, and suspension and emulsion that can be directly injected. A suitable vehicle that can be used for providing the parenteral dosage form of the present disclosure is well known to those skilled in the art. Non-limiting examples of the suitable vehicle include injection water (US Pharmacopoeia); aqueous vehicle such as, without limitation, sodium chloride solution for injection, Ringer's injection solution, dextrose injection solution, dextrose and sodium chloride injection solution, and Ringer's lactate injection solution; water miscible such vehicles as, without limitation, ethyl alcohol, polyethylene glycol, and polypropylene glycol; and non-water-miscible vehicles such as, without limitation, corn oil, cottonseed oil, peanut oil, sesame oil, ethyl oleate, isopropyl myristate, and benzyl benzoate.

A drug can be topically applied to the skin, appendage thereof, or various mucous membranes. Routes that can be used include sublingual, transnasal, transvaginal, intracystic, transrectal, transpreputial, intraocular, cheek, or intra-aural administration. Many dosage forms have been developed to deliver an active ingredient to a site of application to induce a topical action. Non-limiting examples of the topical and mucosal dosage form of the present disclosure include ointment, cream, gel, paste, powder, lotion, spray, liniment, poultice, aerosol, liquid agent, emulsion, suspension, eye drops, other ophthalmic preparations, and other dosage forms known to those skilled in the art. See Remington's Pharmaceutical Sciences, 18th Ed., Mack Publishing, Easton, PA (1990), Introduction to Pharmaceutical Dosage Forms, Lea & Febiger, Philadelphia (1985), and the like. A dosage form suitable for treatment of the mucosal tissue within the oral cavity can be formulated as a gargle or oral gel.

A suitable excipient (e.g., carrier or diluent) and other materials that can be used for providing the topical mucosal dosage form encompassed by the present disclosure: are well known to those skilled in the medicinal field, and are determined in accordance with the specific tissue to which a given pharmaceutical composition or dosage form is applied. Non-limiting examples of typical excipients for forming a liquid agent, emulsion, or gel include water, acetone, ethanol, ethylene glycol, propylene glycol, butane-1,3-diol, isopropyl myristate, isopropyl palmitate, mineral oil, and mixture thereof, which are non-toxic and pharmaceutically acceptable.

A humectant such as an occlusive, moisturizer, mitigant, or a protein rejuvenator can also be added to a pharmaceutical composition or dosage form if desirable.

An occlusive is a substance that physically blocks the loss of moisture within the stratum corneum. Non-limiting examples of the occlusive include petroleum jelly, lanolin, mineral oil, silicone such as dimethicone, zinc oxide, and combinations thereof. An occlusive is preferably petroleum jelly or lanolin, and more preferably petroleum jelly with a minimum concentration of 5%.

A moisturizing agent is a substance that draws water to the skin and theoretically improves the hydration of the stratum corneum upon application the skin. However, water that is drawn to the skin is not from the atmosphere, but is water from another cell. With this type of moisturizing agent, evaporation from the skin can continue and actually exacerbate dryness. Non-limiting examples of the moisturizing agent include glycerin, sorbitol, urea, alpha hydroxyl acid, saccharide, and combinations thereof. Preferred examples of the moisturizing agent include alpha hydroxyl acid such as glycolic acid, lactic acid, malic acid, citric acid, tartaric acid, and the like.

A mitigant is a substance that provides smoothness to the skin by filling the space between skin layers with oil droplets, which generally does not result in blockage unless thickly applied. When used with an emulsifying agent, they can help retain oil and moisture within the stratum corneum. Vitamin E is a general additive that appears to have no effect except as a mitigant. Other vitamins such as Vitamin A and Vitamin D are also added, but the effect thereof is questionable. Non-limiting examples of the mitigant include mineral oil, lanolin, fatty acid, cholesterol, squalene, structured lipids, and combinations thereof.

The timing of administration of the compound of the disclosure and therapeutic agent thereof is not limited. They can be administered simultaneously or at an interval (e.g., different times) to a subject. The compound of the disclosure and therapeutic agent thereof can be prepared as a combined agent. The dosage of such a therapeutic agent can be appropriately selected based on clinically used doses. The ratio of the compound of the disclosure and therapeutic agent thereof can be appropriately selected depending on the subject to be administered, route of administration, target disease, symptom, combination, or the like.

In one embodiment of the present disclosure, the compound of the disclosure, when using a pharmaceutical composition, can be combined at the same time or different time for administration. Such a pharmaceutical composition is also within the scope of the present disclosure.

Such a medicament, formulation, and pharmaceutical composition can be manufactured by mixing the compound of the disclosure and/or additional agent (e.g., anti-rabies gamma globulin formulation, antimicrobial drug, antiviral agent (e.g., ribavirin, amantadine, or the like), sedative (e.g., ketamine, midazolam, etc.), or the like) with any appropriate component, together or separately as a combined agent or separate agents, by using any technology known in the art, and can be formulated using any known technology in the art as an appropriate formulation such as a tablet, capsule, powder, granule, liquid agent, suspension, injection, patch, or poultice. If the compound of the disclosure and/or additional agent (e.g., anti-rabies gamma globulin formulation, antimicrobial drug, antiviral agent (e.g., ribavirin, amantadine, or the like), sedative (e.g., ketamine, midazolam, etc.), or the like) are prepared as separate agents, they can be provided as a kit of two agents. One component can be provided as a single agent, with an instruction (package insert or the like) instructing to combine another component (for the compound of the disclosure, additional agent, and for an additional agent (e.g., anti-rabies gamma globulin formulation, antimicrobial drug, antiviral agent (e.g., ribavirin, amantadine, or the like), sedative (e.g., ketamine, midazolam, etc.), or the like), the compound of the disclosure) at the same time or different times for administration.

If the compound of the disclosure is used as the active ingredient of a medicament, this can be intended for use in not only humans, but also other animals besides humans (cats, dogs, cows, horses, bats, foxes, mongooses, raccoons, and the like).

The toxicity and therapeutic efficacy of the compound of the disclosure can be determined by a standard pharmaceutical procedure in cultured cells or experimental animals by measuring, for example, $LD_{50}$ (lethal dosage for 50% of the population) and $ED_{50}$ (dosage is that therapeutically effective for 50% of the population). The ratio of doses between a toxic effect and therapeutic effect is a therapeutic index, which can be represented as $LD_{50}/ED_{50}$.

A compound exhibiting a high therapeutic index is preferable. While a compound exhibiting a toxic side effect can be used, a delivery system for targeting such a compound to an affected site of tissue must be carefully designed in order to minimize the potential damage to uninfected cells and therefore to reduce side effects.

Data obtained from a cell culture assay or animal test can be used for a prescription within the range of doses for use in humans. Such a dose of a compound is preferably within the range of a circulating concentration including $ED_{50}$ that involves hardly any or no toxicity. A dose can be varied within this range in accordance with the dosage form used and route of administration utilized. For a compound used in the method of the present disclosure, a therapeutically sufficient dosage can be first estimated from a cell culture assay. A dose that can materialize a range of circulating plasma concentration including $IC_{50}$ (i.e., concentration of test compound materializing half of maximum inhibition of symptom) determined in cell culture can be prescribed in an animal model. The dose that is useful in humans can be more accurately determined using such information. The plasma level can be measured by, for example, high performance liquid chromatography.

The compound of the disclosure can be administered orally and at a single dose of about 0.10 to about 150 mg/day in terms of the amount of active ingredient, or the same amount divided into multiple daily doses. The dose can be similarly computed for parenteral, topical, transmucosal (e.g., transnasal, transrectal, or transdermal), or topical administration. The amount of a pharmaceutical composition administered in the method of the present disclosure is determined in accordance with the target of treatment, severity of the disorder or symptom thereof, administration method, dosing frequency, and judgment of a physician. The dosing frequency is within the range from dosing nearly every hour to monthly dosing. In a specific embodiment, dosing is 8 times daily to once every other day, or 1 to 3 times a day. In a specific embodiment, the pharmaceutical composition of the present disclosure is administered chronically, e.g., every day.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

The present disclosure has been described while showing preferred embodiments to facilitate understanding. While the present disclosure is described hereinafter based on the Examples, the above descriptions and the following Examples are provided for the sole purpose of exemplification, not limitation of the present disclosure. Thus, the scope of the present disclosure is not limited to the embodiments and Examples that are specifically described herein and is limited only by the scope of claims.

EXAMPLES

The present disclosure is specifically described based on the Examples. However, the scope of the present disclosure is not limited to the Examples described below. It is understood that the reagent, equipment, etc. that were used can be exchanged with those obtained from a suitable source other than the specific source described in the Examples.

For Thin Layer Chromatography (TLC), Merck's TLC Silica gel 60 F254 (25 glass plate, 20×20 cm) and Fuji Silysia Chemical's CHROMATOREX NH-TLC Plates (20× 20 cm) were used. As the developing solvent, chloroform-methanol mixed solvent system, ethyl acetate-methanol mixed solvent system, or ethyl acetate-hexane mixed solvent system was used. Spots were checked using coloring with UV irradiation, ninhydrin, iodine, or phosphomolybdic acid (ethanol solution). An organic solvent was dried using anhydrous sodium sulfate and anhydrous magnesium sulfate. For column chromatography, Fuji Silysia Chemical's cartridge column CHROMATOREX Q-PACK SI30 (SIZE 10, 20, or 60) and DNH (SIZE 10 or 20) or Shoko Science's Purif-Pack®-EX SI 50 (SIZE 20 or 60) were used in accordance with the amount of raw product to be purified. Silica gel thin layer chromatography for separation (PTLC: Preparative Thin Layer Chromatography) used Merck's PLC Silica gel 60 F254 (20×20 cm; thickness: 0.5 mm; product number: 1.05744.0001; thickness: 1 mm; product number: 1.13895.0001) and Fuji Silysia Chemical's CHROMATOREX NH-PLC05 (20×20 cm; thickness: 0.5 mm). Synthesized compounds were identified by LC/MS (Liquid Chromatography/Mass Spectrometry). The following tables show the retention ($t_R$) and m/z value $[M+1]^+$. For measurement, Shimadzu's LCMS-2020 system was used, and Chemicals Evaluation and Research Institute's L-column 2ODS, 3 μm, 3.0×50 mm was used as the analysis column. The column oven was set to 40° C., and compounds were detected by using both UV absorption (220 nm, 254 nm) and mass spectrometry. Elution condition A or B shown below was used.

Elution Condition A:

Flow rate 1.5 mL/min, mobile phase a=aqueous 0.05% (v/v) trifluoroacetic acid solution, mobile phase b=0.05% (v/v) trifluoroacetic acid containing acetonitrile; 0-0.9 minutes, linear gradient, A:B (95:5)-A:B (10:90), 0.9-2 minutes Elution Condition B:

Flow rate 1.0 mL/min, mobile phase a=aqueous 0.05% (v/v) formic acid solution, mobile phase b=0.05% (v/v) formic acid containing acetonitrile; 0-0.9 minutes, linear gradient, A:B (95:5)-A:B (10:90), 0.9-2 minutes Measurement Condition C:

Shimadzu's LCMS-2020 system was used, and Chemicals Evaluation and Research Institute's L-column 20DS, 3 μm, 3.0×50 mm was used as the analysis column. The column oven was set to 40° C., and the compound was detected by using both UV absorption (220 nm, 254 nm) and mass spectrometry.

Elution condition: flow rate of 1.5 mL/min, mobile phase a=aqueous 0.05% (v/v) trifluoroacetic acid solution, mobile phase b=0.05% (v/v) trifluoroacetic acid containing acetonitrile

TABLE A1

| Time (min) | Ratio of mobile phase b (%) |
|---|---|
| 0.0 | 5 |
| 0.01-0..89 | 5-90 linear gradient |
| 0.9 | 90 |
| 2.00 | 90 |

Measurement Condition D:

The same apparatus as measurement condition C was used. Elution condition: flow rate of 1.5 mL/min, mobile phase a=aqueous 0.05% (v/v) trifluoroacetic acid solution, mobile phase b=0.05% (v/v) trifluoroacetic acid containing acetonitrile

TABLE A2

| Time (min) | Ratio of mobile phase b (%) |
|---|---|
| 0.0 | 0 |
| 0.5 | 0 |
| 0.51-1.39 | 0-70 linear gradient |
| 1.4 | 70 |
| 1.5 | 90 |
| 2.00 | 90 |

Measurement Condition E:

The same apparatus as measurement condition C was used. Elution condition: flow rate of 1.5 mL/min, mobile phase a=5 mM $NH_4HCO_3$ containing water/acetonitrile=900/100 (v/v), mobile phase b=5 mM $NH_4HCO_3$ containing water/acetonitrile=100/900 (v/v)

TABLE A3

| Time (min) | Ratio of mobile phase b (%) |
|---|---|
| 0.0 | 0 |
| 0.5 | 0 |
| 0.51-1.39 | 0-70 linear gradient |
| 1.4 | 70 |
| 1.5 | 90 |
| 2.00 | 90 |

Measurement Condition F:

Waters' Alliance 2695 Separation Module system was used, and YMC's YMC-Triart C18, 5 μm, 3.0×50 mm was used as the analysis column. The column oven was set to 30° C., and the compound was detected using both UV absorption (220 nm) and mass spectrometry.

Elution condition: flow rate of 1.27 mL/min, mobile phase a=aqueous 0.05% (v/v) trifluoroacetic acid solution, mobile phase b=0.05% (v/v) trifluoroacetic acid containing acetonitrile

TABLE A4

| Time (min) | Ratio of mobile phase b (%) |
|---|---|
| 0.0 | 10 |
| 1.0 | 10 |
| 1.0-1.5 | 10-30 gradient |
| 1.5-4.5 | 30-70 gradient |
| 4.5-5.0 | 70-90 gradient |
| 6.0 | 90 |

Measurement Condition G:

The same apparatus as measurement condition F was used.

Elution condition: flow rate of 1.27 mL/min, mobile phase a=aqueous 0.05% (v/v) trifluoroacetic acid solution, mobile phase b=0.05% (v/v) trifluoroacetic acid containing acetonitrile

TABLE A5

| Time (min) | Ratio of mobile phase b (%) |
|---|---|
| 0.0 | 1 |
| 1.0 | 1 |
| 1.0-4.0 | 1-40 gradient |
| 4.0-5.0 | 40-90 gradient |
| 6.0 | 90 |

Measurement Condition H:

Waters' 2767 system was used, and YMC's YMC-Triart C18, 5 μm, 4.6×50 mm was used as the analysis column. The column oven was set to 25° C., and compound was detected using UV absorption (220 nm), mass spectrometry, and ELS (Evaporative Light Scattering).

Elution condition: flow rate of 2 mL/min, mobile phase a=aqueous 0.1% (v/v) trifluoroacetic acid solution, mobile phase b=0.1% (v/v) trifluoroacetic acid containing acetonitrile

TABLE A6

| Time (min) | Ratio of mobile phase b (%) |
|---|---|
| 0.0 | 5 |
| 0.5 | 5 |
| 0.5-3.0 | 5-95 gradient |
| 5.0 | 95 |

Measurement Condition I:

Waters' H-class/SQD2 system was used, and Waters' ACQUITY UPLC BEH C18 1.7 μm, 2.1×50 mm was used as the analysis column. A compound was detected using both UV absorption (220 nm) and mass spectrometry.

Elution condition: flow rate of 0.6 mL/min, mobile phase a=aqueous 0.1% (v/v) formic acid solution, mobile phase b=0.1% (v/v) formic acid containing acetonitrile

TABLE A7

| Time (min) | Ratio of mobile phase b (%) |
|---|---|
| 0.0 | 2 |
| 2.0-2.6 | 2-100 |
| 2.6-3.0 | 100 |

Measurement Condition J:

The same apparatus as measurement condition F was used. Elution condition: flow rate of 1.27 mL/min, mobile phase a=aqueous 0.05% (v/v) trifluoroacetic acid solution, mobile phase b=0.05% (v/v) trifluoroacetic acid containing acetonitrile

TABLE A8

| Time (min) | Ratio of mobile phase b (%) |
|---|---|
| 0.0 | 10 |
| 1.0 | 10 |
| 1.0-2.0 | 10-60 gradient |
| 2.0-5.0 | 60-99 gradient |
| 5.0-6.0 | 99 |

Nuclear Magnetic Resonance (NMR) was measured using Bruker AVANCE III 400 MHZ Spectrometer (resonant frequency: 1H: 400 MHZ, 13C: 100 MHZ) and Bruker AVANCE III 300 MHZ Spectrometer (resonant frequency: 1H: 300 MHZ, 13C: 75 MHZ).

The abbreviations described above and the following abbreviations are also used in the Examples to simplify the description.

s: singlet
d: doublet
t: triplet
m: multiplet
dd: double doublet
J: coupling constant
Hz: Hertz
δ: chemical shift
min: minute
RT: retention time
CDCl$_3$: deuterated chloroform
Me: methyl
Et: ethyl
Pr: propyl
i-Pr: isopropyl
i-Bu: isobutyl
s-Bu and sec-Bu: secondary butyl
$^t$Bu, tBu and tert-Bu: tertiary butyl
i-Pnt: isopentyl
Hxy: n-hexyl
Ac: acetyl
Bz: benzoyl
Bnzl: benzyl
3-Me-Bnzl: 3-methylbenzyl
4-Me-Bnzl: 4-methylbenzyl
4-tBu-Bnzl: 4-(tert-butyl)benzyl
3-MeO-Bnzl: 3-methoxybenzyl
4-MeO-Bnzl: 4-methoxybenzyl
4-OH-Bnzl: 4-hydroxybenzyl
3-F-Bnzl: 3-fluorobenzyl
4-F-Bnzl: 4-fluorobenzyl
3-C$_1$-Bnzl: 3-chlorobenzyl
4-C$_1$-Bnzl: 4-chlorobenzyl
3,4-C$_{12}$-Bnzl: 3,4-dichlorobenzyl
4-tBuO-Bnzl: 4-(tert-butoxy)benzyl
4-Nt-Bnzl: 4-nitrobenzyl
Cbx-E and 2-Cbx-Et: 2-carboxyethyl
Cbm-M: 2-amino-2-oxoethyl or carbamoylmethyl
Cbm-E: 3-amino-3-oxopropyl or 2-carbamoylethyl
tBOC-E: 2-(tert-butoxycarbonyl)ethyl or 3-(tert-butoxy)-3-oxopropyl
Gun-Pr and 3-Gun-Pr: 3-guanidinopropyl
Hdr-M: hydroxymethyl
Hdr-E and 2-OH-Et: 2-hydroxyethyl
tBuO-E and 2-OtBu-Et: 2-(tert-butoxy)ethyl
Ph-Et: 2-phenylethyl
Ph-Pr: 3-phenylpropyl
Ph-Bu: 4-phenylbutyl
Np-M and 1-Npm: naphthalen-1-ylmethyl
2-Npm: naphthalen-2-ylmethyl
Np-E: 2-(naphthalen-1-yl)ethyl
6-Me-Indm: 6-methyl-1H-indol-3-ylmethyl
Boc-6-Me-Indm: 1-tert-butoxycarbonyl-6-methyl-1H-indol-3-ylmethyl
6-F-Indm: 6-fluoro-1H-indol-3-ylmethyl
Boc-6-F-Indm: 1-tert-butoxycarbonyl-6-fluoro-1H-indol-3-ylmethyl
Cpm: cyclopentylmethyl
Chm: cyclohexylmethyl
Chepm: cycloheptylmethyl
Boc and tBOC and $^t$BOC: tert-butoxycarbonyl
TBSO-E and 2-OTBS-Et: 2-(tert-butyldimethylsilyloxy)ethyl

[Chemical Formula 35]

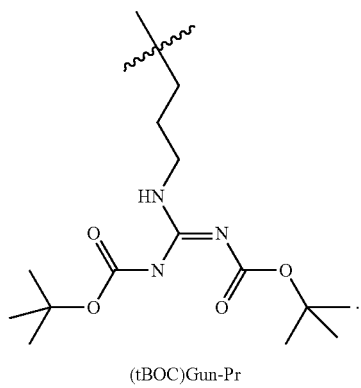

(tBOC)Gun-Pr

Example 1: Synthesis of Compound

Synthesis Example for Compound V

Synthesis of N-cyclohexyl-1,2,4-triazine-3-carboxamide

Ethyl 1,2,4-triazine-3-carboxylate (200 mg, 1.3 mmol) was dissolved in methanol (2.5 mL), and cyclohexylamine (130 mg, 1.3 mmol) was added. The mixture was then stirred for 12 hours at room temperature. Methanol was evaporated under reduced pressure, and the resulting residue was purified by column chromatography (column: CHROMATOREX Q-Pack SI30, SIZE 20, eluent: ethyl acetate-methanol (gradient from 0% to 5%)). A fraction of a compound of interest was concentrated. The aforementioned compound (181 mg, yield: 67%) was obtained as a brown amorphous solid.

Under the same conditions as this reaction, the following compounds were synthesized.

N-(trans-4-methylcyclohexyl)-1,2,4-triazine-3-carboxamide
N-(2,2,6,6-tetramethylpiperidin-4-yl)-1,2,4-triazine-3-carboxamide
N-benzyl-1,2,4-triazine-3-carboxamide
N-isobutyl-1,2,4-triazine-3-carboxamide
N-isopentyl-1,2,4-triazine-3-carboxamide
N-(4-chlorobenzyl)-1,2,4-triazine-3-carboxamide
N-(4-fluorobenzyl)-1,2,4-triazine-3-carboxamide
N-(3-hydroxybenzyl)-1,2,4-triazine-3-carboxamide
N-(4-hydroxybenzyl)-1,2,4-triazine-3-carboxamide Synthesis Example for Compound XV Synthesis of 4-methylpentanal A methylene chloride (40.0 mL) solution of acetic acid (0.0994 mL, 1.30 mmol) and 4-methylpentan-1-ol (1.49 mL, 11.8 mmol) was slowly added dropwise into a methylene chloride (45.0 mL) solution of 1,1,1-triacetoxy-1,1-dihydro-1,2-benziodoxol-3-(1H)-one (Dess-Martin periodinane) (5.25 g, 12.4 mmol) at room temperature. After completion of the addition, the mixture was stirred for another hour, and then diethyl ether (280 mL) was added. An aqueous 1.30M sodium hydroxide solution (200 mL) was added to the organic layer and stirred for 10 minutes at room temperature. The organic layer was washed with an aqueous 1.30M sodium hydroxide solution (90.0 mL) and (50.0 mL). After drying with anhydrous sodium magnesium sulfate, the solvent was carefully evaporated to obtain the aforementioned compound (1.01 g, 86%).

Under the same conditions as this reaction, the following compound was synthesized. 5-methylhexanal

Synthesis Example for Compound III

Synthesis of N-benzylprop-2-en-1-amine (Bromomethyl)benzene (0.992 mL, 8.35 mmol) was gradually added dropwise to a suspension of anhydrous potassium carbonate (1.39 g, 10.0 mmol) and prop-2-en-1-amine (7.53 mL, 100 mmol) and then stirred for 3 hours at room temperature. The solids were filtered and washed with methylene chloride. The combined organic layer was evaporated under reduced pressure. The resulting residue was purified with CHROMATOREX Q-PACK SI30 SIZE 20 (hexane:ethyl acetate=50%:50% to 0%:100%) to obtain the aforementioned compound (934 mg, yield: 76%).

Synthesis Example for Compound III

Synthesis of N-(cyclohexylmethyl) prop-2-en-1-amine

Prop-2-en-1-amine (3.42 g, 60.0 mmol) was added dropwise to a methanol (40.0 mL) solution of cyclohexanecarbaldehyde (7.06 g, 63.0 mmol) while cooling with ice. After the completion of the addition, sodium tetrahydroborate (0.850 g, 22.0 mmol) was resolved and added while cooling with ice, and the mixture was stirred for another hour. Methanol was evaporated under reduced pressure. Ethyl ether was added to the residue. The organic layer was washed with saturated saline and dried with anhydrous sodium sulfate and then concentrated under reduced pressure. The residue was evaporated under reduced pressure to obtain the aforementioned compound (7.35 g, 80%, boiling point 79 to 84° C./9.1 mmHg).

Under the same conditions as this reaction, the following compounds were synthesized.
N-isobutylprop-2-en-1-amine
N-allyl-3-methylbutan-1-amine

Synthesis Example for Compound III

Synthesis of N-allyltetrahydro-2H-pyran-4-amine

Prop-2-en-1-amine (300 mg, 5.3 mmol) was added dropwise to a dichloromethane (7.0 mL) solution of tetrahydro-4H-pyran-4-one (530 mg, 5.3 mmol). Sodium sulfate (750 mg, 5.3 mmol) was added, and the mixture was vigorously stirred for 6 hours at room temperature. Sodium sulfate was filtered out. The resulting filtrate was concentrated under reduced pressure, and methanol was evaporated. The concentrated reaction mixture was redissolved into methanol (7.0 mL). Sodium tetrahydroborate 200 mg, 5.3 mmol) was added while cooling with ice, and the mixture was stirred for another 2 hours. Methanol was evaporated under reduced pressure. Dichloromethane was added to the residue. The organic layer was washed with water and saturated saline and dried with anhydrous sodium sulfate and then concentrated under reduced pressure. The resulting residue was purified by column chromatography (column: Chromatorex Q-Pack SI30, Size 60, eluent: hexane-ethyl acetate (gradient from 20% to 100%) and then ethyl acetate-methanol (gradient from 0% to 15%)) to obtain the aforementioned compound (400 mg, yield: 54%).

Under the same conditions as this reaction, the following compounds were synthesized.
4-((allylamino)methyl) phenol
N-(4-(trifluoromethoxy)benzyl) prop-2-en-1-amine
N-(4-ethoxybenzyl) prop-2-en-1-amine
N-allyl-3-methylbutan-1-amine

Imine Intermediate Synthesis Example: II-5 and II-6

Synthesis of (3S*,3aS*,6R*,7R*,7aS*)-N-benzyl-7-isobutyl-1-(4-methoxybenzyl)-1,2,3,6,7,7a-hexahydro-3aH-3,6-methanopyrrolo[3,2-b]pyridine-3a-carboxamide (II-6) and (3S*,3aR*,6S*,7R*,7aR*)-N-benzyl-7-isobutyl-1-(4-methoxybenzyl)-1,2,3,3a,7,7a-hexahydro-6H-3,6-methanopyrrolo[3,2-c]pyridine-6-carboxamide (II-5)

4A molecular sieves (335 mg), 4-methylpentanal (94.5 mL, 0.93 mmol), and N-(4-methoxybenzylprop-2-en-1-amine (165.5 mg, 0.93 mmol) were added to a chloroform (2 mL) solution of N-benzyl-1,2,4-triazine-3-carboxamide (80 mg, 0.37 mmol), and heated and refluxed for 10 hours. The molecular sieves were filtered and washed twice with chloroform (5.00 mL). The combined organic layer was evaporated under reduced pressure. The resulting residue purified was with CHROMATOREX Q-PACK SI30 SIZE 20 (hexane:ethyl acetate=75%:25% to 0%:100%) and subsequently with CHROMATOREX Q-PACK DNH30 SIZE 10 (hexane:ethyl acetate=100%:0% to 50%:50%) to obtain the aforementioned compounds (II-5) and (II-6) as a mixture of about 1:1 (quantified by 1H NMR) (69.5 mg, yield: 42%, [M+1]$^+$=446).

The synthesized compounds of formula IIB and formula IIF are summarized in the following tables.

TABLE 3-1

| Compound No. | R$_1$ | R$_2$ | R$_3$ | Synthesis method[1] | Reagent | | |
|---|---|---|---|---|---|---|---|
| II-1 | methyl | benzyl | benzyl | II-5 & II-6 | N-allylmethyl-amine | N-benzyl-1,2,4-triazine-3-carboxamide | 3-phenyl-propanal |
| II-2 | 4-chloro-benzyl | benzyl | isobutyl | II-5 & II-6 | N-(4-chloro-benzyl)prop-2-en-1-amine | N-benzyl-1,2,4-triazine-3-carboxamide | 4-methyl-pentanal |

TABLE 3-1-continued

| Compound No. | R₁ | R₂ | R₃ | Synthesis method[1] | Reagent | | |
|---|---|---|---|---|---|---|---|
| II-3 | 4-chlorobenzyl | benzyl | isobutyl | II-5 & II-6 | N-(4-chlorobenzyl)prop-2-en-1-amine | N-benzyl-1,2,4-triazine-3-carboxamide | 4-methylpentanal |
| II-4 | 3-chlorobenzyl | benzyl | isobutyl | II-5 & II-6 | N-(3-chlorobenzyl)prop-2-en-1-amine | N-benzyl-1,2,4-triazine-3-carboxamide | 4-methylpentanal |
| II-5 | 4-methoxybenzyl | benzyl | isobutyl | described in the Examples | N-(4-methoxybenzyl)prop-2-en-1-amine | N-benzyl-1,2,4-triazine-3-carboxamide | 4-methylpentanal |
| II-6 | 4-methoxybenzyl | benzyl | isobutyl | described in the Examples | N-(4-methoxybenzyl)prop-2-en-1-amine | N-benzyl-1,2,4-triazine-3-carboxamide | 4-methylpentanal |
| II-7 | 4-methylbenzyl | benzyl | isobutyl | II-5 & II-6 | N-(4-methoxybenzyl)prop-2-en-1-amine | N-benzyl-1,2,4-triazine-3-carboxamide | 4-methylpentanal |
| II-8 | 4-methylbenzyl | benzyl | isobutyl | II-5 & II-6 | N-(4-methoxybenzyl)prop-2-en-1-amine | N-benzyl-1,2,4-triazine-3-carboxamide | 4-methylpentanal |
| II-9 | benzyl | isobutyl | isobutyl | II-5 & II-6 | N-allylbenzylamine | N-isobutyl-1,2,4-triazine-3-carboxamide | 4-methylpentanal |
| II-10 | benzyl | isobutyl | isobutyl | II-5 & II-6 | N-allylbenzylamine | N-isobutyl-1,2,4-triazine-3-carboxamide | 4-methylpentanal |
| II-11 | isopentyl | isobutyl | benzyl | II-5 & II-6 | N-allylisopentylamine | N-isobutyl-1,2,4-triazine-3-carboxamide | 3-phenylpropanal |
| II-12 | isopentyl | isobutyl | benzyl | II-5 & II-6 | N-allylisopentylamine | N-isobutyl-1,2,4-triazine-3-carboxamide | 3-phenylpropanal |
| II-13 | isobutyl | isobutyl | 4-chlorobenzyl | II-5 & II-6 | N-allylisobutylamine | N-isobutyl-1,2,4-triazine-3-carboxamide | 3-(4-chlorophenyl)propanal |
| II-14 | isobutyl | isobutyl | 4-chlorobenzyl | II-5 & II-6 | N-allylisobutylamine | N-isobutyl-1,2,4-triazine-3-carboxamide | 3-(4-chlorophenyl)propanal |

TABLE 3-2

| | | | | | | | | |
|---|---|---|---|---|---|---|---|---|
| II-15 | isobutyl | | isobutyl | benzyl | II-5 & II-6 | N-allylisobutylamine | N-isobutyl-1,2,4-triazine-3-carboxamide | 3-phenylpropanal |
| II-16 | isobutyl | | isobutyl | isobutyl | II-5 & II-6 | N-allylisobutylamine | N-isobutyl-1,2,4-triazine-3-carboxamide | 4-methylpentanal |
| II-17 | 4-hydroxybenzyl | | benzyl | isobutyl | II-5 & II-6 | N-(4-hydroxybenzyl)prop-2-en-1-amine | N-benzyl-1,2,4-triazine-3-carboxamide | 4-methylpentanal |
| II-18 | isobutyl | | isopentyl | benzyl | II-5 & II-6 | N-allylisobutylamine | N-isopentyl-1,2,4-triazine-3-carboxamide | 3-phenylpropanal |
| II-19 | isobutyl | | isopentyl | benzyl | II-5 & II-6 | N-allylisobutylamine | N-isopentyl-1,2,4-triazine-3-carboxamide | 3-phenylpropanal |
| II-20 | isobutyl | | isobutyl | benzyl | II-5 & II-6 | N-allylisobutylamine | N-isobutyl-1,2,4-triazine-3-carboxamide | 3-phenylpropanal |
| II-21 | isobutyl | | benzyl | isobutyl | II-5 & II-6 | N-allylisobutylamine | N-benzyl-1,2,4-triazine-3-carboxamide | 4-methylpentanal |
| II-22 | isobutyl | | benzyl | isobutyl | II-5 & II-6 | N-allylisobutylamine | N-benzyl-1,2,4-triazine-3-carboxamide | 4-methylpentanal |
| II-23 | isobutyl | | 4-chlorobenzyl | isobutyl | II-5 & II-6 | N-allylisobutylamine | N-(4-chlorobenzyl)-1,2,4-triazine-3-carboxamide | 4-methylpentanal |
| II-24 | isobutyl | | benzyl | isopentyl | II-5 & II-6 | N-allylisobutylamine | N-benzyl-1,2,4-triazine-3-carboxamide | 5-methylhexanal |
| II-25 | isobutyl | | benzyl | isopentyl | II-5 & II-6 | N-allylisobutylamine | N-benzyl-1,2,4-triazine-3-carboxamide | 5-methylhexanal |
| II-26 | isopentyl | | benzyl | isobutyl | II-5 & II-6 | N-allylisopentylamine | N-benzyl-1,2,4-triazine-3-carboxamide | 4-methylpentanal |
| II-27 | isopentyl | | benzyl | isobutyl | II-5 & II-6 | N-allylisopentylamine | N-benzyl-1,2,4-triazine-3-carboxamide | 4-methylpentanal |
| II-28 | 4-(dimethylamino)benzyl | | benzyl | isobutyl | II-5 & II-6 | 4-((allylamino)methyl)-N,N-dimethylaniline | N-benzyl-1,2,4-triazine-3-carboxamide | 4-methylpentanal |
| II-29 | 4-(tert-butyl)benzyl | | benzyl | isobutyl | II-5 & II-6 | N-(4-(tert-butyl)benzyl)prop-2-en-1-amine | N-benzyl-1,2,4-triazine-3-carboxamide | 4-methylpentanal |
| II-30 | 4-hydroxybenzyl | | benzyl | isopentyl | II-5 & II-6 | N-(4-hydroxybenzyl)prop-2-en-1-amine | N-benzyl-1,2,4-triazine-3-carboxamide | 5-methylhexanal |

TABLE 3-3

| | | | | | | | |
|---|---|---|---|---|---|---|---|
| II-31 | isopentyl | 4-chloro-benzyl | isobutyl | II-5 & II-6 | N-allylisopentylamine | N-(4-chlorobenzyl)-1,2,4-triazine-3-carboxamide | 4-methyl-pentanal |
| II-32 | isopentyl | 4-fluoro-benzyl | isobutyl | II-5 & II-6 | N-allylisopentylamine | N-(4-fluorobenzyl)-1,2,4-triazine-3-carboxamide | 4-methyl-pentanal |
| II-33 | 4-(trifluoro-methoxy)benzyl | benzyl | isobutyl | II-5 & II-6 | N-(4-(trifluoromethoxy)benzyl)prop-2-en-1-amine | N-benzyl-1,2,4-triazine-3-carboxamide | 4-methyl-pentanal |
| II-34 | 4-ethoxybenzyl | benzyl | isobutyl | II-5 & II-6 | N-(4-ethoxy-benzyl)prop-2-en-1-amine | N-benzyl-1,2,4-triazine-3-carboxamide | 4-methyl-pentanal |
| II-35 | benzyl | 4-hydroxy-benzyl | isobutyl | II-5 & II-6 | N-allylbenzyl-amine | N-(4-hydroxybenzyl)-1,2,4-triazine-3-carboxamide | 4-methyl-pentanal |
| II-36 | 4-methoxybenzyl | 4-hydroxy-benzyl | isobutyl | II-5 & II-6 | N-(4-methoxy-benzyl)prop-2-en-1-amine | N-(4-hydroxybenzyl)-1,2,4-triazine-3-carboxamide | 4-methyl-pentanal |
| II-37 | 4-(dimethyl-amino)benzyl | 3-hydroxy-benzyl | isobutyl | II-5 & II-6 | N-(3-hydroxy-benzyl)prop-2-en-1-amine | N-(3-hydroxybenzyl)-1,2,4-triazine-3-carboxamide | 4-methyl-pentanal |
| II-38 | 4-(dimethyl-amino)benzyl | 4-hydroxy-benzyl | isobutyl | II-5 & II-6 | N-(4-hydroxy-benzyl)prop-2-en-1-amine | N-(4-hydroxybenzyl)-1,2,4-triazine-3-carboxamide | 4-methyl-pentanal |
| II-39 | 4-(dimethyl-amino)benzyl | 4-hydroxy-benzyl | isobutyl | II-5 & II-6 | N-(4-hydroxy-benzyl)prop-2-en-1-amine | N-(4-hydroxybenzyl)-1,2,4-triazine-3-carboxamide | 4-methyl-pentanal |
| II-40 | benzyl | cyclohexyl | propyl | II-5 & II-6 | N-allylbenzyl-amine | N-cyclohexyl-1,2,4-triazine-3-carboxamide | pentanal |
| II-41 | benzyl | cyclohexyl | propyl | II-5 & II-6 | N-allylbenzyl-amine | N-cyclohexyl-1,2,4-triazine-3-carboxamide | pentanal |
| II-42 | benzyl | trans-4-methyl cyclohexyl | benzyl | II-5 & II-6 | N-allylbenzyl-amine | N-(trans-4-methyl-cyclohexyl)-1,2,4-triazine-3-carboxamide | 3-phenyl-propanal |
| II-43 | benzyl | trans-4-methyl cyclohexyl | benzyl | II-5 & II-6 | N-allylbenzyl-amine | N-(trans-4-methyl-cyclohexyl)-1,2,4-triazine-3-carboxamide | 3-phenyl-propanal |
| II-44 | benzyl | 2,2,6,6-tetra-methyl-piperidin-4-yl | benzyl | II-5 & II-6 | N-allylbenzyl-amine | N-(2,2,6,6-tetramethyl-piperidin-4-yl)-1,2,4-triazine-3-carboxamide | 3-phenyl-propanal |

TABLE 3-4

| | | | | | | | |
|---|---|---|---|---|---|---|---|
| II-45 | benzyl | 2,2,6,6-tetra-methyl-piperidin-4-yl | benzyl | II-5 & II-6 | N-allylbenzyl-amine | N-(2,2,6,6-tetra-methylpiperidin-4-yl)-1,2,4-triazine-3-carboxamide | 3-phenyl-propanal |
| II-46 | cyclohexyl | benzyl | isobutyl | II-5 & II-6 | N-allylcyclo-hexylamine | N-benzyl-1,2,4-triazine-3-carboxamide | 4-methyl-pentanal |
| II-47 | cyclohexyl | benzyl | phenyl | II-5 & II-6 | N-allylcyclo-hexylamine | N-benzyl-1,2,4-triazine-3-carboxamide | 2-phenyl-acetaldehyde |
| II-48 | tetrahydro-2H-pyran-4-yl | benzyl | phenyl | II-5 & II-6 | N-((tetrahydro-2H-pyran-4-yl)methyl)prop-2-en-1-amine | N-benzyl-1,2,4-triazine-3-carboxamide | 2-phenyl-acetaldehyde |
| II-49 | isobutyl | benzyl | phenyl | II-5 & II-6 | N-allylisobutyl amine | N-benzyl-1,2,4-triazine-3-carboxamide | 2-phenyl-acetaldehyde |
| II-50 | isobutyl | benzyl | phenyl | II-5 & II-6 | N-allylisobutyl amine | N-benzyl-1,2,4-triazine-3-carboxamide | 2-phenyl-acetaldehyde |

TABLE 4-1

| Compound No. | Compound name | LCMS $t_R$ (min) | Mass (M + H)⁺ | Analysis method | Yield (%) |
|---|---|---|---|---|---|
| II-1 | (3S,3aS,6R,7R,7aS)-N,7-dibenzyl-1-methyl-5-oxooctahydro-1,2,3,6,7,7a-hexahydro-1,2,3,6,7,7a-hexahydro-3aH-3,6-methanopyrrolo[3,2-b]pyridine-3a-carboxamide | — | 374 | — | 10 |
| II-2 | (3S,3aR,6S,7R,7aR)-N-benzyl-1-(4-chlorobenzyl)-7-isobutyl-1,2,3,3a,7,7a-hexahydro-6H-3,6-methanopyrrolo[3,2-c]pyridine-6-carboxamide | 1.28 | 450 | B | 28 |
| II-3 | (3S,3aS,6R,7R,7aS)-N-benzyl-1-(4-chlorobenzyl)-7-isobutyl-5-oxooctahydro-1,2,3,6,7,7a-hexahydro-3aH-3,6-methanopyrrolo[3,2-b]pyridine-3a-carboxamide | 1.28 | 450 | B | 28 |
| II-4 | (3S,3aR,6S,7R,7aR)-N-benzyl-1-(3-chlorobenzyl)-7-isobutyl-1,2,3,3a,7,7a-hexahydro-6H-3,6-methanopyrrolo[3,2-c]pyridine-6-carboxamide and (3S,3aS,6R,7R,7aS)-N-benzyl-1-(3-chlorobenzyl)-7-isobutyl-5-oxooctahydro-1,2,3,6,7,7a-hexahydro-3aH-3,6-methanopyrrolo[3,2-b]pyridine-3a-carboxamide | 1.30 | 450 | B | 30 |
| II-5 | (3S,3aR,6S,7R,7aR)-N-benzyl-7-isobutyl-1-(4-methoxybenzyl)-1,2,3,3a,7,7a-hexahydro-6H-3,6-methanopyrrolo[3,2-c]pyridine-6-carboxamide | 1.25 | 446 | B | 41 |
| II-6 | (3S,3aS,6R,7R,7aS)-N-benzyl-7-isobutyl-1-(4-methoxybenzyl)-5-oxooctahydro-1,2,3,6,7,7a-hexahydro-3aH-3,6-methanopyrrolo[3,2-b]pyridine-3a-carboxamide | 1.25 | 446 | B | 41 |
| II-7 | (3S*,3aR*,6S*,7R*,7aR*)-N-benzyl-7-isobutyl-1-(4-methylbenzyl)-1,2,3,3a,7,7a-hexahydro-6H-3,6-methanopyrrolo[3,2-c]pyridine-6-carboxamide | 1.27 | 430 | B | 16 |

TABLE 4-2

| Compound No. | Compound name | LCMS $t_R$ (min) | Mass (M + H)⁺ | Analysis method | Yield (%) |
|---|---|---|---|---|---|
| II-8 | (3S*,3aS*,6R*,7R*,7aS*)-N-benzyl-7-isobutyl-1-(4-methylbenzyl)-5-oxooctahydro-1,2,3,6,7,7a-hexahydro-3aH-3,6-methanopyrrolo[3,2-b]pyridine-3a-carboxamide | 1.27 | 430 | B | 15 |
| II-9 | (3S*,3aR*,6S*,7R*,7aR*)-1-benzyl-N,7-diisobutyl-1,2,3,3a,7,7a-hexahydro-6H-3,6-methanopyrrolo[3,2-c]pyridine-6-carboxamide | — | 382 | — | 20 |
| II-10 | (3S,3aS,6R,7R,7aS)-1-benzyl-N,7-diisobutyl-5-oxooctahydro-1,2,3,6,7,7a-hexahydro-3aH-3,6-methanopyrrolo[3,2-b]pyridine-3a-carboxamide | — | 382 | — | 11 |
| II-11 | (3S,3aS,6R,7R,7aS)-7-benzyl-N-isobutyl-1-isopentyl-5-oxooctahydro-1,2,3,6,7,7a-hexahydro-3aH-3,6-methanopyrrolo[3,2-b]pyridine-3a-carboxamide | — | 396 | — | 12 |
| II-12 | (3S*,3aR*,6S*,7R*,7aR*)-7-benzyl-N-isobutyl-1-isopentyl-1,2,3,3a,7,7a-hexahydro-6H-3,6-methanopyrrolo[3,2-c]pyridine-6-carboxamide | — | 396 | — | 12 |
| II-13 | (3S*,3aS*,6R*,7R*,7aS*)-7-(4-chlorobenzyl)-N,1-diisobutyl-5-oxooctahydro-1,2,3,6,7,7a-hexahydro-3aH-3,6-methanopyrrolo[3,2-b]pyridine-3a-carboxamide | — | 416 | — | 17 |
| II-14 | (3S*,3aR*,6S*,7R*,7aR*)-7-(4-chlorobenzyl)-N,1-diisobutyl-1,2,3,3a,7,7a-hexahydro-6H-3,6-methanopyrrolo[3,2-c]pyridine-6-carboxamide | — | 416 | — | 15 |
| II-15 | (3R*,3aS*,6R*,7R*,7aS*)-7-benzyl-N,1-diisobutyl-5-oxooctahydro-1,2,3,6,7,7a-hexahydro-3aH-3,6-methanopyrrolo[3,2-b]pyridine-3a-carboxamide | — | 382 | — | 37 |
| II-16 | (3S*,3aS*,6R*,7R*,7aS*)-N-(4-chlorobenzyl)-1,7-diisobutyl-5-oxooctahydro-1,2,3,6,7,7a-hexahydro-3aH-3,6-methanopyrrolo[3,2-b]pyridine-3a-carboxamide | 1.23 | 416 | B | 27 |
| II-17 | (3S*,3aR*,6S*,7R*,7aR*)-N-benzyl-1-(4-hydroxybenzyl)-7-isobutyl-1,2,3,3a,7,7a-hexahydro-6H-3,6-methanopyrrolo[3,2-c]pyridine-6-carboxamide and (3S*,3aS*,6R*,7R*,7aS*)-N-benzyl-1-(4-hydroxybenzyl)-7-isobutyl-5-oxooctahydro-1,2,3,6,7,7a-hexahydro-3aH-3,6-methanopyrrolo[3,2-b]pyridine-3a-carboxamide | 1.18 | 432 | B | 18 |
| II-18 | (3S,3aR,6S,7R,7aR)-7-benzyl-1-isobutyl-N-isopentyl-1,2,3,3a,7,7a-hexahydro-6H-3,6-methanopyrrolo[3,2-c]pyridine-6-carboxamide | 1.23 | 396 | B | 16 |
| II-19 | (3S,3aS,6R,7R,7aS)-7-benzyl-1-isobutyl-N-isopentyl-5-oxooctahydro-1,2,3,6,7,7a-hexahydro-3aH-3,6-methanopyrrolo[3,2-b]pyridine-3a-carboxamide | 1.28 | 396 | B | 38 |
| II-20 | (3S,3aR,6S,7R,7aR)-7-benzyl-N,1-diisobutyl-1,2,3,3a,7,7a-hexahydro-6H-3,6-methanopyrrolo[3,2-c]pyridine-6-carboxamide | — | 382 | — | 22 |
| II-21 | (3S,3aR,6S,7R,7aR)-N-benzyl-1,7-diisobutyl-1,2,3,3a,7,7a-hexahydro-6H-3,6-methanopyrrolo[3,2-c]pyridine-6-carboxamide | — | 382 | — | 17 |
| II-22 | (3S,3aS,6R,7R,7aS)-N-benzyl-1,7-diisobutyl-5-oxooctahydro-1,2,3,6,7,7a-hexahydro-3aH-3,6-methanopyrrolo[3,2-b]pyridine-3a-carboxamide | — | 382 | — | 37 |
| II-23 | (3S,3aR,6S,7R,7aR)-N-(4-chlorobenzyl)-1,7-diisobutyl-1,2,3,3a,7,7a-hexahydro-6H-3,6-methanopyrrolo[3,2-c]pyridine-6-carboxamide | 1.45 | 416 | B | 13 |
| II-24 | (3S*,3aR*,6S*,7R*,7aR*)-N-benzyl-1-isobutyl-7-isopentyl-1,2,3,3a,7,7a-hexahydro-6H-3,6-methanopyrrolo[3,2-c]pyridine-6-carboxamide | — | -16 | — | 11 |

TABLE 4-3

| Compound No. | Compound name | LCMS $t_R$ (min) | Mass (M + H)⁺ | Analysis method | Yield (%) |
|---|---|---|---|---|---|
| II-25 | (3S*,3aS*,6R*,7R*,7aS*)-N-benzyl-1-isobutyl-7-isopentyl-5-oxooctahydro-1,2,3,6,7,7a-hexahydro-3aH-3,6-methanopyrrolo[3,2-b]pyridine-3a-carboxamide | — | 396 | — | 34 |
| II-26 | (3S,3aR,6S,7R,7aR)-N-benzyl-7-isobutyl-1-isopentyl-1,2,3,3a,7,7a-hexahydro-6H-3,6-methanopyrrolo[3,2-c]pyridine-6-carboxamide and (3S,3aS,6R,7R,7aS)-N-benzyl-7-isobutyl-1-isopentyl-5-oxooctahydro-1,2,3,6,7,7a-hexahydro-3aH-3,6-methanopyrrolo[3,2-b]pyridine-3a-carboxamide | | 396 | | 28 |

TABLE 4-3-continued

| | | | | | |
|---|---|---|---|---|---|
| II-27 | (3S,3aS,6R,7R,7aS)-N-benzyl-7-isobutyl-l-isopentyl-5-oxooctahydro-1,2,3,6,7,7a-hexahydro-3aH-3,6-methanopyrrolo[3,2-b]pyridine-3a-carboxamide | — | 396 | — | 34 |
| II-28 | (3S*,3aR*,6S*,7R*,7aR*)-N-benzyl-l-(4-(dimethylamino)benzyl)-7-isobutyl-1,2,3,3a,7,7a-hexahydro-6H-3,6-methanopyrrolo[3,2-c]pyridine-6-carboxamide and (3S*,3aS*,6R*,7R*,7aS*)-N-benzyl-l-(4-(dimethylamino)benzyl)-7-isobutyl-5-oxooctahydro-1,2,3,6,7,7a-hexahydro-3aH-3,6-methanopyrrolo[3,2-b]pyridine-3a-carboxamide | | 459 | | 77 |
| II-29 | (3S*,3aS*,6R*,7R*,7aS*)-N-benzyl-l-(4-(tert-butyl)benzyl)-7-isobutyl-5-oxooctahydro-1,2,3,6,7,7a-hexahydro-3aH-3,6-methanopyrrolo[3,2-b]pyridine-3a-carboxamide | — | 472 | — | 38 |
| II-30 | (3S*,3aR*,6S*,7R*,7aR*)-N-benzyl-l-(4-hydroxybenzyl)-7-isopentyl-1,2,3,3a,7,7a-hexahydro-6H-3,6-methanopyrrolo[3,2-c]pyridine-6-carboxamide and (3S*,3aS*,6R*,7R*,7aS*)-N-benzyl-l-(4-hydroxybenzyl)-7-isopentyl-5-oxooctahydro-1,2,3,6,7,7a-hexahydro-3aH-3,6-methanopyrrolo[3,2-b]pyridine-3a-carboxamide | 1.22 | 446 | B | 8 |
| II-31 | (3S*,3aS*,6R*,7R*,7aS*)-N-(4-chlorobenzyl)-7-isobutyl-l-isopentyl-5-oxooctahydro-1,2,3,6,7,7a-hexahydro-3aH-3,6-methanopyrrolo[3,2-b]pyridine-3a-carboxamide | — | 430 | — | 74 |
| II-32 | (3S*,3aR*,6S*,7R*,7aR*)-N-(4-fluorobenzyl)-7-isobutyl-l-isopentyl-1,2,3,3a,7,7a-hexahydro-6H-3,6-methanopyrrolo[3,2-c]pyridine-6-carboxamide and (3S*,3aS*,6R*,7R*,7aS*)-N-(4-fluorobenzyl)-7-isobutyl-l-isopentyl-5-oxooctahydro-1,2,3,6,7,7a-hexahydro-3aH-3,6-methanopyrrolo[3,2-b]pyridine-3a-carboxamide | | 414 | | 69 |
| II-33 | (3S*,3aR*,6S*,7R*,7aR*)-N-benzyl-7-isobutyl-4-oxo-l-(4-(trifluoromethoxy)benzyl)octahydro-6H-3,6-methanopyrrolo[3,2-c]pyridine-6-carboxamide and (3S*,3aS*,6R*,7R*,7aS*)-N-benzyl-7-isobutyl-5-oxo-l-(4-(trifluoromethoxy)benzyl)octahydro-1,2,3,6,7,7a-hexahydro-3aH-3,6-methanopyrrolo[3,2-b]pyridine-3a-carboxamide | | 500 | | 50 |
| II-34 | (3S,3aR,6S,7R,7aR)-N-benzyl-l-(4-ethoxybenzyl)-7-isobutyl-1,2,3,3a,7,7a-hexahydro-6H-3,6-methanopyrrolo[3,2-c]pyridine-6-carboxamide and (3S,3aS,6R,7R,7aS)-N-benzyl-l-(4-ethoxybenzyl)-7-isobutyl-5-oxooctahydro-1,2,3,6,7,7a-hexahydro-3aH-3,6-methanopyrrolo[3,2-b] pyridine-3a-carboxamide | | 460 | | 52 |

TABLE 4-4

| | | | | | |
|---|---|---|---|---|---|
| II-35 | (3S,3aR,6S,7R,7aR)-l-benzyl-N-(4-hydroxybenzyl)-7-isobutyl-1,2,3,3a,7,7a-hexahydro-6H-3,6-methanopyrrolo[3,2-c]pyridine-6-carboxamide and (3S,3aS,6R,7R,7aS)-l-benzyl-N-(4-hydroxybenzyl)-7-isobutyl-5-oxooctahydro-1,2,3,6,7,7a-hexahydro-3aH-3,6-methanopyrrolo[3,2-b]pyridine-3a-carboxamide | 1.20 | 432 | B | 84 |
| II-36 | (3S,3aR,6S,7R,7aR)-N-(4-hydroxybenzyl)-7-isobutyl-l-(4-methoxybenzyl)-1,2,3,3a,7,7a-hexahydro-6H-3,6-methanopyrrolo[3,2-c]pyridine-6-carboxamide and (3S,3aS,6R,7R,7aS)-N-(4-hydroxybenzyl)-7-isobutyl-l-(4-methoxybenzyl)-5-oxooctahydro-1,2,3,6,7,7a-hexahydro-3aH-3,6-methanopyrrolo[3,2-b]pyridine-3a-carboxamide | 1.20 | 462 | B | 85 |
| II-37 | (3S,3aR,6S,7R,7aR)-l-(4-(dimethylamino)benzyl)-N-(3-hydroxybenzyl)-7-isobutyl-1,2,3,3a,7,7a-hexahydro-6H-3,6-methanopyrrolo[3,2-c]pyridine-6-carboxamide and (3S,3aS,6R,7R,7aS)-l-(4-(dimethylamino)benzyl)-N-(3-hydroxybenzyl)-7-isobutyl-5-oxooctahydro-1,2,3,6,7,7a-hexahydro-3aH-3,6-methanopyrrolo[3,2-b] pyridine-3a-carboxamide | | 475 | | 47 |
| II-38 | (3S*,3aR*,6S*,7R*,7aR*)-l-(4-(dimethylamino)benzyl)-N-(4-hydroxybenzyl)-7-isobutyl-1,2,3,3a,7,7a-hexahydro-6H-3,6-methanopyrrolo[3,2-c] pyridine-6-carboxamide | — | 475 | — | 48 |
| II-39 | (3S*,3aS*,6R*,7R*,7aS*)-l-(4-(dimethylamino)benzyl)-N-(4-hydroxybenzyl)-7-isobutyl-5-oxooctahydro-1,2,3,6,7,7a-hexahydro-3aH-3,6-methanopyrrolo[3,2-b] pyridine-3a-carboxamide | — | 475 | — | 48 |
| II-40 | (3S*,3aR*,6S*,7R*,7aR*)-l-benzyl-N-cyclohexyl-4-oxo-7-propyloctahydro-6H-3,6-methanopyrrolo[3,2-c] pyridine-6-carboxamide | 1.23 | 394 | B | 30 |
| II-41 | (3S*,3aS*,6R*,7R*,7aS*)-l-benzyl-N-cyclohexyl-5-oxo-7-propyloctahydro-1,2,3,6,7,7a-hexahydro-3aH-3,6-methanopyrrolo[3,2-b]pyridine-3a-carboxamide | 1.23 | 394 | B | 30 |
| II-42 | (3S*,3aR*,6S*,7R*,7aR*)-l,7-dibenzyl-N-((lR,4S)-4-methylcyclohexyl)-1,2,3,3a,7,7a-hexahydro-6H-3,6-methanopyrrolo[3,2-c] pyridine-6-carboxamide | 1.30 | 456 | B | 18 |
| II-43 | (3S*,3aS*,6R*,7R*,7aS*)-l,7-dibenzyl-N-((lR,4S)-4-methylcyclohexyl)-5-oxooctahydro-1,2,3,6,7,7a-hexahydro-3aH-3,6-methanopyrrolo[3,2-b] pyridine-3a-carboxamide | 1.32 | 456 | B | 34 |
| II-44 | (3S,3aS,6R,7R,7aS)-l,7-dibenzyl-5-oxo-N-(2,2,6,6-tetramethylpiperidin-4-yl)octahydro-1,2,3,6,7,7a-hexahydro-3aH-3,6-methanopyrrolo[3,2-b]pyridine-3a-carboxamide | 1.05 | 499 | B | 53 |
| II-45 | (3S,3aR,6S,7R,7aR)-l,7-dibenzyl-4-oxo-N-(2,2,6,6-tetramethylpiperidin-4-yl)octahydro-6H-3,6-methanopyrrolo[3,2-c] pyridine-6-carboxamide | 1.05 | 499 | B | 53 |
| II-46 | (3S,3aS,6R,7R,7aS)-N-benzyl-l-cyclohexyl-7-isobutyl-5-oxooctahydro-1,2,3,6,7,7a-hexahydro-3aH-3,6-methanopyrrolo[3,2-b]pyridine-3a-carboxamide | 1.25 | 428 | B | 33 |
| II-47 | (3S,3aS,6R,7S,7aS)-N-benzyl-l-cyclohexyl-5-oxo-7-phenyloctahydro-1,2,3,6,7,7a-hexahydro-3aH-3,6-methanopyrrolo[3,2-b]pyridine-3a-carboxamide | 1.27 | 408 | B | 4 |
| II-48 | (3S,3aS,6R,7S,7aS)-N-benzyl-5-oxo-7-phenyl-l-(tetrahydro-2H-pyran-4-yl)octahydro-1,2,3,6,7,7a-hexahydro-3aH-3,6-methanopyrrolo[3,2-b]pyridine-3a-carboxamide | 1.20 | 430 | B | 5 |

TABLE 4-5

| II-49 | (3S*,3aR*,6S*,7R*,7aR*)-N-benzyl-1-isobutyl-4-oxo-7-phenyloctahydro-6H-3,6-methanopyrrolo[3,2-c]pyridine-6-carboxamide | 1.18 | 402 | B | 3 |
|---|---|---|---|---|---|
| II-50 | (3S*,3aS*,6R*,7S*,7aS*)-N-benzyl-1-isobutyl-5-oxo-7-phenyloctahydro-1,2,3,6,7,7a-hexahydro-3aH-3,6-methanopyrrolo[3,2-b]pyridine-3a-carboxamide | 1.20 | 402 | B | 22 |

Cyclic Amide Synthesis Example: I-5 and I-6

Synthesis of (3S*,3aS*,6R*,7R*,7aS*)-N-benzyl-7-isobutyl-1-(4-methoxybenzyl)-5-oxooctahydro-3aH-3,6-methanopyrrolo[3,2-b]pyridine-3a-carboxamide (I-6) and (3S*,3aR*,6S*,7R*,7aR*)-N-benzyl-7-isobutyl-1-(4-methoxybenzyl)-4-oxooctahydro-6H-3,6-methanopyrrolo[3,2-c]pyridine-6-carboxamide (I-5)

To a toluene (401 μL) solution of a 1:1 mixture (50.0 mg, 0.100 mmol) of (3S*,3aR*,6S*,7R*,7aR*)-N-benzyl-7-isobutyl-1-(4-methoxybenzyl)-1,2,3,3a,7,7a-hexahydro-6H-3,6-methanopyrrolo[3,2-c]pyridine-6-carboxamide (II-5) and (3S*,3aS*,6R*,7R*,7aS*)-N-benzyl-7-isobutyl-1-(4-methoxybenzyl)-1,2,3,6,7,7a-hexahydro-3aH-3,6-methanopyrrolo[3,2-b]pyridine-3a-carboxamide (II-6), trifluoroacetic acid (15.3 μL, 0.201 mmol), 2,3-dimethyl-2-butene (59.4 μL, 0.501 mmol), aqueous 5 M sodium chlorite solution (30.1 μL, 0.150 mmol), aqueous 5 M sodium dihydrogen phosphate solution (70.2 μL, 0.351 mmol) were added, and the mixture was vigorously stirred for 1 hour at room temperature. Ethyl acetate (1 mL) was added to the reaction mixture. An organic layer was sequentially washed with water (0.5 mL), aqueous 5% sodium thiosulfate solution (0.5 mL), and saturated salt water (0.5 mL) and dried with anhydrous sodium sulfate, and then filtered. Ethyl acetate was evaporated under reduced pressure from the filtrate. The residue including toluene was purified with CHROMATOREX Q-PACK DNH30 SIZE 10 (hexane:ethyl acetate=100%:0% to 0%:100%) to obtain the aforementioned compounds (1-5) (21.4 mg, yield: 46.3%, RT=1.32 minutes (method B), [M+1]$^+$=462) and (I-6) (22.6 mg, yield: 48.9%, RT=1.32 minutes (method B), [M+1]$^+$=462). I-5: $^1$H-NMR spectrum (400 MHZ, CDCl$_3$) δ (ppm): 0.51 (3H, d), 0.65 (3H, d), 0.72-0.85 (1H, m), 0.87-0.93 (1H, m), 1.68-1.76 (3H, m), 2.17 (1H, dd), 2.58-2.70 (3H, m), 2.92 (1H, d), 2.94 (1H, d), 3.60 (1H, d), 3.72 (1H, d), 3.79 (3H, s), 4.40 (1H, dd), 4.55 (1H, dd), 5.97 (1H, br), 6.81-6.83 (2H, m), 7.00 (1H, s), 7.19-7.21 (2H, m), 7.25-7.35 (5H, m). I-6: $^1$H-NMR spectrum (400 MHZ, CDCl$_3$) δ (ppm): 0.91 (3H, d), 0.93 (3H, d), 0.93-1.00 (1H, m), 1.20-1.27 (1H, m), 1.65-1.76 (3H, m), 2.22 (1H, m), 2.28 (1H, t), 2.38 (1H, dd), 2.48 (1H, s), 2.87 (1H, s), 3.24 (1H, dd), 3.58 (1H, d), 3.77 (1H, d), 3.77 (3H, s), 4.46 (2H, m), 6.63 (2H, m), 6.78 (2H, m), 6.90 (1H, s), 7.24-7.38 (5H, m), 9.71 (1H, t).

The synthesized compounds of formula IF or IB are summarized in the following tables.

TABLE 5-1

| Compound No. | R$_1$ | R$_2$ | R$_3$ | Product[1] | Synthesis method | Intermediate |
|---|---|---|---|---|---|---|
| I-1 | methyl | benzyl | benzyl | B | I-5 & I-6 | II-1 |
| I-2 | 4-chlorobenzyl | benzyl | isobutyl | F | I-5 & I-6 | II-2 |
| I-3 | 4-chlorobenzyl | benzyl | isobutyl | B | I-5 & I-6 | II-3 |
| I-4 | 3-chlorobenzyl | benzyl | isobutyl | Mixture of F and B | I-5 & I-6 | II-4 |
| I-5 | 4-methoxybenzyl | benzyl | isobutyl | F | I-5 & I-6 | II-5 |
| I-6 | 4-methoxybenzyl | benzyl | isobutyl | B | described in the Examples | II-6 |
| I-7 | 4-methylbenzyl | benzyl | isobutyl | F | described in the Examples | II-7 |
| I-8 | 4-methylbenzyl | benzyl | isobutyl | B | I-5 & I-6 | II-8 |
| I-9 | benzyl | isobutyl | isobutyl | F | I-5 & I-6 | II-9 |
| I-10 | benzyl | isobutyl | isobutyl | B | I-5 & I-6 | II-10 |
| I-11 | isopentyl | isobutyl | benzyl | B | I-5 & I-6 | II-11 |
| I-12 | isopentyl | isobutyl | benzyl | F | I-5 & I-6 | II-12 |
| I-13 | isobutyl | isobutyl | 4-chlorobenzyl | B | I-5 & I-6 | II-13 |
| I-14 | isobutyl | isobutyl | 4-chlorobenzyl | F | I-5 & I-6 | II-14 |
| I-15 | isobutyl | isobutyl | benzyl | B | I-5 & I-6 | II-15 |
| I-16 | isobutyl | isobutyl | isobutyl | B | I-5 & I-6 | II-16 |
| I-17 | 4-hydroxybenzyl | benzyl | isobutyl | Mixture of F and B | I-5 & I-6 | II-17 |
| I-18 | isobutyl | isopentyl | benzyl | F | I-5 & I-6 | II-18 |
| I-19 | isobutyl | isopentyl | benzyl | B | I-5 & I-6 | II-19 |
| I-20 | isobutyl | isobutyl | benzyl | F | I-5 & I-6 | II-20 |
| I-21 | isobutyl | benzyl | isobutyl | F | I-5 & I-6 | II-21 |
| I-22 | isobutyl | benzyl | isobutyl | B | I-5 & I-6 | II-22 |
| I-23 | isobutyl | 4-chlorobenzyl | isobutyl | F | I-5 & I-6 | II-23 |
| I-24 | isobutyl | benzyl | isopentyl | F | I-5 & I-6 | II-24 |
| I-25 | isobutyl | benzyl | isopentyl | B | I-5 & I-6 | II-25 |
| I-26 | isopentyl | benzyl | isobutyl | Mixture of F and B | I-5 & I-6 | II-26 |
| I-27 | isopentyl | benzyl | isobutyl | B | I-5 & I-6 | II-27 |
| I-28 | 4-(dimethylamino)benzyl | benzyl | isobutyl | Mixture of F and B | I-5 & I-6 | II-28 |

TABLE 5-1-continued

| Compound No. | R₁ | R₂ | R₃ | Product[1] | Synthesis method | Intermediate |
|---|---|---|---|---|---|---|
| I-29 | 4-(tert-butyl)benzyl | benzyl | isobutyl | B | I-5 & I-6 | II-29 |
| I-30 | 4-hydroxybenzyl | benzyl | isopentyl | Mixture of F and B | I-5 & I-6 | II-30 |
| I-31 | isopentyl | 4-chlorobenzyl | isobutyl | B | I-5 & I-6 | II-31 |
| I-32 | isopentyl | 4-fluorobenzyl | isobutyl | Mixture of F and B | I-5 & I-6 | II-32 |
| I-33 | 4-(trifluoromethoxy)benzyl | benzyl | isobutyl | Mixture of F and B | I-5 & I-6 | II-33 |
| I-34 | 4-ethoxybenzyl | benzyl | isobutyl | Mixture of F and B | I-5 & I-6 | II-34 |
| I-35 | benzyl | 4-hydroxybenzyl | isobutyl | Mixture of F and B | I-5 & I-6 | II-35 |
| I-36 | 4-methoxybenzyl | 4-hydroxybenzyl | isobutyl | Mixture of F and B | I-5 & I-6 | II-36 |

TABLE 5-2

| | | | | | | |
|---|---|---|---|---|---|---|
| I-37 | 4-(dimethylamino)benzyl | 3-hydroxybenzyl | isobutyl | Mixture of F and B | I-5 & I-6 | II-37 |
| I-38 | 4-(dimethylamino)benzyl | 4-hydroxybenzyl | isobutyl | F | I-5 & I-6 | II-38 |
| I-39 | 4-(dimethylamino)benzyl | 4-hydroxybenzyl | isobutyl | B | I-5 & I-6 | II-39 |
| I-40 | benzyl | cyclohexyl | propyl | F | I-5 & I-6 | II-40 |
| I-41 | benzyl | cyclohexyl | propyl | B | I-5 & I-6 | II-41 |
| I-42 | benzyl | trans-4-methyl cyclohexyl | benzyl | F | I-5 & I-6 | II-42 |
| I-43 | benzyl | trans-4-methyl cyclohexyl | benzyl | B | I-5 & I-6 | II-43 |
| I-44 | benzyl | 2,2,6,6-tetra-methylpiperidin-4-yl | benzyl | B | described in the Examples | II-44 |
| I-45 | benzyl | 2,2,6,6-tetra-methylpiperidin-4-yl | benzyl | F | described in the Examples | II-45 |
| I-46 | cyclohexyl | benzyl | isobutyl | B | I-5 & I-6 | II-46 |
| I-47 | cyclohexyl | benzyl | phenyl | B | I-5 & I-6 | II-47 |
| I-48 | tetrahydro-2H-pyran-4-yl | benzyl | phenyl | B | I-5 & I-6 | II-48 |
| I-49 | isobutyl | benzyl | phenyl | F | I-5 & I-6 | II-49 |
| I-50 | isobutyl | benzyl | phenyl | B | I-5 & I-6 | II-50 |

[1] F: compound represented by formula IF, B: compound represented by formula IB

TABLE 6-1

| Compound No. | Compound name | LCMS $t_R$ (min) | Mass (M + H)⁺ | Analysis method | Yield (%) |
|---|---|---|---|---|---|
| I-1 | (3S*,3aS*,6R*,7R*,7aS*)-N,7-dibenzyl-1-methyl-5-oxooctahydro-3aH-3,6-methanopyrrolo[3,2-b] pyridine-3a-carboxamide | 1.19 | 390 | B | 31% |
| I-2 | (3S,3aR,6S,7R,7aR)-N-benzyl-1-(4-chlorobenzyl)-7-isobutyl-4-oxooctahydro-6H-3,6-methanopyrrolo[3,2-c]pyridine-6-carboxamide | 1.57 | 466 | B | 26% |
| I-3 | (3S,3aS,6R,7R,7aS)-N-benzyl-1-(4-chlorobenzyl)-7-isobutyl-5-oxooctahydro-3aH-3,6-methanopyrrolo[3,2-b]pyridine-3a-carboxamide | 1.60 | 466 | B | 18% |
| I-4 | (3S*,3aR*,6S*,7R*,7aR*)-N-benzyl-1-(3-chlorobenzyl)-7-isobutyl-4-oxooctahydro-6H-3,6-methanopyrrolo[3,2-c]pyridine-6-carboxamide and (3S*,3aS*,6R*,7R*,7aS*)-N-benzyl-1-(3-chlorobenzyl)-7-isobutyl-5-oxooctahydro-3aH-3,6-methanopyrrolo[3,2-b] pyridine-3a-carboxamide | 1.60 | 466 | B | 57% |
| I-5 | (3S*,3aR*,6S*,7R*,7aR*)-N-benzyl-7-isobutyl-1-(4-methoxybenzyl)-4-oxooctahydro-6H-3,6-methanopyrrolo[3,2-c]pyridine-6-carboxamide | 1.31 | 462 | B | 46% |
| I-6 | (3S*,3aS*,6R*,7R*,7aS*)-N-benzyl-7-isobutyl-1-(4-methoxybenzyl)-5-oxooctahydro-3aH-3,6-methanopyrrolo[3,2-b]pyridine-3a-carboxamide | 1.32 | 462 | B | 49% |
| I-7 | (3S*,3aR*,6S*,7R*,7aR*)-N-benzyl-7-isobutyl-1-(4-methylbenzyl)-4-oxooctahydro-6H-3,6-methanopyrrolo[3,2-c] pyridine-6-carboxamide | 1.42 | 446 | B | 15% |

TABLE 6-2

| | | | | | |
|---|---|---|---|---|---|
| I-8 | (3S*,3aS*,6R*,7R*,7aS*)-N-benzyl-7-isobutyl-l-(4-methylbenzyl)-5-oxooctahydro-3aH-3,6-methanopyrrolo[3,2-b] pyridine-3a-carboxamide | 1.41 | 446 | B | 61% |
| I-9 | (3S ,3aR ,6S ,7R ,7aR )-l-benzyl-N,7-diisobutyl-4-oxooctahydro-6H-3,6-methanopyrrolo[3,2-c]pyridine-6-carboxamide | 1.38 | 398 | B | 13% |
| I-10 | (3S ,3aS ,6R ,7R ,7aS )-l-benzyl-N,7-diisobutyl-5-oxooctahydro-3aH-3,6-methanopyrrolo[3,2-b]pyridine-3a-carboxamide | 1.38 | 398 | B | 13% |
| I-11 | (3S ,3aS ,6R ,7R ,7aS )-7-benzyl-N-isobutyl-l-isopentyl-5-oxooctahydro-3aH-3,6-methanopyrrolo[3,2-b]pyridine-3a-carboxamide | 1.30 | 412 | B | 60% |
| I-12 | (3S ,3aR ,6S ,7R ,7aR )-7-benzyl-N-isobutyl-l-isopentyl-4-oxooctahydro-6H-3,6-methanopyrrolo[3,2-c]pyridine-6-carboxamide | 1.30 | 412 | B | 17% |
| I-13 | (3S ,3aS ,6R ,7R ,7aS )-7-(4-chlorobenzyl)-N,l-diisobutyl-5-oxooctahydro-3aH-3,6-methanopyrrolo[3,2-b] pyridine-3a-carboxamide | 1.52 | 432 | B | 8% |
| I-14 | (3S ,3aR ,6S ,7R ,7aR )-7-(4-chlorobenzyl)-N,l-diisobutyl-4-oxooctahydro-6H-3,6-methanopyrrolo[3,2-c] pyridine-6-carboxamide | 1.51 | 432 | B | 51% |
| I-15 | (3R*,3aS*,6R*,7R*,7aS*)-7-benzyl-N,l-diisobutyl-5-oxooctahydro-3aH-3,6-methanopyrrolo[3,2-b]pyridine-3a-carboxamide | 1.40 | 398 | B | 33% |
| I-16 | (3S*,3aS*,6R*,7R*,7aS*)-N-(4-chlorobenzyl)-l,7-diisobutyl-5-oxooctahydro-3aH-3,6-methanopyrrolo[3,2-b] pyridine-3a-carboxamide | 1.47 | 432 | B | 43% |
| I-17 | (3S*,3aR*,6S*,7R*,7aR*)-N-benzyl-l-(4-hydroxybenzyl)-7-isobutyl-4-oxooctahydro-6H-3,6-methanopyrrolo[3,2-c]pyridine-6-carboxamide and (3S*,3aS*,6R*,7R*,7aS*)-N-benzyl-l-(4-hydroxybenzyl)-7-isobutyl-5-oxooctahydro-3aH-3,6-methanopyrrolo[3,2-b]pyridine-3a-carboxamide | 1.17 | 448 | B | 6% |
| I-18 | (3S*,3aR*,6S*,7R*,7aR*)-7-benzyl-l-isobutyl-N-isopentyl-4-oxooctahydro-6H-3,6-methanopyrrolo[3,2-c]pyridine-6-carboxamide | 1.20 | 412 | B | 47% |
| I-19 | (3S*,3aS*,6R*,7R*,7aS*)-7-benzyl-l-isobutyl-N-isopentyl-5-oxooctahydro-3aH-3,6-methanopyrrolo[3,2-b]pyridine-3a-carboxamide | 1.30 | 412 | B | 15% |
| I-20 | (3S*,3aR*,6S*,7R*,7aR*)-7-benzyl-N,l-diisobutyl-4-oxooctahydro-6H-3,6-methanopyrrolo[3,2-c]pyridine-6-carboxamide | 1.18 | 398 | B | 28% |
| I-21 | (3S ,3aR ,6S ,7R ,7aR )-N-benzyl-l,7-diisobutyl-4-oxooctahydro-6H-3,6-methanopyrrolo[3,2-c]pyridine-6-carboxamide | 1.18 | 398 | B | 27% |
| I-22 | (3S ,3aS ,6R ,7R ,7aS )-N-benzyl-l,7-diisobutyl-5-oxooctahydro-3aH-3,6-methanopyrrolo[3,2-b]pyridine-3a-carboxamide | 1.38 | 398 | B | 24% |
| I-23 | (3S ,3aR ,6S ,7R ,7aR )-N-(4-chlorobenzyl)-l,7-diisobutyl-4-oxooctahydro-6H-3,6-methanopyrrolo[3,2-c] pyridine-6-carboxamide | 1.20 | 432 | B | 24% |
| I-24 | (3S ,3aR ,6S ,7R ,7aR )-N-benzyl-l-isobutyl-7-isopentyl-4-oxooctahydro-6H-3,6-methanopyrrolo[3,2-c]pyridine-6-carboxamide | 1.22 | 412 | B | 10% |
| I-25 | (3S ,3aS ,6R ,7R ,7aS )-N-benzyl-l-isobutyl-7-isopentyl-5-oxooctahydro-3aH-3,6-methanopyrrolo[3,2-b]pyridine-3a-carboxamide | 1.47 | 412 | B | 60% |

TABLE 6-3

| | | | | | |
|---|---|---|---|---|---|
| I-26 | (3S*,3aR*,6S*,7R*,7aR*)-N-benzyl-7-isobutyl-l-isopentyl-4-oxooctahydro-6H-3,6-methanopyrrolo[3,2-c]pyridine-6-carboxamide and (3S*,3aS*,6R*,7R*,7aS*)-N-benzyl-7-isobutyl-l-isopentyl-5-oxooctahydro-3aH-3,6-methanopyrrolo[3,2-b]pyridine-3a-carboxamide | 1.30 | 412 | B | 56% |
| I-27 | (3S*,3aS*,6R*,7R*,7aS*)-N-benzyl-7-isobutyl-l-isopentyl-5-oxooctahydro-3aH-3,6-methanopyrrolo[3,2-b]pyridine-3a-carboxamide | 1.30 | 412 | B | 43% |
| I-28 | (3S*,3aR*,6S*,7R*,7aR*)-N-benzyl-l-(4-(dimethylamino)benzyl)-7-isobutyl-4-oxoocthydro-6H-3,6-methanopyrrolo[3,2-c]pyridine-6-carboxamide and (3S*,3aS*,6R*,7R*,7aS*)-N-benzyl-l-(4-(dimethylamino)benzyl)-7-isobutyl-5-oxooctahydro-3aH-3,6-methanopyrrolo[3,2-b]pyridine-3a-carboxamide | 1.27 | 475 | B | 14% |
| I-29 | (3S*,3aS*,6R*,7R*,7aS*)-N-benzyl-l-(4-(tert-butyl)benzyl)-7-isobutyl-5-oxooctahydro-3aH-3,6-methanopyrrolo[3,2-b]pyridine-3a-carboxamide | 1.57 | 488 | B | 32% |
| I-30 | (3S*,3aR*,6S*,7R*,7aR*)-N-benzyl-l-(4-hydroxybenzyl)-7-isopentyl-4-oxooctahydro-6H-3,6-methanopyrrolo[3,2-c] pyridine-6-carboxamide and (3S*,3aS*,6R*,7R*,7aS*)-N-benzyl-l-(4-hydroxybenzyl)-7-isopentyl-5-oxooctahydro-3aH-3,6-methanopyrrolo[3,2-b]pyridine-3a-carboxamide | 1.20 | 462 | B | 23% |
| I-31 | (3S*,3aS*,6R*,7R*,7aS*)-N-(4-chlorobenzyl)-7-isobutyl-l-isopentyl-5-oxooctahydro-3aH-3,6-methanopyrrolo[3,2-b]pyridine-3a-carboxamide | 1.37 | 446 | B | 48% |
| I-32 | (3S ,3aR ,6S ,7R ,7aR )-N-(4-fluorobenzyl)-7-isobutyl-l-isopentyl-4-oxooctahydro-6H-3,6-methanopyrrolo[3,2-c] pyridine-6-carboxamide and (3S ,3aS ,6R ,7R ,7aS )-N-(4-fluorobenzyl)-7-isobutyl-l-isopentyl-5-oxooctahydro-3aH-3,6-methanopyrrolo[3,2-b]pyridine-3a-carboxamide | 1.31 | 430 | B | 52% |
| I-33 | (3S ,3aR ,6S ,7R ,7aR )-N-benzyl-7-isobutyl-4-oxo-l-(4-(trifluoromethoxy)benzyl)octahydro-6H-3,6-methanopyrrolo[3,2-c]pyridine-6-carboxamide and (3S ,3aS ,6R ,7R ,7aS )-N-benzyl-7-isobutyl-5-oxo-l-(4-(trifluoromethoxy)benzyl)octahydro-3aH-3,6-methanopyrrolo[3,2-b]pyridine-3a-carboxamide | 1.27 | 516 | B | —1% |
| I-34 | (3S ,3aR ,6S ,7R ,7aR )-N-benzyl-l-(4-ethoxybenzyl)-7-isobutyl-4-oxooctahydro-6H-3,6-methanopyrrolo[3,2-c]pyridine-6-carboxamide and (3S ,3aS ,6R ,7R ,7aS )-N-benzyl-l-(4-ethoxybenzyl)-7-isobutyl-5-oxooctahydro-3aH-3,6-methanopyrrolo[3,2-b]pyridine-3a-carboxamide | 1.23 | 476 | B | 0.2% |
| I-35 | (3S ,3aR ,6S ,7R ,7aR )-l-benzyl-N-(4-hydroxybenzyl)-7-isobutyl-4-oxooctahydro-6H-3,6-methanopyrrolo[3,2-c]pyridine-6-carboxamide and (3S ,3aS ,6R ,7R ,7aS )-l-benzyl-N-(4-hydroxybenzyl)-7-isobutyl-5-oxooctahydro-3aH-3,6-methanopyrrolo[3,2-b]pyridine-3a-carboxamide | 1.25 | 448 | B | —3% |

TABLE 6-4

| | | | | |
|---|---|---|---|---|
| I-36 | (3S,3aR,6S,7R,7aR)-N-(4-hydroxybenzyl)-7-isobutyl-l-(4-methoxybenzyl)-4-oxooctahydro-6H-3,6-methanopyrrolo[3,2-c]pyridine-6-carboxamide and (3S,3aS,6R,7R,7aS)-N-(4-hydroxybenzyl)-7-isobutyl-l-(4-methoxybenzyl)-5-oxooctahydro-3aH-3,6-methanopyrrolo[3,2-b]pyridine-3a-carboxamide | 1.20 478 | B | 15% |
| I-37 | (3S*,3aR*,6S*,7R*,7aR*)-l-(4-(dimethylamino)benzyl)-N-(3-hydroxybenzyl)-7-isobutyl-4-oxooctahydro-6H-3,6-methanopyrrolo[3,2-c]pyridine-6-carboxamide and (3S*,3aS*,6R*,7R*,7aS*)-l-(4-(dimethylamino)benzyl)-N-(3-hydroxybenzyl)-7-isobutyl-5-oxooctahydro-3aH-3,6-methanopyrrolo[3,2-b]pyridine-3a-carboxamide | 1.20 491 | B | 3% |
| I-38 | (3S,3aR,6S,7R,7aR)-l-(4-(dimethylamino)benzyl)-N-(4-hydroxybenzyl)-7-isobutyl-4-oxooctahydro-6H-3,6-methanopyrrolo[3,2-c]pyridine-6-carboxamide | 1.13 491 | B | 4% |
| I-39 | (3S,3aS,6R,7R,7aS)-l-(4-(dimethylamino)benzyl)-N-(4-hydroxybenzyl)-7-isobutyl-5-oxooctahydro-3aH-3,6-methanopyrrolo[3,2-b]pyridine-3a-carboxamide | 1.18 491 | B | 4% |
| I-40 | (3S*,3aR*,6S*,7R*,7aR*)-l-benzyl-N-cyclohexyl-4-oxo-7-propyloctahydro-6H-3,6-methanopyrrolo[3,2-c]pyridine-6-carboxamide | 1.17 410 | B | 26% |
| I-41 | (3S*,3aS*,6R*,7R*,7aS*)-l-benzyl-N-cyclohexyl-5-oxo-7-propyloctahydro-3aH-3,6-methanopyrrolo[3,2-b]pyridine-3a-carboxamide | 1.42 410 | B | 34% |
| I-42 | (3S*,3aR*,6S*,7R*,7aR*)-l,7-dibenzyl-N-((lR,4S)-4-methylcyclohexyl)-4-oxooctahydro-6H-3,6-methanopyrrolo[3,2-c]pyridine-6-carboxamide | 1.25 472 | B | 48% |
| I-43 | (3S*,3aS*,6R*,7R*,7aS*)-l,7-dibenzyl-N-((lR,4S)-4-methylcyclohexyl)-5-oxooctahydro-3aH-3,6-methanopyrrolo[3,2-b]pyridine-3a-carboxamide | 1.45 472 | B | 57% |
| I-44 | (3S*,3aS*,6R*,7R*,7aS*)-l,7-dibenzyl-5-oxo-N-(2,2,6,6-tetramethylpiperidin-4-yl)octahydro-3aH-3,6-methanopyrrolo[3,2-b]pyridine-3a-carboxamide | 1.15 515 | B | 27% |
| I-45 | (3S*,3aR*,6S*,7R*,7aR*)-l,7-dibenzyl-4-oxo-N-(2,2,6,6-tetramethylpiperidin-4-yl)octahydro-6H-3,6-methanopyrrolo[3,2-c]pyridine-6-carboxamide | 1.05 515 | B | 13% |
| I-46 | (3S,3aS,6R,7R,7aS)-N-benzyl-l-cyclohexyl-7-isobutyl-5-oxooctahydro-3aH-3,6-methanopyrrolo[3,2-b]pyridine-3a-carboxamide | 1.48 444 | B | 41% |
| I-47 | (3S,3aS,6R,7S,7aS)-N-benzyl-l-cyclohexyl-5-oxo-7-phenyloctahydro-3aH-3,6-methanopyrrolo[3,2-b]pyridine-3a-carboxamide | 1.30 424 | B | 69% |
| I-48 | (3S,3aS,6R,7S,7aS)-N-benzyl-5-oxo-7-phenyl-l-(tetrahydro-2H-pyran-4-yl)octahydro-3aH-3,6-methanopyrrolo[3,2-b] pyridine-3a-carboxamide | 1.35 446 | B | 51% |
| I-49 | (3S,3aR,6S,7R,7aR)-N-benzyl-l-isobutyl-4-oxo-7-phenyloctahydro-6H-3,6-methanopyrrolo[3,2-c]pyridine-6-carboxamide | 1.15 418 | B | 17% |
| I-50 | (3S,3aS,6R,7S,7aS)-N-benzyl-l-isobutyl-5-oxo-7-phenyloctahydro-3aH-3,6-methanopyrrolo[3,2-b]pyridine-3a-carboxamide | 1.48 418 | B | 62% |

Synthesis Example of Compound Wherein $R_4$ is Methyl

Synthesis of tert-butyl 3-((3S*,3aS*,6R*,7R*,7aS*)-3a-(benzylcarbamoyl)-4-methyl-1-(4-nitrobenzyl)-5-oxooctahydro-1H-3,6-methanopyrrolo[3,2-b]pyridin-7-yl) propanoate (IB-358)

First Step

Synthesis of tert-butyl 3-((3S*,3aR*,6S*,7R*,7aR*)-6-(benzylcarbamoyl)-1-(4-nitrobenzyl)-2,2,3a,6,7,7a-hexahydro-1H-3,6-methanopyrrolo[3,2-c]pyridin-7-yl) propanoate (form F) and tert-butyl 3-((3S*,3aS*,6R*,7R*,7aS*)-3a-benzylcarbamoyl)-1-(4-nitrobenzyl)-2,2,3a,6,7,7a-hexahydro-1H-3,6-methanopyrrolo[3,2-b]pyridin-7-yl) propanoate (form B)

Chloroform (7 mL) was added to N-(4-nitrobenzyl) prop-2-en-1-amine (500 mg, 2.6 mmol), tert-butyl 5-oxopentanoate (428 mg, 2.0 mmol), and a molecular sieve 4A (2.0 g), and N-benzyl-1,2,4-triazine-3-carboxamide (526 mg, 3.0 mmol) and chloroform (0.5 mL) were also added. After heating the reaction mixture for 48 hours at 65° C., anhydrous succinic acid (40 mg, 0.4 mmol) was added. The mixture was heated for 4 hours at 65° C. and filtered. The residue obtained by concentrating the filtrate under reduced pressure was purified by elution with eluate 1 (hexane:ethyl acetate=70:25 to 0:100) and subsequently eluate 2 (ethyl acetate:methanol=100:0 to 95:5) by using linked columns of Purif-PACK, NH25, SIZE 20 and CHROMATOREX Q-PACK, Si30, SIZE 60 to obtain the aforementioned compounds, i.e., 131 mg of form F (yield of 9%, RT=0.93 minutes (method C), [M+1]$^+$=533) and 309 mg of form B (yield of 22%, RT=0.96 minutes (method C), [M+1]$^+$=533).

Second Step

Synthesis of (3S*,3aS*,6R*,7R*,7aS*)-3a-(benzylcarbamoyl)-7-(3-(tert-butoxy)-3-oxopropyl)-4-methyl-1-(4-nitrobenzyl)-2,2,3,3a,6,7,7a-hexahydro-1H-3,6-methanopyrrolo[3,2-b]pyridin-4-ium iodide (3S*,3aR*,6S*,7R*,7aR*)-tert-butyl 3-(3a-benzylcarbamoyl)-1-(4-nitrobenzyl)-2,2,3a,6,7,7a-hexahydro-1H-3,6-methanopyrrolo[3,2-b]pyridin-7-yl) propanoate (255 mg, 0.48 mmol) was dissolved in tetrahydrofuran (2.5 mL), and sodium hydrogen carbonate (45 mg, 0.5 mmol) and iodomethane (545 mg, 3.8 mmol) were added. The mixture was heated from 45° C. to 50° C. and stirred for 24 hours. Ethyl acetate was added to the reaction mixture. The mixture was washed twice with saturated salt water. The organic phase was dried with anhydrous sodium sulfate. The anhydrous sodium sulfate was filtered out and the organic phase was concentrated under reduced pressure to obtain the aforementioned compound in a crude form (270 mg, (method C), [M]$^+$=547).

Third Step

Synthesis of tert-butyl 3-((3S*,3aS*,6R*,7R*,7aS*)-3a-(benzylcarbamoyl)-4-methyl-1-(4-nitrobenzyl)-5-oxooctahydro-1H-3,6-methanopyrrolo[3,2-b]pyridin-7-yl) propanoate (IB-358)

The crude (3S*,3aS*,6R*,7R*,7aS*)-3a-(benzylcarbamoyl)-7-(3-(tert-butoxy)-3-oxopropyl)-4-methyl-1-(4-nitrobenzyl)-2,3,3a,6,7,7a-hexahydro-1H-3,6-methanopyrrolo[3,2-b]pyridin-4-ium iodide (270 mg, 0.48 mmol) obtained in the reaction described above was dissolved in tetrahydrofuran (10.6 mL). 2,3-dimethyl-2-butene (202 mg, 2.4 mmol), acetic acid (58 mg, 0.96 mmol), aqueous sodium dihydrogen phosphate solution (5 mol/L solution, 366 µL, 1.68 mmol), and aqueous sodium chlorite solution (5 mol/L, 55 µL, 0.72 mmol) were added. The mixture was stirred overnight at room temperature. The reaction mixture was concentrated, and water and ethyl acetate were added. The mixture was transferred to a separatory funnel and washed with saturated salt water. The organic phase was dried with anhydrous sodium sulfate. The residue resulting from concentration under reduced pressure was purified by elution with eluate 1 (hexane:ethyl acetate=50:50 to 0:100) and subsequently eluate 2 (ethyl acetate:methanol=100:0 to 95:5) using CHROMATOREX Q-PACK, Si30, SIZE 10 to obtain 182 mg of the aforementioned compound (yield 67% (two steps), RT=0.98 minutes (method C), [M+1]$^+$=563).

Synthesis of tert-butyl 3-((3S*,3aS*,6R*,7R*,7aS*)-3a-(benzylcarbamoyl)-4-methyl-5-oxooctahydro-1H-3,6-methanopyrrolo[3,2-b]pyridin-7-yl) propanoate (IB-359)

tert-Butyl 3-((3S*,3aS*,6R*,7R*,7aS*)-3a-(benzylcarbamoyl)-4-methyl-1-(4-nitrobenzyl)-5-oxooctahydro-1H-3,6-methanopyrrolo[3,2-b]pyridin-7-yl) propanoate (98.4 mg, 0.175 mmol) was dissolved in trifluoroethanol (4.8 mL), and palladium on carbon (10%-wet, 38 mg) was added, and the inside of the container was replaced with hydrogen. The mixture was vigorously stirred overnight at room temperature, and the reaction mixture was filtered. The filtrate was concentrated to obtain the aforementioned compound (71.7 mg, yield of 96%, RT=0.79 minutes (method C), [M+1]$^+$=428).

Synthesis of tert-butyl 3-((3S*,3aS*,6S*,7R*,7aS*)-3a-(benzylcarbamoyl)-4-methyl-(3-methylbutanoyl)-5-oxooctahydro-1H-3,6-methanopyrrolo[3,2-b]pyridin-7-yl) propanoate (IB-366)

tert-Butyl 3-((3S*,3aS*,6R*,7R*,7aS*)-3a-(benzylcarbamoyl)-4-methyl-5-oxooctahydro-1H-3,6-methanopyrrolo[3,2-b]pyridin-7-yl) propanoate (10.6 mg, 0.025 mmol) was dissolved in tetrahydrofuran (0.75 mL), and triethylamine (10.1 mg, 0.1 mmol) and 3-methylbutanoyl chloride (4.22 mg, 0.035 mmol) were added. The mixture was stirred for 18 hours at room temperature. Ammonium water (5 ML) was added to the reaction mixture. The mixture was stirred for 1 hour, and then the solvent was evaporated under reduced pressure. Ethyl acetate and water were added to the resulting residue. The mixture was transferred to a separatory funnel. The organic phase was washed with 10% citric acid water, salt water, sodium bicarbonate water, and salt water in order, and the organic layer was dried with anhydrous sodium sulfate. The organic phase was concentrated under reduced pressure, and the residue was purified by TLC (Merck 105715.001, layer thickness of 0.25 mm) (eluent: ethyl acetate) to obtain the aforementioned compound (7.6 mg, yield 59%, RT=1.07 minutes (method C), [M+1]$^+$=512).

Compounds of formulae XXIF and XXIB were also synthesized by the same method described above. The results are summarized in the following tables.

TABLE 6-5

Formula XXIF

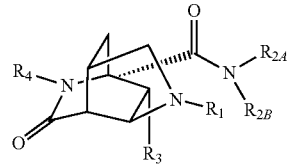

| Compound No. | $R_1$ | $R_{2A}$ | $R_{2B}$ | $R_3$ | $R_4$ | Retention time RT (min) | Mass $(M + H)^+$ | Measurement condition |
|---|---|---|---|---|---|---|---|---|
| IF-51 | i-Bu | H | 1-Npm | Bnzl | H | 0.89 | 482 | C |
| IF-52 | i-Bu | H | i-Pr | Bnzl | H | 0.77 | 384 | C |
| IF-53 | i-Bu | H | 1-Npm | 1-Npm | H | 0.93 | 532 | C |
| IF-54 | i-Bu | H | i-Pr | 1-Npm | H | 0.84 | 434 | C |
| IF-55 | Bnzl | H | i-Bu | 1-Npm | H | 0.89 | 482 | C |
| IF-56 | Bnzl | H | Bnzl | 1-Npm | H | 0.90 | 516 | C |
| IF-57 | Bnzl | H | s-Bu | 1-Npm | H | 0.90 | 482 | C |
| IF-58 | Bnzl | H | 1-Npm | 1-Npm | H | 0.96 | 566 | C |
| IF-59 | i-Bu | H | i-Bu | 4-OH-Bnzl | H | 0.71 | 414 | C |
| IF-60 | i-Bu | H | Bnzl | 4-OH-Bnzl | H | 0.73 | 448 | C |
| IF-61 | i-Bu | H | 2-Cbx-Et | 4-OH-Bnzl | H | 0.57 | 430 | C |
| IF-62 | i-Bu | H | s-Bu | 4-OH-Bnzl | H | 0.71 | 414 | C |
| IF-63 | i-Bu | H | 1-Npm | 4-OH-Bnzl | H | 0.80 | 498 | C |
| IF-64 | i-Bu | H | i-Pr | 4-OH-Bnzl | H | 0.67 | 400 | C |
| IF-65 | i-Bu | H | 1-Npm | 2-Cbx-Et | H | 0.74 | 464 | C |
| IF-66 | Bnzl | H | 4-OH-Bnzl | Bnzl | H | 0.76 | 482 | C |
| IF-67 | Bnzl | H | i-Bu | 4-OH-Bnzl | H | 0.73 | 448 | C |
| IF-68 | Bnzl | H | Bnzl | 4-OH-Bnzl | H | 0.75 | 482 | C |
| IF-69 | Bnzl | H | 2-Cbx-Et | 4-OH-Bnzl | H | 0.61 | 464 | C |
| IF-70 | Bnzl | H | Bnzl | 2-Cbx-Et | H | 0.69 | 448 | C |
| IF-71 | Bnzl | H | 4-OH-Bnzl | 2-Cbx-Et | H | 0.62 | 464 | C |
| IF-72 | Bnzl | H | 1-Npm | 2-Cbx-Et | H | 0.76 | 498 | C |
| IF-73 | Bnzl | H | 4-OH-Bnzl | 1-Npm | H | 0.81 | 532 | C |
| IF-74 | Bnzl | H | 2-Cbx-Et | 1-Npm | H | 0.76 | 498 | C |
| IF-75 | 4-OH-Bnzl | H | Bnzl | Bnzl | H | 0.78 | 482 | C |
| IF-76 | 4-OH-Bnzl | H | 2-Cbx-Et | Bnzl | H | 0.63 | 464 | C |
| IF-77 | 4-OH-Bnzl | H | s-Bu | Bnzl | H | 0.76 | 448 | C |
| IF-78 | 4-OH-Bnzl | H | 1-Npm | Bnzl | H | 0.85 | 532 | C |

TABLE 6-5-continued

Formula XXIF

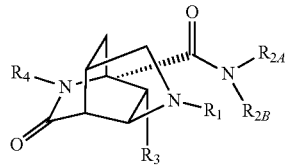

| Compound No. | R1 | R2A | R2B | R3 | R4 | Retention time RT (min) | Mass (M + H)+ | Measurement condition |
|---|---|---|---|---|---|---|---|---|
| IF-79 | 4-OH-Bnzl | H | Bnzl | 2-Cbx-Et | H | 0.65 | 464 | C |
| IF-80 | 4-OH-Bnzl | H | 1-Npm | 2-Cbx-Et | H | 0.73 | 514 | C |
| IF-81 | 4-OH-Bnzl | H | i-Bu | 1-Npm | H | 0.82 | 498 | C |
| IF-82 | 4-OH-Bnzl | H | Bnzl | 1-Npm | H | 0.83 | 532 | C |
| IF-83 | 4-OH-Bnzl | H | 2-Cbx-Et | 1-Npm | H | 0.70 | 514 | C |
| IF-84 | 4-OH-Bnzl | H | s-Bu | 1-Npm | H | 0.82 | 498 | C |
| IF-85 | 4-OH-Bnzl | H | 1-Npm | 1-Npm | H | 0.89 | 582 | C |
| IF-86 | i-Bu | H | s-Bu | Bnzl | H | 0.81 | 398 | C |
| IF-87 | i-Bu | H | i-Bu | 1-Npm | H | 0.87 | 448 | C |
| IF-88 | i-Bu | H | Bnzl | 1-Npm | H | 0.88 | 482 | C |
| IF-89 | Bnzl | H | i-Bu | Bnzl | H | 0.83 | 432 | C |
| IF-90 | Bnzl | H | s-Bu | Bnzl | H | 0.83 | 432 | C |

TABLE 6-6

| Compound No. | R1 | R2A | R2B | R3 | R4 | RT | Mass | Cond |
|---|---|---|---|---|---|---|---|---|
| IF-91 | Bnzl | H | 1-Npm | Bnzl | H | 0.91 | 516 | C |
| IF-92 | Bnzl | H | i-Pr | Bnzl | H | 0.80 | 418 | C |
| IF-93 | Bnzl | H | i-Pr | 1-Npm | H | 0.86 | 468 | C |
| IF-94 | 1-Npm | H | i-Bu | Bnzl | H | 0.88 | 482 | C |
| IF-95 | 1-Npm | H | s-Bu | Bnzl | H | 0.88 | 482 | C |
| IF-96 | 1-Npm | H | i-Pr | Bnzl | H | 0.85 | 468 | C |
| IF-97 | 1-Npm | H | Bnzl | 1-Npm | H | 0.94 | 566 | C |
| IF-98 | 1-Npm | H | s-Bu | 1-Npm | H | 0.93 | 532 | C |
| IF-99 | i-Bu | H | 4-OH-Bnzl | Bnzl | H | 0.74 | 448 | C |
| IF-100 | i-Bu | H | 2-Cbx-Et | Bnzl | H | 0.68 | 414 | C |
| IF-101 | i-Bu | H | i-Bu | 2-Cbx-Et | H | 0.63 | 380 | C |
| IF-102 | i-Bu | H | Bnzl | 2-Cbx-Et | H | 0.66 | 414 | C |
| IF-103 | i-Bu | H | 4-OH-Bnzl | 2-Cbx-Et | H | 0.59 | 430 | C |
| IF-104 | i-Bu | H | i-Pr | 2-Cbx-Et | H | 0.58 | 366 | C |
| IF-105 | i-Bu | H | 4-OH-Bnzl | 1-Npm | H | 0.79 | 498 | C |
| IF-106 | i-Bu | H | 2-Cbx-Et | 1-Npm | H | 0.74 | 464 | C |
| IF-107 | Bnzl | H | 2-Cbx-Et | Bnzl | H | 0.70 | 448 | C |
| IF-108 | Bnzl | H | s-Bu | 4-OH-Bnzl | H | 0.73 | 448 | C |
| IF-109 | Bnzl | H | 1-Npm | 4-OH-Bnzl | H | 0.81 | 532 | C |
| IF-110 | Bnzl | H | i-Pr | 4-OH-Bnzl | H | 0.69 | 434 | C |
| IF-111 | Bnzl | H | s-Bu | 2-Cbx-Et | H | 0.66 | 414 | C |
| IF-112 | Bnzl | H | i-Pr | 2-Cbx-Et | H | 0.62 | 400 | C |
| IF-113 | 4-OH-Bnzl | H | i-Pr | Bnzl | H | 0.73 | 434 | C |
| IF-114 | 4-OH-Bnzl | H | i-Pr | 2-Cbx-Et | H | 0.57 | 416 | C |
| IF-115 | 4-OH-Bnzl | H | i-Pr | 1-Npm | H | 0.79 | 484 | C |
| IF-116 | 2-Cbx-Et | H | i-Bu | Bnzl | H | 0.72 | 414 | C |
| IF-117 | 1-Npm | H | 4-OH-Bnzl | Bnzl | H | 0.81 | 532 | C |
| IF-118 | 1-Npm | H | Bnzl | 4-OH-Bnzl | H | 0.79 | 532 | C |
| IF-119 | 1-Npm | H | 2-Cbx-Et | 4-OH-Bnzl | H | 0.67 | 514 | C |
| IF-120 | 1-Npm | H | s-Bu | 4-OH-Bnzl | H | 0.77 | 498 | C |
| IF-121 | 1-Npm | H | 1-Npm | 4-OH-Bnzl | H | 0.84 | 582 | C |
| IF-122 | 1-Npm | H | i-Pr | 4-OH-Bnzl | H | 0.74 | 484 | C |
| IF-123 | 1-Npm | H | Bnzl | 2-Cbx-Et | H | 0.74 | 498 | C |
| IF-124 | 1-Npm | H | 4-OH-Bnzl | 2-Cbx-Et | H | 0.69 | 514 | C |
| IF-125 | 1-Npm | H | s-Bu | 2-Cbx-Et | H | 0.72 | 464 | C |
| IF-126 | 1-Npm | H | 1-Npm | 2-Cbx-Et | H | 0.80 | 548 | C |
| IF-127 | 1-Npm | H | 4-OH-Bnzl | 1-Npm | H | 0.85 | 582 | C |
| IF-128 | 1-Npm | H | 2-Cbx-Et | 1-Npm | H | 0.81 | 548 | C |
| IF-129 | i-Bu | H | i-Bu | i-Bu | H | 0.80 | 364 | C |
| IF-130 | i-Bu | H | s-Bu | i-Bu | H | 0.80 | 364 | C |
| IF-131 | i-Bu | H | 1-Npm | i-Bu | H | 0.89 | 448 | C |
| IF-132 | i-Bu | H | i-Bu | i-Bu | H | 0.76 | 350 | C |
| IF-133 | i-Bu | H | s-Bu | 1-Npm | H | 0.88 | 448 | C |
| IF-134 | Bnzl | H | Bnzl | i-Bu | H | 0.86 | 432 | C |
| IF-135 | Bnzl | H | 1-Npm | i-Bu | H | 0.94 | 482 | C |
| IF-136 | Bnzl | H | i-Pr | i-Bu | H | 0.82 | 384 | C |
| IF-137 | 1-Npm | H | i-Bu | i-Bu | H | 0.90 | 448 | C |
| IF-138 | 1-Npm | H | Bnzl | i-Bu | H | 0.92 | 482 | C |
| IF-139 | 1-Npm | H | s-Bu | i-Bu | H | 0.91 | 448 | C |
| IF-140 | 1-Npm | H | 1-Npm | i-Bu | H | 0.99 | 532 | C |

TABLE 6-7

| Compound No. | R1 | R2A | R2B | R3 | R4 | RT | Mass | Cond |
|---|---|---|---|---|---|---|---|---|
| IF-141 | 1-Npm | H | i-Pr | i-Bu | H | 0.87 | 434 | C |
| IF-142 | 1-Npm | H | i-Bu | 1-Npm | H | 0.94 | 532 | C |
| IF-143 | 1-Npm | H | i-Pr | 1-Npm | H | 0.90 | 518 | C |
| IF-144 | i-Bu | H | 4-OH-Bnzl | i-Bu | H | 0.73 | 414 | C |
| IF-145 | i-Bu | H | 2-Cbx-Et | i-Bu | H | 0.65 | 380 | C |
| IF-146 | i-Bu | H | 3-Gun-Pr | 4-OH-Bnzl | H | 0.55 | 457 | C |
| IF-147 | i-Bu | H | 1-Npm | 3-Gun-Pr | H | 0.69 | 491 | C |
| IF-148 | Bnzl | H | 4-OH-Bnzl | i-Bu | H | 0.77 | 448 | C |
| IF-149 | Bnzl | H | i-Bu | 2-Cbx-Et | H | 0.67 | 414 | C |
| IF-150 | 2-Cbx-Et | H | Bnzl | i-Bu | H | 0.75 | 414 | C |
| IF-151 | 2-Cbx-Et | H | 4-OH-Bnzl | i-Bu | H | 0.65 | 430 | C |
| IF-152 | 2-Cbx-Et | H | s-Bu | i-Bu | H | 0.72 | 380 | C |
| IF-153 | 2-Cbx-Et | H | 1-Npm | i-Bu | H | 0.81 | 464 | C |
| IF-154 | 2-Cbx-Et | H | i-Pr | i-Bu | H | 0.68 | 366 | C |
| IF-155 | 2-Cbx-Et | H | 1-Npm | Bnzl | H | 0.81 | 498 | C |
| IF-156 | 2-Cbx-Et | H | Bnzl | 4-OH-Bnzl | H | 0.70 | 464 | C |
| IF-157 | 2-Cbx-Et | H | 1-Npm | 4-OH-Bnzl | H | 0.76 | 514 | C |
| IF-158 | 2-Cbx-Et | H | i-Bu | 1-Npm | H | 0.78 | 464 | C |
| IF-159 | 2-Cbx-Et | H | 4-OH-Bnzl | 1-Npm | H | 0.72 | 514 | C |
| IF-160 | 2-Cbx-Et | H | 1-Npm | 1-Npm | H | 0.85 | 548 | C |
| IF-161 | 2-Cbx-Et | H | i-Pr | 1-Npm | H | 0.75 | 450 | C |
| IF-162 | 1-Npm | H | 4-OH-Bnzl | i-Bu | H | 0.82 | 498 | C |
| IF-163 | 1-Npm | H | i-Bu | 4-OH-Bnzl | H | 0.78 | 498 | C |
| IF-164 | 1-Npm | H | i-Bu | 2-Cbx-Et | H | 0.73 | 464 | C |
| IF-165 | 1-Npm | H | i-Pr | 2-Cbx-Et | H | 0.70 | 450 | C |
| IF-166 | 1-Npm | H | 3-Gun-Pr | 1-Npm | H | 0.76 | 575 | C |
| IF-167 | Bnzl | H | i-Bu | i-Bu | H | 0.85 | 398 | C |
| IF-168 | Bnzl | H | s-Bu | i-Bu | H | 0.86 | 398 | C |
| IF-169 | 1-Npm | H | Bnzl | Bnzl | H | 0.90 | 516 | C |
| IF-170 | 1-Npm | H | 1-Npm | Bnzl | H | 0.96 | 566 | C |
| IF-171 | i-Bu | H | 3-Gun-Pr | i-Bu | H | 0.61 | 407 | C |
| IF-172 | i-Bu | H | 3-Gun-Pr | Bnzl | H | 0.64 | 441 | C |
| IF-173 | i-Bu | H | s-Bu | 2-Cbx-Et | H | 0.62 | 380 | C |
| IF-174 | i-Bu | H | i-Bu | 3-Gun-Pr | H | 0.59 | 407 | C |
| IF-175 | i-Bu | H | Bnzl | 3-Gun-Pr | H | 0.61 | 441 | C |
| IF-176 | i-Bu | H | 4-OH-Bnzl | 3-Gun-Pr | H | 0.56 | 457 | C |
| IF-177 | i-Bu | H | s-Bu | 3-Gun-Pr | H | 0.58 | 407 | C |
| IF-178 | i-Bu | H | i-Pr | 3-Gun-Pr | H | 0.55 | 393 | C |
| IF-179 | i-Bu | H | 3-Gun-Pr | 1-Npm | H | 0.69 | 491 | C |
| IF-180 | Bnzl | H | 3-Gun-Pr | i-Bu | H | 0.65 | 441 | C |

TABLE 6-7-continued

| IF-181 | Bnzl | H | 3-Gun-Pr | Bnzl | H | 0.66 | 475 | C |
| IF-182 | Bnzl | H | 3-Gun-Pr | 4-OH-Bnzl | H | 0.58 | 491 | C |
| IF-183 | Bnzl | H | i-Bu | 3-Gun-Pr | H | 0.60 | 441 | C |
| IF-184 | Bnzl | H | Bnzl | 3-Gun-Pr | H | 0.63 | 475 | C |
| IF-185 | Bnzl | H | 4-OH-Bnzl | 3-Gun-Pr | H | 0.58 | 491 | C |
| IF-186 | Bnzl | H | s-Bu | 3-Gun-Pr | H | 0.62 | 441 | C |
| IF-187 | Bnzl | H | 1-Npm | 3-Gun-Pr | H | 0.71 | 525 | C |
| IF-188 | Bnzl | H | 3-Gun-Pr | 1-Npm | H | 0.71 | 525 | C |
| IF-189 | 2-Cbx-Et | H | i-Bu | i-Bu | H | 0.71 | 380 | C |
| IF-190 | 2-Cbx-Et | H | Bnzl | Bnzl | H | 0.74 | 448 | C |

TABLE 6-8

| IF-191 | 2-Cbx-Et | H | 4-OH-Bnzl | Bnzl | H | 0.66 | 464 | C |
| IF-192 | 2-Cbx-Et | H | s-Bu | Bnzl | H | 0.72 | 414 | C |
| IF-193 | 2-Cbx-Et | H | i-Pr | Bnzl | H | 0.68 | 400 | C |
| IF-194 | 2-Cbx-Et | H | i-Bu | 4-OH-Bnzl | H | 0.67 | 430 | C |
| IF-195 | 2-Cbx-Et | H | i-Pr | 4-OH-Bnzl | H | 0.62 | 416 | C |
| IF-196 | 2-Cbx-Et | H | Bnzl | 1-Npm | H | 0.79 | 498 | C |
| IF-197 | 2-Cbx-Et | H | s-Bu | 1-Npm | H | 0.78 | 464 | C |
| IF-198 | 3-Gun-Pr | H | 1-Npm | i-Bu | H | 0.76 | 491 | C |
| IF-199 | 3-Gun-Pr | H | i-Pr | i-Bu | H | 0.64 | 393 | C |
| IF-200 | 3-Gun-Pr | H | 1-Npm | Bnzl | H | 0.75 | 525 | C |
| IF-201 | 3-Gun-Pr | H | i-Pr | Bnzl | H | 0.56 | 427 | C |
| IF-202 | 3-Gun-Pr | H | 1-Npm | 4-OH-Bnzl | H | 0.73 | 541 | C |
| IF-203 | 3-Gun-Pr | H | i-Pr | 4-OH-Bnzl | H | 0.60 | 443 | C |
| IF-204 | 3-Gun-Pr | H | 1-Npm | 1-Npm | H | 0.79 | 575 | C |
| IF-205 | 3-Gun-Pr | H | i-Pr | 1-Npm | H | 0.70 | 477 | C |
| IF-206 | i-Bu | H | i-Bu | 4-tBuO-Bnzl | H | 0.88 | 470 | C |
| IF-207 | i-Bu | H | Bnzl | 4-tBuO-Bnzl | H | 0.89 | 504 | C |
| IF-208 | i-Bu | H | tBOC-E | 4-tBuO-Bnzl | H | 0.91 | 542 | C |
| IF-209 | i-Bu | H | s-Bu | 4-tBuO-Bnzl | H | 0.88 | 470 | C |
| IF-210 | i-Bu | H | 1-Npm | 4-tBuO-Bnzl | H | 0.95 | 554 | C |
| IF-211 | i-Bu | H | i-Pr | 4-tBuO-Bnzl | H | 0.85 | 456 | C |
| IF-212 | i-Bu | H | 1-Npm | tBOC-E | H | 0.91 | 520 | C |
| IF-213 | Bnzl | H | 4-tBuO-Bnzl | Bnzl | H | 0.92 | 538 | C |
| IF-214 | Bnzl | H | i-Bu | 4-tBuO-Bnzl | H | 0.91 | 504 | C |
| IF-215 | Bnzl | H | Bnzl | 4-tBuO-Bnzl | H | 0.91 | 538 | C |
| IF-216 | Bnzl | H | tBOC-E | 4-tBuO-Bnzl | H | 0.93 | 576 | C |
| IF-217 | Bnzl | H | Bnzl | tBOC-E | H | 0.87 | 504 | C |
| IF-218 | Bnzl | H | 4-tBuO-Bnzl | tBOC-E | H | 0.95 | 576 | C |
| IF-219 | Bnzl | H | 1-Npm | tBOC-E | H | 0.94 | 554 | C |
| IF-220 | Bnzl | H | 4-tBuO-Bnzl | 1-Npm | H | 0.97 | 588 | C |
| IF-221 | Bnzl | H | tBOC-E | 1-Npm | H | 0.91 | 554 | C |
| IF-222 | 4-tBuO-Bnzl | H | Bnzl | Bnzl | H | 0.93 | 538 | C |
| IF-223 | 4-tBuO-Bnzl | H | tBOC-E | Bnzl | H | 0.94 | 576 | C |
| IF-224 | 4-tBuO-Bnzl | H | s-Bu | Bnzl | H | 0.92 | 504 | C |
| IF-225 | 4-tBuO-Bnzl | H | 1-Npm | Bnzl | H | 0.99 | 588 | C |
| IF-226 | 4-tBuO-Bnzl | H | Bnzl | tBOC-E | H | 0.96 | 576 | C |
| IF-227 | 4-tBuO-Bnzl | H | 1-Npm | tBOC-E | H | 1.02 | 626 | C |
| IF-228 | 4-tBuO-Bnzl | H | i-Bu | 1-Npm | H | 0.98 | 554 | C |
| IF-229 | 4-tBuO-Bnzl | H | Bnzl | 1-Npm | H | 0.99 | 588 | C |

TABLE 6-9

| IF-230 | 4-tBuO-Bnzl | H | tBOC-E | 1-Npm | H | 1.00 | 626 | C |
| IF-231 | 4-tBuO-Bnzl | H | s-Bu | 1-Npm | H | 0.99 | 554 | C |
| IF-232 | 4-tBuO-Bnzl | H | 1-Npm | 1-Npm | H | 1.04 | 638 | C |
| IF-233 | i-Bu | H | 4-tBuO-Bnzl | Bnzl | H | 0.90 | 504 | C |
| IF-234 | i-Bu | H | tBOC-E | Bnzl | H | 0.84 | 470 | C |
| IF-235 | i-Bu | H | i-Bu | tBOC-E | H | 0.82 | 436 | C |
| IF-236 | i-Bu | H | Bnzl | tBOC-E | H | 0.84 | 470 | C |
| IF-237 | i-Bu | H | 4-tBuO-Bnzl | tBOC-E | H | 0.92 | 542 | C |
| IF-238 | i-Bu | H | i-Pr | tBOC-E | H | 0.79 | 422 | C |
| IF-239 | i-Bu | H | 4-tBuO-Bnzl | 1-Npm | H | 0.95 | 554 | C |
| IF-240 | i-Bu | H | tBOC-E | 1-Npm | H | 0.89 | 520 | C |
| IF-241 | Bnzl | H | tBOC-E | Bnzl | H | 0.86 | 504 | C |
| IF-242 | Bnzl | H | s-Bu | 4-tBuO-Bnzl | H | 0.91 | 504 | C |
| IF-243 | Bnzl | H | 1-Npm | 4-tBuO-Bnzl | H | 0.97 | 588 | C |
| IF-244 | Bnzl | H | i-Pr | 4-tBuO-Bnzl | H | 0.87 | 490 | C |
| IF-245 | Bnzl | H | s-Bu | tBOC-E | H | 0.86 | 470 | C |
| IF-246 | Bnzl | H | i-Pr | tBOC-E | H | 0.83 | 456 | C |
| IF-247 | 4-tBuO-Bnzl | H | i-Pr | Bnzl | H | 0.89 | 490 | C |
| IF-248 | 4-tBuO-Bnzl | H | i-Pr | tBOC-E | H | 0.92 | 528 | C |
| IF-249 | 4-tBuO-Bnzl | H | i-Pr | 1-Npm | H | 0.95 | 540 | C |
| IF-250 | tBOC-E | H | i-Bu | Bnzl | H | 0.87 | 470 | C |
| IF-251 | 1-Npm | H | 4-tBuO-Bnzl | Bnzl | H | 0.96 | 588 | C |
| IF-252 | 1-Npm | H | Bnzl | 4-tBuO-Bnzl | H | 0.96 | 588 | C |

TABLE 6-9-continued

| | | | | | | | | |
|---|---|---|---|---|---|---|---|---|
| IF-253 | 1-Npm | H | tBOC-E | 4-tBuO-Bnzl | H | 0.98 | 626 | C |
| IF-254 | 1-Npm | H | s-Bu | 4-tBuO-Bnzl | H | 0.96 | 554 | C |
| IF-255 | 1-Npm | H | 1-Npm | 4-tBuO-Bnzl | H | 1.02 | 638 | C |
| IF-256 | 1-Npm | H | i-Pr | 4-tBuO-Bnzl | H | 0.92 | 540 | C |
| IF-257 | 1-Npm | H | Bnzl | tBOC-E | H | 0.91 | 554 | C |
| IF-258 | 1-Npm | H | 4-tBuO-Bnzl | tBOC-E | H | 0.99 | 626 | C |
| IF-259 | 1-Npm | H | s-Bu | tBOC-E | H | 0.90 | 520 | C |
| IF-260 | 1-Npm | H | 1-Npm | tBOC-E | H | 0.98 | 604 | C |
| IF-261 | 1-Npm | H | 4-tBuO-Bnzl | 1-Npm | H | 1.01 | 638 | C |
| IF-262 | 1-Npm | H | tBOC-E | 1-Npm | H | 0.95 | 604 | C |
| IF-263 | i-Bu | H | 4-tBuO-Bnzl | i-Bu | H | 0.89 | 470 | C |
| IF-264 | i-Bu | H | tBOC-E | i-Bu | H | 0.83 | 436 | C |
| IF-265 | i-Bu | H | 1-Npm | (tBOC)Gun-Pr | H | 0.97 | 691 | C |

TABLE 6-10

| | | | | | | | | |
|---|---|---|---|---|---|---|---|---|
| IF-266 | Bnzl | H | 4-tBuO-Bnzl | i-Bu | H | 0.95 | 504 | C |
| IF-267 | Bnzl | H | i-Bu | tBOC-E | H | 0.86 | 470 | C |
| IF-268 | tBOC-E | H | Bnzl | i-Bu | H | 0.88 | 470 | C |
| IF-269 | tBOC-E | H | 4-tBuO-Bnzl | i-Bu | H | 0.96 | 542 | C |
| IF-270 | tBOC-E | H | s-Bu | i-Bu | H | 0.87 | 436 | C |
| IF-271 | tBOC-E | H | 1-Npm | i-Bu | H | 0.95 | 520 | C |
| IF-272 | tBOC-E | H | i-Pr | i-Bu | H | 0.84 | 422 | C |
| IF-273 | tBOC-E | H | 1-Npm | Bnzl | H | 0.95 | 554 | C |
| IF-274 | tBOC-E | H | Bnzl | 4-tBuO-Bnzl | H | 0.97 | 576 | C |
| IF-275 | tBOC-E | H | 1-Npm | 4-tBuO-Bnzl | H | 1.03 | 626 | C |
| IF-276 | tBOC-E | H | i-Bu | 1-Npm | H | 0.94 | 520 | C |
| IF-277 | tBOC-E | H | 4-tBuO-Bnzl | 1-Npm | H | 1.02 | 626 | C |
| IF-278 | tBOC-E | H | 1-Npm | 1-Npm | H | 1.01 | 604 | C |
| IF-279 | tBOC-E | H | i-Pr | 1-Npm | H | 0.91 | 506 | C |
| IF-280 | 1-Npm | H | 4-tBuO-Bnzl | i-Bu | H | 0.99 | 554 | C |
| IF-281 | 1-Npm | H | i-Bu | 4-tBuO-Bnzl | H | 0.96 | 554 | C |
| IF-282 | 1-Npm | H | i-Bu | tBOC-E | H | 0.90 | 520 | C |
| IF-283 | 1-Npm | H | i-Pr | tBOC-E | H | 0.88 | 506 | C |
| IF-284 | 1-Npm | H | (tBOC)Gun-Pr | 1-Npm | H | 1.00 | 775 | C |
| IF-285 | i-Bu | H | (tBOC)Gun-Pr | i-Bu | H | 0.90 | 607 | C |
| IF-286 | i-Bu | H | (tBOC)Gun-Pr | Bnzl | H | 0.91 | 641 | C |
| IF-287 | i-Bu | H | s-Bu | tBOC-E | H | 0.84 | 436 | C |
| IF-288 | i-Bu | H | i-Bu | (tBOC)Gun-Pr | H | 0.91 | 607 | C |
| IF-289 | i-Bu | H | Bnzl | (tBOC)Gun-Pr | H | 0.92 | 641 | C |
| IF-290 | i-Bu | H | s-Bu | (tBOC)Gun-Pr | H | 0.90 | 607 | C |
| IF-291 | i-Bu | H | i-Pr | (tBOC)Gun-Pr | H | 0.87 | 593 | C |
| IF-292 | i-Bu | H | (tBOC)Gun-Pr | 1-Npm | H | 0.95 | 691 | C |
| IF-293 | Bnzl | H | (tBOC)Gun-Pr | i-Bu | H | 0.93 | 641 | C |
| IF-294 | Bnzl | H | (tBOC)Gun-Pr | Bnzl | H | 0.92 | 675 | C |
| IF-295 | Bnzl | H | i-Bu | (tBOC)Gun-Pr | H | 0.93 | 641 | C |
| IF-296 | Bnzl | H | Bnzl | (tBOC)Gun-Pr | H | 0.94 | 675 | C |
| IF-297 | Bnzl | H | s-Bu | (tBOC)Gun-Pr | H | 0.94 | 641 | C |
| IF-298 | Bnzl | H | 1-Npm | (tBOC)Gun-Pr | H | 1.07 | 725 | C |

TABLE 6-11

| | | | | | | | | |
|---|---|---|---|---|---|---|---|---|
| IF-299 | Bnzl | H | (tBOC)Gun-Pr | 1-Npm | H | 0.97 | 725 | C |
| IF-300 | tBOC-E | H | i-Bu | i-Bu | H | 0.87 | 436 | C |
| IF-301 | tBOC-E | H | Bnzl | Bnzl | H | 0.90 | 504 | C |
| IF-302 | tBOC-E | H | 4-tBuO-Bnzl | Bnzl | H | 0.98 | 576 | C |
| IF-303 | tBOC-E | H | s-Bu | Bnzl | H | 0.90 | 470 | C |
| IF-304 | tBOC-E | H | i-Pr | Bnzl | H | 0.86 | 456 | C |
| IF-305 | tBOC-E | H | i-Bu | 4-tBuO-Bnzl | H | 0.98 | 542 | C |
| IF-306 | tBOC-E | H | i-Pr | 4-tBuO-Bnzl | H | 0.95 | 528 | C |
| IF-307 | tBOC-E | H | Bnzl | 1-Npm | H | 0.96 | 554 | C |
| IF-308 | tBOC-E | H | s-Bu | 1-Npm | H | 0.96 | 520 | C |
| IF-309 | (tBOC)Gun-Pr | H | 1-Npm | i-Bu | H | 1.05 | 691 | C |
| IF-310 | (tBOC)Gun-Pr | H | i-Pr | i-Bu | H | 0.97 | 593 | C |
| IF-311 | (tBOC)Gun-Pr | H | 1-Npm | Bnzl | H | 1.06 | 725 | C |
| IF-312 | (tBOC)Gun-Pr | H | i-Pr | Bnzl | H | 0.95 | 627 | C |
| IF-313 | (tBOC)Gun-Pr | H | 1-Npm | 1-Npm | H | 1.10 | 775 | C |
| IF-314 | (tBOC)Gun-Pr | H | i-Pr | 1-Npm | H | 1.03 | 677 | C |
| IF-315 | Pr | H | Chm | Bnzl | H | 0.91 | 424 | C |
| IF-316 | 1-Npm | H | heptyl | Ph—Et | H | 1.08 | 538 | C |
| IF-317 | 1-Npm | H | pentyl | Ph—Et | H | 1 | 510 | C |
| IF-318 | 1-Npm | H | cyclohexyl | Ph—Et | H | 1 | 522 | C |
| IF-319 | 1-Npm | H | cyclopentyl | Ph—Et | H | 0.97 | 508 | C |
| IF-320 | 1-Npm | H | Hxy | 4-methylphenethyl | H | 1.08 | 538 | C |
| IF-321 | 1-Npm | H | Hxy | cyclohexylethyl | H | 1.15 | 530 | C |
| IF-322 | 3-tert-butoxypropyl | H | 4-F-Bnzl | 1-Npm | H | 1 | 558 | C |
| IF-323 | 3-(tert-butoxycarbonylamino)propyl | H | 3-(tert-butoxycarbonylamino)propyl | 3-(tert-butoxycarbonylamino)propyl | H | 1 | 767 | C |
| IF-324 | Pr | H | Bnzl | Chm | H | 0.91 | 424.3 | C |
| IF-325 | Pr | H | 2-methylbenzyl | Bnzl | H | 0.87 | 432.2 | C |
| IF-326 | Pr | H | (1,2,3,4-tetrahydronaphthalen-1-yl)methyl | Bnzl | H | 0.95 | 472.3 | C |

TABLE 6-11-continued

| | | | | | | | | |
|---|---|---|---|---|---|---|---|---|
| IF-327 | Pr | H | Cpm | Bnzl | H | 0.87 | 410.3 | C |
| IF-328 | 1-Npm | H | Hxy | 3-methylphenethyl | H | 1.08 | 538.4 | C |

TABLE 6-12

| | | | | | | | | |
|---|---|---|---|---|---|---|---|---|
| IF-329 | Pr | H | Bnzl | Cpm | H | 0.87 | 410.3 | C |
| IF-330 | 1-Npm | H | Hxy | naphthalen-2-ylethyl | H | 1.10 | 574.4 | C |
| IF-331 | 1-Npm | H | Hxy | 4-isopropylphenethyl | H | 1.16 | 566.4 | C |
| IF-332 | 1-Npm | H | β-hydroxyphenethyl | Ph—Et | H | 0.92 | 560.4 | C |
| IF-333 | 1-Npm | H | α-hydroxymethylphenethyl | Ph—Et | H | 0.94 | 574.4 | C |
| IF-334 | 1-Npm | H | α-hydroxymethylphenethyl | Ph—Et | H | 0.92 | 574.4 | C |
| IF-335 | 4-Nt-Bnzl | H | 4-tBuO-Bnzl | tBOC-E | H | 1.03 | 621 | C |
| IF-336 | 4-aminobenzyl | H | 4-tBuO-Bnzl | tBOC-E | H | 0.9 | 591 | C |
| IF-337 | 4-(cyclopentyl carbonylamino) benzyl | H | 4-tBuO-Bnzl | tBOC-E | H | 1.02 | 687 | C |
| IF-338 | 4-(cyclopentyl carbonylamino) benzyl | H | 4-OH-Bnzl | 2-Cbx-Et | H | 0.74 | 575 | C |
| IF-339 | 4-Nt-Bnzl | H | Bnzl | Bnzl | H | 0.91 | 511 | C |
| IF-340 | H | H | Bnzl | Bnzl | H | 0.77 | 376 | C |
| IF-341 | Cpm | H | Bnzl | Bnzl | H | 0.72 | 458 | C |
| IF-342 | cyclohexyl | H | Bnzl | Bnzl | H | 0.9 | 458 | C |
| IF-343 | 4-Nt-Bnzl | H | Hxy | Ph—Et | H | 1.02 | 519 | C |
| IF-344 | H | H | Hxy | Ph—Et | H | 0.87 | 384 | C |
| IF-345 | Isopropyl | H | Bnzl | Bnzl | H | 0.83 | 418 | C |
| IF-346 | s-Bu | H | Bnzl | Bnzl | H | 0.86 | 432 | C |
| IF-347 | Pr | H | Bnzl | Bnzl | H | 0.83 | 418 | C |
| IF-348 | 3-MeO-Bnzl | H | Hxy | Ph—Et | H | 1.02 | 504 | C |
| IF-349 | 2,3-dimethylbenzyl | H | Hxy | Ph—Et | H | 1.04 | 502 | C |
| IF-350 | 5,6,7,8-tetrahydronaphthalen-1-ylmethyl | H | Hxy | Ph—Et | H | 1.1 | 528 | C |
| IF-351 | 4-Nt-Bnzl | H | Bnzl | tBOC-E | Me | 0.9 | 563 | C |
| IF-352 | Ph—Et | H | Bnzl | i-Bu | H | 0.94 | 446.4 | C |
| IF-353 | i-Bu | H | Bnzl | Ph—Et | H | 0.91 | 446.4 | C |
| IF-354 | Bnzl | H | i-Bu | Ph—Et | H | 0.92 | 446.4 | C |
| IF-355 | 4-F-Bnzl | H | i-Bu | Bnzl | H | 0.9 | 450.3 | C |
| IF-356 | i-Bu | H | 4-F-Bnzl | Bnzl | H | 0.89 | 450.4 | C |
| IF-357 | i-Bu | H | i-Pnt | Bnzl | H | 0.9 | 412.4 | C |
| IF-358 | Bnzl | H | i-Pnt | i-Bu | H | 0.95 | 412.4 | C |

TABLE 6-13

| | | | | | | | | |
|---|---|---|---|---|---|---|---|---|
| IF-359 | i-Bu | H | Hxy | Bnzl | H | 0.95 | 426.4 | C |
| IF-360 | 4-F-Bnzl | H | Bnzl | Bnzl | H | 0.91 | 484.3 | C |
| IF-361 | Ph—Et | H | Bnzl | Bnzl | H | 0.92 | 480.3 | C |
| IF-362 | 2-OtBu—Et | H | 4-F-Bnzl | 1-Npm | H | 0.96 | 544.3 | C |
| IF-363 | 2-OH—Et | H | 4-F-Bnzl | 1-Npm | H | 0.84 | 488.2 | C |
| IF-364 | i-Bu | H | Bnzl | Bnzl | H | 0.86 | 432.2 | C |
| IF-365 | Bnzl | H | Bnzl | Bnzl | H | 0.89 | 466.2 | C |
| IF-366 | i-Bu | H | Bnzl | i-Bu | H | 0.85 | 398.3 | C |
| IF-367 | i-Bu | H | i-Bu | Bnzl | H | 0.84 | 398.2 | C |
| IF-368 | Chm | H | Bnzl | Bnzl | H | 0.93 | 472.4 | C |
| IF-369 | 1-Npm | H | 4-F-Bnzl | 2-OTBS—Et | H | 1.11 | 602.3 | C |
| IF-370 | 1-Npm | H | 4-F-Bnzl | 2-OH—Et | H | 0.79 | 488.2 | C |
| IF-371 | i-Pnt | H | Bnzl | Bnzl | H | 0.91 | 446.3 | C |
| IF-372 | Chm | H | 2-OtBu—Et | 1-Npm | H | 0.97 | 532.4 | C |
| IF-373 | Chm | H | 2-OH—Et | 1-Npm | H | 0.83 | 476.3 | C |
| IF-374 | 2-OtBu—Et | H | Bnzl | 1-Npm | H | 0.95 | 526.3 | C |
| IF-375 | 2-OH—Et | H | Bnzl | 1-Npm | H | 0.82 | 470.2 | C |
| IF-376 | tBOC-E | H | Bnzl | Ph—Et | H | 0.95 | 518.3 | C |
| IF-377 | 2-Cbx-Et | H | Bnzl | Ph—Et | H | 0.81 | 462.2 | C |
| IF-378 | i-Pnt | H | Bnzl | Ph—Et | H | 0.92 | 460.3 | C |
| IF-379 | Bnzl | H | i-Bu | i-Pnt | H | 0.91 | 412.3 | C |
| IF-380 | 4-F-Bnzl | H | Bnzl | i-Bu | H | 0.91 | 450.3 | C |
| IF-381 | 2-OtBu—Et | H | Ph—Et | 1-Npm | H | 0.97 | 540.4 | C |

TABLE 6-13-continued

| | | | | | | | | |
|---|---|---|---|---|---|---|---|---|
| IF-382 | 4-tBuO-Bnzl | H | Bnzl | Ph—Et | H | 1.00 | 552.4 | C |
| IF-383 | Ph—Et | H | Hxy | 1-Npm | H | 1.05 | 524.4 | C |
| IF-384 | 4-OH-Bnzl | H | Bnzl | Ph—Et | H | 0.84 | 496.3 | C |
| IF-385 | 2-OH—Et | H | Ph—Et | 1-Npm | H | 0.85 | 484.3 | C |
| IF-386 | (tBOC)Gun-Pr | H | (tBOC)Gun-Pr | (tBOC)Gun-Pr | H | 1.16 | 1093.3 | C |
| IF-387 | 4-tBuO-Bnzl | H | i-Bu | Bnzl | H | 0.98 | 504.4 | C |
| IF-388 | 4-tBuO-Bnzl | H | Bnzl | i-Bu | H | 1.01 | 504.4 | C |
| IF-389 | 4-OH-Bnzl | H | i-Bu | Bnzl | H | 0.81 | 448.2 | C |
| IF-390 | 4-OH-Bnzl | H | Bnzl | i-Bu | H | 0.81 | 448.3 | C |
| IF-391 | i-Bu | H | Ph—Et | Bnzl | H | 0.88 | 446.4 | C |
| IF-392 | Ph—Et | H | i-Bu | Bnzl | H | 0.91 | 446.4 | C |
| IF-393 | Bnzl | H | Ph—Et | i-Bu | H | 0.95 | 446.4 | C |
| IF-394 | i-Pnt | H | i-Bu | Bnzl | H | 0.91 | 412.4 | C |
| IF-395 | Chm | H | i-Bu | Bnzl | H | 0.94 | 438.4 | C |
| IF-396 | Bnzl | H | 4-F-Bnzl | i-Bu | H | 0.92 | 450.3 | C |
| IF-397 | i-Pnt | H | Bnzl | i-Bu | H | 0.91 | 412.4 | C |
| IF-398 | Chm | H | Bnzl | i-Bu | H | 0.95 | 438.4 | C |
| IF-399 | i-Bu | H | Bnzl | i-Pnt | H | 0.89 | 412.4 | C |
| IF-400 | Bnzl | H | Hxy | i-Bu | H | 1.01 | 426.4 | C |
| IF-401 | Ph—Et | H | i-Bu | i-Bu | H | 0.92 | 412.3 | C |
| IF-402 | Ph—Et | H | i-Bu | 1-Npm | H | 0.97 | 496.4 | C |
| IF-403 | Ph—Et | H | i-Bu | 4-tBuO-Bnzl | H | 1.00 | 518.4 | C |
| IF-404 | Ph—Et | H | i-Bu | 2-OTBS—Et | H | 1.07 | 514.4 | C |

TABLE 6-14

| | | | | | | | | |
|---|---|---|---|---|---|---|---|---|
| IF-405 | Ph—Et | H | i-Bu | 2-OH—Et | H | 0.73 | 400.2 | C |
| IF-406 | Ph—Et | H | i-Bu | i-Pnt | H | 0.94 | 426.3 | C |
| IF-407 | Ph—Et | H | i-Bu | 4-OH-Bnzl | H | 0.80 | 462.3 | C |
| IF-408 | Ph—Et | H | 1-Npm | Hxy | H | 1.05 | 524.4 | C |
| IF-409 | 1-Npm | H | Ph—Et | Hxy | H | 1.04 | 524.4 | C |
| IF-410 | Hxy | H | Ph—Et | 1-Npm | H | 1.02 | 524.4 | C |
| IF-411 | Hxy | H | 1-Npm | Ph—Et | H | 1.03 | 524.4 | C |

TABLE 6-15

| Compound No. | $R_1$ | $R_{2A}$ | $R_{2B}$ | $R_3$ | $R_4$ | Retention time RT (min) | Mass $(M + H)^+$ | Measurement condition |
|---|---|---|---|---|---|---|---|---|
| IF-412 | 2-OtBu—Et | H | i-Pr | 1-Npm | H | 3.50 | 478 | F |
| IF-413 | tBOC-E | H | s-Bu | i-Pnt | H | 3.62 | 450 | F |
| IF-414 | 4-F-Bnzl | H | s-Bu | tBOC-E | H | 3.50 | 488 | F |
| IF-415 | i-Pnt | H | 2-OtBu—Et | i-Bu | H | 3.25 | 422 | F |
| IF-416 | Chm | H | 2-OtBu—Et | i-Bu | H | 3.49 | 448 | F |
| IF-417 | Chm | H | 2-OtBu—Et | i-Pnt | H | 3.65 | 462 | F |
| IF-418 | 2-OtBu—Et | H | Hxy | i-Bu | H | 3.85 | 436 | F |
| IF-419 | 2-OtBu—Et | H | Hxy | i-Pnt | H | 4.00 | 450 | F |
| IF-420 | 2-Cbx-Et | H | Bnzl | i-Pnt | H | 4.43 | 428 | G |
| IF-421 | Ph—Et | H | Bnzl | 2-Cbx-Et | H | 4.22 | 462 | G |
| IF-422 | 4-F-Bnzl | H | Bnzl | 2-Cbx-Et | H | 3.98 | 466 | G |
| IF-423 | i-Pnt | H | Bnzl | 2-Cbx-Et | H | 3.95 | 428 | G |
| IF-424 | i-Pnt | H | Bnzl | 2-OH—Et | H | 2.59 | 400 | F |
| IF-425 | Chm | H | Bnzl | 2-Cbx-Et | H | 4.17 | 454 | G |
| IF-426 | Chm | H | Bnzl | 2-OH—Et | H | 2.75 | 426 | F |
| IF-427 | 2-Cbx-Et | H | i-Bu | Ph—Et | H | 4.37 | 428 | G |
| IF-428 | 2-Cbx-Et | H | i-Bu | i-Pnt | H | 4.28 | 394 | G |
| IF-429 | 4-F-Bnzl | H | i-Bu | 2-Cbx-Et | H | 3.77 | 432 | G |
| IF-430 | 2-OH—Et | H | i-Bu | 2-Cbx-Et | H | 3.07 | 368 | G |
| IF-431 | i-Pnt | H | i-Bu | 4-OH-Bnzl | H | 4.28 | 428 | G |
| IF-432 | i-Pnt | H | i-Bu | 2-Cbx-Et | H | 3.72 | 394 | G |
| IF-433 | Chm | H | i-Bu | 4-OH-Bnzl | H | 4.37 | 454 | G |
| IF-434 | Chm | H | i-Bu | 2-Cbx-Et | H | 3.93 | 420 | G |
| IF-435 | 2-Cbx-Et | H | 1-Npm | Ph—Et | H | 4.99 | 512 | G |
| IF-436 | 2-Cbx-Et | H | 1-Npm | i-Pnt | H | 4.89 | 478 | G |
| IF-437 | Ph—Et | H | 1-Npm | 2-Cbx-Et | H | 4.70 | 512 | G |
| IF-438 | 4-F-Bnzl | H | 1-Npm | 2-Cbx-Et | H | 4.57 | 516 | G |
| IF-439 | i-Pnt | H | 1-Npm | 2-Cbx-Et | H | 4.53 | 478 | G |
| IF-440 | Chm | H | 1-Npm | 2-Cbx-Et | H | 4.67 | 504 | G |
| IF-441 | i-Bu | H | i-Pr | 2-OH—Et | H | 0.97 | 338 | F |
| IF-442 | 4-OH-Bnzl | H | i-Pr | Ph—Et | H | 4.39 | 448 | G |
| IF-443 | 4-OH-Bnzl | H | i-Pr | i-Pnt | H | 4.22 | 414 | G |
| IF-444 | 2-Cbx-Et | H | i-Pr | Ph—Et | H | 4.07 | 414 | G |
| IF-445 | Ph—Et | H | i-Pr | 2-Cbx-Et | H | 3.73 | 414 | G |
| IF-446 | Ph—Et | H | i-Pr | 2-OH—Et | H | 2.42 | 386 | F |
| IF-447 | 4-F-Bnzl | H | i-Pr | 2-Cbx-Et | H | 3.52 | 418 | G |

TABLE 6-16

| | | | | | | | |
|---|---|---|---|---|---|---|---|
| IF-448 | 4-F-Bnzl | H | i-Pr | 2-OH—Et | H | 2.12 | 390 | F |
| IF-449 | 2-OH—Et | H | i-Pr | Bnzl | H | 3.82 | 372 | G |
| IF-450 | 2-OH—Et | H | i-Pr | 1-Npm | H | 4.45 | 422 | G |
| IF-451 | 2-OH-Bnzl | H | i-Pr | 4-OH-Bnzl | H | 3.45 | 388 | G |
| IF-452 | 2-OH—Et | H | i-Pr | 2-Cbx-Et | H | 2.68 | 354 | G |
| IF-453 | 2-OH—Et | H | i-Pr | Ph—Et | H | 4.00 | 386 | G |
| IF-454 | 2-OH—Et | H | i-Pr | i-Pnt | H | 3.88 | 352 | G |
| IF-455 | i-Pnt | H | i-Pr | 4-OH-Bnzl | H | 3.97 | 414 | G |
| IF-456 | i-Pnt | H | i-Pr | 2-OH—Et | H | 1.62 | 352 | F |
| IF-457 | Chm | H | i-Pr | i-Bu | H | 3.24 | 390 | F |
| IF-458 | Chm | H | i-Pr | 4-OH-Bnzl | H | 4.07 | 440 | G |
| IF-459 | Chm | H | i-Pr | 2-Cbx-Et | H | 3.70 | 406 | G |
| IF-460 | Chm | H | i-Pr | 2-OH—Et | H | 2.40 | 378 | F |
| IF-461 | Chm | H | i-Pr | i-Pnt | H | 3.42 | 404 | F |
| IF-462 | i-Bu | H | s-Bu | i-Pnt | H | 3.19 | 378 | F |
| IF-463 | 4-OH-Bnzl | H | s-Bu | Ph—Et | H | 4.59 | 462 | G |
| IF-464 | 4-OH-Bnzl | H | s-Bu | i-Pnt | H | 4.47 | 428 | G |
| IF-465 | 2-Cbx-Et | H | s-Bu | Ph—Et | H | 4.34 | 428 | G |
| IF-466 | Ph—Et | H | s-Bu | 2-Cbx-Et | H | 3.97 | 428 | G |
| IF-467 | 2-OH—Et | H | s-Bu | 4-OH-Bnzl | H | 3.65 | 402 | G |
| IF-468 | 2-OH—Et | H | s-Bu | i-Pnt | H | 4.10 | 366 | G |
| IF-469 | i-Pnt | H | s-Bu | i-Bu | H | 3.20 | 378 | F |
| IF-470 | i-Pnt | H | s-Bu | 4-OH-Bnzl | H | 4.22 | 428 | G |
| IF-471 | i-Pnt | H | s-Bu | Ph—Et | H | 3.50 | 426 | F |
| IF-472 | i-Pnt | H | s-Bu | 2-OH—Et | H | 2.37 | 366 | F |
| IF-473 | Chm | H | s-Bu | i-Bu | H | 3.45 | 404 | F |
| IF-474 | Chm | H | s-Bu | 4-OH-Bnzl | H | 4.37 | 454 | G |
| IF-475 | Chm | H | s-Bu | 2-Cbx-Et | H | 3.93 | 420 | G |
| IF-476 | Chm | H | s-Bu | Ph—Et | H | 3.69 | 452 | F |
| IF-477 | Chm | H | s-Bu | 2-OH—Et | H | 2.57 | 392 | F |
| IF-478 | Chm | H | s-Bu | i-Pnt | H | 3.65 | 418 | F |
| IF-479 | i-Bu | H | 4-OH-Bnzl | i-Pnt | H | 4.30 | 428 | G |
| IF-480 | 2-Cbx-Et | H | 4-OH-Bnzl | Ph—Et | H | 3.97 | 478 | G |
| IF-481 | 2-Cbx-Et | H | 4-OH-Bnzl | i-Pnt | H | 3.84 | 444 | G |
| IF-482 | Ph—Et | H | 4-OH-Bnzl | 2-Cbx-Et | H | 3.80 | 478 | G |
| IF-483 | 4-F-Bnzl | H | 4-OH-Bnzl | 2-Cbx-Et | H | 3.57 | 482 | G |
| IF-484 | 2-OH—Et | H | 4-OH-Bnzl | 2-Cbx-Et | H | 2.93 | 418 | G |
| IF-485 | i-Pnt | H | 4-OH-Bnzl | 2-Cbx-Et | H | 3.52 | 444 | G |
| IF-486 | Chm | H | 4-OH-Bnzl | 2-Cbx-Et | H | 3.77 | 470 | G |
| IF-487 | i-Bu | H | 2-Cbx-Et | Ph—Et | H | 4.03 | 428 | G |
| IF-488 | i-Bu | H | 2-Cbx-Et | i-Pnt | H | 3.87 | 394 | G |
| IF-489 | 2-OH—Et | H | 2-Cbx-Et | i-Bu | H | 2.87 | 368 | G |
| IF-490 | 2-OH—Et | H | 2-Cbx-Et | i-Pnt | H | 3.32 | 382 | G |
| IF-491 | i-Pnt | H | 2-Cbx-Et | i-Bu | H | 3.88 | 394 | G |
| IF-492 | i-Pnt | H | 2-Cbx-Et | 4-OH-Bnzl | H | 3.42 | 444 | G |
| IF-493 | Chm | H | 2-Cbx-Et | i-Bu | H | 4.17 | 420 | G |
| IF-494 | Chm | H | 2-Cbx-Et | 4-OH-Bnzl | H | 3.62 | 470 | G |
| IF-495 | Chm | H | 2-Cbx-Et | i-Pnt | H | 4.43 | 434 | G |
| IF-496 | Bnzl | H | 4-F-Bnzl | 4-OH-Bnzl | H | 4.42 | 500 | G |
| IF-497 | Bnzl | H | 4-F-Bnzl | 2-Cbx-Et | H | 4.02 | 466 | G |

TABLE 6-17

| | | | | | | | |
|---|---|---|---|---|---|---|---|
| IF-498 | i-Bu | H | 4-F-Bnzl | 4-OH-Bnzl | H | 4.32 | 466 | G |
| IF-499 | i-Bu | H | 4-F-Bnzl | 2-Cbx-Et | H | 3.82 | 432 | G |
| IF-500 | 1-Npm | H | 4-F-Bnzl | 4-OH-Bnzl | H | 4.75 | 550 | G |
| IF-501 | 1-Npm | H | 4-F-Bnzl | 2-Cbx-Et | H | 4.40 | 516 | G |
| IF-502 | 4-OH-Bnzl | H | 4-F-Bnzl | 2-Cbx-Et | H | 3.75 | 482 | G |
| IF-503 | 4-OH-Bnzl | H | 4-F-Bnzl | Ph—Et | H | 4.80 | 514 | G |
| IF-504 | 4-OH-Bnzl | H | 4-F-Bnzl | i-Pnt | H | 4.68 | 480 | G |
| IF-505 | 2-Cbx-Et | H | 4-F-Bnzl | 4-OH-Bnzl | H | 4.07 | 482 | G |
| IF-506 | 2-Cbx-Et | H | 4-F-Bnzl | Ph—Et | H | 4.65 | 480 | G |
| IF-507 | 2-Cbx-Et | H | 4-F-Bnzl | i-Pnt | H | 4.50 | 446 | G |
| IF-508 | Ph—Et | H | 4-F-Bnzl | 4-OH-Bnzl | H | 4.70 | 514 | G |
| IF-509 | Ph—Et | H | 4-F-Bnzl | 2-Cbx-Et | H | 4.43 | 480 | G |
| IF-510 | 2-OH—Et | H | 4-F-Bnzl | 4-OH-Bnzl | H | 3.95 | 454 | G |
| IF-511 | 2-OH—Et | H | 4-F-Bnzl | 2-Cbx-Et | H | 3.50 | 420 | G |
| IF-512 | i-Pnt | H | 4-F-Bnzl | 4-OH-Bnzl | H | 4.49 | 480 | G |
| IF-513 | i-Pnt | H | 4-F-Bnzl | 2-Cbx-Et | H | 4.10 | 446 | G |
| IF-514 | Chm | H | 4-F-Bnzl | 4-OH-Bnzl | H | 4.64 | 506 | G |
| IF-515 | Chm | H | 4-F-Bnzl | 2-Cbx-Et | H | 4.30 | 472 | G |
| IF-516 | i-Bu | H | i-Pnt | i-Bu | H | 3.24 | 378 | F |
| IF-517 | i-Bu | H | i-Pnt | 2-Cbx-Et | H | 3.80 | 394 | G |
| IF-518 | i-Bu | H | i-Pnt | 2-OH—Et | H | 2.47 | 366 | F |
| IF-519 | 4-OH-Bnzl | H | i-Pnt | 2-Cbx-Et | H | 3.75 | 444 | G |
| IF-520 | 2-Cbx-Et | H | i-Pnt | i-Bu | H | 4.34 | 394 | G |
| IF-521 | 2-Cbx-Et | H | i-Pnt | 4-OH-Bnzl | H | 4.09 | 444 | G |

TABLE 6-17-continued

| | | | | | | | |
|---|---|---|---|---|---|---|---|
| IF-522 | 2-OH—Et | H | i-Pnt | i-Bu | H | 4.20 | 366 | G |
| IF-523 | 2-OH—Et | H | i-Pnt | 2-Cbx-Et | H | 3.48 | 382 | G |
| IF-524 | Chm | H | i-Pnt | i-Bu | H | 3.72 | 418 | F |
| IF-525 | Chm | H | i-Pnt | 2-Cbx-Et | H | 4.30 | 434 | G |
| IF-526 | i-Bu | H | 2-OH—Et | i-Bu | H | 3.47 | 352 | G |
| IF-527 | i-Bu | H | 2-OH—Et | 4-OH-Bnzl | H | 3.02 | 402 | G |
| IF-528 | i-Bu | H | 2-OH—Et | 2-Cbx-Et | H | 2.40 | 368 | G |
| IF-529 | i-Bu | H | 2-OH—Et | i-Pnt | H | 3.80 | 366 | G |
| IF-530 | 1-Npm | H | 2-OH—Et | 4-OH-Bnzl | H | 3.80 | 486 | G |
| IF-531 | 4-OH-Bnzl | H | 2-OH—Et | Bnzl | H | 3.48 | 436 | G |
| IF-532 | 4-OH-Bnzl | H | 2-OH—Et | 1-Npm | H | 3.95 | 486 | G |
| IF-533 | 4-OH-Bnzl | H | 2-OH—Et | 2-Cbx-Et | H | 2.45 | 418 | G |
| IF-534 | 4-OH-Bnzl | H | 2-OH—Et | Ph—Et | H | 3.68 | 450 | G |
| IF-535 | 4-OH-Bnzl | H | 2-OH—Et | i-Pnt | H | 3.47 | 416 | G |
| IF-536 | 2-Cbx-Et | H | 2-OH—Et | Bnzl | H | 3.12 | 402 | G |
| IF-537 | 2-Cbx-Et | H | 2-OH—Et | i-Bu | H | 2.85 | 368 | G |
| IF-538 | 2-Cbx-Et | H | 2-OH—Et | 1-Npm | H | 3.67 | 452 | G |
| IF-539 | 2-Cbx-Et | H | 2-OH—Et | 4-OH-Bnzl | H | 2.75 | 418 | G |
| IF-540 | 2-Cbx-Et | H | 2-OH—Et | Ph—Et | H | 3.37 | 416 | G |
| IF-541 | 2-Cbx-Et | H | 2-OH—Et | i-Pnt | H | 3.23 | 382 | G |
| IF-542 | Ph—Et | H | 2-OH—Et | 2-Cbx-Et | H | 3.29 | 416 | G |
| IF-543 | 4-F-Bnzl | H | 2-OH—Et | 2-Cbx-Et | H | 3.04 | 420 | G |
| IF-544 | i-Bu | H | 2-OH—Et | i-Bu | H | 3.90 | 366 | G |
| IF-545 | i-Pnt | H | 2-OH—Et | 2-Cbx-Et | H | 2.92 | 382 | G |
| IF-546 | Chm | H | 2-OH—Et | i-Bu | H | 4.22 | 392 | G |
| IF-547 | Chm | H | 2-OH—Et | i-Pnt | H | 4.52 | 406 | G |

TABLE 6-18

| | | | | | | | |
|---|---|---|---|---|---|---|---|
| IF-548 | Bnzl | H | Ph—Et | 4-OH-Bnzl | H | 4.50 | 496 | G |
| IF-549 | Bnzl | H | Ph—Et | 2-Cbx-Et | H | 4.05 | 462 | G |
| IF-550 | i-Bu | H | Ph—Et | 4-OH-Bnzl | H | 4.35 | 462 | G |
| IF-551 | i-Bu | H | Ph—Et | 2-Cbx-Et | H | 3.87 | 428 | G |
| IF-552 | 1-Npm | H | Ph—Et | 4-OH-Bnzl | H | 4.78 | 546 | G |
| IF-553 | 1-Npm | H | Ph—Et | 2-Cbx-Et | H | 4.45 | 512 | G |
| IF-554 | 4-OH-Bnzl | H | Ph—Et | 2-Cbx-Et | H | 3.79 | 478 | G |
| IF-555 | 4-OH-Bnzl | H | Ph—Et | i-Pnt | H | 4.75 | 476 | G |
| IF-556 | 2-Cbx-Et | H | Ph—Et | 4-OH-Bnzl | H | 4.10 | 478 | G |
| IF-557 | 2-Cbx-Et | H | Ph—Et | i-Pnt | H | 4.60 | 442 | G |
| IF-558 | 4-F-Bnzl | H | Ph—Et | 4-OH-Bnzl | H | 4.55 | 514 | G |
| IF-559 | 4-F-Bnzl | H | Ph—Et | 2-Cbx-Et | H | 4.17 | 480 | G |
| IF-560 | 2-OH—Et | H | Ph—Et | 4-OH-Bnzl | H | 4.02 | 450 | G |
| IF-561 | 2-OH—Et | H | Ph—Et | 2-Cbx-Et | H | 3.57 | 416 | G |
| IF-562 | i-Pnt | H | Ph—Et | 4-OH-Bnzl | H | 4.53 | 476 | G |
| IF-563 | i-Pnt | H | Ph—Et | 2-Cbx-Et | H | 4.12 | 442 | G |
| IF-564 | Chm | H | Ph—Et | 4-OH-Bnzl | H | 4.65 | 502 | G |
| IF-565 | Chm | H | Ph—Et | 2-Cbx-Et | H | 4.32 | 468 | G |
| IF-566 | Bnzl | H | Hxy | 2-Cbx-Et | H | 4.35 | 442 | G |
| IF-567 | i-Bu | H | Hxy | i-Bu | H | 3.55 | 392 | F |
| IF-568 | i-Bu | H | Hxy | 2-Cbx-Et | H | 4.20 | 408 | G |
| IF-569 | i-Bu | H | Hxy | 2-OH—Et | H | 2.74 | 380 | F |
| IF-570 | i-Bu | H | Hxy | i-Pnt | H | 3.72 | 406 | F |
| IF-571 | 1-Npm | H | Hxy | 2-Cbx-Et | H | 4.70 | 492 | G |
| IF-572 | 4-OH-Bnzl | H | Hxy | 1-Npm | H | 5.20 | 526 | G |
| IF-573 | 4-OH-Bnzl | H | Hxy | 2-Cbx-Et | H | 4.07 | 458 | G |
| IF-574 | 2-Cbx-Et | H | Hxy | i-Bu | H | 4.79 | 408 | G |
| IF-575 | 2-Cbx-Et | H | Hxy | 1-Npm | H | 5.15 | 492 | G |
| IF-576 | 2-Cbx-Et | H | Hxy | 4-OH-Bnzl | H | 4.50 | 458 | G |
| IF-577 | 2-Cbx-Et | H | Hxy | i-Pnt | H | 4.97 | 422 | G |
| IF-578 | 4-F-Bnzl | H | Hxy | 2-Cbx-Et | H | 4.57 | 460 | G |
| IF-579 | 2-OH—Et | H | Hxy | i-Bu | H | 4.68 | 380 | G |
| IF-580 | 2-OH—Et | H | Hxy | 4-OH-Bnzl | H | 4.34 | 430 | G |
| IF-581 | 2-OH—Et | H | Hxy | 2-Cbx-Et | H | 3.90 | 396 | G |
| IF-582 | 2-OH—Et | H | Hxy | i-Pnt | H | 4.92 | 394 | G |
| IF-583 | i-Pnt | H | Hxy | 4-OH-Bnzl | H | 4.85 | 456 | G |
| IF-584 | i-Pnt | H | Hxy | 2-Cbx-Et | H | 4.54 | 422 | G |
| IF-585 | i-Pnt | H | Hxy | 2-OH—Et | H | 2.92 | 394 | F |
| IF-586 | Chm | H | Hxy | i-Bu | H | 4.05 | 432 | F |
| IF-587 | Chm | H | Hxy | 4-OH-Bnzl | H | 4.93 | 482 | G |
| IF-588 | Chm | H | Hxy | 2-Cbx-Et | H | 4.75 | 448 | G |
| IF-589 | Chm | H | Hxy | 2-OH—Et | H | 3.07 | 420 | F |
| IF-590 | Chm | H | Hxy | i-Pnt | H | 4.22 | 446 | F |
| IF-591 | 3-Gun-Pr | H | Bnzl | Ph—Et | H | 4.42 | 489 | G |
| IF-592 | Ph—Et | H | Bnzl | 3-Gun-Pr | H | 4.02 | 489 | G |
| IF-593 | 4-F-Bnzl | H | Bnzl | 3-Gun-Pr | H | 3.70 | 493 | G |
| IF-594 | 2-OH—Et | H | Bnzl | 3-Gun-Pr | H | 3.18 | 429 | G |
| IF-595 | i-Pnt | H | Bnzl | 3-Gun-Pr | H | 3.80 | 455 | G |

TABLE 6-18-continued

| ID | | | | | | | | |
|---|---|---|---|---|---|---|---|---|
| IF-596 | Chm | H | Bnzl | 3-Gun-Pr | H | 3.87 | 481 | G |
| IF-597 | 3-Gun-Pr | H | i-Bu | Ph—Et | H | 4.29 | 455 | G |

TABLE 6-19

| ID | | | | | | | | |
|---|---|---|---|---|---|---|---|---|
| IF-598 | 3-Gun-Pr | H | i-Bu | i-Pnt | H | 4.17 | 421 | G |
| IF-599 | Ph—Et | H | i-Bu | 3-Gun-Pr | H | 3.77 | 455 | G |
| IF-600 | 4-F-Bnzl | H | i-Bu | 3-Gun-Pr | H | 3.57 | 459 | G |
| IF-601 | 2-OH—Et | H | i-Bu | 3-Gun-Pr | H | 2.93 | 395 | G |
| IF-602 | i-Pnt | H | i-Bu | 3-Gun-Pr | H | 3.59 | 421 | G |
| IF-603 | Chm | H | i-Bu | 3-Gun-Pr | H | 3.68 | 447 | G |
| IF-604 | 3-Gun-Pr | H | 1-Npm | i-Pnt | H | 4.79 | 505 | G |
| IF-605 | Ph—Et | H | 1-Npm | 3-Gun-Pr | H | 4.55 | 539 | G |
| IF-606 | 4-F-Bnzl | H | 1-Npm | 3-Gun-Pr | H | 4.43 | 543 | G |
| IF-607 | 2-OH—Et | H | 1-Npm | 3-Gun-Pr | H | 3.77 | 479 | G |
| IF-608 | i-Pnt | H | 1-Npm | 3-Gun-Pr | H | 4.30 | 505 | G |
| IF-609 | Ph—Et | H | i-Pr | 3-Gun-Pr | H | 3.57 | 441 | G |
| IF-610 | 4-F-Bnzl | H | i-Pr | 3-Gun-Pr | H | 3.30 | 445 | G |
| IF-611 | 2-OH—Et | H | i-Pr | 3-Gun-Pr | H | 2.52 | 381 | G |
| IF-612 | i-Pnt | H | i-Pr | 3-Gun-Pr | H | 3.37 | 407 | G |
| IF-613 | Chm | H | i-Pr | 3-Gun-Pr | H | 3.45 | 433 | G |
| IF-614 | 3-Gun-Pr | H | s-Bu | Ph—Et | H | 4.29 | 455 | G |
| IF-615 | Ph—Et | H | s-Bu | 3-Gun-Pr | H | 3.75 | 455 | G |
| IF-616 | 4-F-Bnzl | H | s-Bu | 3-Gun-Pr | H | 3.55 | 459 | G |
| IF-617 | 2-OH—Et | H | s-Bu | 3-Gun-Pr | H | 2.97 | 395 | G |
| IF-618 | i-Pnt | H | s-Bu | 3-Gun-Pr | H | 3.59 | 421 | G |
| IF-619 | Chm | H | s-Bu | 3-Gun-Pr | H | 3.68 | 447 | G |
| IF-620 | 3-Gun-Pr | H | 4-OH-Bnzl | Ph—Et | H | 3.90 | 505 | G |
| IF-621 | Chm | H | 4-OH-Bnzl | 3-Gun-Pr | H | 3.54 | 497 | G |
| IF-622 | i-Bu | H | 3-Gun-Pr | Ph—Et | H | 3.77 | 455 | G |
| IF-623 | i-Bu | H | 3-Gun-Pr | i-Pnt | H | 3.65 | 421 | G |
| IF-624 | 4-OH-Bnzl | H | 3-Gun-Pr | Ph—Et | H | 3.55 | 505 | G |
| IF-625 | 4-OH-Bnzl | H | 3-Gun-Pr | i-Pnt | H | 3.40 | 471 | G |
| IF-626 | Ph—Et | H | 3-Gun-Pr | i-Bu | H | 3.93 | 455 | G |
| IF-627 | Ph—Et | H | 3-Gun-Pr | 1-Npm | H | 4.45 | 539 | G |
| IF-628 | Ph—Et | H | 3-Gun-Pr | 4-OH-Bnzl | H | 3.52 | 505 | G |
| IF-629 | 4-F-Bnzl | H | 3-Gun-Pr | i-Bu | H | 3.84 | 459 | G |
| IF-630 | 4-F-Bnzl | H | 3-Gun-Pr | 1-Npm | H | 4.30 | 543 | G |
| IF-631 | 4-F-Bnzl | H | 3-Gun-Pr | 4-OH-Bnzl | H | 3.32 | 509 | G |
| IF-632 | 4-F-Bnzl | H | 3-Gun-Pr | i-Pnt | H | 4.02 | 473 | G |
| IF-633 | 2-OH—Et | H | 3-Gun-Pr | i-Pnt | H | 3.18 | 409 | G |
| IF-634 | i-Pnt | H | 3-Gun-Pr | Bnzl | H | 3.95 | 455 | G |
| IF-635 | i-Pnt | H | 3-Gun-Pr | i-Bu | H | 3.80 | 421 | G |
| IF-636 | i-Pnt | H | 3-Gun-Pr | 1-Npm | H | 4.39 | 505 | G |
| IF-637 | i-Pnt | H | 3-Gun-Pr | 4-OH-Bnzl | H | 3.25 | 471 | G |
| IF-638 | Chm | H | 3-Gun-Pr | i-Bu | H | 3.98 | 447 | G |
| IF-639 | Chm | H | 3-Gun-Pr | 1-Npm | H | 4.49 | 531 | G |
| IF-640 | Chm | H | 3-Gun-Pr | 4-OH-Bnzl | H | 3.45 | 497 | G |
| IF-641 | Chm | H | 3-Gun-Pr | Ph—Et | H | 4.25 | 495 | G |
| IF-642 | Chm | H | 3-Gun-Pr | i-Pnt | H | 4.17 | 461 | G |
| IF-643 | Bnzl | H | 4-F-Bnzl | 3-Gun-Pr | H | 3.72 | 493 | G |
| IF-644 | i-Bu | H | 4-F-Bnzl | 3-Gun-Pr | H | 3.57 | 459 | G |
| IF-645 | 1-Npm | H | 4-F-Bnzl | 3-Gun-Pr | H | 3.79 | 543 | G |
| IF-646 | 4-OH-Bnzl | H | 4-F-Bnzl | 3-Gun-Pr | H | 3.57 | 509 | G |
| IF-647 | 3-Gun-Pr | H | 4-F-Bnzl | Ph—Et | H | 4.49 | 507 | G |

TABLE 6-20

| ID | | | | | | | | |
|---|---|---|---|---|---|---|---|---|
| IF-648 | 3-Gun-Pr | H | 4-F-Bnzl | i-Pnt | H | 4.39 | 473 | G |
| IF-649 | Ph—Et | H | 4-F-Bnzl | 3-Gun-Pr | H | 4.15 | 507 | G |
| IF-650 | 2-OH—Et | H | 4-F-Bnzl | 3-Gun-Pr | H | 3.30 | 447 | G |
| IF-651 | i-Pnt | H | 4-F-Bnzl | 3-Gun-Pr | H | 3.90 | 473 | G |
| IF-652 | Bnzl | H | i-Pnt | 3-Gun-Pr | H | 3.80 | 455 | G |
| IF-653 | i-Bu | H | i-Pnt | 3-Gun-Pr | H | 3.57 | 421 | G |
| IF-654 | 4-OH-Bnzl | H | i-Pnt | 3-Gun-Pr | H | 3.57 | 471 | G |
| IF-655 | 3-Gun-Pr | H | i-Pnt | 4-OH-Bnzl | H | 4.07 | 471 | G |
| IF-656 | 3-Gun-Pr | H | i-Pnt | Ph—Et | H | 4.54 | 469 | G |
| IF-657 | Ph—Et | H | i-Pnt | 3-Gun-Pr | H | 4.14 | 469 | G |
| IF-658 | 4-F-Bnzl | H | i-Pnt | 3-Gun-Pr | H | 3.90 | 473 | G |
| IF-659 | 2-OH—Et | H | i-Pnt | 3-Gun-Pr | H | 3.27 | 409 | G |
| IF-660 | Chm | H | i-Pnt | 3-Gun-Pr | H | 3.95 | 461 | G |
| IF-661 | 3-Gun-Pr | H | 2-OH—Et | i-Bu | H | 2.85 | 395 | G |
| IF-662 | Bnzl | H | Ph—Et | 3-Gun-Pr | H | 3.88 | 489 | G |
| IF-663 | i-Bu | H | Ph—Et | 3-Gun-Pr | H | 3.77 | 455 | G |

TABLE 6-20-continued

| ID | | | | | | | | |
|---|---|---|---|---|---|---|---|---|
| IF-664 | 4-OH-Bnzl | H | Ph—Et | 3-Gun-Pr | H | 3.74 | 505 | G |
| IF-665 | 3-Gun-Pr | H | Ph—Et | 4-OH-Bnzl | H | 4.07 | 505 | G |
| IF-666 | 3-Gun-Pr | H | Ph—Et | i-Pnt | H | 4.45 | 469 | G |
| IF-667 | 4-F-Bnzl | H | Ph—Et | 3-Gun-Pr | H | 3.92 | 507 | G |
| IF-668 | 2-OH—Et | H | Ph—Et | 3-Gun-Pr | H | 3.47 | 443 | G |
| IF-669 | i-Pnt | H | Ph—Et | 3-Gun-Pr | H | 4.00 | 469 | G |
| IF-670 | Chm | H | Ph—Et | 3-Gun-Pr | H | 4.12 | 495 | G |
| IF-671 | Bnzl | H | Hxy | 3-Gun-Pr | H | 4.17 | 469 | G |
| IF-672 | i-Bu | H | Hxy | 3-Gun-Pr | H | 4.04 | 435 | G |
| IF-673 | 3-Gun-Pr | H | Hxy | Bnzl | H | 4.60 | 469 | G |
| IF-674 | 3-Gun-Pr | H | Hxy | 1-Npm | H | 4.90 | 519 | G |
| IF-675 | 3-Gun-Pr | H | Hxy | 4-OH-Bnzl | H | 4.37 | 485 | G |
| IF-676 | 3-Gun-Pr | H | Hxy | Ph—Et | H | 4.84 | 483 | G |
| IF-677 | 3-Gun-Pr | H | Hxy | i-Pnt | H | 4.75 | 449 | G |
| IF-678 | 2-OH—Et | H | Hxy | 3-Gun-Pr | H | 3.76 | 423 | G |
| IF-679 | i-Pnt | H | Hxy | 3-Gun-Pr | H | 4.24 | 449 | G |
| IF-680 | 2-OtBu—Et | H | i-Bu | 1-Npm | H | 2.89 | 492 | H |
| IF-681 | 2-OtBu—Et | H | i-Bu | 4-tBuO-Bnzl | H | 2.91 | 514 | H |
| IF-682 | 2-OtBu—Et | H | i-Bu | Ph—Et | H | 2.79 | 456 | H |
| IF-683 | 2-OtBu—Et | H | Bnzl | Bnzl | H | 2.76 | 476 | H |
| IF-684 | 2-OtBu—Et | H | Bnzl | i-Bu | H | 2.76 | 442 | H |
| IF-685 | 2-OtBu—Et | H | Bnzl | 4-tBuO-Bnzl | H | 2.94 | 548 | H |
| IF-686 | 2-OtBu—Et | H | 1-Npm | Bnzl | H | 2.95 | 526 | H |
| IF-687 | 2-OtBu—Et | H | 1-Npm | i-Bu | H | 2.94 | 492 | H |
| IF-688 | Bnzl | H | 2-OtBu—Et | i-Bu | H | 2.63 | 476 | H |
| IF-689 | Bnzl | H | 2-OtBu—Et | i-Bu | H | 2.67 | 442 | H |
| IF-690 | Bnzl | H | 2-OtBu—Et | 1-Npm | H | 2.87 | 526 | H |
| IF-691 | Bnzl | H | 2-OtBu—Et | Ph—Et | H | 2.75 | 490 | H |
| IF-692 | Bnzl | H | 2-OtBu—Et | i-Pnt | H | 2.75 | 456 | H |
| IF-693 | i-Bu | H | 2-OtBu—Et | Bnzl | H | 2.63 | 442 | H |
| IF-694 | i-Bu | H | 2-OtBu—Et | 1-Npm | H | 2.81 | 492 | H |
| IF-695 | i-Bu | H | 2-OtBu—Et | Ph—Et | H | 2.69 | 456 | H |
| IF-696 | 1-Npm | H | 2-OtBu—Et | i-Bu | H | 2.83 | 492 | H |
| IF-697 | 1-Npm | H | 2-OtBu—Et | i-Pnt | H | 2.92 | 506 | H |

TABLE 6-21

| ID | | | | | | | | |
|---|---|---|---|---|---|---|---|---|
| IF-698 | 4-tBuO-Bnzl | H | 2-OtBu—Et | i-Bu | H | 2.88 | 514 | H |
| IF-699 | Ph—Et | H | 2-OtBu—Et | Bnzl | H | 2.78 | 490 | H |
| IF-700 | Ph—Et | H | 2-OtBu—Et | i-Bu | H | 2.78 | 456 | H |
| IF-701 | Ph—Et | H | 2-OtBu—Et | 1-Npm | H | 2.92 | 540 | H |
| IF-702 | Ph—Et | H | 2-OtBu—Et | 4-tBuO-Bnzl | H | 2.97 | 562 | H |
| IF-703 | Ph—Et | H | 2-OtBu—Et | i-Pnt | H | 2.84 | 470 | H |
| IF-704 | 4-F-Bnzl | H | 2-OtBu—Et | Bnzl | H | 2.73 | 494 | H |
| IF-705 | 4-F-Bnzl | H | 2-OtBu—Et | i-Bu | H | 2.72 | 460 | H |
| IF-706 | 4-F-Bnzl | H | 2-OtBu—Et | 1-Npm | H | 2.90 | 544 | H |
| IF-707 | 4-F-Bnzl | H | 2-OtBu—Et | 4-tBuO-Bnzl | H | 2.92 | 566 | H |
| IF-708 | 4-F-Bnzl | H | 2-OtBu—Et | Ph—Et | H | 2.78 | 508 | H |
| IF-709 | 4-F-Bnzl | H | 2-OtBu—Et | i-Pnt | H | 2.76 | 474 | H |
| IF-710 | i-Pnt | H | 2-OtBu—Et | Bnzl | H | 2.72 | 456 | H |
| IF-711 | i-Pnt | H | 2-OtBu—Et | 1-Npm | H | 2.88 | 506 | H |
| IF-712 | i-Pnt | H | 2-OtBu—Et | 4-tBuO-Bnzl | H | 2.91 | 528 | H |
| IF-713 | i-Pnt | H | 2-OtBu—Et | Ph—Et | H | 2.78 | 470 | H |
| IF-714 | Chm | H | 2-OtBu—Et | Bnzl | H | 2.79 | 482 | H |
| IF-715 | Chm | H | 2-OtBu—Et | 4-tBuO-Bnzl | H | 3.02 | 554 | H |
| IF-716 | Chm | H | 2-OtBu—Et | Ph—Et | H | 2.88 | 496 | H |
| IF-717 | 4-F-Bnzl | H | i-Pnt | tBOC-E | H | 2.92 | 502 | H |
| IF-718 | Chm | H | i-Pnt | 4-tBuO-Bnzl | H | 3.14 | 524 | H |
| IF-719 | Bnzl | H | Hxy | 4-tBuO-Bnzl | H | 3.15 | 532 | H |
| IF-720 | i-Bu | H | Hxy | 4-tBuO-Bnzl | H | 3.07 | 498 | H |
| IF-721 | 4-tBuO-Bnzl | H | Hxy | Bnzl | H | 3.20 | 532 | H |
| IF-722 | 4-tBuO-Bnzl | H | Hxy | i-Bu | H | 3.25 | 498 | H |

TABLE 6-21-continued

| | | | | | | | | |
|---|---|---|---|---|---|---|---|---|
| IF-723 | 4-tBuO-Bnzl | H | Hxy | Ph—Et | H | 3.26 | 546 | H |
| IF-724 | 4-tBuO-Bnzl | H | Hxy | i-Pnt | H | 3.29 | 512 | H |
| IF-725 | tBOC-E | H | Hxy | Ph—Et | H | 3.11 | 512 | H |
| IF-726 | Ph—Et | H | Hxy | 4-tBuO-Bnzl | H | 3.29 | 546 | H |
| IF-727 | 2-OtBu—Et | H | Hxy | Bnzl | H | 2.96 | 470 | H |
| IF-728 | 2-OH—Et | H | i-Bu | Bnzl | H | 2.37 | 386 | H |
| IF-729 | 2-OH—Et | H | i-Bu | i-Bu | H | 2.30 | 352 | H |
| IF-730 | 2-OH—Et | H | i-Bu | 1-Npm | H | 2.53 | 436 | H |
| IF-731 | 2-OH—Et | H | i-Bu | 4-OH-Bnzl | H | 2.27 | 402 | H |
| IF-732 | 2-OH—Et | H | i-Bu | Ph—Et | H | 2.46 | 400 | H |
| IF-733 | 2-OH—Et | H | i-Bu | i-Pnt | H | 2.41 | 366 | H |
| IF-734 | 2-OH—Et | H | Bnzl | Bnzl | H | 2.43 | 420 | H |
| IF-735 | 2-OH—Et | H | Bnzl | i-Bu | H | 2.39 | 386 | H |
| IF-736 | 2-OH—Et | H | Bnzl | 4-OH-Bnzl | H | 2.30 | 436 | H |
| IF-737 | 2-OH—Et | H | Bnzl | Ph—Et | H | 2.51 | 434 | H |
| IF-738 | 2-OH—Et | H | Bnzl | i-Pnt | H | 2.48 | 400 | H |
| IF-739 | 2-OH—Et | H | 1-Npm | Bnzl | H | 2.60 | 470 | H |
| IF-740 | 2-OH—Et | H | 1-Npm | i-Bu | H | 2.57 | 436 | H |
| IF-741 | Bnzl | H | 2-OH—Et | Bnzl | H | 2.31 | 420 | H |
| IF-742 | Bnzl | H | 2-OH—Et | i-Bu | H | 2.28 | 386 | H |
| IF-743 | Bnzl | H | 2-OH—Et | 1-Npm | H | 2.47 | 470 | H |
| IF-744 | Bnzl | H | 2-OH—Et | Ph—Et | H | 2.41 | 434 | H |
| IF-745 | Bnzl | H | 2-OH—Et | i-Pnt | H | 2.39 | 400 | H |
| IF-746 | i-Bu | H | 2-OH—Et | Bnzl | H | 2.28 | 386 | H |
| IF-747 | i-Bu | H | 2-OH—Et | 1-Npm | H | 2.43 | 436 | H |

TABLE 6-22

| | | | | | | | | |
|---|---|---|---|---|---|---|---|---|
| IF-748 | i-Bu | H | 2-OH—Et | Ph—Et | H | 2.33 | 400 | H |
| IF-749 | 1-Npm | H | 2-OH—Et | i-Bu | H | 2.45 | 436 | H |
| IF-750 | 1-Npm | H | 2-OH—Et | i-Pnt | H | 2.52 | 450 | H |
| IF-751 | 4-OH-Bnzl | H | 2-OH—Et | i-Bu | H | 2.11 | 402 | H |
| IF-752 | Ph—Et | H | 2-OH—Et | Bnzl | H | 2.44 | 434 | H |
| IF-753 | Ph—Et | H | 2-OH—Et | i-Bu | H | 2.39 | 400 | H |
| IF-754 | Ph—Et | H | 2-OH—Et | 1-Npm | H | 2.57 | 484 | H |
| IF-755 | Ph—Et | H | 2-OH—Et | 4-OH-Bnzl | H | 2.22 | 450 | H |
| IF-756 | Ph—Et | H | 2-OH—Et | i-Pnt | H | 2.47 | 414 | H |
| IF-757 | 4-F-Bnzl | H | 2-OH—Et | Bnzl | H | 2.38 | 438 | H |
| IF-758 | 4-F-Bnzl | H | 2-OH—Et | i-Bu | H | 2.34 | 404 | H |
| IF-759 | 4-F-Bnzl | H | 2-OH—Et | 1-Npm | H | 2.53 | 488 | H |
| IF-760 | 4-F-Bnzl | H | 2-OH—Et | 4-OH-Bnzl | H | 2.15 | 454 | H |
| IF-761 | 4-F-Bnzl | H | 2-OH—Et | Ph—Et | H | 2.46 | 452 | H |
| IF-762 | 4-F-Bnzl | H | 2-OH—Et | i-Pnt | H | 2.40 | 418 | H |
| IF-763 | i-Pnt | H | 2-OH—Et | Bnzl | H | 2.38 | 400 | H |
| IF-764 | i-Pnt | H | 2-OH—Et | 1-Npm | H | 2.51 | 450 | H |
| IF-765 | i-Pnt | H | 2-OH—Et | 4-OH-Bnzl | H | 2.15 | 416 | H |
| IF-766 | i-Pnt | H | 2-OH—Et | Ph—Et | H | 2.44 | 414 | H |
| IF-767 | Chm | H | 2-OH—Et | Bnzl | H | 2.44 | 426 | H |
| IF-768 | Chm | H | 2-OH—Et | 4-OH-Bnzl | H | 2.21 | 442 | H |
| IF-769 | Chm | H | 2-OH—Et | Ph—Et | H | 2.52 | 440 | H |
| IF-770 | 4-F-Bnzl | H | i-Pnt | 2-Cbx-Et | H | 2.42 | 446 | H |
| IF-771 | Chm | H | i-Pnt | 4-OH-Bnzl | H | 2.63 | 468 | H |
| IF-772 | Bnzl | H | Hxy | 4-OH-Bnzl | H | 2.67 | 476 | H |
| IF-773 | i-Bu | H | Hxy | 4-OH-Bnzl | H | 2.61 | 442 | H |
| IF-774 | 4-OH-Bnzl | H | Hxy | Bnzl | H | 2.74 | 476 | H |
| IF-775 | 4-OH-Bnzl | H | Hxy | i-Bu | H | 2.71 | 442 | H |
| IF-776 | 4-OH-Bnzl | H | Hxy | Ph—Et | H | 2.78 | 490 | H |
| IF-777 | 4-OH-Bnzl | H | Hxy | i-Pnt | H | 2.76 | 456 | H |
| IF-778 | 2-Cbx-Et | H | Hxy | Ph—Et | H | 2.69 | 456 | H |
| IF-779 | Ph—Et | H | Hxy | 4-OH-Bnzl | H | 2.76 | 490 | H |
| IF-780 | 2-OH—Et | H | Hxy | Bnzl | H | 2.62 | 414 | H |
| IF-781 | 2-OH—Et | H | Hxy | Ph—Et | H | 2.68 | 428 | H |
| IF-782 | 1-tert-butoxy-carbonyl-6-methyl-1H-indol-3-ylmethyl | H | cycloheptylmethyl | i-Bu | H | 1.55 | 605 | B |
| IF-783 | 6-methyl-1H-indol-3-ylmethyl | H | cycloheptylmethyl | i-Bu | H | 1.32 | 505 | B |
| IF-784 | 1-tert-butoxy-carbonyl-6-fluoro-1H-indol-3-ylmethyl | H | cycloheptylmethyl | i-Bu | H | 1.61 | 609 | B |
| IF-785 | 6-fluoro-1H-indol-3-ylmethyl | H | cycloheptylmethyl | i-Bu | H | 1.31 | 509 | B |
| IF-786 | Chm | H | pentyl | 3-Me-Bnzl | H | 1.02 | 466.3 | C |
| IF-787 | 1-Npm | H | β-hydroxyphenethyl | Ph—Et | H | 0.92 | 560 | C |

TABLE 6-23

| | | | | | | | | |
|---|---|---|---|---|---|---|---|---|
| IF-788 | 1-Npm | H | α-hydroxymethyl-phenethyl | Ph—Et | H | 0.94 | 574 | C |
| IF-789 | 1-Npm | H | α-hydroxymethyl-phenethyl | Ph—Et | H | 0.92 | 574 | C |
| IF-790 | 2-trifluoro-methylbenzyl | H | 4-tBuO-Bnzl | i-Bu | H | 1.05 | 572.3 | C |
| IF-791 | 2-trifluoro-methylbenzyl | H | 4-OH-Bnzl | i-Bu | H | 0.85 | 516.3 | C |
| IF-792 | 3-benzyloxybenzyl | H | 4-tBuO-Bnzl | i-Bu | H | 1.14 | 610.4 | C |
| IF-793 | 3-benzyloxybenzyl | H | 4-OH-Bnzl | i-Bu | H | 0.93 | 554.4 | C |
| IF-794 | Chm | H | pentyl | Bnzl | H | 0.97 | 452.3 | C |
| IF-795 | cycloheptylmethyl | H | pentyl | Bnzl | H | 1.01 | 466.3 | C |
| IF-796 | cycloheptylmethyl | H | pentyl | 3-Me-Bnzl | H | 1.05 | 480.4 | C |
| IF-797 | cyclopentylmethyl | H | Bnzl | Chm | H | 0.98 | 464.3 | C |
| IF-798 | 4-Me-Bnzl | H | 4-methoxybutyl | Pr | H | 0.81 | 428.3 | C |
| IF-799 | 4-Cl-Bnzl | H | 4-methoxybutyl | Pr | H | 0.83 | 448.2 | C |
| IF-800 | 3-Gun-Pr | H | 3-Gun-Pr | 3-Gun-Pr | H | 0.39 | 493.3 | C |

TABLE 6-24

Table XXIB

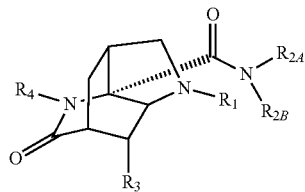

| Compound No. | $R_1$ | $R_{2A}$ | $R_{2B}$ | $R_3$ | $R_4$ | Retention time RT (min) | Mass $(M + H)^+$ | Measurement condition |
|---|---|---|---|---|---|---|---|---|
| IB-51 | i-Bu | H | 1-Npm | Bnzl | H | 0.91 | 482 | C |
| IB-52 | i-Bu | H | i-Pr | Bnzl | H | 0.77 | 384 | C |
| IB-53 | i-Bu | H | 1-Npm | 1-Npm | H | 0.97 | 532 | C |
| IB-54 | i-Bu | H | i-Pr | 1-Npm | H | 0.84 | 434 | C |
| IB-55 | Bnzl | H | i-Bu | 1-Npm | H | 0.93 | 482 | C |
| IB-56 | Bnzl | H | Bnzl | 1-Npm | H | 0.94 | 516 | C |
| IB-57 | Bnzl | H | s-Bu | 1-Npm | H | 0.94 | 482 | C |
| IB-58 | Bnzl | H | 1-Npm | 1-Npm | H | 1.02 | 566 | C |
| IB-59 | Bnzl | H | i-Pr | 1-Npm | H | 0.88 | 468 | C |
| IB-60 | i-Bu | H | i-Bu | 4-OH-Bnzl | H | 0.72 | 414 | C |
| IB-61 | i-Bu | H | Bnzl | 4-OH-Bnzl | H | 0.75 | 448 | C |
| IB-62 | i-Bu | H | 2-Cbx-Et | 4-OH-Bnzl | H | 0.60 | 430 | C |
| IB-63 | i-Bu | H | s-Bu | 4-OH-Bnzl | H | 0.72 | 414 | C |
| IB-64 | i-Bu | H | 1-Npm | 4-OH-Bnzl | H | 0.82 | 498 | C |
| IB-65 | i-Bu | H | i-Pr | 4-OH-Bnzl | H | 0.67 | 400 | C |
| IB-66 | i-Bu | H | 1-Npm | 2-Cbx-Et | H | 0.78 | 464 | C |
| IB-67 | i-Bu | H | i-Pr | 2-Cbx-Et | H | 0.61 | 366 | C |
| IB-68 | Bnzl | H | 4-OH-Bnzl | Bnzl | H | 0.81 | 482 | C |
| IB-69 | Bnzl | H | i-Bu | 4-OH-Bnzl | H | 0.78 | 448 | C |
| IB-70 | Bnzl | H | Bnzl | 4-OH-Bnzl | H | 0.80 | 482 | C |
| IB-71 | Bnzl | H | 2-Cbx-Et | 4-OH-Bnzl | H | 0.66 | 464 | C |
| IB-72 | Bnzl | H | Bnzl | 2-Cbx-Et | H | 0.73 | 448 | C |
| IB-73 | Bnzl | H | 4-OH-Bnzl | 2-Cbx-Et | H | 0.65 | 464 | C |
| IB-74 | Bnzl | H | 1-Npm | 2-Cbx-Et | H | 0.81 | 498 | C |
| IB-75 | Bnzl | H | 4-OH-Bnzl | 1-Npm | H | 0.86 | 532 | C |
| IB-76 | Bnzl | H | 2-Cbx-Et | 1-Npm | H | 0.80 | 498 | C |
| IB-77 | 4-OH-Bnzl | H | i-Bu | Bnzl | H | 0.75 | 448 | C |
| IB-78 | 4-OH-Bnzl | H | Bnzl | Bnzl | H | 0.77 | 482 | C |
| IB-79 | 4-OH-Bnzl | H | 1-Npm | Bnzl | H | 0.83 | 532 | C |
| IB-80 | 4-OH-Bnzl | H | Bnzl | 2-Cbx-Et | H | 0.68 | 464 | C |

TABLE 6-25

| | | | | | | | |
|---|---|---|---|---|---|---|---|
| IB-81 | 4-OH-Bnzl | H | 1-Npm | 2-Cbx-Et | H | 0.75 | 514 C |
| IB-82 | 4-OH-Bnzl | H | i-Bu | 1-Npm | H | 0.79 | 498 C |
| IB-83 | 4-OH-Bnzl | H | Bnzl | 1-Npm | H | 0.81 | 532 C |
| IB-84 | 4-OH-Bnzl | H | 2-Cbx-Et | 1-Npm | H | 0.71 | 514 C |
| IB-85 | 4-OH-Bnzl | H | s-Bu | 1-Npm | H | 0.80 | 498 C |
| IB-86 | 4-OH-Bnzl | H | 1-Npm | 1-Npm | H | 0.87 | 582 C |
| IB-87 | i-Bu | H | s-Bu | Bnzl | H | 0.81 | 398 C |
| IB-88 | i-Bu | H | i-Bu | 1-Npm | H | 0.88 | 448 C |
| IB-89 | i-Bu | H | Bnzl | 1-Npm | H | 0.89 | 482 C |
| IB-90 | Bnzl | H | i-Bu | Bnzl | H | 0.87 | 432 C |

TABLE 6-25-continued

| | | | | | | | | |
|---|---|---|---|---|---|---|---|---|
| IB-91 | Bnzl | H | s-Bu | Bnzl | H | 0.86 | 432 | C |
| IB-92 | Bnzl | H | 1-Npm | Bnzl | H | 0.97 | 516 | C |
| IB-93 | Bnzl | H | i-Pr | Bnzl | H | 0.82 | 418 | C |
| IB-94 | 1-Npm | H | s-Bu | Bnzl | H | 1.05 | 482 | C |
| IB-95 | 1-Npm | H | Bnzl | 1-Npm | H | 1.12 | 566 | C |
| IB-96 | 1-Npm | H | s-Bu | 1-Npm | H | 1.11 | 532 | C |
| IB-97 | i-Bu | H | 4-OH-Bnzl | Bnzl | H | 0.76 | 448 | C |
| IB-98 | i-Bu | H | 2-Cbx-Et | Bnzl | H | 0.71 | 414 | C |
| IB-99 | i-Bu | H | i-Pr | 2-Cbx-Et | H | 0.67 | 380 | C |
| IB-100 | i-Bu | H | Bnzl | 2-Cbx-Et | H | 0.71 | 414 | C |
| IB-101 | i-Bu | H | 4-OH-Bnzl | 2-Cbx-Et | H | 0.62 | 430 | C |
| IB-102 | i-Bu | H | s-Bu | 2-Cbx-Et | H | 0.67 | 380 | C |
| IB-103 | i-Bu | H | 4-OH-Bnzl | 1-Npm | H | 0.82 | 498 | C |
| IB-104 | i-Bu | H | 2-Cbx-Et | 1-Npm | H | 0.77 | 464 | C |
| IB-105 | Bnzl | H | 2-Cbx-Et | Bnzl | H | 0.74 | 448 | C |
| IB-106 | Bnzl | H | s-Bu | 4-OH-Bnzl | H | 0.78 | 448 | C |
| IB-107 | Bnzl | H | 1-Npm | 4-OH-Bnzl | H | 0.88 | 532 | C |
| IB-108 | Bnzl | H | i-Pr | 4-OH-Bnzl | H | 0.74 | 434 | C |
| IB-109 | Bnzl | H | s-Bu | 2-Cbx-Et | H | 0.70 | 414 | C |
| IB-110 | Bnzl | H | i-Pr | 2-Cbx-Et | H | 0.66 | 400 | C |
| IB-111 | 4-OH-Bnzl | H | i-Pr | Bnzl | H | 0.71 | 434 | C |
| IB-112 | 4-OH-Bnzl | H | i-Pr | 2-Cbx-Et | H | 0.60 | 416 | C |
| IB-113 | 4-OH-Bnzl | H | i-Pr | 1-Npm | H | 0.76 | 484 | C |
| IB-114 | 2-Cbx-Et | H | i-Bu | Bnzl | H | 0.68 | 414 | C |
| IB-115 | 2-Cbx-Et | H | Bnzl | Bnzl | H | 0.72 | 448 | C |
| IB-116 | 2-Cbx-Et | H | 4-OH-Bnzl | Bnzl | H | 0.65 | 464 | C |
| IB-117 | 2-Cbx-Et | H | s-Bu | Bnzl | H | 0.67 | 414 | C |
| IB-118 | 2-Cbx-Et | H | 1-Npm | Bnzl | H | 0.78 | 498 | C |
| IB-119 | 2-Cbx-Et | H | i-Bu | 4-OH-Bnzl | H | 0.62 | 430 | C |
| IB-120 | 2-Cbx-Et | H | Bnzl | 4-OH-Bnzl | H | 0.65 | 464 | C |
| IB-121 | 2-Cbx-Et | H | s-Bu | 4-OH-Bnzl | H | 0.61 | 430 | C |
| IB-122 | 2-Cbx-Et | H | 1-Npm | 4-OH-Bnzl | H | 0.74 | 514 | C |
| IB-123 | 2-Cbx-Et | H | i-Pr | 4-OH-Bnzl | H | 0.57 | 416 | C |
| IB-124 | 2-Cbx-Et | H | i-Bu | 1-Npm | H | 0.75 | 464 | C |
| IB-125 | 2-Cbx-Et | H | 4-OH-Bnzl | 1-Npm | H | 0.73 | 514 | C |
| IB-126 | 2-Cbx-Et | H | s-Bu | 1-Npm | H | 0.74 | 464 | C |
| IB-127 | 2-Cbx-Et | H | 1-Npm | 1-Npm | H | 0.84 | 548 | C |
| IB-128 | 1-Npm | H | 4-OH-Bnzl | Bnzl | H | 0.95 | 532 | C |
| IB-129 | 1-Npm | H | Bnzl | 4-OH-Bnzl | H | 0.94 | 532 | C |
| IB-130 | 1-Npm | H | 2-Cbx-Et | 4-OH-Bnzl | H | 0.75 | 514 | C |

TABLE 6-26

| | | | | | | | | |
|---|---|---|---|---|---|---|---|---|
| IB-131 | 1-Npm | H | s-Bu | 4-OH-Bnzl | H | 0.92 | 498 | C |
| IB-132 | 1-Npm | H | 1-Npm | 4-OH-Bnzl | H | 1.01 | 582 | C |
| IB-133 | 1-Npm | H | i-Pr | 4-OH-Bnzl | H | 0.85 | 484 | C |
| IB-134 | 1-Npm | H | i-Bu | 2-Cbx-Et | H | 0.85 | 464 | C |
| IB-135 | 1-Npm | H | Bnzl | 2-Cbx-Et | H | 0.86 | 498 | C |
| IB-136 | 1-Npm | H | 4-OH-Bnzl | 2-Cbx-Et | H | 0.76 | 514 | C |
| IB-137 | 1-Npm | H | s-Bu | 2-Cbx-Et | H | 0.84 | 464 | C |
| IB-138 | 1-Npm | H | 1-Npm | 2-Cbx-Et | H | 0.94 | 548 | C |
| IB-139 | 1-Npm | H | 4-OH-Bnzl | 1-Npm | H | 1.01 | 582 | C |
| IB-140 | 1-Npm | H | 2-Cbx-Et | 1-Npm | H | 0.91 | 548 | C |
| IB-141 | i-Bu | H | i-Bu | i-Bu | H | 0.79 | 364 | C |
| IB-142 | i-Bu | H | s-Bu | i-Bu | H | 0.78 | 364 | C |
| IB-143 | i-Bu | H | 1-Npm | i-Bu | H | 0.89 | 448 | C |
| IB-144 | i-Bu | H | i-Pr | i-Bu | H | 0.74 | 350 | C |
| IB-145 | i-Bu | H | s-Bu | 1-Npm | H | 0.88 | 448 | C |
| IB-146 | Bnzl | H | i-Bu | i-Bu | H | 0.82 | 398 | C |
| IB-147 | Bnzl | H | Bnzl | i-Bu | H | 0.84 | 432 | C |
| IB-148 | Bnzl | H | s-Bu | i-Bu | H | 0.81 | 398 | C |
| IB-149 | Bnzl | H | 1-Npm | i-Bu | H | 0.90 | 482 | C |
| IB-150 | Bnzl | H | i-Pr | i-Bu | H | 0.78 | 384 | C |
| IB-151 | 1-Npm | H | Bnzl | i-Bu | H | 0.98 | 482 | C |
| IB-152 | 1-Npm | H | i-Bu | Bnzl | H | 1.07 | 482 | C |
| IB-153 | 1-Npm | H | i-Bu | 1-Npm | H | 1.13 | 532 | C |
| IB-154 | 1-Npm | H | i-Pr | 1-Npm | H | 1.06 | 518 | C |
| IB-155 | i-Bu | H | 4-OH-Bnzl | i-Bu | H | 0.74 | 414 | C |
| IB-156 | i-Bu | H | 2-Cbx-Et | i-Bu | H | 0.68 | 380 | C |
| IB-157 | i-Bu | H | 3-Gun-Pr | 4-OH-Bnzl | H | 0.56 | 457 | C |
| IB-158 | i-Bu | H | 1-Npm | 3-Gun-Pr | H | 0.73 | 491 | C |
| IB-159 | Bnzl | H | 4-OH-Bnzl | i-Bu | H | 0.77 | 448 | C |
| IB-160 | Bnzl | H | i-Bu | 3-Gun-Pr | H | 0.64 | 441 | C |
| IB-161 | Bnzl | H | 4-OH-Bnzl | 3-Gun-Pr | H | 0.60 | 491 | C |
| IB-162 | 2-Cbx-Et | H | i-Bu | i-Bu | H | 0.65 | 380 | C |
| IB-163 | 2-Cbx-Et | H | Bnzl | i-Bu | H | 0.69 | 414 | C |
| IB-164 | 2-Cbx-Et | H | 4-OH-Bnzl | i-Bu | H | 0.62 | 430 | C |

TABLE 6-26-continued

| | | | | | | | | |
|---|---|---|---|---|---|---|---|---|
| IB-165 | 2-Cbx-Et | H | s-Bu | i-Bu | H | 0.64 | 380 | C |
| IB-166 | 2-Cbx-Et | H | 1-Npm | i-Bu | H | 0.77 | 464 | C |
| IB-167 | 2-Cbx-Et | H | i-Pr | i-Bu | H | 0.61 | 366 | C |
| IB-168 | 2-Cbx-Et | H | Bnzl | 1-Npm | H | 0.78 | 498 | C |
| IB-169 | 2-Cbx-Et | H | i-Pr | 1-Npm | H | 0.72 | 450 | C |
| IB-170 | 1-Npm | H | 3-Gun-Pr | Bnzl | H | 0.79 | 525 | C |
| IB-171 | 1-Npm | H | i-Bu | 4-OH-Bnzl | H | 0.93 | 498 | C |
| IB-172 | 1-Npm | H | i-Pr | 2-Cbx-Et | H | 0.78 | 450 | C |
| IB-173 | 1-Npm | H | 1-Npm | 3-Gun-Pr | H | 0.84 | 575 | C |
| IB-174 | 1-Npm | H | i-Pr | 3-Gun-Pr | H | 0.71 | 477 | C |
| IB-175 | 1-Npm | H | 3-Gun-Pr | 1-Npm | H | 0.83 | 575 | C |
| IB-176 | 1-Npm | H | 1-Npm | i-Bu | H | 1.06 | 532 | C |
| IB-177 | 1-Npm | H | Bnzl | Bnzl | H | 1.08 | 516 | C |
| IB-178 | 1-Npm | H | 1-Npm | Bnzl | H | 1.16 | 566 | C |
| IB-179 | i-Bu | H | 3-Gun-Pr | i-Bu | H | 0.62 | 407 | C |
| IB-180 | i-Bu | H | 3-Gun-Pr | Bnzl | H | 0.65 | 441 | C |

TABLE 6-27

| | | | | | | | | |
|---|---|---|---|---|---|---|---|---|
| IB-181 | i-Bu | H | i-Bu | 3-Gun-Pr | H | 0.61 | 407 | C |
| IB-182 | i-Bu | H | Bnzl | 3-Gun-Pr | H | 0.65 | 441 | C |
| IB-183 | i-Bu | H | 4-OH-Bnzl | 3-Gun-Pr | H | 0.58 | 457 | C |
| IB-184 | i-Bu | H | s-Bu | 3-Gun-Pr | H | 0.61 | 407 | C |
| IB-185 | i-Bu | H | i-Pr | 3-Gun-Pr | H | 0.57 | 393 | C |
| IB-186 | i-Bu | H | 3-Gun-Pr | 1-Npm | H | 0.71 | 491 | C |
| IB-187 | Bnzl | H | 3-Gun-Pr | i-Bu | H | 0.66 | 441 | C |
| IB-188 | Bnzl | H | 3-Gun-Pr | Bnzl | H | 0.69 | 475 | C |
| IB-189 | Bnzl | H | 3-Gun-Pr | 4-OH-Bnzl | H | 0.61 | 491 | C |
| IB-190 | Bnzl | H | i-Bu | 2-Cbx-Et | H | 0.71 | 414 | C |
| IB-191 | Bnzl | H | Bnzl | 3-Gun-Pr | H | 0.67 | 475 | C |
| IB-192 | Bnzl | H | s-Bu | 3-Gun-Pr | H | 0.64 | 441 | C |
| IB-193 | Bnzl | H | i-Pr | 3-Gun-Pr | H | 0.59 | 427 | C |
| IB-194 | Bnzl | H | 3-Gun-Pr | 1-Npm | H | 0.74 | 525 | C |
| IB-195 | 2-Cbx-Et | H | i-Pr | Bnzl | H | 0.64 | 400 | C |
| IB-196 | 3-Gun-Pr | H | 1-Npm | i-Bu | H | 0.67 | 491 | C |
| IB-197 | 3-Gun-Pr | H | i-Pr | i-Bu | H | 0.54 | 393 | C |
| IB-198 | 3-Gun-Pr | H | 1-Npm | Bnzl | H | 0.68 | 525 | C |
| IB-199 | 3-Gun-Pr | H | i-Pr | Bnzl | H | 0.55 | 427 | C |
| IB-200 | 3-Gun-Pr | H | 1-Npm | 4-OH-Bnzl | H | 0.66 | 541 | C |
| IB-201 | 3-Gun-Pr | H | i-Pr | 4-OH-Bnzl | H | 0.52 | 443 | C |
| IB-202 | 3-Gun-Pr | H | 1-Npm | 1-Npm | H | 0.72 | 575 | C |
| IB-203 | 3-Gun-Pr | H | i-Pr | 1-Npm | H | 0.61 | 477 | C |
| IB-204 | 1-Npm | H | 3-Gun-Pr | i-Bu | H | 0.73 | 491 | C |
| IB-205 | i-Bu | H | i-Bu | 4-tBuO-Bnzl | H | 0.88 | 470 | C |
| IB-206 | i-Bu | H | Bnzl | 4-tBuO-Bnzl | H | 0.90 | 504 | C |
| IB-207 | i-Bu | H | tBOC-E | 4-tBuO-Bnzl | H | 0.91 | 542 | C |
| IB-208 | i-Bu | H | s-Bu | 4-tBuO-Bnzl | H | 0.89 | 470 | C |
| IB-209 | i-Bu | H | 1-Npm | 4-tBuO-Bnzl | H | 0.97 | 554 | C |
| IB-210 | i-Bu | H | i-Pr | 4-tBuO-Bnzl | H | 0.85 | 456 | C |
| IB-211 | i-Bu | H | 1-Npm | tBOC-E | H | 0.93 | 520 | C |
| IB-212 | i-Bu | H | i-Pr | tBOC-E | H | 0.79 | 422 | C |
| IB-213 | Bnzl | H | 4-tBuO-Bnzl | Bnzl | H | 0.96 | 538 | C |
| IB-214 | Bnzl | H | i-Bu | 4-tBuO-Bnzl | H | 0.95 | 504 | C |
| IB-215 | Bnzl | H | Bnzl | 4-tBuO-Bnzl | H | 0.97 | 538 | C |
| IB-216 | Bnzl | H | tBOC-E | 4-tBuO-Bnzl | H | 0.97 | 576 | C |
| IB-217 | Bnzl | H | Bnzl | tBOC-E | H | 0.87 | 504 | C |
| IB-218 | Bnzl | H | 4-tBuO-Bnzl | tBOC-E | H | 0.94 | 576 | C |
| IB-219 | Bnzl | H | 1-Npm | tBOC-E | H | 0.94 | 554 | C |
| IB-220 | Bnzl | H | tBOC-E | 1-Npm | H | 0.95 | 554 | C |
| IB-221 | 4-tBuO-Bnzl | H | i-Bu | Bnzl | H | 0.94 | 504 | C |
| IB-222 | 4-tBuO-Bnzl | H | Bnzl | Bnzl | H | 0.95 | 538 | C |
| IB-223 | 4-tBuO-Bnzl | H | 1-Npm | Bnzl | H | 1.03 | 588 | C |
| IB-224 | 4-tBuO-Bnzl | H | Bnzl | tBOC-E | H | 0.94 | 576 | C |

TABLE 6-28

| | | | | | | | | |
|---|---|---|---|---|---|---|---|---|
| IB-225 | 4-tBuO-Bnzl | H | 1-Npm | tBOC-E | H | 1.00 | 626 | C |
| IB-226 | 4-tBuO-Bnzl | H | i-Bu | 1-Npm | H | 0.99 | 554 | C |

TABLE 6-28-continued

| | | | | | | | |
|---|---|---|---|---|---|---|---|
| IB-227 | 4-tBuO-Bnzl | H | Bnzl | 1-Npm | H | 1.00 | 588 C |
| IB-228 | 4-tBuO-Bnzl | H | tBOC-E | 1-Npm | H | 1.01 | 626 C |
| IB-229 | 4-tBuO-Bnzl | H | s-Bu | 1-Npm | H | 1.00 | 554 C |
| IB-230 | 4-tBuO-Bnzl | H | 1-Npm | 1-Npm | H | 1.07 | 638 C |
| IB-231 | i-Bu | H | 4-tBuO-Bnzl | Bnzl | H | 0.91 | 504 C |
| IB-232 | i-Bu | H | tBOC-E | Bnzl | H | 0.85 | 470 C |
| IB-233 | i-Bu | H | i-Bu | tBOC-E | H | 0.83 | 436 C |
| IB-234 | i-Bu | H | Bnzl | tBOC-E | H | 0.85 | 470 C |
| IB-235 | i-Bu | H | 4-tBuO-Bnzl | tBOC-E | H | 0.93 | 542 C |
| IB-236 | i-Bu | H | s-Bu | tBOC-E | H | 0.83 | 436 C |
| IB-237 | i-Bu | H | 4-tBuO-Bnzl | 1-Npm | H | 0.96 | 554 C |
| IB-238 | i-Bu | H | tBOC-E | 1-Npm | H | 0.90 | 520 C |
| IB-239 | Bnzl | H | tBOC-E | Bnzl | H | 0.90 | 504 C |
| IB-240 | Bnzl | H | s-Bu | 4-tBuO-Bnzl | H | 0.94 | 504 C |
| IB-241 | Bnzl | H | 1-Npm | 4-tBuO-Bnzl | H | 1.05 | 588 C |
| IB-242 | Bnzl | H | i-Pr | 4-tBuO-Bnzl | H | 0.91 | 490 C |
| IB-243 | Bnzl | H | s-Bu | tBOC-E | H | 0.85 | 470 C |
| IB-244 | Bnzl | H | i-Pr | tBOC-E | H | 0.81 | 456 C |
| IB-245 | 4-tBuO-Bnzl | H | i-Pr | Bnzl | H | 0.90 | 490 C |
| IB-246 | 4-tBuO-Bnzl | H | i-Pr | tBOC-E | H | 0.90 | 528 C |
| IB-247 | 4-tBuO-Bnzl | H | i-Pr | 1-Npm | H | 0.95 | 540 C |
| IB-248 | tBOC-E | H | i-Bu | Bnzl | H | 0.88 | 470 C |
| IB-249 | tBOC-E | H | Bnzl | Bnzl | H | 0.90 | 504 C |
| IB-250 | tBOC-E | H | 4-tBuO-Bnzl | Bnzl | H | 0.97 | 576 C |
| IB-251 | tBOC-E | H | s-Bu | Bnzl | H | 0.86 | 470 C |
| IB-252 | tBOC-E | H | 1-Npm | Bnzl | H | 0.96 | 554 C |
| IB-253 | tBOC-E | H | i-Bu | 4-tBuO-Bnzl | H | 0.95 | 542 C |
| IB-254 | tBOC-E | H | Bnzl | 4-tBuO-Bnzl | H | 0.97 | 576 C |
| IB-255 | tBOC-E | H | s-Bu | 4-tBuO-Bnzl | H | 0.94 | 542 C |
| IB-256 | tBOC-E | H | 1-Npm | 4-tBuO-Bnzl | H | 1.03 | 626 C |
| IB-257 | tBOC-E | H | i-Pr | 4-tBuO-Bnzl | H | 0.91 | 528 C |
| IB-258 | tBOC-E | H | i-Bu | 1-Npm | H | 0.93 | 520 C |
| IB-259 | tBOC-E | H | 4-tBuO-Bnzl | 1-Npm | H | 1.02 | 626 C |
| IB-260 | tBOC-E | H | s-Bu | 1-Npm | H | 0.91 | 520 C |
| IB-261 | tBOC-E | H | 1-Npm | 1-Npm | H | 1.02 | 604 C |

TABLE 6-29

| | | | | | | | |
|---|---|---|---|---|---|---|---|
| IB-262 | 1-Npm | H | 4-tBuO-Bnzl | Bnzl | H | 1.13 | 588 C |
| IB-263 | 1-Npm | H | Bnzl | 4-tBuO-Bnzl | H | 1.13 | 588 C |
| IB-264 | 1-Npm | H | tBOC-E | 4-tBuO-Bnzl | H | 1.12 | 626 C |
| IB-265 | 1-Npm | H | s-Bu | 4-tBuO-Bnzl | H | 1.12 | 554 C |
| IB-266 | 1-Npm | H | 1-Npm | 4-tBuO-Bnzl | H | 1.22 | 638 C |
| IB-267 | 1-Npm | H | i-Pr | 4-tBuO-Bnzl | H | 1.05 | 540 C |
| IB-268 | 1-Npm | H | i-Bu | tBOC-E | H | 1.02 | 520 C |
| IB-269 | 1-Npm | H | Bnzl | tBOC-E | H | 1.03 | 554 C |
| IB-270 | 1-Npm | H | 4-tBuO-Bnzl | tBOC-E | H | 1.10 | 626 C |
| IB-271 | 1-Npm | H | s-Bu | tBOC-E | H | 0.98 | 520 C |
| IB-272 | 1-Npm | H | 1-Npm | tBOC-E | H | 1.10 | 604 C |
| IB-273 | 1-Npm | H | 4-tBuO-Bnzl | 1-Npm | H | 1.19 | 638 C |
| IB-274 | 1-Npm | H | tBOC-E | 1-Npm | H | 1.10 | 604 C |
| IB-275 | i-Bu | H | 4-tBuO-Bnzl | i-Bu | H | 0.89 | 470 C |
| IB-276 | i-Bu | H | tBOC-E | i-Bu | H | 0.83 | 436 C |
| IB-277 | i-Bu | H | 1-Npm | (tBOC)Gun-Pr | H | 0.97 | 691 C |
| IB-278 | Bnzl | H | 4-tBuO-Bnzl | i-Bu | H | 0.91 | 504 C |
| IB-279 | Bnzl | H | i-Bu | (tBOC)Gun-Pr | H | 0.93 | 641 C |
| IB-280 | tBOC-E | H | i-Bu | i-Bu | H | 0.87 | 436 C |
| IB-281 | tBOC-E | H | Bnzl | i-Bu | H | 0.89 | 470 C |
| IB-282 | tBOC-E | H | 4-tBuO-Bnzl | i-Bu | H | 0.96 | 542 C |
| IB-283 | tBOC-E | H | s-Bu | i-Bu | H | 0.85 | 436 C |
| IB-284 | tBOC-E | H | 1-Npm | i-Bu | H | 0.95 | 520 C |
| IB-285 | tBOC-E | H | i-Pr | i-Bu | H | 0.82 | 422 C |
| IB-286 | tBOC-E | H | Bnzl | 1-Npm | H | 0.97 | 554 C |
| IB-287 | tBOC-E | H | i-Pr | 1-Npm | H | 0.90 | 506 C |
| IB-288 | 1-Npm | H | (tBOC)Gun-Pr | Bnzl | H | 1.06 | 725 C |
| IB-289 | 1-Npm | H | i-Bu | 4-tBuO-Bnzl | H | 1.15 | 554 C |
| IB-290 | 1-Npm | H | i-Pr | tBOC-E | H | 0.96 | 506 C |
| IB-291 | 1-Npm | H | 1-Npm | (tBOC)Gun-Pr | H | 1.08 | 775 C |
| IB-292 | 1-Npm | H | i-Pr | (tBOC)Gun-Pr | H | 0.97 | 677 C |
| IB-293 | 1-Npm | H | (tBOC)Gun-Pr | 1-Npm | H | 1.11 | 775 C |
| IB-294 | i-Bu | H | (tBOC)Gun-Pr | i-Bu | H | 0.90 | 607 C |
| IB-295 | i-Bu | H | (tBOC)Gun-Pr | Bnzl | H | 0.91 | 641 C |
| IB-296 | i-Bu | H | i-Bu | (tBOC)Gun-Pr | H | 0.89 | 607 C |

TABLE 6-30

| | | | | | | | |
|---|---|---|---|---|---|---|---|
| IB-297 | i-Bu | H | Bnzl | (tBOC)Gun-Pr | H | 0.90 | 641 C |
| IB-298 | i-Bu | H | s-Bu | (tBOC)Gun-Pr | H | 0.89 | 607 C |
| IB-299 | i-Bu | H | i-Pr | (tBOC)Gun-Pr | H | 0.86 | 593 C |
| IB-300 | i-Bu | H | (tBOC)Gun-Pr | 1-Npm | H | 0.96 | 691 C |
| IB-301 | Bnzl | H | (tBOC)Gun-Pr | i-Bu | H | 0.91 | 641 C |
| IB-302 | Bnzl | H | (tBOC)Gun-Pr | Bnzl | H | 0.94 | 675 C |
| IB-303 | Bnzl | H | i-Bu | tBOC-E | H | 1.06 | 725 C |
| IB-304 | Bnzl | H | Bnzl | (tBOC)Gun-Pr | H | 0.93 | 675 C |
| IB-305 | Bnzl | H | s-Bu | (tBOC)Gun-Pr | H | 0.92 | 641 C |
| IB-306 | Bnzl | H | i-Pr | (tBOC)Gun-Pr | H | 0.88 | 627 C |
| IB-307 | Bnzl | H | (tBOC)Gun-Pr | 1-Npm | H | 0.98 | 725 C |
| IB-308 | tBOC-E | H | i-Pr | Bnzl | H | 0.85 | 456 C |
| IB-309 | (tBOC)Gun-Pr | H | 1-Npm | i-Bu | H | 1.03 | 691 C |
| IB-310 | (tBOC)Gun-Pr | H | i-Pr | i-Bu | H | 0.95 | 593 C |
| IB-311 | (tBOC)Gun-Pr | H | 1-Npm | Bnzl | H | 1.04 | 725 C |
| IB-312 | (tBOC)Gun-Pr | H | i-Pr | Bnzl | H | 0.96 | 627 C |
| IB-313 | (tBOC)Gun-Pr | H | 1-Npm | 1-Npm | H | 1.07 | 775 C |
| IB-314 | (tBOC)Gun-Pr | H | i-Pr | 1-Npm | H | 1.00 | 677 C |
| IB-315 | 1-Npm | H | (tBOC)Gun-Pr | i-Bu | H | 1.00 | 691 C |
| IB-316 | Pr | H | Chm | Bnzl | H | 0.88 | 424.3 C |
| IB-317 | tBuO-E | H | 4-fluorophenethyl | 1-Npm | H | 0.99 | 558.3 C |
| IB-318 | Hdr-E | H | 4-fluorophenethyl | 1-Npm | H | 0.83 | 502.3 C |
| IB-319 | 1-Npm | H | heptyl | Ph—Et | H | 1.16 | 538.5 C |
| IB-320 | 1-Npm | H | pentyl | Ph—Et | H | 1.08 | 510.4 C |
| IB-321 | 1-Npm | H | cyclohexyl | Ph—Et | H | 1.06 | 522.4 C |
| IB-322 | 1-Npm | H | cyclopentyl | Ph—Et | H | 1.02 | 508.3 C |
| IB-323 | 1-Npm | H | pyrrolidine † | Ph—Et | H | 0.88 | 494.3 C |
| IB-324 | 1-Npm | H | Hxy | 4-methylphenethyl | H | 1.15 | 538.4 C |

TABLE 6-31

| | | | | | | | | |
|---|---|---|---|---|---|---|---|---|
| IB-325 | 1-Npm | H | Hxy | cyclohexylethyl | H | 1.18 | 530.4 | C |
| IB-326 | tBuO-E | H | 4-Cl-Bnzl | 1-Npm | H | 1 | 560.3 | C |
| IB-327 | 3-tert-butoxypropyl | H | 4-F-Bnzl | 1-Npm | H | 0.96 | 558.4 | C |
| IB-328 | Hdr-E | H | 4-Cl-Bnzl | 1-Npm | H | 0.87 | 504.2 | C |
| IB-329 | 3-hydroxypropyl | H | 4-F-Bnzl | 1-Npm | H | 0.83 | 502.3 | C |
| IB-330 | 3-(tert-butoxycarbonylamino)propyl | H | 3-(tert-butoxy-carbonyl-amino)propyl | 3-(tert-butoxy-carbonylamino) propyl | H | 0.99 | 767.6 | C |
| IB-331 | Pr | H | Bnzl | Chm | H | 0.88 | 424.3 | C |
| IB-332 | Pr | H | 2-methylbenzyl | Bnzl | H | 0.85 | 432.3 | C |
| IB-333 | Pr | H | (1,2,3,4-tetra-hydronaph-thalen-1-yl) methyl | Bnzl | H | 0.92 | 472.3 | C |
| IB-334 | Pr | H | Cpm | Bnzl | H | 0.85 | 410.3 | C |
| IB-335 | 1-Npm | H | Hxy | 3-methylphenethyl | H | 1.15 | 538.4 | C |
| IB-336 | Pr | H | Bnzl | Cpm | H | 0.84 | 410.3 | C |
| IB-337 | 1-Npm | H | Hxy | naphthalen-2-yl ethyl | H | 1.17 | 574.4 | C |
| IB-338 | 1-Npm | H | Hxy | 4-isopropylphen-ethyl | H | 1.22 | 566.4 | C |
| IB-339 | 1-Npm | H | β-hydroxy-phenethyl | Ph—Et | H | 0.98 | 560.3 | C |
| IB-340 | 1-Npm | H | α-hydroxy-methylphenethyl | Ph—Et | H | 0.94 | 574.3 | C |
| IB-341 | 1-Npm | H | α-hydroxymethyl-phenethyl | Ph—Et | H | 1.03 | 574.3 | C |
| IB-342 | Cpm | H | 4-tBuO-Bnzl | tBOC-E | H | 1.02 | 568 | C |
| IB-343 | Cpm | H | 4-OH-Bnzl | 2-Cbx-Et | H | 0.71 | 456 | C |
| IB-344 | 4-Nt-Bnzl | H | 4-tBuO-Bnzl | tBOC-E | H | 1.08 | 621 | C |
| IB-345 | 4-Nt-Bnzl | H | Bnzl | Bnzl | H | 1.01 | 511 | C |
| IB-346 | H | H | Bnzl | Bnzl | H | 0.72 | 376 | C |
| IB-347 | 4-Nt-Bnzl | H | Hxy | Ph—Et | H | 1.04 | 519 | C |
| IB-348 | Cpm | H | Bnzl | Bnzl | H | 0.9 | 458 | C |
| IB-349 | cyclohexyl | H | Bnzl | Bnzl | H | 0.88 | 458 | C |
| IB-350 | H | H | Hxy | Ph—Et | H | 0.82 | 384 | C |
| IB-351 | isopropyl | H | Bnzl | Bnzl | H | 0.8 | 418 | C |
| IB-352 | s-Bu | H | Bnzl | Bnzl | H | 0.83 | 432 | C |
| IB-353 | 3-MeO-Bnzl | H | Hxy | Ph—Et | H | 0.98 | 504 | C |

TABLE 6-32

| | | | | | | | | |
|---|---|---|---|---|---|---|---|---|
| IB-354 | 2,3-dimethylbenzyl | H | Hxy | Ph—Et | H | 1.05 | 502 | C |
| IB-355 | 5,6,7,8-tetrahydro-naphthalen-1-yl methyl | H | Hxy | Ph—Et | H | 1.09 | 528 | C |
| IB-356 | Pr | H | Bnzl | Bnzl | H | 0.82 | 418 | C |
| IB-357 | 1-Npm | H | Bnzl | isobutyl | Me | 0.98 | 496 | C |
| IB-358 | 4-Nt-Bnzl | H | Bnzl | tBOC-E | Me | 0.98 | 563 | C |
| IB-359 | H | H | Bnzl | tBOC-E | Me | 0.79 | 428 | C |
| IB-360 | phenylacetyl | H | Bnzl | tBOC-E | Me | 1.08 | 546 | C |
| IB-361 | phenylacetyl | H | Bnzl | 2-Cbx-Et | Me | 0.9 | 490 | C |
| IB-362 | 4-aminobenzyl | H | Bnzl | tBOC-E | Me | 0.82 | 533 | C |
| IB-363 | benzoyl | H | Bnzl | Bnzl | H | 0.99 | 480 | C |
| IB-364 | phenylacetyl | H | Bnzl | Bnzl | H | 0.99 1.02 | 494 | C |
| IB-365 | phenoxycarbonyl | H | Bnzl | Bnzl | H | 1.06 | 496 | C |
| IB-366 | isovaleryl | H | Bnzl | tBOC-E | Me | 1.07 | 512 | C |
| IB-367 | isopropyloxycarbonyl | H | Bnzl | tBOC-E | Me | 1.07 | 514 | C |
| IB-368 | Ph—Et | H | Bnzl | i-Bu | H | 0.9 | 446.5 | C |
| IB-369 | i-Bu | H | Bnzl | Ph—Et | H | 0.92 | 446.4 | C |
| IB-370 | Bnzl | H | i-Bu | Ph—Et | H | 0.92 | 446.4 | C |
| IB-371 | 4-F-Bnzl | H | i-Bu | Bnzl | H | 0.94 | 450.3 | C |
| IB-372 | i-Bu | H | 4-F-Bnzl | Bnzl | H | 0.9 | 450.3 | C |
| IB-373 | i-Bu | H | i-Pnt | Bnzl | H | 0.9 | 412.4 | C |
| IB-374 | Bnzl | H | i-Pnt | i-Bu | H | 0.9 | 412.4 | C |
| IB-375 | i-Bu | H | Hxy | Bnzl | H | 0.95 | 426.4 | C |
| IB-376 | 4-F-Bnzl | H | Bnzl | Bnzl | H | 0.95 | 484.3 | C |
| IB-377 | Ph—Et | H | Bnzl | Bnzl | H | 0.92 | 480.3 | C |
| IB-378 | 2-OtBu—Et | H | 4-F-Bnzl | 1-Npm | H | 0.99 | 544.3 | C |
| IB-379 | 2-OH—Et | H | 4-F-Bnzl | 1-Npm | H | 0.82 | 488.2 | C |
| IB-380 | i-Bu | H | Bnzl | Bnzl | H | 0.88 | 432.2 | C |
| IB-381 | Bnzl | H | Bnzl | Bnzl | H | 0.93 | 466.2 | C |
| IB-382 | i-Bu | H | Bnzl | i-Bu | H | 0.85 | 398.2 | C |
| IB-383 | i-Bu | H | i-Bu | Bnzl | H | 0.85 | 398.2 | C |
| IB-384 | Chm | H | Bnzl | Bnzl | H | 0.96 | 472.3 | C |

TABLE 6-32-continued

| | | | | | | | |
|---|---|---|---|---|---|---|---|
| IB-385 | 1-Npm | H | 4-F-Bnzl | 2-OTBS-Et | H | 1.26 | 602.3 C |
| IB-386 | 1-Npm | H | 4-F-Bnzl | 2—OH—Et | H | 0.89 | 488.2 C |
| IB-387 | i-Pnt | H | Bnzl | Bnzl | H | 0.89 | 446.3 C |
| IB-388 | Chm | H | 2-OtBu-Et | 1-Npm | H | 1 | 532.4 C |
| IB-389 | Chm | H | 2-OH—Et | 1-Npm | H | 0.86 | 476.3 C |
| IB-390 | 2—OtBu—Et | H | Bnzl | 1-Npm | H | 0.98 | 526.3 C |
| IB-391 | 2—OH—Et | H | Bnzl | 1-Npm | H | 0.8 | 470.2 C |
| IB-392 | tBOC-E | H | Bnzl | Ph—Et | H | 0.96 | 518.3 C |
| IB-393 | 2-Cbx-Et | H | Bnzl | Ph—Et | H | 0.78 | 462.2 C |

TABLE 6-33

| | | | | | | | |
|---|---|---|---|---|---|---|---|
| IB-394 | i-Pnt | H | Bnzl | Ph—Et | H | 0.91 | 460.3 C |
| IB-395 | Bnzl | H | i-Bu | i-Pnt | H | 0.89 | 412.3 C |
| IB-396 | 4-F-Bnzl | H | Bnzl | i-Bu | H | 0.88 | 450.2 C |
| IB-397 | 2-OtBu-Et | H | Ph—Et | 1-Npm | H | 0.98 | 540.4 C |
| IB-398 | 4-tBuO-Bnzl | H | Bnzl | Ph—Et | H | 0.98 | 552.4 C |
| IB-399 | Ph—Et | H | Hxy | 1-Npm | H | 1.03 | 524.4 C |
| IB-400 | 4-OH-Bnzl | H | Bnzl | Ph—Et | H | 0.81 | 496.3 C |
| IB-401 | 2—OH—Et | H | Ph—Et | 1-Npm | H | 0.82 | 484.3 C |
| IB-402 | (tBOC)Gun-Pr | H | (tBOC)Gun-Pr | (tBOC)Gun-Pr | H | 1.13 | 1093.3 C |
| IB-403 | 4-tBuO-Bnzl | H | Bnzl | i-Bu | H | 0.97 | 504.4 C |
| IB-404 | 4-OH-Bnzl | H | Bnzl | i-Bu | H | 0.79 | 448.3 C |
| IB-405 | i-Bu | H | Ph—Et | Bnzl | H | 0.89 | 446.4 C |
| IB-406 | Ph—Et | H | i-Bu | Bnzl | H | 0.90 | 446.4 C |
| IB-407 | Bnzl | H | Ph—Et | i-Bu | H | 0.91 | 446.4 C |
| IB-408 | i-Pnt | H | i-Bu | Bnzl | H | 0.90 | 412.4 C |
| IB-409 | Chm | H | i-Bu | Bnzl | H | 0.96 | 438.4 C |
| IB-410 | Bnzl | H | 4-F-Bnzl | i-Bu | H | 0.90 | 450.3 C |
| IB-411 | i-Pnt | H | Bnzl | i-Bu | H | 0.89 | 412.4 C |
| IB-412 | Chm | H | Bnzl | i-Bu | H | 0.94 | 438.4 C |
| IB-413 | i-Bu | H | Bnzl | i-Pnt | H | 0.90 | 412.4 C |
| IB-414 | Bnzl | H | Hxy | i-Bu | H | 0.95 | 426.4 C |
| IB-415 | Ph—Et | H | i-Bu | i-Bu | H | 0.89 | 412.4 C |
| IB-416 | Ph—Et | H | i-Bu | 1-Npm | H | 0.97 | 496.3 C |
| IB-417 | Ph—Et | H | i-Bu | 4-tBuO-Bnzl | H | 0.98 | 518.4 C |
| IB-418 | Ph—Et | H | i-Bu | 2-OTBS-Et | H | 1.06 | 514.4 C |
| IB-419 | Ph—Et | H | i-Bu | i-Pnt | H | 0.93 | 426.3 C |
| IB-420 | Ph—Et | H | i-Bu | 4-OH-Bnzl | H | 0.82 | 462.3 C |
| IB-421 | Ph—Et | H | i-Bu | 4-OH—Et | H | 0.76 | 400.2 C |
| IB-422 | Ph—Et | H | 1-Npm | Hxy | H | 1.03 | 524.4 C |
| IB-423 | 1-Npm | H | Ph—Et | Hxy | H | 1.11 | 524.4 C |
| IB-424 | Hxy | H | Ph—Et | 1-Npm | H | 1.00 | 524.4 C |
| IB-425 | Hxy | H | 1-Npm | Ph—Et | H | 1.01 | 524.4 C |

† Ring formed together by R2A and R2B

TABLE 6-34

| Compound No. | $R_1$ | $R_{2A}$ | $R_{2B}$ | $R_3$ | $R_4$ | Retention time RT (min) | Mass $(M + H)^+$ | Measurement condition |
|---|---|---|---|---|---|---|---|---|
| IB-426 | 2-OtBu-Et | H | Bnzl | tBOC-E | H | 3.63 | 514 | F |
| IB-427 | Ph-Et | H | i-Bu | tBOC-E | H | 3.62 | 484 | F |
| IB-428 | 2-OtBu-Et | H | i-Pr | Bnzl | H | 3.20 | 428 | F |
| IB-429 | 2-OtBu-Et | H | i-Pr | i-Bu | H | 3.04 | 394 | F |
| IB-430 | 2-OtBu-Et | H | i-Pr | 1-Npm | H | 3.60 | 478 | F |
| IB-431 | 2-OtBu-Et | H | i-Pr | Ph-Et | H | 3.32 | 442 | F |
| IB-432 | Ph-Et | H | 4-tBuO-Bnzl | tBOC-E | H | 4.14 | 590 | F |
| IB-433 | 2-OtBu-Et | H | i-Pnt | i-Bu | H | 3.45 | 422 | F |
| IB-434 | i-Bu | H | 2-OtBu-Et | i-Bu | H | 2.95 | 408 | F |

TABLE 6-35

| | | | | | | | | |
|---|---|---|---|---|---|---|---|---|
| IB-435 | i-Bu | H | 2-OtBu-Et | i-Pnt | H | 3.25 | 422 | F |
| IB-436 | i-Pnt | H | 2-OtBu-Et | i-Bu | H | 3.24 | 422 | F |
| IB-437 | Chm | H | 2-OtBu-Et | i-Bu | H | 3.42 | 448 | F |
| IB-438 | Chm | H | 2-OtBu-Et | i-Pnt | H | 3.75 | 462 | F |
| IB-439 | Ph-Et | H | Hxy | tBOC-E | H | 4.09 | 512 | F |
| IB-440 | 2-OtBu-Et | H | Hxy | i-Bu | H | 3.80 | 436 | F |
| IB-441 | 2-OtBu-Et | H | Hxy | i-Pnt | H | 3.99 | 450 | F |
| IB-442 | 2-Cbx-Et | H | Bnzl | i-Pnt | H | 4.17 | 428 | G |
| IB-443 | Ph-Et | H | Bnzl | 2-Cbx-Et | H | 4.47 | 462 | G |
| IB-444 | 4-F-Bnzl | H | Bnzl | 2-Cbx-Et | H | 4.30 | 466 | G |

TABLE 6-35-continued

| | | | | | | | | |
|---|---|---|---|---|---|---|---|---|
| IB-445 | i-Pnt | H | Bnzl | 2-Cbx-Et | H | 4.24 | 428 | G |
| IB-446 | i-Pnt | H | Bnzl | 2-OH-Et | H | 2.70 | 400 | F |
| IB-447 | Chm | H | Bnzl | 2-Cbx-Et | H | 4.47 | 454 | G |
| IB-448 | Chm | H | Bnzl | 2-OH-Et | H | 2.88 | 426 | F |
| IB-449 | 2-Cbx-Et | H | i-Bu | Ph-Et | H | 4.05 | 428 | G |
| IB-450 | 2-Cbx-Et | H | i-Bu | i-Pnt | H | 3.90 | 394 | G |
| IB-451 | 4-F-Bnzl | H | i-Bu | 2-Cbx-Et | H | 4.03 | 432 | G |
| IB-452 | i-Pnt | H | i-Bu | 4-OH-Bnzl | H | 4.22 | 428 | G |
| IB-453 | i-Pnt | H | i-Bu | 2-Cbx-Et | H | 4.00 | 394 | G |
| IB-454 | Chm | H | i-Bu | 4-OH-Bnzl | H | 4.57 | 454 | G |
| IB-455 | Chm | H | i-Bu | 2-Cbx-Et | H | 4.27 | 420 | G |
| IB-456 | 2-Cbx-Et | H | 1-Npm | Ph-Et | H | 4.77 | 512 | G |
| IB-457 | 2-Cbx-Et | H | 1-Npm | 2-OH-Et | H | 3.93 | 452 | G |
| IB-458 | 2-Cbx-Et | H | 1-Npm | i-Pnt | H | 4.67 | 478 | G |
| IB-459 | Ph-Et | H | 1-Npm | 2-Cbx-Et | H | 4.93 | 512 | G |
| IB-460 | 4-F-Bnzl | H | 1-Npm | 2-Cbx-Et | H | 4.84 | 516 | G |
| IB-461 | 2-OH-Et | H | 1-Npm | 2-Cbx-Et | H | 3.97 | 452 | G |
| IB-462 | i-Pnt | H | 1-Npm | 2-Cbx-Et | H | 4.75 | 478 | G |
| IB-463 | Chm | H | 1-Npm | 2-Cbx-Et | H | 4.97 | 504 | G |
| IB-464 | i-Bu | H | i-Pr | 2-OH-Et | H | 1.00 | 338 | F |
| IB-465 | 4-OH-Bnzl | H | i-Pr | Ph-Et | H | 4.20 | 448 | G |
| IB-466 | 4-OH-Bnzl | H | i-Pr | 2-OH-Et | H | 3.35 | 388 | G |
| IB-467 | 4-OH-Bnzl | H | i-Pr | i-Pnt | H | 4.07 | 414 | G |
| IB-468 | 2-Cbx-Et | H | i-Pr | Ph-Et | H | 3.79 | 414 | G |
| IB-469 | 2-Cbx-Et | H | i-Pr | i-Pnt | H | 3.62 | 380 | G |
| IB-470 | Ph-Et | H | i-Pr | 2-Cbx-Et | H | 3.95 | 414 | G |
| IB-471 | Ph-Et | H | i-Pr | 2-OH-Et | H | 2.54 | 386 | F |
| IB-472 | 4-F-Bnzl | H | i-Pr | 2-Cbx-Et | H | 3.77 | 418 | G |
| IB-473 | 4-F-Bnzl | H | i-Pr | 2-OH-Et | H | 2.45 | 390 | F |
| IB-474 | 2-OH-Et | H | i-Pr | Bnzl | H | 3.54 | 372 | G |
| IB-475 | 2-OH-Et | H | i-Pr | i-Bu | H | 3.20 | 338 | G |
| IB-476 | 2-OH-Et | H | i-Pr | 1-Npm | H | 4.18 | 422 | G |
| IB-477 | 2-OH-Et | H | i-Pr | 4-OH-Bnzl | H | 3.02 | 388 | G |
| IB-478 | 2-OH-Et | H | i-Pr | Ph-Et | H | 3.80 | 386 | G |
| IB-479 | i-Pnt | H | i-Pr | i-Bu | H | 2.92 | 364 | F |
| IB-480 | i-Pnt | H | i-Pr | 4-OH-Bnzl | H | 3.95 | 414 | G |
| IB-481 | i-Pnt | H | i-Pr | 2-Cbx-Et | H | 3.70 | 380 | G |
| IB-482 | i-Pnt | H | i-Pr | 2-OH-Et | H | 2.34 | 352 | F |
| IB-483 | Chm | H | i-Pr | i-Bu | H | 3.13 | 390 | F |
| IB-484 | Chm | H | i-Pr | 4-OH-Bnzl | H | 4.25 | 440 | G |
| IB-485 | Chm | H | i-Pr | 2-Cbx-Et | H | 3.95 | 406 | G |

TABLE 6-36

| | | | | | | | | |
|---|---|---|---|---|---|---|---|---|
| IB-486 | Chm | H | i-Pr | 2-OH-Et | H | 2.55 | 378 | F |
| IB-487 | Chm | H | i-Pr | i-Pnt | H | 3.38 | 404 | F |
| IB-488 | i-Bu | H | s-Bu | i-Pnt | H | 3.15 | 378 | F |
| IB-489 | 4-OH-Bnzl | H | s-Bu | Ph-Et | H | 4.42 | 462 | G |
| IB-490 | 4-OH-Bnzl | H | s-Bu | 2-OH-Et | H | 3.63 | 402 | G |
| IB-491 | 4-OH-Bnzl | H | s-Bu | i-Pnt | H | 4.30 | 428 | G |
| IB-492 | 2-Cbx-Et | H | s-Bu | Ph-Et | H | 4.04 | 428 | G |
| IB-493 | 2-Cbx-Et | H | s-Bu | i-Pnt | H | 3.93 | 394 | G |
| IB-494 | Ph-Et | H | s-Bu | 2-Cbx-Et | H | 4.20 | 428 | G |
| IB-495 | 4-F-Bnzl | H | s-Bu | 2-Cbx-Et | H | 4.07 | 432 | G |
| IB-496 | 2-OH-Et | H | s-Bu | 4-OH-Bnzl | H | 3.30 | 402 | G |
| IB-497 | 2-OH-Et | H | s-Bu | 2-Cbx-Et | H | 2.77 | 368 | G |
| IB-498 | i-Pnt | H | s-Bu | i-Bu | H | 3.09 | 378 | F |
| IB-499 | i-Pnt | H | s-Bu | 4-OH-Bnzl | H | 4.20 | 428 | G |
| IB-500 | i-Pnt | H | s-Bu | 2-Cbx-Et | H | 3.97 | 394 | G |
| IB-501 | i-Pnt | H | s-Bu | Ph-Et | H | 3.49 | 426 | F |
| IB-502 | i-Pnt | H | s-Bu | 2-OH-Et | H | 2.55 | 366 | F |
| IB-503 | Chm | H | s-Bu | i-Bu | H | 3.40 | 404 | F |
| IB-504 | Chm | H | s-Bu | 4-OH-Bnzl | H | 4.55 | 454 | G |
| IB-505 | Chm | H | s-Bu | 2-Cbx-Et | H | 4.22 | 420 | G |
| IB-506 | Chm | H | s-Bu | Ph-Et | H | 3.65 | 452 | F |
| IB-507 | Chm | H | s-Bu | 2-OH-Et | H | 2.72 | 392 | F |
| IB-508 | Chm | H | s-Bu | i-Pnt | H | 3.70 | 418 | F |
| IB-509 | i-Bu | H | 4-OH-Bnzl | i-Pnt | H | 4.43 | 428 | G |
| IB-510 | 2-Cbx-Et | H | 4-OH-Bnzl | Ph-Et | H | 3.92 | 478 | G |
| IB-511 | 2-Cbx-Et | H | 4-OH-Bnzl | i-Pnt | H | 3.79 | 444 | G |
| IB-512 | 4-F-Bnzl | H | 4-OH-Bnzl | 2-Cbx-Et | H | 3.80 | 482 | G |
| IB-513 | 2-OH-Et | H | 4-OH-Bnzl | 2-Cbx-Et | H | 2.78 | 418 | G |
| IB-514 | i-Pnt | H | 4-OH-Bnzl | 2-Cbx-Et | H | 3.72 | 444 | G |
| IB-515 | Chm | H | 4-OH-Bnzl | 2-Cbx-Et | H | 3.97 | 470 | G |
| IB-516 | i-Bu | H | 2-Cbx-Et | Ph-Et | H | 4.14 | 428 | G |
| IB-517 | i-Bu | H | 2-Cbx-Et | i-Pnt | H | 4.09 | 394 | G |
| IB-518 | 2-OH-Et | H | 2-Cbx-Et | i-Bu | H | 2.85 | 368 | G |

TABLE 6-36-continued

| | | | | | | | | |
|---|---|---|---|---|---|---|---|---|
| IB-519 | 2-OH-Et | H | 2-Cbx-Et | i-Pnt | H | 3.32 | 382 | G |
| IB-520 | i-Pnt | H | 2-Cbx-Et | i-Bu | H | 4.05 | 394 | G |
| IB-521 | i-Pnt | H | 2-Cbx-Et | 4-OH-Bnzl | H | 3.55 | 444 | G |
| IB-522 | Chm | H | 2-Cbx-Et | i-Bu | H | 4.37 | 420 | G |
| IB-523 | Chm | H | 2-Cbx-Et | 4-OH-Bnzl | H | 3.84 | 470 | G |
| IB-524 | Chm | H | 2-Cbx-Et | i-Pnt | H | 4.60 | 434 | G |
| IB-525 | Bnzl | H | 4-F-Bnzl | 4-OH-Bnzl | H | 4.74 | 500 | G |
| IB-526 | Bnzl | H | 4-F-Bnzl | 2-Cbx-Et | H | 4.27 | 466 | G |
| IB-527 | i-Bu | H | 4-F-Bnzl | 4-OH-Bnzl | H | 4.39 | 466 | G |
| IB-528 | i-Bu | H | 4-F-Bnzl | 2-Cbx-Et | H | 4.02 | 432 | G |
| IB-529 | 1-Npm | H | 4-F-Bnzl | 4-OH-Bnzl | H | 5.27 | 550 | G |
| IB-530 | 1-Npm | H | 4-F-Bnzl | 2-Cbx-Et | H | 5.02 | 516 | G |
| IB-531 | 4-OH-Bnzl | H | 4-F-Bnzl | 2-Cbx-Et | H | 3.95 | 482 | G |
| IB-532 | 4-OH-Bnzl | H | 4-F-Bnzl | Ph-Et | H | 4.72 | 514 | G |
| IB-533 | 4-OH-Bnzl | H | 4-F-Bnzl | 2-OH-Et | H | 3.92 | 454 | G |
| IB-534 | 4-OH-Bnzl | H | 4-F-Bnzl | i-Pnt | H | 4.60 | 480 | G |
| IB-535 | 2-Cbx-Et | H | 4-F-Bnzl | 4-OH-Bnzl | H | 3.77 | 482 | G |
| IB-536 | 2-Cbx-Et | H | 4-F-Bnzl | Ph-Et | H | 4.40 | 480 | G |

TABLE 6-37

| | | | | | | | | |
|---|---|---|---|---|---|---|---|---|
| IB-537 | 2-Cbx-Et | H | 4-F-Bnzl | i-Pnt | H | 4.27 | 446 | G |
| IB-538 | Ph-Et | H | 4-F-Bnzl | 4-OH-Bnzl | H | 4.78 | 514 | G |
| IB-539 | Ph-Et | H | 4-F-Bnzl | 2-Cbx-Et | H | 4.53 | 480 | G |
| IB-540 | 2-OH-Et | H | 4-F-Bnzl | 4-OH-Bnzl | H | 3.70 | 454 | G |
| IB-541 | i-Pnt | H | 4-F-Bnzl | 4-OH-Bnzl | H | 4.52 | 480 | G |
| IB-542 | i-Pnt | H | 4-F-Bnzl | 2-Cbx-Et | H | 4.37 | 446 | G |
| IB-543 | Chm | H | 4-F-Bnzl | 4-OH-Bnzl | H | 4.84 | 506 | G |
| IB-544 | Chm | H | 4-F-Bnzl | 2-Cbx-Et | H | 4.59 | 472 | G |
| IB-545 | i-Bu | H | i-Pnt | i-Bu | H | 3.12 | 378 | F |
| IB-546 | i-Bu | H | i-Pnt | 2-Cbx-Et | H | 4.03 | 394 | G |
| IB-547 | i-Bu | H | i-Pnt | 2-OH-Et | H | 2.57 | 366 | F |
| IB-548 | 4-OH-Bnzl | H | i-Pnt | 2-Cbx-Et | H | 3.98 | 444 | G |
| IB-549 | 2-Cbx-Et | H | i-Pnt | i-Bu | H | 3.90 | 394 | G |
| IB-550 | 2-Cbx-Et | H | i-Pnt | 4-OH-Bnzl | H | 3.73 | 444 | G |
| IB-551 | 2-OH-Et | H | i-Pnt | i-Bu | H | 3.92 | 366 | G |
| IB-552 | Chm | H | i-Pnt | i-Bu | H | 3.54 | 418 | F |
| IB-553 | Chm | H | i-Pnt | 2-Cbx-Et | H | 4.60 | 434 | G |
| IB-554 | Bnzl | H | 2-OH-Et | 2-Cbx-Et | H | 3.05 | 402 | G |
| IB-555 | i-Bu | H | 2-OH-Et | i-Bu | H | 3.67 | 352 | G |
| IB-556 | i-Bu | H | 2-OH-Et | 4-OH-Bnzl | H | 3.17 | 402 | G |
| IB-557 | 1-Npm | H | 2-OH-Et | 4-OH-Bnzl | H | 4.15 | 486 | G |
| IB-558 | 4-OH-Bnzl | H | 2-OH-Et | Bnzl | H | 3.60 | 436 | G |
| IB-559 | 4-OH-Bnzl | H | 2-OH-Et | 1-Npm | H | 4.02 | 486 | G |
| IB-560 | 4-OH-Bnzl | H | 2-OH-Et | Ph-Et | H | 3.70 | 450 | G |
| IB-561 | 4-OH-Bnzl | H | 2-OH-Et | i-Pnt | H | 3.52 | 416 | G |
| IB-562 | 2-Cbx-Et | H | 2-OH-Et | 1-Npm | H | 3.80 | 452 | G |
| IB-563 | 2-Cbx-Et | H | 2-OH-Et | 4-OH-Bnzl | H | 2.62 | 418 | G |
| IB-564 | i-Pnt | H | 2-OH-Et | i-Bu | H | 4.04 | 366 | G |
| IB-565 | Chm | H | 2-OH-Et | i-Bu | H | 4.35 | 392 | G |
| IB-566 | Chm | H | 2-OH-Et | i-Pnt | H | 4.64 | 406 | G |
| IB-567 | Bnzl | H | Ph-Et | 4-OH-Bnzl | H | 4.72 | 496 | G |
| IB-568 | Bnzl | H | Ph-Et | 2-Cbx-Et | H | 4.34 | 463 | G |
| IB-569 | i-Bu | H | Ph-Et | 4-OH-Bnzl | H | 4.37 | 462 | G |
| IB-570 | i-Bu | H | Ph-Et | 2-Cbx-Et | H | 4.03 | 428 | G |
| IB-571 | 1-Npm | H | Ph-Et | 4-OH-Bnzl | H | 5.28 | 546 | G |
| IB-572 | 4-OH-Bnzl | H | Ph-Et | 2-OH-Et | H | 3.93 | 450 | G |
| IB-573 | 4-OH-Bnzl | H | Ph-Et | i-Pnt | H | 4.60 | 476 | G |
| IB-574 | 2-Cbx-Et | H | Ph-Et | 4-OH-Bnzl | H | 3.80 | 478 | G |
| IB-575 | 2-Cbx-Et | H | Ph-Et | i-Pnt | H | 4.22 | 442 | G |
| IB-576 | 4-F-Bnzl | H | Ph-Et | 4-OH-Bnzl | H | 4.78 | 514 | G |
| IB-577 | 4-F-Bnzl | H | Ph-Et | 2-Cbx-Et | H | 4.42 | 480 | G |
| IB-578 | 2-OH-Et | H | Ph-Et | 4-OH-Bnzl | H | 3.77 | 450 | G |
| IB-579 | i-Pnt | H | Ph-Et | 4-OH-Bnzl | H | 4.55 | 476 | G |
| IB-580 | i-Pnt | H | Ph-Et | 2-Cbx-Et | H | 4.32 | 442 | G |
| IB-581 | Chm | H | Ph-Et | 4-OH-Bnzl | H | 4.85 | 502 | G |
| IB-582 | Chm | H | Ph-Et | 2-Cbx-Et | H | 4.59 | 468 | G |
| IB-583 | Bnzl | H | Hxy | 2-Cbx-Et | H | 4.64 | 464 | G |
| IB-584 | i-Bu | H | Hxy | i-Bu | H | 3.42 | 392 | F |
| IB-585 | i-Bu | H | Hxy | 2-Cbx-Et | H | 4.40 | 408 | G |
| IB-586 | i-Bu | H | Hxy | 2-OH-Et | H | 2.82 | 380 | F |
| IB-587 | i-Bu | H | Hxy | i-Pnt | H | 3.77 | 406 | F |

TABLE 6-38

| | | | | | | | |
|---|---|---|---|---|---|---|---|
| IB-588 | 4-OH-Bnzl | H | Hxy | 1-Npm | H | 5.15 | 526 | G |
| IB-589 | 4-OH-Bnzl | H | Hxy | 2-Cbx-Et | H | 4.42 | 458 | G |
| IB-590 | 2-Cbx-Et | H | Hxy | i-Bu | H | 4.43 | 408 | G |
| IB-591 | 2-Cbx-Et | H | Hxy | 1-Npm | H | 5.00 | 492 | G |
| IB-592 | 2-Cbx-Et | H | Hxy | 4-OH-Bnzl | H | 4.25 | 458 | G |
| IB-593 | 2-Cbx-Et | H | Hxy | i-Pnt | H | 4.67 | 422 | G |
| IB-594 | 4-F-Bnzl | H | Hxy | 2-Cbx-Et | H | 4.80 | 460 | G |
| IB-595 | 2-OH-Et | H | Hxy | i-Bu | H | 4.39 | 380 | G |
| IB-596 | 2-OH-Et | H | Hxy | 4-OH-Bnzl | H | 4.05 | 430 | G |
| IB-597 | 2-OH-Et | H | Hxy | i-Pnt | H | 4.65 | 394 | G |
| IB-598 | i-Pnt | H | Hxy | i-Bu | H | 3.65 | 406 | F |
| IB-599 | i-Pnt | H | Hxy | 4-OH-Bnzl | H | 4.85 | 456 | G |
| IB-600 | i-Pnt | H | Hxy | 2-Cbx-Et | H | 4.77 | 422 | G |
| IB-601 | i-Pnt | H | Hxy | 2-OH-Et | H | 3.04 | 394 | F |
| IB-602 | Chm | H | Hxy | i-Bu | H | 3.92 | 432 | F |
| IB-603 | Chm | H | Hxy | 4-OH-Bnzl | H | 5.09 | 482 | G |
| IB-604 | Chm | H | Hxy | 2-Cbx-Et | H | 4.97 | 448 | G |
| IB-605 | Chm | H | Hxy | 2-OH-Et | H | 3.22 | 420 | F |
| IB-606 | Chm | H | Hxy | i-Pnt | H | 4.10 | 446 | F |
| IB-607 | 3-Gun-Pr | H | Bnzl | Ph-Et | H | 3.87 | 489 | G |
| IB-608 | 3-Gun-Pr | H | Bnzl | 2-OH-Et | H | 3.00 | 429 | G |
| IB-609 | 3-Gun-Pr | H | Bnzl | i-Pnt | H | 3.67 | 455 | G |
| IB-610 | Ph-Et | H | Bnzl | 3-Gun-Pr | H | 4.24 | 489 | G |
| IB-611 | 4-F-Bnzl | H | Bnzl | 3-Gun-Pr | H | 3.92 | 493 | G |
| IB-612 | 2-OH-Et | H | Bnzl | 3-Gun-Pr | H | 3.12 | 429 | G |
| IB-613 | Chm | H | Bnzl | 3-Gun-Pr | H | 4.18 | 481 | G |
| IB-614 | 3-Gun-Pr | H | i-Bu | Ph-Et | H | 3.65 | 455 | G |
| IB-615 | 3-Gun-Pr | H | i-Bu | i-Pnt | H | 3.54 | 421 | G |
| IB-616 | Ph-Et | H | i-Bu | 3-Gun-Pr | H | 4.04 | 455 | G |
| IB-617 | 4-F-Bnzl | H | i-Bu | 3-Gun-Pr | H | 3.75 | 459 | G |
| IB-618 | 2-OH-Et | H | i-Bu | 3-Gun-Pr | H | 2.68 | 395 | G |
| IB-619 | i-Pnt | H | i-Bu | 3-Gun-Pr | H | 3.72 | 421 | G |
| IB-620 | Chm | H | i-Bu | 3-Gun-Pr | H | 4.02 | 447 | G |
| IB-621 | 3-Gun-Pr | H | 1-Npm | Ph-Et | H | 4.37 | 539 | G |
| IB-622 | 3-Gun-Pr | H | 1-Npm | i-Pnt | H | 4.24 | 505 | G |
| IB-623 | Ph-Et | H | 1-Npm | 3-Gun-Pr | H | 4.62 | 539 | G |
| IB-624 | 4-F-Bnzl | H | 1-Npm | 3-Gun-Pr | H | 4.60 | 543 | G |
| IB-625 | 2-OH-Et | H | 1-Npm | 3-Gun-Pr | H | 3.75 | 479 | G |
| IB-626 | i-Pnt | H | 1-Npm | 3-Gun-Pr | H | 4.52 | 505 | G |
| IB-627 | Chm | H | 1-Npm | 3-Gun-Pr | H | 4.70 | 531 | G |
| IB-628 | 3-Gun-Pr | H | i-Pr | 2-OH-Et | H | 1.17 | 381 | G |
| IB-629 | 3-Gun-Pr | H | i-Pr | i-Pnt | H | 3.34 | 407 | G |
| IB-630 | Ph-Et | H | i-Pr | 3-Gun-Pr | H | 3.72 | 441 | G |
| IB-631 | 4-F-Bnzl | H | i-Pr | 3-Gun-Pr | H | 3.37 | 445 | G |
| IB-632 | 2-OH-Et | H | i-Pr | 3-Gun-Pr | H | 1.41 | 381 | G |
| IB-633 | i-Pnt | H | i-Pr | 3-Gun-Pr | H | 3.45 | 407 | G |
| IB-634 | Chm | H | i-Pr | 3-Gun-Pr | H | 3.69 | 433 | G |
| IB-635 | 3-Gun-Pr | H | s-Bu | Ph-Et | H | 3.69 | 455 | G |
| IB-636 | Ph-Et | H | s-Bu | 3-Gun-Pr | H | 4.00 | 455 | G |
| IB-637 | 2-OH-Et | H | s-Bu | 3-Gun-Pr | H | 2.67 | 395 | G |
| IB-638 | i-Pnt | H | s-Bu | 3-Gun-Pr | H | 3.67 | 421 | G |

TABLE 6-39

| | | | | | | | |
|---|---|---|---|---|---|---|---|
| IB-639 | Chm | H | s-Bu | 3-Gun-Pr | H | 3.97 | 447 | G |
| IB-640 | 3-Gun-Pr | H | 4-OH-Bnzl | Ph-Et | H | 3.59 | 505 | G |
| IB-641 | Ph-Et | H | 4-OH-Bnzl | 3-Gun-Pr | H | 3.82 | 505 | G |
| IB-642 | 4-F-Bnzl | H | 4-OH-Bnzl | 3-Gun-Pr | H | 3.59 | 509 | G |
| IB-643 | 2-OH-Et | H | 4-OH-Bnzl | 3-Gun-Pr | H | 2.68 | 445 | G |
| IB-644 | i-Pnt | H | 4-OH-Bnzl | 3-Gun-Pr | H | 3.52 | 471 | G |
| IB-645 | Chm | H | 4-OH-Bnzl | 3-Gun-Pr | H | 3.77 | 497 | G |
| IB-646 | Bnzl | H | 3-Gun-Pr | 2-OH-Et | H | 2.97 | 429 | G |
| IB-647 | i-Bu | H | 3-Gun-Pr | Ph-Et | H | 3.95 | 455 | G |
| IB-648 | i-Bu | H | 3-Gun-Pr | 2-OH-Et | H | 2.59 | 395 | G |
| IB-649 | i-Bu | H | 3-Gun-Pr | i-Pnt | H | 3.82 | 421 | G |
| IB-650 | 1-Npm | H | 3-Gun-Pr | Ph-Et | H | 4.68 | 539 | G |
| IB-651 | 4-OH-Bnzl | H | 3-Gun-Pr | Ph-Et | H | 3.63 | 505 | G |
| IB-652 | 4-OH-Bnzl | H | 3-Gun-Pr | 2-OH-Et | H | 2.70 | 445 | G |
| IB-653 | 4-OH-Bnzl | H | 3-Gun-Pr | i-Pnt | H | 3.50 | 471 | G |
| IB-654 | Ph-Et | H | 3-Gun-Pr | i-Bu | H | 4.02 | 455 | G |
| IB-655 | Ph-Et | H | 3-Gun-Pr | 1-Npm | H | 4.55 | 539 | G |
| IB-656 | Ph-Et | H | 3-Gun-Pr | 4-OH-Bnzl | H | 3.59 | 505 | G |
| IB-657 | Ph-Et | H | 3-Gun-Pr | i-Pnt | H | 4.27 | 469 | G |
| IB-658 | 4-F-Bnzl | H | 3-Gun-Pr | i-Bu | H | 3.92 | 459 | G |
| IB-659 | 4-F-Bnzl | H | 3-Gun-Pr | 1-Npm | H | 4.52 | 543 | G |
| IB-660 | 4-F-Bnzl | H | 3-Gun-Pr | 4-OH-Bnzl | H | 3.59 | 509 | G |
| IB-661 | 4-F-Bnzl | H | 3-Gun-Pr | i-Pnt | H | 4.17 | 473 | G |

TABLE 6-39-continued

| | | | | | | | |
|---|---|---|---|---|---|---|---|
| IB-662 | 2-OH-Et | H | 3-Gun-Pr | i-Bu | H | 2.72 | 395 | G |
| IB-663 | 2-OH-Et | H | 3-Gun-Pr | i-Pnt | H | 3.15 | 409 | G |
| IB-664 | i-Pnt | H | 3-Gun-Pr | Bnzl | H | 4.02 | 455 | G |
| IB-665 | i-Pnt | H | 3-Gun-Pr | i-Bu | H | 3.82 | 421 | G |
| IB-666 | i-Pnt | H | 3-Gun-Pr | 1-Npm | H | 4.40 | 505 | G |
| IB-667 | i-Pnt | H | 3-Gun-Pr | 4-OH-Bnzl | H | 3.34 | 471 | G |
| IB-668 | Chm | H | 3-Gun-Pr | Bnzl | H | 4.27 | 481 | G |
| IB-669 | Chm | H | 3-Gun-Pr | i-Bu | H | 4.10 | 447 | G |
| IB-670 | Chm | H | 3-Gun-Pr | 1-Npm | H | 4.64 | 531 | G |
| IB-671 | Chm | H | 3-Gun-Pr | 4-OH-Bnzl | H | 3.63 | 497 | G |
| IB-672 | Chm | H | 3-Gun-Pr | Ph-Et | H | 4.42 | 495 | G |
| IB-673 | Chm | H | 3-Gun-Pr | 2-OH-Et | H | 3.22 | 435 | G |
| IB-674 | Chm | H | 3-Gun-Pr | i-Pnt | H | 4.34 | 461 | G |
| IB-675 | Bnzl | H | 4-F-Bnzl | 3-Gun-Pr | H | 4.00 | 493 | G |
| IB-676 | i-Bu | H | 4-F-Bnzl | 3-Gun-Pr | H | 3.74 | 459 | G |
| IB-677 | 1-Npm | H | 4-F-Bnzl | 3-Gun-Pr | H | 4.75 | 543 | G |
| IB-678 | 4-OH-Bnzl | H | 4-F-Bnzl | 3-Gun-Pr | H | 3.80 | 509 | G |
| IB-679 | 3-Gun-Pr | H | 4-F-Bnzl | Ph-Et | H | 3.94 | 507 | G |
| IB-680 | 3-Gun-Pr | H | 4-F-Bnzl | i-Pnt | H | 3.82 | 473 | G |
| IB-681 | Ph-Et | H | 4-F-Bnzl | 3-Gun-Pr | H | 4.35 | 507 | G |
| IB-682 | 2-OH-Et | H | 4-F-Bnzl | 3-Gun-Pr | H | 3.27 | 447 | G |
| IB-683 | i-Pnt | H | 4-F-Bnzl | 3-Gun-Pr | H | 4.12 | 473 | G |
| IB-684 | Chm | H | 4-F-Bnzl | 3-Gun-Pr | H | 4.32 | 499 | G |
| IB-685 | Bnzl | H | i-Pnt | 3-Gun-Pr | H | 3.88 | 455 | G |
| IB-686 | i-Bu | H | i-Pnt | 3-Gun-Pr | H | 3.72 | 421 | G |
| IB-687 | 1-Npm | H | i-Pnt | 3-Gun-Pr | H | 4.72 | 505 | G |
| IB-688 | 4-OH-Bnzl | H | i-Pnt | 3-Gun-Pr | H | 3.72 | 471 | G |
| IB-689 | 3-Gun-Pr | H | i-Pnt | 4-OH-Bnzl | H | 3.47 | 471 | G |

TABLE 6-40

| | | | | | | | |
|---|---|---|---|---|---|---|---|
| IB-690 | 3-Gun-Pr | H | i-Pnt | Ph-Et | H | 3.97 | 469 | G |
| IB-691 | Ph-Et | H | i-Pnt | 3-Gun-Pr | H | 4.22 | 469 | G |
| IB-692 | 4-F-Bnzl | H | i-Pnt | 3-Gun-Pr | H | 4.07 | 473 | G |
| IB-693 | 2-OH-Et | H | i-Pnt | 3-Gun-Pr | H | 3.13 | 409 | G |
| IB-694 | Chm | H | i-Pnt | 3-Gun-Pr | H | 4.30 | 461 | G |
| IB-695 | Bnzl | H | 2-OH-Et | 3-Gun-Pr | H | 2.84 | 429 | G |
| IB-696 | i-Bu | H | 2-OH-Et | 3-Gun-Pr | H | 2.52 | 395 | G |
| IB-697 | 1-Npm | H | 2-OH-Et | 3-Gun-Pr | H | 3.42 | 479 | G |
| IB-698 | 4-OH-Bnzl | H | 2-OH-Et | 3-Gun-Pr | H | 2.65 | 445 | G |
| IB-699 | 3-Gun-Pr | H | 2-OH-Et | i-Bu | H | 2.72 | 395 | G |
| IB-700 | 4-F-Bnzl | H | 2-OH-Et | 3-Gun-Pr | H | 2.92 | 447 | G |
| IB-701 | i-Pnt | H | 2-OH-Et | 3-Gun-Pr | H | 2.99 | 409 | G |
| IB-702 | Chm | H | 2-OH-Et | 3-Gun-Pr | H | 3.24 | 435 | G |
| IB-703 | Bnzl | H | Ph-Et | 3-Gun-Pr | H | 3.90 | 489 | G |
| IB-704 | i-Bu | H | Ph-Et | 3-Gun-Pr | H | 3.75 | 455 | G |
| IB-705 | 1-Npm | H | Ph-Et | 3-Gun-Pr | H | 4.65 | 539 | G |
| IB-706 | 4-OH-Bnzl | H | Ph-Et | 3-Gun-Pr | H | 3.73 | 505 | G |
| IB-707 | 3-Gun-Pr | H | Ph-Et | i-Pnt | H | 3.85 | 469 | G |
| IB-708 | 4-F-Bnzl | H | Ph-Et | 3-Gun-Pr | H | 3.97 | 507 | G |
| IB-709 | 2-OH-Et | H | Ph-Et | 3-Gun-Pr | H | 3.29 | 443 | G |
| IB-710 | i-Pnt | H | Ph-Et | 3-Gun-Pr | H | 4.02 | 469 | G |
| IB-711 | Chm | H | Ph-Et | 3-Gun-Pr | H | 4.22 | 495 | G |
| IB-712 | Bnzl | H | Hxy | 3-Gun-Pr | H | 4.18 | 469 | G |
| IB-713 | i-Bu | H | Hxy | 3-Gun-Pr | H | 4.05 | 435 | G |
| IB-714 | 1-Npm | H | Hxy | 3-Gun-Pr | H | 5.07 | 519 | G |
| IB-715 | 4-OH-Bnzl | H | Hxy | 3-Gun-Pr | H | 4.17 | 485 | G |
| IB-716 | 3-Gun-Pr | H | Hxy | Bnzl | H | 4.07 | 469 | G |
| IB-717 | 3-Gun-Pr | H | Hxy | 1-Npm | H | 4.30 | 519 | G |
| IB-718 | 3-Gun-Pr | H | Hxy | 4-OH-Bnzl | H | 3.85 | 485 | G |
| IB-719 | 3-Gun-Pr | H | Hxy | Ph-Et | H | 4.29 | 483 | G |
| IB-720 | 3-Gun-Pr | H | Hxy | i-Pnt | H | 4.20 | 449 | G |
| IB-721 | Ph-Et | H | Hxy | 3-Gun-Pr | H | 4.62 | 483 | G |
| IB-722 | 4-F-Bnzl | H | Hxy | 3-Gun-Pr | H | 4.43 | 487 | G |
| IB-723 | 2-OH-Et | H | Hxy | 3-Gun-Pr | H | 3.69 | 423 | G |
| IB-724 | i-Pnt | H | Hxy | 3-Gun-Pr | H | 4.47 | 449 | G |
| IB-725 | Chm | H | Hxy | 3-Gun-Pr | H | 4.52 | 475 | G |
| IB-726 | 2-OtBu-Et | H | i-Bu | Bnzl | H | 2.76 | 492 | H |
| IB-727 | 2-OtBu-Et | H | i-Bu | 1-Npm | H | 2.94 | 492 | H |
| IB-728 | 2-OtBu-Et | H | Bnzl | i-Pnt | H | 2.85 | 456 | H |
| IB-729 | 2-OtBu-Et | H | 1-Npm | Bnzl | H | 3.03 | 526 | H |
| IB-730 | 2-OtBu-Et | H | 1-Npm | i-Bu | H | 2.94 | 492 | H |
| IB-731 | Bnzl | H | 2-OtBu-Et | Bnzl | H | 2.78 | 476 | H |
| IB-732 | Bnzl | H | 2-OtBu-Et | i-Bu | H | 2.66 | 442 | H |
| IB-733 | Bnzl | H | 2-OtBu-Et | 1-Npm | H | 2.92 | 526 | H |
| IB-734 | Bnzl | H | 2-OtBu-Et | Ph-Et | H | 2.77 | 490 | H |
| IB-735 | Bnzl | H | 2-OtBu-Et | i-Pnt | H | 2.74 | 456 | H |

TABLE 6-40-continued

| | | | | | | | | |
|---|---|---|---|---|---|---|---|---|
| IB-736 | i-Bu | H | 2-OtBu-Et | Bnzl | H | 2.65 | 442 | H |
| IB-737 | i-Bu | H | 2-OtBu-Et | 1-Npm | H | 2.83 | 492 | H |
| IB-738 | i-Bu | H | 2-OtBu-Et | Ph-Et | H | 2.72 | 456 | H |
| IB-739 | 1-Npm | H | 2-OtBu-Et | Bnzl | H | 3.22 | 526 | H |
| IB-740 | 1-Npm | H | 2-OtBu-Et | i-Bu | H | 2.94 | 492 | H |

TABLE 6-41

| | | | | | | | | |
|---|---|---|---|---|---|---|---|---|
| IB-741 | 1-Npm | H | 2-OtBu-Et | Ph-Et | H | 3.09 | 540 | H |
| IB-742 | 1-Npm | H | 2-OtBu-Et | i-Pnt | H | 3.05 | 506 | H |
| IB-743 | 4-tBuO-Bnzl | H | 2-OtBu-Et | i-Bu | H | 2.86 | 514 | H |
| IB-744 | Ph-Et | H | 2-OtBu-Et | Bnzl | H | 2.78 | 490 | H |
| IB-745 | Ph-Et | H | 2-OtBu-Et | i-Bu | H | 2.74 | 456 | H |
| IB-746 | Ph-Et | H | 2-OtBu-Et | 4-tBuO-Bnzl | H | 2.95 | 562 | H |
| IB-747 | Ph-Et | H | 2-OtBu-Et | i-Pnt | H | 2.82 | 470 | H |
| IB-748 | 4-F-Bnzl | H | 2-OtBu-Et | Bnzl | H | 2.78 | 494 | H |
| IB-749 | 4-F-Bnzl | H | 2-OtBu-Et | i-Bu | H | 2.67 | 460 | H |
| IB-750 | 4-F-Bnzl | H | 2-OtBu-Et | 1-Npm | H | 2.93 | 544 | H |
| IB-751 | 4-F-Bnzl | H | 2-OtBu-Et | Ph-Et | H | 2.80 | 508 | H |
| IB-752 | 4-F-Bnzl | H | 2-OtBu-Et | i-Pnt | H | 2.74 | 474 | H |
| IB-753 | i-Pnt | H | 2-OtBu-Et | Bnzl | H | 2.72 | 456 | H |
| IB-754 | i-Pnt | H | 2-OtBu-Et | 1-Npm | H | 2.88 | 506 | H |
| IB-755 | Chm | H | 2-OtBu-Et | Bnzl | H | 2.88 | 482 | H |
| IB-756 | Chm | H | 2-OtBu-Et | 4-tBuO-Bnzl | H | 3.08 | 554 | H |
| IB-757 | Chm | H | 2-OtBu-Et | Ph-Et | H | 2.90 | 496 | H |
| IB-758 | 4-F-Bnzl | H | i-Pnt | tBOC-E | H | 2.85 | 502 | H |
| IB-759 | Chm | H | i-Pnt | 4-tBuO-Bnzl | H | 3.18 | 524 | H |
| IB-760 | Bnzl | H | Hxy | 4-tBuO-Bnzl | H | 3.18 | 532 | H |
| IB-761 | i-Bu | H | Hxy | 4-tBuO-Bnzl | H | 3.05 | 498 | H |

TABLE 6-41-continued

| | | | | | | | | |
|---|---|---|---|---|---|---|---|---|
| IB-762 | 4-tBuO-Bnzl | H | Hxy | Bnzl | H | 3.20 | 532 | H |
| IB-763 | 4-tBuO-Bnzl | H | Hxy | Ph-Et | H | 3.17 | 546 | H |
| IB-764 | 4-tBuO-Bnzl | H | Hxy | i-Pnt | H | 3.17 | 512 | H |
| IB-765 | tBOC-E | H | Hxy | Ph-Et | H | 3.06 | 512 | H |
| IB-766 | Ph-Et | H | Hxy | 4-tBuO-Bnzl | H | 3.17 | 546 | H |
| IB-767 | 2-OtBu-Et | H | Hxy | Bnzl | H | 3.01 | 470 | H |
| IB-768 | 2-OtBu-Et | H | Hxy | Ph-Et | H | 3.04 | 484 | H |
| IB-769 | 2-OH-Et | H | i-Bu | Bnzl | H | 2.31 | 386 | H |
| IB-770 | 2-OH-Et | H | i-Bu | 1-Npm | H | 2.49 | 436 | H |
| IB-771 | 2-OH-Et | H | Bnzl | i-Pnt | H | 2.42 | 400 | H |
| IB-772 | 2-OH-Et | H | 1-Npm | Bnzl | H | 2.58 | 470 | H |
| IB-773 | 2-OH-Et | H | 1-Npm | i-Bu | H | 2.52 | 436 | H |
| IB-774 | Bnzl | H | 2-OH-Et | Bnzl | H | 2.42 | 420 | H |
| IB-775 | Bnzl | H | 2-OH-Et | i-Bu | H | 2.32 | 386 | H |
| IB-776 | Bnzl | H | 2-OH-Et | 1-Npm | H | 2.54 | 470 | H |
| IB-777 | Bnzl | H | 2-OH-Et | Ph-Et | H | 2.44 | 434 | H |
| IB-778 | Bnzl | H | 2-OH-Et | i-Pnt | H | 2.41 | 400 | H |
| IB-779 | i-Bu | H | 2-OH-Et | Bnzl | H | 2.29 | 386 | H |
| IB-780 | i-Bu | H | 2-OH-Et | 1-Npm | H | 2.47 | 436 | H |
| IB-781 | i-Bu | H | 2-OH-Et | Ph-Et | H | 2.38 | 400 | H |
| IB-782 | 1-Npm | H | 2-OH-Et | Bnzl | H | 2.61 | 470 | H |
| IB-783 | 1-Npm | H | 2-OH-Et | i-Bu | H | 2.49 | 436 | H |
| IB-784 | 1-Npm | H | 2-OH-Et | Ph-Et | H | 2.62 | 484 | H |
| IB-785 | 1-Npm | H | 2-OH-Et | i-Pnt | H | 2.58 | 450 | H |
| IB-786 | 4-OH-Bnzl | H | 2-OH-Et | i-Bu | H | 2.13 | 402 | H |
| IB-787 | Ph-Et | H | 2-OH-Et | Bnzl | H | 2.47 | 434 | H |
| IB-788 | Ph-Et | H | 2-OH-Et | i-Bu | H | 2.40 | 400 | H |
| IB-789 | Ph-Et | H | 2-OH-Et | 1-Npm | H | 2.60 | 484 | H |
| IB-790 | Ph-Et | H | 2-OH-Et | 4-OH-Bnzl | H | 2.26 | 450 | H |
| IB-791 | Ph-Et | H | 2-OH-Et | i-Pnt | H | 2.51 | 414 | H |

TABLE 6-42

| | | | | | | | | |
|---|---|---|---|---|---|---|---|---|
| IB-792 | 4-F-Bnzl | H | 2-OH-Et | Bnzl | H | 2.42 | 438 | H |
| IB-793 | 4-F-Bnzl | H | 2-OH-Et | i-Bu | H | 2.36 | 404 | H |
| IB-794 | 4-F-Bnzl | H | 2-OH-Et | 1-Npm | H | 2.57 | 488 | H |
| IB-795 | 4-F-Bnzl | H | 2-OH-Et | 4-OH-Bnzl | H | 2.22 | 454 | H |
| IB-796 | 4-F-Bnzl | H | 2-OH-Et | Ph-Et | H | 2.45 | 452 | H |
| IB-797 | i-Pnt | H | 2-OH-Et | Bnzl | H | 2.41 | 400 | H |
| IB-798 | i-Pnt | H | 2-OH-Et | 1-Npm | H | 2.54 | 450 | H |
| IB-799 | i-Pnt | H | 2-OH-Et | 4-OH-Bnzl | H | 2.17 | 416 | H |
| IB-800 | Chm | H | 2-OH-Et | Bnzl | H | 2.53 | 426 | H |
| IB-801 | Chm | H | 2-OH-Et | 4-OH-Bnzl | H | 2.29 | 442 | H |
| IB-802 | Chm | H | 2-OH-Et | Ph-Et | H | 2.58 | 440 | H |
| IB-803 | 4-F-Bnzl | H | i-Pnt | 2-Cbx-Et | H | 2.48 | 446 | H |
| IB-804 | Chm | H | i-Pnt | 4-OH-Bnzl | H | 2.71 | 468 | H |
| IB-805 | Bnzl | H | Hxy | 4-OH-Bnzl | H | 2.76 | 476 | H |
| IB-806 | i-Bu | H | Hxy | 4-OH-Bnzl | H | 2.64 | 442 | H |
| IB-807 | 4-OH-Bnzl | H | Hxy | Bnzl | H | 2.72 | 476 | H |
| IB-808 | 4-OH-Bnzl | H | Hxy | Ph-Et | H | 2.74 | 490 | H |
| IB-809 | 4-OH-Bnzl | H | Hxy | i-Pnt | H | 2.69 | 456 | H |
| IB-810 | 2-Cbx-Et | H | Hxy | Ph-Et | H | 2.63 | 456 | H |
| IB-811 | Ph-Et | H | Hxy | 4-OH-Bnzl | H | 2.76 | 490 | H |
| IB-812 | 2-OH-Et | H | Hxy | Bnzl | H | 2.57 | 414 | H |
| IB-813 | 2-OH-Et | H | Hxy | Ph-Et | H | 2.63 | 428 | H |
| IB-814 | 1-tert-butoxycarbonyl-6-methyl-1H-indol-3-ylmethyl | H | cycloheptylmethyl | i-Bu | H | 2.4 | 605 | B |
| IB-815 | 6-methyl-1H-indol-3-ylmethyl | H | cycloheptylmethyl | i-Bu | H | 1.44 | 505 | B |
| IB-816 | 1-tert-butoxycarbonyl-6-fluoro-1H-indol-3-ylmethyl | H | cycloheptylmethyl | i-Bu | H | 2.23 | 609 | B |
| IB-817 | 6-fluoro-1H-indol-3-ylmethyl | H | cycloheptylmethyl | i-Bu | H | 1.42 | 509 | B |
| IB-818 | Chm | H | pentyl | 3-Me-Bnzl | H | 1.01 | 466.3 | C |
| IB-819 | 1-Npm | H | β-hydroxyphenethyl | Ph-Et | H | 0.98 | 560 | C |
| IB-820 | 1-Npm | H | α-hydroxymethylphenethyl | Ph-Et | H | 0.94 | 574 | C |
| IB-821 | 1-Npm | H | α-hydroxymethylphenethyl | Ph-Et | H | 1.03 | 574 | C |
| IB-822 | 2-trifluoromethylbenzyl | H | 4-tBuO-Bnzl | i-Bu | H | 1.22 | 572.3 | C |
| IB-823 | 2-trifluoromethylbenzyl | H | 4-OH-Bnzl | i-Bu | H | 1.01 | 516.3 | C |
| IB-824 | 3-benzyloxybenzyl | H | 4-tBuO-Bnzl | i-Bu | H | 1.06 | 610.4 | C |
| IB-825 | 3-benzyloxybenzyl | H | 4-OH-Bnzl | i-Bu | H | 0.92 | 554.3 | C |
| IB-826 | Chm | H | pentyl | Bnzl | H | 0.99 | 452.3 | C |
| IB-827 | cycloheptylmethyl | H | pentyl | Bnzl | H | 1.03 | 466.4 | C |

TABLE 6-43

| IB-828 | cycloheptylmethyl | H | pentyl | 3-Me-Bnzl | H | 1.05 | 480.4 | C |
| IB-829 | cyclopentylmethyl | H | Bnzl | Chm | H | 0.97 | 464.3 | C |
| IB-830 | 4-Me-Bnzl | H | 4-methoxybutyl | Pr | H | 0.81 | 428.3 | C |
| IB-831 | 4-Cl-Bnzl | H | 4-methoxybutyl | Pr | H | 0.83 | 448.2 | C |
| IB-832 | 3-Gun-Pr | H | 3-Gun-Pr | 3-Gun-Pr | H | 0.36 | 493.3 | C |

Example 2

(1) Synthesis of N-(2,2,6,6-tetramethylpiperidin-4-yl)-1,2,4-triazine-3-carboxamide 200 mg of ethyl 1,2,4-triazine-3-carboxylate was dissolved in 2.5 mL of methanol, and 204 mg of 4-amino-2,2,6,6-tetramethylpyridine was added. The mixture was then stirred for 12 hours at room temperature. Methanol was evaporated under reduced pressure, and the resulting residue was purified with CHROMATOREX Q-PACK SI30 SIZE 20 (chloroform:methanol=100%:0% to 80%:20%) to obtain N-(2,2,6,6-tetramethylpiperidin-4-yl)-1,2,4-triazine-3-carboxamide (124 mg, yield: 36%).

(2) Synthesis of (3S*,3aS*,6R*,7R*,7aS*)-1,7-dibenzyl-5-oxo-N-(2,2,6,6-tetramethylpiperidin-4-yl) octahydro-1,2,3,6,7,7a-hexahydro-3aH-3,6-methanopyrrolo[3,2-b]pyridine-3a-carboxamide (II-44) and (3S*,3aR*,6S*,7R*,7aR*)-1,7-dibenzyl-4-oxo-N-(2,2,6,6-tetramethylpiperidin-4-yl) octahydro-6H-3,6-methanopyrrolo[3,2-c]pyridine-6-carboxamide (II-45)

335 mg of 4A molecular sieves, 112 mg of N-allylbenzylamine, and 102 mg of 3-phenylpropanal were added to 2 mL of chloroform solution of 80 mg of N-(2,2,6,6-tetramethylpiperidin-4-yl)-1,2,4-triazine-3-carboxamide. The mixture was refluxed by heating for 12 hours. Molecular sieves were filtered and washed twice with chloroform. The combined organic layer was evaporated under reduced pressure, and the resulting residue was purified with CHROMATOREX Q-PACK SI30 SIZE 20 (hexane:ethyl acetate=75%:25% to 0%:100%) and subsequently with CHROMATOREX Q-PACK DNH30 SIZE 10 (hexane:ethyl acetate=100%:0% to 50%:50%) to obtain the aforementioned compounds (II-44) and (II-45) as about 1:1 mixture (quantified by 1H NMR) (80.3 mg, yield: 53%, [M+1]$^+$=499).

(3) Synthesis of (3S*,3aS*,6R*,7R*,7aS*)-1,7-dibenzyl-5-oxo-N-(2,2,6,6-tetramethylpiperidin-4-yl) octahydro-3aH-3,6-methanopyrrolo[3,2-b]pyridine-3a-carboxamide (I-44) and (3S*,3aR*,6S*,7R*,7aR*)-1,7-dibenzyl-4-oxo-N-(2,2,6,6-tetramethylpiperidin-4-yl) octahydro-6H-3,6-methanopyrrolo[3,2-c]pyridine-6-carboxamide (I-45)

6.1 μL of trifluoroacetic acid, 23.8 μL of 2,3-dimethyl-2-butene, 12 μL of aqueous 5 M sodium chlorite solution, and 28.1 μL of aqueous 5 M sodium dihydrogen phosphate solution were added to 0.16 mL toluene solution of 20 mg mixture of II-44 and II-45. The mixture was vigorously stirred for 1 hour at room temperature. 1.0 mL of ethyl acetate was added to the reaction mixture. The organic layer was sequentially washed with 0.5 mL of saturated sodium hydrogen carbonate water, 0.5 mL of aqueous 5% sodium thiosulfate solution, and 0.5 mL of saturated salt water, dried with anhydrous sodium sulfate, and then filtered. Ethyl acetate was evaporated under reduced pressure from the filtrate, and the residue including toluene was purified with CHROMATOREX Q-PACK DNH30 SIZE 10 (hexane:ethyl acetate=100%:0% to 0%:100%) to obtain the aforementioned compounds (1-44) (5.6 mg, yield: 27.0%, RT=1.15 minutes (method B), [M+1]$^+$=515) and (1-45) (2.7 mg, yield: 13.2%, RT=1.05 minutes (method B), [M+1]$^+$=515).

Example 3

(1) Synthesis of N-(pyridin-4-yl)methyl-1,2,4-triazine-3-carboxamide

Ethyl 1,2,4-triazine-3-carboxylate was dissolved in methanol, and 4-aminopyridine was added. The mixture was then stirred at room temperature. Methanol was evaporated under reduced pressure, and the resulting residue was purified by column chromatography. A fraction of the compound of interest was concentrated to obtain the aforementioned compound.

(2) Synthesis of (3S*,3aS*,6R*,7R*,7aS*)-N-(pyridin-4-yl)methyl-1,7-diisobutyl-1,2,3,6,7,7a-hexahydro-3aH-3,6-methanopyrrolo[3,2-b]pyridine-3a-carboxamide and (3S*,3aR*,6S*,7R*,7aR*)-N-(pyridin-4-yl)methyl-1,7-diisobutyl-1,2,3,3a,7,7a-hexahydro-6H-3,6-methanopyrrolo[3,2-c]pyridine-6-carboxamide 4A molecular sieves, 4-methylpentanal, and N-isobutyl prop-2-en-1-amine were added to a chloroform solution of N-(pyridin-4-yl)methyl-1,2,4-triazine-3-carboxamide, and the mixture was refluxed by heating. The molecular sieves were filtered and washed twice with chloroform. The combined organic layer was evaporated under reduced pressure, and the resulting residue was purified to obtain the aforementioned compound as a mixture.

(3) Synthesis of (3S*,3aS*,6R*,7R*,7aS*)-N-(pyridin-4-yl)methyl-1,7-diisobutyl-5-oxooctahydro-3aH-3,6-methanopyrrolo[3,2-b]pyridine-3a-carboxamide and (3S*,3aR*,6S*,7R*,7aR*)-N-(pyridin-4-yl)methyl-1,7-diisobutyl-4-oxooctahydro-6H-3,6-methanopyrrolo[3,2-c]pyridine-6-carboxamide Trifluoroacetic acid, 2,3-dimethyl-2-butene, aqueous 5 M sodium chlorite solution, and aqueous 5 M sodium dihydrogen phosphate solution were added to a toluene solution of a mixture of (3S*,3aS*,6R*,7R*,7aS*)-N-(pyridin-4-yl)methyl-1,7-diisobutyl-1,2,3,6,7,7a-hexahydro-3aH-3,6-methanopyrrolo[3,2-b]pyridine-3a-carboxamide and (3S*,3aR*,6S*,7R*,7aR*)-N-(pyridin-4-yl)methyl-1,7-diisobutyl-1,2,3,3a,7,7a-hexahydro-6H-3,6-methanopyrrolo[3,2-c]pyridine-6-carboxamide. The mixture was vigorously stirred at room temperature. Ethyl acetate was added to the reaction mixture. The organic layer was sequentially washed with water, aqueous 5% sodium thiosulfate solution, and saturated salt water, dried with anhydrous sodium sulfate, and filtered. Ethyl acetate was evaporated under reduced pressure from the filtrate. The residue including toluene was purified in a column to obtain the aforementioned compound.

The following compounds are synthesized under the same conditions as this reaction.

(3S*,3aS*,6R*,7R*,7aS*)-N-(pyridin-3-yl)methyl-1,7-di-isobutyl-1,2,3,6,7,7a-hexahydro-3aH-3,6-methanopyrrolo[3,2-b]pyridine-3a-carboxamide, (3S*,3aR*,6S*,7R*,7aR*)-N-(pyridin-3-yl)methyl-1,7-di-isobutyl-1,2,3,3a,7,7a-hexahydro-6H-3,6-methanopyrrolo[3,2-c]pyridine-6-carboxamide, (3S*,3aS*,6R*,7R*,7aS*)-N-(pyridin-2-yl)methyl-1,7-di-isobutyl-1,2,3,6,7,7a-hexahydro-3aH-3,6-methanopyrrolo[3,2-b]pyridine-3a-carboxamide, (3S*,3aR*,6S*,7R*,7aR*)-N-(pyridin-2-yl)methyl-1,7-di-isobutyl-1,2,3,3a,7,7a-hexahydro-6H-3,6-methanopyrrolo[3,2-c]pyridine-6-carboxamide, (3S*,3aS*,6R*,7R*,7aS*)-N-(2-thienyl)methyl-1,7-di-isobutyl-1,2,3,6,7,7a-hexahydro-3aH-3,6-methanopyrrolo[3,2-b]pyridine-3a-carboxamide, (3S*,3aR*,6S*,7R*,7aR*)-N-(2-thienyl)methyl-1,7-di-isobutyl-1,2,3,3a,7,7a-hexahydro-6H-3,6-methanopyrrolo[3,2-c]pyridine-6-carboxamide, (3S*,3aS*,6R*,7R*,7aS*)-N-(3-thienyl)methyl-1,7-di-isobutyl-1,2,3,6,7,7a-hexahydro-3aH-3,6-methanopyrrolo[3,2-b]pyridine-3a-carboxamide, and (3S*,3aR*,6S*,7R*,7aR*)-N-(3-thienyl)methyl-1,7-di-isobutyl-1,2,3,3a,7,7a-hexahydro-6H-3,6-methanopyrrolo[3,2-c]pyridine-6-carboxamide.

Example 4: Assay Method for Anti-Rabies Virus Activity

In the Example described above, each tested compound prepared as a 10 mM with DMSO was first diluted to 100 µM or 40 µM with 10% fetal bovine serum-supplemented Eagle's minimal essential medium (hereinafter, medium), and further diluted with the medium to the final concentration of interest. Fifty microliters of the diluted medium was added dropwise to each well of a 96-well plate. Furthermore, 50 µl of medium comprising $4 \times 10^2$ infectious units of the recombinant rabies virus 1088 strain expressing Gaussia Luciferase (GLuc) (1088/GLuc) and $4 \times 10^4$ Neuro-2a cells were added to each well. The plate was shaken for 30 seconds with a multiple microplate mixer NS-4P (AS ONE Corporation) and then cultured for 3 days at 37° C. in the presence of 5% $CO_2$. After incubation, 25 µL of coelenterazine, which is a substrate of the luciferase, was added dropwise to each well of the plate, and the plate was immediately loaded into a luminescent plate reader LuMate (Awareness Technology) and shaken for 10 seconds. The relative light unit (RLU) was then measured.

The compounds synthesized in the Example described above were tested. It was found that the compounds described in the following table exhibited anti-rabies virus activity that is equal to or greater than $IC_{50}$=30 µM of T-705 (generic name: Favipiravir), which is examined as an anti-rabies antiviral drug.

TABLE 7

| Compound No. | Compound name |
| --- | --- |
| I-2 | (3S ,3aR ,6S ,7R ,7aR )-N-benzyl-l-(4-chlorobenzyl)-7-isobutyl-4-oxooctahydro-6H-3,6-methanopyrrolo[3,2-c]pyridine-6-carboxamide |
| I-3 | (3S*,3aS*,6R*,7R*,7aS*)-N-benzyl-l-(4-chlorobenzyl)-7-isobutyl-5-oxooctahydro-3aH-3,6-methanopyrrolo[3,2-b]pyridine-3a-carboxamide |
| I-4 | Mixture of (3S*,3aR*,6S*,7R*,7aR*)-N-benzyl-l-(3-chlorobenzyl)-7-isobutyl-4-oxooctahydro-6H-3,6-methanopyrrolo[3,2-c]pyridine-6-carboxamide and (3S*,3aS*,6R*,7R*,7aS*)-N-benzyl-l-(3-chlorobenzyl)-7-isobutyl-5-oxooctahydro-3aH-3,6-methanopyrrolo[3,2-b]pyridine-3a-carboxamide |
| I-5 | (3S*,3aS*,6R*,7R*,7aS*)-N-benzyl-l-(3-chlorobenzyl)-7-isobutyl-5-oxooctahydro-3aH-3,6-methanopyrrolo[3,2-b]pyridine-3a-carboxamide |
| I-6 | (3S ,3aR ,6S ,7R ,7aR )-N-benzyl-7-isobutyl-l-(4-methoxybenzyl)-4-oxooctahydro-6H-3,6-methanopyrrolo[3,2-c] pyridine-6-carboxamide |
| I-22 | (3S ,3aS ,6R ,7R ,7aS )-N-benzyl-l,7-diisobutyl-5-oxooctahydro-3aH-3,6-methanopyrrolo[3,2-b]pyridine-3a-carboxamide |
| I-25 | (3S*,3aS*,6R*,7R*,7aS*)-N-benzyl-l-isobutyl-7-isopentyl-5-oxooctahydro-3aH-3,6-methanopyrrolo[3,2-b]pyridine-3a-carboxamide |
| I-26 | Mixture of (3S*,3aR*,6S*,7R*,7aR*)-N-benzyl-7-isobutyl-l-isopentyl-4-oxooctahydro-6H-3,6-methanopyrrolo[3,2-c]pyridine-6-carboxamide and (3S*,3aS*,6R*,7R*,7aS*)-N-benzyl-7-isobutyl-l-isopentyl-5-oxooctahydro-3aH-3,6-methanopyrrolo[3,2-b]pyridine-3a-carboxamide |
| I-27 | (3S*,3aS*,6R*,7R*,7aS*)-N-benzyl-7-isobutyl-l-isopentyl-5-oxooctahydro-3aH-3,6-methanopyrrolo[3,2-b]pyridine-3a-carboxamide |
| I-29 | (3S*,3aS*,6R*,7R*,7aS*)-N-benzyl-l-(4-(tert-butyl)benzyl)-7-isobutyl-5-oxooctahydro-3aH-3,6-methanopyrrolo[3,2-b]pyridine-3a-carboxamide |

The following table shows anti-rabies activity of compounds of formula IF, formula IB, formula XXIF, or formula XXIB. The compounds are classified as A if $IC_{50}$ is 5 UM or less, B if greater than 5 μM and less than or equal to 10 μM, and C if greater than 10 μm and less than or equal to 30 μM. The 'na' indicates not applicable.

[Table 8]

TABLE 8

| Compound No. | $R_1$ | $R_{2A}$ | $R_{2B}$ | $R_3$ | $R_4$ | Anti-rabies activity |
| --- | --- | --- | --- | --- | --- | --- |
| 1-2 | 4-Cl-Bnzl | H | Bnzl | i-Bu | H | C |
| 1-3 | 4-Cl-Bnzl | H | Bnzl | i-Bu | H | C |
| 1-4 | 3-Cl-Bnzl | H | Bnzl | i-Bu | H | A |
| 1-5 | 4-MeO-Bnzl | H | Bnzl | i-Bu | H | A |
| 1-6 | 4-MeO-Bnzl | H | Bnzl | i-Bu | H | B |
| 1-7 | 4-Me-Bnzl | H | Bnzl | i-Bu | H | C |
| 1-8 | 4-Me-Bnzl | H | Bnzl | i-Bu | H | C |
| 1-9 | Bnzl | H | i-Bu | i-Bu | H | na |
| 1-10 | Bnzl | H | i-Bu | i-Bu | H | na |
| 1-15 | i-Bu | H | i-Bu | Bnzl | H | na |
| 1-16 | i-Bu | H | i-Bu | i-Bu | H | C |
| 1-17 | 4-OH-Bnzl | H | Bnzl | i-Bu | H | na |
| 1-18 | i-Bu | H | i-Pnt | Bnzl | H | na |
| 1-19 | i-Bu | H | i-Pnt | Bnzl | H | na |
| 1-20 | i-Bu | H | i-Bu | Bnzl | H | na |
| 1-21 | i-Bu | H | Bnzl | i-Bu | H | na |
| 1-22 | i-Bu | H | Bnzl | i-Bu | H | C |
| 1-23 | i-Bu | H | 4-Cl-Bnzl | i-Bu | H | C |
| 1-24 | i-Bu | H | Bnzl | i-Pnt | H | na |
| 1-25 | i-Bu | H | Bnzl | i-Pnt | H | C |
| 1-26 | i-Pnt | H | Bnzl | i-Bu | H | C |
| 1-27 | i-Pnt | H | Bnzl | i-Bu | H | C |
| 1-28 | 4-(dimethylamino)benzyl | H | Bnzl | i-Bu | H | na |
| 1-29 | 4-tBu-Bnzl | H | Bnzl | i-Bu | H | C |
| 1-30 | 4-OH-Bnzl | H | Bnzl | i-Pnt | H | na |
| 1-31 | i-Pnt | H | 4-Cl-Bnzl | i-Bu | H | C |
| 1-32 | i-Pnt | H | 4-F-Bnzl | i-Bu | H | C |
| 1-33 | 4-(trifluoromethoxy)benzyl | H | Bnzl | i-Bu | H | na |
| 1-34 | 4-ethoxybenzyl | H | Bnzl | i-Bu | H | na |
| 1-35 | Bnzl | H | 4-OH-Bnzl | i-Bu | H | na |
| 1-36 | 4-MeO-Bnzl | H | 4-OH-Bnzl | i-Bu | H | na |
| 1-37 | 4-(dimethylamino)benzyl | H | 3-OH-Bnzl | i-Bu | H | na |
| 1-38 | 4-(dimethylamino)benzyl | H | 4-OH-Bnzl | i-Bu | H | na |
| 1-39 | 4-(dimethylamino)benzyl | H | 4-OH-Bnzl | i-Bu | H | na |
| IF-782 | Boc-6-Me-Indm | H | Chepm | i-Bu | H | C |
| IF-783 | 6-Me-Indm | H | Chepm | i-Bu | H | na |
| IF-784 | Boc-6-F-Indm | H | Chepm | i-Bu | H | na |
| IF-785 | 6-F-Indm | H | Chepm | i-Bu | H | na |
| IB-814 | Boc-6-Me-Indm | H | Chepm | i-Bu | H | C |
| IB-815 | 6-Me-Indm | H | Chepm | i-Bu | H | na |
| IB-816 | Boc-6-F-Indm | H | Chepm | i-Bu | H | na |
| IB-817 | 6-F-Indm | H | Chepm | i-Bu | H | C |

[Note]

As disclosed above, the present disclosure is exemplified by the use of its preferred embodiments. However, it is understood that the scope of the present disclosure should be interpreted based solely on the Claims. It is also understood that any patent, any patent application, and any other references cited herein should be incorporated herein by reference in the same manner as the contents are specifically described herein. The present application claims priority to Japanese Patent Application No. 2019-103958 filed on Jun. 3, 2019 and Japanese Patent Application No. 2020-23653 filed on Feb. 14, 2020 in Japan. The entire content thereof is incorporated herein by reference.

INDUSTRIAL APPLICABILITY

The present disclosure is useful in the field of rabies therapy and prevention.

The invention claimed is:
1. A compound represented by formula XXIF:

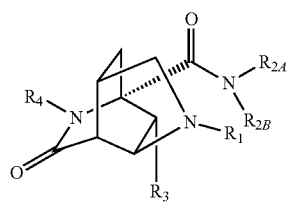

Formula XXIF or an enantiomer thereof, or a salt thereof, or a solvate thereof, wherein
$R_1$, $R_3$, and $R_4$ are each independently
hydrogen,
an optionally substituted hydrocarbon group,
an optionally substituted heterocycle,
optionally substituted carbonyl, or
an optionally substituted functional group, and
$R_{2A}$ and $R_{2B}$ are each independently
hydrogen,
an optionally substituted hydrocarbon group,
an optionally substituted heterocycle,
optionally substituted carbonyl, or
an optionally substituted functional group, or
$R_{2A}$ and $R_{2B}$, together with the nitrogen atom to which they are attached, form a heterocycle, wherein the heterocycles are each independently optionally substituted.

2. A compound represented by formula XXIB:

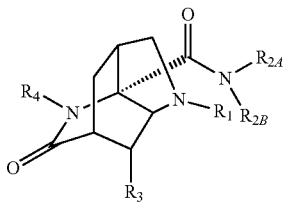

Formula XXIB or an enantiomer thereof, or a salt thereof, or a solvate thereof, wherein
$R_1$, $R_3$, and $R_4$ are each independently
hydrogen,
an optionally substituted hydrocarbon group,
an optionally substituted heterocycle,
optionally substituted carbonyl, or
an optionally substituted functional group, and
$R_{2A}$ and $R_{2B}$ are each independently
hydrogen,
an optionally substituted hydrocarbon group,
an optionally substituted heterocycle,
optionally substituted carbonyl, or
an optionally substituted functional group, or
$R_{2A}$ and $R_{2B}$, together with the nitrogen atom to which they are attached, form a heterocycle, wherein the heterocycles are each independently optionally substituted.

3. The compound, or an enantiomer thereof, or a salt thereof, or a solvate thereof according to claim 1, wherein
the alkyl, alkenyl, alkynyl, cycloalkyl, heterocycloalkyl, aryl, heteroaryl, and carbonyl of $R_1$, $R_3$, and $R_4$ are each independently optionally substituted with one to the maximum substitutable number of the same or different substituents selected from substituent group I, and
the alkyl, alkenyl, alkynyl, cycloalkyl, heterocycloalkyl, aryl, heteroaryl, carbonyl, and the non-aryl heterocycle and the heteroaryl ring of $R_{2A}$ and $R_{2B}$ are each independently optionally substituted with one to the maximum substitutable number of the same or different substituents selected from substituent group I.

4. The compound, or an enantiomer thereof, or a salt thereof, or a solvate thereof according to claim 1, wherein
$R_1$, $R_3$, and $R_4$ are each independently
hydrogen,
optionally substituted alkyl,
optionally substituted cycloalkyl,
optionally substituted heterocycloalkyl,
optionally substituted aryl,
optionally substituted heteroaryl, or
optionally substituted carbonyl, and
$R_{2A}$ and $R_{2B}$ are each independently
hydrogen,
optionally substituted alkyl,
optionally substituted cycloalkyl,
optionally substituted heterocycloalkyl,
optionally substituted aryl,
optionally substituted heteroaryl, or
optionally substituted carbonyl, or
$R_{2A}$ and $R_{2B}$, together with the nitrogen atom to which they are attached, form a non-aryl heterocycle or a heteroaryl ring,
wherein the non-aryl heterocycle and the heteroaryl ring are each independently optionally substituted.

5. The compound, or an enantiomer thereof, or a salt thereof, or a solvate thereof according to claim 1, wherein
$R_1$, $R_3$, and $R_4$ are each independently
hydrogen,
optionally substituted alkyl,
optionally substituted arylalkyl,
optionally substituted heteroarylalkyl,
optionally substituted cycloalkyl,
optionally substituted heterocycloalkyl,
optionally substituted aryl,
formyl,
optionally substituted alkylcarbonyl,
optionally substituted alkoxycarbonyl,
optionally substituted arylcarbonyl,
optionally substituted aryloxycarbonyl,
optionally substituted heteroarylcarbonyl,
optionally substituted heteroaryloxycarbonyl,
optionally substituted cycloalkylcarbonyl,
optionally substituted cycloalkyloxycarbonyl,
optionally substituted heterocycloalkylcarbonyl,
optionally substituted heterocycloalkyloxycarbonyl,
carbamoyl,
optionally substituted alkylcarbamoyl,
optionally substituted alkoxycarbamoyl,
optionally substituted arylcarbamoyl,
optionally substituted heteroarylcarbamoyl,
optionally substituted cycloalkylcarbamoyl, or
optionally substituted heterocycloalkylcarbamoyl,
wherein the groups of $R_1$, $R_3$, and $R_4$ are optionally substituted with one to the maximum substitutable number of the same or different substituents selected from substituent group II, and
$R_{2A}$ and $R_{2B}$ are each independently
hydrogen,
optionally substituted alkyl,
optionally substituted arylalkyl,
optionally substituted cycloalkyl,
optionally substituted heterocycloalkyl,
formyl,
optionally substituted alkylcarbonyl,
optionally substituted alkoxycarbonyl,
optionally substituted arylcarbonyl,
optionally substituted aryloxycarbonyl,
optionally substituted heteroarylcarbonyl, optionally substituted heteroaryloxycarbonyl,
optionally substituted cycloalkylcarbonyl,
optionally substituted cycloalkyloxycarbonyl,
optionally substituted heterocycloalkylcarbonyl,
optionally substituted heterocycloalkyloxycarbonyl,
carbamoyl,
optionally substituted alkylcarbamoyl,
optionally substituted alkoxycarbamoyl,
optionally substituted arylcarbamoyl,
optionally substituted heteroarylcarbamoyl,
optionally substituted cycloalkylcarbamoyl, or
optionally substituted heterocycloalkylcarbamoyl,
wherein the groups of $R_{2A}$ and $R_{2B}$ are optionally substituted with one to the maximum substitutable number of the same or different substituents selected from substituent group II, or
$R_{2A}$ and $R_{2B}$, together with the nitrogen atom to which they are attached, form a non-aryl heterocycle or a heteroaryl ring,
wherein the non-aryl heterocycle and the heteroaryl ring are each independently optionally substituted with one to the maximum substitutable number of the same or different substituents selected from substituent group II.

6. The compound, or an enantiomer thereof, or a salt thereof, or a solvate thereof according to claim 1, wherein $R_1$ and $R_4$ are each independently
hydrogen,
optionally substituted alkyl,
optionally substituted arylalkyl,
optionally substituted heteroarylalkyl,
optionally substituted cycloalkyl,
optionally substituted heterocycloalkyl,
formyl,
optionally substituted alkylcarbonyl,
optionally substituted alkoxycarbonyl,
optionally substituted arylcarbonyl,
optionally substituted aryloxycarbonyl,
optionally substituted cycloalkylcarbonyl,
optionally substituted cycloalkyloxycarbonyl,
optionally substituted heterocycloalkylcarbonyl,
optionally substituted heterocycloalkyloxycarbonyl,
carbamoyl,
optionally substituted alkylcarbamoyl,
optionally substituted alkoxycarbamoyl,
optionally substituted arylcarbamoyl,
optionally substituted heteroarylcarbamoyl,
optionally substituted cycloalkylcarbamoyl, or
optionally substituted heterocycloalkylcarbamoyl,
wherein the groups of $R_1$ and $R_4$ are optionally substituted with one to the maximum substitutable number of the same or different substituents selected from substituent group III.

7. The compound, or an enantiomer thereof, or a salt thereof, or a solvate thereof according to claim 1, wherein $R_1$ and $R_4$ are each independently
hydrogen,
optionally substituted alkyl,
optionally substituted arylalkyl,
optionally substituted heteroarylalkyl,
optionally substituted heterocycloalkyl,
formyl,
optionally substituted alkylcarbonyl,
optionally substituted alkoxycarbonyl,
optionally substituted arylcarbonyl, or
optionally substituted aryloxycarbonyl,
wherein the groups of $R_1$ and $R_4$ are optionally substituted with one to the maximum substitutable number of the same or different substituents selected from substituent group III.

8. The compound, or an enantiomer thereof, or a salt thereof, or a solvate thereof according to claim 1, wherein $R_1$ is
hydrogen;
alkyl;
alkyl substituted with one to the maximum substitutable number of the same or different substituents selected from the group consisting of hydroxy, substituted oxy, formyl, substituted carbonyl, amino, substituted amino, cycloalkyl, and substituted cycloalkyl;
arylalkyl;
arylalkyl substituted with one to the maximum substitutable number of the same or different substituents selected from the group consisting of halogen, alkyl, substituted alkyl, hydroxy, substituted oxy, amino, substituted amino, and nitro;
heteroarylalkyl;
heteroarylalkyl substituted with one to the maximum substitutable number of the same or different substituents selected from the group consisting of halogen, alkyl, substituted alkyl, hydroxy, substituted oxy, amino, substituted amino, and nitro;
cycloalkyl;
substituted cycloalkyl;
heterocycloalkyl;
substituted heterocycloalkyl; or
substituted carbonyl,
wherein the substituted oxy, substituted carbonyl, substituted amino, substituted cycloalkyl, substituted heterocycloalkyl, and substituted alkyl each independently have one to the maximum substitutable number of the same or different substituents selected from substituent group IV.

9. The compound, or an enantiomer thereof, or a salt thereof, or a solvate thereof according to claim 1, wherein $R_3$ is
alkyl;
alkyl substituted with one to the maximum substitutable number of the same or different substituents selected from the group consisting of hydroxy, substituted oxy, substituted carbonyl, amino, substituted amino, cycloalkyl, and substituted cycloalkyl;
arylalkyl;
arylalkyl substituted with one to the maximum substitutable number of the same or different substituents selected from the group consisting of halogen, alkyl, substituted alkyl, hydroxy, and substituted oxy;
aryl; or
substituted aryl,
wherein the substituted oxy, substituted carbonyl, substituted amino, substituted cycloalkyl, substituted alkyl, and substituted aryl each independently have one to the maximum substitutable number of the same or different substituents selected from substituent group IV.

10. The compound, or an enantiomer thereof, or a salt thereof, or a solvate thereof according to claim 1, wherein $R_{2A}$ and $R_{2B}$ are each independently
hydrogen;
alkyl;
alkyl substituted with one to the maximum substitutable number of the same or different substituents selected from the group consisting of hydroxy, substituted oxy, amino, substituted amino, cycloalkyl, and substituted cycloalkyl;

arylalkyl;

arylalkyl substituted with one to the maximum substitutable number of the same or different substituents selected from the group consisting of halogen, alkyl, substituted alkyl, hydroxy, and substituted oxy;

cycloalkyl;

substituted cycloalkyl;

heterocycloalkyl; or substituted heterocycloalkyl, wherein the substituted oxy, substituted amino, substituted alkyl, substituted cycloalkyl, and substituted heterocycloalkyl each independently have one to the maximum substitutable number of the same or different substituents selected from substituent group IV, or $R_{2A}$ and $R_{2B}$, together with the nitrogen atom to which they are attached, form a non-aryl heterocycle, wherein the non-aryl heterocycle is optionally substituted with one to the maximum substitutable number of the same or different substituents selected from substituent group VI.

11. The compound, or an enantiomer thereof, or a salt thereof, or a solvate thereof according to claim 1, wherein $R_4$ is hydrogen, alkyl, or substituted alkyl, wherein the substituted alkyl has one to the maximum substitutable number of the same or different substituents selected from the group consisting of halogen, carboxy, carbamoyl, amino, alkylamino, aryl, nitroaryl, and alkoxycarbonylamino.

12. The compound, or an enantiomer thereof, or a salt thereof, or a solvate thereof according to claim 1, wherein $R_1$ is hydrogen, methyl, propyl, isopropyl, isobutyl, sec-butyl, isopentyl, hexyl, amidinoaminopropyl, (tert-butoxycarbonyl-substituted amidinoamino) propyl, tert-butoxyethyl, tert-butoxypropyl, tert-butoxycarbonylethyl, carboxyethyl, hydroxyethyl, hydroxypropyl, tert-butoxycarbonylaminopropyl, cyclopentylmethyl, cyclohexylmethyl, cycloheptylmethyl, 5,6,7,8-tetrahydronaphthalenylmethyl, benzyl, phenylethyl, naphthalenylmethyl, fluorobenzyl, chlorobenzyl, methylbenzyl, dimethylbenzyl, tert-butylbenzyl, methoxybenzyl, ethoxybenzyl, tert-butoxybenzyl, trifluoromethylbenzyl, (trifluoromethoxy)benzyl, benzyloxybenzyl, aminobenzyl, (dimethylamino)benzyl, (cyclopentylcarbonylamino)benzyl, 6-methyl-1H-indol-3-ylmethyl, 6-fluoro-1H-indol-3-ylmethyl, 1-tert-butoxycarbonyl-6-methyl-1H-indol-3-ylmethyl, 1-tert-butoxycarbonyl-6-fluoro-1H-indol-3-ylmethyl, nitrobenzyl, hydroxybenzyl, cyclohexyl, isovaleryl, phenylacetyl, benzoyl, isopropyloxycarbonyl, phenoxycarbonyl, or tetrahydro-2H-pyranyl.

13. The compound, or an enantiomer thereof, or a salt thereof, or a solvate thereof according to claim 1, wherein $R_1$ is alkyl, substituted arylalkyl, or substituted heteroarylalkyl, $R_{2A}$ is hydrogen, and $R_{2B}$ is alkyl, arylalkyl, substituted arylalkyl, or optionally substituted cycloalkylalkyl, $R_3$ is alkyl, and $R_4$ is hydrogen.

14. The compound, or an enantiomer thereof, or a salt thereof, or a solvate thereof according to claim 1, wherein:

the compound is selected from the group consisting of:

(3S*,3aR*,6S*,7R*,7aR*)-N-benzyl-1-(4-chlorobenzyl)-7-isobutyl-4-oxooctahydro-6H-3,6-methanopyrrolo[3,2-c]pyridine-6-carboxamide;
(3S*,3aR*,6S*,7R*,7aR*)-N-benzyl-1-(3-chlorobenzyl)-7-isobutyl-4-oxooctahydro-6H-3,6-methanopyrrolo[3,2-c]pyridine-6-carboxamide, and
(3S*,3aS*,6R*,7R*,7aS*)-N-benzyl-1-(3-chlorobenzyl)-7-isobutyl-5-oxooctahydro-3aH-3,6-methanopyrrolo[3,2-b]pyridine-3a-carboxamide;
(3S*,3aR*,6S*,7R*,7aR*)-N-benzyl-7-isobutyl-1-(4-methoxybenzyl)-4-oxooctahydro-6H-3,6-methanopyrrolo[3,2-c]pyridine-6-carboxamide;
(3S*,3aR*,6S*,7R*,7aR*)-N-benzyl-7-isobutyl-1-(4-methylbenzyl)-4-oxooctahydro-6H-3,6-methanopyrrolo[3,2-c]pyridine-6-carboxamide;
(3S*,3aR*,6S*,7R*,7aR*)-7-benzyl-N-isobutyl-1-isopentyl-4-oxooctahydro-6H-3,6-methanopyrrolo[3,2-c]pyridine-6-carboxamide;
(3S*,3aR*,6S*,7R*,7aR*)-7-(4-chlorobenzyl)-N,1-diisobutyl-4-oxooctahydro-6H-3,6-methanopyrrolo[3,2-c]pyridine-6-carboxamide;
(3S*,3aR*,6S*,7R*,7aR*)-N-benzyl-1-(4-hydroxybenzyl)-7-isobutyl-4-oxooctahydro-6H-3,6-methanopyrrolo[3,2-c]pyridine-6-carboxamide, and
(3S*,3aS*,6R*,7R*,7aS*)-N-benzyl-1-(4-hydroxybenzyl)-7-isobutyl-5-oxooctahydro-3aH-3,6-methanopyrrolo[3,2-b]pyridine-3a-carboxamide;
(3S*,3aR*,6S*,7R*,7aR*)-7-benzyl-1-isobutyl-N-isopentyl-4-oxooctahydro-6H-3,6-methanopyrrolo[3,2-c]pyridine-6-carboxamide;
(3S*,3aR*,6S*,7R*,7aR*)-7-benzyl-N,1-diisobutyl-4-oxooctahydro-6H-3,6-methanopyrrolo[3,2-c]pyridine-6-carboxamide;
(3S*,3aR*,6S*,7R*,7aR*)-N-benzyl-1,7-diisobutyl-4-oxooctahydro-6H-3,6-methanopyrrolo[3,2-c]pyridine-6-carboxamide;
(3S*,3aR*,6S*,7R*,7aR*)-N-(4-chlorobenzyl)-1,7-diisobutyl-4-oxooctahydro-6H-3,6-methanopyrrolo[3,2-c]pyridine-6-carboxamide;
(3S*,3aR*,6S*,7R*,7aR*)-N-benzyl-1-isobutyl-7-isopentyl-4-oxooctahydro-6H-3,6-methanopyrrolo[3,2-c]pyridine-6-carboxamide;
(3S*,3aR*,6S*,7R*,7aR*)-N-benzyl-7-isobutyl-1-isopentyl-4-oxooctahydro-6H-3,6-methanopyrrolo[3,2-c]pyridine-6-carboxamide, and
(3S*,3aS*,6R*,7R*,7aS*)-N-benzyl-7-isobutyl-1-isopentyl-5-oxooctahydro-3aH-3,6-methanopyrrolo[3,2-b]pyridine-3a-carboxamide;
(3S*,3aR*,6S*,7R*,7aR*)-N-benzyl-1-(4-(dimethylamino)benzyl)-7-isobutyl-4-oxooctahydro-6H-3,6-methanopyrrolo[3,2-c]pyridine-6-carboxamide, and
(3S*,3aS*,6R*,7R*,7aS*)-N-benzyl-1-(4-(dimethylamino)benzyl)-7-isobutyl-5-oxooctahydro-3aH-3,6-methanopyrrolo[3,2-b]pyridine-3a-carboxamide;
(3S*,3aR*,6S*,7R*,7aR*)-N-benzyl-1-(4-hydroxybenzyl)-7-isopentyl-4-oxooctahydro-6H-3,6-methanopyrrolo[3,2-c]pyridine-6-carboxamide, and
(3S*,3aS*,6R*,7R*,7aS*)-N-benzyl-1-(4-hydroxybenzyl)-7-isopentyl-5-oxooctahydro-3aH-3,6-methanopyrrolo[3,2-b]pyridine-3a-carboxamide;
(3S*,3aR*,6S*,7R*,7aR*)-N-(4-fluorobenzyl)-7-isobutyl-1-isopentyl-4-oxooctahydro-6H-3,6-methanopyrrolo[3,2-c]pyridine-6-carboxamide, and
(3S*,3aS*,6R*,7R*,7aS*)-N-(4-fluorobenzyl)-7-isobutyl-1-isopentyl-5-oxooctahydro-3aH-3,6-methanopyrrolo[3,2-b]pyridine-3a-carboxamide;
(3S*,3aR*,6S*,7R*,7aR*)-N-benzyl-7-isobutyl-4-oxo-1-(4-(trifluorobenzyl)octahydro-6H-3,6-methanopyrrolo[3,2-c]pyridine-6-carboxamide, and
(3S*,3aS*,6R*,7R*,7aS*)-N-benzyl-7-isobutyl-5-oxo-1-(4-(trifluoromethoxy)benzyl)octahydro-3aH-3,6-methanopyrrolo[3,2-b]pyridine-3a-carboxamide;
(3S*,3aR*,6S*,7R*,7aR*)-N-benzyl-1-(4-ethoxybenzyl)-7-isobutyl-4-oxooctahydro-6H-3,6-methanopyrrolo[3,2-c]pyridine-6-carboxamide, and -continued (3S*,3aS*,6R*,7R*,7aS*)-N-benzyl-1-(4-ethoxybenzyl)-7-isobutyl-5-oxooctahydro-3aH-3,6-methanopyrrolo[3,2-b]pyridine-3a-carboxamide;
(3S*,3aR*,6S*,7R*,7aR*)-1-benzyl-N-(4-hydroxybenzyl)-7-isobutyl-4-oxooctahydro-6H-3,6-methanopyrrolo[3,2-c]pyridine-6-carboxamide, and
(3S*,3aS*,6R*,7R*,7aS*)-1-benzyl-N-(4-hydroxybenzyl)-7-isobutyl-5-oxooctahydro-3aH-3,6-methanopyrrolo[3,2-b]pyridine-3a-carboxamide;
(3S*,3aR*,6S*,7R*,7aR*)-N-(4-hydroxybenzyl)-7-isobutyl-1-(4-methoxybenzyl)-4-oxooctahydro-6H-3,6-methanopyrrolo[3,2-c]pyridine-6-carboxamide, and
(3S*,3aS*,6R*,7R*,7aS*)-N-(4-hydroxybenzyl)-7-isobutyl-1-(4-methoxybenzyl)-5-oxooctahydro-3aH-3,6-methanopyrrolo[3,2-b]pyridine-3a-carboxamide;
(3S*,3aR*,6S*,7R*,7aR*)-1-(4-(dimethylamino)benzyl)-N-(3-hydroxybenzyl)-7-isobutyl-4-oxooctahydro-6H-3,6-methanopyrrolo[3,2-c]pyridine-6-carboxamide, and
(3S*,3aS*,6R*,7R*,7aS*)-1-(4-(dimethylamino)benzyl)-N-(3-hydroxybenzyl)-7-isobutyl-5-oxooctahydro-3aH-3,6-methanopyrrolo[3,2-b]pyridine-3a-carboxamide;
(3S*,3aR*,6S*,7R*,7aR*)-1-(4-(dimethylamino)benzyl)-N-(4-hydroxybenzyl)-7-isobutyl-4-oxooctahydro-6H-3,6-methanopyrrolo[3,2-c]pyridine-6-carboxamide;
(3S*,3aR*,6S*,7R*,7aR*)-1-benzyl-N-cyclohexyl-4-oxo-7-propyloctahydro-6H-3,6-methanopyrrolo[3,2-c]pyridine-6-carboxamide;
(3S*,3aR*,6S*,7R*,7aR*)-1,7-dibenzyl-N-((1R,4S)-4-methylcyclohexyl)-4-oxooctahydro-6H-3,6-methanopyrrolo[3,2-c]pyridine-6-carboxamide;
(3S*,3aR*,6S*,7R*,7aR*)-1,7-dibenzyl-4-oxo-N-(2,2,6,6-tetramethylpiperidin-4-yl)octahydro-6H-3,6-methanopyrrolo[3,2-c]pyridine-6-carboxamide; and
(3S*,3aR*,6S*,7R*,7aR*)-N-benzyl-1-isobutyl-4-oxo-7-phenyloctahydro-6H-3,6-methanopyrrolo[3,2-c]pyridine-6-carboxamide, or the compound is a compound of Formula XXIF:

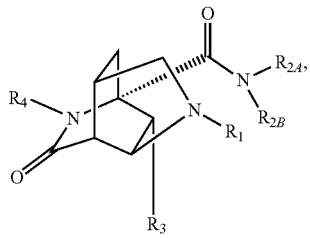

(XXIF)

wherein $R_1$, $R_{2A}$, $R_{2B}$, $R_3$ and $R_4$ are as defined below:

| $R_1$ | $R_{2A}$ | $R_{2B}$ | $R_3$ | $R_4$ |
|---|---|---|---|---|
| i-Bu | H | 1-Npm | Bnzl | H |
| i-Bu | H | i-Pr | Bnzl | H |
| i-Bu | H | 1-Npm | 1-Npm | H |
| i-Bu | H | i-Pr | 1-Npm | H |
| Bnzl | H | i-Bu | 1-Npm | H |
| Bnzl | H | Bnzl | 1-Npm | H |
| Bnzl | H | s-Bu | 1-Npm | H |
| Bnzl | H | 1-Npm | 1-Npm | H |
| i-Bu | H | i-Bu | 4-OH-Bnzl | H |
| i-Bu | H | Bnzl | 4-OH-Bnzl | H |
| i-Bu | H | 2-Cbx-Et | 4-OH-Bnzl | H |
| i-Bu | H | s-Bu | 4-OH-Bnzl | H |
| i-Bu | H | 1-Npm | 4-OH-Bnzl | H |
| i-Bu | H | i-Pr | 4-OH-Bnzl | H |
| i-Bu | H | 1-Npm | 2-Cbx-Et | H |
| Bnzl | H | 4-OH-Bnzl | Bnzl | H |
| Bnzl | H | i-Bu | 4-OH-Bnzl | H |
| Bnzl | H | Bnzl | 4-OH-Bnzl | H |
| Bnzl | H | 2-Cbx-Et | 4-OH-Bnzl | H |
| Bnzl | H | Bnzl | 2-Cbx-Et | H |
| Bnzl | H | 4-OH-Bnzl | 2-Cbx-Et | H |
| Bnzl | H | 1-Npm | 2-Cbx-Et | H |
| Bnzl | H | 4-OH-Bnzl | 1-Npm | H |
| Bnzl | H | 2-Cbx-Et | 1-Npm | H |
| 4-OH-Bnzl | H | Bnzl | Bnzl | H |
| 4-OH-Bnzl | H | 2-Cbx-Et | Bnzl | H |
| 4-OH-Bnzl | H | s-Bu | Bnzl | H |
| 4-OH-Bnzl | H | 1-Npm | Bnzl | H |
| 4-OH-Bnzl | H | Bnzl | 2-Cbx-Et | H |
| 4-OH-Bnzl | H | 1-Npm | 2-Cbx-Et | H |
| 4-OH-Bnzl | H | i-Bu | 1-Npm | H |
| 4-OH-Bnzl | H | Bnzl | 1-Npm | H |
| 4-OH-Bnzl | H | 2-Cbx-Et | 1-Npm | H |
| 4-OH-Bnzl | H | s-Bu | 1-Npm | H |
| 4-OH-Bnzl | H | 1-Npm | 1-Npm | H |
| i-Bu | H | s-Bu | Bnzl | H |
| i-Bu | H | i-Bu | 1-Npm | H |
| i-Bu | H | Bnzl | 1-Npm | H |
| Bnzl | H | i-Bu | Bnzl | H |
| Bnzl | H | s-Bu | Bnzl | H |
| Bnzl | H | 1-Npm | Bnzl | H |
| Bnzl | H | i-Pr | Bnzl | H |
| Bnzl | H | i-Pr | 1-Npm | H |
| 1-Npm | H | i-Bu | Bnzl | H |
| 1-Npm | H | s-Bu | Bnzl | H |
| 1-Npm | H | i-Pr | Bnzl | H |
| 1-Npm | H | Bnzl | 1-Npm | H |
| 1-Npm | H | s-Bu | 1-Npm | H |
| i-Bu | H | 4-OH-Bnzl | Bnzl | H |
| i-Bu | H | 2-Cbx-Et | Bnzl | H |
| i-Bu | H | i-Bu | 2-Cbx-Et | H |
| i-Bu | H | Bnzl | 2-Cbx-Et | H |
| i-Bu | H | 4-OH-Bnzl | 2-Cbx-Et | H |
| i-Bu | H | i-Pr | 2-Cbx-Et | H |
| i-Bu | H | 4-OH-Bnzl | 1-Npm | H |
| i-Bu | H | 2-Cbx-Et | 1-Npm | H |
| Bnzl | H | 2-Cbx-Et | Bnzl | H |
| Bnzl | H | s-Bu | 4-OH-Bnzl | H |
| Bnzl | H | 1-Npm | 4-OH-Bnzl | H |
| Bnzl | H | i-Pr | 4-OH-Bnzl | H |
| Bnzl | H | s-Bu | 2-Cbx-Et | H |
| Bnzl | H | i-Pr | 2-Cbx-Et | H |
| 4-OH-Bnzl | H | i-Pr | Bnzl | H |
| 4-OH-Bnzl | H | i-Pr | 2-Cbx-Et | H |
| 4-OH-Bnzl | H | i-Pr | 1-Npm | H |
| 2-Cbx-Et | H | i-Bu | Bnzl | H |
| 1-Npm | H | 4-OH-Bnzl | Bnzl | H |
| 1-Npm | H | Bnzl | 4-OH-Bnzl | H |
| 1-Npm | H | 2-Cbx-Et | 4-OH-Bnzl | H |
| 1-Npm | H | s-Bu | 4-OH-Bnzl | H |
| 1-Npm | H | 1-Npm | 4-OH-Bnzl | H |
| 1-Npm | H | i-Pr | 4-OH-Bnzl | H |
| 1-Npm | H | Bnzl | 2-Cbx-Et | H |
| 1-Npm | H | 4-OH-Bnzl | 2-Cbx-Et | H |
| 1-Npm | H | s-Bu | 2-Cbx-Et | H |
| 1-Npm | H | 1-Npm | 2-Cbx-Et | H |
| 1-Npm | H | 4-OH-Bnzl | 1-Npm | H |
| 1-Npm | H | 2-Cbx-Et | 1-Npm | H |
| i-Bu | H | i-Bu | i-Bu | H |
| i-Bu | H | s-Bu | i-Bu | H |
| i-Bu | H | 1-Npm | i-Bu | H |
| i-Bu | H | i-Pr | i-Bu | H |
| i-Bu | H | s-Bu | 1-Npm | H |
| Bnzl | H | Bnzl | i-Bu | H |
| Bnzl | H | 1-Npm | i-Bu | H |
| Bnzl | H | i-Pr | i-Bu | H |
| 1-Npm | H | i-Bu | i-Bu | H |
| 1-Npm | H | Bnzl | i-Bu | H |
| 1-Npm | H | s-Bu | i-Bu | H |
| 1-Npm | H | 1-Npm | i-Bu | H |
| 1-Npm | H | i-Bu | 1-Npm | H |
| 1-Npm | H | i-Pr | 1-Npm | H |
| i-Bu | H | 4-OH-Bnzl | i-Bu | H |
| i-Bu | H | 2-Cbx-Et | i-Bu | H |
| i-Bu | H | 3-Gun-Pr | 4-OH-Bnzl | H |

| R₁ | R₂ₐ | R₂ᵦ | R₃ | R₄ |
|---|---|---|---|---|
| i-Bu | H | 1-Npm | 3-Gun-Pr | H |
| Bnzl | H | 4-OH-Bnzl | i-Bu | H |
| Bnzl | H | i-Bu | 2-Cbx-Et | H |
| 2-Cbx-Et | H | Bnzl | i-Bu | H |
| 2-Cbx-Et | H | 4-OH-Bnzl | i-Bu | H |
| 2-Cbx-Et | H | s-Bu | i-Bu | H |
| 2-Cbx-Et | H | 1-Npm | i-Bu | H |
| 2-Cbx-Et | H | i-Pr | i-Bu | H |
| 2-Cbx-Et | H | 1-Npm | Bnzl | H |
| 2-Cbx-Et | H | Bnzl | 4-OH-Bnzl | H |
| 2-Cbx-Et | H | 1-Npm | 4-OH-Bnzl | H |
| 2-Cbx-Et | H | i-Bu | 1-Npm | H |
| 2-Cbx-Et | H | 4-OH-Bnzl | 1-Npm | H |
| 2-Cbx-Et | H | 1-Npm | 1-Npm | H |
| 2-Cbx-Et | H | i-Pr | 1-Npm | H |
| 1-Npm | H | 4-OH-Bnzl | i-Bu | H |
| 1-Npm | H | i-Bu | 4-OH-Bnzl | H |
| 1-Npm | H | i-Bu | 2-Cbx-Et | H |
| 1-Npm | H | i-Pr | 2-Cbx-Et | H |
| 1-Npm | H | 3-Gun-Pr | 1-Npm | H |
| Bnzl | H | i-Bu | i-Bu | H |
| Bnzl | H | s-Bu | i-Bu | H |
| 1-Npm | H | Bnzl | Bnzl | H |
| 1-Npm | H | i-Bu | Bnzl | H |
| i-Bu | H | 3-Gun-Pr | i-Bu | H |
| i-Bu | H | 3-Gun-Pr | Bnzl | H |
| i-Bu | H | s-Bu | 2-Cbx-Et | H |
| i-Bu | H | i-Bu | 3-Gun-Pr | H |
| i-Bu | H | Bnzl | 3-Gun-Pr | H |
| i-Bu | H | 4-OH-Bnzl | 3-Gun-Pr | H |
| i-Bu | H | s-Bu | 3-Gun-Pr | H |
| i-Bu | H | i-Pr | 3-Gun-Pr | H |
| i-Bu | H | 3-Gun-Pr | 1-Npm | H |
| Bnzl | H | 3-Gun-Pr | i-Bu | H |
| Bnzl | H | 3-Gun-Pr | Bnzl | H |
| Bnzl | H | 3-Gun-Pr | 4-OH-Bnzl | H |
| Bnzl | H | i-Bu | 3-Gun-Pr | H |
| Bnzl | H | Bnzl | 3-Gun-Pr | H |
| Bnzl | H | 4-OH-Bnzl | 3-Gun-Pr | H |
| Bnzl | H | s-Bu | 3-Gun-Pr | H |
| Bnzl | H | 1-Npm | 3-Gun-Pr | H |
| Bnzl | H | 3-Gun-Pr | 1-Npm | H |
| 2-Cbx-Et | H | i-Bu | i-Bu | H |
| 2-Cbx-Et | H | Bnzl | Bnzl | H |
| 2-Cbx-Et | H | 4-OH-Bnzl | Bnzl | H |
| 2-Cbx-Et | H | s-Bu | Bnzl | H |
| 2-Cbx-Et | H | i-Pr | Bnzl | H |
| 2-Cbx-Et | H | i-Bu | 4-OH-Bnzl | H |
| 2-Cbx-Et | H | i-Pr | 4-OH-Bnzl | H |
| 2-Cbx-Et | H | Bnzl | 1-Npm | H |
| 2-Cbx-Et | H | s-Bu | 1-Npm | H |
| 3-Gun-Pr | H | 1-Npm | i-Bu | H |
| 3-Gun-Pr | H | i-Pr | i-Bu | H |
| 3-Gun-Pr | H | 1-Npm | Bnzl | H |
| 3-Gun-Pr | H | i-Pr | Bnzl | H |
| 3-Gun-Pr | H | 1-Npm | 4-OH-Bnzl | H |
| 3-Gun-Pr | H | i-Pr | 4-OH-Bnzl | H |
| 3-Gun-Pr | H | 1-Npm | 1-Npm | H |
| 3-Gun-Pr | H | i-Pr | 1-Npm | H |
| i-Bu | H | i-Bu | 4-tBuO-Bnzl | H |
| i-Bu | H | Bnzl | 4-tBuO-Bnzl | H |
| i-Bu | H | tBOC-E | 4-tBuO-Bnzl | H |
| i-Bu | H | s-Bu | 4-tBuO-Bnzl | H |
| i-Bu | H | 1-Npm | 4-tBuO-Bnzl | H |
| i-Bu | H | i-Pr | 4-tBuO-Bnzl | H |
| i-Bu | H | 1-Npm | tBOC-E | H |
| Bnzl | H | 4-tBuO-Bnzl | Bnzl | H |
| Bnzl | H | i-Bu | 4-tBuO-Bnzl | H |
| Bnzl | H | Bnzl | 4-tBuO-Bnzl | H |
| Bnzl | H | tBOC-E | 4-tBuO-Bnzl | H |
| Bnzl | H | Bnzl | tBOC-E | H |
| Bnzl | H | 4-tBuO-Bnzl | tBOC-E | H |
| Bnzl | H | 1-Npm | tBOC-E | H |
| Bnzl | H | 4-tBuO-Bnzl | 1-Npm | H |
| Bnzl | H | tBOC-E | 1-Npm | H |
| 4-tBuO-Bnzl | H | Bnzl | Bnzl | H |
| 4-tBuO-Bnzl | H | tBOC-E | Bnzl | H |

| R₁ | R₂ₐ | R₂ᵦ | R₃ | R₄ |
|---|---|---|---|---|
| 4-tBuO-Bnzl | H | s-Bu | Bnzl | H |
| 4-tBuO-Bnzl | H | 1-Npm | Bnzl | H |
| 4-tBuO-Bnzl | H | Bnzl | tBOC-E | H |
| 4-tBuO-Bnzl | H | 1-Npm | tBOC-E | H |
| 4-tBuO-Bnzl | H | i-Bu | 1-Npm | H |
| 4-tBuO-Bnzl | H | Bnzl | 1-Npm | H |
| 4-tBuO-Bnzl | H | tBOC-E | 1-Npm | H |
| 4-tBuO-Bnzl | H | s-Bu | 1-Npm | H |
| 4-tBuO-Bnzl | H | 1-Npm | 1-Npm | H |
| i-Bu | H | 4-tBuO-Bnzl | Bnzl | H |
| i-Bu | H | tBOC-E | Bnzl | H |
| i-Bu | H | i-Bu | tBOC-E | H |
| i-Bu | H | Bnzl | tBOC-E | H |
| i-Bu | H | 4-tBuO-Bnzl | tBOC-E | H |
| i-Bu | H | i-Pr | tBOC-E | H |
| i-Bu | H | 4-tBuO-Bnzl | 1-Npm | H |
| i-Bu | H | tBOC-E | 1-Npm | H |
| Bnzl | H | tBOC-E | Bnzl | H |
| Bnzl | H | s-Bu | 4-tBuO-Bnzl | H |
| Bnzl | H | 1-Npm | 4-tBuO-Bnzl | H |
| Bnzl | H | i-Pr | 4-tBuO-Bnzl | H |
| Bnzl | H | s-Bu | tBOC-E | H |
| Bnzl | H | i-Pr | tBOC-E | H |
| 4-tBuO-Bnzl | H | i-Pr | Bnzl | H |
| 4-tBuO-Bnzl | H | i-Pr | tBOC-E | H |
| 4-tBuO-Bnzl | H | i-Pr | 1-Npm | H |
| tBOC-E | H | i-Bu | Bnzl | H |
| 1-Npm | H | 4-tBuO-Bnzl | Bnzl | H |
| 1-Npm | H | Bnzl | 4-tBuO-Bnzl | H |
| 1-Npm | H | tBOC-E | 4-tBuO-Bnzl | H |
| 1-Npm | H | s-Bu | 4-tBuO-Bnzl | H |
| 1-Npm | H | 1-Npm | 4-tBuO-Bnzl | H |
| 1-Npm | H | i-Pr | 4-tBuO-Bnzl | H |
| 1-Npm | H | Bnzl | tBOC-E | H |
| 1-Npm | H | 4-tBuO-Bnzl | tBOC-E | H |
| 1-Npm | H | s-Bu | tBOC-E | H |
| 1-Npm | H | 1-Npm | tBOC-E | H |
| 1-Npm | H | 4-tBuO-Bnzl | 1-Npm | H |
| 1-Npm | H | tBOC-E | 1-Npm | H |
| i-Bu | H | 4-tBuO-Bnzl | i-Bu | H |
| i-Bu | H | tBOC-E | i-Bu | H |
| i-Bu | H | 1-Npm | (tBOC)Gun-Pr | H |
| Bnzl | H | 4-tBuO-Bnzl | i-Bu | H |
| Bnzl | H | i-Bu | tBOC-E | H |
| tBOC-E | H | Bnzl | i-Bu | H |
| tBOC-E | H | 4-tBuO-Bnzl | i-Bu | H |
| tBOC-E | H | s-Bu | i-Bu | H |
| tBOC-E | H | 1-Npm | i-Bu | H |
| tBOC-E | H | i-Pr | i-Bu | H |
| tBOC-E | H | 1-Npm | Bnzl | H |
| tBOC-E | H | Bnzl | 4-tBuO-Bnzl | H |
| tBOC-E | H | 1-Npm | 4-tBuO-Bnzl | H |
| tBOC-E | H | i-Bu | 1-Npm | H |
| tBOC-E | H | 4-tBuO-Bnzl | 1-Npm | H |
| tBOC-E | H | 1-Npm | 1-Npm | H |
| tBOC-E | H | i-Pr | 1-Npm | H |
| 1-Npm | H | 4-tBuO-Bnzl | i-Bu | H |
| 1-Npm | H | i-Bu | 4-tBuO-Bnzl | H |
| 1-Npm | H | i-Bu | tBOC-E | H |
| 1-Npm | H | i-Pr | tBOC-E | H |
| 1-Npm | H | (tBOC)Gun-Pr | 1-Npm | H |
| i-Bu | H | (tBOC)Gun-Pr | i-Bu | H |
| i-Bu | H | (tBOC)Gun-Pr | Bnzl | H |
| i-Bu | H | s-Bu | tBOC-E | H |
| i-Bu | H | i-Bu | (tBOC)Gun-Pr | H |
| i-Bu | H | Bnzl | (tBOC)Gun-Pr | H |
| i-Bu | H | s-Bu | (tBOC)Gun-Pr | H |
| i-Bu | H | i-Pr | (tBOC)Gun-Pr | H |
| i-Bu | H | (tBOC)Gun-Pr | 1-Npm | H |
| Bnzl | H | (tBOC)Gun-Pr | i-Bu | H |
| Bnzl | H | (tBOC)Gun-Pr | Bnzl | H |
| Bnzl | H | i-Bu | (tBOC)Gun-Pr | H |
| Bnzl | H | Bnzl | (tBOC)Gun-Pr | H |
| Bnzl | H | s-Bu | (tBOC)Gun-Pr | H |
| Bnzl | H | 1-Npm | (tBOC)Gun-Pr | H |
| Bnzl | H | (tBOC)Gun-Pr | 1-Npm | H |
| tBOC-E | H | i-Bu | i-Bu | H |

-continued

| R₁ | R₂ₐ | R₂ᵦ | R₃ | R₄ |
|---|---|---|---|---|
| tBOC-E | H | Bnzl | Bnzl | H |
| tBOC-E | H | 4-tBuO-Bnzl | Bnzl | H |
| tBOC-E | H | s-Bu | Bnzl | H |
| tBOC-E | H | i-Pr | Bnzl | H |
| tBOC-E | H | i-Bu | 4-tBuO-Bnzl | H |
| tBOC-E | H | i-Pr | 4-tBuO-Bnzl | H |
| tBOC-E | H | Bnzl | 1-Npm | H |
| tBOC-E | H | s-Bu | 1-Npm | H |
| (tBOC)Gun-Pr | H | 1-Npm | i-Bu | H |
| (tBOC)Gun-Pr | H | i-Pr | i-Bu | H |
| (tBOC)Gun-Pr | H | 1-Npm | Bnzl | H |
| (tBOC)Gun-Pr | H | i-Pr | Bnzl | H |
| (tBOC)Gun-Pr | H | 1-Npm | 1-Npm | H |
| (tBOC)Gun-Pr | H | i-Pr | 1-Npm | H |
| Pr | H | Chm | Bnzl | H |
| 1-Npm | H | heptyl | Ph-Et | H |
| 1-Npm | H | pentyl | Ph-Et | H |
| 1-Npm | H | cyclohexyl | Ph-Et | H |
| 1-Npm | H | cyclopentyl | Ph-Et | H |
| 1-Npm | H | Hxy | 4-methylphenethyl | H |
| 1-Npm | H | Hxy | cyclohexylethyl | H |
| 3-tert-butoxy-propyl | H | 4-F-Bnzl | 1-Npm | H |
| 3-(tert-butoxy-carbonylamino)propyl | H | 3-(tert-butoxy-carbonylamino)propyl | 3-(tert-butoxycarbonyl amino)propyl | H |
| Pr | H | Bnzl | Chm | H |
| Pr | H | 2-methylbenzyl | Bnzl | H |
| Pr | H | (1,2,3,4-tetrahydro naphthalen-1-yl)methyl | Bnzl | H |
| Pr | H | Cpm | Bnzl | H |
| 1-Npm | H | Hxy | 3-methylphenethyl | H |
| Pr | H | Bnzl | Cpm | H |
| 1-Npm | H | Hxy | naphthalen-2-yl ethyl | H |
| 1-Npm | H | Hxy | 4-isopropyl-phenethyl | H |
| 1-Npm | H | β-hydroxyphenethyl | Ph-Et | H |
| 1-Npm | H | α-hydroxymethyl phenethyl | Ph-Et | H |
| 1-Npm | H | α-hydroxymethyl phenethyl | Ph-Et | H |
| 4-Nt-Bnzl | H | 4-tBuO-Bnzl | tBOC-E | H |
| 4-aminobenzyl | H | 4-tBuO-Bnzl | tBOC-E | H |
| 4-(cyclopentyl-carbonylamino)benzyl | H | 4-tBuO-Bnzl | tBOC-E | H |
| 4-(cyclopentyl-carbonylamino)benzyl | H | 4-OH-Bnzl | 2-Cbx-Et | H |
| 4-Nt-Bnzl | H | Bnzl | Bnzl | H |
| H | H | Bnzl | Bnzl | H |
| Cpm | H | Bnzl | Bnzl | H |
| cyclohexyl | H | Bnzl | Bnzl | H |
| 4-Nt-Bnzl | H | Hxy | Ph-Et | H |
| H | H | Hxy | Ph-Et | H |
| Isopropyl | H | Bnzl | Bnzl | H |
| s-Bu | H | Bnzl | Bnzl | H |
| Pr | H | Bnzl | Bnzl | H |
| 3-MeO-Bnzl | H | Hxy | Ph-Et | H |
| 2,3-dimethylbenzyl | H | Hxy | Ph-Et | H |
| 5,6,7,8-tetrahydro-naphthalen-1-yl-methyl | H | Hxy | Ph-Et | H |
| 4-Nt-Bnzl | H | Bnzl | tBOC-E | H |
| Ph-Et | H | Bnzl | i-Bu | H |
| i-Bu | H | Bnzl | Ph-Et | H |
| Bnzl | H | i-Bu | Ph-Et | H |
| 4-F-Bnzl | H | i-Bu | Bnzl | H |
| i-Bu | H | 4-F-Bnzl | Bnzl | H |
| i-Bu | H | i-Pnt | Bnzl | H |
| Bnzl | H | i-Pnt | i-Bu | H |
| i-Bu | H | Hxy | Bnzl | H |
| 4-F-Bnzl | H | Bnzl | Bnzl | H |
| Ph-Et | H | Bnzl | Bnzl | H |
| 2-OtBu-Et | H | 4-F-Bnzl | 1-Npm | H |
| 2-OH-Et | H | 4-F-Bnzl | 1-Npm | H |
| i-Bu | H | Bnzl | Bnzl | H |
| Bnzl | H | Bnzl | Bnzl | H |
| i-Bu | H | Bnzl | i-Bu | H |
| i-Bu | H | i-Bu | Bnzl | H |
| Chm | H | Bnzl | Bnzl | H |
| 1-Npm | H | 4-F-Bnzl | 2-OTBS-Et | H |
| 1-Npm | H | 4-F-Bnzl | 2-OH-Et | H |
| i-Pnt | H | Bnzl | Bnzl | H |
| Chm | H | 2-OtBu-Et | 1-Npm | H |
| Chm | H | 2-OH-Et | 1-Npm | H |
| 2-OtBu-Et | H | Bnzl | 1-Npm | H |
| 2-OH-Et | H | Bnzl | 1-Npm | H |
| tBOC-E | H | Bnzl | Ph-Et | H |
| 2-Cbx-Et | H | Bnzl | Ph-Et | H |
| i-Pnt | H | Bnzl | Ph-Et | H |
| i-Bu | H | Bnzl | i-Pnt | H |
| 4-F-Bnzl | H | Bnzl | i-Bu | H |
| 2-OtBu-Et | H | Ph-Et | 1-Npm | H |
| 4-tBuO-Bnzl | H | Bnzl | Ph-Et | H |
| Ph-Et | H | Hxy | 1-Npm | H |
| 4-OH-Bnzl | H | Bnzl | Ph-Et | H |
| 2-OH-Et | H | Ph-Et | 1-Npm | H |
| (tBOC)Gun-Pr | H | (tBOC)Gun-Pr | (tBOC)Gun-Pr | H |
| 4-tBuO-Bnzl | H | i-Bu | Bnzl | H |
| 4-tBuO-Bnzl | H | Bnzl | i-Bu | H |
| 4-OH-Bnzl | H | i-Bu | Bnzl | H |
| 4-OH-Bnzl | H | Bnzl | i-Bu | H |
| i-Bu | H | Ph-Et | Bnzl | H |
| Ph-Et | H | i-Bu | Bnzl | H |
| Bnzl | H | Ph-Et | i-Bu | H |
| i-Pnt | H | i-Bu | Bnzl | H |
| Chm | H | i-Bu | Bnzl | H |
| Bnzl | H | 4-F-Bnzl | i-Bu | H |
| i-Pnt | H | Bnzl | i-Bu | H |
| Chm | H | Bnzl | i-Bu | H |
| i-Bu | H | Bnzl | i-Pnt | H |
| Bnzl | H | Hxy | i-Bu | H |
| Ph-Et | H | i-Bu | i-Bu | H |
| Ph-Et | H | i-Bu | 1-Npm | H |
| Ph-Et | H | i-Bu | 4-tBuO-Bnzl | H |
| Ph-Et | H | i-Bu | 2-OTBS-Et | H |
| Ph-Et | H | i-Bu | 2-OH-Et | H |
| Ph-Et | H | i-Bu | i-Pnt | H |
| Ph-Et | H | i-Bu | 4-OH-Bnzl | H |
| Ph-Et | H | 1-Npm | Hxy | H |
| 1-Npm | H | Ph-Et | Hxy | H |
| Hxy | H | Ph-Et | 1-Npm | H |
| Hxy | H | 1-Npm | Ph-Et | H |
| 2-OtBu-Et | H | i-Pr | 1-Npm | H |
| tBOC-E | H | s-Bu | i-Pnt | H |
| 4-F-Bnzl | H | s-Bu | tBOC-E | H |
| i-Pnt | H | 2-OtBu-Et | i-Bu | H |
| Chm | H | 2-OtBu-Et | i-Bu | H |
| Chm | H | 2-OtBu-Et | i-Pnt | H |
| 2-OtBu-Et | H | Hxy | i-Bu | H |
| 2-OtBu-Et | H | Hxy | i-Pnt | H |
| 2-Cbx-Et | H | Bnzl | i-Pnt | H |
| Ph-Et | H | Bnzl | 2-Cbx-Et | H |
| 4-F-Bnzl | H | Bnzl | 2-Cbx-Et | H |
| i-Pnt | H | Bnzl | 2-Cbx-Et | H |
| i-Pnt | H | Bnzl | 2-OH-Et | H |
| Chm | H | Bnzl | 2-Cbx-Et | H |
| Chm | H | Bnzl | 2-OH-Et | H |
| 2-Cbx-Et | H | i-Bu | Ph-Et | H |
| 2-Cbx-Et | H | i-Bu | i-Pnt | H |
| 4-F-Bnzl | H | i-Bu | 2-Cbx-Et | H |
| 2-OH-Et | H | i-Bu | 2-Cbx-Et | H |
| i-Pnt | H | i-Bu | 4-OH-Bnzl | H |
| i-Pnt | H | i-Bu | 2-Cbx-Et | H |
| Chm | H | i-Bu | 4-OH-Bnzl | H |
| Chm | H | i-Bu | 2-Cbx-Et | H |
| 2-Cbx-Et | H | 1-Npm | Ph-Et | H |
| 2-Cbx-Et | H | 1-Npm | i-Pnt | H |
| Ph-Et | H | 1-Npm | 2-Cbx-Et | H |
| 4-F-Bnzl | H | 1-Npm | 2-Cbx-Et | H |
| i-Pnt | H | 1-Npm | 2-Cbx-Et | H |
| Chm | H | 1-Npm | 2-Cbx-Et | H |

| R₁ | R₂ₐ | R₂ᵦ | R₃ | R₄ |
|---|---|---|---|---|
| i-Bu | H | i-Pr | 2-OH-Et | H |
| 4-OH-Bnzl | H | i-Pr | Ph-Et | H |
| 4-OH-Bnzl | H | i-Pr | i-Pnt | H |
| 2-Cbx-Et | H | i-Pr | Ph-Et | H |
| Ph-Et | H | i-Pr | 2-Cbx-Et | H |
| Ph-Et | H | i-Pr | 2-OH-Et | H |
| 4-F-Bnzl | H | i-Pr | 2-Cbx-Et | H |
| 4-F-Bnzl | H | i-Pr | 2-OH-Et | H |
| 2-OH-Et | H | i-Pr | Bnzl | H |
| 2-OH-Et | H | i-Pr | 1-Npm | H |
| 2-OH-Et | H | i-Pr | 4-OH-Bnzl | H |
| 2-OH-Et | H | i-Pr | 2-Cbx-Et | H |
| 2-OH-Et | H | i-Pr | Ph-Et | H |
| 2-OH-Et | H | i-Pr | i-Pnt | H |
| i-Pnt | H | i-Pr | 4-OH-Bnzl | H |
| i-Pnt | H | i-Pr | 2-OH-Et | H |
| Chm | H | i-Pr | i-Bu | H |
| Chm | H | i-Pr | 4-OH-Bnzl | H |
| Chm | H | i-Pr | 2-Cbx-Et | H |
| Chm | H | i-Pr | 2-OH-Et | H |
| Chm | H | i-Pr | i-Pnt | H |
| i-Bu | H | s-Bu | i-Pnt | H |
| 4-OH-Bnzl | H | s-Bu | Ph-Et | H |
| 4-OH-Bnzl | H | s-Bu | i-Pnt | H |
| 2-Cbx-Et | H | s-Bu | Ph-Et | H |
| Ph-Et | H | s-Bu | 2-Cbx-Et | H |
| 2-OH-Et | H | s-Bu | 4-OH-Bnzl | H |
| 2-OH-Et | H | s-Bu | i-Pnt | H |
| i-Pnt | H | s-Bu | i-Bu | H |
| i-Pnt | H | s-Bu | 4-OH-Bnzl | H |
| i-Pnt | H | s-Bu | Ph-Et | H |
| i-Pnt | H | s-Bu | 2-OH-Et | H |
| Chm | H | s-Bu | i-Bu | H |
| Chm | H | s-Bu | 4-OH-Bnzl | H |
| Chm | H | s-Bu | 2-Cbx-Et | H |
| Chm | H | s-Bu | Ph-Et | H |
| Chm | H | s-Bu | 2-OH-Et | H |
| Chm | H | s-Bu | i-Pnt | H |
| i-Bu | H | 4-OH-Bnzl | i-Pnt | H |
| 2-Cbx-Et | H | 4-OH-Bnzl | Ph-Et | H |
| 2-Cbx-Et | H | 4-OH-Bnzl | i-Pnt | H |
| Ph-Et | H | 4-OH-Bnzl | 2-Cbx-Et | H |
| 4-F-Bnzl | H | 4-OH-Bnzl | 2-Cbx-Et | H |
| 2-OH-Et | H | 4-OH-Bnzl | 2-Cbx-Et | H |
| i-Pnt | H | 4-OH-Bnzl | 2-Cbx-Et | H |
| Chm | H | 4-OH-Bnzl | 2-Cbx-Et | H |
| i-Bu | H | 2-Cbx-Et | Ph-Et | H |
| i-Bu | H | 2-Cbx-Et | i-Pnt | H |
| 2-OH-Et | H | 2-Cbx-Et | i-Bu | H |
| 2-OH-Et | H | 2-Cbx-Et | i-Pnt | H |
| i-Pnt | H | 2-Cbx-Et | i-Bu | H |
| i-Pnt | H | 2-Cbx-Et | 4-OH-Bnzl | H |
| Chm | H | 2-Cbx-Et | i-Bu | H |
| Chm | H | 2-Cbx-Et | 4-OH-Bnzl | H |
| Chm | H | 2-Cbx-Et | i-Pnt | H |
| Bnzl | H | 4-F-Bnzl | 4-OH-Bnzl | H |
| Bnzl | H | 4-F-Bnzl | 2-Cbx-Et | H |
| i-Bu | H | 4-F-Bnzl | 4-OH-Bnzl | H |
| i-Bu | H | 4-F-Bnzl | 2-Cbx-Et | H |
| 1-Npm | H | 4-F-Bnzl | 4-OH-Bnzl | H |
| 1-Npm | H | 4-F-Bnzl | 2-Cbx-Et | H |
| 4-OH-Bnzl | H | 4-F-Bnzl | 2-Cbx-Et | H |
| 4-OH-Bnzl | H | 4-F-Bnzl | Ph-Et | H |
| 4-OH-Bnzl | H | 4-F-Bnzl | i-Pnt | H |
| 2-Cbx-Et | H | 4-F-Bnzl | 4-OH-Bnzl | H |
| 2-Cbx-Et | H | 4-F-Bnzl | Ph-Et | H |
| 2-Cbx-Et | H | 4-F-Bnzl | i-Pnt | H |
| Ph-Et | H | 4-F-Bnzl | 4-OH-Bnzl | H |
| Ph-Et | H | 4-F-Bnzl | 2-Cbx-Et | H |
| 2-OH-Et | H | 4-F-Bnzl | 4-OH-Bnzl | H |
| 2-OH-Et | H | 4-F-Bnzl | 2-Cbx-Et | H |
| i-Pnt | H | 4-F-Bnzl | 4-OH-Bnzl | H |
| i-Pnt | H | 4-F-Bnzl | 2-Cbx-Et | H |
| Chm | H | 4-F-Bnzl | 4-OH-Bnzl | H |
| Chm | H | 4-F-Bnzl | 2-Cbx-Et | H |
| i-Bu | H | i-Pnt | i-Bu | H |
| i-Bu | H | i-Pnt | 2-Cbx-Et | H |
| i-Bu | H | i-Pnt | 2-OH-Et | H |
| 4-OH-Bnzl | H | i-Pnt | 2-Cbx-Et | H |
| 2-Cbx-Et | H | i-Pnt | i-Bu | H |
| 2-Cbx-Et | H | i-Pnt | 4-OH-Bnzl | H |
| 2-OH-Et | H | i-Pnt | i-Bu | H |
| 2-OH-Et | H | i-Pnt | 2-Cbx-Et | H |
| Chm | H | i-Pnt | i-Bu | H |
| Chm | H | i-Pnt | 2-Cbx-Et | H |
| i-Bu | H | 2-OH-Et | i-Bu | H |
| i-Bu | H | 2-OH-Et | 4-OH-Bnzl | H |
| i-Bu | H | 2-OH-Et | 2-Cbx-Et | H |
| i-Bu | H | 2-OH-Et | i-Pnt | H |
| 1-Npm | H | 2-OH-Et | 4-OH-Bnzl | H |
| 4-OH-Bnzl | H | 2-OH-Et | Bnzl | H |
| 4-OH-Bnzl | H | 2-OH-Et | 1-Npm | H |
| 4-OH-Bnzl | H | 2-OH-Et | 2-Cbx-Et | H |
| 4-OH-Bnzl | H | 2-OH-Et | Ph-Et | H |
| 4-OH-Bnzl | H | 2-OH-Et | i-Pnt | H |
| 2-Cbx-Et | H | 2-OH-Et | Bnzl | H |
| 2-Cbx-Et | H | 2-OH-Et | i-Bu | H |
| 2-Cbx-Et | H | 2-OH-Et | 1-Npm | H |
| 2-Cbx-Et | H | 2-OH-Et | 4-OH-Bnzl | H |
| 2-Cbx-Et | H | 2-OH-Et | Ph-Et | H |
| 2-Cbx-Et | H | 2-OH-Et | i-Pnt | H |
| Ph-Et | H | 2-OH-Et | 2-Cbx-Et | H |
| 4-F-Bnzl | H | 2-OH-Et | 2-Cbx-Et | H |
| i-Pnt | H | 2-OH-Et | i-Bu | H |
| i-Pnt | H | 2-OH-Et | 2-Cbx-Et | H |
| Chm | H | 2-OH-Et | i-Bu | H |
| Chm | H | 2-OH-Et | i-Pnt | H |
| Bnzl | H | Ph-Et | 4-OH-Bnzl | H |
| Bnzl | H | Ph-Et | 2-Cbx-Et | H |
| i-Bu | H | Ph-Et | 4-OH-Bnzl | H |
| i-Bu | H | Ph-Et | 2-Cbx-Et | H |
| 1-Npm | H | Ph-Et | 4-OH-Bnzl | H |
| 1-Npm | H | Ph-Et | 2-Cbx-Et | H |
| 4-OH-Bnzl | H | Ph-Et | 2-Cbx-Et | H |
| 4-OH-Bnzl | H | Ph-Et | i-Pnt | H |
| 2-Cbx-Et | H | Ph-Et | 4-OH-Bnzl | H |
| 2-Cbx-Et | H | Ph-Et | i-Pnt | H |
| 4-F-Bnzl | H | Ph-Et | 4-OH-Bnzl | H |
| 4-F-Bnzl | H | Ph-Et | 2-Cbx-Et | H |
| 2-OH-Et | H | Ph-Et | 4-OH-Bnzl | H |
| 2-OH-Et | H | Ph-Et | 2-Cbx-Et | H |
| i-Pnt | H | Ph-Et | 4-OH-Bnzl | H |
| i-Pnt | H | Ph-Et | 2-Cbx-Et | H |
| Chm | H | Ph-Et | 4-OH-Bnzl | H |
| Chm | H | Ph-Et | 2-Cbx-Et | H |
| Bnzl | H | Hxy | 2-Cbx-Et | H |
| i-Bu | H | Hxy | i-Bu | H |
| i-Bu | H | Hxy | 2-Cbx-Et | H |
| i-Bu | H | Hxy | 2-OH-Et | H |
| i-Bu | H | Hxy | i-Pnt | H |
| 1-Npm | H | Hxy | 2-Cbx-Et | H |
| 4-OH-Bnzl | H | Hxy | 1-Npm | H |
| 4-OH-Bnzl | H | Hxy | 2-Cbx-Et | H |
| 2-Cbx-Et | H | Hxy | i-Bu | H |
| 2-Cbx-Et | H | Hxy | 1-Npm | H |
| 2-Cbx-Et | H | Hxy | 4-OH-Bnzl | H |
| 2-Cbx-Et | H | Hxy | i-Pnt | H |
| 4-F-Bnzl | H | Hxy | 2-Cbx-Et | H |
| 2-OH-Et | H | Hxy | i-Bu | H |
| 2-OH-Et | H | Hxy | 4-OH-Bnzl | H |
| 2-OH-Et | H | Hxy | 2-Cbx-Et | H |
| 2-OH-Et | H | Hxy | i-Pnt | H |
| i-Pnt | H | Hxy | 4-OH-Bnzl | H |
| i-Pnt | H | Hxy | 2-Cbx-Et | H |
| i-Pnt | H | Hxy | 2-OH-Et | H |
| Chm | H | Hxy | i-Bu | H |
| Chm | H | Hxy | 4-OH-Bnzl | H |
| Chm | H | Hxy | 2-Cbx-Et | H |
| Chm | H | Hxy | 2-OH-Et | H |
| Chm | H | Hxy | i-Pnt | H |
| 3-Gun-Pr | H | Bnzl | Ph-Et | H |
| Ph-Et | H | Bnzl | 3-Gun-Pr | H |
| 4-F-Bnzl | H | Bnzl | 3-Gun-Pr | H |
| 2-OH-Et | H | Bnzl | 3-Gun-Pr | H |

-continued

| R₁ | R₂ₐ | R₂ᵦ | R₃ | R₄ |
|---|---|---|---|---|
| i-Pnt | H | Bnzl | 3-Gun-Pr | H |
| Chm | H | Bnzl | 3-Gun-Pr | H |
| 3-Gun-Pr | H | i-Bu | Ph-Et | H |
| 3-Gun-Pr | H | i-Bu | i-Pnt | H |
| Ph-Et | H | i-Bu | 3-Gun-Pr | H |
| 4-F-Bnzl | H | i-Bu | 3-Gun-Pr | H |
| 2-OH-Et | H | i-Bu | 3-Gun-Pr | H |
| i-Pnt | H | i-Bu | 3-Gun-Pr | H |
| Chm | H | i-Bu | 3-Gun-Pr | H |
| 3-Gun-Pr | H | 1-Npm | i-Pnt | H |
| Ph-Et | H | 1-Npm | 3-Gun-Pr | H |
| 4-F-Bnzl | H | 1-Npm | 3-Gun-Pr | H |
| 2-OH-Et | H | 1-Npm | 3-Gun-Pr | H |
| i-Pnt | H | 1-Npm | 3-Gun-Pr | H |
| Ph-Et | H | i-Pr | 3-Gun-Pr | H |
| 4-F-Bnzl | H | i-Pr | 3-Gun-Pr | H |
| 2-OH-Et | H | i-Pr | 3-Gun-Pr | H |
| i-Pnt | H | i-Pr | 3-Gun-Pr | H |
| Chm | H | i-Pr | 3-Gun-Pr | H |
| 3-Gun-Pr | H | s-Bu | Ph-Et | H |
| Ph-Et | H | s-Bu | 3-Gun-Pr | H |
| 4-F-Bnzl | H | s-Bu | 3-Gun-Pr | H |
| 2-OH-Et | H | s-Bu | 3-Gun-Pr | H |
| i-Pnt | H | s-Bu | 3-Gun-Pr | H |
| Chm | H | s-Bu | 3-Gun-Pr | H |
| 3-Gun-Pr | H | 4-OH-Bnzl | Ph-Et | H |
| Chm | H | 4-OH-Bnzl | 3-Gun-Pr | H |
| i-Bu | H | 3-Gun-Pr | Ph-Et | H |
| i-Bu | H | 3-Gun-Pr | i-Pnt | H |
| 4-OH-Bnzl | H | 3-Gun-Pr | Ph-Et | H |
| 4-OH-Bnzl | H | 3-Gun-Pr | i-Pnt | H |
| Ph-Et | H | 3-Gun-Pr | i-Bu | H |
| Ph-Et | H | 3-Gun-Pr | 1-Npm | H |
| Ph-Et | H | 3-Gun-Pr | 4-OH-Bnzl | H |
| 4-F-Bnzl | H | 3-Gun-Pr | i-Bu | H |
| 4-F-Bnzl | H | 3-Gun-Pr | 1-Npm | H |
| 4-F-Bnzl | H | 3-Gun-Pr | 4-OH-Bnzl | H |
| 4-F-Bnzl | H | 3-Gun-Pr | i-Pnt | H |
| 2-OH-Et | H | 3-Gun-Pr | i-Pnt | H |
| i-Pnt | H | 3-Gun-Pr | Bnzl | H |
| i-Pnt | H | 3-Gun-Pr | i-Bu | H |
| i-Pnt | H | 3-Gun-Pr | 1-Npm | H |
| i-Pnt | H | 3-Gun-Pr | 4-OH-Bnzl | H |
| Chm | H | 3-Gun-Pr | i-Bu | H |
| Chm | H | 3-Gun-Pr | 1-Npm | H |
| Chm | H | 3-Gun-Pr | 4-OH-Bnzl | H |
| Chm | H | 3-Gun-Pr | Ph-Et | H |
| Chm | H | 3-Gun-Pr | i-Pnt | H |
| Bnzl | H | 4-F-Bnzl | 3-Gun-Pr | H |
| i-Bu | H | 4-F-Bnzl | 3-Gun-Pr | H |
| 1-Npm | H | 4-F-Bnzl | 3-Gun-Pr | H |
| 4-OH-Bnzl | H | 4-F-Bnzl | 3-Gun-Pr | H |
| 3-Gun-Pr | H | 4-F-Bnzl | Ph-Et | H |
| 4-tBuO-Bnzl | H | 2-OtBu-Et | i-Bu | H |
| Ph-Et | H | 2-OtBu-Et | Bnzl | H |
| Ph-Et | H | 2-OtBu-Et | i-Bu | H |
| Ph-Et | H | 2-OtBu-Et | 1-Npm | H |
| Ph-Et | H | 2-OtBu-Et | 4-tBuO-Bnzl | H |
| Ph-Et | H | 2-OtBu-Et | i-Pnt | H |
| 4-F-Bnzl | H | 2-OtBu-Et | Bnzl | H |
| 4-F-Bnzl | H | 2-OtBu-Et | i-Bu | H |
| 4-F-Bnzl | H | 2-OtBu-Et | 1-Npm | H |
| 4-F-Bnzl | H | 2-OtBu-Et | 4-tBuO-Bnzl | H |
| 4-F-Bnzl | H | 2-OtBu-Et | Ph-Et | H |
| 4-F-Bnzl | H | 2-OtBu-Et | i-Pnt | H |
| i-Pnt | H | 2-OtBu-Et | Bnzl | H |
| i-Pnt | H | 2-OtBu-Et | 1-Npm | H |
| i-Pnt | H | 2-OtBu-Et | 4-tBuO-Bnzl | H |
| i-Pnt | H | 2-OtBu-Et | Ph-Et | H |
| Chm | H | 2-OtBu-Et | Bnzl | H |
| Chm | H | 2-OtBu-Et | 4-tBuO-Bnzl | H |
| Chm | H | 2-OtBu-Et | Ph-Et | H |
| 4-F-Bnzl | H | i-Pnt | tBOC-E | H |
| Chm | H | i-Pnt | 4-tBuO-Bnzl | H |
| Bnzl | H | Hxy | 4-tBuO-Bnzl | H |
| i-Bu | H | Hxy | 4-tBuO-Bnzl | H |
| 4-tBuO-Bnzl | H | Hxy | Bnzl | H |
| 4-tBuO-Bnzl | H | Hxy | i-Bu | H |
| 4-tBuO-Bnzl | H | Hxy | Ph-Et | H |
| 4-tBuO-Bnzl | H | Hxy | i-Pnt | H |
| tBOC-E | H | Hxy | Ph-Et | H |
| Ph-Et | H | Hxy | 4-tBuO-Bnzl | H |
| 2-OtBu-Et | H | Hxy | Bnzl | H |
| 2-OH-Et | H | i-Bu | Bnzl | H |
| 2-OH-Et | H | i-Bu | i-Bu | H |
| 2-OH-Et | H | i-Bu | 1-Npm | H |
| 2-OH-Et | H | i-Bu | 4-OH-Bnzl | H |
| 2-OH-Et | H | i-Bu | Ph-Et | H |
| 2-OH-Et | H | i-Bu | i-Pnt | H |
| 2-OH-Et | H | Bnzl | Bnzl | H |
| 2-OH-Et | H | Bnzl | i-Bu | H |
| 2-OH-Et | H | Bnzl | 4-OH-Bnzl | H |
| 2-OH-Et | H | Bnzl | Ph-Et | H |
| 2-OH-Et | H | Bnzl | i-Pnt | H |
| 2-OH-Et | H | 1-Npm | Bnzl | H |
| 2-OH-Et | H | 1-Npm | i-Bu | H |
| Bnzl | H | 2-OH-Et | Bnzl | H |
| Bnzl | H | 2-OH-Et | i-Bu | H |
| Bnzl | H | 2-OH-Et | 1-Npm | H |
| Bnzl | H | 2-OH-Et | Ph-Et | H |
| Bnzl | H | 2-OH-Et | i-Pnt | H |
| i-Bu | H | 2-OH-Et | Bnzl | H |
| i-Bu | H | 2-OH-Et | 1-Npm | H |
| i-Bu | H | 2-OH-Et | Ph-Et | H |
| 1-Npm | H | 2-OH-Et | i-Bu | H |
| 1-Npm | H | 2-OH-Et | i-Pnt | H |
| 4-OH-Bnzl | H | 2-OH-Et | i-Bu | H |
| Ph-Et | H | 2-OH-Et | Bnzl | H |
| Ph-Et | H | 2-OH-Et | i-Bu | H |
| Ph-Et | H | 2-OH-Et | 1-Npm | H |
| Ph-Et | H | 2-OH-Et | 4-OH-Bnzl | H |
| Ph-Et | H | 2-OH-Et | i-Pnt | H |
| 4-F-Bnzl | H | 2-OH-Et | Bnzl | H |
| 4-F-Bnzl | H | 2-OH-Et | i-Bu | H |
| 4-F-Bnzl | H | 2-OH-Et | 1-Npm | H |
| 4-F-Bnzl | H | 2-OH-Et | 4-OH-Bnzl | H |
| 4-F-Bnzl | H | 2-OH-Et | Ph-Et | H |
| 4-F-Bnzl | H | 2-OH-Et | i-Pnt | H |
| i-Pnt | H | 2-OH-Et | Bnzl | H |
| i-Pnt | H | 2-OH-Et | 1-Npm | H |
| i-Pnt | H | 2-OH-Et | 4-OH-Bnzl | H |
| i-Pnt | H | 2-OH-Et | Ph-Et | H |
| Chm | H | 2-OH-Et | Bnzl | H |
| Chm | H | 2-OH-Et | 4-OH-Bnzl | H |
| Chm | H | 2-OH-Et | Ph-Et | H |
| 4-F-Bnzl | H | i-Pnt | 2-Cbx-Et | H |
| Chm | H | i-Pnt | 4-OH-Bnzl | H |
| Bnzl | H | Hxy | 4-OH-Bnzl | H |
| i-Bu | H | Hxy | 4-OH-Bnzl | H |
| 4-OH-Bnzl | H | Hxy | Bnzl | H |
| 4-OH-Bnzl | H | Hxy | i-Bu | H |
| 4-OH-Bnzl | H | Hxy | Ph-Et | H |
| 4-OH-Bnzl | H | Hxy | i-Pnt | H |
| 2-Cbx-Et | H | Hxy | Ph-Et | H |
| Ph-Et | H | Hxy | 4-OH-Bnzl | H |
| 2-OH-Et | H | Hxy | Bnzl | H |
| 2-OH-Et | H | Hxy | Ph-Et | H |
| 1-tert-butoxycarbonyl-6-methyl-1H-indol-3-ylmethyl | H | cycloheptylmethyl | i-Bu | H |
| 6-methyl-1H-indol-3-ylmethyl | H | cycloheptylmethyl | i-Bu | H |
| 1-tert-butoxycarbonyl-6-fluoro-1H-indol-3-ylmethyl | H | cycloheptylmethyl | i-Bu | H |
| 6-fluoro-1H-indol-3-ylmethyl | H | cycloheptylmethyl | i-Bu | H |
| Chm | H | pentyl | 3-Me-Bnzl | H |
| 1-Npm | H | β-hydroxyphenethyl | Ph-Et | H |
| 1-Npm | H | α-hydroxymethyl-phenethyl | Ph-Et | H |
| 1-Npm | H | α-hydroxymethyl phenethyl | Ph-Et | H |

-continued

| $R_1$ | $R_{2A}$ | $R_{2B}$ | $R_3$ | $R_4$ |
|---|---|---|---|---|
| 2-trifluoromethyl-benzyl | H | 4-tBuO-Bnzl | i-Bu | H |
| 2-trifluoromethyl-benzyl | H | 4-OH-Bnzl | i-Bu | H |
| 3-benzyloxybenzyl | H | 4-tBuO-Bnzl | i-Bu | H |
| 3-benzyloxybenzyl | H | 4-OH-Bnzl | i-Bu | H |
| Chm | H | pentyl | Bnzl | H |
| cycloheptylmethyl | H | pentyl | Bnzl | H |
| cycloheptylmethyl | H | pentyl | 3-Me-Bnzl | H |
| cyclopentylmethyl | H | Bnzl | Chm | H |
| 4-Me-Bnzl | H | 4-methoxybutyl | Pr | H |
| 4-Cl-Bnzl | H | 4-methoxybutyl | Pr | H |
| 3-Gun-Pr | H | 3-Gun-Pr | 3-Gun-Pr | H |
| 1-Npm | H | α-hydroxymethyl phenethyl | Ph-Et | H |
| 1-Npm | H | α-hydroxymethyl phenethyl | Ph-Et | H |
| 2-trifluoromethyl-benzyl | H | 4-tBuO-Bnzl | i-Bu | H |
| 2-trifluoromethyl-benzyl | H | 4-OH-Bnzl | i-Bu | H |
| 3-benzyloxybenzyl | H | 4-tBuO-Bnzl | i-Bu | H |
| 3-benzyloxybenzyl | H | 4-OH-Bnzl | i-Bu | H |
| Chm | H | pentyl | Bnzl | H |
| cycloheptylmethyl | H | pentyl | Bnzl | H |
| cycloheptylmethyl | H | pentyl | 3-Me-Bnzl | H |
| cyclopentylmethyl | H | Bnzl | Chm | H |
| 4-Me-Bnzl | H | 4-methoxybutyl | Pr | H |
| 4-Cl-Bnzl | H | 4-methoxybutyl | Pr | H |
| 3-Gun-Pr | H | 3-Gun-Pr | 3-Gun-Pr | H. |

15. A pharmaceutical composition comprising the compound or an enantiomer thereof, or a pharmaceutically acceptable salt thereof, or a solvate thereof according to claim 1 and a pharmaceutically acceptable carrier.

16. A method for preventing or treating an infection with Lyssavirus, characterized by administering, to a patient in need thereof, a therapeutically effective amount of the compound or an enantiomer thereof, or a pharmaceutically acceptable salt thereof, or a solvate thereof according to claim 1.

17. The method according to claim 16, wherein the infection with Lyssavirus is rabies.

18. The compound or an enantiomer thereof, or a salt thereof, or a solvate thereof according to claim 2, wherein
the alkyl, alkenyl, alkynyl, cycloalkyl, heterocycloalkyl, aryl, heteroaryl, and carbonyl of $R_1$, $R_3$, and $R_4$ are each independently optionally substituted with one to the maximum substitutable number of the same or different substituents selected from substituent group I, and
the alkyl, alkenyl, alkynyl, cycloalkyl, heterocycloalkyl, aryl, heteroaryl, carbonyl, and the non-aryl heterocycle and the heteroaryl ring of $R_{2A}$ and $R_{2B}$ are each independently optionally substituted with one to the maximum substitutable number of the same or different substituents selected from substituent group I.

19. The compound, or an enantiomer thereof, or a salt thereof, or a solvate thereof according to claim 2, wherein
$R_1$, $R_3$, and $R_4$ are each independently
hydrogen,
optionally substituted alkyl,
optionally substituted cycloalkyl,
optionally substituted heterocycloalkyl,
optionally substituted aryl,
optionally substituted heteroaryl, or
optionally substituted carbonyl, and $R_{2A}$ and $R_{2B}$ are each independently
hydrogen,
optionally substituted alkyl,
optionally substituted cycloalkyl,
optionally substituted heterocycloalkyl,
optionally substituted aryl,
optionally substituted heteroaryl, or
optionally substituted carbonyl, or $R_{2A}$ and $R_{2B}$, together with the nitrogen atom to which they are attached, form a non-aryl heterocycle or a heteroaryl ring,
wherein the non-aryl heterocycle and the heteroaryl ring are each independently optionally substituted.

20. The compound, or an enantiomer thereof, or a salt thereof, or a solvate thereof according to claim 2, wherein
$R_1$, $R_3$, and $R_4$ are each independently
hydrogen,
optionally substituted alkyl,
optionally substituted arylalkyl,
optionally substituted heteroarylalkyl,
optionally substituted cycloalkyl,
optionally substituted heterocycloalkyl,
optionally substituted aryl,
formyl,
optionally substituted alkylcarbonyl,
optionally substituted alkoxycarbonyl,
optionally substituted arylcarbonyl,
optionally substituted aryloxycarbonyl,
optionally substituted heteroarylcarbonyl,
optionally substituted heteroaryloxycarbonyl,
optionally substituted cycloalkylcarbonyl,
optionally substituted cycloalkyloxycarbonyl,
optionally substituted heterocycloalkylcarbonyl,
optionally substituted heterocycloalkyloxycarbonyl,
carbamoyl,
optionally substituted alkylcarbamoyl,
optionally substituted alkoxycarbamoyl,
optionally substituted arylcarbamoyl,
optionally substituted heteroarylcarbamoyl,
optionally substituted cycloalkylcarbamoyl, or
optionally substituted heterocycloalkylcarbamoyl,
wherein the groups of $R_1$, $R_3$, and $R_4$ are optionally substituted with one to the maximum substitutable number of the same or different substituents selected from substituent group II, and $R_{2A}$ and $R_{2B}$ are each independently
hydrogen,
optionally substituted alkyl,
optionally substituted arylalkyl,
optionally substituted cycloalkyl,
optionally substituted heterocycloalkyl,
formyl,
optionally substituted alkylcarbonyl,
optionally substituted alkoxycarbonyl,
optionally substituted arylcarbonyl,
optionally substituted aryloxycarbonyl,
optionally substituted heteroarylcarbonyl,
optionally substituted heteroaryloxycarbonyl,
optionally substituted cycloalkylcarbonyl,
optionally substituted cycloalkyloxycarbonyl,
optionally substituted heterocycloalkylcarbonyl,
optionally substituted heterocycloalkyloxycarbonyl,
carbamoyl,
optionally substituted alkylcarbamoyl,
optionally substituted alkoxycarbamoyl,
optionally substituted arylcarbamoyl,
optionally substituted heteroarylcarbamoyl, optionally substituted cycloalkylcarbamoyl, or
optionally substituted heterocycloalkylcarbamoyl,
wherein the groups of $R_{2A}$ and $R_{2B}$ are optionally substituted with one to the maximum substitutable number of the same or different substituents selected from substituent group II, or
$R_{2A}$ and $R_{2B}$, together with the nitrogen atom to which they are attached, form a non-aryl heterocycle or a heteroaryl ring,
wherein the non-aryl heterocycle and the heteroaryl ring are each independently optionally substituted with one to the maximum substitutable number of the same or different substituents selected from substituent group II.

21. The compound, or an enantiomer thereof, or a salt thereof, or a solvate thereof according to claim 2, wherein $R_1$ and $R_4$ are each independently
hydrogen,
optionally substituted alkyl,
optionally substituted arylalkyl,
optionally substituted heteroarylalkyl,
optionally substituted cycloalkyl,
optionally substituted heterocycloalkyl,
formyl,
optionally substituted alkylcarbonyl,
optionally substituted alkoxycarbonyl,
optionally substituted arylcarbonyl,
optionally substituted aryloxycarbonyl,
optionally substituted cycloalkylcarbonyl,
optionally substituted cycloalkyloxycarbonyl,
optionally substituted heterocycloalkylcarbonyl,
optionally substituted heterocycloalkyloxycarbonyl,
carbamoyl,
optionally substituted alkylcarbamoyl,
optionally substituted alkoxycarbamoyl,
optionally substituted arylcarbamoyl,
optionally substituted heteroarylcarbamoyl,
optionally substituted cycloalkylcarbamoyl, or
optionally substituted heterocycloalkylcarbamoyl,
wherein the groups of $R_1$ and $R_4$ are optionally substituted with one to the maximum substitutable number of the same or different substituents selected from substituent group III.

22. The compound, or an enantiomer thereof, or a salt thereof, or a solvate thereof according to claim 2, wherein $R_1$ and $R_4$ are each independently
hydrogen,
optionally substituted alkyl,
optionally substituted arylalkyl,
optionally substituted heteroarylalkyl,
optionally substituted heterocycloalkyl,
formyl,
optionally substituted alkylcarbonyl,
optionally substituted alkoxycarbonyl,
optionally substituted arylcarbonyl, or
optionally substituted aryloxycarbonyl,
wherein the groups of $R_1$ and $R_4$ are optionally substituted with one to the maximum substitutable number of the same or different substituents selected from substituent group III.

23. The compound, or an enantiomer thereof, or a salt thereof, or a solvate thereof according to claim 2, wherein $R_1$ is
hydrogen;
alkyl;
alkyl substituted with one to the maximum substitutable number of the same or different substituents selected from the group consisting of hydroxy, substituted oxy, formyl, substituted carbonyl, amino, substituted amino, cycloalkyl, and substituted cycloalkyl;
arylalkyl;
arylalkyl substituted with one to the maximum substitutable number of the same or different substituents selected from the group consisting of halogen, alkyl, substituted alkyl, hydroxy, substituted oxy, amino, substituted amino, and nitro;
heteroarylalkyl;
heteroarylalkyl substituted with one to the maximum substitutable number of the same or different substituents selected from the group consisting of halogen, alkyl, substituted alkyl, hydroxy, substituted oxy, amino, substituted amino, and nitro;
cycloalkyl;
substituted cycloalkyl;
heterocycloalkyl;
substituted heterocycloalkyl; or
substituted carbonyl,
wherein the substituted oxy, substituted carbonyl, substituted amino, substituted cycloalkyl, substituted heterocycloalkyl, and substituted alkyl each independently have one to the maximum substitutable number of the same or different substituents selected from substituent group IV.

24. The compound, or an enantiomer thereof, or a salt thereof, or a solvate thereof according to claim 2, wherein $R_3$ is
alkyl;
alkyl substituted with one to the maximum substitutable number of the same or different substituents selected from the group consisting of hydroxy, substituted oxy, substituted carbonyl, amino, substituted amino, cycloalkyl, and substituted cycloalkyl;
arylalkyl;
arylalkyl substituted with one to the maximum substitutable number of the same or different substituents selected from the group consisting of halogen, alkyl, substituted alkyl, hydroxy, and substituted oxy;
aryl; or
substituted aryl,
wherein the substituted oxy, substituted carbonyl, substituted amino, substituted cycloalkyl, substituted alkyl, and substituted aryl each independently have one to the maximum substitutable number of the same or different substituents selected from substituent group IV.

25. The compound, or an enantiomer thereof, or a salt thereof, or a solvate thereof according to claim 2, wherein $R_{2A}$ and $R_{2B}$ are each independently
hydrogen;
alkyl;
alkyl substituted with one to the maximum substitutable number of the same or different substituents selected from the group consisting of hydroxy, substituted oxy, amino, substituted amino, cycloalkyl, and substituted cycloalkyl;
arylalkyl;
arylalkyl substituted with one to the maximum substitutable number of the same or different substituents selected from the group consisting of halogen, alkyl, substituted alkyl, hydroxy, and substituted oxy;
cycloalkyl;
substituted cycloalkyl;
heterocycloalkyl; or
substituted heterocycloalkyl, wherein the substituted oxy, substituted amino, substituted alkyl, substituted cycloalkyl, and substituted heterocycloalkyl each independently have one to the maximum substitutable number of the same or different substituents selected from substituent group IV, or $R_{2A}$ and $R_{2B}$, together with the nitrogen atom to which they are attached, form a non-aryl heterocycle, wherein the non-aryl heterocycle is optionally substituted with one to the maximum substitutable number of the same or different substituents selected from substituent group VI.

26. The compound, or an enantiomer thereof, or a salt thereof, or a solvate thereof according to claim 2, wherein $R_4$ is hydrogen, alkyl, or substituted alkyl, wherein the substituted alkyl has one to the maximum substitutable number of the same or different substituents selected from the group consisting of halogen, carboxy, carbamoyl, amino, alkylamino, aryl, nitroaryl, and alkoxycarbonylamino.

27. The compound, or an enantiomer thereof, or a salt thereof, or a solvate thereof according to claim 2, wherein $R_1$ is hydrogen, methyl, propyl, isopropyl, isobutyl, sec-butyl, isopentyl, hexyl, amidinoaminopropyl, (tert-butoxycarbonyl-substituted amidinoamino) propyl, tert-butoxyethyl, tert-butoxypropyl, tert-butoxycarbonylethyl, carboxyethyl, hydroxyethyl, hydroxypropyl, tert-butoxycarbonylaminopropyl, cyclopentylmethyl, cyclohexylmethyl, cycloheptylmethyl, 5,6,7,8-tetrahydronaphthalenylmethyl, benzyl, phenylethyl, naphthalenylmethyl, fluorobenzyl, chlorobenzyl, methylbenzyl, dimethylbenzyl, tert-butylbenzyl, methoxybenzyl, ethoxybenzyl, tert-butoxybenzyl, trifluoromethylbenzyl, (trifluoromethoxy)benzyl, benzyloxybenzyl, aminobenzyl, (dimethylamino)benzyl, (cyclopentylcarbonylamino)benzyl, 6-methyl-1H-indol-3-ylmethyl, 6-fluoro-1H-indol-3-ylmethyl, 1-tert-butoxycarbonyl-6-methyl-1H-indol-3-ylmethyl, 1-tert-butoxycarbonyl-6-fluoro-1H-indol-3-ylmethyl, nitrobenzyl, hydroxybenzyl, cyclohexyl, isovaleryl, phenylacetyl, benzoyl, isopropyloxycarbonyl, phenoxycarbonyl, or tetrahydro-2H-pyranyl.

28. The compound, or an enantiomer thereof, or a salt thereof, or a solvate thereof according to claim 2, wherein
$R_1$ is alkyl, substituted arylalkyl, or substituted heteroarylalkyl,
$R_{2A}$ is hydrogen, and $R_{2B}$ is alkyl, arylalkyl, substituted arylalkyl, or optionally substituted cycloalkylalkyl,
$R_3$ is alkyl, and
$R_4$ is hydrogen.

29. The compound or an enantiomer thereof, or a salt thereof, or a solvate thereof according to claim 2, wherein:
the compound is selected from the group consisting of;

(3S*,3aS*,6R*,7R*,7aS*)-N,7-dibenzyl-1-methyl-5-oxooctahydro-3aH-3,6-methanopyrrolo[3,2-b]pyridine-3a-carboxamide;
(3S*,3aS*,6R*,7R*,7aS*)-N-benzyl-1-(4-chlorobenzyl)-7-isobutyl-5-oxooctahydro-3aH-3,6-methanopyrrolo[3,2-b]pyridine-3a-carboxamide;
(3S*,3aR*,6S*,7R*,7aR*)-N-benzyl-1-(3-chlorobenzyl)-7-isobutyl-4-oxooctahydro-6H-3,6-methanopyrrolo[3,2-c]pyridine-6-carboxamide, and
(3S*,3aS*,6R*,7R*,7aS*)-N-benzyl-1-(3-chlorobenzyl)-7-isobutyl-5-oxooctahydro-3aH-3,6-methanopyrrolo[3,2-b]pyridine-3a-carboxamide;
(3S*,3aS*,6R*,7R*,7aS*)-N-benzyl-7-isobutyl-1-(4-methoxybenzyl)-5-oxooctahydro-3aH-3,6-methanopyrrolo[3,2-b]pyridine-3a-carboxamide;
(3S*,3aS*,6R*,7R*,7aS*)-N-benzyl-7-isobutyl-1-(4-methylbenzyl)-5-oxooctahydro-3aH-3,6-methanopyrrolo[3,2-b]pyridine-3a-carboxamide;
(3S*,3aS*,6R*,7R*,7aS*)-1-benzyl-N,7-diisobutyl-5-oxooctahydro-3aH-3,6-methanopyrrolo[3,2-b]pyridine-3a-carboxamide;
(3S*,3aS*,6R*,7R*,7aS*)-7-benzyl-N-isobutyl-1-isopentyl-5-oxooctahydro-3aH-3,6-methanopyrrolo[3,2-b]pyridine-3a-carboxamide;
(3S*,3aS*,6R*,7R*,7aS*)-7-(4-chlorobenzyl)-N,1-diisobutyl-5-oxooctahydro-3aH-3,6-methanopyrrolo[3,2-b]pyridine-3a-carboxamide;
(3R*,3aS*,6R*,7R*,7aS*)-7-benzyl-N,1-diisobutyl-5-oxooctahydro-3aH-3,6-methanopyrrolo[3,2-b]pyridine-3a-carboxamide;
(3S*,3aS*,6R*,7R*,7aS*)-N-(4-chlorobenzyl)-1,7-diisobutyl-5-oxooctahydro-3aH-3,6-methanopyrrolo[3,2-b]pyridine-3a-carboxamide;
(3S*,3aR*,6S*,7R*,7aR*)-N-benzyl-1-(4-hydroxybenzyl)-7-isobutyl-4-oxooctahydro-6H-3,6-methanopyrrolo[3,2-c]pyridine-6-carboxamide, and
(3S*,3aS*,6R*,7R*,7aS*)-N-benzyl-1-(4-hydroxybenzyl)-7-isobutyl-5-oxooctahydro-3aH-3,6-methanopyrrolo[3,2-b]pyridine-3a-carboxamide;
(3S*,3aS*,6R*,7R*,7aS*)-7-benzyl-1-isobutyl-N-isopentyl-5-oxooctahydro-3aH-3,6-methanopyrrolo[3,2-b]pyridine-3a-carboxamide;
(3S*,3aS*,6R*,7R*,7aS*)-N-benzyl-1,7-diisobutyl-5-oxooctahydro-3aH-3,6-methanopyrrolo[3,2-b]pyridine-3a-carboxamide;
(3S*,3aS*,6R*,7R*,7aS*)-N-benzyl-1-isobutyl-7-isopentyl-5-oxooctahydro-3aH-3,6-methanopyrrolo[3,2-b]pyridine-3a-carboxamide;
(3S*,3aR*,6S*,7R*,7aR*)-N-benzyl-7-isobutyl-1-isopentyl-4-oxooctahydro-6H-3,6-methanopyrrolo[3,2-c]pyridine-6-carboxamide, and
(3S*,3aS*,6R*,7R*,7aS*)-N-benzyl-7-isobutyl-1-isopentyl-5-oxooctahydro-3aH-3,6-methanopyrrolo[3,2-b]pyridine-3a-carboxamide;
(3S*,3aS*,6R*,7R*,7aS*)-N-benzyl-7-isobutyl-1-isopentyl-5-oxooctahydro-3aH-3,6-methanopyrrolo[3,2-b]pyridine-3a-carboxamide;
(3S*,3aR*,6S*,7R*,7aR*)-N-benzyl-1-(4-(dimethylamino)benzyl)-7-isobutyl-4-oxooctahydro-6H-3,6-methanopyrrolo[3,2-c]pyridine-6-carboxamide, and
(3S*,3aS*,6R*,7R*,7aS*)-N-benzyl-1-(4-(dimethylamino)benzyl)-7-isobutyl-5-oxooctahydro-3aH-3,6-methanopyrrolo[3,2-b]pyridine-3a-carboxamide;
(3S*,3aS*,6R*,7R*,7aS*)-N-benzyl-1-(4-(tert-butyl)benzyl)-7-isobutyl-5-oxooctahydro-3aH-3,6-methanopyrrolo[3,2-b]pyridine-3a-carboxamide;
(3S*,3aR*,6S*,7R*,7aR*)-N-benzyl-1-(4-hydroxybenzyl)-7-isopentyl-4-oxooctahydro-6H-3,6-methanopyrrolo[3,2-c]pyridine-6-carboxamide, and
(3S*,3aS*,6R*,7R*,7aS*)-N-benzyl-1-(4-hydroxybenzyl)-7-isopentyl-5-oxooctahydro-3aH-3,6-methanopyrrolo[3,2-b]pyridine-3a-carboxamide;

-continued (3S*,3aS*,6R*,7R*,7aS*)-N-(4-chlorobenzyl)-7-isobutyl-1-isopentyl-5-oxooctahydro-3aH-3,6-methanopyrrolo[3,2-b]pyridine-3a-carboxamide;
(3S*,3aR*,6S*,7R*,7aR*)-N-(4-fluorobenzyl)-7-isobutyl-1-isopentyl-4-oxooctahydro-6H-3,6-methanopyrrolo[3,2-c]pyridine-6-carboxamide, and
(3S*,3aS*,6R*,7R*,7aS*)-N-(4-fluorobenzyl)-7-isobutyl-1-isopentyl-5-oxooctahydro-3aH-3,6-methanopyrrolo[3,2-b]pyridine-3a-carboxamide;
(3S*,3aR*,6S*,7R*,7aR*)-N-benzyl-7-isobutyl-4-oxo-1-(4-(trifluoromethoxy)benzyl)octahydro-6H-3,6-methanopyrrolo[3,2-c]pyridine-6-carboxamide, and
(3S*,3aS*,6R*,7R*,7aS*)-N-benzyl-7-isobutyl-5-oxo-1-(4-(trifluoromethoxy)benzyl)octahydro-3aH-3,6-methanopyrrolo[3,2-b]pyridine-3a-carboxamide;
(3S*,3aR*,6S*,7R*,7aR*)-N-benzyl-1-(4-ethoxybenzyl)-7-isobutyl-4-oxooctahydro-6H-3,6-methanopyrrolo[3,2-c]pyridine-6-carboxamide, and
(3S*,3aS*,6R*,7R*,7aS*)-N-benzyl-1-(4-ethoxybenzyl)-7-isobutyl-5-oxooctahydro-3aH-3,6-methanopyrrolo[3,2-b]pyridine-3a-carboxamide;
(3S*,3aR*,6S*,7R*,7aR*)-1-benzyl-N-(4-hydroxybenzyl)-7-isobutyl-4-oxooctahydro-6H-3,6-methanopyrrolo[3,2-c]pyridine-6-carboxamide, and
(3S*,3aS*,6R*,7R*,7aS*)-1-benzyl-N-(4-hydroxybenzyl)-7-isobutyl-5-oxooctahydro-3aH-3,6-methanopyrrolo[3,2-b]pyridine-3a-carboxamide;
(3S*,3aR*,6S*,7R*,7aR*)-N-(4-hydroxybenzyl)-7-isobutyl-1-(4-methoxybenzyl)-4-oxooctahydro-6H-3,6-methanopyrrolo[3,2-c]pyridine-6-carboxamide, and
(3S*,3aS*,6R*,7R*,7aS*)-N-(4-hydroxybenzyl)-7-isobutyl-1-(4-methoxybenzyl)-5-oxooctahydro-3aH-3,6-methanopyrrolo[3,2-b]pyridine-3a-carboxamide;
(3S*,3aR*,6S*,7R*,7aR*)-1-(4-(dimethylamino)benzyl)-N-(3-hydroxybenzyl)-7-isobutyl-4-oxooctahydro-6H-3,6-methanopyrrolo[3,2-c]pyridine-6-carboxamide, and
(3S*,3aS*,6R*,7R*,7aS*)-1-(4-(dimethylamino)benzyl)-N-(3-hydroxybenzyl)-7-isobutyl-5-oxooctahydro-3aH-3,6-methanopyrrolo[3,2-b]pyridine-3a-carboxamide;
(3S*,3aS*,6R*,7R*,7aS*)-1-(4-(dimethylamino)benzyl)-N-(4-hydroxybenzyl)-7-isobutyl-5-oxooctahydro-3aH-3,6-methanopyrrolo[3,2-b]pyridine-3a-carboxamide;
(3S*,3aS*,6R*,7R*,7aS*)-1-benzyl-N-cyclohexyl-5-oxo-7-propyloctahydro-3aH-3,6-methanopyrrolo[3,2-b]pyridine-3a-carboxamide;
(3S*,3aS*,6R*,7R*,7aS*)-1,7-dibenzyl-N-((1R,4S)-4-methylcyclohexyl)-5-oxooctahydro-3aH-3,6-methanopyrrolo[3,2-b]pyridine-3a-carboxamide;
(3S*,3aS*,6R*,7R*,7aS*)-1,7-dibenzyl-5-oxo-N-(2,2,6,6-tetramethylpiperidin-4-yl)octahydro-3aH-3,6-methanopyrrolo[3,2-b]pyridine-3a-carboxamide;
(3S*,3aS*,6R*,7R*,7aS*)-N-benzyl-1-cyclohexyl-7-isobutyl-5-oxooctahydro-3aH-3,6-methanopyrrolo[3,2-b]pyridine-3a-carboxamide;;
(3S*,3aS*,6R*,7S*,7aS*)-N-benzyl-1-cyclohexyl-5-oxo-7-phenyloctahydro-3aH-3,6-methanopyrrolo[3,2-b]pyridine-3a-carboxamide
(3S*,3aS*,6R*,7S*,7aS*)-N-benzyl-5-oxo-7-phenyl-1-(tetrahydro-2H-pyran-4-yl)octahydro-3aH-3,6-methanopyrrolo[3,2-b]pyridine-3a-carboxamide; and
(3S*,3aS*,6R*,7S*,7aS*)-N-benzyl-1-isobutyl-5-oxo-7-phenyloctahydro-3aH-3,6-methanopyrrolo[3,2-b]pyridine-3a-carboxamide, or the compound is a compound of Formula XXIB:

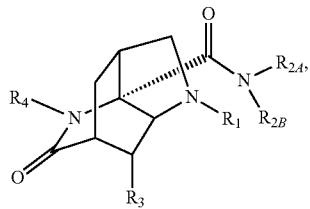

(XXIB)

wherein $R_1$, $R_{2A}$, $R_{2B}$, $R_3$ and $R_4$ are as defined below:

| $R_1$ | $R_{2A}$ | $R_{2B}$ | $R_3$ | $R_4$ |
|---|---|---|---|---|
| i-Bu | H | 1-Npm | Bnzl | H |
| i-Bu | H | i-Pr | Bnzl | H |
| i-Bu | H | 1-Npm | 1-Npm | H |
| i-Bu | H | i-Pr | 1-Npm | H |
| Bnzl | H | i-Bu | 1-Npm | H |
| Bnzl | H | Bnzl | 1-Npm | H |
| Bnzl | H | s-Bu | 1-Npm | H |
| Bnzl | H | 1-Npm | 1-Npm | H |
| Bnzl | H | i-Pr | 1-Npm | H |
| i-Bu | H | i-Bu | 4-OH-Bnzl | H |
| i-Bu | H | Bnzl | 4-OH-Bnzl | H |
| i-Bu | H | 2-Cbx-Et | 4-OH-Bnzl | H |
| i-Bu | H | s-Bu | 4-OH-Bnzl | H |

-continued

| R₁ | R₂ₐ | R₂ᵦ | R₃ | R₄ |
|---|---|---|---|---|
| i-Bu | H | 1-Npm | 4-OH-Bnzl | H |
| i-Bu | H | i-Pr | 4-OH-Bnzl | H |
| i-Bu | H | 1-Npm | 2-Cbx-Et | H |
| i-Bu | H | i-Pr | 2-Cbx-Et | H |
| Bnzl | H | 4-OH-Bnzl | Bnzl | H |
| Bnzl | H | i-Bu | 4-OH-Bnzl | H |
| Bnzl | H | Bnzl | 4-OH-Bnzl | H |
| Bnzl | H | 2-Cbx-Et | 4-OH-Bnzl | H |
| Bnzl | H | Bnzl | 2-Cbx-Et | H |
| Bnzl | H | 4-OH-Bnzl | 2-Cbx-Et | H |
| Bnzl | H | 1-Npm | 2-Cbx-Et | H |
| Bnzl | H | 4-OH-Bnzl | 1-Npm | H |
| Bnzl | H | 2-Cbx-Et | 1-Npm | H |
| 4-OH-Bnzl | H | i-Bu | Bnzl | H |
| 4-OH-Bnzl | H | Bnzl | Bnzl | H |
| 4-OH-Bnzl | H | 1-Npm | Bnzl | H |
| 4-OH-Bnzl | H | Bnzl | 2-Cbx-Et | H |
| i-Bu | H | 1-Npm | Bnzl | H |
| i-Bu | H | i-Pr | Bnzl | H |
| i-Bu | H | 1-Npm | 1-Npm | H |
| i-Bu | H | i-Pr | 1-Npm | H |
| Bnzl | H | i-Bu | 1-Npm | H |
| Bnzl | H | Bnzl | 1-Npm | H |
| Bnzl | H | s-Bu | 1-Npm | H |
| Bnzl | H | 1-Npm | 1-Npm | H |
| Bnzl | H | i-Pr | 1-Npm | H |
| i-Bu | H | i-Bu | 4-OH-Bnzl | H |
| i-Bu | H | Bnzl | 4-OH-Bnzl | H |
| i-Bu | H | 2-Cbx-Et | 4-OH-Bnzl | H |
| i-Bu | H | s-Bu | 4-OH-Bnzl | H |
| i-Bu | H | 1-Npm | 4-OH-Bnzl | H |
| i-Bu | H | i-Pr | 4-OH-Bnzl | H |
| i-Bu | H | 1-Npm | 2-Cbx-Et | H |
| i-Bu | H | i-Pr | 2-Cbx-Et | H |
| Bnzl | H | 4-OH-Bnzl | Bnzl | H |
| Bnzl | H | i-Bu | 4-OH-Bnzl | H |
| Bnzl | H | Bnzl | 4-OH-Bnzl | H |
| Bnzl | H | 2-Cbx-Et | 4-OH-Bnzl | H |
| Bnzl | H | Bnzl | 2-Cbx-Et | H |
| Bnzl | H | 4-OH-Bnzl | 2-Cbx-Et | H |
| Bnzl | H | 1-Npm | 2-Cbx-Et | H |
| Bnzl | H | 4-OH-Bnzl | 1-Npm | H |
| Bnzl | H | 2-Cbx-Et | 1-Npm | H |
| 4-OH-Bnzl | H | i-Bu | Bnzl | H |
| 4-OH-Bnzl | H | Bnzl | Bnzl | H |
| 4-OH-Bnzl | H | 1-Npm | Bnzl | H |
| 4-OH-Bnzl | H | Bnzl | 2-Cbx-Et | H |
| 4-OH-Bnzl | H | 1-Npm | 2-Cbx-Et | H |
| 4-OH-Bnzl | H | i-Bu | 1-Npm | H |
| 4-OH-Bnzl | H | Bnzl | 1-Npm | H |
| 4-OH-Bnzl | H | 2-Cbx-Et | 1-Npm | H |
| 4-OH-Bnzl | H | s-Bu | 1-Npm | H |
| 4-OH-Bnzl | H | 1-Npm | 1-Npm | H |
| i-Bu | H | s-Bu | Bnzl | H |
| i-Bu | H | i-Bu | 1-Npm | H |
| i-Bu | H | Bnzl | 1-Npm | H |
| Bnzl | H | i-Bu | Bnzl | H |
| Bnzl | H | s-Bu | Bnzl | H |
| Bnzl | H | 1-Npm | Bnzl | H |
| Bnzl | H | i-Pr | Bnzl | H |
| 1-Npm | H | s-Bu | Bnzl | H |
| 1-Npm | H | Bnzl | 1-Npm | H |
| 1-Npm | H | s-Bu | 1-Npm | H |
| i-Bu | H | 4-OH-Bnzl | Bnzl | H |
| i-Bu | H | 2-Cbx-Et | Bnzl | H |
| i-Bu | H | i-Bu | 2-Cbx-Et | H |
| i-Bu | H | Bnzl | 2-Cbx-Et | H |
| i-Bu | H | 4-OH-Bnzl | 2-Cbx-Et | H |
| i-Bu | H | s-Bu | 2-Cbx-Et | H |
| i-Bu | H | 4-OH-Bnzl | 1-Npm | H |
| i-Bu | H | 2-Cbx-Et | 1-Npm | H |
| Bnzl | H | 2-Cbx-Et | Bnzl | H |
| Bnzl | H | s-Bu | 4-OH-Bnzl | H |
| Bnzl | H | 1-Npm | 4-OH-Bnzl | H |
| Bnzl | H | i-Pr | 4-OH-Bnzl | H |
| Bnzl | H | s-Bu | 2-Cbx-Et | H |
| Bnzl | H | i-Pr | 2-Cbx-Et | H |

-continued

| R₁ | R₂ₐ | R₂ᵦ | R₃ | R₄ |
|---|---|---|---|---|
| 4-OH-Bnzl | H | i-Pr | Bnzl | H |
| 4-OH-Bnzl | H | i-Pr | 2-Cbx-Et | H |
| 4-OH-Bnzl | H | i-Pr | 1-Npm | H |
| 2-Cbx-Et | H | i-Bu | Bnzl | H |
| 2-Cbx-Et | H | Bnzl | Bnzl | H |
| 2-Cbx-Et | H | 4-OH-Bnzl | Bnzl | H |
| 2-Cbx-Et | H | s-Bu | Bnzl | H |
| 2-Cbx-Et | H | 1-Npm | Bnzl | H |
| 2-Cbx-Et | H | i-Bu | 4-OH-Bnzl | H |
| 2-Cbx-Et | H | Bnzl | 4-OH-Bnzl | H |
| 2-Cbx-Et | H | s-Bu | 4-OH-Bnzl | H |
| 2-Cbx-Et | H | 1-Npm | 4-OH-Bnzl | H |
| 2-Cbx-Et | H | i-Pr | 4-OH-Bnzl | H |
| 2-Cbx-Et | H | i-Bu | 1-Npm | H |
| 2-Cbx-Et | H | 4-OH-Bnzl | 1-Npm | H |
| 2-Cbx-Et | H | s-Bu | 1-Npm | H |
| 2-Cbx-Et | H | 1-Npm | 1-Npm | H |
| 1-Npm | H | 4-OH-Bnzl | Bnzl | H |
| 1-Npm | H | Bnzl | 4-OH-Bnzl | H |
| 1-Npm | H | 2-Cbx-Et | 4-OH-Bnzl | H |
| 1-Npm | H | s-Bu | 4-OH-Bnzl | H |
| 1-Npm | H | 1-Npm | 4-OH-Bnzl | H |
| 1-Npm | H | i-Pr | 4-OH-Bnzl | H |
| 1-Npm | H | i-Bu | 2-Cbx-Et | H |
| 1-Npm | H | Bnzl | 2-Cbx-Et | H |
| 1-Npm | H | 4-OH-Bnzl | 2-Cbx-Et | H |
| 1-Npm | H | s-Bu | 2-Cbx-Et | H |
| 1-Npm | H | 1-Npm | 2-Cbx-Et | H |
| 1-Npm | H | 4-OH-Bnzl | 1-Npm | H |
| 1-Npm | H | 2-Cbx-Et | 1-Npm | H |
| i-Bu | H | i-Bu | i-Bu | H |
| i-Bu | H | s-Bu | i-Bu | H |
| i-Bu | H | 1-Npm | i-Bu | H |
| i-Bu | H | i-Pr | i-Bu | H |
| i-Bu | H | s-Bu | 1-Npm | H |
| Bnzl | H | i-Bu | i-Bu | H |
| Bnzl | H | Bnzl | i-Bu | H |
| Bnzl | H | s-Bu | i-Bu | H |
| Bnzl | H | 1-Npm | i-Bu | H |
| Bnzl | H | i-Pr | i-Bu | H |
| 1-Npm | H | Bnzl | i-Bu | H |
| 1-Npm | H | i-Bu | Bnzl | H |
| 1-Npm | H | i-Bu | 1-Npm | H |
| 1-Npm | H | i-Pr | 1-Npm | H |
| i-Bu | H | 4-OH-Bnzl | i-Bu | H |
| i-Bu | H | 2-Cbx-Et | i-Bu | H |
| i-Bu | H | 3-Gun-Pr | 4-OH-Bnzl | H |
| i-Bu | H | 1-Npm | 3-Gun-Pr | H |
| Bnzl | H | 4-OH-Bnzl | i-Bu | H |
| Bnzl | H | i-Bu | 3-Gun-Pr | H |
| Bnzl | H | 4-OH-Bnzl | 3-Gun-Pr | H |
| 2-Cbx-Et | H | i-Bu | i-Bu | H |
| 2-Cbx-Et | H | Bnzl | i-Bu | H |
| 2-Cbx-Et | H | 4-OH-Bnzl | i-Bu | H |
| 2-Cbx-Et | H | s-Bu | i-Bu | H |
| 2-Cbx-Et | H | 1-Npm | i-Bu | H |
| 2-Cbx-Et | H | i-Pr | i-Bu | H |
| 2-Cbx-Et | H | Bnzl | 1-Npm | H |
| 2-Cbx-Et | H | i-Pr | 1-Npm | H |
| 1-Npm | H | 3-Gun-Pr | Bnzl | H |
| 1-Npm | H | i-Bu | 4-OH-Bnzl | H |
| 1-Npm | H | i-Pr | 2-Cbx-Et | H |
| 1-Npm | H | 1-Npm | 3-Gun-Pr | H |
| 1-Npm | H | i-Pr | 3-Gun-Pr | H |
| 1-Npm | H | 3-Gun-Pr | 1-Npm | H |
| 1-Npm | H | 1-Npm | i-Bu | H |
| 1-Npm | H | Bnzl | Bnzl | H |
| 1-Npm | H | 1-Npm | Bnzl | H |
| i-Bu | H | 3-Gun-Pr | i-Bu | H |
| i-Bu | H | 3-Gun-Pr | Bnzl | H |
| i-Bu | H | i-Bu | 3-Gun-Pr | H |
| i-Bu | H | Bnzl | 3-Gun-Pr | H |
| i-Bu | H | 4-OH-Bnzl | 3-Gun-Pr | H |
| i-Bu | H | s-Bu | 3-Gun-Pr | H |
| i-Bu | H | i-Pr | 3-Gun-Pr | H |
| i-Bu | H | 3-Gun-Pr | 1-Npm | H |
| Bnzl | H | 3-Gun-Pr | i-Bu | H |

-continued

| $R_1$ | $R_{2A}$ | $R_{2B}$ | $R_3$ | $R_4$ |
|---|---|---|---|---|
| Bnzl | H | 3-Gun-Pr | Bnzl | H |
| Bnzl | H | 3-Gun-Pr | 4-OH-Bnzl | H |
| Bnzl | H | i-Bu | 2-Cbx-Et | H |
| Bnzl | H | Bnzl | 3-Gun-Pr | H |
| Bnzl | H | s-Bu | 3-Gun-Pr | H |
| Bnzl | H | i-Pr | 3-Gun-Pr | H |
| Bnzl | H | 3-Gun-Pr | 1-Npm | H |
| 2-Cbx-Et | H | i-Pr | Bnzl | H |
| 3-Gun-Pr | H | 1-Npm | i-Bu | H |
| 3-Gun-Pr | H | i-Pr | i-Bu | H |
| 3-Gun-Pr | H | 1-Npm | Bnzl | H |
| 3-Gun-Pr | H | i-Pr | Bnzl | H |
| 3-Gun-Pr | H | 1-Npm | 4-OH-Bnzl | H |
| 3-Gun-Pr | H | i-Pr | 4-OH-Bnzl | H |
| 3-Gun-Pr | H | 1-Npm | 1-Npm | H |
| 3-Gun-Pr | H | i-Pr | 1-Npm | H |
| 1-Npm | H | 3-Gun-Pr | i-Bu | H |
| i-Bu | H | i-Bu | 4-tBuO-Bnzl | H |
| i-Bu | H | Bnzl | 4-tBuO-Bnzl | H |
| i-Bu | H | tBOC-E | 4-tBuO-Bnzl | H |
| i-Bu | H | s-Bu | 4-tBuO-Bnzl | H |
| i-Bu | H | 1-Npm | 4-tBuO-Bnzl | H |
| i-Bu | H | i-Pr | 4-tBuO-Bnzl | H |
| i-Bu | H | 1-Npm | tBOC-E | H |
| i-Bu | H | i-Pr | tBOC-E | H |
| Bnzl | H | 4-tBuO-Bnzl | Bnzl | H |
| Bnzl | H | i-Bu | 4-tBuO-Bnzl | H |
| Bnzl | H | Bnzl | 4-tBuO-Bnzl | H |
| Bnzl | H | tBOC-E | 4-tBuO-Bnzl | H |
| Bnzl | H | Bnzl | tBOC-E | H |
| Bnzl | H | 4-tBuO-Bnzl | tBOC-E | H |
| Bnzl | H | 1-Npm | tBOC-E | H |
| Bnzl | H | tBOC-E | 1-Npm | H |
| 4-tBuO-Bnzl | H | i-Bu | Bnzl | H |
| 4-tBuO-Bnzl | H | Bnzl | Bnzl | H |
| 4-tBuO-Bnzl | H | 1-Npm | Bnzl | H |
| 4-tBuO-Bnzl | H | Bnzl | tBOC-E | H |
| 4-tBuO-Bnzl | H | 1-Npm | tBOC-E | H |
| 4-tBuO-Bnzl | H | i-Bu | 1-Npm | H |
| 4-tBuO-Bnzl | H | Bnzl | 1-Npm | H |
| 4-tBuO-Bnzl | H | tBOC-E | 1-Npm | H |
| 4-tBuO-Bnzl | H | s-Bu | 1-Npm | H |
| 4-tBuO-Bnzl | H | 1-Npm | 1-Npm | H |
| i-Bu | H | 4-tBuO-Bnzl | Bnzl | H |
| i-Bu | H | tBOC-E | Bnzl | H |
| i-Bu | H | i-Bu | tBOC-E | H |
| i-Bu | H | Bnzl | tBOC-E | H |
| i-Bu | H | 4-tBuO-Bnzl | tBOC-E | H |
| i-Bu | H | s-Bu | tBOC-E | H |
| i-Bu | H | 4-tBuO-Bnzl | 1-Npm | H |
| i-Bu | H | tBOC-E | 1-Npm | H |
| Bnzl | H | tBOC-E | Bnzl | H |
| Bnzl | H | s-Bu | 4-tBuO-Bnzl | H |
| Bnzl | H | 1-Npm | 4-tBuO-Bnzl | H |
| Bnzl | H | i-Pr | 4-tBuO-Bnzl | H |
| Bnzl | H | s-Bu | tBOC-E | H |
| Bnzl | H | i-Pr | tBOC-E | H |
| 4-tBuO-Bnzl | H | i-Pr | Bnzl | H |
| 4-tBuO-Bnzl | H | i-Pr | tBOC-E | H |
| 4-tBuO-Bnzl | H | i-Pr | 1-Npm | H |
| tBOC-E | H | i-Bu | Bnzl | H |
| tBOC-E | H | Bnzl | Bnzl | H |
| tBOC-E | H | 4-tBuO-Bnzl | Bnzl | H |
| tBOC-E | H | s-Bu | Bnzl | H |
| tBOC-E | H | 1-Npm | Bnzl | H |
| tBOC-E | H | i-Bu | 4-tBuO-Bnzl | H |
| tBOC-E | H | Bnzl | 4-tBuO-Bnzl | H |
| tBOC-E | H | s-Bu | 4-tBuO-Bnzl | H |
| tBOC-E | H | 1-Npm | 4-tBuO-Bnzl | H |
| tBOC-E | H | i-Pr | 4-tBuO-Bnzl | H |
| tBOC-E | H | i-Bu | 1-Npm | H |
| tBOC-E | H | 4-tBuO-Bnzl | 1-Npm | H |
| tBOC-E | H | s-Bu | 1-Npm | H |
| tBOC-E | H | 1-Npm | 1-Npm | H |
| 1-Npm | H | 4-tBuO-Bnzl | Bnzl | H |
| 1-Npm | H | Bnzl | 4-tBuO-Bnzl | H |
| 1-Npm | H | tBOC-E | 4-tBuO-Bnzl | H |

-continued

| R₁ | R₂ₐ | R₂ᵦ | R₃ | R₄ |
|---|---|---|---|---|
| 1-Npm | H | s-Bu | 4-tBuO-Bnzl | H |
| 1-Npm | H | 1-Npm | 4-tBuO-Bnzl | H |
| 1-Npm | H | i-Pr | 4-tBuO-Bnzl | H |
| 1-Npm | H | i-Bu | tBOC-E | H |
| 1-Npm | H | Bnzl | tBOC-E | H |
| 1-Npm | H | 4-tBuO-Bnzl | tBOC-E | H |
| 1-Npm | H | s-Bu | tBOC-E | H |
| 1-Npm | H | 1-Npm | tBOC-E | H |
| 1-Npm | H | 4-tBuO-Bnzl | 1-Npm | H |
| 1-Npm | H | tBOC-E | 1-Npm | H |
| i-Bu | H | 4-tBuO-Bnzl | i-Bu | H |
| i-Bu | H | tBOC-E | i-Bu | H |
| i-Bu | H | 1-Npm | (tBOC)Gun-Pr | H |
| Bnzl | H | 4-tBuO-Bnzl | i-Bu | H |
| Bnzl | H | i-Bu | (tBOC)Gun-Pr | H |
| tBOC-E | H | i-Bu | i-Bu | H |
| tBOC-E | H | Bnzl | i-Bu | H |
| tBOC-E | H | 4-tBuO-Bnzl | i-Bu | H |
| tBOC-E | H | S-Bu | i-Bu | H |
| tBOC-E | H | 1-Npm | i-Bu | H |
| tBOC-E | H | i-Pr | i-Bu | H |
| tBOC-E | H | Bnzl | 1-Npm | H |
| tBOC-E | H | i-Pr | 1-Npm | H |
| 1-Npm | H | (tBOC)Gun-Pr | Bnzl | H |
| 1-Npm | H | i-Bu | 4-tBuO-Bnzl | H |
| 1-Npm | H | i-Pr | tBOC-E | H |
| 1-Npm | H | 1-Npm | (tBOC)Gun-Pr | H |
| 1-Npm | H | i-Pr | (tBOC)Gun-Pr | H |
| 1-Npm | H | (tBOC)Gun-Pr | 1-Npm | H |
| i-Bu | H | (tBOC)Gun-Pr | i-Bu | H |
| i-Bu | H | (tBOC)Gun-Pr | Bnzl | H |
| i-Bu | H | i-Bu | (tBOC)Gun-Pr | H |
| i-Bu | H | Bnzl | (tBOC)Gun-Pr | H |
| i-Bu | H | s-Bu | (tBOC)Gun-Pr | H |
| i-Bu | H | i-Pr | (tBOC)Gun-Pr | H |
| i-Bu | H | (tBOC)Gun-Pr | 1-Npm | H |
| Bnzl | H | (tBOC)Gun-Pr | i-Bu | H |
| Bnzl | H | (tBOC)Gun-Pr | Bnzl | H |
| Bnzl | H | i-Bu | tBOC-E | H |
| Bnzl | H | Bnzl | (tBOC)Gun-Pr | H |
| Bnzl | H | s-Bu | (tBOC)Gun-Pr | H |
| Bnzl | H | i-Pr | (tBOC)Gun-Pr | H |
| Bnzl | H | (tBOC)Gun-Pr | 1-Npm | H |
| tBOC-E | H | i-Pr | Bnzl | H |
| (tBOC)Gun-Pr | H | 1-Npm | i-Bu | H |
| (tBOC)Gun-Pr | H | i-Pr | i-Bu | H |
| (tBOC)Gun-Pr | H | 1-Npm | Bnzl | H |
| (tBOC)Gun-Pr | H | i-Pr | Bnzl | H |
| (tBOC)Gun-Pr | H | 1-Npm | 1-Npm | H |
| (tBOC)Gun-Pr | H | i-Pr | 1-Npm | H |
| 1-Npm | H | (tBOC)Gun-Pr | i-Bu | H |
| Pr | H | Chm | Bnzl | H |
| tBuO-E | H | 4-fluorophenethyl | 1-Npm | H |
| Hdr-E | H | 4-fluorophenethyl | 1-Npm | H |
| 1-Npm | H | heptyl | Ph—Et | H |
| 1-Npm | H | pentyl | Ph—Et | H |
| 1-Npm | H | cyclohexyl | Ph—Et | H |
| 1-Npm | H | cyclopentyl | Ph—Et | H |
| 1-Npm | pyrrolidine† | Ph—Et | H | |
| 1-Npm | H | Hxy | 4-methylphenethyl | H |
| 1-Npm | H | Hxy | cyclohexylethyl | H |
| tBuO-E | H | 4-Cl-Bnzl | 1-Npm | H |
| 3-tert-butoxypropyl | H | 4-F-Bnzl | 1-Npm | H |
| Hdr-E | H | 4-Cl-Bnzl | 1-Npm | H |
| 3-hydroxypropyl | H | 4-F-Bnzl | 1-Npm | H |
| 3-(tert-butoxycarbonyl-amino)propyl | H | 3-(tert-butoxycarbonyl-amino)propyl | 3-(tert-butoxycarbonyl-amino)propyl | H |
| Pr | H | Bnzl | Chm | H |
| Pr | H | 2-methylbenzyl | Bnzl | H |
| Pr | H | (1,2,3,4-tetrahydronaphthalen-1-yl)methyl | Bnzl | H |
| Pr | H | Cpm | Bnzl | H |
| 1-Npm | H | Hxy | 3-methylphenethyl | H |
| Pr | H | Bnzl | Cpm | H |
| 1-Npm | H | Hxy | naphthalen-2-yl ethyl | H |
| 1-Npm | H | Hxy | 4-isopropylphenethyl | H |

-continued

| R₁ | R₂ₐ | R₂ᵦ | R₃ | R₄ |
|---|---|---|---|---|
| 1-Npm | H | β-hydroxyphenethyl | Ph—Et | H |
| 1-Npm | H | α-hydroxymethyl phenethyl | Ph—Et | H |
| 1-Npm | H | α-hydroxymethyl phenethyl | Ph—Et | H |
| Cpm | H | 4-tBuO-Bnzl | tBOC-E | H |
| Cpm | H | 4-OH-Bnzl | 2-Cbx-Et | H |
| 4-Nt-Bnzl | H | 4-tBuO-Bnzl | tBOC-E | H |
| 4-Nt-Bnzl | H | Bnzl | Bnzl | H |
| H | H | Bnzl | Bnzl | H |
| 4-Nt-Bnzl | H | Hxy | Ph—Et | H |
| Cpm | H | Bnzl | Bnzl | H |
| cyclohexyl | H | Bnzl | Bnzl | H |
| H | H | Hxy | Ph—Et | H |
| isopropyl | H | Bnzl | Bnzl | H |
| s-Bu | H | Bnzl | Bnzl | H |
| 3-MeO-Bnzl | H | Hxy | Ph—Et | H |
| 2,3-dimethylbenzyl | H | Hxy | Ph—Et | H |
| 5,6,7,8-tetrahydro-naphthalen-1-ylmethyl | H | Hxy | Ph—Et | H |
| Pr | H | Bnzl | Bnzl | H |
| 1-Npm | H | Bnzl | isobutyl | Me |
| 4-Nt-Bnzl | H | Bnzl | tBOC-E | Me |
| H | H | Bnzl | tBOC-E | Me |
| phenylacetyl | H | Bnzl | tBOC-E | Me |
| phenylacetyl | H | Bnzl | 2-Cbx-Et | Me |
| 4-aminobenzyl | H | Bnzl | tBOC-E | Me |
| benzoyl | H | Bnzl | Bnzl | H |
| phenylacetyl | H | Bnzl | Bnzl | H |
| phenoxycarbonyl | H | Bnzl | Bnzl | H |
| isovaleryl | H | Bnzl | tBOC-E | Me |
| isopropyloxycarbonyl | H | Bnzl | tBOC-E | Me |
| Ph—Et | H | Bnzl | i-Bu | H |
| i-Bu | H | Bnzl | Ph—Et | H |
| Bnzl | H | i-Bu | Ph—Et | H |
| 4-F-Bnzl | H | i-Bu | Bnzl | H |
| i-Bu | H | 4-F-Bnzl | Bnzl | H |
| i-Bu | H | i-Pnt | Bnzl | H |
| Bnzl | H | i-Pnt | i-Bu | H |
| i-Bu | H | Hxy | Bnzl | H |
| 4-F-Bnzl | H | Bnzl | Bnzl | H |
| Ph—Et | H | Bnzl | Bnzl | H |
| 2-OtBu—Et | H | 4-F-Bnzl | 1-Npm | H |
| 2-OH—Et | H | 4-F-Bnzl | 1-Npm | H |
| i-Bu | H | Bnzl | Bnzl | H |
| Bnzl | H | Bnzl | Bnzl | H |
| i-Bu | H | Bnzl | i-Bu | H |
| i-Bu | H | i-Bu | Bnzl | H |
| Chm | H | Bnzl | Bnzl | H |
| 1-Npm | H | 4-F-Bnzl | 2-OTBS-Et | H |
| 1-Npm | H | 4-F-Bnzl | 2-OH—Et | H |
| i-Pnt | H | Bnzl | Bnzl | H |
| Chm | H | 2-OtBu—Et | 1-Npm | H |
| Chm | H | 2-OH—Et | 1-Npm | H |
| 2-OtBu—Et | H | Bnzl | 1-Npm | H |
| 2-OH—Et | H | Bnzl | 1-Npm | H |
| tBOC-E | H | Bnzl | Ph—Et | H |
| 2-Cbx-Et | H | Bnzl | Ph—Et | H |
| i-Pnt | H | Bnzl | Ph—Et | H |
| Bnzl | H | i-Bu | i-Pnt | H |
| 4-F-Bnzl | H | Bnzl | i-Bu | H |
| 2-OtBu—Et | H | Ph—Et | 1-Npm | H |
| 4-tBuO-Bnzl | H | Bnzl | Ph—Et | H |
| Ph—Et | H | Hxy | 1-Npm | H |
| 4-OH-Bnzl | H | Bnzl | Ph—Et | H |
| 2-OH—Et | H | Ph—Et | 1-Npm | H |
| (tBOC)Gun-Pr | H | (tBOC)Gun-Pr | (tBOC)Gun-Pr | H |
| 4-tBuO-Bnzl | H | Bnzl | i-Bu | H |
| 4-OH-Bnzl | H | Bnzl | i-Bu | H |
| i-Bu | H | Ph—Et | Bnzl | H |
| Ph—Et | H | i-Bu | Bnzl | H |
| Bnzl | H | Ph—Et | i-Bu | H |
| i-Pnt | H | i-Bu | Bnzl | H |
| Chm | H | i-Bu | Bnzl | H |
| Bnzl | H | 4-F-Bnzl | i-Bu | H |
| i-Pnt | H | Bnzl | i-Bu | H |
| Chm | H | Bnzl | i-Bu | H |

-continued

| R₁ | R₂ₐ | R₂ᵦ | R₃ | R₄ |
|---|---|---|---|---|
| i-Bu | H | Bnzl | i-Pnt | H |
| Bnzl | H | Hxy | i-Bu | H |
| Ph—Et | H | i-Bu | i-Bu | H |
| Ph—Et | H | i-Bu | 1-Npm | H |
| Ph—Et | H | i-Bu | 4-tBuO-Bnzl | H |
| Ph—Et | H | i-Bu | 2-OTBS-Et | H |
| Ph—Et | H | i-Bu | i-Pnt | H |
| Ph—Et | H | i-Bu | 4-OH-Bnzl | H |
| Ph—Et | H | i-Bu | 4-OH—Et | H |
| Ph—Et | H | 1-Npm | Hxy | H |
| 1-Npm | H | Ph—Et | Hxy | H |
| Hxy | H | Ph—Et | 1-Npm | H |
| Hxy | H | 1-Npm | Ph—Et | H |
| 2-OtBu—Et | H | Bnzl | tBOC-E | H |
| Ph—Et | H | i-Bu | tBOC-E | H |
| 2-OtBu—Et | H | i-Pr | Bnzl | H |
| 2-OtBu—Et | H | i-Pr | i-Bu | H |
| 2-OtBu—Et | H | i-Pr | 1-Npm | H |
| 2-OtBu—Et | H | i-Pr | Ph—Et | H |
| Ph—Et | H | 4-tBuO-Bnzl | tBOC-E | H |
| 2-OtBu—Et | H | i-Pnt | i-Bu | H |
| i-Bu | H | 2-OtBu—Et | i-Bu | H |
| i-Bu | H | 2-OtBu—Et | i-Pnt | H |
| i-Pnt | H | 2-OtBu—Et | i-Bu | H |
| Chm | H | 2-OtBu—Et | i-Bu | H |
| Chm | H | 2-OtBu—Et | i-Pnt | H |
| Ph—Et | H | Hxy | tBOC-E | H |
| 2-OtBu—Et | H | Hxy | i-Bu | H |
| 2-OtBu—Et | H | Hxy | i-Pnt | H |
| 2-Cbx-Et | H | Bnzl | i-Pnt | H |
| Ph—Et | H | Bnzl | 2-Cbx-Et | H |
| 4-F-Bnzl | H | Bnzl | 2-Cbx-Et | H |
| i-Pnt | H | Bnzl | 2-Cbx-Et | H |
| i-Pnt | H | Bnzl | 2-OH—Et | H |
| Chm | H | Bnzl | 2-Cbx-Et | H |
| Chm | H | Bnzl | 2-OH—Et | H |
| 2-Cbx-Et | H | i-Bu | Ph—Et | H |
| 2-Cbx-Et | H | i-Bu | i-Pnt | H |
| 4-F-Bnzl | H | i-Bu | 2-Cbx-Et | H |
| i-Pnt | H | i-Bu | 4-OH-Bnzl | H |
| i-Pnt | H | i-Bu | 2-Cbx-Et | H |
| Chm | H | i-Bu | 4-OH-Bnzl | H |
| Chm | H | i-Bu | 2-Cbx-Et | H |
| 2-Cbx-Et | H | 1-Npm | Ph—Et | H |
| 2-Cbx-Et | H | 1-Npm | 2-OH—Et | H |
| 2-Cbx-Et | H | 1-Npm | i-Pnt | H |
| Ph—Et | H | 1-Npm | 2-Cbx-Et | H |
| 4-F-Bnzl | H | 1-Npm | 2-Cbx-Et | H |
| 2-OH—Et | H | 1-Npm | 2-Cbx-Et | H |
| i-Pnt | H | 1-Npm | 2-Cbx-Et | H |
| Chm | H | 1-Npm | 2-Cbx-Et | H |
| i-Bu | H | i-Pr | 2-OH—Et | H |
| 4-OH-Bnzl | H | i-Pr | Ph—Et | H |
| 4-OH-Bnzl | H | i-Pr | 2-OH—Et | H |
| 4-OH-Bnzl | H | i-Pr | i-Pnt | H |
| 2-Cbx-Et | H | i-Pr | Ph—Et | H |
| 2-Cbx-Et | H | i-Pr | i-Pnt | H |
| Ph—Et | H | i-Pr | 2-Cbx-Et | H |
| Ph—Et | H | i-Pr | 2-OH—Et | H |
| 4-F-Bnzl | H | i-Pr | 2-Cbx-Et | H |
| 4-F-Bnzl | H | i-Pr | 2-OH—Et | H |
| 2-OH—Et | H | i-Pr | Bnzl | H |
| 2-OH—Et | H | i-Pr | i-Bu | H |
| 2-OH—Et | H | i-Pr | 1-Npm | H |
| 2-OH—Et | H | i-Pr | 4-OH-Bnzl | H |
| 2-OH—Et | H | i-Pr | Ph—Et | H |
| i-Pnt | H | i-Pr | i-Bu | H |
| i-Pnt | H | i-Pr | 4-OH-Bnzl | H |
| i-Pnt | H | i-Pr | 2-Cbx-Et | H |
| i-Pnt | H | i-Pr | 2-OH—Et | H |
| Chm | H | i-Pr | i-Bu | H |
| Chm | H | i-Pr | 4-OH-Bnzl | H |
| Chm | H | i-Pr | 2-Cbx-Et | H |
| Chm | H | i-Pr | 2-OH—Et | H |
| Chm | H | i-Pr | i-Pnt | H |
| i-Bu | H | s-Bu | i-Pnt | H |
| 4-OH-Bnzl | H | s-Bu | Ph—Et | H |

| R₁ | R₂ₐ | R₂ᵦ | R₃ | R₄ |
| --- | --- | --- | --- | --- |
| 4-OH-Bnzl | H | s-Bu | 2-OH—Et | H |
| 4-OH-Bnzl | H | s-Bu | i-Pnt | H |
| 2-Cbx-Et | H | s-Bu | Ph—Et | H |
| 2-Cbx-Et | H | s-Bu | i-Pnt | H |
| Ph—Et | H | s-Bu | 2-Cbx-Et | H |
| 4-F-Bnzl | H | s-Bu | 2-Cbx-Et | H |
| 2-OH—Et | H | s-Bu | 4-OH-Bnzl | H |
| 2-OH—Et | H | s-Bu | 2-Cbx-Et | H |
| i-Pnt | H | s-Bu | i-Bu | H |
| i-Pnt | H | s-Bu | 4-OH-Bnzl | H |
| i-Pnt | H | s-Bu | 2-Cbx-Et | H |
| i-Pnt | H | s-Bu | Ph—Et | H |
| i-Pnt | H | s-Bu | 2-OH—Et | H |
| Chm | H | s-Bu | i-Bu | H |
| Chm | H | s-Bu | 4-OH-Bnzl | H |
| Chm | H | s-Bu | 2-Cbx-Et | H |
| Chm | H | s-Bu | Ph—Et | H |
| Chm | H | s-Bu | 2-OH—Et | H |
| Chm | H | s-Bu | i-Pnt | H |
| i-Bu | H | 4-OH-Bnzl | i-Pnt | H |
| 2-Cbx-Et | H | 4-OH-Bnzl | Ph—Et | H |
| 2-Cbx-Et | H | 4-OH-Bnzl | i-Pnt | H |
| 4-F-Bnzl | H | 4-OH-Bnzl | 2-Cbx-Et | H |
| 2-OH—Et | H | 4-OH-Bnzl | 2-Cbx-Et | H |
| i-Pnt | H | 4-OH-Bnzl | 2-Cbx-Et | H |
| Chm | H | 4-OH-Bnzl | 2-Cbx-Et | H |
| i-Bu | H | 2-Cbx-Et | Ph—Et | H |
| i-Bu | H | 2-Cbx-Et | i-Pnt | H |
| 2-OH—Et | H | 2-Cbx-Et | i-Bu | H |
| 2-OH—Et | H | 2-Cbx-Et | i-Pnt | H |
| i-Pnt | H | 2-Cbx-Et | i-Bu | H |
| i-Pnt | H | 2-Cbx-Et | 4-OH-Bnzl | H |
| Chm | H | 2-Cbx-Et | i-Bu | H |
| Chm | H | 2-Cbx-Et | 4-OH-Bnzl | H |
| Chm | H | 2-Cbx-Et | i-Pnt | H |
| Bnzl | H | 4-F-Bnzl | 4-OH-Bnzl | H |
| Bnzl | H | 4-F-Bnzl | 2-Cbx-Et | H |
| i-Bu | H | 4-F-Bnzl | 4-OH-Bnzl | H |
| i-Bu | H | 4-F-Bnzl | 2-Cbx-Et | H |
| 1-Npm | H | 4-F-Bnzl | 4-OH-Bnzl | H |
| 1-Npm | H | 4-F-Bnzl | 2-Cbx-Et | H |
| 4-OH-Bnzl | H | 4-F-Bnzl | 2-Cbx-Et | H |
| 4-OH-Bnzl | H | 4-F-Bnzl | Ph—Et | H |
| 4-OH-Bnzl | H | 4-F-Bnzl | 2-OH—Et | H |
| 4-OH-Bnzl | H | 4-F-Bnzl | i-Pnt | H |
| 2-Cbx-Et | H | 4-F-Bnzl | 4-OH-Bnzl | H |
| 2-Cbx-Et | H | 4-F-Bnzl | Ph—Et | H |
| 2-Cbx-Et | H | 4-F-Bnzl | i-Pnt | H |
| Ph—Et | H | 4-F-Bnzl | 4-OH-Bnzl | H |
| Ph—Et | H | 4-F-Bnzl | 2-Cbx-Et | H |
| 2-OH—Et | H | 4-F-Bnzl | 4-OH-Bnzl | H |
| i-Pnt | H | 4-F-Bnzl | 4-OH-Bnzl | H |
| i-Pnt | H | 4-F-Bnzl | 2-Cbx-Et | H |
| Chm | H | 4-F-Bnzl | 4-OH-Bnzl | H |
| Chm | H | 4-F-Bnzl | 2-Cbx-Et | H |
| i-Bu | H | i-Pnt | i-Bu | H |
| i-Bu | H | i-Pnt | 2-Cbx-Et | H |
| i-Bu | H | i-Pnt | 2-OH—Et | H |
| 4-OH-Bnzl | H | i-Pnt | 2-Cbx-Et | H |
| 2-Cbx-Et | H | i-Pnt | i-Bu | H |
| 2-Cbx-Et | H | i-Pnt | 4-OH-Bnzl | H |
| 2-OH—Et | H | i-Pnt | i-Bu | H |
| Chm | H | i-Pnt | i-Bu | H |
| Chm | H | i-Pnt | 2-Cbx-Et | H |
| Bnzl | H | 2-OH—Et | 2-Cbx-Et | H |
| i-Bu | H | 2-OH—Et | i-Bu | H |
| i-Bu | H | 2-OH—Et | 4-OH-Bnzl | H |
| 1-Npm | H | 2-OH—Et | 4-OH-Bnzl | H |
| 4-OH-Bnzl | H | 2-OH—Et | Bnzl | H |
| 4-OH-Bnzl | H | 2-OH—Et | 1-Npm | H |
| 4-OH-Bnzl | H | 2-OH—Et | Ph—Et | H |
| 4-OH-Bnzl | H | 2-OH—Et | i-Pnt | H |
| 2-Cbx-Et | H | 2-OH—Et | 1-Npm | H |
| 2-Cbx-Et | H | 2-OH—Et | 4-OH-Bnzl | H |
| i-Pnt | H | 2-OH—Et | i-Bu | H |
| Chm | H | 2-OH—Et | i-Bu | H |
| Chm | H | 2-OH—Et | i-Pnt | H |

-continued

| R₁ | R₂ₐ | R₂ᵦ | R₃ | R₄ |
|---|---|---|---|---|
| Bnzl | H | Ph—Et | 4-OH-Bnzl | H |
| Bnzl | H | Ph—Et | 2-Cbx-Et | H |
| i-Bu | H | Ph—Et | 4-OH-Bnzl | H |
| i-Bu | H | Ph—Et | 2-Cbx-Et | H |
| 1-Npm | H | Ph—Et | 4-OH-Bnzl | H |
| 4-OH-Bnzl | H | Ph—Et | 2-OH—Et | H |
| 4-OH-Bnzl | H | Ph—Et | i-Pnt | H |
| 2-Cbx-Et | H | Ph—Et | 4-OH-Bnzl | H |
| 2-Cbx-Et | H | Ph—Et | i-Pnt | H |
| 4-F-Bnzl | H | Ph—Et | 4-OH-Bnzl | H |
| 4-F-Bnzl | H | Ph—Et | 2-Cbx-Et | H |
| 2-OH—Et | H | Ph—Et | 4-OH-Bnzl | H |
| i-Pnt | H | Ph—Et | 4-OH-Bnzl | H |
| i-Pnt | H | Ph—Et | 2-Cbx-Et | H |
| Chm | H | Ph—Et | 4-OH-Bnzl | H |
| Chm | H | Ph—Et | 2-Cbx-Et | H |
| Bnzl | H | Hxy | 2-Cbx-Et | H |
| i-Bu | H | Hxy | i-Bu | H |
| i-Bu | H | Hxy | 2-Cbx-Et | H |
| i-Bu | H | Hxy | 2-OH—Et | H |
| i-Bu | H | Hxy | i-Pnt | H |
| 4-OH-Bnzl | H | Hxy | 1-Npm | H |
| 4-OH-Bnzl | H | Hxy | 2-Cbx-Et | H |
| 2-Cbx-Et | H | Hxy | i-Bu | H |
| 2-Cbx-Et | H | Hxy | 1-Npm | H |
| 2-Cbx-Et | H | Hxy | 4-OH-Bnzl | H |
| 2-Cbx-Et | H | Hxy | i-Pnt | H |
| 4-F-Bnzl | H | Hxy | 2-Cbx-Et | H |
| 2-OH—Et | H | Hxy | i-Bu | H |
| 2-OH—Et | H | Hxy | 4-OH-Bnzl | H |
| 2-OH—Et | H | Hxy | i-Pnt | H |
| i-Pnt | H | Hxy | i-Bu | H |
| i-Pnt | H | Hxy | 4-OH-Bnzl | H |
| i-Pnt | H | Hxy | 2-Cbx-Et | H |
| i-Pnt | H | Hxy | 2-OH—Et | H |
| Chm | H | Hxy | i-Bu | H |
| Chm | H | Hxy | 4-OH-Bnzl | H |
| Chm | H | Hxy | 2-Cbx-Et | H |
| Chm | H | Hxy | 2-OH—Et | H |
| Chm | H | Hxy | i-Pnt | H |
| 3-Gun-Pr | H | Bnzl | Ph—Et | H |
| 3-Gun-Pr | H | Bnzl | 2-OH—Et | H |
| 3-Gun-Pr | H | Bnzl | i-Pnt | H |
| Ph—Et | H | Bnzl | 3-Gun-Pr | H |
| 4-F-Bnzl | H | Bnzl | 3-Gun-Pr | H |
| 2-OH—Et | H | Bnzl | 3-Gun-Pr | H |
| Chm | H | Bnzl | 3-Gun-Pr | H |
| 3-Gun-Pr | H | i-Bu | Ph—Et | H |
| 3-Gun-Pr | H | i-Bu | i-Pnt | H |
| Ph—Et | H | i-Bu | 3-Gun-Pr | H |
| 4-F-Bnzl | H | i-Bu | 3-Gun-Pr | H |
| 2-OH—Et | H | i-Bu | 3-Gun-Pr | H |
| i-Pnt | H | i-Bu | 3-Gun-Pr | H |
| Chm | H | i-Bu | 3-Gun-Pr | H |
| 3-Gun-Pr | H | 1-Npm | Ph—Et | H |
| 3-Gun-Pr | H | 1-Npm | i-Pnt | H |
| Ph—Et | H | 1-Npm | 3-Gun-Pr | H |
| 4-F-Bnzl | H | 1-Npm | 3-Gun-Pr | H |
| 2-OH—Et | H | 1-Npm | 3-Gun-Pr | H |
| i-Pnt | H | 1-Npm | 3-Gun-Pr | H |
| Chm | H | 1-Npm | 3-Gun-Pr | H |
| 3-Gun-Pr | H | i-Pr | 2-OH—Et | H |
| 3-Gun-Pr | H | i-Pr | i-Pnt | H |
| Ph—Et | H | i-Pr | 3-Gun-Pr | H |
| 4-F-Bnzl | H | i-Pr | 3-Gun-Pr | H |
| 2-OH—Et | H | i-Pr | 3-Gun-Pr | H |
| i-Pnt | H | i-Pr | 3-Gun-Pr | H |
| Chm | H | i-Pr | 3-Gun-Pr | H |
| 3-Gun-Pr | H | s-Bu | Ph—Et | H |
| Ph—Et | H | s-Bu | 3-Gun-Pr | H |
| 2-OH—Et | H | s-Bu | 3-Gun-Pr | H |
| i-Pnt | H | s-Bu | 3-Gun-Pr | H |
| Chm | H | s-Bu | 3-Gun-Pr | H |
| 3-Gun-Pr | H | 4-OH-Bnzl | Ph—Et | H |
| Ph—Et | H | 4-OH-Bnzl | 3-Gun-Pr | H |
| 4-F-Bnzl | H | 4-OH-Bnzl | 3-Gun-Pr | H |
| 2-OH—Et | H | 4-OH-Bnzl | 3-Gun-Pr | H |

| R₁ | R₂ₐ | R₂ᵦ | R₃ | R₄ |
|---|---|---|---|---|
| i-Pnt | H | 4-OH-Bnzl | 3-Gun-Pr | H |
| Chm | H | 4-OH-Bnzl | 3-Gun-Pr | H |
| Bnzl | H | 3-Gun-Pr | 2-OH—Et | H |
| i-Bu | H | 3-Gun-Pr | Ph—Et | H |
| i-Bu | H | 3-Gun-Pr | 2-OH—Et | H |
| i-Bu | H | 3-Gun-Pr | i-Pnt | H |
| 1-Npm | H | 3-Gun-Pr | Ph—Et | H |
| 4-OH-Bnzl | H | 3-Gun-Pr | Ph—Et | H |
| 4-OH-Bnzl | H | 3-Gun-Pr | 2-OH—Et | H |
| 4-OH-Bnzl | H | 3-Gun-Pr | i-Pnt | H |
| Ph—Et | H | 3-Gun-Pr | i-Bu | H |
| Ph—Et | H | 3-Gun-Pr | 1-Npm | H |
| Ph—Et | H | 3-Gun-Pr | 4-OH-Bnzl | H |
| Ph—Et | H | 3-Gun-Pr | i-Pnt | H |
| 4-F-Bnzl | H | 3-Gun-Pr | i-Bu | H |
| 4-F-Bnzl | H | 3-Gun-Pr | 1-Npm | H |
| 4-F-Bnzl | H | 3-Gun-Pr | 4-OH-Bnzl | H |
| 4-F-Bnzl | H | 3-Gun-Pr | i-Pnt | H |
| 2-OH—Et | H | 3-Gun-Pr | i-Bu | H |
| 2-OH—Et | H | 3-Gun-Pr | i-Pnt | H |
| i-Pnt | H | 3-Gun-Pr | Bnzl | H |
| i-Pnt | H | 3-Gun-Pr | i-Bu | H |
| i-Pnt | H | 3-Gun-Pr | 1-Npm | H |
| i-Pnt | H | 3-Gun-Pr | 4-OH-Bnzl | H |
| Chm | H | 3-Gun-Pr | Bnzl | H |
| Chm | H | 3-Gun-Pr | i-Bu | H |
| Chm | H | 3-Gun-Pr | 1-Npm | H |
| Chm | H | 3-Gun-Pr | 4-OH-Bnzl | H |
| Chm | H | 3-Gun-Pr | Ph—Et | H |
| Chm | H | 3-Gun-Pr | 2-OH—Et | H |
| Chm | H | 3-Gun-Pr | i-Pnt | H |
| Bnzl | H | 4-F-Bnzl | 3-Gun-Pr | H |
| i-Bu | H | 4-F-Bnzl | 3-Gun-Pr | H |
| 1-Npm | H | 4-F-Bnzl | 3-Gun-Pr | H |
| 4-OH-Bnzl | H | 4-F-Bnzl | 3-Gun-Pr | H |
| 3-Gun-Pr | H | 4-F-Bnzl | Ph—Et | H |
| 3-Gun-Pr | H | 4-F-Bnzl | i-Pnt | H |
| Ph—Et | H | 4-F-Bnzl | 3-Gun-Pr | H |
| 2-OH—Et | H | 4-F-Bnzl | 3-Gun-Pr | H |
| i-Pnt | H | 4-F-Bnzl | 3-Gun-Pr | H |
| Chm | H | 4-F-Bnzl | 3-Gun-Pr | H |
| Bnzl | H | i-Pnt | 3-Gun-Pr | H |
| i-Bu | H | i-Pnt | 3-Gun-Pr | H |
| 1-Npm | H | i-Pnt | 3-Gun-Pr | H |
| 4-OH-Bnzl | H | i-Pnt | 3-Gun-Pr | H |
| 3-Gun-Pr | H | i-Pnt | 4-OH-Bnzl | H |
| 3-Gun-Pr | H | i-Pnt | Ph—Et | H |
| Ph—Et | H | i-Pnt | 3-Gun-Pr | H |
| 4-F-Bnzl | H | i-Pnt | 3-Gun-Pr | H |
| 2-OH—Et | H | i-Pnt | 3-Gun-Pr | H |
| Chm | H | i-Pnt | 3-Gun-Pr | H |
| Bnzl | H | 2-OH—Et | 3-Gun-Pr | H |
| i-Bu | H | 2-OH—Et | 3-Gun-Pr | H |
| 1-Npm | H | 2-OH—Et | 3-Gun-Pr | H |
| 4-OH-Bnzl | H | 2-OH—Et | 3-Gun-Pr | H |
| 3-Gun-Pr | H | 2-OH—Et | i-Bu | H |
| 4-F-Bnzl | H | 2-OH—Et | 3-Gun-Pr | H |
| i-Pnt | H | 2-OH—Et | 3-Gun-Pr | H |
| Chm | H | 2-OH—Et | 3-Gun-Pr | H |
| Bnzl | H | Ph—Et | 3-Gun-Pr | H |
| i-Bu | H | Ph—Et | 3-Gun-Pr | H |
| 1-Npm | H | Ph—Et | 3-Gun-Pr | H |
| 4-OH-Bnzl | H | Ph—Et | 3-Gun-Pr | H |
| 3-Gun-Pr | H | Ph—Et | i-Pnt | H |
| 4-F-Bnzl | H | Ph—Et | 3-Gun-Pr | H |
| 2-OH—Et | H | Ph—Et | 3-Gun-Pr | H |
| i-Pnt | H | Ph—Et | 3-Gun-Pr | H |
| Chm | H | Ph—Et | 3-Gun-Pr | H |
| Bnzl | H | Hxy | 3-Gun-Pr | H |
| i-Bu | H | Hxy | 3-Gun-Pr | H |
| 1-Npm | H | Hxy | 3-Gun-Pr | H |
| 4-OH-Bnzl | H | Hxy | 3-Gun-Pr | H |
| 3-Gun-Pr | H | Hxy | Bnzl | H |
| 3-Gun-Pr | H | Hxy | 1-Npm | H |
| 3-Gun-Pr | H | Hxy | 4-OH-Bnzl | H |
| 3-Gun-Pr | H | Hxy | Ph—Et | H |
| 3-Gun-Pr | H | Hxy | i-Pnt | H |

-continued

| $R_1$ | $R_{2A}$ | $R_{2B}$ | $R_3$ | $R_4$ |
|---|---|---|---|---|
| Ph—Et | H | Hxy | 3-Gun-Pr | H |
| 4-F-Bnzl | H | Hxy | 3-Gun-Pr | H |
| 2-OH—Et | H | Hxy | 3-Gun-Pr | H |
| i-Pnt | H | Hxy | 3-Gun-Pr | H |
| Chm | H | Hxy | 3-Gun-Pr | H |
| 2-OtBu—Et | H | i-Bu | Bnzl | H |
| 2-OtBu—Et | H | i-Bu | 1-Npm | H |
| 2-OtBu—Et | H | Bnzl | i-Pnt | H |
| 2-OtBu—Et | H | 1-Npm | Bnzl | H |
| 2-OtBu—Et | H | 1-Npm | i-Bu | H |
| Bnzl | H | 2-OtBu—Et | Bnzl | H |
| Bnzl | H | 2-OtBu—Et | i-Bu | H |
| Bnzl | H | 2-OtBu—Et | 1-Npm | H |
| Bnzl | H | 2-OtBu—Et | Ph—Et | H |
| Bnzl | H | 2-OtBu—Et | i-Pnt | H |
| i-Bu | H | 2-OtBu—Et | Bnzl | H |
| i-Bu | H | 2-OtBu—Et | 1-Npm | H |
| i-Bu | H | 2-OtBu—Et | Ph—Et | H |
| 1-Npm | H | 2-OtBu—Et | Bnzl | H |
| 1-Npm | H | 2-OtBu—Et | i-Bu | H |
| 1-Npm | H | 2-OtBu—Et | Ph—Et | H |
| 1-Npm | H | 2-OtBu—Et | i-Pnt | H |
| 4-tBuO-Bnzl | H | 2-OtBu—Et | i-Bu | H |
| Ph—Et | H | 2-OtBu—Et | Bnzl | H |
| Ph—Et | H | 2-OtBu—Et | i-Bu | H |
| Ph—Et | H | 2-OtBu—Et | 4-tBuO-Bnzl | H |
| Ph—Et | H | 2-OtBu—Et | i-Pnt | H |
| 4-F-Bnzl | H | 2-OtBu—Et | Bnzl | H |
| 4-F-Bnzl | H | 2-OtBu—Et | i-Bu | H |
| 4-F-Bnzl | H | 2-OtBu—Et | 1-Npm | H |
| 4-F-Bnzl | H | 2-OtBu—Et | Ph—Et | H |
| 4-F-Bnzl | H | 2-OtBu—Et | i-Pnt | H |
| i-Pnt | H | 2-OtBu—Et | Bnzl | H |
| i-Pnt | H | 2-OtBu—Et | 1-Npm | H |
| Chm | H | 2-OtBu—Et | Bnzl | H |
| Chm | H | 2-OtBu—Et | 4-tBuO-Bnzl | H |
| Chm | H | 2-OtBu—Et | Ph—Et | H |
| 4-F-Bnzl | H | i-Pnt | tBOC-E | H |
| Chm | H | i-Pnt | 4-tBuO-Bnzl | H |
| Bnzl | H | Hxy | 4-tBuO-Bnzl | H |
| i-Bu | H | Hxy | 4-tBuO-Bnzl | H |
| 4-tBuO-Bnzl | H | Hxy | Bnzl | H |
| 4-tBuO-Bnzl | H | Hxy | Ph—Et | H |
| 4-tBuO-Bnzl | H | Hxy | i-Pnt | H |
| tBOC-E | H | Hxy | Ph—Et | H |
| Ph-Et | H | Hxy | 4-tBuO-Bnzl | H |
| 2-OtBu—Et | H | Hxy | Bnzl | H |
| 2-OtBu—Et | H | Hxy | Ph—Et | H |
| 2-OH—Et | H | i-Bu | Bnzl | H |
| 2-OH—Et | H | i-Bu | 1-Npm | H |
| 2-OH—Et | H | Bnzl | i-Pnt | H |
| 2-OH—Et | H | 1-Npm | Bnzl | H |
| 2-OH—Et | H | 1-Npm | i-Bu | H |
| Bnzl | H | 2-OH—Et | Bnzl | H |
| Bnzl | H | 2-OH—Et | i-Bu | H |
| Bnzl | H | 2-OH—Et | 1-Npm | H |
| Bnzl | H | 2-OH—Et | Ph—Et | H |
| Bnzl | H | 2-OH—Et | i-Pnt | H |
| i-Bu | H | 2-OH—Et | Bnzl | H |
| i-Bu | H | 2-OH—Et | 1-Npm | H |
| i-Bu | H | 2-OH—Et | Ph—Et | H |
| 1-Npm | H | 2-OH—Et | Bnzl | H |
| 1-Npm | H | 2-OH—Et | i-Bu | H |
| 1-Npm | H | 2-OH—Et | Ph—Et | H |
| 1-Npm | H | 2-OH—Et | i-Pnt | H |
| 4-OH-Bnzl | H | 2-OH—Et | i-Bu | H |
| Ph—Et | H | 2-OH—Et | Bnzl | H |
| Ph—Et | H | 2-OH—Et | i-Bu | H |
| Ph—Et | H | 2-OH—Et | 1-Npm | H |
| Ph—Et | H | 2-OH—Et | 4-OH-Bnzl | H |
| Ph—Et | H | 2-OH—Et | i-Pnt | H |
| 4-F-Bnzl | H | 2-OH—Et | Bnzl | H |
| 4-F-Bnzl | H | 2-OH—Et | i-Bu | H |
| 4-F-Bnzl | H | 2-OH—Et | 1-Npm | H |
| 4-F-Bnzl | H | 2-OH—Et | 4-OH-Bnzl | H |
| 4-F-Bnzl | H | 2-OH—Et | Ph—Et | H |
| i-Pnt | H | 2-OH—Et | Bnzl | H |

-continued

| R₁ | R₂ₐ | R₂ᵦ | R₃ | R₄ |
|---|---|---|---|---|
| i-Pnt | H | 2-OH—Et | 1-Npm | H |
| i-Pnt | H | 2-OH—Et | 4-OH-Bnzl | H |
| Chm | H | 2-OH—Et | Bnzl | H |
| Chm | H | 2-OH—Et | 4-OH-Bnzl | H |
| Chm | H | 2-OH—Et | Ph—Et | H |
| 4-F-Bnzl | H | i-Pnt | 2-Cbx-Et | H |
| Chm | H | i-Pnt | 4-OH-Bnzl | H |
| Bnzl | H | Hxy | 4-OH-Bnzl | H |
| i-Bu | H | Hxy | 4-OH-Bnzl | H |
| 4-OH-Bnzl | H | Hxy | Bnzl | H |
| 4-OH-Bnzl | H | Hxy | Ph—Et | H |
| 4-OH-Bnzl | H | Hxy | i-Pnt | H |
| 2-Cbx-Et | H | Hxy | Ph—Et | H |
| Ph—Et | H | Hxy | 4-OH-Bnzl | H |
| 2-OH—Et | H | Hxy | Bnzl | H |
| 2-OH—Et | H | Hxy | Ph—Et | H |
| 1-tert-butoxycarbonyl-6-methyl-1H-indol-3-ylmethyl | H | cycloheptylmethyl | i-Bu | H |
| 6-methyl-1H-indol-3-ylmethyl | H | cycloheptylmethyl | i-Bu | H |
| 1-tert-butoxycarbonyl-6-fluoro-1H-indol-3-ylmethyl | H | cycloheptylmethyl | i-Bu | H |
| 6-fluoro-1H-indol-3-ylmethyl | H | cycloheptylmethyl | i-Bu | H |
| Chm | H | pentyl | 3-Me-Bnzl | H |
| 1-Npm | H | β-hydroxyphenethyl | Ph—Et | H |
| 1-Npm | H | α-hydroxymethyl-phenethyl | Ph—Et | H |
| 1-Npm | H | α-hydroxymethyl-phenethyl | Ph—Et | H |
| 2-trifluoromethylbenzyl | H | 4-tBuO-Bnzl | i-Bu | H |
| 2-trifluoromethylbenzyl | H | 4-OH-Bnzl | i-Bu | H |
| 3-benzyloxybenzyl | H | 4-tBuO-Bnzl | i-Bu | H |
| 3-benzyloxybenzyl | H | 4-OH-Bnzl | i-Bu | H |
| Chm | H | pentyl | Bnzl | H |
| cycloheptylmethyl | H | pentyl | Bnzl | H |
| cycloheptylmethyl | H | pentyl | 3-Me-Bnzl | H |
| cyclopentylmethyl | H | Bnzl | Chm | H |
| 4-Me-Bnzl | H | 4-methoxybutyl | Pr | H |
| 4-Cl-Bnzl | H | 4-methoxybutyl | Pr | H |
| 3-Gun-Pr | H | 3-Gun-Pr | 3-Gun-Pr | H |

†Ring formed together by R₂ₐ and R₂ᵦ.

30. A pharmaceutical composition comprising the compound or an enantiomer thereof or a pharmaceutically acceptable salt thereof according to claim 2 and a pharmaceutically acceptable carrier.

31. A method for preventing or treating an infection with Lyssavirus, characterized by administering, to a patient in need thereof, a therapeutically effective amount of the compound or an enantiomer thereof, or a pharmaceutically acceptable salt thereof, or a solvate thereof according to claim 2.

32. The method according to claim 31, wherein the infection with Lyssavirus is rabies.

* * * * *